US009556197B2

(12) United States Patent
Li et al.

(10) Patent No.: US 9,556,197 B2
(45) Date of Patent: Jan. 31, 2017

(54) FURO- AND THIENO-PYRIDINE CARBOXAMIDE COMPOUNDS USEFUL AS PIM KINASE INHIBITORS

(71) Applicant: Incyte Corporation, Wilmington, DE (US)

(72) Inventors: Yun-Long Li, Chadds Ford, PA (US); David M. Burns, Glen Mills, PA (US); Hao Feng, Aston, PA (US); Taisheng Huang, Wilmington, DE (US); Song Mei, Wilmington, DE (US); Jun Pan, Media, PA (US); Oleg Vechorkin, Wilmington, DE (US); Hai-Fen Ye, Newark, DE (US); Wenyu Zhu, Media, PA (US); Maria Rafalski, Greenville, DE (US); Anlai Wang, Wilmington, DE (US); Chu-Biao Xue, Hockessin, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 14/465,910

(22) Filed: Aug. 22, 2014

(65) Prior Publication Data
US 2015/0057265 A1    Feb. 26, 2015

Related U.S. Application Data

(60) Provisional application No. 61/869,442, filed on Aug. 23, 2013.

(51) Int. Cl.
*C07D 495/04* (2006.01)
*C07D 491/048* (2006.01)

(52) U.S. Cl.
CPC ......... *C07D 495/04* (2013.01); *C07D 491/048* (2013.01)

(58) Field of Classification Search
CPC .................................................. C07D 495/04
See application file for complete search history.

(56) References Cited

U.S. PATENT DOCUMENTS

| 8,168,794 | B2 | 5/2012 | Burger et al. |
| 8,329,732 | B2 | 12/2012 | Burger et al. |
| 9,278,950 | B2 | 3/2016 | Li et al. |
| 2011/0059961 | A1 | 3/2011 | Wang et al. |
| 2012/0114663 | A1 | 5/2012 | Gelfand et al. |
| 2014/0086941 | A1 | 3/2014 | Reddy et al. |
| 2014/0088117 | A1 | 3/2014 | Burch et al. |
| 2014/0163000 | A1* | 6/2014 | Ahmad ................ C07D 487/04 514/210.18 |
| 2014/0200216 | A1 | 7/2014 | Li et al. |
| 2014/0200227 | A1 | 7/2014 | Xue et al. |
| 2015/0329534 | A1 | 11/2015 | Xue et al. |
| 2016/0009714 | A1 | 1/2016 | Sun et al. |
| 2016/0009726 | A1 | 1/2016 | Vechorkin et al. |
| 2016/0137626 | A1 | 5/2016 | Li et al. |

FOREIGN PATENT DOCUMENTS

| CN | 103664878 | 3/2014 |
| EP | 2637650 | 9/2013 |
| EP | 2743269 | 6/2014 |
| WO | WO 02/00196 | 1/2002 |
| WO | WO 02/055489 | 7/2002 |
| WO | WO 02/093173 | 11/2002 |
| WO | WO 03/106681 | 12/2003 |
| WO | WO 2004/024895 | 3/2004 |
| WO | WO 2004/090106 | 10/2004 |
| WO | WO 2005/028624 | 3/2005 |
| WO | WO 2005/033310 | 4/2005 |
| WO | WO 2006/006569 | 1/2006 |
| WO | WO 2006/071960 | 7/2006 |
| WO | WO 2006/078228 | 7/2006 |
| WO | WO 2007/002433 | 1/2007 |
| WO | WO 2007/011760 | 1/2007 |
| WO | WO 2007/041712 | 4/2007 |
| WO | WO 2007/044724 | 4/2007 |
| WO | WO 2007/048065 | 4/2007 |
| WO | WO 2007/052843 | 5/2007 |
| WO | WO 2007/084857 | 7/2007 |
| WO | WO 2007/131191 | 11/2007 |
| WO | WO 2008/002676 | 1/2008 |
| WO | WO 2008/022164 | 2/2008 |
| WO | WO 2008/045252 | 4/2008 |
| WO | WO 2008/054749 | 5/2008 |
| WO | WO 2008/058126 | 5/2008 |
| WO | WO 2008/082839 | 7/2008 |
| WO | WO 2008/082840 | 7/2008 |
| WO | WO 2008/106692 | 9/2008 |
| WO | WO 2008/121687 | 10/2008 |
| WO | WO 2008/124323 | 10/2008 |
| WO | WO 2008/127728 | 10/2008 |
| WO | WO 2008/133955 | 11/2008 |
| WO | WO 2008/143759 | 11/2008 |
| WO | WO 2009/014637 | 1/2009 |

(Continued)

OTHER PUBLICATIONS

Michelotti et. al. "Two classes of p38a MAP kinase inhibitors having a common diphenylether core but exhibiting divergent binding modes" 2005, 15, 5274-5279.*

Jiang et. al. "3,5-Disubstituted quinolines as novel c-Jun N-terminal kinase inhibitors." Bioorganic & Medicinal Chemistry Letters 2007, 17, 6378-6382.*

Liu et. al. "Synthesis and SAR of 1,9-dihydro-9-hydroxypyrazolo[3,4-b]quinolin-4-ones as novel, selective c-Jun N-terminal kinase inhibitors" Bioorganic & Medicinal Chemistry Letters 2006, 16, 2590-2594.*

(Continued)

*Primary Examiner* — David K O'Dell
(74) *Attorney, Agent, or Firm* — Fish & Richardson P.C.

(57) ABSTRACT

The present disclosure describes furo- and thieno-pyridine carboxamide compounds, as well as their compositions and methods of use. The compounds inhibit the activity of the Pim kinases, and are useful in the treatment of diseases related to the activity of Pim kinases including, e.g., cancer and other diseases.

48 Claims, No Drawings

(56) References Cited

FOREIGN PATENT DOCUMENTS

| | | |
|---|---|---|
| WO | WO 2009/017701 | 2/2009 |
| WO | WO 2009/064486 | 5/2009 |
| WO | WO 2009/065080 | 5/2009 |
| WO | WO 2009/108912 | 9/2009 |
| WO | WO 2009/109576 | 9/2009 |
| WO | WO 2009/151845 | 12/2009 |
| WO | WO 2010/000978 | 1/2010 |
| WO | WO 2010/001169 | 1/2010 |
| WO | WO 2010/002933 | 1/2010 |
| WO | WO 2010/022076 | 2/2010 |
| WO | WO 2010/022081 | 2/2010 |
| WO | WO 2010/026121 | 3/2010 |
| WO | WO 2010/026122 | 3/2010 |
| WO | WO 2010/026124 | 3/2010 |
| WO | WO 2010/048314 | 4/2010 |
| WO | WO 2010/057833 | 5/2010 |
| WO | WO 2010/071885 | 6/2010 |
| WO | WO 2010/135401 | 11/2010 |
| WO | WO 2010/135571 | 11/2010 |
| WO | WO 2010/135581 | 11/2010 |
| WO | WO 2010/148351 | 12/2010 |
| WO | WO 2011/025859 | 3/2011 |
| WO | WO 2011/029802 | 3/2011 |
| WO | WO 2011/031979 | 3/2011 |
| WO | WO 2011/035019 | 3/2011 |
| WO | WO 2011/035022 | 3/2011 |
| WO | WO 2011/053861 | 5/2011 |
| WO | WO 2011/057784 | 5/2011 |
| WO | WO 2011/058139 | 5/2011 |
| WO | WO 2011/060295 | 5/2011 |
| WO | WO 2011/063398 | 5/2011 |
| WO | WO 2011/068667 | 6/2011 |
| WO | WO 2011/075613 | 6/2011 |
| WO | WO 2011/079274 | 6/2011 |
| WO | WO 2011/101643 | 8/2011 |
| WO | WO 2011/124580 | 10/2011 |
| WO | WO 2012/004217 | 1/2012 |
| WO | WO 2012007375 A1 * | 1/2012 |
| WO | WO 2012/015474 | 2/2012 |
| WO | WO 2012/016217 | 2/2012 |
| WO | WO 2012/064981 | 5/2012 |
| WO | WO 2012/065297 | 5/2012 |
| WO | WO 2012/065546 | 5/2012 |
| WO | WO 2012/078777 | 6/2012 |
| WO | WO 2012/080990 | 6/2012 |
| WO | WO 2012/101029 | 8/2012 |
| WO | WO 2012/101032 | 8/2012 |
| WO | WO 2012/120415 | 9/2012 |
| WO | WO 2012/120428 | 9/2012 |
| WO | WO 2012/129338 | 9/2012 |
| WO | WO 2012/137089 | 10/2012 |
| WO | WO 2012/139930 | 10/2012 |
| WO | WO 2012/145617 | 10/2012 |
| WO | WO 2012/146933 | 11/2012 |
| WO | WO 2012/146936 | 11/2012 |
| WO | WO 2012/148775 | 11/2012 |
| WO | WO 2012/154274 | 11/2012 |
| WO | WO 2012/156367 | 11/2012 |
| WO | WO 2012/156756 | 11/2012 |
| WO | WO 2012/163942 | 12/2012 |
| WO | WO 2012/170827 | 12/2012 |
| WO | WO 2012/175591 | 12/2012 |
| WO | WO 2013/013188 | 1/2013 |
| WO | WO 2013/020369 | 2/2013 |
| WO | WO 2013/20370 | 2/2013 |
| WO | WO 2013/020371 | 2/2013 |
| WO | WO 2013/024002 | 2/2013 |
| WO | WO 2013/034570 | 3/2013 |
| WO | WO 2013/041634 | 3/2013 |
| WO | WO 2013/045461 | 4/2013 |
| WO | WO 2013/050446 | 4/2013 |
| WO | WO 2013/050448 | 4/2013 |
| WO | WO 2013/130660 | 9/2013 |
| WO | WO 2013/134079 | 9/2013 |
| WO | WO 2013/066684 | 10/2013 |
| WO | WO 2013/144189 | 10/2013 |
| WO | WO 2013/149909 | 10/2013 |
| WO | WO 2013/175388 | 11/2013 |
| WO | WO 2014/001377 | 1/2014 |
| WO | WO 2014/022752 | 2/2014 |
| WO | WO 2014/033630 | 3/2014 |
| WO | WO 2014/033631 | 3/2014 |
| WO | WO 2014/048939 | 4/2014 |
| WO | WO 2014/053568 | 4/2014 |
| WO | WO 2014/076162 | 5/2014 |
| WO | WO 2014/099880 | 6/2014 |
| WO | WO 2014089379 A9 * | 6/2014 |
| WO | WO 2014/110574 | 7/2014 |

OTHER PUBLICATIONS

Miyazaki et. al. "Design and effective synthesis of novel templates, 3,7-diphenyl-4- amino-thieno and furo-[3,2-c]pyridines as protein kinase inhibitors and in vitro evaluation targeting angiogenetic kinases" Bioorganic & Medicinal Chemistry Letters 2007, 17, 250-254.*

Mulvihill et. al. "Novel 2-phenylquinolin-7-yl-derived imidazo[1,5-a]pyrazines as potent insulin-like growth factor-I receptor (IGF-IR) inhibitors" Bioorganic & Medicinal Chemistry 2008, 16, 1359-1375.*

Burger "Structure Guided Optimization, in Vitro Activity, and in Vivo Activity of Pan-PIM Kinase Inhibitors" ACS Med. Chem. Lett. 2013, 4, 1193-1197.*

Bamborough "Assessment of Chemical Coverage of Kinome Space and Its Implications for Kinase Drug Discovery" J. Med. Chem. 2008, 51, 7898-7914.*

Simone, Oncology: Introduction, Cecil Textbook of Medicine, 20th Edition, 1996 vol. 1, pp. 1004-1010.*

Konstantinos Makrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.*

Chaichian "Targeted Therapies in Systemic Lupus Erythematosus: State-of-the-Art Review" J Clin Cell Immunol 2013, S6, 1- 8.*

Georg Pilz, "Modern multiple sclerosis treatment—what is approved, what is on the horizon" Drug Discovery Today Dec. 2008, vol. 13, Nos. 23/24 1013-1025.*

Merkel, "PIM1 kinase as a target for cancer therapy" Expert Opin. Investig. Drugs [Early Online] 2012, 1-12.*

Damia "Contemporary pre-clinical development of anticancer agents—What are the optimal preclinical models?" European Journal of Cancer 2009, 45, 2768-2781.*

Sharma "Cell line-based platforms to evaluate the therapeutic efficacy of candidate anticancer agents" Nature Reviews Cancer Apr. 2010, vol. 10, 241-253.*

Ocana, A. "Preclinical development of molecular targeted agents for cancer" Nat. Rev. Clin. Oncol. 2011, 8, 200-209.*

Johnson, et. al. "Relationships between drug activity in Nci preclinical in vitro and in vivo models and early clinical trials." British Journal of Cancer 2001, 84, 1424-1431.*

International Search Report and Written Opinion in International Application No. PCT/US2014/011487, mailed Apr. 4, 2014, 11 pages.

International Search Report and Written Opinion in International Application No. PCT/US2014/011486, mailed Mar. 17, 2014, 12 pages.

International Search Report and Written Opinion in International Application No. PCT/US2014/052214, mailed Oct. 28, 2014, 13 pages.

Amson et al., "The human protooncogene product p33pim is expressed during fetal hematopoiesis and in diverse leukemias," Proc. Nat. Acad. Sci., USA, 1989, 86:8857-61.

Berge et al., "Pharmaceutical Salts," J. Pharm. Sci., 1977, 66(1):1-19.

(56) References Cited

OTHER PUBLICATIONS

Blom et al., "Optimizing Preparative LC-MS Configurations and Methods for Parallel Synthesis Purification," J. Comb. Chem., 2003, 5:670-83.
Blom et al., "Preparative LC-MS Purification: Improved Compound Specific Method Optimization," J. Comb. Chem., 2004, 6:874-883.
Blom, "Two-Pump At Column Dilution Configuration for Preparative Liquid Chromatography—Mass Spectrometry," J. Comb. Chem., 2002, 4:295-301.
Burger et al. "Structure Guided Optimization, in Vitro Activity, and in Vivo Activity of Pan-PIM Kinase Inhibitors," ACS Med Chem Lett., 2013, 4:1193-1197.
Chen et al., "Pim kinase inhibitor, SGI-1776, induces apoptosis in chronic lymphocytic leukemia cells," Blood, 2009, 114:4150-57.
Claudio et al., "A molecular compendium of genes expressed in multiple myeloma," Blood, 2002, 100:2175-86.
Davis et al., "Small Molecule Dual Antagonist of Pim 1 and 3 Kinases Ameliorate Experimental Autoimmune Encephalomyelitis," $26^{th}$ Congress of the European Committee for Treatment and Research in Multiple Sclerosis, Oct. 13-16, 2010, Gothenburg, Sweden, Poster P436.
Dorwald F. A. Side Reactions in Organic Synthesis, 2005, Wiley: VCH, Weinheim p. IX of Preface pg. 1-15.
Fujii et al., "Aberrant expression of serine-threonine kinase Pim-3 in hepatocellular carcinoma development and its role in the proliferation of human hepatoma cell lines," Int. J. Canc., 2005, 114:209-18.
Gomez-Abad et al., "PIM2 inhibition as a rational therapeutic approach in B-cell lymphoma," Blood, 2011, 118:5517-27.
Gu and Li, "A concise synthesis of (2S,4R)- and (2S,4S)-4-methylglutamic acid," Tetrahedron Lett., 2003, 44:3203-3205.
Hsi et al., "Ki67 and PIM1 expression predict outcome in mantle cell lymphoma treated with high dose therapy, stem cell transplantation and rituximab: a Cancer and Leukemia Group B 59909 correlative science study," Leuk. Lymph., 2008, 49:2081-90.
Hsu et al., "Pim-1 knockdown potentiates paclitaxel-induced apoptosis in human hormone-refractory prostate cancers through inhibition of NHEJ DNA repair," Cancer Lett., 2012, 319:214-222.
Huang et al., "Structure-based design and optimization of 2-aminothiazole-4-carboxamide as a new class of CHK1 inhibitors," Bioorganic Med Chem Lett., Mar. 2013, 23(9):2590-2594.
Isaac et al., "The oncogenic PIM kinase family regulates drug resistance through multiple mechanisms," Drug Resis. Updates, 2011, 14:203-11.
Ishchenko et al., "Structure-based design of low-nanomolar PIM kinase inhibitors," Bioorg Med Chem Lett., 2015, 25:474-480.
Li et al., "Pim-3, a Proto-Oncogene with Serine/Threonine Kinase Activity, is Aberrantly Expressed in Human Pancreatic Cancer and Phosphorylates Bad to Block Bad-Mediated Apoptosis in Human Pancreatic Cancer Cell Lines," Canc. Res., 2006, 66:6741-7.
Liu et al., "Overexpression of Pim-1 is associated with poor prognosis in patients with esophageal squamous cell carcinoma," J. Surg. Oncol., 2010,102:683-88.
Merkel et al., "PIM1 kinase as a target for cancer therapy," Exp. Opin. Investig. Drugs, 2012, 21:425-38.
Mikkers et al., "Mice deficient for all PIM kinases display reduced body size and impaired responses to hematopoietic growth factors," Mol. Cell. Biol., 2004, 24:6104-15.
Mikkers et al., "High-throughput retroviral tagging to identify components of specific signaling pathways in cancer," Nature Genet., 2002, 32:153-159.
Mizuki et al., "Suppression of myeloid transcription factors and induction of STAT response genes by AML-specific Flt3 mutations," Blood, 2003, 101:3164-73.
Morwick, "Pim kinase inhibitors: a survey of the patent literature," Exp. Opin. Ther. Patents, 2010, 20(2):193-212.

Peltola et al., "Pim-1 kinase expression predicts radiation response in squamocellular carcinoma of head and neck and is under the control of epidermal growth factor receptor," Neoplasia, 2009, 11:629-36.
Peturssion, "Protecting Groups in Carbohydrate Chemistry," J. Chem. Educ., 1997, 74(11):1297- 1303.
Ravin, "Preformulation," Remington's Pharmaceutical Sciences, $17^{th}$ Ed., (Mack Publishing Company, Easton, 1985), p. 1409-1423.
Robinson et al., "A Dual PIM 1/3 Kinase Inhibitor Demonstrates Efficacy in Murine Models of Lupus and Multiple Sclerosis," J. Immunol , 2012, 188:119.9.
Schatz, et al., "Targeting cap-dependent translation blocks converging survival signals by AKT and PIM kinases in lymphoma," J. Exp. Med., 2011, 208:1799-1807.
Shen et al , "Inhibition of Pim-1 kinase ameliorates dextran sodium sulfate-induced colitis in mice," Dig. Dis. Sci., 2012, 57:1822-31.
Shinto et al., "Moloney murine leukemia virus infection accelerates lymphomagenesis in Eµ-bc1-2 transfenic mice," Oncogene, 1995, 11:1729-36.
Swords et al., "The Pim kinases: new targets for drug development," Curr. Drug Targets, 2011, 12(14):2059-66.
Venkatesh et al., "Role of the Development Scientist in Compound Lead Selection and Optimization," J. Pharm. Sci., 2000, 89:145-54.
Wang et al , "Inhibition of Pim1 kinase prevents peanut allergy by enhancing Runx3 expression and suppressing T(H)2 and T(H)17 T-cell differentiation," J. All. Clin. Immunol., 2012, 130:932-44.
Yang et al., "Proviral integration site 2 is required for interleukin-6 expression induced by interleukin-1, tumour necrosis factor-α and lipopolysaccharide," Immunol , 2010, 131:174-182.
Zippo, et al., "PIM1-dependent phosphorylation of histone H3 at serine 10 is required for MYC-dependent transcriptional activation and oncogenic transformation," Nature Cell Biol., 2007, 9:932-44.
Arunesh et al., "Small molecule inhibitors of PIM1 kinase: Jul. 2009 to Feb. 2013 patent update," Expert Opin Ther Pat, Jan. 2014, 24(1): 5-17.
Chan et al., "New N- and O-arylations with phenylboronic acids and cupric acetate," Tetrahedron Letters, May 1998, 39(19): 2933-2936.
Freshney, Culture of Animal Cells, A Manual of Basic Technique, Alan R. Liss, Inc., 1983, New York, P4.
International Preliminary Report on Patentability in International Application No. PCT/US2014/011486, mailed Jul. 21, 2015, 7 pages.
International Preliminary Report on Patentability in International Application No. PCT/US2014/011487, mailed Jul. 23, 2015, 6 pages.
International Search Report and Written Opinion in International Application No. PCT/US2015/040146, dated Oct. 5, 2015, 12 pages.
Kelly et al., "Targeting PIM kinase activity significantly augments the efficacy of cytarabine," British Journal of Haematology, 2011, 156, 129-152.
Lam et al., "New aryl/heteroaryl C N bond cross-coupling reactions via arylboronic acid/cupric acetate arylation," Tetrahedron Letters, May 1998, 39(19): 2941-2944.
Ogawa et al., "Insights from Pim1 structure for anti-cancer drug design," Expert Opin Drug Discov, Dec. 2012, 7(12): 1177-92.
Search Report, Jul. 2, 2014, 6 pages.
Search Report, Jul. 8, 2014, 4 pages.
Search Report, Jul. 3, 2014, 4 pages.
United States Office Action in U.S. Appl. No. 14/155,134, mailed Jul. 27, 2015, 12 pages.
Blanco-Aparicio, Biochemical Pharmacology, vol. 85, pp. 629-643, 2013.
International Preliminary Report on Patentability in International Application No. PCT/US2014/052214, dated Feb. 23, 2016, 7 pages.

* cited by examiner

FURO- AND THIENO-PYRIDINE CARBOXAMIDE COMPOUNDS USEFUL AS PIM KINASE INHIBITORS

CROSS-REFERENCE TO RELATED APPLICATIONS

This application claims the benefit of U.S. Provisional Application Ser. No. 61/869,442, filed Aug. 23, 2013, the disclosure of which is incorporated herein by reference in its entirety.

TECHNICAL FIELD

The present application is concerned with pharmaceutically useful compounds. The disclosure provides new compounds as well as their compositions and methods of use. The compounds inhibit the activity of Pim kinases and are therefore useful in the treatment of diseases related to the activity of Pim kinases including, e.g., cancers and other diseases.

BACKGROUND

Protein kinases regulate diverse biological processes including cell growth, survival, differentiation, organ formation, morphogenesis, neovascularization, tissue repair, and regeneration, among others. Protein kinases also play specialized roles in a host of human diseases including cancer. The three members of the Pim kinase family, one example of a protein kinase family, were initially identified as preferential integration sites of Moloney leukemia virus in mouse models of cancer. Although possessing modest but measurable oncogenic activity alone, they potentiate pro-proliferative and pro-survival oncogenes, e.g., causing a dramatic acceleration of lymphomagenesis in Myc-transgenic or Bcl2-transgenic mice. Mikkers et al., *Nature Genet.*, 2002, 32, 153-159; Shinto et al., *Oncogene*, 1995, 11, 1729-35.

The three non-receptor serine/threonine kinases Pim1, Pim2 and Pim3 regulate cell proliferation and survival by impacting gene transcription and protein translation. Zippo, et al., *Nature Cell Biol.*, 2007, 9, 932-44; Schatz, et al., *J. Exp. Med.*, 2011, 208, 1799-1807. As opposed to numerous other protein kinases which require activation by phosphorylation, the Pim kinases are constitutively activated and family members have overlapping substrate targets and biological functions, with differences between family members dictated, in part, by their varied tissue distribution. Expression of the Pim kinases is induced by cytokines and growth factors. Among the cytokines activating Pim kinase expression are cytokines which signal through the JAK/STAT pathway. Pim kinases act in parallel to the PI3K/AKT pathway, and they share several phosphorylation targets (e.g., pBAD, p4EBP1). Inhibitors of Pim kinases may therefore potentiate regimens including inhibitors of either the JAK pathway or the PI3K/AKT pathway.

Overexpression of Pim kinases is detected in a wide variety of hematologic and solid cancers. Overexpression of various family members have been noted in multiple myeloma, AML, pancreatic and hepatocellular cancers. Claudio et al., *Blood*, 2002, 100, 2175-86; Amson et al., *Proc. Nat. Acad. Sci.*, USA, 1989, 86, 8857-61; Mizuki et al., *Blood*, 2003, 101, 3164-73; Li et al., *Canc. Res.*, 2006, 66, 6741-7; Fujii et al., *Int. J. Canc.*, 2005, 114, 209-18. Pim1 overexpression is associated with poor prognosis in mantle cell lymphoma, esophageal and head and neck cancers. Hsi et al., *Leuk. Lymph.*, 2008, 49, 2081-90; Liu et al., *J. Surg. Oncol.*, 2010, 102, 683-88; Peltola et al., *Neoplasia*, 2009, 11, 629-36. Pim2 overexpression is associated with an aggressive clinical course in a subset of DLBCL patients. Gomez-Abad et al., *Blood*, 2011, 118, 5517-27. Overexpression is often seen where Myc is overexpressed and Pim kinases can convey resistance to traditional chemotherapeutic agents and radiation. Chen et al., *Blood*, 2009, 114, 4150-57; Isaac et al., *Drug Resis. Updates*, 2011, 14, 203-11; Hsu et al., *Cancer Lett.*, 2012, 319, 214; Peltola et al., *Neoplasia*, 2009, 11, 629-36.

As such, these data indicate that inhibition of Pim kinases will be useful to provide therapeutic benefit in cancer patients.

Data from mice deficient for one or multiple Pim kinase family members suggests that pan-Pim inhibitor would have a favorable toxicity profile. Triple knockout mice are viable, but are slightly smaller than their wild type littermates. Mikkers et al., *Mol. Cell. Biol.*, 2004, 24. 6104-15. Since Pim kinases are also involved in a variety of immunologic and inflammatory responses and these indications require drug agents with fewer side effects, Pim kinase inhibitors are expected to be useful in treating patients with colitis (Shen et al., *Dig. Dis. Sci.*, 2012, 57, 1822-31), peanut allergy (Wang et al., *J. All. Clin. Immunol.*, 2012, 130, 932-44), multiple sclerosis and lupus (Davis et al., "Small Molecule Dual Antagonist of Pim 1 and 3 Kinases Ameliorate Experimental Autoimmune Encephalomyelitis", 26th Congress of the European Committee for Treatment and Research in Multiple Sclerosis, 13-16 Oct. 2010, Gothenburg, Sweden, Poster P436; Robinson et al., *J. Immunol.*, 2012, 188, 119.9) and rheumatoid arthritis (Yang et al., *Immunol.* 2010, 131, 174-182) and other immunological and inflammatory disorders.

The Pim kinases have therefore been identified as useful targets for drug development efforts. Swords et al., *Curr. Drug Targets*, 2011, 12(14), 2059-66; Merkel et al., *Exp. Opin. Investig. Drugs*, 2012, 21, 425-38; Morwick et al., *Exp. Opin. Ther. Patents*, 2010, 20(2), 193-212.

Accordingly, there is a need for new compounds that inhibit Pim kinases. The present application describes new inhibitors of Pim kinases that are useful for treating diseases associated with the expression or activity of one or more Pim kinases, e.g., cancer and other diseases.

SUMMARY

The present disclosure provides, inter alia, a compound of Formula (I):

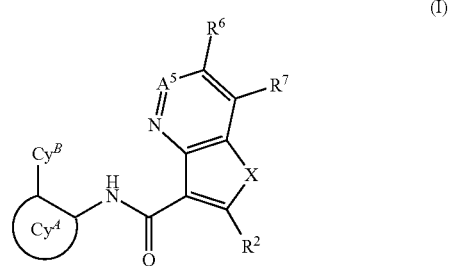

or a pharmaceutically acceptable salt thereof; wherein the variables are as defined below.

The present disclosure also provides a composition comprising a compound of Formula (I), or a pharmaceutically acceptable salt thereof, and at least one pharmaceutically acceptable carrier.

The present disclosure also provides methods of treating cancer and other diseases comprising administering to a patient a therapeutically effective amount of a compound of Formula (I), or a pharmaceutically acceptable salt thereof.

The details of one or more embodiments are set forth in the description below. Other features, objects and advantages will be apparent from the description and from the claims.

DETAILED DESCRIPTION

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

I. Compounds

The present disclosure provides, inter alia, a compound of Formula (I):

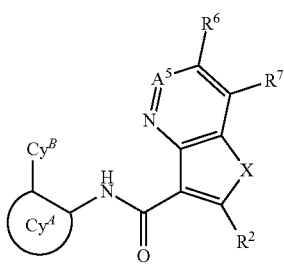

or a pharmaceutically acceptable salt thereof, wherein:

X is S or O;

$A^5$ is N or C—$R^5$;

$Cy^A$ is a 5 to 6 membered monocyclic heteroaryl group, wherein the ring atoms of the heteroaryl group forming $Cy^A$ consist of carbon atoms and 1, 2, or 3 heteroatoms selected from N, O and S, and wherein the 5 to 6 membered monocyclic heteroaryl group forming $Cy^A$ is unsubstituted or substituted with 1, 2, or 3 $R^A$;

each $R^A$ is independently selected from $R^{A1}$, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)R^{b1}$ and $S(=O)_2NR^{c1}R^{d1}$;

each $R^{A1}$ is independently selected from $C_{1-6}$ alkyl, $C_{2-6}$ alkenyl and $C_{2-6}$ alkynyl, wherein each $C_{1-6}$ alkyl, $C_{2-6}$ alkenyl and $C_{2-6}$ alkynyl forming $R^{A1}$ is unsubstituted or substituted with 1, 2, 3, 4 or 5 substituents independently selected from halogen, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$;

$Cy^B$ is $C_{6-10}$ aryl, $C_{3-7}$ cycloalkyl, 5-10 membered heteroaryl or 4-10 membered heterocycloalkyl wherein the ring atoms of the ring atoms of the heteroaryl or heterocycloalkyl forming $Cy^B$ consist of carbon atoms and 1, 2 or 3 heteroatoms selected from O, N and S, and wherein each of said $C_{6-10}$ aryl, $C_{3-7}$ cycloalkyl, 5-10 membered heteroaryl or 4-10 membered heterocycloalkyl forming $Cy^B$ is unsubstituted or substituted with 1, 2, 3, 4 or 5 $R^B$;

each $R^B$ is independently selected from $R^{B1}$, $R^{B2}$, halogen, $C_{1-6}$ haloalkyl, CN, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $NR^{c2}R^{d2}$, $NR^{c2}C(=O)R^{b2}$, $NR^{c2}C(=O)NR^{c2}R^{d2}$, $NR^{c2}C(=O)OR^{a2}$, $C(=NR^{e2})NR^{c2}R^{d2}$, $NR^{c2}C(=NR^{e2})NR^{c2}R^{d2}$, $S(=O)R^{b2}$, $S(=O)NR^{c2}R^{d2}$, $S(=O)_2R^{b2}$, $NR^{c2}S(=O)_2R^{b2}$ and $S(=O)_2NR^{c2}R^{d2}$;

each $R^{B1}$ is independently selected from $C_{1-6}$ alkyl, $C_{2-6}$ alkenyl and $C_{2-6}$ alkynyl, wherein each of said $C_{1-6}$ alkyl, $C_{2-6}$ alkenyl and $C_{2-6}$ alkynyl of $R^{B1}$ is unsubstituted or substituted with 1, 2, 3, 4 or 5 $R^{B3}$;

each $R^{B2}$ is independently selected from $C_{6-10}$ aryl, $C_{3-7}$ cycloalkyl, 5-10 membered heteroaryl and 4-10 membered heterocycloalkyl, wherein each of said $C_{6-10}$ aryl, $C_{3-7}$ cycloalkyl, 5-10 membered heteroaryl and 4-10 membered heterocycloalkyl forming $R^{B2}$ is unsubstituted or substituted with 1, 2, 3, 4 or 5 $R^{B4}$;

each $R^{B3}$ is independently selected from $R^{B2}$, halogen, $C_{1-6}$ haloalkyl, CN, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $NR^{c2}R^{d2}$, $NR^{c2}C(=O)R^{b2}$, $NR^{c2}C(=O)NR^{c2}R^{d2}$, $NR^{c2}C(=O)OR^{a2}$, $C(=NR^{e2})NR^{c2}R^{d2}$, $NR^{c2}C(=NR^{e2})NR^{c2}R^{d2}$, $S(=O)R^{b2}$, $S(=O)NR^{c2}R^{d2}$, $S(=O)_2R^{b2}$, $NR^{c2}S(=O)_2R^{b2}$ and $S(=O)_2NR^{c2}R^{d2}$;

each $R^{B4}$ is independently selected from halogen, $C_{1-6}$ haloalkyl, CN, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $NR^{c2}R^{d2}$, $NR^{c2}C(=O)R^{b2}$, $NR^{c2}C(=O)NR^{c2}R^{d2}$, $NR^{c2}C(=O)OR^{a2}$, $C(=NR^{e2})NR^{c2}R^{d2}$, $NR^{c2}C(=NR^{e2})NR^{c2}R^{d2}$, $S(=O)R^{b2}$, $S(=O)NR^{c2}R^{d2}$, $S(=O)_2R^{b2}$, $NR^{c2}S(=O)_2R^{b2}$ and $S(=O)_2NR^{c2}R^{d2}$;

$R^2$ is H, halogen or $NH_2$;

$R^5$ is H, halogen, $R^{5A}$, $C_{1-6}$ haloalkyl, CN, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $C(=NR^{e3})NR^{c3}R^{d3}$, $NR^{c3}C(=NR^{e3})NR^{c3}R^{d3}$, $S(=O)R^{b3}$, $S(=O)NR^{c3}R^{d3}$, $S(=O)_2R^{b3}$, $NR^{c3}S(=O)_2R^{b3}$ or $S(=O)_2NR^{c3}R^{d3}$;

$R^{5A}$ is $C_{1-6}$ alkyl, $C_{2-6}$ alkenyl, $C_{2-6}$ alkynyl, $C_{3-7}$ cycloalkyl or phenyl, wherein each of said $C_{1-6}$ alkyl, $C_{2-6}$ alkenyl, $C_{2-6}$ alkynyl, $C_{3-7}$ cycloalkyl or phenyl forming $R^{5A}$ is unsubstituted or substituted with 1, 2, 3, 4 or 5 substituents independently selected from halogen, CN, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C$ $(=O)NR^{c3}R^{d3}$, $NR^{c3}C(=O)OR^{a3}$, $C(=NR^{e3})NR^{c3}R^{d3}$, $NR^{c3}C(=NR^{e3})NR^{c3}R^{d3}$, $S(=O)R^{b3}$, $S(=O)NR^{c3}R^{d3}$, $S(=O)_2R^{b3}$, $NR^{c3}S(=O)_2R^{b3}$ and $S(=O)_2NR^{c3}R^{d3}$;

$R^6$ is H, halogen, $R^{6A}$, $C_{1-6}$ haloalkyl, CN, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$, $NR^{c4}C(=O)R^{b4}$, $NR^{c4}C(=O)NR^{c4}R^{d4}$, $NR^{c4}C(=O)OR^{a4}$, $C(=NR^{e4})NR^{c4}R^{d4}$, $NR^{c4}C(=NR^{e4})NR^{c4}R^{d4}$, $S(=O)R^{b4}$, $S(=O)NR^{c4}R^{d4}$, $S(=O)_2R^{b4}$, $NR^{c4}S(=O)_2R^{b4}$ or $S(=O)_2NR^{c4}R^{d4}$;

$R^{6A}$ is $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkyl-, $C_{6-10}$ aryl-$C_{1-4}$ alkyl-, 5-10 membered heteroaryl-$C_{1-4}$ alkyl- or 4-10 membered heterocycloalkyl-$C_{1-4}$ alkyl-, wherein each of said $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkyl-, $C_{6-10}$ aryl-$C_{1-4}$ alkyl-, 5-10 membered heteroaryl-$C_{1-4}$ alkyl- or 4-10 membered heterocycloalkyl-$C_{1-4}$ alkyl-forming $R^{6A}$ is unsubstituted or substituted with 1, 2, 3, 4 or 5 substituents independently selected from $C_{1-6}$ alkyl, halogen, $C_{1-6}$ haloalkyl, CN, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$, $NR^{c4}C(=O)R^{b4}$, $NR^{c4}C(=O)NR^{c4}R^{d4}$, $NR^{c4}C(=O)OR^{a4}$, $C(=NR^{e4})NR^{c4}R^{d4}$, $NR^{c4}C(=NR^{e4})NR^{c4}R^{d4}$, $S(=O)R^{b4}$, $S(=O)NR^{c4}R^{d4}$, $S(=O)_2R^{b4}$, $NR^{c4}S(=O)_2R^{b4}$ and $S(=O)_2NR^{c4}R^{d4}$;

$R^7$ is H, halogen, $R^{7A}$, $C_{1-6}$ haloalkyl, CN, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)NR^{c5}R^{d5}$, $NR^{c5}C(=O)OR^{a5}$, $C(=NR^{e5})NR^{c5}R^{d5}$, $NR^{c5}C(=NR^{e5})NR^{c5}R^{d5}$, $S(=O)R^{b5}$, $S(=O)NR^{c5}R^{d5}$, $S(=O)_2R^{b5}$, $NR^{c5}S(=O)_2R^{b5}$ or $S(=O)_2NR^{c5}R^{d5}$;

$R^{7A}$ is $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkyl-, $C_{6-10}$ aryl-$C_{1-4}$ alkyl-, 5-10 membered heteroaryl-$C_{1-4}$ alkyl- or 4-10 membered heterocycloalkyl-$C_{1-4}$ alkyl-, wherein each of said $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkyl-, $C_{6-10}$ aryl-$C_{1-4}$ alkyl-, 5-10 membered heteroaryl-$C_{1-4}$ alkyl- or 4-10 membered heterocycloalkyl-$C_{1-4}$ alkyl-forming $R^{7A}$ is unsubstituted or substituted with 1, 2, 3, 4 or 5 substituents independently selected from $C_{1-6}$ alkyl, halogen, $C_{1-6}$ haloalkyl, CN, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)NR^{c5}R^{d5}$, $NR^{c5}C(=O)OR^{a5}$, $C(=NR^{e5})NR^{c5}R^{d5}$, $NR^{c5}C(=NR^{e5})NR^{c5}R^{d5}$, $S(=O)R^{b5}$, $S(=O)NR^{c5}R^{d5}$, $S(=O)_2R^{b5}$, $NR^{c5}S(=O)_2R^{b5}$ and $S(=O)_2NR^{c5}R^{d5}$;

$R^{a1}$, $R^{b1}$, $R^{c1}$ and $R^{d1}$ are each independently selected from H, $C_{1-6}$ alkyl, $C_{2-6}$ alkenyl and $C_{2-6}$ alkynyl;

$R^{a2}$, $R^{b2}$, $R^{c2}$ and $R^{d2}$ are each independently selected from H, $C_{1-6}$ alkyl, $C_{2-6}$ alkenyl and $C_{2-6}$ alkynyl;

$R^{a3}$, $R^{b3}$, $R^{c3}$ and $R^{d3}$ are each independently selected from H, $C_{1-6}$ alkyl, $C_{2-6}$ alkenyl and $C_{2-6}$ alkynyl;

$R^{a4}$, $R^{b4}$, $R^{c4}$ and $R^{d4}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a4}$, $R^{b4}$, $R^{c4}$ and $R^{d4}$ are each unsubstituted or substituted with 1, 2, 3, 4 or 5 substituents independently selected from $C_{1-6}$ alkyl, halo, CN, $OR^{a6}$, $SR^{a6}$, $C(=O)R^{b6}$, $C(=O)NR^{c6}R^{d6}$, $C(=O)OR^{a6}$, $OC(=O)R^{b6}$, $OC(=O)NR^{c6}R^{d6}$, $NR^{c6}R^{d6}$, $NR^{c6}C(=O)R^{b6}$, $NR^{c6}C(=O)NR^{c6}R^{d6}$, $NR^{c6}C(=O)OR^{a6}$, $C(=NR^{e6})NR^{c6}R^{d6}$, $NR^{c6}C(=NR^{e6})NR^{c6}R^{d6}$, $S(=O)R^{b6}$, $S(=O)NR^{c6}R^{d6}$, $S(=O)_2R^{b6}$, $NR^{c6}S(=O)_2R^{b6}$ and $S(=O)_2NR^{c6}R^{d6}$;

or $R^{c4}$ and $R^{d4}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from $C_{1-6}$ alkyl, halo, CN, $OR^{a6}$, $SR^{a6}$, $C(=O)R^{b6}$, $C(=O)NR^{c6}R^{d6}$, $C(=O)OR^{a6}$, $OC(=O)R^{b6}$, $OC(=O)NR^{c6}R^{d6}$, $NR^{c6}R^{d6}$, $NR^{c6}C(=O)R^{b6}$, $NR^{c6}C(=O)NR^{c6}R^{d6}$, $NR^{c6}C(=O)OR^{a6}$, $C(=NR^{e6})NR^{c6}R^{d6}$, $NR^{c6}C(=NR^{e6})NR^{c6}R^{d6}$, $S(=O)R^{b6}$, $S(=O)NR^{c6}R^{d6}$, $S(=O)_2R^{b6}$, $NR^{c6}S(=O)_2R^{b6}$ and $S(=O)_2NR^{c6}R^{d6}$;

$R^{a5}$, $R^{b5}$, $R^{c5}$ and $R^{d5}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a5}$, $R^{b5}$, $R^{c5}$ and $R^{d5}$ are each unsubstituted or substituted with 1, 2, 3, 4 or 5 substituents independently selected from $C_{1-6}$ alkyl, halo, CN, $OR^{a6}$, $SR^{a6}$, $C(=O)R^{b6}$, $C(=O)NR^{c6}R^{d6}$, $C(=O)OR^{a6}$, $OC(=O)R^{b6}$, $OC(=O)NR^{c6}R^{d6}$, $NR^{c6}R^{d6}$, $NR^{c6}C(=O)R^{b6}$, $NR^{c6}C(=O)OR^{a6}$, $C(=NR^{e6})NR^{c6}R^{d6}$, $NR^{c6}C(=NR^{e6})NR^{c6}R^{d6}$, $S(=O)R^{b6}$, $S(=O)NR^{c6}R^{d6}$, $S(=O)_2R^{b6}$, $NR^{c6}S(=O)_2R^{b6}$ and $S(=O)_2NR^{c6}R^{d6}$;

or $R^{c5}$ and $R^{d5}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from $C_{1-6}$ alkyl, halo, CN, $OR^{a6}$, $SR^{a6}$, $C(=O)R^{b6}$, $C(=O)NR^{c6}R^{d6}$, $C(=O)OR^{a6}$, $OC(=O)R^{b6}$, $OC(=O)NR^{c6}R^{d6}$, $NR^{c6}R^{d6}$, $NR^{c6}C(=O)R^{b6}$, $NR^{c6}C(=O)NR^{c6}R^{d6}$, $NR^{c6}C(=O)OR^{a6}$, $C(=NR^{e6})NR^{c6}R^{d6}$, $NR^{c6}C(=NR^{e6})NR^{c6}R^{d6}$, $S(=O)R^{b6}$, $S(=O)NR^{c6}R^{d6}$, $S(=O)_2R^{b6}$, $NR^{c6}S(=O)_2R^{b6}$ and $S(=O)_2NR^{c6}R^{d6}$;

$R^{a6}$, $R^{b6}$, $R^{c6}$ and $R^{d6}$ are each independently selected from H, $C_{1-6}$ alkyl, $C_{1-6}$ haloalkyl, $C_{2-6}$ alkenyl, $C_{2-6}$ alkynyl, $C_{6-10}$ aryl, 5-10 membered heteroaryl, $C_{3-7}$ cycloalkyl and 4-10 membered heterocycloalkyl, wherein said $C_{1-6}$ alkyl, $C_{2-6}$ alkenyl, $C_{2-6}$ alkynyl, $C_{6-10}$ aryl, 5-10 membered heteroaryl, $C_{3-7}$ cycloalkyl and 4-10 membered heterocycloalkyl forming $R^{a6}$, $R^{b6}$, $R^{c6}$ and $R^{d6}$ are each optionally substituted with 1, 2 or 3 substituents independently selected from OH, CN, amino, $NH(C_{1-6}$ alkyl), $N(C_{1-6}$ alkyl)$_2$, halo, $C_{1-6}$ alkyl, $C_{1-6}$ alkoxy, $C_{1-6}$ haloalkyl and $C_{1-6}$ haloalkoxy;

or $R^{c6}$ and $R^{d6}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, $NH(C_{1-6}$ alkyl), $N(C_{1-6}$ alkyl)$_2$, halo, $C_{1-6}$ alkyl, $C_{1-6}$ alkoxy, $C_{1-6}$ haloalkyl and $C_{1-6}$ haloalkoxy; and $R^{e1}$, $R^{e2}$, $R^{e3}$, $R^{e4}$, $R^{e5}$ and $R^{e6}$ are each, independently, H, $C_{1-4}$ alkyl, CN or $NO_2$.

In the Formula (I), $Cy^B$ and the group:

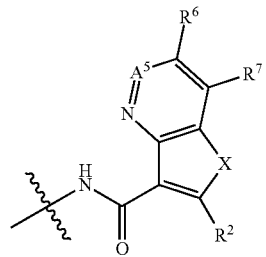

are attached to adjacent carbon atoms of $Cy^A$.

In some embodiments, X is O.

In some embodiments, X is S.

In some embodiments, $Cy^A$ is a 5 or 6-membered monocyclic heteroaryl group wherein the ring atoms consist of carbon atoms and 1, or 2 heteroatoms selected from N, O and S and wherein $Cy^A$ is unsubstituted or substituted with 1, 2, or 3 $R^A$.

In some embodiments, $Cy^A$ is a 5 or 6-membered monocyclic heteroaryl group, the ring atoms of which consist of carbon atoms and 1 or 2 nitrogen atoms and wherein $Cy^A$ is unsubstituted or substituted with 1, 2, or 3 $R^A$.

In some embodiments, $Cy^A$ is a pyrazolyl or pyridinyl ring wherein $Cy^A$ is unsubstituted or substituted with 1, 2, or 3 $R^A$.

In some embodiments, $Cy^A$ is a pyridin-3-yl or 1H-pyrazol-4-yl ring wherein $Cy^A$ is unsubstituted or substituted with 1 or 2 $R^A$.

In some embodiments, $Cy^A$ is a pyridinyl ring wherein $Cy^A$ is unsubstituted or substituted with 1, 2, or 3 $R^A$.

In some embodiments, $Cy^A$ is a pyridin-3-yl ring wherein $Cy^A$ is unsubstituted or substituted with 1 or 2 $R^A$.

In some embodiments, $Cy^A$ is a 1H-pyrazol-4-yl ring wherein $Cy^A$ is unsubstituted or substituted with 1 or 2 $R^A$.

In some embodiments, $Cy^A$ is unsubstituted.

In some embodiments, $Cy^A$ is substituted with 1, 2, or 3 $R^A$.

In some embodiments, $Cy^A$ is substituted with 1 or 2 $R^A$.

In some embodiments, $Cy^A$ is substituted with 1 $R^A$.

In some embodiments, each $R^A$ is independently selected from $C_{1-6}$ alkyl, $C_{2-6}$ alkenyl and $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=)NR^{c1}R^{d1}$, $NR^{c1}C(=O)OR^{a1}$, $C(NR^{e1})NR^{c1}R^{d1}$, $NR^{c1}C(=NR^{e1})NR^{c1}R^{d1}$, $S(=O)R^{b1}$, $S(=O)NR^{c1}R^{d1}$ $S(=O)_2R^{b1}$, $NR^{c1}S(=O)_2R^{b1}$ and $S(=O)_2NR^{c1}R^{d1}$.

In some embodiments, each $R^A$ is $C_{1-6}$ alkyl.

In some embodiments, each $R^A$ is methyl.

In some embodiments, $Cy^A$ is a pyridin-3-yl, 5-methyl-pyridin-3-yl, or 1-methyl-1H-pyrazol-4-yl ring.

In some embodiments, $Cy^B$ is unsubstituted $C_{6-10}$ aryl or $C_{6-10}$ aryl substituted with 1, 2, 3, 4 or 5 $R^B$.

In some embodiments, $Cy^B$ is unsubstituted $C_{3-7}$ cycloalkyl or $C_{3-7}$ cycloalkyl substituted with 1, 2, 3, 4 or 5 $R^B$.

In some embodiments, $Cy^B$ is unsubstituted cyclohexyl substituted with 1, 2, 3, or 4 $R^B$.

In some embodiments, $Cy^B$ is unsubstituted cyclohexyl substituted with 1, 2, 3, or 4 $R^B$ wherein $R^B$ is at each occurrence selected from F, Cl, methyl, ethyl, cyclopropyl, $CF_3$, CN, OH, methoxy and $NH_2$.

In some embodiments, $Cy^B$ is unsubstituted 5-10 membered heteroaryl or 5-10 membered heteroaryl substituted with 1, 2, 3, 4 or 5 $R^B$.

In some embodiments, $Cy^B$ is unsubstituted 4-10 membered heterocycloalkyl or 4-10 membered heterocycloalkyl substituted with 1, 2, 3, 4 or 5 $R^B$.

In some embodiments, $Cy^B$ is unsubstituted 4-10 membered heterocycloalkyl or 4-10 membered heterocycloalkyl substituted with 1, 2, 3 or 4 $R^B$.

In some embodiments, $Cy^B$ is unsubstituted 4-7 membered heterocycloalkyl or 4-7 membered heterocycloalkyl substituted with 1, 2, 3 or 4 $R^B$.

In some embodiments, $Cy^B$ is unsubstituted 4-7 membered heterocycloalkyl or 4-7 membered heterocycloalkyl substituted with 1, 2, or 3 $R^B$.

In some embodiments, $Cy^B$ is 4-7 membered heterocycloalkyl wherein the ring atoms of the heterocycloalkyl forming $Cy^B$ consist of carbon atoms and 1 or 2 nitrogen atoms, and wherein the 4-7 membered heterocycloalkyl forming $Cy^B$ is unsubstituted or substituted with 1, 2, 3 or 4 $R^B$.

In some embodiments, $Cy^B$ is a pyrrolidine, piperidine, azepane or 1,4-diazepane ring, wherein the pyrrolidine, piperidine, azepane or 1,4-diazepane ring forming $Cy^B$ is unsubstituted or substituted with 1, 2 or 3 $R^B$.

In some embodiments, a ring nitrogen atom of $Cy^B$ forms the bond connecting $Cy^B$ to the remainder of the molecule.

In some embodiments, each $R^B$ is independently selected from halogen, $C_{1-6}$ alkyl, $C_{1-6}$ haloalkyl, $C_{3-7}$ cycloalkyl, CN, $OR^{a2}$ and $NR^{c2}R^{d2}$.

In some embodiments, each $R^B$ is independently selected from halogen, $C_{1-6}$ alkyl, $C_{1-6}$ haloalkyl, $C_{3-7}$ cycloalkyl, CN, $OR^{a2}$ and $NR^{c2}R^{d2}$.

In some embodiments, each $R^B$ is independently selected from methyl, ethyl, cyclopropyl, $CF_3$, OH and $NH_2$.

In some embodiments, $Cy^B$ is a piperidin-1-yl ring substituted at the 3-position by an amino group. $Cy^B$ can be, e.g., 3-aminopiperidin-1-yl, 3-amino-4-hydroxypiperidinyl or 3-amino-4-hydroxy-5-methylpiperidinyl.

In some embodiments, the configuration of the carbon atom at the 3-position of the piperidin-1-yl ring forming $Cy^B$ is (S) when the carbon atom at the 2-position of the piperidin-1-yl ring forming $Cy^B$ has a higher Cahn-Ingold-Prelog priority than the carbon atom at the 4-position and (R) when the carbon atom at the 4-position of the piperidin-1-yl ring forming $Cy^B$ has a higher Cahn-Ingold-Prelog priority than the carbon atom at the 4-position. $Cy^B$ can be, e.g., (3S)-aminopiperidin-1-yl, (3R,4R)-3-amino-4-hydroxypiperidinyl, (3R,4S)-3-amino-4-hydroxypiperidinyl, (3R,4R,5R)-3-amino-4-hydroxy-5-methylpiperidinyl, (3R,4R,5S)-3-amino-4-hydroxy-5-methylpiperidinyl, (3R,4S,5R)-3-amino-4-hydroxy-5-methylpiperidinyl or (3R,4S,5S)-3-amino-4-hydroxy-5-methylpiperidinyl.

In some embodiments, the configuration of the carbon atom at the 3-position of the piperidin-1-yl ring forming $Cy^B$ is (R) when the carbon atom at the 2-position of the piperidin-1-yl ring forming $Cy^B$ has a higher Cahn-Ingold-Prelog priority than the carbon atom at the 4-position and (S) when the carbon atom at the 4-position of the piperidin-1-yl ring forming $Cy^B$ has a higher Cahn-Ingold-Prelog priority than the carbon atom at the 4-position. $Cy^B$ can be, e.g., (3R)-aminopiperidin-1-yl, (3S,4S)-3-amino-4-hydroxypiperidinyl, (3S,4R)-3-amino-4-hydroxypiperidinyl, (3S,4R,5R)-3-amino-4-hydroxy-5-methylpiperidinyl, (3S,4R,5S)-3-amino-4-hydroxy-5-methylpiperidinyl, (3S,4S,5R)-3-amino-4-hydroxy-5-methylpiperidinyl or (3S,4S,5S)-3-amino-4-hydroxy-5-methylpiperidinyl.

In some embodiments, $Cy^B$ is a hetereocycloalkyl group of the following Formula (B-1):

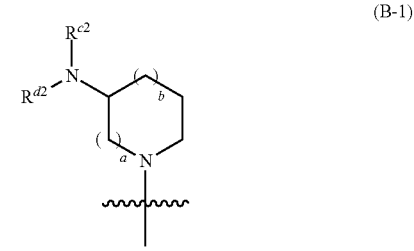

(B-1)

wherein:
$R^{c2}$ is H, $C_{1-6}$ alkyl or $OC(=O)C_{1-6}$ alkyl;
$R^{d2}$ is H or $C_{1-6}$ alkyl;
a is 1 or 2;
b is 0, 1 or 2; and
the sum of a and b is 1, 2 or 3; and
wherein the heterocycloalkyl group of Formula (B-1) is further substituted by 0, 1, 2, or 3 $R^B$, wherein $R^B$ is independently, at each occurrence, selected from F, Cl, methyl, ethyl, cyclopropyl, $CF_3$, CN, OH, and methoxy.

In some embodiments, $Cy^B$ is a group of Formula $Cy^B$-1:

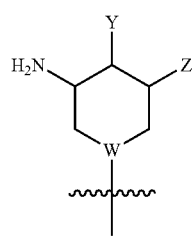
($Cy^B$-1)

wherein:
W is N or CH;
Y is H or OH; and
Z is H, $C_{1-6}$ alkyl, $C_{1-3}$ haloalkyl, or $C_{3-7}$ cycloalkyl.

In some embodiments $Cy^B$ is a group of Formula $Cy^B$-2:

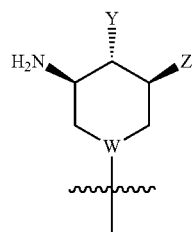
($Cy^B$-2)

wherein:
W is N or CH;
Y is H or OH; and
Z is H, $C_{1-6}$ alkyl, $C_{1-3}$ haloalkyl, or $C_{3-7}$ cycloalkyl.

In some embodiments, W is N.
In some embodiments, W is CH.
In some embodiments, $Cy^B$ is a group of Formula $Cy^B$-3:

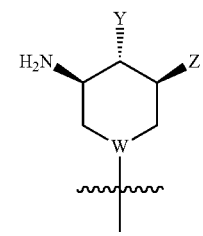
(CyB-3)

In some embodiments, $Cy^B$ is a group of Formula $Cy^B$-4:

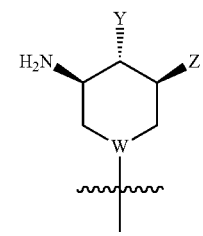
(CyB-4)

In some embodiments, Y is H.
In some embodiments, Y is OH.

In some embodiments, Z is H.
In some embodiments, Z is $C_{1-6}$ alkyl.
In some embodiments, Z is methyl.
In some embodiments, Z is $C_{1-3}$ haloalkyl.
In some embodiments, Z is trifluoromethyl.
In some embodiments, Z is $C_{3-7}$ cycloalkyl.
In some embodiments, Z is cyclopropyl.

In some embodiments, $Cy^B$ is a group selected from groups of the following Formulae (B-2) to (B-12):

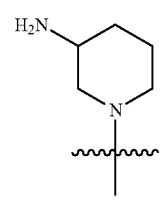
(B-2)

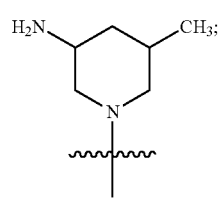
(B-3)

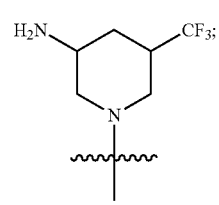
(B-4)

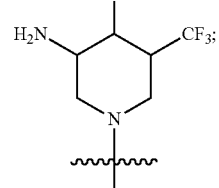
(B-5)

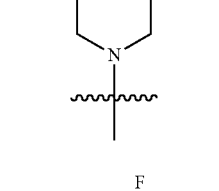
(B-6)

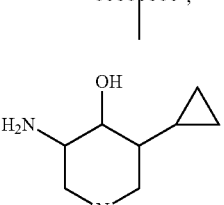
(B-7)

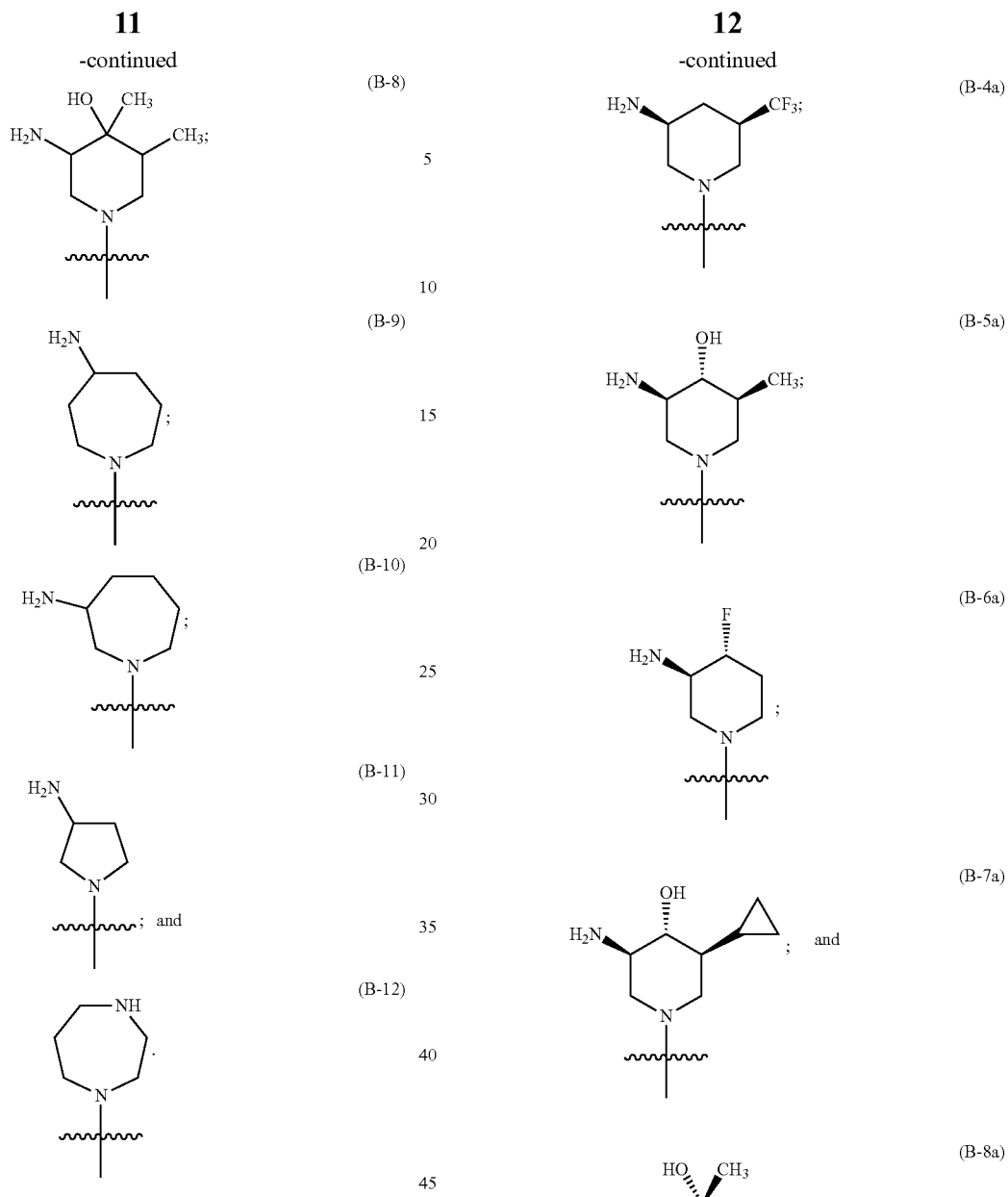
In some embodiments, $Cy^B$ is a group selected from groups of the following Formulae (B-2a) to (B-8a):
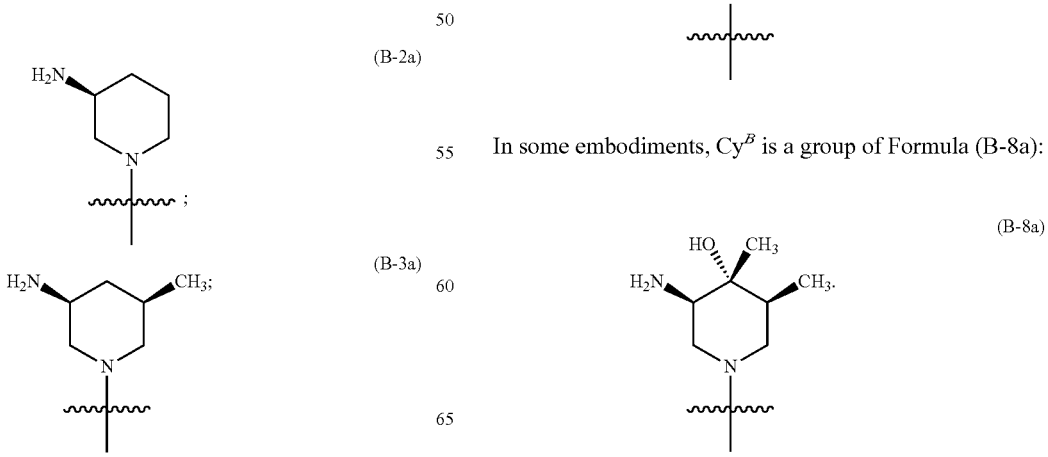
In some embodiments, $Cy^B$ is a group of Formula (B-8a):

In some embodiments, Cy$^B$ is a group of Formula (B-7a):
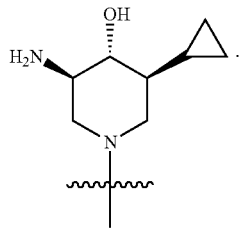
(B-7a)
In some embodiments, Cy$^B$ is a group of Formula (B-5a):
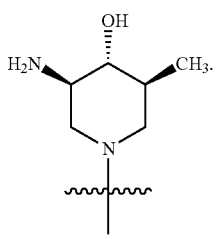
(B-5a)
In some embodiments, Cy$^B$ is a group of Formula (B-4a):
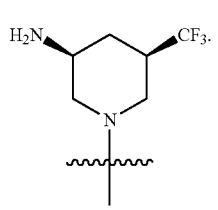
(B-4a)
In some embodiments, Cy$^B$ is a group of Formula (B-3a):
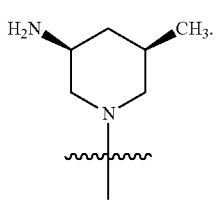
(B-3a)
In some embodiments, Cy$^B$ is a group selected from groups of the following Formulae (B-101) to (B-130):
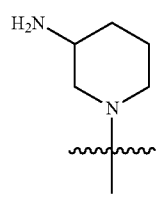
(B-101)
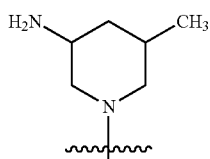
(B-102)
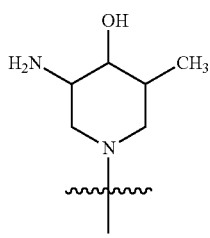
(B-103)
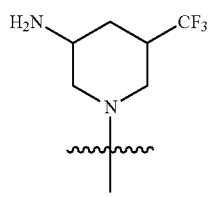
(B-104)
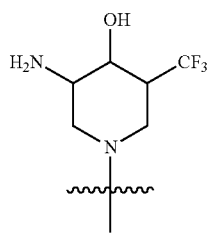
(B-105)
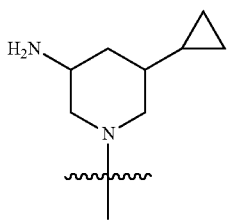
(B-106)
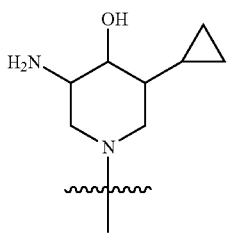
(B-107)
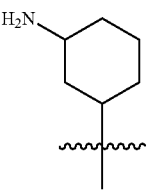
(B-108)

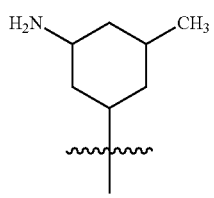 (B-109)
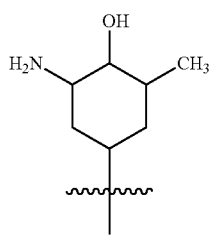 (B-110)
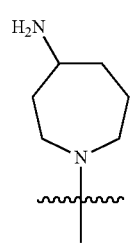 (B-111)
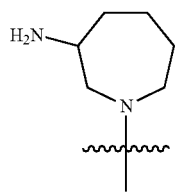 (B-112)
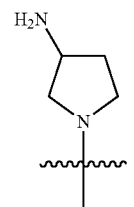 (B-113)
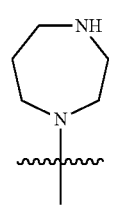 (B-114)
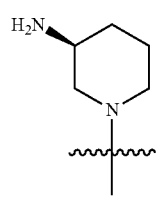 (B-115)
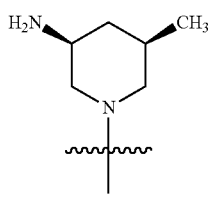 (B-116)
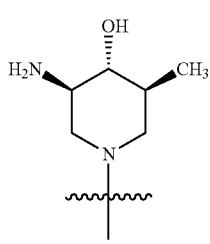 (B-117)
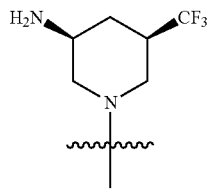 (B-118)
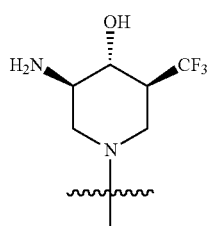 (B-119)
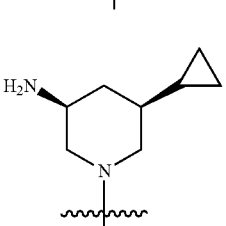 (B-120)
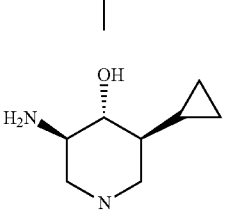 (B-121)
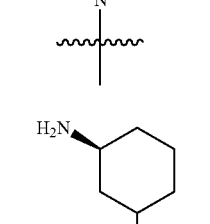 (B-122)

-continued (B-123) 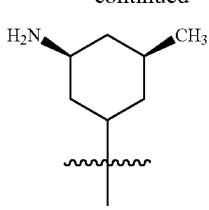

(B-124) 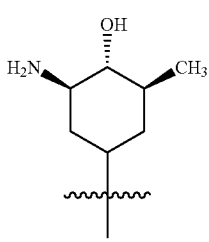

(B-125) 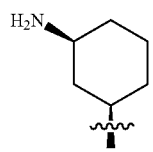

(B-126) 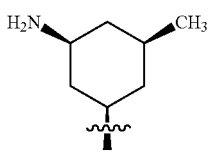

(B-127) 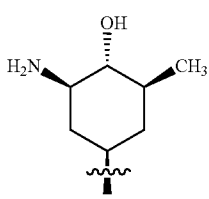

(B-128) 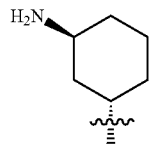

(B-129) 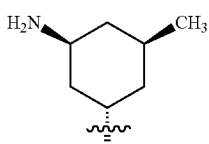

(B-130) 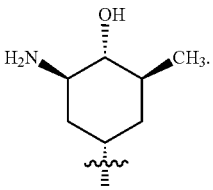

In some embodiments, $Cy^B$ is 4-7 membered heterocycloalkyl wherein the ring atoms of the heterocycloalkyl forming $Cy^B$ consist of carbon atoms and 1 or 2 nitrogen atoms, and wherein the 4-7 membered heterocycloalkyl forming $Cy^B$ is unsubstituted or substituted with 1, 2 or 3 substituents independently selected from F, Cl, methyl, ethyl, cyclopropyl, $CF_3$, CN, OH, methoxy and $NH_2$.

In some embodiments, $Cy^B$ is selected from piperidine-1-yl, azepan-1-yl, 1,4-diazepan-1-yl, and pyrrolidine-1-yl, wherein each of said piperidine-1-yl, azepan-1-yl, 1,4-diazepan-1-yl, and pyrrolidine-1-yl, forming $Cy^B$ is unsubstituted or substituted with 1, 2 or 3 substituents independently selected from F, Cl, methyl, ethyl, cyclopropyl, $CF_3$, CN, OH, methoxy and $NH_2$.

In some embodiments, $Cy^B$ is unsubstituted piperidin-1-yl or piperidin-1-yl substituted with 1, 2 or 3 substituents independently selected from F, Cl, methyl, ethyl, cyclopropyl, $CF_3$, CN, OH, methoxy and $NH_2$.

In some embodiments, $Cy^B$ is unsubstituted piperidin-1-yl or piperidin-1-yl substituted with 1, 2 or 3 substituents independently selected from methyl, cyclopropyl, $CF_3$, OH and $NH_2$.

In some embodiments, $Cy^B$ is unsubstituted azepan-1-yl or azepan-1-yl substituted with 1, 2 or 3 substituents independently selected from F, Cl, methyl, ethyl, $CF_3$, CN, OH, methoxy and $NH_2$.

In some embodiments, $Cy^B$ is unsubstituted azepan-1-yl or azepan-1-yl substituted with 1, 2 or 3 substituents independently selected from methyl, cyclopropyl, OH and $NH_2$.

In some embodiments, $Cy^B$ is unsubstituted 1,4-diazepan-1-yl or 1,4-diazepan-1-yl substituted with 1, 2 or 3 substituents independently selected from F, Cl, methyl, ethyl, cyclopropyl, $CF_3$, CN, OH, methoxy and $NH_2$.

In some embodiments, $Cy^B$ is unsubstituted 1,4-diazepan-1-yl or 1,4-diazepan-1-yl substituted with 1, 2 or 3 substituents independently selected from methyl, cyclopropyl, $CF_3$, OH and $NH_2$.

In some embodiments, $Cy^B$ is unsubstituted pyrrolidin-1-yl or pyrrolidin-1-yl substituted with 1, 2 or 3 substituents independently selected from F, Cl, methyl, ethyl, cyclopropyl, $CF_3$, CN, OH, methoxy and $NH_2$.

In some embodiments, $Cy^B$ is unsubstituted pyrrolidin-1-yl or pyrrolidin-1-yl substituted with 1, 2 or 3 substituents independently selected from methyl, cyclopropyl, $CF_3$, OH and $NH_2$.

In some embodiments, the group

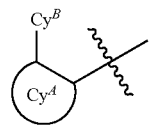

is selected from:

(Cy-1)

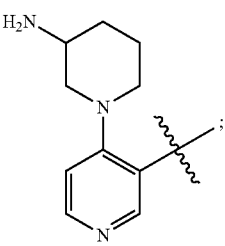

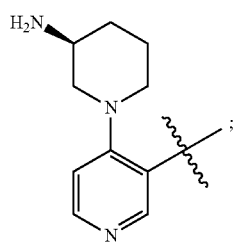 (Cy-2)
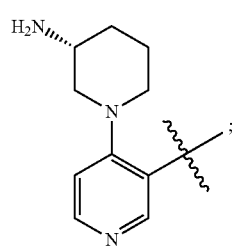 (Cy-3)
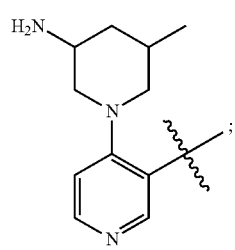 (Cy-4)
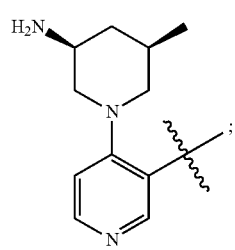 (Cy-5)
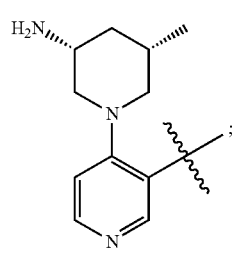 (Cy-6)
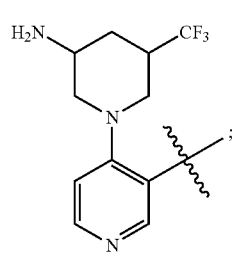 (Cy-7)
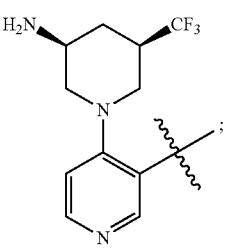 (Cy-8)
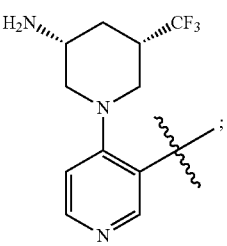 (Cy-9)
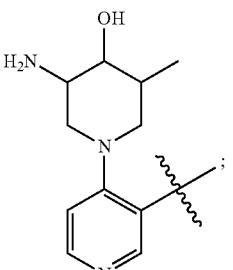 (Cy-10)
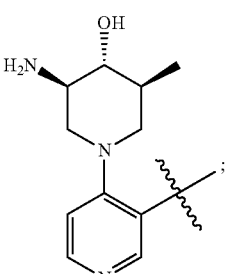 (Cy-11)
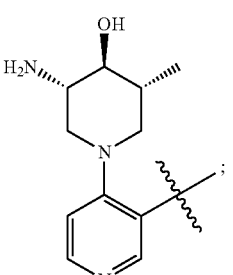 (Cy-12)
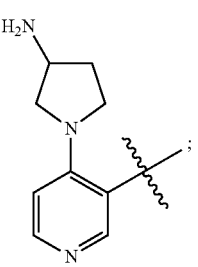 (Cy-13)

(Cy-14) 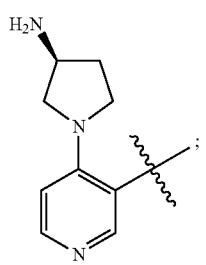
(Cy-15) 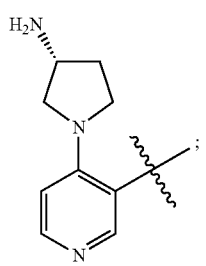
(Cy-16) 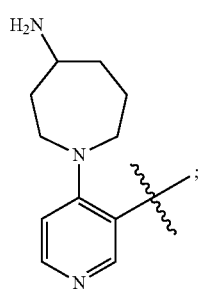
(Cy-17) 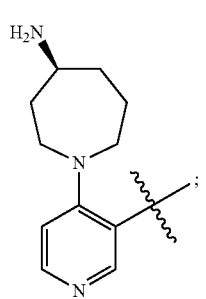
(Cy-18) 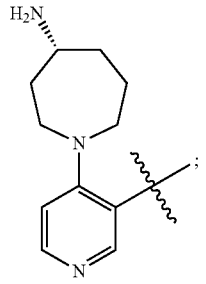
(Cy-19) 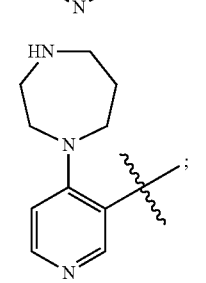
(Cy-20) 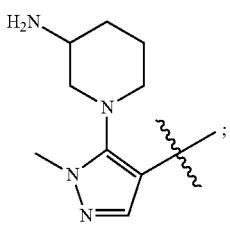
(Cy-21) 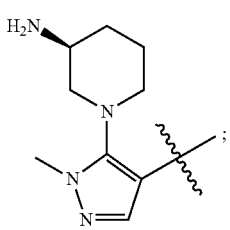
(Cy-22) 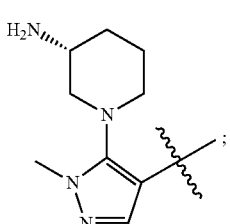
(Cy-23) 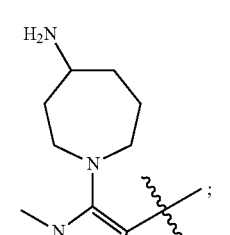
(Cy-24) 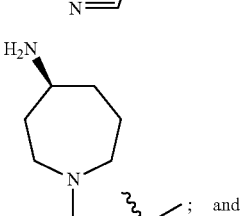; and
(Cy-25) 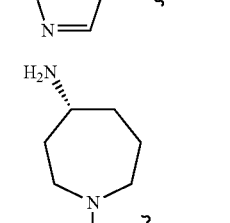.
In some embodiments, $R^2$ is $NH_2$.
In some embodiments, $A^5$ is N.
In some embodiments, $A^5$ is $CR^5$.
In some embodiments, $R^5$ is H, halogen, $R^{5A}$, CN or $OR^{a3}$.

In some embodiments, $R^{5A}$ is $C_{1-6}$ alkyl, $C_{2-6}$ alkenyl, $C_{2-6}$ alkynyl, $C_{1-6}$ haloalkyl, $C_{3-7}$ cycloalkyl or phenyl, wherein each of said $C_{1-6}$ alkyl, $C_{2-6}$ alkenyl, $C_{2-6}$ alkynyl, $C_{3-7}$ cycloalkyl or phenyl forming $R^{5A}$ is unsubstituted or substituted with 1, 2 or 3 substituents independently selected from halogen, CN and $OR^{a3}$.

In some embodiments, e is H or $C_{1-6}$ alkyl.

In some embodiments, $R^5$ is H, halogen, $C_{1-6}$ alkyl, $C_{2-6}$ alkenyl, $C_{2-6}$ alkynyl, $C_{1-6}$ haloalkyl, $C_{3-7}$ cycloalkyl, phenyl, $R^{5A}$, CN, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $C(=NR^{e3})NR^{c3}R^{d3}$, $NR^{c3}C(=NR^{e3})NR^{c3}R^{d3}$, $S(=O)R^{b3}$, $S(=O)NR^{c3}R^{d3}$, $S(=O)_2R^{b3}$, $NR^{c3}S(=O)_2R^{b3}$ or $S(=O)_2NR^{c3}R^{d3}$.

In some embodiments, $R^5$ is H, halogen or $C_{1-6}$ alkyl.
In some embodiments, $R^5$ is H, Cl or methyl.
In some embodiments, $R^5$ is H.

In some embodiments, $R^6$ is H, halogen, $R^{6A}$, $C_{1-6}$ haloalkyl, CN or $OR^{a4}$.

In some embodiments, $R^6$ is $R^{6A}$.

In some embodiments, $R^6$ is H, halogen, $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkyl-, $C_{6-10}$ aryl-$C_{1-4}$ alkyl-, 5-10 membered heteroaryl-$C_{1-4}$ alkyl- or 4-10 membered heterocycloalkyl-$C_{1-4}$ alkyl-, $C_{1-6}$ haloalkyl, CN, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$, $NR^{c4}C(=O)R^{b4}$, $NR^{c4}C(=O)NR^{c4}R^{d4}$, $NR^{c4}C(=O)OR^{a4}$, $C(=NR^{e4})NR^{c4}R^{d4}$, $NR^{c4}C(=NR^{e4})NR^{c4}R^{d4}$, $S(=O)R^{b4}$, $S(=O)NR^{c4}R^{d4}$, $S(=O)_2R^{b4}$, $NR^{c4}S(=O)_2R^{b4}$ or $S(=O)_2NR^{c4}R^{d4}$.

In some embodiments, $R^6$ is H, halogen or $C_{1-6}$ alkyl, OH, $OC_{1-6}$ alkyl, $OC_{3-7}$ cycloalkyl, $C_{1-6}$ haloalkyl, $C_{6-10}$ aryl, 5-6-membered heteroaryl or 4-7 membered heterocycloalkyl, In some embodiments, $R^6$ is H, F, Cl, Br, methyl, ethyl, propyl, isopropyl, $CF_3$, OH, OMe, OEt, On-Pr, Oi-Pr, Ocyclopropyl, phenyl, 2,6-difluorophenyl, 3,5-dimethylisoxazol-4-yl, 1,3-thiazol-2-yl, 1-methylazetidin-3-yl, 1-isopropylazetidin-3-yl, methoxymethyl or tetrahydro-2H-pyran-4-yl, In some embodiments, $R^6$ is H.

In some embodiments, $R^{6A}$ is $C_{1-6}$ alkyl, $C_{2-6}$ alkenyl, $C_{2-6}$ alkynyl, $C_{3-7}$ cycloalkyl, phenyl, 5-6 membered heteroaryl or 4-7 membered heterocycloalkyl, wherein each of said $C_{1-6}$ alkyl, $C_{2-6}$ alkenyl, $C_{2-6}$ alkynyl, $C_{3-7}$ cycloalkyl, phenyl, 5-6 membered heteroaryl or 4-7 membered heterocycloalkyl forming $R^{6A}$ is unsubstituted or substituted with 1, 2, 3, 4 or 5 substituents independently selected from $C_{1-6}$ alkyl, halogen, CN and $OR^{a4}$.

In some embodiments, $R^{6A}$ is unsubstituted phenyl or phenyl substituted with 1, 2, 3, 4 or 5 substituents independently selected from $C_{1-6}$ alkyl, halogen, CN and $OR^{a4}$.

In some embodiments, $R^{6A}$ is unsubstituted phenyl or phenyl 2,6-disubstituted with substituents independently selected from $C_{1-6}$ alkyl, halogen, CN and $OR^{a4}$.

In some embodiments, $R^{a4}$ is H or $C_{1-6}$ alkyl.

In some embodiments, $R^7$ is H, halogen, $R^{7A}$, $C_{1-6}$ haloalkyl, CN, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)NR^{c5}R^{d5}$, $NR^{c5}C(=O)OR^{a5}$, $C(=NR^{e5})NR^{c5}R^{d5}$, $NR^{c5}C(=NR^{e5})NR^{c5}R^{d5}$, $S(=O)R^{b5}$, $S(=O)NR^{c5}R^{d5}$, $S(=O)_2R^{b5}$, $NR^{c5}S(=O)_2R^{b5}$ or $S(=O)_2NR^{c5}R^{d5}$.

In some embodiments, $R^7$ is H, halogen, $R^{7A}$, $C_{1-6}$ haloalkyl, CN or $OR^{a5}$.

In some embodiments, $R^{7A}$ is $C_{1-6}$ alkyl, $C_{2-6}$ alkenyl, $C_{2-6}$ alkynyl, $C_{3-7}$ cycloalkyl and phenyl wherein each is $C_{1-6}$ alkyl, $C_{2-6}$ alkenyl, $C_{2-6}$ alkynyl, $C_{3-7}$ cycloalkyl and phenyl forming R7A is unsubstituted or substituted with 1, 2, 3, 4 or 5 substituents independently selected from $C_{1-6}$ alkyl, halogen, $C_{1-6}$ haloalkyl, CN, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)NR^{c5}R^{d5}$, $NR^{c5}C(=O)OR^{a5}$, $C(=NR^{e5})NR^{c5}R^{d5}$, $NR^{c5}C(=NR^{e5})NR^{c5}R^{d5}$, $S(=O)R^{b5}$, $S(=O)NR^{c5}R^{d5}$, $S(=O)_2R^{b5}$, $NR^{c5}S(=O)_2R^{b5}$ and $S(=O)_2NR^{c5}R^{d5}$.

In some embodiments, $R^{a5}$ is H or $C_{1-6}$ alkyl.

In some embodiments, $R^7$ is H, halogen, $C_{1-6}$ alkyl, $C_{1-6}$ haloalkyl or $O(C_{1-6}$ alkyl).

In some embodiments, $R^7$ is H, Cl, methyl, ethyl, $CF_3$, OMe, OEt, On-Pr or Oi-Pr.

In some embodiments, $R^7$ is H.

In some embodiments, the compound is a compound of Formula (I-A):

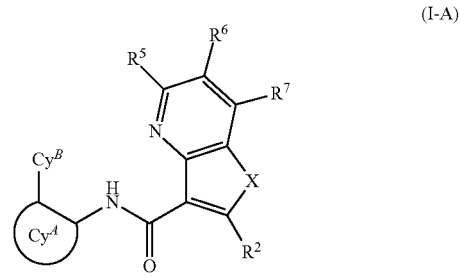

(I-A)

or a pharmaceutically acceptable salt thereof, wherein:
X is S or O;
$Cy^A$ is a 5 to 6 membered monocyclic heteroaryl group wherein the ring atoms of the heteroaryl group forming $Cy^A$ consist of carbon atoms and 1, 2, or 3 atoms selected from N, O and S, and wherein the 5 to 6 membered monocyclic heteroaryl group forming $Cy^A$ is unsubstituted or substituted with 1, 2 or 3 $R^A$;
each $R^A$ is independently selected from halogen, CN, OH, $C_{1-6}$ alkyl, $C_{1-6}$ haloalkyl and alkoxy;
$Cy^B$ is $C_{3-7}$ cycloalkyl or 4-10 membered heterocycloalkyl wherein the ring atoms of the heterocycloalkyl forming $Cy^B$ consist of carbon atoms and 1, 2 or 3 heteroatoms selected from O, N and S, wherein each of said $C_{3-7}$ cycloalkyl or 4-10 membered heterocycloalkyl forming $Cy^B$ is unsubstituted or substituted with 1, 2, 3, 4 or 5 $R^B$;
each $R^B$ is independently selected from halogen, $C_{1-6}$ alkyl, $C_{1-6}$ haloalkyl, $C_{3-7}$ cycloalkyl, CN, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $NR^{c2}R^{d2}$, $NR^{c2}C(=O)R^{b2}$, $NR^{c2}C(=O)NR^{c2}R^{d2}$, $NR^{c2}C(=O)OR^{a2}$, $C(=NR^{e2})NR^{c2}R^{d2}$, $NR^{c2}C(=NR^{e2})NR^{c2}R^{d2}$, $S(=O)R^{b2}$, $S(=O)NR^{c2}R^{d2}$, $S(=O)_2R^{b2}$, $NR^{c2}S(=O)_2R^{b2}$ and $S(=O)_2NR^{c2}R^{d2}$;
$R^2$ is H, halogen or $NH_2$;
$R^5$ is H, halogen, $R^{5A}$, $C_{1-6}$ haloalkyl, CN, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)OR^{a3}$, $C(=NR^{e3})NR^{c3}R^{d3}$, $NR^{c3}C(=NR^{e3})NR^{c3}R^{d3}$, $S(=O)R^{b3}$, $S(=O)NR^{c3}R^{d3}$, $S(=O)_2R^{b3}$, $NR^{c3}S(=O)_2R^{b3}$ or $S(=O)_2NR^{c3}R^{d3}$;
$R^{5A}$ is $C_{1-6}$ alkyl, $C_{2-6}$ alkenyl, $C_{2-6}$ alkynyl, $C_{3-7}$ cycloalkyl or phenyl wherein each of said $C_{1-6}$ alkyl, $C_{2-6}$ alkenyl, $C_{2-6}$ alkynyl, $C_{3-7}$ cycloalkyl or phenyl forming $R^{5A}$ is unsubstituted or substituted with 1, 2, 3, 4 or 5 substituents independently selected from halogen, CN, OR$^{a3}$, SR$^{a3}$, C(=O)R$^{b3}$, C(=O)NR$^{c3}$R$^{d3}$, C(=O)OR$^{a3}$, OC(=O)R$^{b3}$, OC(=O)NR$^{c3}$R$^{d3}$, NR$^{c3}$R$^{d3}$, NR$^{c3}$C(=O)R$^{b3}$, NR$^{c3}$C(=O)NR$^{c3}$R$^{d3}$, NR$^{c3}$C(=O)OR$^{a3}$, C(=NR$^{e3}$)NR$^{c3}$R$^{d3}$, NR$^{c3}$C(=NR$^{e3}$)NR$^{c3}$R$^{d3}$, S(=O)R$^{b3}$, S(=O)NR$^{c3}$R$^{d3}$, S(=O)$_2$R$^{b3}$, NR$^{c3}$S(=O)$_2$R$^{b3}$ and S(=O)$_2$NR$^{c3}$R$^{d3}$;

R$^6$ is H, halogen, R$^{6A}$, C$_{1-6}$ haloalkyl, CN, OR$^{a4}$, SR$^{a4}$, C(=O)R$^{b4}$, C(=O)NR$^{c4}$R$^{d4}$, C(=O)OR$^{a4}$, OC(=O)R$^{b4}$, OC(=O)NR$^{c4}$R$^{d4}$, NR$^{c4}$R$^{d4}$, NR$^{c4}$C(=O)R$^{b4}$, NR$^{c4}$C(=O)NR$^{c4}$R$^{d4}$, NR$^{c4}$C(=O)OR$^{a4}$, C(=NR$^{e4}$)NR$^{c4}$R$^{d4}$, NR$^{c4}$C(=NR$^{e4}$)NR$^{c4}$R$^{d4}$, S(=O)R$^{b4}$, S(=O)NR$^{c4}$R$^{d4}$, S(=O)$_2$R$^{b4}$, NR$^{c4}$S(=O)$_2$R$^{b4}$ or S(=O)$_2$NR$^{c4}$R$^{d4}$;

R$^{6A}$ is C$_{1-6}$ alkyl, C$_{2-6}$ alkenyl, C$_{2-6}$ alkynyl, C$_{3-7}$ cycloalkyl, C$_{6-10}$ aryl, 5-10 membered heteroaryl, 4-10 membered heterocycloalkyl, C$_{3-7}$ cycloalkyl-C$_{1-4}$ alkyl-, C$_{6-10}$ aryl-C$_{1-4}$ alkyl-, 5-10 membered heteroaryl-C$_{1-4}$ alkyl- or 4-10 membered heterocycloalkyl-C$_{1-4}$ alkyl- wherein each of said C$_{1-6}$ alkyl, C$_{2-6}$ alkenyl, C$_{2-6}$ alkynyl, C$_{3-7}$ cycloalkyl, C$_{6-10}$ aryl, 5-10 membered heteroaryl, 4-10 membered heterocycloalkyl, C$_{3-7}$ cycloalkyl-C$_{1-4}$ alkyl-, C$_{6-10}$ aryl-C$_{1-4}$ alkyl-, 5-10 membered heteroaryl-C$_{1-4}$ alkyl- or 4-10 membered heterocycloalkyl-C$_{1-4}$ alkyl-forming R$^{6A}$ is unsubstituted or substituted with 1, 2, 3, 4 or 5 substituents independently selected from C$_{1-6}$ alkyl, halogen, C$_{1-6}$ haloalkyl, CN, OR$^{a4}$, SR$^{a4}$, C(=O)R$^{b4}$, C(=O)NR$^{c4}$R$^{d4}$, C(=O)OR$^{a4}$, OC(=O)R$^{b4}$, OC(=O)NR$^{c4}$R$^{d4}$, NR$^{c4}$R$^{d4}$, NR$^{c4}$C(=O)R$^{b4}$, NR$^{c4}$C(=O)NR$^{c4}$R$^{d4}$, NR$^{c4}$C(=O)OR$^{a4}$, C(=NR$^{e4}$)NR$^{c4}$R$^{d4}$, NR$^{c4}$C(=NR$^{e4}$)NR$^{c4}$R$^{d4}$, S(=O)R$^{b4}$, S(=O)NR$^{c4}$R$^{d4}$, S(=O)$_2$R$^{b4}$, NR$^{c4}$S(=O)$_2$R$^{b4}$ and S(=O)$_2$NR$^{c4}$R$^{d4}$;

R$^7$ is H, halogen, R$^{7A}$, C$_{1-6}$ haloalkyl, CN, OR$^{a5}$, SR$^{a5}$, C(=O)R$^{b5}$, C(=O)NR$^{c5}$R$^{d5}$, C(=O)OR$^{a5}$, OC(=O)R$^{b5}$, OC(=O)NR$^{c5}$R$^{d5}$, NR$^{c5}$R$^{d5}$, NR$^{c5}$C(=O)R$^{b5}$, NR$^{c5}$C(=O)NR$^{c5}$R$^{d5}$, NR$^{c5}$C(=O)OR$^{a5}$, C(=NR$^{e5}$)NR$^{c5}$R$^{d5}$, NR$^{c5}$C(=NR$^{e5}$)NR$^{c5}$R$^{d5}$, S(=O)R$^{b5}$, S(=O)NR$^{c5}$R$^{d5}$, S(=O)$_2$R$^{b5}$, NR$^{c5}$S(=O)$_2$R$^{b5}$ or S(=O)$_2$NR$^{c5}$R$^{d5}$;

R$^{7A}$ is C$_{1-6}$ alkyl, C$_{2-6}$ alkenyl, C$_{2-6}$ alkynyl, C$_{3-7}$ cycloalkyl, C$_{6-10}$ aryl, 5-10 membered heteroaryl, 4-10 membered heterocycloalkyl, C$_{3-7}$ cycloalkyl-C$_{1-4}$ alkyl-, C$_{6-10}$ aryl-C$_{1-4}$ alkyl-, 5-10 membered heteroaryl-C$_{1-4}$ alkyl- or 4-10 membered heterocycloalkyl-C$_{1-4}$ alkyl-, wherein each of said C$_{1-6}$ alkyl, C$_{2-6}$ alkenyl, C$_{2-6}$ alkynyl, C$_{3-7}$ cycloalkyl, C$_{6-10}$ aryl, 5-10 membered heteroaryl, 4-10 membered heterocycloalkyl, C$_{3-7}$ cycloalkyl-C$_{1-4}$ alkyl-, C$_{6-10}$ aryl-C$_{1-4}$ alkyl-, 5-10 membered heteroaryl-C$_{1-4}$ alkyl- and 4-10 membered heterocycloalkyl-C$_{1-4}$ alkyl-forming R$^{7A}$ is unsubstituted or substituted with 1, 2, 3, 4 or 5 substituents independently selected from C$_{1-6}$ alkyl, halogen, C$_{1-6}$ haloalkyl, CN, OR$^{a5}$, SR$^{a5}$, C(=O)R$^{b5}$, C(=O)NR$^{c5}$R$^{d5}$, C(=O)OR$^{a5}$, OC(=O)R$^{b5}$, OC(=O)NR$^{c5}$R$^{d5}$, NR$^{c5}$R$^{d5}$, NR$^{c5}$C(=O)R$^{b5}$, NR$^{c5}$C(=O)NR$^{c5}$R$^{d5}$, NR$^{c5}$C(=O)OR$^{a5}$, C(=NR$^{e5}$)NR$^{c5}$R$^{d5}$, NR$^{c5}$C(=NR$^{e5}$)NR$^{c5}$R$^{d5}$, S(=O)R$^{b5}$, S(=O)NR$^{c5}$R$^{d5}$, S(=O)$_2$R$^{b5}$, NR$^{c5}$S(=O)$_2$R$^{b5}$ and S(=O)$_2$NR$^{c5}$R$^{d5}$;

R$^{a1}$, R$^{b1}$, R$^{c1}$ and R$^{d1}$ are each independently selected from H, C$_{1-6}$ alkyl, C$_{2-6}$ alkenyl and C$_{2-6}$ alkynyl;

R$^{a2}$, R$^{b2}$, R$^{c2}$ and R$^{d2}$ are each independently selected from H, C$_{1-6}$ alkyl, C$_{2-6}$ alkenyl and C$_{2-6}$ alkynyl;

R$^{a1}$, R$^{b3}$, R$^{c3}$ and R$^{d3}$ are each independently selected from H, C$_{1-6}$ alkyl, C$_{2-6}$ alkenyl and C$_{2-6}$ alkynyl;

R$^{a4}$, R$^{b4}$, R$^{c4}$ and R$^{d4}$ are each independently selected from H, C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl forming R$^{a4}$, R$^{b4}$, R$^{c4}$ and R$^{d4}$ are each unsubstituted or substituted with 1, 2, 3, 4 or 5 substituents independently selected from C$_{1-6}$ alkyl, halo, CN, OR$^{a6}$, SR$^{a6}$, C(=O)R$^{b6}$, C(=O)NR$^{c6}$R$^{d6}$, C(=O)OR$^{a6}$, OC(=O)R$^{b6}$, OC(=O)NR$^{c6}$R$^{d6}$, NR$^{c6}$R$^{d6}$, NR$^{c6}$C(=O)R$^{b6}$, NR$^{c6}$C(=O)NR$^{c6}$R$^{d6}$, NR$^{c6}$C(=O)OR$^{a6}$, C(=NR$^{e6}$)NR$^{c6}$R$^{d6}$, NR$^{c6}$C(=NR$^{e6}$)NR$^{c6}$R$^{d6}$, S(=O)R$^{b6}$, S(=O)NR$^{c6}$R$^{d6}$, S(=O)$_2$R$^{b6}$, NR$^{c6}$S(=O)$_2$R$^{b6}$ and S(=O)$_2$NR$^{c6}$R$^{d6}$;

or R$^{c4}$ and R$^{d4}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from C$_{1-6}$ alkyl, halo, CN, OR$^{a6}$, SR$^{a6}$, C(=O)R$^{b6}$, C(=O)NR$^{c6}$R$^{d6}$, C(=O) OR$^{a6}$, OC(=O)R$^{b6}$, OC(=O)NR$^{c6}$R$^{d6}$, NR$^{c6}$R$^{d6}$, NR$^{c6}$C(=O)R$^{b6}$, NR$^{c6}$C(=O)NR$^{c6}$R$^{d6}$, NR$^{c6}$C(=O)OR$^{a6}$, C(=NR$^{e6}$)NR$^{c6}$R$^{d6}$, NR$^{c6}$C(=NR$^{e6}$)NR$^{c6}$R$^{d6}$, S(=O)R$^{b6}$, S(=O)NR$^{c6}$R$^{d6}$, S(=O)$_2$R$^{b6}$, NR$^{c6}$S(=O)$_2$R$^{b6}$ and S(=O)$_2$NR$^{c6}$R$^{d6}$;

R$^{a5}$, R$^{b5}$, R$^{c5}$ and R$^{d5}$ are each independently selected from H, C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl forming R$^{a5}$, R$^{b5}$, R$^{c5}$ and R$^{d5}$ are each unsubstituted or substituted with 1, 2, 3, 4 or 5 substituents independently selected from C$_{1-6}$ alkyl, halo, CN, OR$^{a6}$, SR$^{a6}$, C(=O)R$^{b6}$, C(=O)NR$^{c6}$R$^{d6}$, C(=O)OR$^{a6}$, OC(=O) R$^{b6}$, OC(=O)NR$^{c6}$R$^{d6}$, NR$^{c6}$R$^{d6}$, NR$^{c6}$C(=O)R$^{b6}$, NR$^{c6}$C(=O)NR$^{c6}$R$^{d6}$, NR$^{c6}$C(=O)OR$^{a6}$, C(=NR$^{e6}$)NR$^{c6}$R$^{d6}$, NR$^{c6}$C(=NR$^{e6}$)NR$^{c6}$R$^{d6}$, S(=O)R$^{b6}$, S(=O)NR$^{c6}$R$^{d6}$, S(=O)$_2$R$^{b6}$, NR$^{c6}$S(=O)$_2$R$^{b6}$ and S(=O)$_2$NR$^{c6}$R$^{d6}$;

or R$^{c5}$ and R$^{d5}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from C$_{1-6}$ alkyl, halo, CN, OR$^{a6}$, SR$^{a6}$, C(=O)R$^{b6}$, C(=O)NR$^{c6}$R$^{d6}$, C(=O) OR$^{a6}$, OC(=O)R$^{b6}$, OC(=O)NR$^{c6}$R$^{d6}$, NR$^{c6}$R$^{d6}$, NR$^{c6}$C(=O)R$^{b6}$, NR$^{c6}$C(=O)NR$^{c6}$R$^{d6}$, NR$^{c6}$C(=O)OR$^{a6}$, C(=NR$^{e6}$)NR$^{c6}$R$^{d6}$, NR$^{c6}$C(=NR$^{e6}$)NR$^{c6}$R$^{d6}$, S(=O)R$^{b6}$, S(=O)NR$^{c6}$R$^{d6}$, S(=O)$_2$R$^{b6}$, NR$^{c6}$S(=O)$_2$R$^{b6}$ and S(=O)$_2$NR$^{c6}$R$^{d6}$;

R$^{a6}$, R$^{b6}$, R$^{c6}$ and R$^{d6}$ are each independently selected from H, C$_{1-6}$ alkyl, C$_{1-6}$ haloalkyl, C$_{2-6}$ alkenyl, C$_{2-6}$ alkynyl, aryl, C$_{6-10}$ aryl, 5-10 membered heteroaryl, C$_{3-7}$ cycloalkyl and 4-10 membered heterocycloalkyl, wherein said C$_{1-6}$ alkyl, C$_{2-6}$ alkenyl, C$_{2-6}$ alkynyl C$_{6-10}$ aryl, 5-10 membered heteroaryl, C$_{3-7}$ cycloalkyl and 4-10 membered heterocycloalkyl forming R$^{a6}$, R$^{b6}$, R$^{c6}$ and R$^{d6}$ are each optionally substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl and C$_{1-6}$ haloalkoxy;

or R$^{c6}$ and R$^{d6}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl and C$_{1-6}$ haloalkoxy; and R$^{e1}$, R$^{e2}$, R$^{e3}$, R$^{e4}$, R$^{e5}$ and R$^{e6}$ are each, independently, H, C$_{1-4}$ alkyl, CN or NO$_2$.

In some embodiments, the compound is a compound of Formula (I-A):

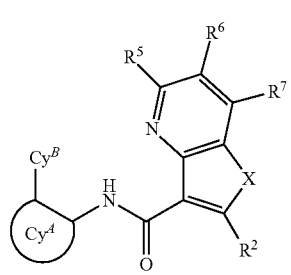

(I-A)

or a pharmaceutically acceptable salt thereof, wherein:

X is S or O;

Cy$^A$ is a 5 to 6 membered monocyclic heteroaryl group wherein the ring atoms of the heteroaryl group forming Cy$^A$ consist of carbon atoms and 1 or 2 atoms selected from N, O and S, and wherein the 5 to 6 membered monocyclic heteroaryl group forming Cy$^A$ is unsubstituted or substituted with 1, 2 or 3 R$^A$;

each R$^A$ is independently selected from halogen, CN, OH, C$_{1-6}$ alkyl, C$_{1-6}$ haloalkyl and C$_{1-6}$ alkoxy;

Cy$^B$ is 4-7 membered heterocycloalkyl wherein the ring atoms of the heterocycloalkyl forming Cy$^B$ consist of carbon atoms and 1 or 2 nitrogen atoms, wherein each of said 4-7 membered heterocycloalkyl forming Cy$^B$ is unsubstituted or substituted with 1, 2 or 3 R$^B$;

each R$^B$ is independently selected from halogen, C$_{1-6}$ alkyl, C$_{1-6}$ haloalkyl, C$_{3-7}$ cycloalkyl, CN, OH, C$_{1-6}$ alkoxy and NH$_2$;

R$^2$ is H, halogen or NH$_2$;

R$^5$ is H, halogen, R$^{5A}$, C$_{1-6}$ haloalkyl, CN or OR$^{a3}$;

R$^{5A}$ is C$_{1-6}$ alkyl, C$_{2-6}$ alkenyl, C$_{2-6}$ alkynyl, C$_{3-7}$ cycloalkyl or phenyl wherein each of said C$_{1-6}$ alkyl, C$_{2-6}$ alkenyl, C$_{2-6}$ alkynyl, C$_{3-7}$ cycloalkyl or phenyl forming R$^{5A}$ is unsubstituted or substituted with 1, 2 or 3 substituents independently selected from halogen, CN and OR$^{a3}$;

R$^6$ is H, halogen, R$^{6A}$, C$_{1-6}$ haloalkyl, CN or OR$^{a4}$;

R$^{6A}$ is C$_{1-6}$ alkyl, C$_{2-6}$ alkenyl, C$_{2-6}$ alkynyl, C$_{3-7}$ cycloalkyl, phenyl, 5-6 membered heteroaryl or 4-7 membered heterocycloalkyl, wherein each of said C$_{1-6}$ alkyl, C$_{2-6}$ alkenyl, C$_{2-6}$ alkynyl, C$_{3-7}$ cycloalkyl, phenyl, 5-6 membered heteroaryl or 4-7 membered heterocycloalkyl forming R$^{6A}$ is unsubstituted or substituted with 1, 2, 3, 4 or 5 substituents independently selected from C$_{1-6}$ alkyl, halogen, CN and OR$^{a4}$;

R$^7$ is H, halogen, R$^{7A}$, C$_{1-6}$ haloalkyl, CN or OR$^{a5}$;

R$^{7A}$ is C$_{1-6}$ alkyl, C$_{2-6}$ alkenyl, C$_{2-6}$ alkynyl, C$_{3-7}$ cycloalkyl, phenyl, 5-6 membered heteroaryl or 4-7 membered heterocycloalkyl forming R$^{7A}$ is unsubstituted or substituted with 1, 2, 3, 4 or 5 substituents independently selected from H, C$_{1-6}$ alkyl, halogen, CN and OR$^{a5}$;

each R$^{a3}$ is independently selected from H, C$_{1-6}$ alkyl, C$_{2-6}$ alkenyl, C$_{2-6}$ alkynyl and C$_{3-7}$ cycloalkyl;

each R$^{a4}$ is independently selected from H, C$_{1-6}$ alkyl, C$_{1-6}$ haloalkyl, C$_{2-6}$ alkenyl and C$_{2-6}$ alkynyl; and each R$^{a5}$ is independently selected from H, C$_{1-6}$ alkyl, C$_{1-6}$ haloalkyl, C$_{2-6}$ alkenyl and C$_{2-6}$ alkynyl.

Embodiments of the compounds of Formula (I-A) may have any of the features described above for embodiments of the compounds of Formula (I), or any combination thereof.

In some embodiments, the compound is a compound of Formula (II-1):

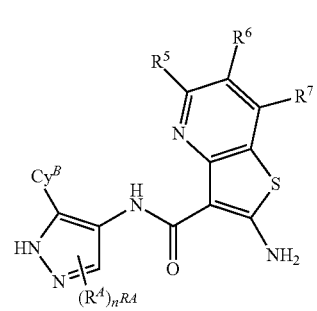

(II-1)

or a pharmaceutically acceptable salt thereof, wherein n$^{RA}$ is 0, 1 or 2.

In some embodiments, the compound is a compound of Formula (II-2):

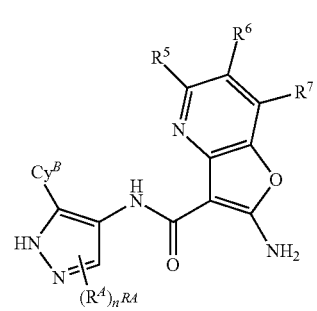

(II-2)

or a pharmaceutically acceptable salt thereof, wherein n$^{RA}$ is 0, 1 or 2.

In some embodiments, the compound is a compound of Formula (II-3):

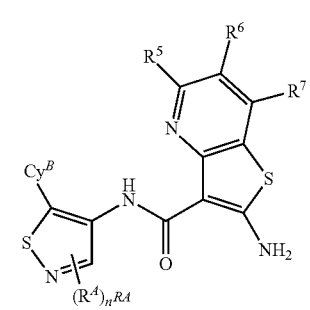

(II-3)

or a pharmaceutically acceptable salt thereof, wherein n$^{RA}$ is 0 or 1.

In some embodiments, the compound is a compound of Formula (II-4):

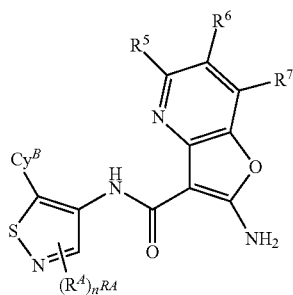

(II-4)

or a pharmaceutically acceptable salt thereof, wherein $n^{RA}$ is 0 or 1.

In some embodiments, the compound is a compound of Formula (II-5):

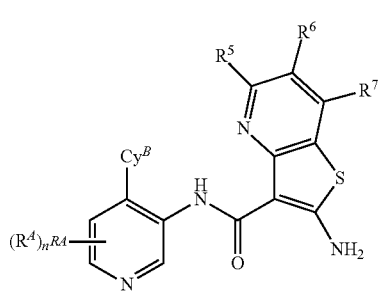

(II-5)

or a pharmaceutically acceptable salt thereof, wherein $n^{RA}$ is 0, 1, 2 or 3.

In some embodiments, the compound is a compound of Formula (II-6):

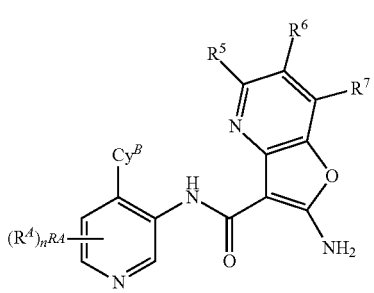

(II-6)

or a pharmaceutically acceptable salt thereof, wherein $n^{RA}$ is 0, 1, 2 or 3.

Embodiments of the compounds of Formula (II-1), (II-2), (II-3), (II-4), (II-5) and (II-6), may have any of the features described above for embodiments of the compounds of Formula (I) and (I-A), or any combination thereof.

In some embodiments of the compounds of Formulae (II-1), (II-2), (II-3), (II-4), (II-5) and (II-6), $n^{RA}$ is 0.

In some embodiments of the compounds of Formulae (II-1), (II-2), (II-3), (II-4), (II-5) and (II-6), $n^{RA}$ is 1.

In some embodiments of the compounds described above, each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a6}$, $R^{b6}$, $R^{c6}$ and $R^{d6}$ is independently selected from H and $C_{1-6}$ alkyl.

In some embodiments of the compounds described above, each $R^{e1}$, $R^{e2}$, $R^{e3}$, $R^{e4}$, $R^{e5}$ and $R^{e6}$ is independently selected from H and $C_{1-6}$ alkyl.

In some embodiments of the compounds described above, each $R^{e1}$, $R^{e2}$, $R^{e3}$, $R^{e4}$, $R^{e5}$ and $R^{e6}$ is H.

The compounds of Formula (I) include the following compounds, and pharmaceutically acceptable salts thereof:

2-amino-N-[5-(4-aminoazepan-1-yl)-1-methyl-1H-pyrazol-4-yl]thieno[3,2-b]pyridine-3-carboxamide;
2-amino-N-[5-((4S)-4-aminoazepan-1-yl)-1-methyl-1H-pyrazol-4-yl]thieno[3,2-b]pyridine-3-carboxamide;
2-amino-N-[5-((4R)-4-aminoazepan-1-yl)-1-methyl-1H-pyrazol-4-yl]thieno[3,2-b]pyridine-3-carboxamide;
2-amino-N-{5-[3-aminopiperidin-1-yl]-1-methyl-1H-pyrazol-4-yl}thieno[3,2-b]pyridine-3-carboxamide;
2-amino-N-{5-[(3S)-3-aminopiperidin-1-yl]-1-methyl-1H-pyrazol-4-yl}thieno[3,2-b]pyridine-3-carboxamide;
2-amino-N-{5-[(3R)-3-aminopiperidin-1-yl]-1-methyl-1H-pyrazol-4-yl}thieno[3,2-b]pyridine-3-carboxamide;
2-amino-N-[5-(1,4-diazepan-1-yl)-1-methyl-1H-pyrazol-4-yl]thieno[3,2-b]pyridine-3-carboxamide;
2-amino-N-[5-(3-amino-2,3-dihydro-1H-inden-5-yl)-1-methyl-1H-pyrazol-4-yl]thieno[3,2-b]pyridine-3-carboxamide;
2-amino-N-[5-((3S)-3-amino-2,3-dihydro-1H-inden-5-yl)-1-methyl-1H-pyrazol-4-yl]thieno[3,2-b]pyridine-3-carboxamide;
2-amino-N-[5-((3R)-3-amino-2,3-dihydro-1H-inden-5-yl)-1-methyl-1H-pyrazol-4-yl]thieno[3,2-b]pyridine-3-carboxamide;
2-amino-N-{4-[3-aminopiperidin-1-yl]pyridin-3-yl}thieno[3,2-b]pyridine-3-carboxamide;
2-amino-N-{4-[(3S)-3-aminopiperidin-1-yl]pyridin-3-yl}thieno[3,2-b]pyridine-3-carboxamide;
2-amino-N-{4-[(3R)-3-aminopiperidin-1-yl]pyridin-3-yl}thieno[3,2-b]pyridine-3-carboxamide;
2-amino-N-[4-(1,4-diazepan-1-yl)pyridin-3-yl]thieno[3,2-b]pyridine-3-carboxamide;
2-amino-N-[4-(4-aminoazepan-1-yl)pyridin-3-yl]thieno[3,2-b]pyridine-3-carboxamide;
2-amino-N-[4-((4S)-4-aminoazepan-1-yl)pyridin-3-yl]thieno[3,2-b]pyridine-3-carboxamide;
2-amino-N-[4-((4R)-4-aminoazepan-1-yl)pyridin-3-yl]thieno[3,2-b]pyridine-3-carboxamide;
2-amino-N-{4-[3-aminopiperidin-1-yl]pyridin-3-yl}-6-methoxythieno[3,2-b]pyridine-3-carboxamide;
2-amino-N-{4-[(3S)-3-aminopiperidin-1-yl]pyridin-3-yl}-6-methoxythieno[3,2-b]pyridine-3-carboxamide;
2-amino-N-{4-[(3R)-3-aminopiperidin-1-yl]pyridin-3-yl}-6-methoxythieno[3,2-b]pyridine-3-carboxamide;
2-amino-N-[5-(4-aminoazepan-1-yl)-1-methyl-1H-pyrazol-4-yl]-6-methoxythieno[3,2-b]pyridine-3-carboxamide;
2-amino-N-[5-((4S)-4-aminoazepan-1-yl)-1-methyl-1H-pyrazol-4-yl]-6-methoxythieno[3,2-b]pyridine-3-carboxamide;
2-amino-N-[5-((4R)-4-aminoazepan-1-yl)-1-methyl-1H-pyrazol-4-yl]-6-methoxythieno[3,2-b]pyridine-3-carboxamide;
2-amino-N-{4-[3-aminopiperidin-1-yl]pyridin-3-yl}-6-cyclopropoxythieno[3,2-b]pyridine-3-carboxamide;
2-amino-N-{4-[(3S)-3-aminopiperidin-1-yl]pyridin-3-yl}-6-cyclopropoxythieno[3,2-b]pyridine-3-carboxamide;
2-amino-N-{4-[(3R)-3-aminopiperidin-1-yl]pyridin-3-yl}-6-cyclopropoxythieno[3,2-b]pyridine-3-carboxamide;
2-amino-N-{4-[(3-amino-5-methyl-piperidin-1-yl]pyridin-3-yl}-thieno[3,2-b]pyridine-3-carboxamide;

2-amino-N-{4-[(cis-3-amino-5-methyl-piperidin-1-yl]pyridin-3-yl}-thieno[3,2-b]pyridine-3-carboxamide;
2-amino-N-{4-[(3S,5R)-3-amino-5-methyl-piperidin-1-yl]pyridin-3-yl}-thieno[3,2-b]pyridine-3-carboxamide;
2-amino-N-{4-[(3-aminopiperidin-1-yl]pyridin-3-yl}-7-methoxythieno[3,2-b]pyridine-3-carboxamide;
2-amino-N-{4-[(3S)-3-aminopiperidin-1-yl]pyridin-3-yl}-7-methoxythieno[3,2-b]pyridine-3-carboxamide;
2-amino-N-{4-[(3R)-3-aminopiperidin-1-yl]pyridin-3-yl}-7-methoxythieno[3,2-b]pyridine-3-carboxamide;
2-amino-N-[5-(4-aminoazepan-1-yl)-1-methyl-1H-pyrazol-4-yl]-7-methoxythieno[3,2-b]pyridine-3-carboxamide;
2-amino-N-[5-((4S)-4-aminoazepan-1-yl)-1-methyl-1H-pyrazol-4-yl]-7-methoxythieno[3,2-b]pyridine-3-carboxamide;
2-amino-N-[5-((4R)-4-aminoazepan-1-yl)-1-methyl-1H-pyrazol-4-yl]-7-methoxythieno[3,2-b]pyridine-3-carboxamide;
2-amino-N-{4-[3-aminopiperidin-1-yl]pyridin-3-yl}-7-isopropoxythieno[3,2-b]pyridine-3-carboxamide;
2-amino-N-{4-[(3S)-3-aminopiperidin-1-yl]pyridin-3-yl}-7-isopropoxythieno[3,2-b]pyridine-3-carboxamide;
2-amino-N-{4-[(3R)-3-aminopiperidin-1-yl]pyridin-3-yl}-7-isopropoxythieno[3,2-b]pyridine-3-carboxamide;
2-amino-N-[5-(4-aminoazepan-1-yl)-1-methyl-1H-pyrazol-4-yl]-7-isopropoxythieno[3,2-b]pyridine-3-carboxamide;
2-amino-N-[5-((4S)-4-aminoazepan-1-yl)-1-methyl-1H-pyrazol-4-yl]-7-isopropoxythieno[3,2-b]pyridine-3-carboxamide;
2-amino-N-[5-((4R)-4-aminoazepan-1-yl)-1-methyl-1H-pyrazol-4-yl]-7-isopropoxythieno[3,2-b]pyridine-3-carboxamide;
2-amino-N-{4-[3-aminopiperidin-1-yl]pyridin-3-yl}-7-ethoxythieno[3,2-b]pyridine-3-carboxamide;
2-amino-N-{4-[(3S)-3-aminopiperidin-1-yl]pyridin-3-yl}-7-ethoxythieno[3,2-b]pyridine-3-carboxamide;
2-amino-N-{4-[(3R)-3-aminopiperidin-1-yl]pyridin-3-yl}-7-ethoxythieno[3,2-b]pyridine-3-carboxamide;
2-amino-N-{4-[3-aminopiperidin-1-yl]pyridin-3-yl}-6-ethylthieno[3,2-b]pyridine-3-carboxamide;
2-amino-N-{4-[(3S)-3-aminopiperidin-1-yl]pyridin-3-yl}-6-ethylthieno[3,2-b]pyridine-3-carboxamide;
2-amino-N-{4-[(3R)-3-aminopiperidin-1-yl]pyridin-3-yl}-6-ethylthieno[3,2-b]pyridine-3-carboxamide;
2-amino-N-[5-(4-aminoazepan-1-yl)-1-methyl-1H-pyrazol-4-yl]-6-ethylthieno[3,2-b]pyridine-3-carboxamide;
2-amino-N-[5-((4S)-4-aminoazepan-1-yl)-1-methyl-1H-pyrazol-4-yl]-6-ethylthieno[3,2-b]pyridine-3-carboxamide;
2-amino-N-[5-((4R)-4-aminoazepan-1-yl)-1-methyl-1H-pyrazol-4-yl]-6-ethylthieno[3,2-b]pyridine-3-carboxamide;
2-amino-N-{4-[3-aminopiperidin-1-yl]pyridin-3-yl}-6-phenylthieno[3,2-b]pyridine-3-carboxamide;
2-amino-N-{4-[3-aminopiperidin-1-yl]pyridin-3-yl}-6-phenylthieno[3,2-b]pyridine-3-carboxamide;
2-amino-N-{4-[(3S)-3-aminopiperidin-1-yl]pyridin-3-yl}-6-phenylthieno[3,2-b]pyridine-3-carboxamide;
2-amino-N-{4-[(3R)-3-aminopiperidin-1-yl]pyridin-3-yl}-6-phenylthieno[3,2-b]pyridine-3-carboxamide;
2-amino-N-[5-(4-aminoazepan-1-yl)-1-methyl-1H-pyrazol-4-yl]-6-phenylthieno[3,2-b]pyridine-3-carboxamide;
2-amino-N-[5-((4S)-4-aminoazepan-1-yl)-1-methyl-1H-pyrazol-4-yl]-6-phenylthieno[3,2-b]pyridine-3-carboxamide;
2-amino-N-[5-((4R)-4-aminoazepan-1-yl)-1-methyl-1H-pyrazol-4-yl]-6-phenylthieno[3,2-b]pyridine-3-carboxamide;
2-amino-N-{4-[3-aminopiperidin-1-yl]pyridin-3-yl}-6-(2,6-difluorophenyl)-thieno[3,2-b]pyridine-3-carboxamide;
2-amino-N-{4-[(3S)-3-aminopiperidin-1-yl]pyridin-3-yl}-6-(2,6-difluorophenyl)-thieno[3,2-b]pyridine-3-carboxamide;
2-amino-N-{4-[(3R)-3-aminopiperidin-1-yl]pyridin-3-yl}-6-(2,6-difluorophenyl)-thieno[3,2-b]pyridine-3-carboxamide;
2-amino-N-[5-(4-aminoazepan-1-yl)-1-methyl-1H-pyrazol-4-yl]-6-(2,6-difluorophenyl)-thieno[3,2-b]pyridine-3-carboxamide;
2-amino-N-[5-((4S)-4-aminoazepan-1-yl)-1-methyl-1H-pyrazol-4-yl]-6-(2,6-difluorophenyl)-thieno[3,2-b]pyridine-3-carboxamide;
2-amino-N-[5-((4R)-4-aminoazepan-1-yl)-1-methyl-1H-pyrazol-4-yl]-6-(2,6-difluorophenyl)-thieno[3,2-b]pyridine-3-carboxamide;
2-amino-N-{4-[3-aminopiperidin-1-yl]pyridin-3-yl}-6-(3,5-dimethylisoxazol-4-yl)-thieno[3,2-b]pyridine-3-carboxamide;
2-amino-N-{4-[(3S)-3-aminopiperidin-1-yl]pyridin-3-yl}-6-(3,5-dimethylisoxazol-4-yl)-thieno[3,2-b]pyridine-3-carboxamide;
2-amino-N-{4-[(3R)-3-aminopiperidin-1-yl]pyridin-3-yl}-6-(3,5-dimethylisoxazol-4-yl)-thieno[3,2-b]pyridine-3-carboxamide;
2-amino-N-[5-(4-aminoazepan-1-yl)-1-methyl-1H-pyrazol-4-yl]-6-(3,5-dimethylisoxazol-4-yl)-thieno[3,2-b]pyridine-3-carboxamide;
2-amino-N-[5-((4S)-4-aminoazepan-1-yl)-1-methyl-1H-pyrazol-4-yl]-6-(3,5-dimethylisoxazol-4-yl)-thieno[3,2-b]pyridine-3-carboxamide;
2-amino-N-[5-((4R)-4-aminoazepan-1-yl)-1-methyl-1H-pyrazol-4-yl]-6-(3,5-dimethylisoxazol-4-yl)-thieno[3,2-b]pyridine-3-carboxamide;
2-amino-N-[5-(4-aminoazepan-1-yl)-1-methyl-1H-pyrazol-4-yl]-6-(1,3-thiazol-2-yl)-thieno[3,2-b]pyridine-3-carboxamide;
2-amino-N-[5-((4S)-4-aminoazepan-1-yl)-1-methyl-1H-pyrazol-4-yl]-6-(1,3-thiazol-2-yl)-thieno[3,2-b]pyridine-3-carboxamide;
2-amino-N-[5-((4R)-4-aminoazepan-1-yl)-1-methyl-1H-pyrazol-4-yl]-6-(1,3-thiazol-2-yl)-thieno[3,2-b]pyridine-3-carboxamide;
2-amino-N-{4-[3-aminopiperidin-1-yl]pyridin-3-yl}-6-(1-methylazetidin-3-yl)thieno[3,2-b]pyridine-3-carboxamide;
2-amino-N-{4-[(3S)-3-aminopiperidin-1-yl]pyridin-3-yl}-6-(1-methylazetidin-3-yl)thieno[3,2-b]pyridine-3-carboxamide;
2-amino-N-{4-[(3R)-3-aminopiperidin-1-yl]pyridin-3-yl}-6-(1-methylazetidin-3-yl)thieno[3,2-b]pyridine-3-carboxamide;
2-amino-N-[5-(4-aminoazepan-1-yl)-1-methyl-1H-pyrazol-4-yl]-6-(1-methylazetidin-3-yl)thieno[3,2-b]pyridine-3-carboxamide;
2-amino-N-[5-((4S)-4-aminoazepan-1-yl)-1-methyl-1H-pyrazol-4-yl]-6-(1-methylazetidin-3-yl)thieno[3,2-b]pyridine-3-carboxamide;
2-amino-N-[5-((4R)-4-aminoazepan-1-yl)-1-methyl-1H-pyrazol-4-yl]-6-(1-methylazetidin-3-yl)thieno[3,2-b]pyridine-3-carboxamide;

2-amino-N-{4-[(3-aminopiperidin-1-yl]pyridin-3-yl}-6-(1-isopropylazetidin-3-yl)thieno[3,2-b]pyridine-3-carboxamide;

2-amino-N-{4-[(3S)-3-aminopiperidin-1-yl]pyridin-3-yl}-6-(1-isopropylazetidin-3-yl)thieno[3,2-b]pyridine-3-carboxamide;

2-amino-N-{4-[(3R)-3-aminopiperidin-1-yl]pyridin-3-yl}-6-(1-isopropylazetidin-3-yl)thieno[3,2-b]pyridine-3-carboxamide;

2-amino-N-{4-[(3-aminopiperidin-1-yl]pyridin-3-yl}-6-(methoxymethyl)thieno[3,2-b]pyridine-3-carboxamide;

2-amino-N-{4-[(3S)-3-aminopiperidin-1-yl]pyridin-3-yl}-6-(methoxymethyl)thieno[3,2-b]pyridine-3-carboxamide;

2-amino-N-{4-[(3R)-3-aminopiperidin-1-yl]pyridin-3-yl}-6-(methoxymethyl)thieno[3,2-b]pyridine-3-carboxamide;

2-amino-N-{4-[3-aminopiperidin-1-yl]pyridin-3-yl}-6-(tetrahydro-2H-pyran-4-yl)thieno[3,2-b]pyridine-3-carboxamide;

2-amino-N-{4-[(3S)-3-aminopiperidin-1-yl]pyridin-3-yl}-6-(tetrahydro-2H-pyran-4-yl)thieno[3,2-b]pyridine-3-carboxamide;

2-amino-N-{4-[(3R)-3-aminopiperidin-1-yl]pyridin-3-yl}-6-(tetrahydro-2H-pyran-4-yl)thieno[3,2-b]pyridine-3-carboxamide;

2-amino-N-{4-[3-aminopiperidin-1-yl]pyridin-3-yl}-6-fluoro-thieno[3,2-b]pyridine-3-carboxamide;

2-amino-N-{4-[(3S)-3-aminopiperidin-1-yl]pyridin-3-yl}-6-fluoro-thieno[3,2-b]pyridine-3-carboxamide;

2-amino-N-{4-[(3R)-3-aminopiperidin-1-yl]pyridin-3-yl}-6-fluoro-thieno[3,2-b]pyridine-3-carboxamide;

2-amino-N-[5-(4-aminoazepan-1-yl)-1-methyl-1H-pyrazol-4-yl]-6-fluoro-thieno[3,2-b]pyridine-3-carboxamide;

2-amino-N-[5-((4S)-4-aminoazepan-1-yl)-1-methyl-1H-pyrazol-4-yl]-6-fluoro-thieno[3,2-b]pyridine-3-carboxamide;

2-amino-N-[5-((4R)-4-aminoazepan-1-yl)-1-methyl-1H-pyrazol-4-yl]-6-fluoro-thieno[3,2-b]pyridine-3-carboxamide;

2-amino-N-{4-[3-aminopiperidin-1-yl]pyridin-3-yl}-7-trifluoromethyl-thieno[3,2-b]pyridine-3-carboxamide;

2-amino-N-{4-[(3S)-3-aminopiperidin-1-yl]pyridin-3-yl}-7-trifluoromethyl-thieno[3,2-b]pyridine-3-carboxamide;

2-amino-N-{4-[(3R)-3-aminopiperidin-1-yl]pyridin-3-yl}-7-trifluoromethyl-thieno[3,2-b]pyridine-3-carboxamide;

2-amino-N-[5-(4-aminoazepan-1-yl)-1-methyl-1H-pyrazol-4-yl]-5-chlorothieno[3,2-b]pyridine-3-carboxamide;

2-amino-N-[5-((4S)-4-aminoazepan-1-yl)-1-methyl-1H-pyrazol-4-yl]-5-chlorothieno[3,2-b]pyridine-3-carboxamide;

2-amino-N-[5-((4R)-4-aminoazepan-1-yl)-1-methyl-1H-pyrazol-4-yl]-5-chlorothieno[3,2-b]pyridine-3-carboxamide;

2-amino-N-[4-(3-aminopiperidin-1-yl)pyridin-3-yl]-5-chlorothieno[3,2-b]pyridine-3-carboxamide;

2-amino-N-[4-((3S)-3-aminopiperidin-1-yl)pyridin-3-yl]-5-chlorothieno[3,2-b]pyridine-3-carboxamide;

2-amino-N-[4-((3R)-3-aminopiperidin-1-yl)pyridin-3-yl]-5-chlorothieno[3,2-b]pyridine-3-carboxamide;

2-amino-N-{5-[(3-aminopiperidin-1-yl]-1-methyl-1H-pyrazol-4-yl}-5-chlorothieno[3,2-b]pyridine-3-carboxamide;

2-amino-N-{5-[(3S)-3-aminopiperidin-1-yl]-1-methyl-1H-pyrazol-4-yl}-5-chlorothieno[3,2-b]pyridine-3-carboxamide;

2-amino-N-{5-[(3R)-3-aminopiperidin-1-yl]-1-methyl-1H-pyrazol-4-yl}-5-chlorothieno[3,2-b]pyridine-3-carboxamide;

2-amino-N-[4-(3-aminopiperidin-1-yl)pyridin-3-yl]-5-methylthieno[3,2-b]pyridine-3-carboxamide;

2-amino-N-[4-((3S)-3-aminopiperidin-1-yl)pyridin-3-yl]-5-methylthieno[3,2-b]pyridine-3-carboxamide;

2-amino-N-[4-((3R)-3-aminopiperidin-1-yl)pyridin-3-yl]-5-methylthieno[3,2-b]pyridine-3-carboxamide;

2-amino-N-[5-(4-aminoazepan-1-yl)-1-methyl-1H-pyrazol-4-yl]-5-methylthieno[3,2-b]pyridine-3-carboxamide;

2-amino-N-[5-((4S)-4-aminoazepan-1-yl)-1-methyl-1H-pyrazol-4-yl]-5-methylthieno[3,2-b]pyridine-3-carboxamide;

2-amino-N-[5-((4R)-4-aminoazepan-1-yl)-1-methyl-1H-pyrazol-4-yl]-5-methylthieno[3,2-b]pyridine-3-carboxamide;

2-amino-N-[5-(4-aminoazepan-1-yl)-1-methyl-1H-pyrazol-4-yl]-5-phenylthieno[3,2-b]pyridine-3-carboxamide;

2-amino-N-[5-((4S)-4-aminoazepan-1-yl)-1-methyl-1H-pyrazol-4-yl]-5-phenylthieno[3,2-b]pyridine-3-carboxamide;

2-amino-N-[5-((4R)-4-aminoazepan-1-yl)-1-methyl-1H-pyrazol-4-yl]-5-phenylthieno[3,2-b]pyridine-3-carboxamide;

2-amino-N-{4-[3-aminopiperidin-1-yl]pyridin-3-yl}furo[3,2-b]pyridine-3-carboxamide;

2-amino-N-{4-[(3S)-3-aminopiperidin-1-yl]pyridin-3-yl}furo[3,2-b]pyridine-3-carboxamide;

2-amino-N-{4-[(3R)-3-aminopiperidin-1-yl]pyridin-3-yl}furo[3,2-b]pyridine-3-carboxamide;

2-amino-N-[5-(4-aminoazepan-1-yl)-1-methyl-1H-pyrazol-4-yl]furo[3,2-b]pyridine-3-carboxamide;

2-amino-N-[5-((4S)-4-aminoazepan-1-yl)-1-methyl-1H-pyrazol-4-yl]furo[3,2-b]pyridine-3-carboxamide;

2-amino-N-[5-((4R)-4-aminoazepan-1-yl)-1-methyl-1H-pyrazol-4-yl]furo[3,2-b]pyridine-3-carboxamide;

2-amino-N-{4-[(3-aminopiperidin-1-yl]pyridin-3-yl}-6-ethylfuro[3,2-b]pyridine-3-carboxamide;

2-amino-N-{4-[(3S)-3-aminopiperidin-1-yl]pyridin-3-yl}-6-ethylfuro[3,2-b]pyridine-3-carboxamide;

2-amino-N-{4-[(3R)-3-aminopiperidin-1-yl]pyridin-3-yl}-6-ethylfuro[3,2-b]pyridine-3-carboxamide;

2-amino-N-{4-[3-aminopiperidin-1-yl]pyridin-3-yl}-6-(trifluoromethyl)furo[3,2-b]pyridine-3-carboxamide;

2-amino-N-{4-[(3S)-3-aminopiperidin-1-yl]pyridin-3-yl}-6-(trifluoromethyl)furo[3,2-b]pyridine-3-carboxamide;

2-amino-N-{4-[(3R)-3-aminopiperidin-1-yl]pyridin-3-yl}-6-(trifluoromethyl)furo[3,2-b]pyridine-3-carboxamide;

2-amino-N-{4-[(3-aminopiperidin-1-yl]pyridin-3-yl}-6-methyl-furo[3,2-b]pyridine-3-carboxamide;

2-amino-N-{4-[(3S)-3-aminopiperidin-1-yl]pyridin-3-yl}-6-methyl-furo[3,2-b]pyridine-3-carboxamide;

2-amino-N-{4-[(3R)-3-aminopiperidin-1-yl]pyridin-3-yl}-6-methyl-furo[3,2-b]pyridine-3-carboxamide;

2-amino-N-{4-[3-aminopiperidin-1-yl]pyridin-3-yl}-6-(iso-propyl)furo[3,2-b]pyridine-3-carboxamide;

2-amino-N-{4-[(3S)-3-aminopiperidin-1-yl]pyridin-3-yl}-6-(iso-propyl)furo[3,2-b]pyridine-3-carboxamide;

2-amino-N-{4-[(3R)-3-aminopiperidin-1-yl]pyridin-3-yl}-6-(iso-propyl)furo[3,2-b]pyridine-3-carboxamide;

2-amino-N-{4-[3-aminopiperidin-1-yl]pyridin-3-yl}-6-(propyl)furo[3,2-b]pyridine-3-carboxamide;

2-amino-N-{4-[(3S)-3-aminopiperidin-1-yl]pyridin-3-yl}-6-(propyl)furo[3,2-b]pyridine-3-carboxamide;

2-amino-N-{4-[(3R)-3-aminopiperidin-1-yl]pyridin-3-yl}-6-(propyl)furo[3,2-b]pyridine-3-carboxamide;

2-amino-N-{4-[3-aminopiperidin-1-yl]pyridin-3-yl}-6-fluoro-furo[3,2-b]pyridine-3-carboxamide;

2-amino-N-{4-[(3S)-3-aminopiperidin-1-yl]pyridin-3-yl}-6-fluoro-furo[3,2-b]pyridine-3-carboxamide;
2-amino-N-{4-[(3R)-3-aminopiperidin-1-yl]pyridin-3-yl}-6-fluoro-furo[3,2-b]pyridine-3-carboxamide;
2-amino-N-{4-[3-aminopiperidin-1-yl]pyridin-3-yl}-6-chloro-furo[3,2-b]pyridine-3-carboxamide;
2-amino-N-{4-[(3S)-3-aminopiperidin-1-yl]pyridin-3-yl}-6-chloro-furo[3,2-b]pyridine-3-carboxamide;
2-amino-N-{4-[(3R)-3-aminopiperidin-1-yl]pyridin-3-yl}-6-chloro-furo[3,2-b]pyridine-3-carboxamide;
2-amino-N-{4-[3-aminopiperidin-1-yl]pyridin-3-yl}-6-bromo-furo[3,2-b]pyridine-3-carboxamide;
2-amino-N-{4-[(3S)-3-aminopiperidin-1-yl]pyridin-3-yl}-6-bromo-furo[3,2-b]pyridine-3-carboxamide;
2-amino-N-{4-[(3R)-3-aminopiperidin-1-yl]pyridin-3-yl}-6-bromo-furo[3,2-b]pyridine-3-carboxamide;
2-amino-N-{4-[3-aminopiperidin-1-yl]pyridin-3-yl}-7-methyl-furo[3,2-b]pyridine-3-carboxamide;
2-amino-N-{4-[(3S)-3-aminopiperidin-1-yl]pyridin-3-yl}-7-methyl-furo[3,2-b]pyridine-3-carboxamide;
2-amino-N-{4-[(3R)-3-aminopiperidin-1-yl]pyridin-3-yl}-7-methyl-furo[3,2-b]pyridine-3-carboxamide;
2-amino-N-[5-(4-aminoazepan-1-yl)-1-methyl-1H-pyrazol-4-yl]-6-trifluoromethyl-furo[3,2-b]pyridine-3-carboxamide;
2-amino-N-[5-((4S)-4-aminoazepan-1-yl)-1-methyl-1H-pyrazol-4-yl]-6-trifluoromethyl-furo[3,2-b]pyridine-3-carboxamide;
2-amino-N-[5-((4R)-4-aminoazepan-1-yl)-1-methyl-1H-pyrazol-4-yl]-6-trifluoromethyl-furo[3,2-b]pyridine-3-carboxamide;
2-amino-N-[5-(4-aminoazepan-1-yl)-1-methyl-1H-pyrazol-4-yl]-6-chlorofuro[3,2-b]pyridine-3-carboxamide;
2-amino-N-[5-((4S)-4-aminoazepan-1-yl)-1-methyl-1H-pyrazol-4-yl]-6-chlorofuro[3,2-b]pyridine-3-carboxamide;
2-amino-N-[5-((4R)-4-aminoazepan-1-yl)-1-methyl-1H-pyrazol-4-yl]-6-chlorofuro[3,2-b]pyridine-3-carboxamide;
2-amino-N-[5-(4-aminoazepan-1-yl)-1-methyl-1H-pyrazol-4-yl]-7-chlorofuro[3,2-b]pyridine-3-carboxamide;
2-amino-N-[5-((4S)-4-aminoazepan-1-yl)-1-methyl-1H-pyrazol-4-yl]-7-chlorofuro[3,2-b]pyridine-3-carboxamide;
2-amino-N-[5-((4R)-4-aminoazepan-1-yl)-1-methyl-1H-pyrazol-4-yl]-7-chlorofuro[3,2-b]pyridine-3-carboxamide;
2-amino-N-[5-(4-aminoazepan-1-yl)-1-methyl-1H-pyrazol-4-yl]-6-propylfuro[3,2-b]pyridine-3-carboxamide;
2-amino-N-[5-((4S)-4-aminoazepan-1-yl)-1-methyl-1H-pyrazol-4-yl]-6-propylfuro[3,2-b]pyridine-3-carboxamide;
2-amino-N-[5-((4R)-4-aminoazepan-1-yl)-1-methyl-1H-pyrazol-4-yl]-6-propylfuro[3,2-b]pyridine-3-carboxamide;
2-amino-N-{4-[3-amino-5-(trifluoromethyl)piperidin-1-yl]pyridin-3-yl}-furo[3,2-b]pyridine-3-carboxamide;
2-amino-N-{4-[cis-3-amino-5-(trifluoromethyl)piperidin-1-yl]pyridin-3-yl}-furo[3,2-b]pyridine-3-carboxamide;
2-amino-N-{4-[(3S,5R)-3-amino-5-(trifluoromethyl)piperidin-1-yl]pyridin-3-yl}-furo[3,2-b]pyridine-3-carboxamide;
2-amino-N-{4-[3-amino-5-(trifluoromethyl)piperidin-1-yl]pyridin-3-yl}-6-trifluoromethyl-furo[3,2-b]pyridine-3-carboxamide;
2-amino-N-{4-[cis-3-amino-5-(trifluoromethyl)piperidin-1-yl]pyridin-3-yl}-6-trifluoromethyl-furo[3,2-b]pyridine-3-carboxamide;
2-amino-N-{4-[(3S,5R)-3-amino-5-(trifluoromethyl)piperidin-1-yl]pyridin-3-yl}-6-trifluoromethyl-furo[3,2-b]pyridine-3-carboxamide;
2-amino-N-{4-[3-amino-5-(trifluoromethyl)piperidin-1-yl]pyridin-3-yl}-6-chlorofuro[3,2-b]pyridine-3-carboxamide;
2-amino-N-{4-[cis-3-amino-5-(trifluoromethyl)piperidin-1-yl]pyridin-3-yl}-6-chlorofuro[3,2-b]pyridine-3-carboxamide;
2-amino-N-{4-[(3S,5R)-3-amino-5-(trifluoromethyl)piperidin-1-yl]pyridin-3-yl}-6-chlorofuro[3,2-b]pyridine-3-carboxamide;
2-amino-N-{4-[3-amino-5-(trifluoromethyl)piperidin-1-yl]pyridin-3-yl}-6-fluorofuro[3,2-b]pyridine-3-carboxamide
2-amino-N-{4-[cis-3-amino-5-(trifluoromethyl)piperidin-1-yl]pyridin-3-yl}-6-fluorofuro[3,2-b]pyridine-3-carboxamide;
2-amino-N-{4-[(3S,5R)-3-amino-5-(trifluoromethyl)piperidin-1-yl]pyridin-3-yl}-6-fluorofuro[3,2-b]pyridine-3-carboxamide;
2-amino-N-{4-[3-aminopyrrolidin-1-yl]-5-methylpyridin-3-yl}furo[3,2-b]pyridine-3-carboxamide;
2-amino-N-{4-[(3S)-3-aminopyrrolidin-1-yl]-5-methylpyridin-3-yl}furo[3,2-b]pyridine-3-carboxamide;
2-amino-N-{4-[(3R)-3-aminopyrrolidin-1-yl]-5-methylpyridin-3-yl}furo[3,2-b]pyridine-3-carboxamide;
2-amino-N-{4-[3-amino-5-methyl-piperidin-1-yl]pyridin-3-yl}-furo[3,2-b]pyridine-3-carboxamide;
2-amino-N-{4-[cis-3-amino-5-methyl-piperidin-1-yl]pyridin-3-yl}-furo[3,2-b]pyridine-3-carboxamide;
2-amino-N-{4-[(3S,5R)-3-amino-5-methyl-piperidin-1-yl]pyridin-3-yl}-furo[3,2-b]pyridine-3-carboxamide;
2-amino-N-{4-[3-amino-4-hydroxy-5-methylpiperidin-1-yl]pyridin-3-yl}-6-chlorofuro[3,2-b]pyridine-3-carboxamide;
2-amino-N-{4-[(3R,4R,5S)-3-amino-4-hydroxy-5-methyl-piperidin-1-yl]pyridin-3-yl}-6-chlorofuro[3,2-b]pyridine-3-carboxamide;
2-amino-N-{4-[3-amino-4-hydroxy-5-methylpiperidin-1-yl]pyridin-3-yl}-6-propylfuro[3,2-b]pyridine-3-carboxamide;
2-amino-N-{4-[(3R,4R,5S)-3-amino-4-hydroxy-5-methyl-piperidin-1-yl]pyridin-3-yl}-6-propylfuro[3,2-b]pyridine-3-carboxamide;
2-amino-N-{4-[3-amino-4-hydroxy-5-methylpiperidin-1-yl]pyridin-3-yl}-6-(trifluoromethyl)furo[3,2-b]pyridine-3-carboxamide;
2-amino-N-{4-[(3R,4R,5S)-3-amino-4-hydroxy-5-methyl-piperidin-1-yl]pyridin-3-yl}-6-(trifluoromethyl)furo[3,2-b]pyridine-3-carboxamide;
2-amino-N-{4-[3-amino-5-(trifluoromethyl)piperidin-1-yl]pyridin-3-yl}-6-propylfuro[3,2-b]pyridine-3-carboxamide;
2-amino-N-{4-[cis-3-amino-5-(trifluoromethyl)piperidin-1-yl]pyridin-3-yl}-6-propylfuro[3,2-b]pyridine-3-carboxamide;
2-amino-N-{4-[(3S,5R)-3-amino-5-(trifluoromethyl)piperidin-1-yl]pyridin-3-yl}-6-propylfuro[3,2-b]pyridine-3-carboxamide;
2-amino-N-{4-[3-amino-5-methyl-piperidin-1-yl]pyridin-3-yl}-6-propylfuro[3,2-b]pyridine-3-carboxamide;
2-amino-N-{4-[cis-3-amino-5-methyl-piperidin-1-yl]pyridin-3-yl}-6-propylfuro[3,2-b]pyridine-3-carboxamide;

2-amino-N-{4-[(3S,5R)-3-amino-5-methyl-piperidin-1-yl]pyridin-3-yl}-6-propylfuro[3,2-b]pyridine-3-carboxamide;
2-amino-N-{4-[3-amino-5-methyl-piperidin-1-yl]pyridin-3-yl}-6-fluorofuro[3,2-b]pyridine-3-carboxamide;
2-amino-N-{4-[cis-3-amino-5-methyl-piperidin-1-yl]pyridin-3-yl}-6-fluorofuro[3,2-b]pyridine-3-carboxamide;
2-amino-N-{4-[(3S,5R)-3-amino-5-methyl-piperidin-1-yl]pyridin-3-yl}-6-fluorofuro[3,2-b]pyridine-3-carboxamide;
2-amino-N-{4-[(3-amino-5-methyl-piperidin-1-yl]pyridin-3-yl}-6-chlorofuro[3,2-b]pyridine-3-carboxamide;
2-amino-N-{4-[cis3-amino-5-methyl-piperidin-1-yl]pyridin-3-yl}-6-chlorofuro[3,2-b]pyridine-3-carboxamide;
2-amino-N-{4-[(3S,5R)-3-amino-5-methyl-piperidin-1-yl]pyridin-3-yl}-6-chlorofuro[3,2-b]pyridine-3-carboxamide;
2-amino-N-{4-[3-amino-5-methyl-piperidin-1-yl]pyridin-3-yl}-6-(trifluoromethyl)-furo[3,2-b]pyridine-3-carboxamide;
2-amino-N-{4-[cis-3-amino-5-methyl-piperidin-1-yl]pyridin-3-yl}-6-(trifluoromethyl)-furo[3,2-b]pyridine-3-carboxamide;
2-amino-N-{4-[(3S,5R)-3-amino-5-methyl-piperidin-1-yl]pyridin-3-yl}-6-(trifluoromethyl)-furo[3,2-b]pyridine-3-carboxamide;
2-amino-N-{4-[3-amino-4-hydroxy-5-methylpiperidin-1-yl]pyridin-3-yl}-furo[3,2-b]pyridine-3-carboxamide;
2-amino-N-{4-[(3R,4R,5S)-3-amino-4-hydroxy-5-methylpiperidin-1-yl]pyridin-3-yl}-furo[3,2-b]pyridine-3-carboxamide;
2-amino-N-{4-[3-amino-4-hydroxy-5-methylpiperidin-1-yl]pyridin-3-yl}-6-isopropylfuro[3,2-b]pyridine-3-carboxamide;
2-amino-N-{4-[(3R,4R,5S)-3-amino-4-hydroxy-5-methylpiperidin-1-yl]pyridin-3-yl}-6-isopropylfuro[3,2-b]pyridine-3-carboxamide;
2-amino-N-{5-methyl-4-[3-amino-4-hydroxy-5-methylpiperidin-1-yl]pyridin-3-yl}-furo[3,2-b]pyridine-3-carboxamide;
2-amino-N-{5-methyl-4-[(3R,4R,5S)-3-amino-4-hydroxy-5-methylpiperidin-1-yl]pyridin-3-yl}-furo[3,2-b]pyridine-3-carboxamide;
2-amino-N-{5-methyl-4-[3-amino-4-hydroxy-5-methylpiperidin-1-yl]pyridin-3-yl}-6-propylfuro[3,2-b]pyridine-3-carboxamide;
2-amino-N-{5-methyl-4-[(3R,4R,5S)-3-amino-4-hydroxy-5-methylpiperidin-1-yl]pyridin-3-yl}-6-propylfuro[3,2-b]pyridine-3-carboxamide;
2-amino-N-{5-methyl-4-[3-amino-4-hydroxy-5-methylpiperidin-1-yl]pyridin-3-yl}-6-chlorofuro[3,2-b]pyridine-3-carboxamide;
2-amino-N-{5-methyl-4-[(3R,4R,5S)-3-amino-4-hydroxy-5-methylpiperidin-1-yl]pyridin-3-yl}-6-chlorofuro[3,2-b]pyridine-3-carboxamide;
2-amino-N-{5-methyl-4-[3-amino-4-hydroxy-5-methylpiperidin-1-yl]pyridin-3-yl}-6-(trifluoromethyl)-furo[3,2-b]pyridine-3-carboxamide;
2-amino-N-{5-methyl-4-[(3R,4R,5S)-3-amino-4-hydroxy-5-methylpiperidin-1-yl]pyridin-3-yl}-6-(trifluoromethyl)-furo[3,2-b]pyridine-3-carboxamide;
2-amino-N-{4-[3-amino-4-fluoro-piperidin-1-yl]pyridin-3-yl}-6-propylfuro[3,2-b]pyridine-3-carboxamide;
2-amino-N-{4-[trans-3-amino-4-fluoro-piperidin-1-yl]pyridin-3-yl}-6-propylfuro[3,2-b]pyridine-3-carboxamide;
2-amino-N-{4-[(3R,4R)-3-amino-4-fluoro-piperidin-1-yl]pyridin-3-yl}-6-propylfuro[3,2-b]pyridine-3-carboxamide;
2-amino-N-{4-[3-aminopiperidin-1-yl]pyridin-3-yl}-7-chloro-furo[3,2-b]pyridine-3-carboxamide;
2-amino-N-{4-[(3S)-3-aminopiperidin-1-yl]pyridin-3-yl}-7-chloro-furo[3,2-b]pyridine-3-carboxamide;
2-amino-N-{4-[(3R)-3-aminopiperidin-1-yl]pyridin-3-yl}-7-chloro-furo[3,2-b]pyridine-3-carboxamide;
2-amino-N-{4-[3-amino-5-cyclopropyl-4-hydroxypiperidin-1-yl]pyridin-3-yl}-6-propylfuro[3,2-b]pyridine-3-carboxamide;
2-amino-N-{4-[(3R,4R,5S)-3-amino-5-cyclopropyl-4-hydroxypiperidin-1-yl]pyridin-3-yl}-6-propylfuro[3,2-b]pyridine-3-carboxamide;
2-amino-N-(4-(3-amino-4-hydroxy-4,5-dimethylcyclohexyl)pyridin-3-yl)furo[3,2-b]pyridine-3-carboxamide;
2-amino-N-(4-((1R,3R,4R,5S)-3-amino-4-hydroxy-4,5-dimethylcyclohexyl)pyridin-3-yl)furo[3,2-b]pyridine-3-carboxamide;
2-amino-N-(4-(3-amino-4-hydroxy-4,5-dimethylcyclohexyl)pyridin-3-yl)-6-propylfuro[3,2-b]pyridine-3-carboxamide;
2-amino-N-(4-((1R,3R,4R,5S)-3-amino-4-hydroxy-4,5-dimethylcyclohexyl)pyridin-3-yl)-6-propylfuro[3,2-b]pyridine-3-carboxamide;
2-amino-N-{4-[3-amino-4-hydroxy-4,5-dimethylpiperidin-1-yl]pyridin-3-yl}-6-propylfuro[3,2-b]pyridine-3-carboxamide;
2-amino-N-{4-[(3R,4R,5S)-3-amino-4-hydroxy-4,5-dimethylpiperidin-1-yl]pyridin-3-yl}-6-propylfuro[3,2-b]pyridine-3-carboxamide;
2-amino-N-{4-[3-amino-4-hydroxy-4,5-dimethylpiperidin-1-yl]pyridin-3-yl}-6-propylfuro[3,2-b]pyridine-3-carboxamide;
2-amino-N-{4-[(3R,4S,5S)-3-amino-4-hydroxy-4,5-dimethylpiperidin-1-yl]pyridin-3-yl}-6-propylfuro[3,2-b]pyridine-3-carboxamide;
2-amino-N-{4-[3-amino-4-hydroxy-5-(trifluoromethyl)piperidin-1-yl]pyridin-3-yl}furo[3,2-b]pyridine-3-carboxamide;
2-amino-N-{4-[(3R,4R,5S)-3-amino-4-hydroxy-5-(trifluoromethyl)piperidin-1-yl]pyridin-3-yl}furo[3,2-b]pyridine-3-carboxamide;
2-amino-N-{5-[3-aminopiperidin-1-yl]isothiazol-4-yl}thieno[3,2-b]pyridine-3-carboxamide;
2-amino-N-{5-[(3S)-3-aminopiperidin-1-yl]isothiazol-4-yl}thieno[3,2-b]pyridine-3-carboxamide;
2-amino-N-{5-[(3R)-3-aminopiperidin-1-yl]isothiazol-4-yl}thieno[3,2-b]pyridine-3-carboxamide;
2-amino-N-{5-[3-amino-5-(trifluoromethyl)piperidin-1-yl]-1-methyl-1H-pyrazol-4-yl}-6-(tetrahydro-2H-pyran-4-yl)furo[3,2-b]pyridine-3-carboxamide;
2-amino-N-{5-[trans-3-amino-5-(trifluoromethyl)piperidin-1-yl]-1-methyl-1H-pyrazol-4-yl}-6-(tetrahydro-2H-pyran-4-yl)furo[3,2-b]pyridine-3-carboxamide;
2-amino-N-{5-[(3S,5R)-3-amino-5-(trifluoromethyl)piperidin-1-yl]-1-methyl-1H-pyrazol-4-yl}-6-(tetrahydro-2H-pyran-4-yl)furo[3,2-b]pyridine-3-carboxamide;
2-amino-N-{5-[3-amino-5-(trifluoromethyl)piperidin-1-yl]isothiazol-4-yl}-6-(tetrahydro-2H-pyran-4-yl)furo[3,2-b]pyridine-3-carboxamide;
2-amino-N-{5-[trans-3-amino-5-(trifluoromethyl)piperidin-1-yl]isothiazol-4-yl}-6-(tetrahydro-2H-pyran-4-yl)furo[3,2-b]pyridine-3-carboxamide;

2-amino-N-{5-[(3S,5R)-3-amino-5-(trifluoromethyl)piperidin-1-yl]isothiazol-4-yl}-6-(tetrahydro-2H-pyran-4-yl)furo[3,2-b]pyridine-3-carboxamide;

2-amino-N-{4-[3-amino-5-(trifluoromethyl)piperidin-1-yl]pyridin-3-yl}-6-(tetrahydro-2H-pyran-4-yl)furo[3,2-b]pyridine-3-carboxamide;

2-amino-N-{4-[trans-3-amino-5-(trifluoromethyl)piperidin-1-yl]pyridin-3-yl}-6-(tetrahydro-2H-pyran-4-yl)furo[3,2-b]pyridine-3-carboxamide;

2-amino-N-{4-[(3S,5R)-3-amino-5-(trifluoromethyl)piperidin-1-yl]pyridin-3-yl}-6-(tetrahydro-2H-pyran-4-yl)furo[3,2-b]pyridine-3-carboxamide;

2-amino-N-{4-[3-amino-5-(trifluoromethyl)piperidin-1-yl]pyridin-3-yl}-6-(1-methylpiperidin-4-yl)furo[3,2-b]pyridine-3-carboxamide;

2-amino-N-{4-[cis-3-amino-5-(trifluoromethyl)piperidin-1-yl]pyridin-3-yl}-6-(1-methylpiperidin-4-yl)furo[3,2-b]pyridine-3-carboxamide;

2-amino-N-{4-[(3S,5R)-3-amino-5-(trifluoromethyl)piperidin-1-yl]pyridin-3-yl}-6-(1-methylpiperidin-4-yl)furo[3,2-b]pyridine-3-carboxamide;

2-amino-N-{5-[3-amino-5-(trifluoromethyl)piperidin-1-yl]-1-methyl-1H-pyrazol-4-yl}-6-(1-methylpiperidin-4-yl)furo[3,2-b]pyridine-3-carboxamide;

2-amino-N-{5-[cis-3-amino-5-(trifluoromethyl)piperidin-1-yl]-1-methyl-1H-pyrazol-4-yl}-6-(1-methylpiperidin-4-yl)furo[3,2-b]pyridine-3-carboxamide;

2-amino-N-{5-[(3S,5R)-3-amino-5-(trifluoromethyl)piperidin-1-yl]-1-methyl-1H-pyrazol-4-yl}-6-(1-methylpiperidin-4-yl)furo[3,2-b]pyridine-3-carboxamide;

2-amino-N-{4-[3-amino-5-methylpiperidin-1-yl]pyridin-3-yl}-6-(tetrahydro-2H-pyran-4-yl)furo[3,2-b]pyridine-3-carboxamide;

2-amino-N-{4-[cis-3-amino-5-methylpiperidin-1-yl]pyridin-3-yl}-6-(tetrahydro-2H-pyran-4-yl)furo[3,2-b]pyridine-3-carboxamide;

2-amino-N-{4-[(3S,5R)-3-amino-5-methylpiperidin-1-yl]pyridin-3-yl}-6-(tetrahydro-2H-pyran-4-yl)furo[3,2-b]pyridine-3-carboxamide;

2-amino-N-{5-[3-amino-5-methylpiperidin-1-yl]isothiazol-4-yl}-6-(tetrahydro-2H-pyran-4-yl)furo[3,2-b]pyridine-3-carboxamide;

2-amino-N-{5-[cis-3-amino-5-methylpiperidin-1-yl]isothiazol-4-yl}-6-(tetrahydro-2H-pyran-4-yl)furo[3,2-b]pyridine-3-carboxamide;

2-amino-N-{5-[(3S,5R)-3-amino-5-methylpiperidin-1-yl]isothiazol-4-yl}-6-(tetrahydro-2H-pyran-4-yl)furo[3,2-b]pyridine-3-carboxamide;

2-amino-N-{4-[3-amino-5-methylpiperidin-1-yl]pyridin-3-yl}-6-cyclobutylfuro[3,2-b]pyridine-3-carboxamide;

2-amino-N-{4-[cis-3-amino-5-methylpiperidin-1-yl]pyridin-3-yl}-6-cyclobutylfuro[3,2-b]pyridine-3-carboxamide;

2-amino-N-{4-[(3S,5R)-3-amino-5-methylpiperidin-1-yl]pyridin-3-yl}-6-cyclobutylfuro[3,2-b]pyridine-3-carboxamide;

2-amino-N-{4-[3-amino-5-(trifluoromethyl)piperidin-1-yl]pyridin-3-yl}-6-cyclobutylfuro[3,2-b]pyridine-3-carboxamide;

2-amino-N-{4-[cis-3-amino-5-(trifluoromethyl)piperidin-1-yl]pyridin-3-yl}-6-cyclobutylfuro[3,2-b]pyridine-3-carboxamide;

2-amino-N-{4-[(3S,5R)-3-amino-5-(trifluoromethyl)piperidin-1-yl]pyridin-3-yl}-6-cyclobutylfuro[3,2-b]pyridine-3-carboxamide;

2-amino-N-{4-[3-amino-5-(trifluoromethyl)piperidin-1-yl]pyridin-3-yl}-6-[(3-fluoroazetidin-1-yl)methyl]furo[3,2-b]pyridine-3-carboxamide;

2-amino-N-{4-[cis-3-amino-5-(trifluoromethyl)piperidin-1-yl]pyridin-3-yl}-6-[(3-fluoroazetidin-1-yl)methyl]furo[3,2-b]pyridine-3-carboxamide;

2-amino-N-{4-[(3S,5R)-3-amino-5-(trifluoromethyl)piperidin-1-yl]pyridin-3-yl}-6-[(3-fluoroazetidin-1-yl)methyl]furo[3,2-b]pyridine-3-carboxamide;

2-amino-N-{4-[3-amino-5-(trifluoromethyl)piperidin-1-yl]pyridin-3-yl}-6-[(3,3-difluoroazetidin-1-yl)methyl]furo[3,2-b]pyridine-3-carboxamide;

2-amino-N-{4-[cis-3-amino-5-(trifluoromethyl)piperidin-1-yl]pyridin-3-yl}-6-[(3,3-difluoroazetidin-1-yl)methyl]furo[3,2-b]pyridine-3-carboxamide;

2-amino-N-{4-[(3S,5R)-3-amino-5-(trifluoromethyl)piperidin-1-yl]pyridin-3-yl}-6-[(3,3-difluoroazetidin-1-yl)methyl]furo[3,2-b]pyridine-3-carboxamide;

2-amino-N-{4-[3-amino-5-(trifluoromethyl)piperidin-1-yl]pyridin-3-yl}-6-[(3-hydroxyazetidin-1-yl)methyl]furo[3,2-b]pyridine-3-carboxamide;

2-amino-N-{4-[cis-3-amino-5-(trifluoromethyl)piperidin-1-yl]pyridin-3-yl}-6-[(3-hydroxyazetidin-1-yl)methyl]furo[3,2-b]pyridine-3-carboxamide;

2-amino-N-{4-[(3S,5R)-3-amino-5-(trifluoromethyl)piperidin-1-yl]pyridin-3-yl}-6-[(3-hydroxyazetidin-1-yl)methyl]furo[3,2-b]pyridine-3-carboxamide;

2-amino-N-{4-[3-amino-5-methyl-4-(1H-1,2,3-triazol-1-yl)piperidin-1-yl]pyridin-3-yl}-6-isopropylfuro[3,2-b]pyridine-3-carboxamide;

2-amino-N-{4-[(3R,4S,5S)-3-amino-5-methyl-4-(1H-1,2,3-triazol-1-yl)piperidin-1-yl]pyridin-3-yl}-6-isopropylfuro[3,2-b]pyridine-3-carboxamide;

2-amino-N-{4-[3-amino-5-(trifluoromethyl)piperidin-1-yl]pyridin-3-yl}-6-[(3-methoxypyrrolidin-1-yl)methyl]furo[3,2-b]pyridine-3-carboxamide;

2-amino-N-{4-[cis-3-amino-5-(trifluoromethyl)piperidin-1-yl]pyridin-3-yl}-6-[(3-methoxypyrrolidin-1-yl)methyl]furo[3,2-b]pyridine-3-carboxamide;

2-amino-N-{4-[(3S,5R)-3-amino-5-(trifluoromethyl)piperidin-1-yl]pyridin-3-yl}-6-[(3-methoxypyrrolidin-1-yl)methyl]furo[3,2-b]pyridine-3-carboxamide;

2-amino-N-{4-[3-amino-5-(trifluoromethyl)piperidin-1-yl]pyridin-3-yl}-6-[(3-ethoxypyrrolidin-1-yl)methyl]furo[3,2-b]pyridine-3-carboxamide;

2-amino-N-{4-[cis-3-amino-5-(trifluoromethyl)piperidin-1-yl]pyridin-3-yl}-6-[(3-ethoxypyrrolidin-1-yl)methyl]furo[3,2-b]pyridine-3-carboxamide;

2-amino-N-{4-[(3S,5R)-3-amino-5-(trifluoromethyl)piperidin-1-yl]pyridin-3-yl}-6-[(3-ethoxypyrrolidin-1-yl)methyl]furo[3,2-b]pyridine-3-carboxamide;

2-amino-N-{4-[3-amino-5-(trifluoromethyl)piperidin-1-yl]pyridin-3-yl}-6-{[(3R)-3-fluoropyrrolidin-1-yl]methyl}furo[3,2-b]pyridine-3-carboxamide;

2-amino-N-{4-[cis-3-amino-5-(trifluoromethyl)piperidin-1-yl]pyridin-3-yl}-6-{[(3R)-3-fluoropyrrolidin-1-yl]methyl}furo[3,2-b]pyridine-3-carboxamide;

2-amino-N-{4-[(3S,5R)-3-amino-5-(trifluoromethyl)piperidin-1-yl]pyridin-3-yl}-6-{[(3R)-3-fluoropyrrolidin-1-yl]methyl}furo[3,2-b]pyridine-3-carboxamide;

2-amino-N-{4-[3-amino-5-(trifluoromethyl)piperidin-1-yl]pyridin-3-yl}-6-{[(3S)-3-fluoropyrrolidin-1-yl]methyl}furo[3,2-b]pyridine-3-carboxamide;

2-amino-N-{4-[cis-3-amino-5-(trifluoromethyl)piperidin-1-yl]pyridin-3-yl}-6-{[(3S)-3-fluoropyrrolidin-1-yl]methyl}furo[3,2-b]pyridine-3-carboxamide;

2-amino-N-{4-[(3S,5R)-3-amino-5-(trifluoromethyl)piperidin-1-yl]pyridin-3-yl}-6-{[(3S)-3-fluoropyrrolidin-1-yl]methyl}furo[3,2-b]pyridine-3-carboxamide;
2-amino-N-{4-[3-amino-5-(trifluoromethyl)piperidin-1-yl]pyridin-3-yl}-6-[(4-methoxypiperidin-1-yl)methyl]furo[3,2-b]pyridine-3-carboxamide;
2-amino-N-{4-[cis-3-amino-5-(trifluoromethyl)piperidin-1-yl]pyridin-3-yl}-6-[(4-methoxypiperidin-1-yl)methyl]furo[3,2-b]pyridine-3-carboxamide;
2-amino-N-{4-[(3S,5R)-3-amino-5-(trifluoromethyl)piperidin-1-yl]pyridin-3-yl}-6-[(4-methoxypiperidin-1-yl)methyl]furo[3,2-b]pyridine-3-carboxamide;
2-amino-N-{4-[3-amino-5-(trifluoromethyl)piperidin-1-yl]pyridin-3-yl}-6-[(4-methylpiperazin-1-yl)methyl]furo[3,2-b]pyridine-3-carboxamide;
2-amino-N-{4-[cis-3-amino-5-(trifluoromethyl)piperidin-1-yl]pyridin-3-yl}-6-[(4-methylpiperazin-1-yl)methyl]furo[3,2-b]pyridine-3-carboxamide;
2-amino-N-{4-[(3S,5R)-3-amino-5-(trifluoromethyl)piperidin-1-yl]pyridin-3-yl}-6-[(4-methylpiperazin-1-yl)methyl]furo[3,2-b]pyridine-3-carboxamide;
2-amino-N-{4-[3-amino-5-(trifluoromethyl)piperidin-1-yl]pyridin-3-yl}-6-(1-methyl-1H-pyrazol-4-yl)furo[3,2-b]pyridine-3-carboxamide;
2-amino-N-{4-[cis-3-amino-5-(trifluoromethyl)piperidin-1-yl]pyridin-3-yl}-6-(1-methyl-1H-pyrazol-4-yl)furo[3,2-b]pyridine-3-carboxamide;
2-amino-N-{4-[(3S,5R)-3-amino-5-(trifluoromethyl)piperidin-1-yl]pyridin-3-yl}-6-(1-methyl-1H-pyrazol-4-yl)furo[3,2-b]pyridine-3-carboxamide;
2-amino-N-{4-[3-amino-5-methylpiperidin-1-yl]pyridin-3-yl}-6-(1-methyl-1H-pyrazol-4-yl)furo[3,2-b]pyridine-3-carboxamide;
2-amino-N-{4-[cis)-3-amino-5-methylpiperidin-1-yl]pyridin-3-yl}-6-(1-methyl-1H-pyrazol-4-yl)furo[3,2-b]pyridine-3-carboxamide;
2-amino-N-{4-[(3S,5R)-3-amino-5-methylpiperidin-1-yl]pyridin-3-yl}-6-(1-methyl-1H-pyrazol-4-yl)furo[3,2-b]pyridine-3-carboxamide;
2-amino-N-{4-[(3S,5R)-3-amino-5-(trifluoromethyl)piperidin-1-yl]pyridin-3-yl}-6-pyrimidin-5-ylfuro[3,2-b]pyridine-3-carboxamide;
2-amino-N-{4-[3-amino-5-(trifluoromethyl)piperidin-1-yl]pyridin-3-yl}-6-pyrimidin-5-ylfuro[3,2-b]pyridine-3-carboxamide;
2-amino-N-{4-[cis-3-amino-5-(trifluoromethyl)piperidin-1-yl]pyridin-3-yl}-6-pyrimidin-5-ylfuro[3,2-b]pyridine-3-carboxamide;
2-amino-N-{4-[3-amino-5-methylpiperidin-1-yl]pyridin-3-yl}-6-pyrimidin-5-ylfuro[3,2-b]pyridine-3-carboxamide;
2-amino-N-{4-[cis-3-amino-5-methylpiperidin-1-yl]pyridin-3-yl}-6-pyrimidin-5-ylfuro[3,2-b]pyridine-3-carboxamide;
2-amino-N-{4-[(3S,5R)-3-amino-5-methylpiperidin-1-yl]pyridin-3-yl}-6-pyrimidin-5-ylfuro[3,2-b]pyridine-3-carboxamide;
2-amino-N-{4-[3-amino-5-(trifluoromethyl)piperidin-1-yl]pyridin-3-yl}-6-cyclopropylfuro[3,2-b]pyridine-3-carboxamide;
2-amino-N-{4-[cis-3-amino-5-(trifluoromethyl)piperidin-1-yl]pyridin-3-yl}-6-cyclopropylfuro[3,2-b]pyridine-3-carboxamide;
2-amino-N-{4-[(3S,5R)-3-amino-5-(trifluoromethyl)piperidin-1-yl]pyridin-3-yl}-6-cyclopropylfuro[3,2-b]pyridine-3-carboxamide;
2-amino-N-{4-[3-amino-5-methylpiperidin-1-yl]pyridin-3-yl}-6-cyclopropylfuro[3,2-b]pyridine-3-carboxamide;
2-amino-N-{4-[cis-3-amino-5-methylpiperidin-1-yl]pyridin-3-yl}-6-cyclopropylfuro[3,2-b]pyridine-3-carboxamide;
2-amino-N-{4-[(3S,5R)-3-amino-5-methylpiperidin-1-yl]pyridin-3-yl}-6-cyclopropylfuro[3,2-b]pyridine-3-carboxamide;
2-amino-N-{4-[3-amino-5-(trifluoromethyl)piperidin-1-yl]pyridin-3-yl}-6-methylfuro[3,2-b]pyridine-3-carboxamide;
2-amino-N-{4-[cis-3-amino-5-(trifluoromethyl)piperidin-1-yl]pyridin-3-yl}-6-methylfuro[3,2-b]pyridine-3-carboxamide;
2-amino-N-{4-[(3S,5R)-3-amino-5-(trifluoromethyl)piperidin-1-yl]pyridin-3-yl}-6-methylfuro[3,2-b]pyridine-3-carboxamide;
2-amino-N-{4-[3-amino-5-methylpiperidin-1-yl]pyridin-3-yl}-6-methylfuro[3,2-b]pyridine-3-carboxamide;
2-amino-N-{4-[cis-3-amino-5-methylpiperidin-1-yl]pyridin-3-yl}-6-methylfuro[3,2-b]pyridine-3-carboxamide;
2-amino-N-{4-[(3S,5R)-3-amino-5-methylpiperidin-1-yl]pyridin-3-yl}-6-methylfuro[3,2-b]pyridine-3-carboxamide;
2-amino-N-{4-[3-amino-5-methylpiperidin-1-yl]pyridin-3-yl}-6-ethylfuro[3,2-b]pyridine-3-carboxamide;
2-amino-N-{4-[cis-3-amino-5-methylpiperidin-1-yl]pyridin-3-yl}-6-ethylfuro[3,2-b]pyridine-3-carboxamide;
2-amino-N-{4-[(3S,5R)-3-amino-5-methylpiperidin-1-yl]pyridin-3-yl}-6-ethylfuro[3,2-b]pyridine-3-carboxamide;
2-amino-N-{4-[3-amino-5-(trifluoromethyl)piperidin-1-yl]pyridin-3-yl}-6-ethylfuro[3,2-b]pyridine-3-carboxamide;
2-amino-N-{4-[cis)-3-amino-5-(trifluoromethyl)piperidin-1-yl]pyridin-3-yl}-6-ethylfuro[3,2-b]pyridine-3-carboxamide;
2-amino-N-{4-[(3S,5R)-3-amino-5-(trifluoromethyl)piperidin-1-yl]pyridin-3-yl}-6-ethylfuro[3,2-b]pyridine-3-carboxamide;
2-amino-N-{4-[3-amino-5-methylpiperidin-1-yl]pyridin-3-yl}-6-(2,6-difluorophenyl)furo[3,2-b]pyridine-3-carboxamide;
2-amino-N-{4-[cis-3-amino-5-methylpiperidin-1-yl]pyridin-3-yl}-6-(2,6-difluorophenyl)furo[3,2-b]pyridine-3-carboxamide;
2-amino-N-{4-[(3S,5R)-3-amino-5-methylpiperidin-1-yl]pyridin-3-yl}-6-(2,6-difluorophenyl)furo[3,2-b]pyridine-3-carboxamide;
2-amino-N-(4-(3-amino-5-methylpiperidin-1-yl)pyridin-3-yl)-6-(difluoromethoxy)furo[3,2-b]pyridine-3-carboxamide;
2-amino-N-(4-(cis-3-amino-5-methylpiperidin-1-yl)pyridin-3-yl)-6-(difluoromethoxy)furo[3,2-b]pyridine-3-carboxamide;
2-amino-N-(4-((3S,5R)-3-amino-5-methylpiperidin-1-yl)pyridin-3-yl)-6-(difluoromethoxy)furo[3,2-b]pyridine-3-carboxamide;
2-amino-N-(4-(3-amino-5-methylpiperidin-1-yl)pyridin-3-yl)-6-isopropoxyfuro[3,2-b]pyridine-3-carboxamide;
2-amino-N-(4-(cis-3-amino-5-methylpiperidin-1-yl)pyridin-3-yl)-6-isopropoxyfuro[3,2-b]pyridine-3-carboxamide;
2-amino-N-(4-((3S,5R)-3-amino-5-methylpiperidin-1-yl)pyridin-3-yl)-6-isopropoxyfuro[3,2-b]pyridine-3-carboxamide;
2-amino-N-(4-(3-amino-5-methylpiperidin-1-yl)pyridin-3-yl)-6-(tetrahydrofuran-3-yl)furo[3,2-b]pyridine-3-carboxamide;

2-amino-N-(4-(cis-3-amino-5-methylpiperidin-1-yl)pyridin-3-yl)-6-(tetrahydrofuran-3-yl)furo[3,2-b]pyridine-3-carboxamide;

2-amino-N-(4-((3S,5R)-3-amino-5-methylpiperidin-1-yl)pyridin-3-yl)-6-(tetrahydrofuran-3-yl)furo[3,2-b]pyridine-3-carboxamide;

2-amino-N-{4-[3-amino-5-(trifluoromethyl)piperidin-1-yl]pyridin-3-yl}-6-(tetrahydrofuran-3-yl)furo[3,2-b]pyridine-3-carboxamide;

2-amino-N-{4-[cis-3-amino-5-(trifluoromethyl)piperidin-1-yl]pyridin-3-yl}-6-(tetrahydrofuran-3-yl)furo[3,2-b]pyridine-3-carboxamide;

2-amino-N-{4-[(3S,5R)-3-amino-5-(trifluoromethyl)piperidin-1-yl]pyridin-3-yl}-6-(tetrahydrofuran-3-yl)furo[3,2-b]pyridine-3-carboxamide;

2-amino-N-{4-[3-amino-4-hydroxy-5-methylpiperidin-1-yl]pyridin-3-yl}-6-cyclobutylfuro[3,2-b]pyridine-3-carboxamide;

2-amino-N-{4-[(3R,4R,5S)-3-amino-4-hydroxy-5-methylpiperidin-1-yl]pyridin-3-yl}-6-cyclobutylfuro[3,2-b]pyridine-3-carboxamide;

2-amino-N-{4-[3-amino-5-cyclopropyl-4-hydroxypiperidin-1-yl]pyridin-3-yl}-6-cyclobutylfuro[3,2-b]pyridine-3-carboxamide;

2-amino-N-{4-[(3R,4R,5S)-3-amino-5-cyclopropyl-4-hydroxypiperidin-1-yl]pyridin-3-yl}-6-cyclobutylfuro[3,2-b]pyridine-3-carboxamide;

2-amino-N-{4-[3-amino-5-(trifluoromethyl)piperidin-1-yl]pyridin-3-yl}-6-{6-[(methylamino)carbonyl]pyridin-3-yl}furo[3,2-b]pyridine-3-carboxamide;

2-amino-N-{4-[cis-3-amino-5-(trifluoromethyl)piperidin-1-yl]pyridin-3-yl}-6-{6-[(methylamino)carbonyl]pyridin-3-yl}furo[3,2-b]pyridine-3-carboxamide;

2-amino-N-{4-[(3S,5R)-3-amino-5-(trifluoromethyl)piperidin-1-yl]pyridin-3-yl}-6-{6-[(methylamino)carbonyl]pyridin-3-yl}furo[3,2-b]pyridine-3-carboxamide;

2-amino-N-(4-(3-amino-5-methylpiperidin-1-yl)pyridin-3-yl)-6-(6-(methylcarbamoyl)pyridin-3-yl)furo[3,2-b]pyridine-3-carboxamide;

2-amino-N-(4-(cis-3-amino-5-methylpiperidin-1-yl)pyridin-3-yl)-6-(6-(methylcarbamoyl)pyridin-3-yl)furo[3,2-b]pyridine-3-carboxamide;

2-amino-N-(4-((3S,5R)-3-amino-5-methylpiperidin-1-yl)pyridin-3-yl)-6-(6-(methylcarbamoyl)pyridin-3-yl)furo[3,2-b]pyridine-3-carboxamide;

2-amino-N-(4-(3-amino-5-cyclopropyl-4-hydroxypiperidin-1-yl)pyridin-3-yl)-6-cyclopropylfuro[3,2-b]pyridine-3-carboxamide;

2-amino-N-(4-((3R,4R,5S)-3-amino-5-cyclopropyl-4-hydroxypiperidin-1-yl)pyridin-3-yl)-6-cyclopropylfuro[3,2-b]pyridine-3-carboxamide;

2-amino-N-(4-(3-amino-5-cyclopropyl-4-hydroxypiperidin-1-yl)pyridin-3-yl)-6-(trifluoromethyl)furo[3,2-b]pyridine-3-carboxamide;

2-amino-N-(4-((3R,4R,5S)-3-amino-5-cyclopropyl-4-hydroxypiperidin-1-yl)pyridin-3-yl)-6-(trifluoromethyl)furo[3,2-b]pyridine-3-carboxamide;

2-amino-N-{4-[3-amino-5-methylcyclohexyl]pyridin-3-yl}-6-isopropylfuro[3,2-b]pyridine-3-carboxamide;

2-amino-N-{4-[(1R,3S,5S)-3-amino-5-methylcyclohexyl]pyridin-3-yl}-6-isopropylfuro[3,2-b]pyridine-3-carboxamide;

2-amino-N-{4-[3-amino-5-(trifluoromethyl)piperidin-1-yl]pyridin-3-yl}-6-(3-methoxypropyl)furo[3,2-b]pyridine-3-carboxamide;

2-amino-N-{4-[cis-3-amino-5-(trifluoromethyl)piperidin-1-yl]pyridin-3-yl}-6-(3-methoxypropyl)furo[3,2-b]pyridine-3-carboxamide;

2-amino-N-{4-[(3S,5R)-3-amino-5-(trifluoromethyl)piperidin-1-yl]pyridin-3-yl}-6-(3-methoxypropyl)furo[3,2-b]pyridine-3-carboxamide;

2-amino-N-{4-[3-amino-5-(trifluoromethyl)piperidin-1-yl]pyridin-3-yl}-6-(3-morpholin-4-ylpropyl)furo[3,2-b]pyridine-3-carboxamide;

2-amino-N-{4-[cis-3-amino-5-(trifluoromethyl)piperidin-1-yl]pyridin-3-yl}-6-(3-morpholin-4-ylpropyl)furo[3,2-b]pyridine-3-carboxamide;

2-amino-N-{4-[(3S,5R)-3-amino-5-(trifluoromethyl)piperidin-1-yl]pyridin-3-yl}-6-(3-morpholin-4-ylpropyl)furo[3,2-b]pyridine-3-carboxamide;

2-amino-N-{4-[3-amino-5-methylcyclohexyl]pyridin-3-yl}-6-cyclopropylfuro[3,2-b]pyridine-3-carboxamide;

2-amino-N-{4-[(1R,3S,5S)-3-amino-5-methylcyclohexyl]pyridin-3-yl}-6-cyclopropylfuro[3,2-b]pyridine-3-carboxamide;

2-amino-N-{4-[(1S,3R,5R)-3-amino-5-methylcyclohexyl]pyridin-3-yl}-6-cyclopropylfuro[3,2-b]pyridine-3-carboxamide;

2-amino-N-{4-[3-amino-5-methylpiperidin-1-yl]pyridin-3-yl}-6-(3-methoxypropyl)furo[3,2-b]pyridine-3-carboxamide;

2-amino-N-{4-[cis-3-amino-5-methylpiperidin-1-yl]pyridin-3-yl}-6-(3-methoxypropyl)furo[3,2-b]pyridine-3-carboxamide;

2-amino-N-{4-[(3S,5R)-3-amino-5-methylpiperidin-1-yl]pyridin-3-yl}-6-(3-methoxypropyl)furo[3,2-b]pyridine-3-carboxamide;

2-amino-N-{4-[3-amino-5-(trifluoromethyl)piperidin-1-yl]pyridin-3-yl}-6-[3-(dimethylamino)propyl]furo[3,2-b]pyridine-3-carboxamide;

2-amino-N-{4-[cis-3-amino-5-(trifluoromethyl)piperidin-1-yl]pyridin-3-yl}-6-[3-(dimethylamino)propyl]furo[3,2-b]pyridine-3-carboxamide;

2-amino-N-{4-[(3S,5R)-3-amino-5-(trifluoromethyl)piperidin-1-yl]pyridin-3-yl}-6-[3-(dimethylamino)propyl]furo[3,2-b]pyridine-3-carboxamide;

2-amino-N-{4-[3-amino-5-(trifluoromethyl)cyclohexyl]pyridin-3-yl}furo[3,2-b]pyridine-3-carboxamide;

2-amino-N-{4-[(1R,3R,5S)-3-amino-5-(trifluoromethyl)cyclohexyl]pyridin-3-yl}furo[3,2-b]pyridine-3-carboxamide;

2-amino-N-{4-[3-amino-4-hydroxy-5-methylpiperidin-1-yl]pyridin-3-yl}-6-(3-fluoropropyl)furo[3,2-b]pyridine-3-carboxamide;

2-amino-N-{4-[cis-3-amino-4-hydroxy-5-methylpiperidin-1-yl]pyridin-3-yl}-6-(3-fluoropropyl)furo[3,2-b]pyridine-3-carboxamide;

2-amino-N-{4-[(3R,5S)-3-amino-4-hydroxy-5-methylpiperidin-1-yl]pyridin-3-yl}-6-(3-fluoropropyl)furo[3,2-b]pyridine-3-carboxamide;

2-amino-N-{4-[3-amino-5-(trifluoromethyl)piperidin-1-yl]pyridin-3-yl}-6-{2-[3-fluoropyrrolidin-1-yl]ethyl}furo[3,2-b]pyridine-3-carboxamide;

2-amino-N-{4-[cis-3-amino-5-(trifluoromethyl)piperidin-1-yl]pyridin-3-yl}-6-{2-[3-fluoropyrrolidin-1-yl]ethyl}furo[3,2-b]pyridine-3-carboxamide;

2-amino-N-{4-[(3S,5R)-3-amino-5-(trifluoromethyl)piperidin-1-yl]pyridin-3-yl}-6-{2-[(3R)-3-fluoropyrrolidin-1-yl]ethyl}furo[3,2-b]pyridine-3-carboxamide;

2-amino-N-(4-(3-amino-4-hydroxy-5-methylpiperidin-1-yl)pyridin-3-yl)-6-isopropylthieno[3,2-b]pyridine-3-carboxamide;

2-amino-N-(4-((3R,4R,5S)-3-amino-4-hydroxy-5-methylpiperidin-1-yl)pyridin-3-yl)-6-isopropylthieno[3,2-b]pyridine-3-carboxamide;
2-amino-N-(4-(3-amino-4-hydroxy-5-methylpiperidin-1-yl)pyridin-3-yl)-6-propylthieno[3,2-b]pyridine-3-carboxamide;
2-amino-N-(4-((3R,4R,5S)-3-amino-4-hydroxy-5-methylpiperidin-1-yl)pyridin-3-yl)-6-propylthieno[3,2-b]pyridine-3-carboxamide;
6-(acetylamino)-2-amino-N-{4-[3-amino-4-hydroxy-5-methylpiperidin-1-yl]pyridin-3-yl}thieno[3,2-b]pyridine-3-carboxamide;
6-(acetylamino)-2-amino-N-{4-[(3R,4R,5S)-3-amino-4-hydroxy-5-methylpiperidin-1-yl]pyridin-3-yl}thieno[3,2-b]pyridine-3-carboxamide;
2-amino-N-(4-(3-amino-4-hydroxy-5-methylpiperidin-1-yl)pyridin-3-yl)-6-(cyclopropanecarboxamido)thieno[3,2-b]pyridine-3-carboxamide;
2-amino-N-(4-((3R,4R,5S)-3-amino-4-hydroxy-5-methylpiperidin-1-yl)pyridin-3-yl)-6-(cyclopropanecarboxamido)thieno[3,2-b]pyridine-3-carboxamide;
2-amino-N-(4-(3-amino-4-hydroxy-5-methylpiperidin-1-yl)pyridin-3-yl)-6-isobutyramidothieno[3,2-b]pyridine-3-carboxamide;
2-amino-N-(4-((3R,4R,5S)-3-amino-4-hydroxy-5-methylpiperidin-1-yl)pyridin-3-yl)-6-isobutyramidothieno[3,2-b]pyridine-3-carboxamide;
2-amino-N-(4-(3-amino-5-(trifluoromethyl)piperidin-1-yl)pyridin-3-yl)-6-morpholinothieno[3,2-b]pyridine-3-carboxamide;
2-amino-N-(4-(cis-3-amino-5-(trifluoromethyl)piperidin-1-yl)pyridin-3-yl)-6-morpholinothieno[3,2-b]pyridine-3-carboxamide; and
2-amino-N-(4-((3S,5R)-3-amino-5-(trifluoromethyl)piperidin-1-yl)pyridin-3-yl)-6-morpholinothieno[3,2-b]pyridine-3-carboxamide.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated that features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups are described. It is specifically intended that each linking substituent include both the forward and backward forms of the linking substituent. For example, —NR(CR'R")$_n$— includes both —NR(CR'R")$_n$— and +(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. The term "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chain or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_n$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The terms "halo" or "halogen", used alone or in combination with other terms, refers to fluoro, chloro, bromo and iodo.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "amino" refers to a group of formula —$NH_2$.

The term "carbamyl" refers to a group of formula C(=O)$NH_2$.

The term "carbonyl", employed alone or in combination with other terms, refers to a —C(=O)— group, which also may be written as C(O).

The term "carbonyl", employed alone or in combination with other terms, refers to a —C(=O)— group.

The term "carboxy" refers to a group of formula —C(=O)OH.

The term "oxo" refers to oxygen as a divalent substituent, forming a carbonyl group, or attached to a heteroatom forming a sulfoxide or sulfone group, or an N-oxide group.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, indenyl and the like. In some embodiments, aryl groups have from 6 to 10 carbon atoms. In some embodiments, the aryl group is phenyl.

The term "heteroaryl" or "heteroaromatic", employed alone or in combination with other terms, refers to a monocyclic or polycyclic aromatic heterocycle having at least one heteroatom ring member selected from sulfur, oxygen and nitrogen. In some embodiments, the heteroaryl is 5- to 10-membered $C_{1-9}$ heteroaryl, which is monocyclic or bicyclic and which has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1, 2, 3, or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, imidazo[1,2-b]pyridazine, purine, furopyridine (e.g., furo[3,2-b]pyridine), thienopyridine (e.g. thieno[3,2-b]pyridine) or the like.

A five-membered heteroaryl ring is a heteroaryl group having five ring atoms wherein one or more (e.g., 1, 2, 3 or 4) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "cycloalkyl", employed alone or in combination with other terms, refers to a non-aromatic, saturated, monocyclic, bicyclic or polycyclic hydrocarbon ring system, including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cyclopentenyl, cyclohexenyl, cyclohexadienyl, norbornyl, norpinyl, bicyclo[2.1.1]hexanyl, bicyclo[1.1.1]pentanyl and the like. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like, for example indanyl or tetrahydronaphthyl. A cycloalkyl group containing a fused aromatic ring can be attached through any ring-forming atom including a ring-forming atom of the fused aromatic ring.

The term "heterocycloalkyl", employed alone or in combination with other terms, refers to non-aromatic ring or ring system, which may optionally contain one or more alkenylene groups as part of the ring structure, which has at least one heteroatom ring member independently selected from nitrogen, sulfur oxygen and phosphorus, and which has 4-10 ring members, 4-7 ring members or 4-6 ring members. Included in heterocycloalkyl are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Examples of heterocycloalkyl groups include azetidine, pyrrolidine, piperidine, piperazine, morpholine, thiomorpholine, pyran, azepane, tetrahydropyran, tetrahydrofuran, dihydropyran, dihydrofuran and the like. Ring-forming carbon atoms and heteroatoms of a heterocycloalkyl group can be optionally substituted by oxo or sulfido (e.g., C(=O), S(=O), C(S) or S(=O)$_2$, etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 1,2,3,4-tetrahydroquinoline, dihydrobenzofuran, azetidine, azepane, diazepan (e.g., 1,4-diazepan), pyrrolidine, piperidine, piperazine, morpholine, thiomorpholine, pyran, tetrahydrofuran and di- and tetra-hydropyran.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone enol pairs, amide-imidic acid pairs, lactam lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers and isotopes of the structures depicted.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

The following abbreviations may be used herein: AcOH (acetic acid); Ac$_2$O (acetic anhydride); Al$_2$O$_3$ (aluminium oxide); aq. (aqueous); atm. (atmosphere(s)); Boc (t-butoxycarbonyl); Boc$_2$O (di-tert-butyldicarbonate); BOP ((benzotriazol-1-yloxy)tris(dimethylamino)phosphonium hexafluorophosphate); br (broad); c-Pr (cyclopropyl); Cbz (carboxybenzyl); calc. (calculated); CeCl$_3$.7H$_2$O (cerium (III) chloride heptahydrate); Cs$_2$CO$_3$ (cesium carbonate); CuI (copper (I) iodide); d (doublet); dd (doublet of doublets); DCM (dichloromethane); DIPEA (N,N-diisopropylethylamine); DMAP (4-dimethylaminopyridine); DMF (N,N-dimethylformamide); DMSO (dimethylsulfoxide); Et (ethyl); EtOAc (ethyl acetate); EtOH (ethanol); Fmoc (9-fluorenylmethylmethoxycarbonyl); g (gram(s)); h (hour(s)); H$_2$ (hydrogen gas); H$_2$O$_2$ (hydrogen peroxide); HATU (N,N,N',N'-tetramethyl-O-(7-azabenzotriazol-1-yl) uronium hexafluorophosphate); HBr (hydrogen bromide); HCl (hydrochloric acid or hydrogen chloride); HPLC (high performance liquid chromatography); Hz (hertz); i-Pr (isopropyl); i-PrOH (isopropyl alcohol); J (coupling constant); KOAc (potassium acetate); K$_3$PO$_4$ (potassium phosphate); K$_3$PO$_4$.H$_2$O (tripotassium phosphate hydrate); LCMS (liquid chromatography-mass spectrometry); LiAlH$_4$ (lithium tetrahydroaluminate); LiBH$_4$ (lithium tetrahydroborate); LiOH (lithium hydroxide); LiOH.H$_2$O (lithium hydroxide monohydrate); m (multiplet); M (molar); mCPBA (m-chloroperbenzoic acid); Me (methyl); MeCN (acetonitrile); MeOH (methanol); MgSO$_4$ (magnesium sulfate); MS (mass spectrometry); mg (milligram(s)); min. (minutes(s)); mL (milliliter(s)); mmol (millimole(s)); N (normal); N$_2$ (nitrogen gas); NaHCO$_3$ (sodium bicarbonate); NaIO$_4$ (sodium metaperiodate); NaN$_3$ (sodium azide); NaOH (sodium hydroxide); Na$_2$SO$_4$ (sodium sulfate); n-Bu (n-butyl); n-BuLi (n-butyllithium); NH$_4$Cl (ammonium chloride); NH$_4$OH (ammonium hydroxide); nM (nanomolar); NMR (nuclear magnetic resonance spectroscopy); Pd (palladium); Pd(dppf)Cl$_2$ ([1,1'-bis(diphenylphosphino)ferrocene]palladium(II) dichloride); Pd(OAc)$_2$ (palladium acetate); Pd(tBu$_3$P)$_2$ (bis(tri-tert-butylphosphine)palladium); pM (picomolar); Pd(PPh$_3$)$_4$ (tetrakis(triphenylphosphine)palladium(0)); PPh$_3$ (triphenylphosphine); psi (pounds per square inch); PTFE (polytetrafluoroethylene); RP-HPLC (reverse phase high performance liquid chromatography); s (singlet); t (triplet or tertiary); tert (tertiary); tt (triplet of triplets); TBAF (tetra-n-butylammoniumfluoride); t-Bu (tert-butyl); TEA (triethylamine); TFA (trifluoroacetic acid); THF (tetrahydrofuran); μg (microgram(s)); μL (microliter(s)); μm (micromolar); wt % (weight percent).

II. Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, Protecting Group Chemistry, (Oxford University Press, 2000); Smith et al., *March's Advanced Organic Chemistry: Reactions, Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) can be prepared, e.g., using a process as illustrated in Scheme 1. In the process depicted in Scheme 1, a suitable aromatic amine of formula 1-1 is reacted with an acid of formula 1-2 under conditions suitable for forming an amide bond to provide the compound of Formula (I). Suitable combinations for forming the amide bond include, e.g., the methods used to form amide bonds in peptides as described, e.g., in Jones, *Amino Acid and Peptide Synthesis*, 2$^{nd}$ Ed., Oxford University Press, 2002; and Jones, *The Chemical Synthesis of Peptides (International Series of Monographs on Chemistry)* (Oxford University Press, 1994). An example of a suitable coupling agent is HATU/DIPEA.

hydrogen peroxide or peroxycarboxylic acids such as mCPBA. The N-oxide can then be converted to the 2-cyano-substituted compound 2-3, e.g., via treatment with trimethylsilyl cyanide. Reaction of the cyanide 2-3 with a suitable substituted carboxylic acid derivative (wherein X is O or S and R is a suitable carboxylic acid protecting group such as a $C_{1-6}$ alkyl group) then results in the formation of a fused furan or thiophane ring in the compound 2-5. Completion of the synthesis then requires conversion of the carboxylic acid and amino groups of the compound 2-5 to the required functional groups of the compound of formula 1-2. In Scheme 2, the amino group of compound 2-5 is converted to a bromo group in compound 2-6 via diazotization of compound 2-5 and reaction of an intermediate diazo compound with copper (I) bromide. The protected carboxyl group of compound 2-6 is converted to a protected amino group (wherein OCOR' is a suitable carbamate protecting group wherein R' is, e.g., a $C_{1-6}$ alkyl group such as tert-butyl) in compound 2-7 via a Curtius rearrangement. The conversion of compound 2-6 can be carried out, e.g., by deprotection of the $CO_2R$ group (e.g., via hydrolysis using a base such as lithium hydroxide or potassium carbonate) followed by reaction of the resulting carboxylic acid with diphenylphosphonic azide in the presence of a suitable alcohol (e.g., tert-butanol). Finally, the carboxylic acid group of compound 2-8 can be introduced by bromine-lithium exchange (using a suitable organolithium reagent such as n-BuLi) followed by reaction of the resulting lithium compound with carbon dioxide, or via reaction with carbon monoxide in an organometallically-catalyzed carbonylation reaction (e.g., reaction with CO/MeOH in the presence of a suitable catalyst such as [1,1'-bis(diphenylphosphino)ferrocene]dichloropalladium(II), complex with dichloromethane (followed by hydrolysis of the resulting ester). Compound 2-8 corresponds to the compound of formula 1-2 wherein $R^2$ is a protected amino group. The amino group of compound 2-8 can be converted to alternative $R^2$ groups via suitable functional group interconversion reactions of the amino group (e.g., via diazotization-reduction or diazotization-halogenation).

Scheme 1

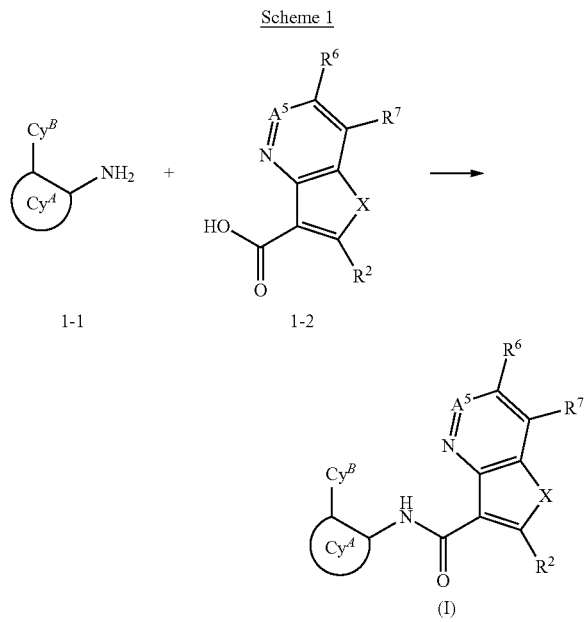

Compounds of formula 1-2 (or synthetic equivalents thereof) may be prepared, e.g., as shown in Scheme 2. In Scheme 2, a suitably substituted compound of formula 2-1 having a leaving group (e.g. chloro) at the 3-position adjacent to the $R^7$ group is oxidized to an N-oxide 2-2. Suitable oxidizing agents include, e.g., peroxy compounds such as Scheme 2

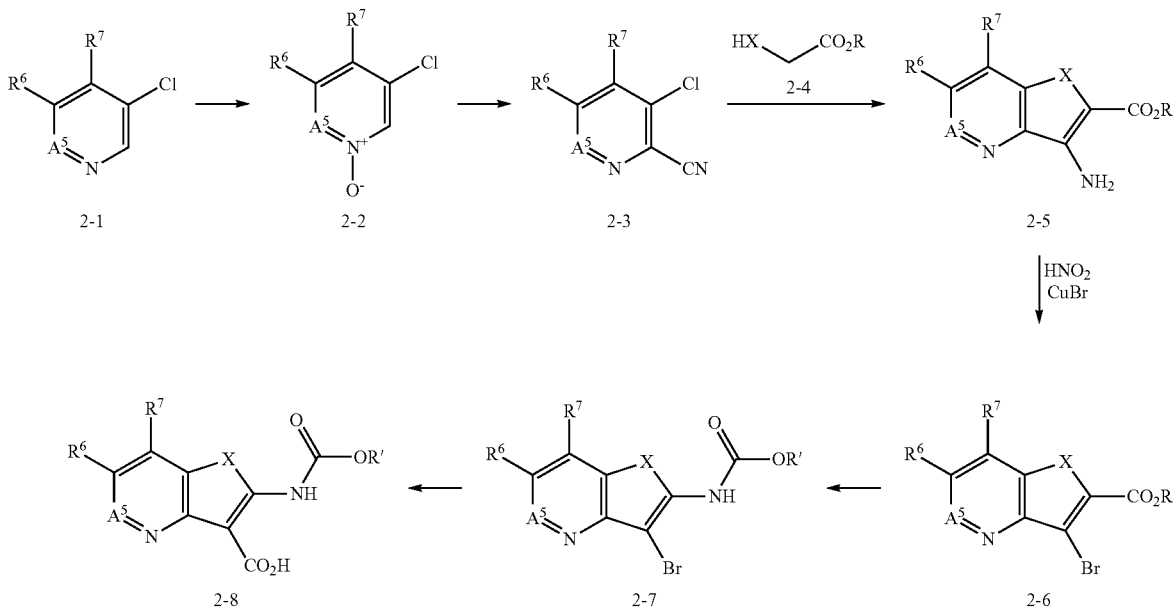

Compounds of formula 1-2 (or synthetic equivalents thereof) wherein X is O may be prepared, e.g., as shown in Scheme 3. In Scheme 3, a suitably substituted compound of formula 3-1 having hydroxy at the 3-position adjacent to the $R^7$ group is oxidized to an N-oxide 3-2. Suitable oxidizing agents include, e.g., peroxy compounds such as hydrogen peroxide or peroxycarboxylic acids such as mCPBA. The N-oxide can then be converted to the substituted compound 3-3, e.g., via treatment with acetic anhydride followed by a suitable cyanoacetate compound, e.g., an alkyl cyanoacetate such as ethyl cyanoacetate (R=$C_{1-6}$ alkyl, e.g., ethyl). Ring closure to form the fused furan ring of compound 3-4 can then be carried out under suitable conditions such as the use of an acid catalyst such as concentrated sulfuric acid. Compound 3-4 corresponds to the compound of formula 1-2 wherein X is O, $R^2$ is a protected amino group. The amino group of compound 3-4 can be converted to alternative $R^2$ groups via suitable functional group interconversion reactions of the amino group (e.g., via diazotization-reduction or diazotization-halogenation).

Compounds of formula 1-2 (or synthetic equivalents thereof) wherein X is S may be prepared, e.g., as shown in Scheme 4. The intermolecular cyclization of substituted 2-cyanopyridine (4-1) (wherein Hal is a halogen), e.g., with methylthioglycolate in the presence of potassium carbonate in acetonitrile can be used to prepare a substituted 7-amino-6-methoxycarbonylthienopyridine (4-2), which can be treated, e.g., with copper(I) bromide and sodium nitrite in 48% HBr aqueous solution to generate substituted 7-bromo-6-methoxycarbonylthienopyridine (4-3). Hydrolysis of 4-3, e.g., with lithium hydroxide followed by Curtius rearrangement can be employed to provide 7-bromo-6-tert-butoxycarbonylaminothienopyridine (4-5), which can be converted to the substituted thienopyridinyl carboxylic acid (4-7), e.g., by treatment of 4-5 with n-BuLi followed up with the treatment of $CO_2$, or by carboxylation of 4-5 with monocarboxide in the presence of palladium catalyst in methanol followed by hydrolysis with lithium hydroxide.

Scheme 3

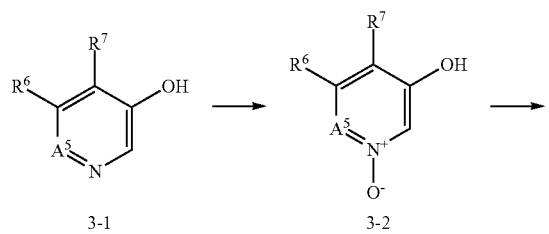

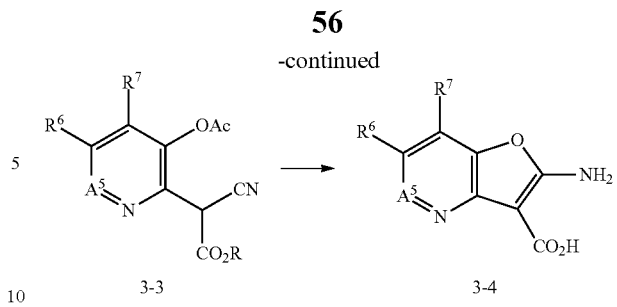

Scheme 4

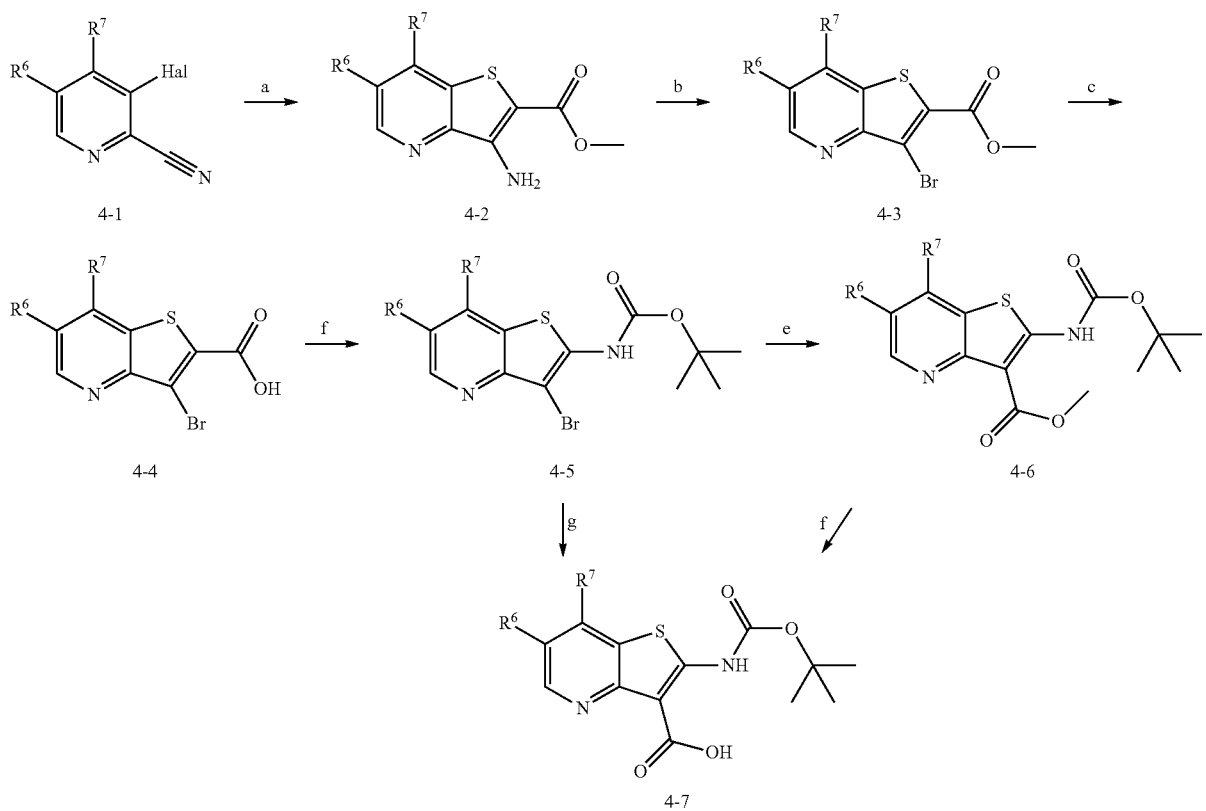

Reagents: a: methylthioglycolate, $K_2CO_3$, MeCN; b: CuBr, $NaNO_2$, HBr, $H_2O$; c: LiOH, $H_2O$, THF, MeOH; d: DPPA, DIEA, t-BuOH; e: $(DPPF)_2PdCl_2$, CO, MeOH, TEA; f: LiOH, $H_2O$, THF, MeOH; g: n-BuLi, dry ice.

Compounds of formula 1-2 (or synthetic equivalents thereof) wherein X is O may be prepared, e.g., as shown in Scheme 5. Substituted 3-hydroxypyridine (5-1) was treated with mCPBA in DCM to generated substituted 3-hydroxypyridine N-oxide (5-2), which was dissolved in acetic anhydride followed by treatment with ethyl cyanoacetate and concentrated sulfuric acid sequentially to produce substituted 6-amino-7-ethoxycarbonyl-furopyridine (5-4) smoothly. The amino group on 5-4 was easily protected by Boc protection group to give the compound (5-5), which was hydrolyzed by treatment with lithium hydroxide to afford substituted furopyridinyl carboxylic acid (5-6) in good yield.

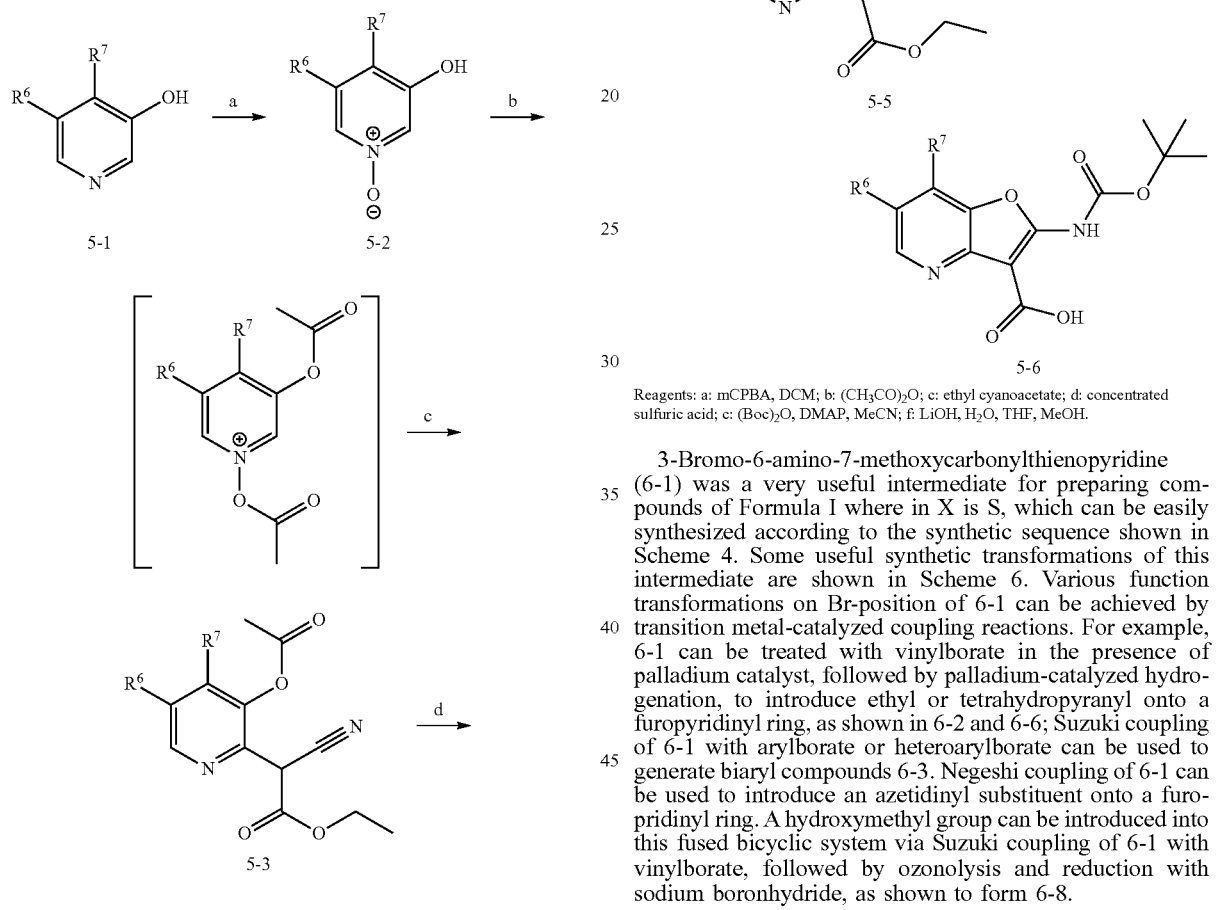

Reagents: a: mCPBA, DCM; b: (CH$_3$CO)$_2$O; c: ethyl cyanoacetate; d: concentrated sulfuric acid; e: (Boc)$_2$O, DMAP, MeCN; f: LiOH, H$_2$O, THF, MeOH.

3-Bromo-6-amino-7-methoxycarbonylthienopyridine (6-1) was a very useful intermediate for preparing compounds of Formula I where in X is S, which can be easily synthesized according to the synthetic sequence shown in Scheme 4. Some useful synthetic transformations of this intermediate are shown in Scheme 6. Various function transformations on Br-position of 6-1 can be achieved by transition metal-catalyzed coupling reactions. For example, 6-1 can be treated with vinylborate in the presence of palladium catalyst, followed by palladium-catalyzed hydrogenation, to introduce ethyl or tetrahydropyranyl onto a furopyridinyl ring, as shown in 6-2 and 6-6; Suzuki coupling of 6-1 with arylborate or heteroarylborate can be used to generate biaryl compounds 6-3. Negeshi coupling of 6-1 can be used to introduce an azetidinyl substituent onto a furopridinyl ring. A hydroxymethyl group can be introduced into this fused bicyclic system via Suzuki coupling of 6-1 with vinylborate, followed by ozonolysis and reduction with sodium boronhydride, as shown to form 6-8.

Scheme 6

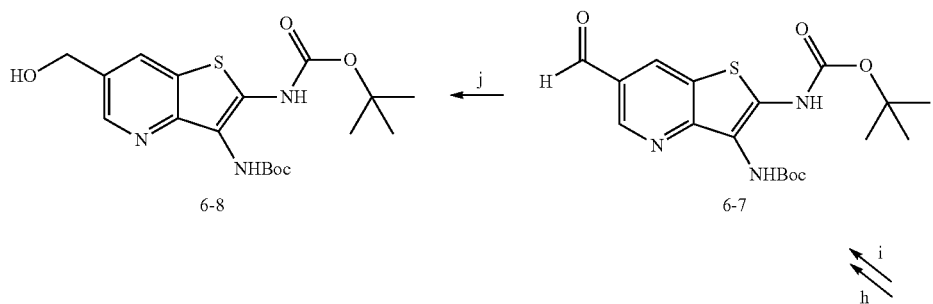

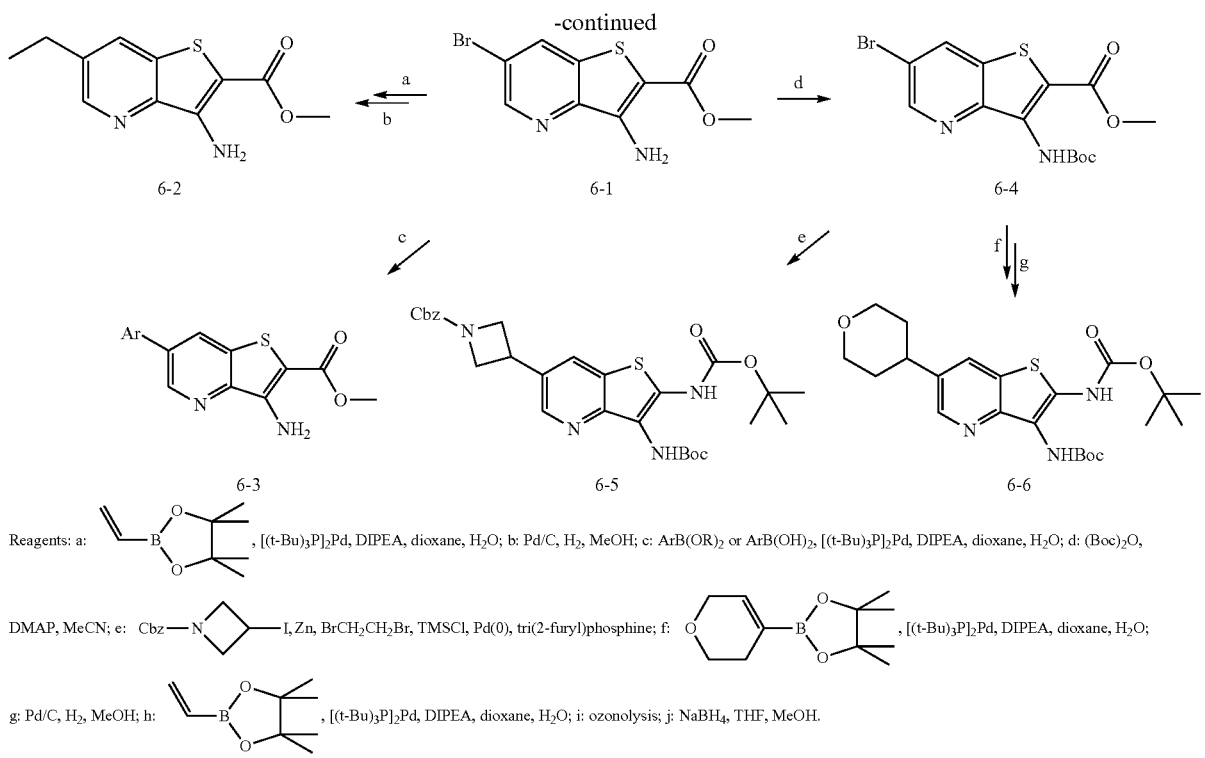

Compounds of formula 1-1 can be prepared, e.g., as shown in Scheme 7. Coupling of a compound of formula 7-1, wherein L is a suitable leaving group, with an appropriate group $Cy^B$ can be achieved with methods known to one skilled in the art, such as direct coupling or Buchwald-Hartwig coupling when $Cy^B$ is attached to $Cy^A$ through nitrogen; or Suzuki coupling when $Cy^B$ is attached to $Cy^A$ through carbon.

Scheme 7

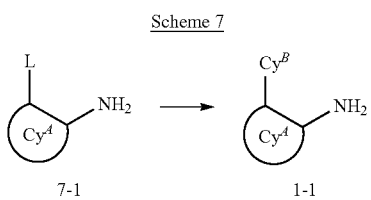

For the synthesis of particular compounds, the general schemes described above can be modified. For example, the products or intermediates can be modified to introduce particular functional groups. Alternatively, the substituents can be modified at any step of the overall synthesis by methods know to one skilled in the art, e.g., as described by Larock, *Comprehensive Organic Transformations: A Guide to Functional Group Preparations* (Wiley, 1999); and Katritzky et al. (Ed.), *Comprehensive Organic Functional Group Transformations* (Pergamon Press 1996).

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (*Journal of Heterocyclic Chemistry*, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

III. Uses of the Compounds

Compounds of the invention can inhibit the activity of one or more members of the Pim kinase family and, thus, are useful in treating diseases and disorders associated with activity of Pim kinases. For the uses described herein, any of the compounds of the invention, including any of the embodiments thereof, may be used.

The compounds of the invention can inhibit one or more of Pim1, Pim2 and Pim3. In some embodiments the compounds are selective for one Pim kinase over another. "Selective" means that the compound binds to or inhibits a Pim kinase with greater affinity or potency, respectively, compared to a reference enzyme, such as another Pim kinase. For example, the compounds can be selective for Pim1 over Pim2 and Pim3, selective for Pim2 over Pim1 and Pim3, or selective for Pim3 over Pim1 and Pim2. In some embodiments, the compounds inhibit all of the Pim family members (e.g., Pim1, Pim2 and Pim3). In some embodiments, the compounds can be selective for Pim over other kinases such as receptor and non-receptor Ser/Thr kinases such as Akt1, Akt2, Akt3, TGF-βR, PKA, PKG, PKC, CaM-kinase, phosphorylase kinase, MEKK, ERK, MAPK and mTOR; receptor Tyr kinases such as EGFR, HER2, HER3, HER4, INS-R, IGF-1R, IR-R, PDGFαR, PDGFl3R, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2; and non-receptor Tyr kinases such as Src, Fyn, Lck, Fgr, Btk, Fak, SYK, FRK, JAK or ABL. In general, selectivity can be at least about 5-fold, at least about 10-fold, at least about 20-fold, at least about 50-fold, at least about 100-fold, at least about 200-fold, at least about 500-fold or at least about 1000-fold. The method of inhibiting a Pim1, Pim2 or Pim3 kinase includes contacting the appropriate enzyme with the compound of Formula (I), or any of the embodiments thereof, or a pharmaceutically acceptable salt thereof.

Thus, the present disclosure provides methods of treating a Pim kinase-associated disease or disorder in an individual (e.g., patient) by administering to the individual in need of such treatment a therapeutically effective amount or dose of a compound of Formula (I), or any of the embodiments thereof, or a pharmaceutical composition thereof. The present disclosure also provides a compound of Formula (I), or any of the embodiments thereof, or a pharmaceutical composition thereof, for use in treating a Pim kinase-associated disease or disorder. Also provided is the use of a compound of Formula (I), or any of the embodiments thereof, or a pharmaceutical composition thereof, in the manufacture of a medicament for treating a Pim kinase-associated disease or disorder.

A Pim kinase-associated disease can include any disease, disorder or condition that is directly or indirectly linked to expression or activity of the Pim kinase, including overexpression and/or abnormal activity levels. Abnormal activity levels can be determined by comparing activity level in normal, healthy tissue or cells with activity level in diseased cells. A Pim kinase-associated disease can also include any disease, disorder or condition that can be prevented, ameliorated, inhibited or cured by modulating Pim kinase activity. In some embodiments, the disease is characterized by the abnormal activity or expression (e.g., overexpression) of one or more Pim1, Pim2 and Pim3. In some embodiments, the disease is characterized by mutant Pim1, Pim2 or Pim3. A Pim kinase associated disease can also refer to any disease, disorder or condition wherein modulating the expression or activity of one or more Pim kinases is beneficial.

Pim kinase associated diseases that can be treated using the compounds of the invention include cancer, including, in particular, cancers in which Pim kinases are upregulated or an oncogene, e.g., Myc or BCL2, is activated. Pim kinase associated diseases include solid tumors, e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head or neck, thyroid cancer, glioblastoma, sarcoma, bladder cancer, etc. Pim kinase associated diseases also include hematological cancers, e.g., lymphoma, leukemia such as acute lymphoblastic leukemia (ALL), acute myelogenous leukemia (AML), chronic lymphocytic leukemia (CLL), chronic myelogenous leukemia (CML), diffuse large B-cell lymphoma (DLBCL), mantle cell lymphoma, non-Hodgkin lymphoma (including relapsed non-Hodgkin lymphoma, refractory non-Hodgkin lymphoma and recurrent follicular non-Hodgkin lymphoma), Hodgkin lymphoma and multiple myeloma.

Pim kinase associated diseases that can be treated using the compounds of the invention also include myeloproliferative disorders such as polycythemia vera (PV), essential thrombocythemia (ET), chronic myelogenous leukemia (CML) and the like. The myeloproliferative disorder can be myelofibrosis such as primary myelofibrosis (PMF), myelofibrosis with myeloid metaplasia (MMM), post-polycythemia vera/essential thrombocythemia myelo fibrosis (Post-PV/ET MF), post-essential thrombocythemia myelofibrosis (Post-ET MF) or post-polycythemia vera myelofibrosis (Post-PV MF).

Pim kinase-associated diseases that can be treated with compounds according to the invention also include immune disorders such as autoimmune diseases. The immune disorders include multiple sclerosis, rheumatoid arthritis, allergy, food allergy, asthma, lupus, inflammatory bowel disease and ulcerative colitis.

Pim kinase-associated diseases that can be treated with compounds according to the invention also include atherosclerosis.

The compounds of the invention can also be used to inhibit disease processes in which Pim-kinases are involved, including angiogenesis and tumor metastasis.

Due to the fact that Pim kinases are regulated by the JAK/STAT pathway, the compounds of the invention are useful to treat diseases in which modulating JAK/STAT signaling is beneficial. Thus, other diseases that can be treated using the compounds of the invention include Crohn's disease, irritable bowel syndrome, pancreatitis, diverticulosis, Grave's disease, juvenile rheumatoid arthritis, osteoarthritis, psoriatic arthritis, ankylosing spondylitis, myasthenia gravis, vasculitis, autoimmune thyroiditis, dermatitis, psoriasis, scleroderma, systemic sclerosis, vitiligo, graft versus host disease, Sjogren's syndrome, glomerulonephritis and diabetes mellitus (type I).

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

The term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different kinase inhibitors, exhibiting different preferences in the kinases which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

Accordingly, the Pim inhibitors of the present invention can be used in combination with one or more other kinase inhibitors for the treatment of diseases, such as cancer, that are impacted by multiple signaling pathways. For example, the compounds of the invention can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the Pim inhibitors of the invention can be combined with inhibitors of kinases associated with the PIK3/Akt/mTOR signaling pathway, such as PI3K, Akt (including Akt1, Akt2 and Akt3) and mTOR kinases.

The Pim inhibitors of the present invention can further be used in combination with other methods of treating cancers, for example by chemotherapy, irradiation or surgery. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, do farabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

The Pim inhibitors of the present invention can further be used in combination with one or more anti-inflammatory agents, steroids, immunosuppressants or therapeutic antibodies.

When more than one pharmaceutical agent is administered to a patient, they can be administered simultaneously, sequentially, or in combination (e.g., for more than two agents).

IV. Formulation, Dosage Forms and Administration

When employed as pharmaceuticals, the compounds of the invention can be administered in the form of pharmaceutical compositions. Thus the present disclosure provides a composition comprising a compound Formula (I), or a pharmaceutically acceptable salt thereof, or any of the embodiments thereof, and at least one pharmaceutically acceptable carrier. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

V. Labeled Compounds and Assay Methods

The compounds of the invention can further be useful in investigations of biological processes, including kinase signaling, in normal and abnormal tissues. Thus, another aspect of the present invention relates to labeled compounds of the invention (radio-labeled, fluorescent-labeled, etc.) that would be useful not only in imaging techniques but also in assays, both in vitro and in vivo, for localizing and quantitating Pim kinases in tissue samples, including human, and for identifying Pim kinase ligands by inhibition binding of a labeled compound. Accordingly, the present invention includes Pim kinase assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro Pim kinase labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is to be understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$. In some embodiments, the compound incorporates 1, 2 or 3 deuterium atoms. Synthetic methods for incorporating radio-isotopes into organic compounds are known in the art.

Specifically, a labeled compound of the invention can be used in a screening assay to identify and/or evaluate compounds. For example, a newly synthesized or identified compound (i.e., test compound) which is labeled can be evaluated for its ability to bind a Pim-kinase by monitoring its concentration variation when contacting with the Pim kinase, through tracking of the labeling. For example, a test compound (labeled) can be evaluated for its ability to reduce binding of another compound which is known to bind to a Pim kinase (i.e., standard compound). Accordingly, the ability of a test compound to compete with the standard compound for binding to the Pim kinase directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

VI. Kits

The present disclosure also includes pharmaceutical kits useful, e.g., in the treatment or prevention of Pim kinase-associated diseases or disorders, such as cancer, which include one or more containers containing a pharmaceutical composition comprising a therapeutically effective amount of a compound of Formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be Pim-kinase inhibitors according to at least one assay described herein.

EXAMPLES

Experimental procedures for compounds of the invention are provided below. Open Access Preparative LCMS Purification of some of the compounds prepared was performed on Waters mass directed fractionation systems. The basic equipment setup, protocols, and control software for the operation of these systems have been described in detail in literature. See, e. *g., Blom, "Two-Pump At Column Dilution Configuration for Preparative LCMS", *J. Combi. Chem.,* 2002, 4, 295-301; Blom et al., "Optimizing Preparative LCMS Configurations and Methods for Parallel Synthesis Purification", *J. Combi. Chem.,* 2003, 5, 670-83; and Blom et al., "Preparative LCMS Purification: Improved Compound Specific Method Optimization", *J. Combi. Chem.*, 2004, 6, 874-883. The compounds separated were typically subjected to analytical liquid chromatography mass spectrometry (LCMS) for purity under the following conditions: Instrument: Agilent 1100 series, LCMSD, Column: Waters SunFire™ $C_{18}$ 5 μm, 2.1×5.0 mm, Buffers: mobile phase A: 0.025% TFA in water and mobile phase B: 0.025% TFA in MeCN; gradient 2% to 80% of B in 3 min. with flow rate 1.5 mL/min.

Some of the compounds prepared were also separated on a preparative scale by reverse-phase high performance liquid chromatography (RP-HPLC) with MS detector or flash chromatography (silica gel) as indicated in the Examples.

Typical preparative reverse-phase high performance liquid chromatography (RP-HPLC) column conditions set out below in Methods A and B.

Unless otherwise indicated, the example compounds were purified by preparative HPLC using acidic conditions (method A) and were obtained as a TFA salt, or using basic conditions (method B) and were obtained as a free base.

Method A:
Column: Waters SunFire™ C18, 5 μm particle size, 30×100 mm;
Mobile phase: water (0.1% TFA)/MeCN
Flow rate: 60 mL/min.
Gradient: 5 min. or 12 min. from 5% MeCN/95% water to 100% MeCN Method B:
Column: Waters XBridge™ C18, 5 μm particle size, 30×100 mm;
Mobile phase: water (0.15% NH$_4$OH)/MeCN
Flow rate: 60 mL/min.
Gradient: 5 min or 12 min from 5% MeCN/95% water to 100% MeCN The example compounds and intermediates below containing one or more chiral centers were obtained in enantiomerically pure form or as scalemic or racemic mixtures, unless otherwise specified.

Intermediate 1: tert-Butyl [1-(4-amino-1-methyl-1H-pyrazol-5-yl)azepan-4-yl]carbamate

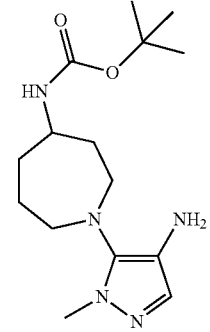

Step A. 1-Methyl-4-nitro-1H-pyrazole

A mixture of 4-nitro-1H-pyrazole (10.0 g, 88.4 mmol, commercially available from Aldrich), 1.0 M aq. NaOH (400.0 mL, 400.0 mmol) and dimethyl sulfate (62 mL, 660 mmol) was stirred at room temperature for 72 h. The mixture was extracted with DCM (2×300 mL). The combined extracts were dried over Na$_2$SO$_4$, filtered and evaporated under reduced pressure to give 11.2 g (96.1% yield) of the sub-title compound as a white solid. LCMS calc. for C$_4$H$_6$N$_3$O$_2$ (M+H)$^+$: m/z=128.1. found: 128.1.

Step B. 5-Chloro-1-methyl-4-nitro-1H-pyrazole

To 1 L three-neck flask 1-methyl-4-nitro-1H-pyrazole (10.8 g, 85.0 mmol) and THF (30 mL) were added. The mixture was cooled to −78° C. and 1.0 M lithium hexamethyldisilazide in THF (222 mL) was added dropwise via an addition funnel over 20 min. The brown mixture was stirred for 30 min. and then allowed to warm to −45° C. over 30 min. The mixture was cooled back down to −78° C. and hexachloroethane (26.4 g, 111 mmol) dissolved in THF (20 mL) was added via an addition funnel over 15 min. The mixture was stirred for 2.5 h and then allowed to warm from −78° C. to 40° C. and the reaction was monitored by LCMS. Upon the completion of the reaction, the reaction was quenched with a solution of NH$_4$Cl (450 mL) and then EtOAc (300 mL) was added. The organic phase was separated and the aqueous layer was extracted with EtOAc. The combined extracts were dried over Na$_2$SO$_4$, filtered and concentrated under reduced pressure give an oil residue, which was further purified by column chromatography on silica gel using CombiFlash® apparatus eluting with EtOAc/hexane (50-100%). The purification gave 10.8 g (78.7% yield) of the sub-title compound as a white solid. LCMS calc. for C$_4$H$_5$ClN$_3$O$_2$(M+H)$^+$: m/z=162.0. found: 162.0.

Step C. tert-Butyl [1-(1-methyl-4-nitro-1H-pyrazol-5-yl)azepan-4-yl]carbamate

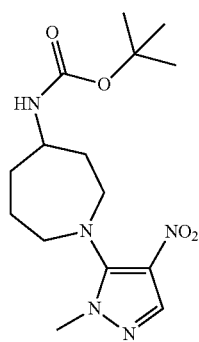 [SMILES: Cn1ncc(N)c1N1CCCC(NC(=O)OC(C)(C)C)CC1]

A mixture of 5-chloro-1-methyl-4-nitro-1H-pyrazole (0.400 g, 2.48 mmol), tert-butyl azepan-4-yl carbamate (0.58 g, 2.7 mmol), EtOH (3 mL) and DIPEA (1.6 mL, 9.2 mmol) was irradiated in a microwave oven for 1 h at 130° C. The mixture was concentrated under reduced pressure and the residue was purified by column chromatography on silica gel using CombiFlash® apparatus, eluting with EtOAc/hexane (10-60%). The purification gave 0.580 g (69.0% yield) of the sub-title compound as a colorless oil. LCMS calc. for C$_{11}$H$_{18}$N$_5$O$_4$ (M+H-t-Bu+H)$^+$: m/z=284.2. found: 284.1.

Step D. tert-Butyl [1-(4-amino-1-methyl-1H-pyrazol-5-yl)azepan-4-yl]carbamate

A mixture of tert-butyl [1-(1-methyl-4-nitro-1H-pyrazol-5-yl)azepan-4-yl]carbamate (0.580 g, 1.71 mmol), iron powder (0.38 g, 6.8 mmol), NH$_4$Cl (0.46 g, 8.5 mmol), EtOH (10 mL) and water (1.2 mL) was heated at 60° C. for 60 min. When the reaction was complete, the mixture was allowed to cool and filtered through a diatomaceous earth pad. The pad was washed with EtOAc and NaHCO$_3$ solution. The organic layer was then washed with water and brine, dried over Na$_2$SO$_4$, filtered and concentrated under reduced pressure to give 0.468 g (88.5% yield) of the title compound as a reddish oil. LCMS calc. for C$_{15}$H$_{28}$N$_5$O$_2$ (M+H)$^+$: m/z=310.2. found: 310.2.

Intermediate 2: tert-Butyl [(3S)-1-(4-amino-1-methyl-1H-pyrazol-5-yl)piperidin-3-yl]carbamate

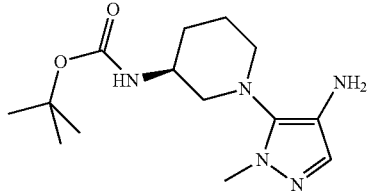 [SMILES: Cn1ncc(N)c1N1CCC[C@H](NC(=O)OC(C)(C)C)C1]

Step A. tert-Butyl [(3S)-1-(1-methyl-4-nitro-1H-pyrazol-5-yl)piperidin-3-yl]carbamate

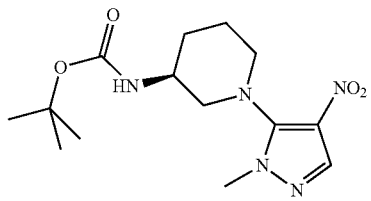 [SMILES: Cn1ncc([N+](=O)[O-])c1N1CCC[C@H](NC(=O)OC(C)(C)C)C1]

A mixture of 5-chloro-1-methyl-4-nitro-1H-pyrazole (0.323 g, 2.00 mmol) (prepared as described for Intermediate 1, Step A and B), tert-butyl (3S)-piperidin-3-ylcarbamate (0.400 g, 2.00 mmol) and DIPEA (0.632 mL, 3.63 mmol) in EtOH (1 mL) was heated under microwave irradiation at 130° C. for 1 h. The reaction mixture was concentrated under reduced pressure and the residue was purified by column chromatography on silica gel using CombiFlash® apparatus eluting with EtOAc/hexane (50-100%). The purification afforded 0.488 g (75.1% yield) of the sub-title compound as a yellow solid. LCMS calc. for C$_{10}$H$_{16}$N$_5$O$_4$ (M+H-t-Bu+H)$^+$: m/z=270.1. found: 270.1.

Step B. tert-Butyl [(3S)-1-(4-amino-1-methyl-1H-pyrazol-5-yl)piperidin-3-yl]carbamate A mixture of tert-butyl [(3S)-1-(1-methyl-4-nitro-1H-pyrazol-5-yl)piperidin-3-yl]carbamate (0.480 g, 1.48 mmol), iron powder (0.33 g, 5.9 mmol), NH$_4$Cl (0.39 g, 7.4 mmol), EtOH (10 mL) and water (0.9 mL) was heated at 60° C. for 60 min. When the reaction was complete, the reaction mixture was allowed to cool and filtered through a diatomaceous earth pad. The pad was washed with EtOAc and NaHCO$_3$ solution. The organic layers were washed with water and brine, dried over Na$_2$SO$_4$, filtered and concentrated under reduced pressure to give 0.402 g (92.2% yield) of the title compound as a brown solid. LCMS calc. for C$_{14}$H$_{26}$N$_5$O$_2$ (M+H)$^+$: m/z=296.2. found: 296.2.

Intermediate 3: tert-Butyl [(3R)-1-(4-amino-1-methyl-1H-pyrazol-5-yl)piperidin-3-yl]carbamate

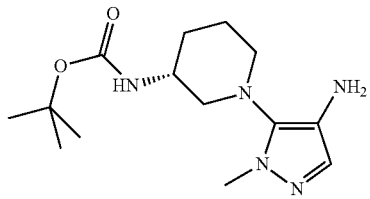 [SMILES: Cn1ncc(N)c1N1CCC[C@@H](NC(=O)OC(C)(C)C)C1]

Intermediate 3 was synthesized as described for Intermediate 2 except using tert-butyl (3R)-piperidin-3-ylcarbamate instead of tert-butyl (3S)-piperidin-3-ylcarbamate.

Intermediate 4: tert-Butyl 4-(4-amino-1-methyl-1H-pyrazol-5-yl)-1,4-diazepane-1-carboxylate

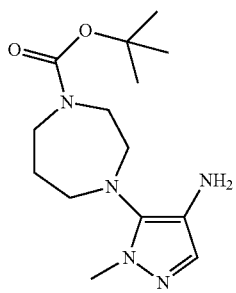 [SMILES: Cn1ncc([N+](=O)[O-])c1N1CCCN(C(=O)OC(C)(C)C)CC1]

Step A. tert-Butyl 4-(1-methyl-4-nitro-1H-pyrazol-5-yl)-1,4-diazepane-1-carboxylate

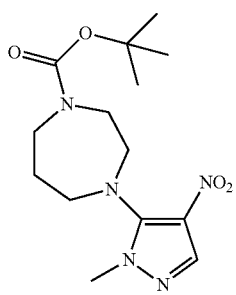

A mixture of 5-chloro-1-methyl-4-nitro-1H-pyrazole (0.403 g, 2.50 mmol) (prepared as described for Intermediate 1, Step A and B), tert-butyl 1,4-diazepane-1-carboxylate (0.500 g, 2.50 mmol) and DIPEA (0.791 mL, 4.54 mmol) in EtOH (2 mL) was heated under microwave irradiation at 130° C. for 1 h. The mixture was concentrated under reduced pressure and the resulting residue was purified by column chromatography on silica gel using CombiFlash® apparatus eluting with EtOAc/hexane (50-100%). The purification afforded 0.572 g (70.4% yield) of the sub-title compound as a yellow oil. LCMS calc. for $C_{14}H_{23}N_5O_4Na$ (M+Na)$^+$: m/z=348.2. found: 348.1.

Step B. tert-Butyl 4-(4-amino-1-methyl-1H-pyrazol-5-yl)-1,4-diazepane-1-carboxylate A mixture of tert-butyl 4-(1-methyl-4-nitro-1H-pyrazol-5-yl)-1,4-diazepane-1-carboxylate (0.550 g, 1.69 mmol), iron powder (0.38 g, 6.8 mmol), NH$_4$Cl (0.45 g, 8.4 mmol), EtOH (10 mL) and water (1 mL) was heated at 60° C. for 60 min. When the reaction was complete, the mixture was allowed to cool and filtered through a diatomaceous earth pad. The cake was washed with EtOAc and NaHCO$_3$ solution. The organic layers were washed with water and brine, dried over Na$_2$SO$_4$, filtered and concentrated under reduced pressure to give 0.466 g (93.3% yield) of the title compound as a brown solid. LCMS calc. for $C_{14}H_{26}N_5O_2$ (M+H)$^+$: m/z=296.2. found: 296.2.

Intermediate 5: tert-Butyl [6-(4-amino-1-methyl-1H-pyrazol-5-yl)-2,3-dihydro-1H-inden-1-yl]carbamate

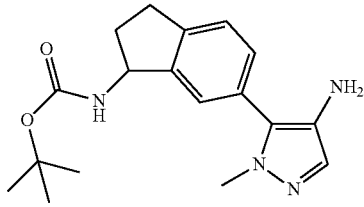

Step A. tert-Butyl (6-bromo-2,3-dihydro-1H-inden-1-yl)carbamate

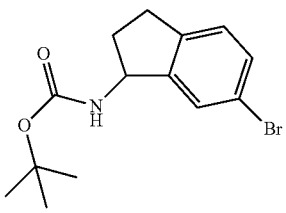

A mixture of 6-bromoindan-1-amine (0.500 g, 2.36 mmol), Boc$_2$O (0.679 g, 3.11 mmol) and TEA (0.657 mL, 4.72 mmol) in THF (6 mL) was stirred at room temperature for 1 h. The reaction mixture was concentrated under reduced pressure and the residue was purified by column chromatography on silica gel using CombiFlash® apparatus eluting with EtOAc/hexane (20-70%). The purification gave 0.724 g (98.4% yield) of the sub-title compound as an off-white solid. LCMS calc. for $C_{10}H_{11}BrNO_2$ (M+H-t-Bu+H)$^+$: m/z=256.0. found: 256.0.

Step B. tert-Butyl [6-(4,4,5,5-tetramethyl-1,3,2-dioxaborolan-2-yl)-2,3-dihydro-1H-inden-1-yl]carbamate A mixture containing tert-butyl (6-bromo-2,3-dihydro-1H-inden-1-yl)carbamate (0.700 g, 2.24 mmol), 4,4,5,5,4',4',5',5'-octamethyl-[2,2']bi[[1,3,2]dioxaborolanyl] (1.14 g, 4.48 mmol) and [1,1'-bis(diphenylphosphino)ferrocene]dichloropalladium(II), complex with dichloromethane (1:1) (0.18 g, 0.22 mmol) and KOAc (0.660 g, 6.73 mmol) was stirred at 130° C. in a sealed tube for 1 h. The mixture was then diluted with 20 mL of EtOAc and filtered through a plug of diatomaceous earth. The solvent was removed under reduced pressure. The residue was purified by column chromatography on silica gel using CombiFlash® apparatus eluting with EtOAc/hexane (0-40%). The purification gave 0.790 g (98.1% yield) of the sub-title compound as a yellowish oil. LCMS calc. for $C_{16}H_{23}BNO_4$(M+H-t-Bu+H)$^+$: m/z=304.2. found: 304.2.

Step C. tert-Butyl [6-(1-methyl-4-nitro-1H-pyrazol-5-yl)-2,3-dihydro-1H-inden-1-yl]carbamate

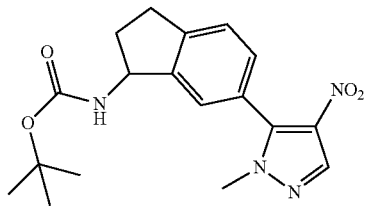 [SMILES: Cn1ncc(N)c1-c1ccc2c(c1)C(NC(=O)OC(C)(C)C)CC2]

A mixture of 5-chloro-1-methyl-4-nitro-1H-pyrazole (50.0 mg, 0.310 mmol), tert-butyl [6-(4,4,5,5-tetramethyl-1,3,2-dioxaborolan-2-yl)-2,3-dihydro-1H-inden-1-yl]carbamate (111.2 mg, 0.3095 mmol), Pd(PPh$_3$)$_4$ (36 mg, 0.031 mmol) and 2.0 M aq. Na$_2$CO$_3$ (0.46 mL, 0.93 mmol) in 1,4-dioxane (2 mL) was heated under microwave irradiation at 130° C. for 15 min. The reaction mixture was filtered through a pad of diatomaceous earth and the pad was rinsed with EtOAc. The filtrate was concentrated under reduced pressure and the residue was purified by column chromatography on silica gel using CombiFlash® apparatus eluting with EtOAc/hexane (20-100%). The purification gave 40 mg (40% yield) of the sub-title compound as a colorless oil. LCMS calc. for $C_{18}H_{23}N_4O_4$ (M+H)$^+$: m/z=359.2. found: 359.2.

Step D. tert-Butyl [6-(4-amino-1-methyl-1H-pyrazol-5-yl)-2,3-dihydro-1H-inden-1-yl]carbamate A mixture of tert-butyl [6-(1-methyl-4-nitro-1H-pyrazol-5-yl)-2,3-dihydro-1H-inden-1-yl]carbamate (125 mg, 0.349 mmol), iron powder (77.9 mg, 1.40 mmol), NH$_4$Cl (93.3 mg, 1.74 mmol) in EtOH (3 mL) and water (0.3 mL) was heated under reflux for 2 h. The reaction mixture was allowed to cool to room temperature and neutralized to pH=9 with saturated aq. NaHCO$_3$, filtered through a pad of diatomaceous earth and rinsed with EtOAc. The organic layer was washed with water and brine, dried over Na$_2$SO$_4$, filtered and concentrated under reduced pressure to give 113 mg (98.6% yield) of the title compound as a reddish oil. LCMS calc. for $C_{18}H_{25}N_4O_2$ (M+H)$^+$: m/z=329.2. found: 329.1.

Intermediate 6: tert-Butyl [(3S)-1-(3-aminopyridin-4-yl)piperidin-3-yl]carbamate

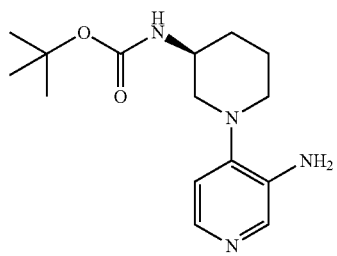

Step A. tert-Butyl [(3S)-1-(3-nitropyridin-4-yl)piperidin-3-yl]carbamate

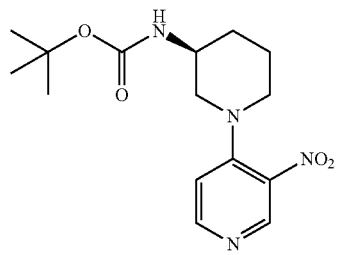 [SMILES: CC(C)(C)OC(=O)N[C@H]1CCCN(c2ccncc2N)C1]

A mixture of 4-chloro-3-nitropyridine (1.11 g, 6.99 mmol), tert-butyl (3S)-piperidin-3-ylcarbamate (1.40 g, 6.99 mmol) and DIPEA (3.65 mL, 21.0 mmol) in EtOH (6 mL) was heated under microwave irradiation at 80° C. for 1 h. The mixture was concentrated under reduced pressure and the residue was purified by column chromatography on silica gel using CombiFlash® apparatus eluting with EtOAc/hexane (50-100%). The purification gave 2.18 g (96.7% yield) of the sub-title compound as a yellow solid. LCMS calc. for $C_{15}H_{23}N_4O_4$ (M+H)$^+$: m/z=323.2. found: 323.0.

Step B. tert-Butyl [(3S)-1-(3-aminopyridin-4-yl)piperidin-3-yl]carbamate

A mixture of tert-butyl [(3S)-1-(3-nitropyridin-4-yl)piperidin-3-yl]carbamate (2.10 g, 6.51 mmol), iron powder (1.46 g, 26.0 mmol), NH$_4$Cl (1.74 g, 32.6 mmol), EtOH (40 mL) and water (4.4 mL) was heated at 60° C. for 60 min. When the reaction was complete, the mixture was allowed to cool, filtered through a diatomaceous earth pad, washed with EtOAc, saturated aq. NaHCO$_3$ solution. The organic layer was washed with water and brine, dried over Na$_2$SO$_4$, filtered and concentrated under reduced pressure to give 1.78 g (93.4% yield) of the title compound as a yellowish solid. LCMS calc. for $C_{15}H_{25}N_4O_2$ (M+H)$^+$: m/z=293.2. found: 293.2.

Intermediate 7: tert-Butyl [(3R)-1-(3-aminopyridin-4-yl)piperidin-3-yl]carbamate

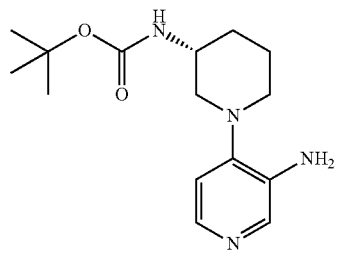 [SMILES: CC(C)(C)OC(=O)N[C@@H]1CCCN(c2ccncc2N)C1]

Intermediate 7 was synthesized by an analogous procedure to that described in Intermediate 6, using tert-butyl (3R)-piperidin-3-ylcarbamate instead of tert-butyl (3S)-piperidin-3-ylcarbamate.

Intermediate 8: tert-Butyl 4-(3-aminopyridin-4-yl)-1,4-diazepane-1-carboxylate

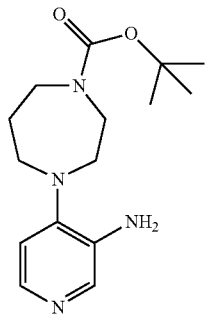

Step A. tert-Butyl 4-(3-nitropyridin-4-yl)-1,4-diazepane-1-carboxylate

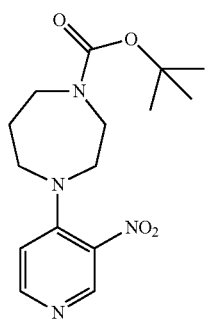 [SMILES: CC(C)(C)OC(=O)N1CCCN(c2ccncc2[N+](=O)[O-])CC1]

A mixture of 4-chloro-3-nitropyridine (0.500 g, 3.15 mmol), tert-butyl 1,4-diazepane-1-carboxylate (0.632 g, 3.15 mmol) and DIPEA (2.0 mL, 12 mmol) in EtOH (4 mL) was irradiated in a microwave oven for 1 h at 130° C. The reaction mixture was concentrated under reduced pressure and the residue was purified by column chromatography on silica gel using CombiFlash® apparatus eluting with EtOAc/hexane (50-100%). The purification gave 0.818 g (80.5% yield) of the sub-title compound as a yellow solid. LCMS calc. for $C_{15}H_{23}N_4O_4$ $(M+H)^+$: m/z=323.2. found: 323.2.

Step B. tert-Butyl 4-(3-aminopyridin-4-yl)-1,4-diazepane-1-carboxylate

A mixture of tert-butyl 4-(3-nitropyridin-4-yl)-1,4-diazepane-1-carboxylate (0.600 g, 1.86 mmol), iron powder (0.42 g, 7.4 mmol), $NH_4Cl$ (0.50 g, 9.3 mmol), EtOH (10 mL) and water (1 mL) was heated at 100° C. for 2 h. When the reaction was complete, the reaction mixture was allowed to cool and filtered through a diatomaceous earth pad. The pad was washed with EtOAc and saturated aq. $NaHCO_3$ solution. The organic layers were washed with water and brine, dried over $Na_2SO_4$, filtered and concentrated under reduced pressure to give 0.524 g (96.3% yield) of the title compound as a brown solid. LCMS calc. for $C_{15}H_{25}N_4O_2$ $(M+H)^+$: m/z=293.2. found: 293.2.

Intermediate 9: tert-Butyl [1-(3-aminopyridin-4-yl)azepan-4-yl]carbamate

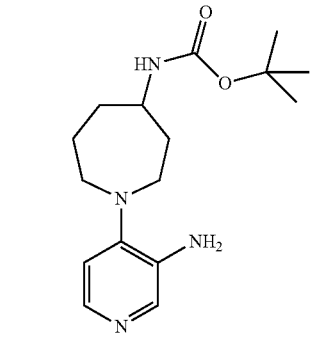

Step A. tert-Butyl [1-(3-nitropyridin-4-yl)azepan-4-yl]carbamate

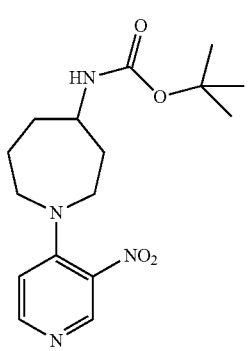 [SMILES: CC(C)(C)OC(=O)NC1CCCN(c2ccncc2[N+](=O)[O-])CC1]

A mixture of 4-chloro-3-nitropyridine (0.500 g, 3.15 mmol), tert-butyl azepan-4-yl carbamate (0.676 g, 3.15 mmol) and DIPEA (2.0 mL, 12 mmol) in EtOH (4 mL) was irradiated in a microwave oven for 1 h at 130° C. The reaction mixture was concentrated under reduced pressure and the residue was purified by column chromatography on silica gel using CombiFlash® apparatus eluting with EtOAc/hexane (10-60%). The purification gave 0.920 g (86.7% yield) of the sub-title compound as a yellowish oil. LCMS calc. for $C_{16}H_{25}N_4O_4$ $(M+H)^+$: m/z=337.2. found: 337.1.

Step B. tert-Butyl [1-(3-aminopyridin-4-yl)azepan-4-yl]carbamate

A mixture of tert-butyl [1-(3-nitropyridin-4-yl)azepan-4-yl]carbamate (0.600 g, 1.78 mmol), iron powder (0.40 g, 7.1 mmol), $NH_4Cl$ (0.48 g, 8.9 mmol), EtOH (10 mL) and water (1 mL) was heated at 100° C. for 3 h. When the reaction was complete, the reaction mixture was allowed to cool and filtered through a diatomaceous earth pad. The pad was washed with EtOAc and saturated aqueous $NaHCO_3$ solution. The organic layers were washed with water and brine, dried over $Na_2SO_4$ and filtered to give 0.518 g (94.8% yield) of the title compound as a brown solid. LCMS calc. for $C_{16}H_{27}N_4O_2$ $(M+H)^+$: m/z=307.2. found: 307.2.

Intermediate 10: tert-Butyl [(3R)-1-(3-aminopyridin-4-yl)pyrrolidin-3-yl]carbamate

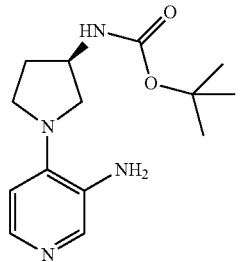

Step A. tert-Butyl [(3R)-1-(3-nitropyridin-4-yl)pyrrolidin-3-yl]carbamate

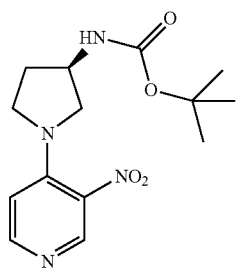 [SMILES: CC(C)(C)OC(=O)N[C@@H]1CCN(c2ccncc2[N+](=O)[O-])C1]

A mixture of 4-chloro-3-nitropyridine (0.500 g, 3.15 mmol), tert-butyl (3R)-pyrrolidin-3-ylcarbamate (0.587 g, 3.15 mmol) and DIPEA (1.10 mL, 6.31 mmol) in EtOH (4 mL) was irradiated in a microwave oven for 1 h at 130° C. The reaction mixture was concentrated under reduced pressure and the residue was purified by column chromatography on silica gel using CombiFlash® apparatus eluting with EtOAc/hexane (50-100%). The purification gave 0.710 g (73.0% yield) of the sub-title compound as a yellow solid. LCMS calc. for $C_{14}H_{21}N_4O_4(M+H)^+$: m/z=309.2. found: 309.1.

Step B. tert-Butyl [(3R)-1-(3-aminopyridin-4-yl)pyrrolidin-3-yl]carbamate

A mixture of tert-butyl [(3R)-1-(3-nitropyridin-4-yl)pyrrolidin-3-yl]carbamate (0.521 g, 1.69 mmol), iron powder (0.38 g, 6.8 mmol), NH$_4$Cl (0.45 g, 8.4 mmol), EtOH (10 mL) and water (1 mL) was heated at 60° C. for 60 min. When the reaction was complete, the reaction mixture was allowed to cool and filtered through a diatomaceous earth pad. The pad was washed with EtOAc and saturated aqueous NaHCO$_3$ solution. The organic layers were washed with water and brine, dried over Na$_2$SO$_4$, filtered and concentrated under reduced pressure to give 0.432 g (91.8% yield) of the title compound as a brown solid. LCMS calc. for $C_{14}H_{23}N_4O_2$ (M+H)$^+$: m/z=279.2. found: 279.2.

Intermediate 11: tert-Butyl [(3S)-1-(3-aminopyridin-4-yl)pyrrolidin-3-yl]carbamate

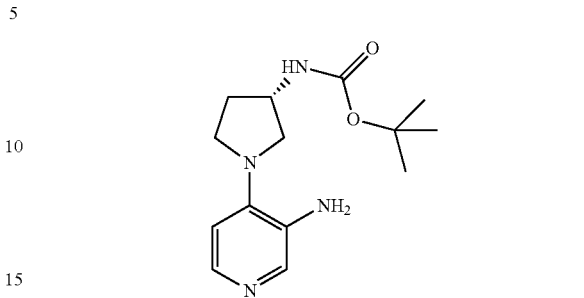

Step A. tert-Butyl [(3S)-1-(3-nitropyridin-4-yl)pyrrolidin-3-yl]carbamate

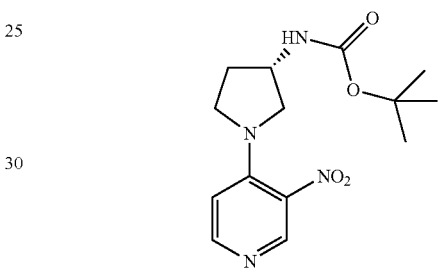

A mixture of 4-chloro-3-nitropyridine (0.500 g, 3.15 mmol), tert-butyl (3S)-pyrrolidin-3-yl carbamate (0.587 g, 3.15 mmol) and DIPEA (2.0 mL, 12 mmol) in EtOH (4 mL) was irradiated in a microwave oven for 1 h at 130° C. The reaction mixture was concentrated under reduced pressure and the residue was purified by column chromatography on silica gel using CombiFlash® apparatus eluting with EtOAc/hexane (50-100%). The purification gave 0.698 g (71.8% yield) of the sub-title compound as a yellow solid. LCMS calc. for $C_{14}H_{21}N_4O_4(M+H)^+$: m/z=: 309.2. found: 309.2.

Step B. tert-Butyl [(3S)-1-(3-aminopyridin-4-yl)pyrrolidin-3-yl]carbamate

A mixture of tert-butyl [(3S)-1-(3-nitropyridin-4-yl)pyrrolidin-3-yl]carbamate (0.521 g, 1.69 mmol), iron powder (0.38 g, 6.8 mmol), NH$_4$Cl (0.45 g, 8.4 mmol), EtOH (10 mL) and water (1 mL) was heated at 60° C. for 60 min. When the reaction was complete, the mixture was allowed to cool and filtered through a diatomaceous earth pad. The pad was washed with EtOAc and saturated aq. NaHCO$_3$ solution. The organic layers were washed with water and brine, dried over Na$_2$SO$_4$, filtered and concentrated under reduced pressure to give 0.428 g (91% yield) of the title compound as a brown solid. LCMS calc. for $C_{14}H_{23}N_4O_2$ (M+H)$^+$: m/z=: 279.2. found: 279.1.

Intermediate 12: tert-Butyl [(3S)-1-(3-amino-5-methyl-pyridin-4-yl)pyrrolidin-3-yl]carbamate

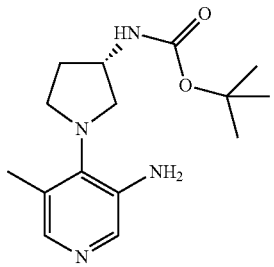 [SMILES: Cc1cncc(N)c1N1CC[C@H](NC(=O)OC(C)(C)C)C1]

Step A. tert-Butyl [(3S)-1-(3-nitro-5-methyl-pyridin-4-yl)pyrrolidin-3-yl]carbamate

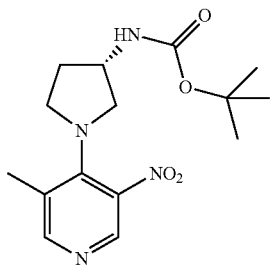 [SMILES: Cc1cncc([N+](=O)[O-])c1N1CC[C@H](NC(=O)OC(C)(C)C)C1]

A mixture of 4-chloro-3-methyl-5-nitropyridine (1.0 g, 5.8 mmol), tert-butyl (3S)-pyrrolidin-3-yl carbamate (1.1 g, 5.8 mmol), DIPEA (2.0 mL) and N-methylpyrrolidinone (6.0 mL) was heated at 160° C. for 60 min. in a microwave oven. The reaction mixture was concentrated under reduced pressure and the residue was purified by column chromatography on silica gel using CombiFlash® apparatus eluting with EtOAc/hexane (50-100%). The purification gave 1.8 g (96% yield) of the sub-title compound as a yellow solid. LCMS calc. for $C_{15}H_{23}N_4O_4$ (M+H)$^+$: m/z=323.2. found: 323.1.

Step B. tert-Butyl [(3S)-1-(3-amino-5-methyl-pyridin-4-yl)pyrrolidin-3-yl]carbamate A mixture of tert-butyl [(3S)-1-(3-nitro-5-methyl-pyridin-4-yl)pyrrolidin-3-yl]carbamate (0.556 g, 1.69 mmol), iron powder (0.38 g, 6.8 mmol), AcOH (10 mL) and water (1 mL) was heated at 60° C. for 60 min. When the reaction was complete, the mixture was allowed to cool, concentrated under reduced pressure and diluted with EtOAc. The resulting mixture was filtered through a diatomaceous earth pad. The filtrate was concentrated under reduced pressure and the residue was dissolved in 1 M aq. NaOH, extracted with EtOAc (100 mL×3). The combined organic layers were washed with water and brine, dried over $Na_2SO_4$, filtered and concentrated under reduced pressure to give 0.435 g (91% yield) of the title compound as a brown solid. LCMS calc. for $C_{15}H_{25}N_4O_2$(M+H)$^+$: m/z=293.1. found: 293.1.

Intermediate 13: tert-Butyl [(3S,5R)-1-(3-aminopyridin-4-yl)-5-trifluoromethyl-piperidin-3-yl]carbamate

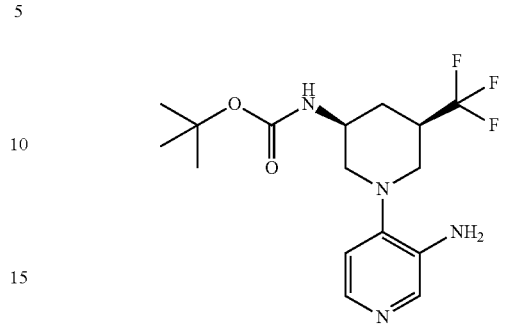

Step A. tert-butyl [(3S,5R)-1-(3-nitropyridin-4-yl)-5-(trifluoromethyl)piperidin-3-yl]carbamate

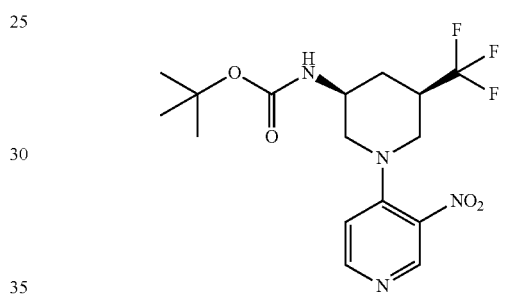

A mixture of 4-chloro-3-nitropyridine (580 mg, 3.6 mmol), tert-butyl [(3S,5R)-5-(trifluoromethyl)piperidin-3-yl]carbamate (800 mg, 3 mmol), i-PrOH (5.0 mL) and DIPEA (1.0 mL, 6.0 mmol) was stirred at 80° C. overnight. The reaction mixture was concentrated under reduced pressure and the residue was purified by column chromatography on silica gel using CombiFlash® apparatus eluting with EtOAc/hexane (50-100%). The purification gave 1.0 g (80% yield) of the sub-title compound as a yellow solid. LCMS calc. for $C_{16}H_{22}F_3N_4O_4$(M+H)$^+$: m/z=: 391.2. found: 391.1.

Step B. tert-butyl [(3S,5R)-1-(3-aminopyridin-4-yl)-5-(trifluoromethyl)piperidin-3-yl]carbamate A mixture of tert-butyl [(3S,5R)-1-(3-nitropyridin-4-yl)-5-(trifluoromethyl)piperidin-3-yl]carbamate (1 g, 2 mmol), iron powder (0.57 g, 10 mmol), AcOH (16 mL) and water (2 mL) was stirred at room temperature for 60 min. When the reaction was complete, the mixture was allowed to cool, concentrated under reduced pressure and diluted with EtOAc. The resulting mixture was filtered through a diatomaceous earth pad. The filtrate was concentrated under reduced pressure, and the residue was dissolved in 1 M NaOH aqueous solution and extracted with EtOAc (100 mL×3). The combined organic layers were washed with water and brine, dried over $Na_2SO_4$, filtered and concentrated under reduced pressure to give 0.9 g (100% yield) of the title compound as a brown solid. LCMS calc. for $C_{16}H_{24}F_3N_4O_2$(M+H)$^+$: m/z=: 361.2. found: 361.1.

Intermediate 14: tert-Butyl [(3S,4S)-1-(3-amin-opyridin-4-yl)-4-fluoro-piperidin-3-yl]carbamate

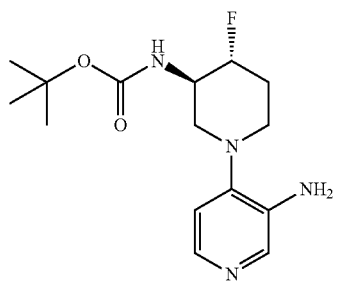 [SMILES: CC(C)(C)OC(=O)N[C@@H]1CN(c2ccncc2[N+](=O)[O-])CC[C@H]1F]

Step A. tert-butyl [(3S,4S)-4-fluoro-1-(3-nitropyridin-4-yl)piperidin-3-yl]carbamate

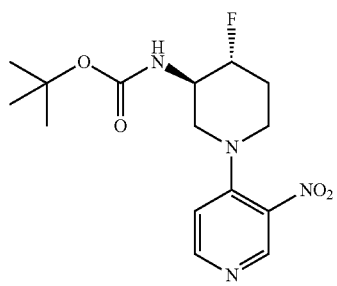

A mixture of 4-chloro-3-nitropyridine (750 mg, 4.7 mmol), tert-butyl [(3S,4S)-4-fluoropiperidin-3-yl]carbamate (1 g, 4 mmol), i-PrOH (5.0 mL) and DIPEA (1.6 mL, 9.2 mmol) was stirred at 80° C. overnight. The reaction mixture was concentrated under reduced pressure and the residue was purified by column chromatography on silica gel using CombiFlash® apparatus eluting with EtOAc/hexane (50-100%). The purification gave 1.9 g (95% yield) of the sub-title compound as a yellow solid. LCMS calc. for $C_{15}H_{22}FN_4O_4(M+H)^+$: m/z=: 341.2. found: 341.1.

Step B. tert-butyl [(3S,4S)-1-(3-aminopyridin-4-yl)-4-fluoropiperidin-3-yl]carbamate A mixture of tert-butyl [(3S,4S)-4-fluoro-1-(3-nitropyridin-4-yl)piperidin-3-yl]carbamate (900 mg, 2 mmol), iron powder (0.57 g, 10 mmol), AcOH (16 mL) and water (2 mL) was stirred at room temperature for 60 min. When the reaction was complete, the mixture was allowed to cool, concentrated under reduced pressure and diluted with EtOAc. The resulting mixture was filtered through a diatomaceous earth pad. The filtrate was concentrated under reduced pressure, and the residue was dissolved in 1 M aq. NaOH and extracted with EtOAc (100 mL×3). The combined organic layers were washed with water and brine, dried over $Na_2SO_4$, filtered and concentrated under reduced pressure to give 0.6 g (80% yield) of the title compound as a brown solid. LCMS calc. for $C_{15}H_{24}FN_4O_2(M+H)^+$: m/z=: 311.2. found: 311.1.

Intermediate 15: tert-Butyl [(3S,5R)-1-(3-amin-opyridin-4-yl)-5-methyl-piperidin-3-yl]carbamate

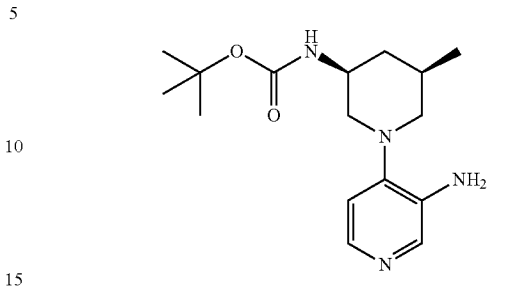

Step A. 1-tert-butyl 2-methyl (2S,4R)-4-methyl-5-oxopyrrolidine-1,2-dicarboxylate

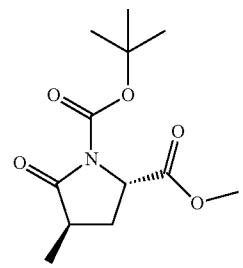 [SMILES: COC(=O)[C@@H]1C[C@@H](C)C(=O)N1C(=O)OC(C)(C)C]

A solution of 1-tert-butyl 2-methyl (2S)-5-oxopyrrolidine-1,2-dicarboxylate (16.1 g, 66.2 mmol) in THF (100 mL) was cooled to −78° C. Lithium hexamethyldisilazide in THF (1.0 M; 68.2 mL, 68.2 mmol) was added dropwise over 5 min. The resulting mixture was stirred at −78° C. for 35 min., then methyl iodide (10.0 mL, 160 mmol) was added. The reaction was allowed to warm to room temperature slowly overnight. The reaction was quenched with AcOH (7.5 mL, 130 mmol) and water (5 mL) and then concentrated under reduced pressure. The concentrated residue was further diluted with water and extracted with EtOAc (3 times). The combined extracts were washed with water and brine, dried ($Na_2SO_4$), filtered and concentrated under reduced pressure. The residue was purified by silica gel column and eluted with 0-50% EtOAc/Hex over 45 min. Fractions were checked by TLC ($MoSO_4$ stain) and LCMS. 6.1 g (35% yield) of the sub-title compound was obtained. LCMS calc. for $C_7H_{12}NO_3(M+H-Boc+H)^+$: m/z=158.1. found: 158.1.

Step B. tert-butyl [(1S,3R)-4-hydroxy-1-(hydroxymethyl)-3-methylbutyl]carbamate

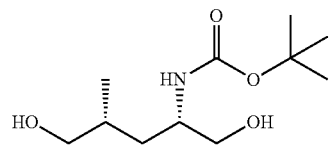 [SMILES: C[C@@H](CO)C[C@@H](CO)NC(=O)OC(C)(C)C]

A solution of 1-tert-butyl 2-methyl (2S,4R)-4-methyl-5-oxopyrrolidine-1,2-dicarboxylate (11.0 g, 42.8 mmol) in THF (100 mL) was cooled to 0° C. then $LiBH_4$ (2.8 g, 130 mmol) and then EtOH (22 mL) were added. The mixture was slowly allowed to warm to room temperature and stirred for 4 h. The reaction was quenched with water then extracted with EtOAc (3 times). The combined extracts were dried (Na₂SO₄), filtered, and concentrated under reduced pressure to give 4.5 g (45% yield) of the crude sub-title compound. The crude product was used without further purification.

Step C. tert-butyl [(3S,5R)-1-benzyl-5-methylpiperidin-3-yl]carbamate

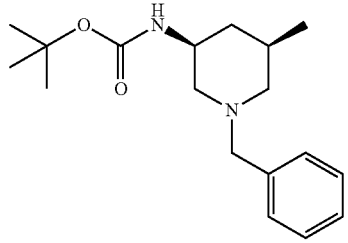 [SMILES: C[C@@H]1C[C@H](NC(=O)OC(C)(C)C)CN(Cc2ccccc2)C1]

A solution of tert-butyl [(1S,3R)-4-hydroxy-1-(hydroxymethyl)-3-methylbutyl]carbamate (9.50 g, 40.7 mmol) in DCM (200 mL) was cooled to 0° C. TEA (23 mL, 160 mmol) was added followed by dropwise addition of methanesulfonyl chloride (9.4 mL, 120 mmol). The clear solution became cloudy and yellow. The mixture was stirred at 0° C. for 1 h. The mixture was diluted with DCM and washed with saturated aq. NaHCO₃ and water. The organic layer was dried (Na₂SO₄), filtered and concentrated under reduced pressure to give an intermediate mesylate as a yellow oil that was used immediately for the next step.

The intermediate mesylate and benzylamine (90 mL, 800 mmol) were combined in microwave vial, sealed and heated at 70° C. overnight. After 18 h, the mixture was quenched with 10% aq. NaOH. The mixture was extracted with hexanes (3 times). The combined extracts were washed with brine, dried (MgSO₄), filtered and concentrated under reduced pressure. The residue was purified on a silica gel column and eluted with 0-40% EtOAc/hexane over 34 min. to give 6.0 g (49% yield) of the sub-title compound as a white solid. LCMS calc. for $C_{18}H_{29}N_2O_2$ (M+H)⁺: m/z=305.2. found: 305.1.

Step D. tert-butyl [(3S,5R)-5-methylpiperidin-3-yl]carbamate

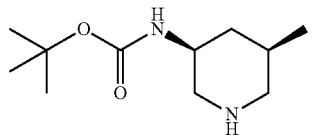

A mixture of tert-butyl [(3S,5R)-1-benzyl-5-methylpiperidin-3-yl]carbamate (4.5 g, 15 mmol), AcOH (2.0 mL, 35 mmol) and 10% Pd on carbon (1.6 g, 1.5 mmol) in EtOH (100 mL) was stirred in a Par-shaker under H₂ (50 psi) overnight. The mixture was filtered through a pad of diatomaceous earth and concentrated under reduced pressure. The residue was diluted with DCM (500 ml) and washed with saturated aq. NaHCO₃ solution. The aqueous layer was extracted twice with DCM. The combined DCM extract was dried over Na₂SO₄, concentrated under reduced pressure to give 2.2 g (67% yield) of the sub-title compound as a white solid. LCMS calc. for $C_{11}H_{23}N_2O_2$(M+H)⁺: m/z=: 215.2. found: 215.1.

Step E. tert-butyl [(3S,5R)-5-methyl-1-(3-nitropyridin-4-yl)piperidin-3-yl]carbamate

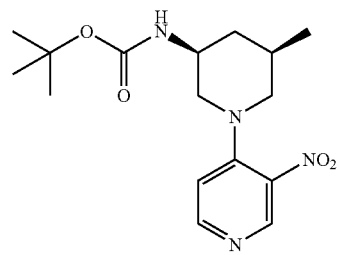 [SMILES: C[C@@H]1C[C@H](NC(=O)OC(C)(C)C)CN(c2ccncc2[N+](=O)[O-])C1]

A mixture of 4-chloro-3-nitropyridine (740 mg, 4.7 mmol), tert-butyl [(3S,5R)-5-methylpiperidin-3-yl]carbamate (1000.0 mg, 4.67 mmol) and DIPEA (2.4 mL, 14 mmol) was irradiated in a microwave oven for 1 h at 130° C. The reaction mixture was concentrated under reduced pressure and the residue was purified by column chromatography on silica gel using CombiFlash® apparatus eluting with EtOAc/hexane (10-60%). The purification gave 1.21 g (80% yield) of the sub-title compound as a colorless oil. LCMS calc. for $C_{16}H_{25}N_4O_4$(M+H)⁺: m/z=337.2. found: 337.1.

Step F. tert-butyl [(3S,5R)-1-(3-aminopyridin-4-yl)-5-methylpiperidin-3-yl]carbamate A mixture of tert-butyl [(3S,5R)-5-methyl-1-(3-nitropyridin-4-yl)piperidin-3-yl]carbamate (100 mg, 0.3 mmol), iron powder (0.072 g, 1.3 mmol), AcOH (2.0 mL, 35 mmol) and water (0.2 mL, 10 mmol) was stirred at room temperature for 60 min. When the reaction was complete, the reaction mixture was concentrated under reduced pressure, diluted with EtOAc, filtered through a pad of diatomaceous earth, washed with aqueous NaHCO₃ solution, water and brine, dried over Na₂SO₄ and concentrated under reduced pressure to give 60 mg (60% yield) of the title compound as a brown solid. LCMS calc. for $C_{16}H_{27}N_4O_2$ (M+H)⁺: m/z=307.1. found: 307.1.

Intermediate 16: tert-butyl ((3R,4R,5S)-1-(3-aminopyridin-4-yl)-4-{[tert-butyl(dimethyl)silyl]oxy}-5-methylpiperidin-3-yl)carbamate

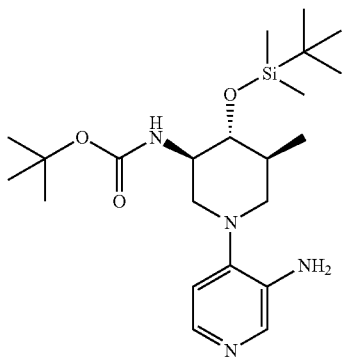 [SMILES: C[C@H]1CN(c2ccncc2N)C[C@@H](NC(=O)OC(C)(C)C)[C@@H]1O[Si](C)(C)C(C)(C)C]

Step A. tert-butyl (4R)-4-{(1R,2R)-3-[(4R)-4-benzyl-2-oxo-1,3-oxazolidin-3-yl]-1-hydroxy-2-methyl-3-oxopropyl}-2,2-dimethyl-1,3-oxazolidine-3-carboxylate

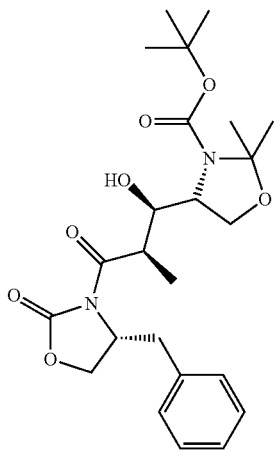

To a solution of (R)-3-(1-oxopropyl)-4-benzyl-2-oxazolidinone (12 g, 51 mmol) in DCM (300 mL) (0.13 M), 1.0 M titanium tetrachloride in DCM (51 mL, 51 mmol) was added at −40° C. The mixture was stirred at −40° C. for 10 min. (yellow suspension), then DIPEA (22 mL, 130 mmol) was added (dark red solution). The mixture was stirred at 0° C. for 20 min. tert-Butyl (4R)-4-formyl-2,2-dimethyl-1,3-oxazolidine-3-carboxylate (12 g, 51 mmol) in DCM (100 mL) (0.5 M) was then added dropwise and the resulting mixture was stirred for 1.5 h at 0° C. LCMS showed 2 peaks with desired mass, one major and the other minor (5:2). The reaction mixture was quenched by the addition of aq. NH$_4$Cl solution and the mixture was extracted with DCM. The organic phase was separated, washed with brine, dried over MgSO$_4$, concentrated under reduced pressure and purified by chromatography on silica gel (0-40% EtOAc/hexane) to give 8 g (30% yield) of the sub-title compound as a colorless oil. LCMS calc. for $C_{24}H_{35}N_2O_7$ (M+H)$^+$: m/z=463.2. found: 463.1.

Step B. tert-butyl (4R)-4-((1R,2R)-3-[(4R)-4-benzyl-2-oxo-1,3-oxazolidin-3-yl]-1-{[tert-butyl(dimethyl)silyl]oxy}-2-methyl-3-oxopropyl)-2,2-dimethyl-1,3-oxazolidine-3-carboxylate

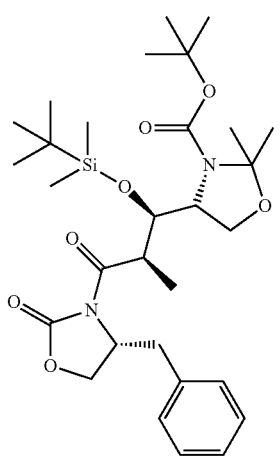

To a solution of tert-butyl (4R)-4-{(1R,2R)-3-[(4R)-4-benzyl-2-oxo-1,3-oxazolidin-3-yl]-1-hydroxy-2-methyl-3-oxopropyl}-2,2-dimethyl-1,3-oxazolidine-3-carboxylate (12.1 g, 26.2 mmol) and 2,6-lutidine (5.4 mL, 47 mmol) in DCM (260 mL) (0.1 M) was added tert-butyldimethylsilyl trifluoromethanesulfonate (8.41 mL, 36.6 mmol) at −40° C. The mixture was stirred at −40° C. for 2 h. The reaction mixture was diluted with DCM, washed with saturated aq. NaHCO$_3$ solution, dried over Na$_2$SO$_4$, concentrated under reduced pressure and purified by chromatography on silica gel (0-20% EtOAc/hexane) to give 14 g (92.8% yield) of the sub-title compound as a colorless gel. LCMS calc. for $C_{25}H_{41}N_2O_5Si$(M+H-Boc+H)$^+$: m/z=477.3. found: 477.1.

Step C. tert-butyl (4R)-4-((1R,2S)-1-{[tert-butyl(dimethyl)silyl]oxy}-3-hydroxy-2-methylpropyl)-2,2-dimethyl-1,3-oxazolidine-3-carboxylate

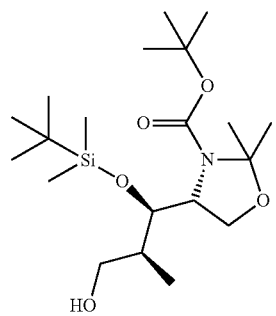

To a solution of tert-butyl (4R)-4-((1R,2R)-3-[(4R)-4-benzyl-2-oxo-1,3-oxazolidin-3-yl]-1-{[tert-butyl(dimethyl)silyl]oxy}-2-methyl-3-oxopropyl)-2,2-dimethyl-1,3-oxazolidine-3-carboxylate (14.0 g, 24.3 mmol) and EtOH (4.2 mL, 73 mmol) in THF (300 mL) (0.09 M) was added LiBH$_4$ (1.6 g, 73 mmol) at −30° C. The mixture allowed to warm to 0° C. and stirred overnight. The reaction mixture was diluted with ether and 1 M NaOH was added. The resulting mixture was extracted with EtOAc and the organic extract was washed with brine, dried over Na$_2$SO$_4$, concentrated under reduced pressure and purified by chromatography on silica gel (0-20% EtOAc/hexane) to give 4.1 g (42% yield) of the sub-title compound as a colorless oil. LCMS calc. for $C_{15}H_{34}NO_3Si$(M+H-Boc+H)$^+$: m/z=304.2. found: 304.1.

Step D. tert-butyl (4R)-4-((1R,2S)-3-azido-1-{[tert-butyl(dimethyl)silyl]oxy}-2-methylpropyl)-2,2-dimethyl-1,3-oxazolidine-3-carboxylate

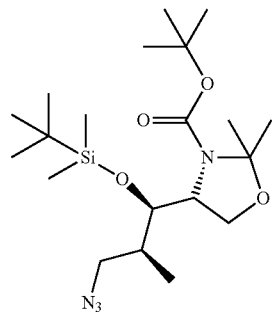

To a mixture of tert-butyl (4R)-4-((1R,2S)-1-{[tert-butyl(dimethyl)silyl]oxy}-3-hydroxy-2-methylpropyl)-2,2-dimethyl-1,3-oxazolidine-3-carboxylate (8.20 g, 20.3 mmol), diisopropyl azodicarboxylate (8.0 mL, 41 mmol) and PPh$_3$ (11 g, 41 mmol) in THF (100 mL) (0.18 M), diphenylphosphonic azide (8.8 mL, 41 mmol) was added. The mixture was stirred at room temperature overnight. The mixture was concentrated under reduced pressure, and the residue was purified by chromatography on silica gel (0-15% EtOAc/hexane) to give 5.2 g (60% yield) of the sub-title compound as a yellowish oil. LCMS calc. for $C_{20}H_{41}N_4O_4Si(M+H)^+$: m/z=429.3. found: 429.1.

Step E. tert-butyl [(1R,2R,3S)-4-azido-2-{[tert-butyl(dimethyl)silyl]oxy}-1-(hydroxymethyl)-3-methylbutyl]carbamate

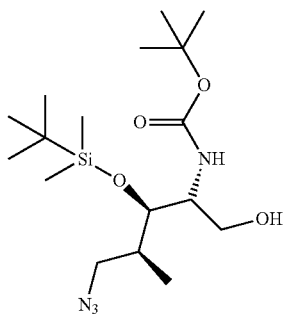

A solution of tert-butyl (4R)-4-((1R,2S)-3-azido-1-{[tert-butyl(dimethyl)silyl]oxy}-2-methylpropyl)-2,2-dimethyl-1,3-oxazolidine-3-carboxylate (10.5 g, 24.5 mmol) in EtOH (70 mL) was added pyridinium p-toluenesulfonate (12.3 g, 49.0 mmol) and the mixture was heated under reflux for 2 days.

The volatiles were removed under reduced pressure and the residue was dissolved in DCM (200 mL) (0.1 M). To the resulting solution were added DIPEA (8.53 mL, 49.0 mmol) and Boc$_2$O (6.42 g, 29.4 mmol). The reaction mixture was stirred at room temperature for 5 h. The mixture was concentrated under reduced pressure and purified by chromatography on silica gel (0-25% EtOAc/Hexane) to give 5.8 g (61% yield) of the sub-title compound as a colorless oil. LCMS calc. for $C_{12}H_{29}N_4O_2Si(M+H-Boc+H)^+$: m/z=289.2. found: 289.1.

Step F. (2R,3R,4S)-5-azido-2-[(tert-butoxycarbonyl)amino]-3-{[tert-butyl(dimethyl)silyl]oxy}-4-methylpentyl methanesulfonate

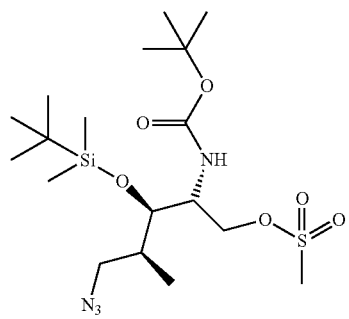

To a solution of tert-butyl [(1R,2R,3S)-4-azido-2-{[tert-butyl(dimethyl)silyl]oxy}-1-(hydroxymethyl)-3-methylbutyl]carbamate (5.80 g, 14.9 mmol) in pyridine (75 mL) at 0° C. was added methanesulfonyl chloride (1.50 mL, 19.4 mmol) and DMAP (0.36 g, 3.0 mmol). The mixture was stirred at 0° C. for 1 h. The solution was diluted with EtOAc, washed with saturated NaHCO$_3$ solution, concentrated under reduced pressure and purified by chromatography on silica gel (0-25% EtOAc/Hexane) to give 4.8 g (69% yield) of the sub-title compound as a colorless oil. LCMS calc. for $C_{13}H_{31}N_4O_4SSi(M+H-Boc)^+$: m/z=367.2. found: 367.2.

Step G. tert-butyl ((3R,4R,5S)-4-{[tert-butyl(dimethyl)silyl]oxy}-5-methylpiperidin-3-yl)carbamate

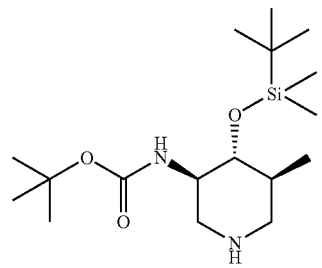 [SMILES: C[C@H]1CNC[C@@H](NC(=O)OC(C)(C)C)[C@@H]1O[Si](C)(C)C(C)(C)C]

A solution of (2R,3R,4S)-5-azido-2-[(tert-butoxycarbonyl)amino]-3-{[tert-butyl(dimethyl)silyl]oxy}-4-methylpentyl methanesulfonate (4.25 g, 9.11 mmol) in MeOH (100 mL) (0.09M) was deoxygenated with a stream of N$_2$ for 20 min. DIPEA (4.0 mL, 23 mmol) was added, followed by mixture of 10% palladium on carbon (0.97 g, 0.91 mmol). The reaction mixture was stirred under a balloon containing H$_2$ for 2 h. The solution was filtered through a pad of diatomaceous earth and rinsed with MeOH. The filtrate was concentrated under reduced pressure to give 2.10 g (66% yield) of the sub-title compound as a white solid. LCMS calc. for $C_{17}H_{37}N_2O_3Si(M+H)^+$: m/z=345.3. found: 345.1.

Step H. tert-butyl [(3R,4R,5S)-4-{[tert-butyl(dimethyl)silyl]oxy}-5-methyl-1-(3-nitropyridin-4-yl)piperidin-3-yl]carbamate

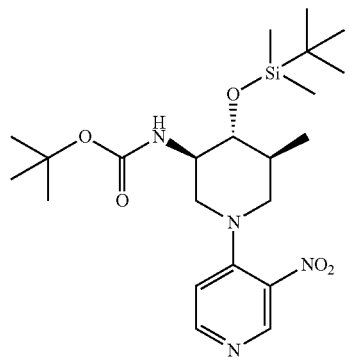 [SMILES: C[C@H]1CN(c2ccncc2[N+](=O)[O-])C[C@@H](NC(=O)OC(C)(C)C)[C@@H]1O[Si](C)(C)C(C)(C)C]

A mixture of 4-chloro-3-nitropyridine (150.0 mg, 0.9461 mmol) and tert-butyl ((3R,4R,5S)-4-{[tert-butyl(dimethyl)silyl]oxy}-5-methylpiperidin-3-yl)carbamate (300.0 mg, 0.8707 mmol) and TEA (0.3763 mL, 2.700 mmol) in i-PrOH (10.0 mL) was stirred at 60° C. for 2 h. The reaction mixture was concentrated under reduced pressure and the residue was purified by column chromatography on silica gel using CombiFlash® apparatus (eluting with 0 to 30% EtOAc in hexane) to give 100 mg (24% yield) of the sub-title compound. LCMS calc. for $C_{22}H_{39}N_4O_5Si(M+H)^+$: m/z=467.3. found: 467.1.

Step I. tert-butyl ((3R,4R,5S)-1-(3-aminopyridin-4-yl)-4-{[tert-butyl(dimethyl)silyl]oxy}-5-methylpiperidin-3-yl)carbamate A mixture of tert-butyl [(3R,4R,5S)-4-{[tert-butyl(dimethyl)silyl]oxy}-5-methyl-1-(3-nitropyridin-4-yl)piperidin-3-yl]carbamate (100.00 mg, 0.27858 mmol), AcOH (10.00 mL) and iron powder (558.4 mg, 9.999 mmol) was stirred at ambient temperature for 2 h. The mixture was diluted with 30 mL of EtOAc and filtered through a pad of diatomaceous earth. The combined organic filtrate was concentrated under reduced pressure. The residue was diluted with EtOAc and washed with aq. Na₂CO₃ solution and 0.2 M NaOH. The organic phase was concentrated under reduced pressure to give 50 mg (47% yield) of the title compound. LCMS calc. for $C_{22}H_{41}N_4O_3Si(M+H)^+$: m/z=437.3. found: 437.1.

Intermediate 17: tert-butyl ((3R,4R,5S)-1-(3-amino-5-methyl-pyridin-4-yl)-4-{[tert-butyl(dimethyl)silyl]oxy}-5-methylpiperidin-3-yl)carbamate

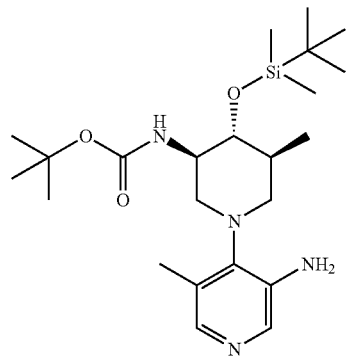 [SMILES: Cc1cncc(N)c1N1C[C@H](C)[C@@H](O[Si](C)(C)C(C)(C)C)[C@H](NC(=O)OC(C)(C)C)C1]

Step A. tert-butyl [(3R,4R,5S)-4-{[tert-butyl(dimethyl)silyl]oxy}-5-methyl-1-(3-nitro-5-methyl-pyridin-4-yl)piperidin-3-yl]carbamate

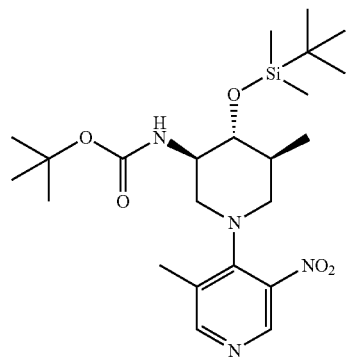

A mixture of 4-chloro-3-methyl-5-nitropyridine (110.2 mg, 0.6385 mmol), tert-butyl ((3R,4R,5S)-4-{[tert-butyl(dimethyl)silyl]oxy}-5-methylpiperidin-3-yl)carbamate (200.00 mg, 0.58044 mmol) and TEA (0.243 mL, 1.74 mmol) in i-PrOH (10.0 mL, 131 mmol) was stirred at 80° C. overnight. The reaction mixture was concentrated under reduced pressure and purified by column chromatography on silica gel using CombiFlash® apparatus (0 to 30% EtOAc in hexane) to give 178 mg (64% yield) of the sub-title compound. LCMS calc. for $C_{23}H_{41}N_4O_5Si(M+H)^+$: m/z=481.3. found: 481.1.

Step B. tert-butyl ((3R,4R,5S)-1-(3-amino-5-methyl-pyridin-4-yl)-4-{[tert-butyl(dimethyl)silyl]oxy}-5-methylpiperidin-3-yl)carbamate

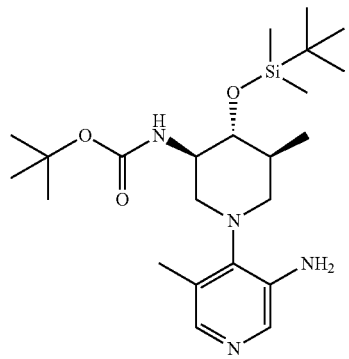 [SMILES: Cc1cncc([N+](=O)[O-])c1N1C[C@H](C)[C@@H](O[Si](C)(C)C(C)(C)C)[C@H](NC(=O)OC(C)(C)C)C1]

To a solution of tert-butyl [(3R,4R,5S)-4-{[tert-butyl(dimethyl)silyl]oxy}-5-methyl-1-(3-methyl-5-nitropyridin-4-yl)piperidin-3-yl]carbamate (150.0 mg, 0.3121 mmol) in AcOH (20 mL) and water (2 mL) was added iron (174.3 mg, 3.121 mmol). The mixture was stirred at room temperature for 2 h. The reaction mixture was diluted with EtOAc (100 mL), filtered through a diatomaceous earth pad and concentrated at 20° C. under reduced pressure. The residue was diluted with EtOAc (100 mL) again and washed with 1 M NaOH aqueous solution. The organic extract was dried over Na₂SO₄, filtered and concentrated under reduced pressure to give 120 mg (85% yield) of the title compound. LCMS calc. for $C_{23}H_{43}N_4O_3Si(M+H)^+$: m/z=451.3. found: 451.1.

Example 1

2-Amino-N-[5-(4-aminoazepan-1-yl)-1-methyl-1H-pyrazol-4-yl]thieno[3,2-b]pyridine-3-carboxamide

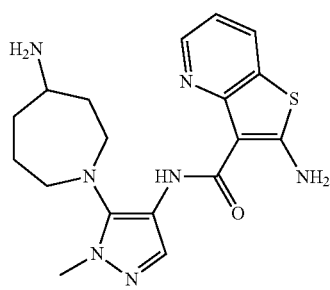 [SMILES: Cn1ncc(NC(=O)c2c(N)sc3cccnc23)c1N1CCCC(N)CC1]

Step A. Methyl 3-bromothieno[3,2-b]pyridine-2-carboxylate

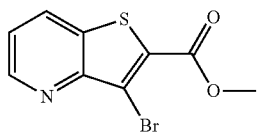

To a solution of copper (I) bromide (1.450 g, 10.10 mmol) in HBr (24 mL, 210 mmol) at 0-5° C., methyl 3-aminothieno[3,2-b]pyridine-2-carboxylate (2.00 g, 9.60 mmol) was added. To the mixture at this temperature a solution of sodium nitrite (0.796 g, 11.5 mmol) in water (12 mL) was added dropwise over 30 min. The reaction was continued at 0-5° C. for 1 h. The reaction mixture was slowly poured into iced water containing 20 g of NaHCO$_3$ and extracted with DCM (2 times). The combined organic phases were washed with water and brine, dried over Na$_2$SO$_4$, concentrated under reduced pressure to give 2.41 g (92.2% yield) of the sub-title compound as a yellow solid. LCMS calc. for C$_9$H$_7$BrNO$_2$S (M+H)$^+$: m/z=271.9. found: 272.0.

Step B. 3-Bromothieno[3,2-b]pyridine-2-carboxylic acid

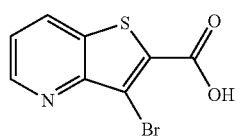 [SMILES: O=C(O)c1sc2cccnc2c1Br]

A solution of methyl 3-bromothieno[3,2-b]pyridine-2-carboxylate (2.41 g, 8.86 mmol), LiOH (0.800 g, 33.4 mmol), THF (60 mL), water (10 mL) and MeOH (10 mL) was stirred at ambient temperature for 3 h. The solution was concentrated under reduced pressure. The residue was adjusted to pH=6 with 1 M HCl. The solid formed was filtered to give 2.09 g (91.4% yield) of the sub-title compound as a yellowish solid. LCMS calc. for C$_8$H$_5$BrNO$_2$S (M+H)$^+$: m/z=257.9. found: 258.0.

Step C. tert-Butyl (3-bromothieno[3,2-b]pyridin-2-yl)carbamate

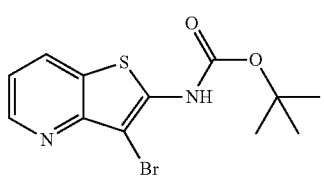 [SMILES: CC(C)(C)OC(=O)Nc1sc2cccnc2c1Br]

A mixture of 3-bromothieno[3,2-b]pyridine-2-carboxylic acid (2.060 g, 7.982 mmol), diphenylphosphonic azide (2.13 mL, 9.89 mmol) and DIPEA (1.53 mL, 8.81 mmol) in tert-butyl alcohol (20 mL) was heated under reflux overnight. The mixture was concentrated under reduced pressure and the residue was purified by column chromatography on silica gel using CombiFlash® apparatus eluting with EtOAc/hexane (50-100%). The purification gave 1.71 g (65.1% yield) of the sub-title compound as a yellow solid. LCMS calc. for C$_{12}$H$_{14}$BrN$_2$O$_2$S (M+H)$^+$: m/z=329.0. found: 329.0.

Step D. 2-[(tert-Butoxycarbonyl)amino]thieno[3,2-b]pyridine-3-carboxylic acid

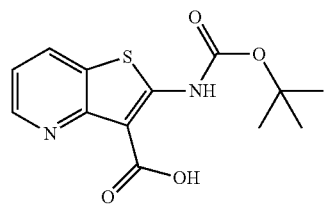 [SMILES: CC(C)(C)OC(=O)Nc1sc2cccnc2c1C(=O)O]

To a solution of tert-butyl (3-bromothieno[3,2-b]pyridin-2-yl)carbamate (0.400 g, 1.22 mmol) in THF (5 mL) at −78° C. was added 1.6 M n-BuLi in hexane (1.90 mL, 3.04 mmol). The mixture was stirred at −78° C. for 30 min. The solution was poured into dry ice. The mixture was adjusted to pH=6 with 1 M aq. HCl solution and extracted with DCM. The organic phase was washed with water and brine, dried over Na$_2$SO$_4$, filtered and concentrated under reduced pressure. The residue was purified by preparative LCMS (pH=10). The purification afforded 35 mg (9.8% yield) of the sub-title compound as a white solid. LCMS calc. for C$_{13}$H$_{15}$N$_2$O$_4$S (M+H)$^+$: m/z=295.1. found: 295.0.

Step E. 2-Amino-N-[5-(4-aminoazepan-1-yl)-1-methyl-1H-pyrazol-4-yl]-thieno[3,2-b]pyridine-3-carboxamide A mixture of tert-butyl [1-(4-amino-1-methyl-1H-pyrazol-5-yl)azepan-4-yl]carbamate (26.3 mg, 0.0849 mmol), 2-[(tert-butoxycarbonyl)amino]thieno[3,2-b]pyridine-3-carboxylic acid (25.0 mg, 0.0849 mmol), HATU (42.0 mg, 0.110 mmol) and DIPEA (44 µL, 0.25 mmol) in DMF (0.9 mL) was stirred at ambient temperature overnight and quenched with brine, and extracted with EtOAc. The organic phase was concentrated under reduced pressure and the residue was purified by preparative LCMS (pH=2) to give the intermediate, tert-butyl (3-{[(5-{4-[(tert-butoxycarbonyl)amino]azepan-1-yl}-1-methyl-1H-pyrazol-4-yl)amino]carbonyl}thieno[3,2-b]pyridin-2-yl)carbamate. LCMS calc. for C$_{28}$H$_{40}$N$_7$O$_5$S (M+H)$^+$: m/z=586.3. found: 586.1.

To the purified intermediate, DCM (0.4 mL) and TFA (0.4 mL) were added. The reaction mixture was stirred for 60 min. and then concentrated under reduced pressure. The residue was neutralized with one drop of NH$_4$OH in water to pH=8-9. Purification by preparative LCMS (pH=10) afforded the title compound as a white powder. LCMS calc. for C$_{18}$H$_{24}$N$_7$OS (M+H)$^+$: m/z=386.2. found: 386.1.

Example 2

2-Amino-N-{5-[(3S)-3-aminopiperidin-1-yl]-1-methyl-1H-pyrazol-4-yl}thieno[3,2-b]pyridine-3-carboxamide

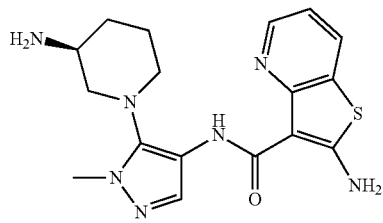 [SMILES: Cn1ncc(NC(=O)c2c(N)sc3cccnc23)c1N1CCC[C@H](N)C1]

Example 2 was synthesized by using an analogous procedure to that described in Example 1, except using Intermediate 2 instead of Intermediate 1 in Step E (Example 1). LCMS calc. for $C_{17}H_{22}N_7OS$ (M+H)$^+$: m/z=372.2. found: 372.1.

Example 3

2-Amino-N-{5-[(3R)-3-aminopiperidin-1-yl]-1-methyl-1H-pyrazol-4-yl}thieno[3,2-b]pyridine-3-carboxamide

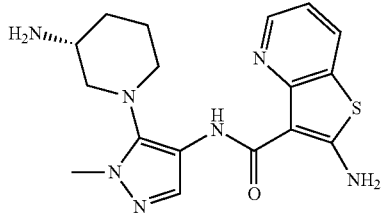 [SMILES: Cn1ncc(NC(=O)c2c(N)sc3cccnc23)c1N1CCC[C@@H](N)C1]

Example 3 was synthesized using an analogous procedure to that described in Example 1, except using Intermediate 3 instead of Intermediate 1 in Step E (Example 1). LCMS calc. for $C_{17}H_{22}N_7OS$ (M+H)$^+$: m/z=372.2. found: 372.1.

Example 4

2-Amino-N-[5-(1,4-diazepan-1-yl)-1-methyl-1H-pyrazol-4-yl]thieno[3,2-b]pyridine-3-carboxamide

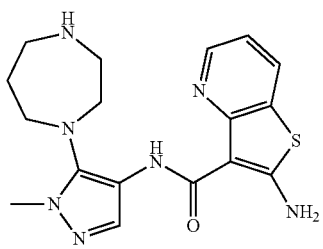 [SMILES: Cn1ncc(NC(=O)c2c(N)sc3cccnc23)c1N1CCCNCC1]

Example 4 was synthesized an analogous procedure to that described in Example 1 except using Intermediate 4 instead of Intermediate 1 in Step E (Example 1). LCMS calc. for $C_{17}H_{22}N_7OS$ (M+H)$^+$: m/z=372.2. found: 372.1.

Example 5

2-Amino-N-[5-(3-amino-2,3-dihydro-1H-inden-5-yl)-1-methyl-1H-pyrazol-4-yl]thieno[3,2-b]pyridine-3-carboxamide

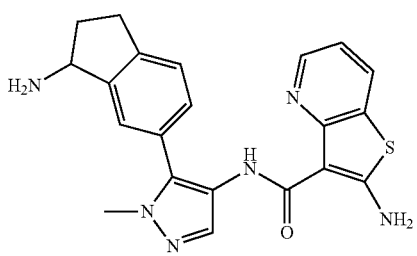 [SMILES: Cn1ncc(NC(=O)c2c(N)sc3cccnc23)c1-c1ccc2c(c1)C(N)CC2]

Example 5 was synthesized using an analogous procedure to that described in Example 1, except using Intermediate 5 instead of Intermediate 1 in Step E (Example 1). LCMS calc. for $C_{21}H_{21}N_6OS$ (M+H)$^+$: m/z=405.1. found: 405.1.

Example 6

2-Amino-N-{4-[(3S)-3-aminopiperidin-1-yl]pyridin-3-yl}thieno[3,2-b]pyridine-3-carboxamide

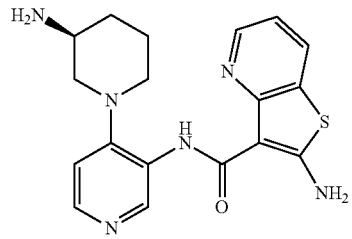

A mixture of tert-butyl [(3S)-1-(3-aminopyridin-4-yl)piperidin-3-yl]carbamate (49.7 mg, 0.170 mmol), 2-[(tert-butoxycarbonyl)amino]thieno[3,2-b]pyridine-3-carboxylic acid (50.0 mg, 0.170 mmol), HATU (83.97 mg, 0.2208 mmol) and DIPEA (0.089 mL, 0.51 mmol) in DMF (0.8 mL) was stirred at ambient temperature overnight. The reaction was quenched with brine, then extracted with EtOAc. The organic phase was concentrated under reduced pressure and the residue was purified by preparative LCMS (pH=2) to give the intermediate compound, tert-butyl (3-{[(4-{(3S)-3-[(tert-butoxycarbonyl)amino]piperidin-1-yl}pyridin-3-yl)amino]carbonyl}thieno[3,2-b]pyridin-2-yl)carbamate. LCMS calc. for $C_{28}H_{37}N_6O_5S$ (M+H)$^+$: m/z=569.3. found: 569.1.

To the purified intermediate DCM (0.8 mL) was added followed by TFA (0.8 mL). The reaction mixture was stirred at ambient temperature for 60 min. and concentrated under reduced pressure. The residue was neutralized with one drop of NH$_4$OH in water to pH=8-9. Purification by preparative LCMS (pH=10) afforded the title compound as a white powder. LCMS calc. for $C_{18}H_{21}N_6OS$ (M+H)$^+$: m/z=369.1. found: 369.1.

Example 7

2-Amino-N-{4-[(3R)-3-aminopiperidin-1-yl]pyridin-3-yl}thieno[3,2-b]pyridine-3-carboxamide

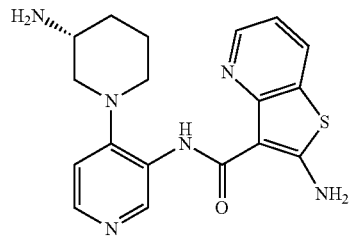 [SMILES: Nc1sc2cccnc2c1C(=O)Nc1cnccc1N1CCC[C@@H](N)C1]

Example 7 was synthesized using an analogous procedure to that described in Example 6, except using Intermediate 7 instead of Intermediate 6 (Example 6). LCMS calc. for $C_{18}H_{21}N_6OS$ (M+H)$^+$: m/z=369.1. found: 369.1.

Example 8

2-Amino-N-[4-(1,4-diazepan-1-yl)pyridin-3-yl]thieno[3,2-b]pyridine-3-carboxamide

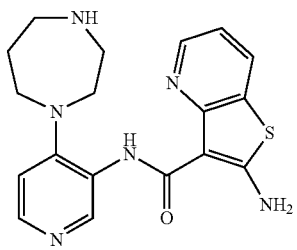 [SMILES: Nc1sc2cccnc2c1C(=O)Nc1cnccc1N1CCCNCC1]

Example 8 was synthesized using an analogous procedure to that described in Example 6, except using Intermediate 8 instead of Intermediate 6 (Example 6). LCMS calc. for $C_{18}H_{21}N_6OS$ (M+H)$^+$: m/z=369.1. found: 369.1.

Example 9

2-Amino-N-[4-(4-aminoazepan-1-yl)pyridin-3-yl]thieno[3,2-b]pyridine-3-carboxamide

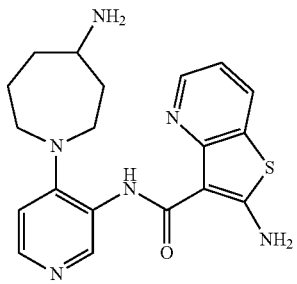 [SMILES: Nc1sc2cccnc2c1C(=O)Nc1cnccc1N1CCCC(N)CC1]

Example 9 was synthesized using an analogous procedure to that described in Example 6, except using Intermediate 9 instead of Intermediate 6 (Example 6). LCMS calc. for $C_{19}H_{23}N_6OS$ (M+H)$^+$: m/z=383.2. found: 383.1.

Example 12

2-Amino-N-{4-[(3S)-3-aminopiperidin-1-yl]pyridin-3-yl}-6-methoxythieno[3,2-b]pyridine-3-carboxamide

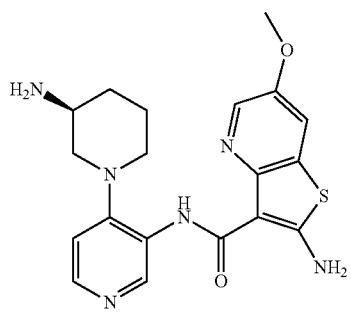 [SMILES: COc1cnc2c(C(=O)Nc3cnccc3N3CCC[C@H](N)C3)c(N)sc2c1]

Step A. 3-Chloro-5-methoxypyridine 1-oxide

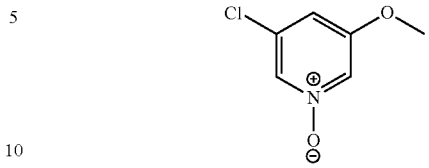

A mixture of 3-chloro-5-methoxypyridine (2.00 g, 13.9 mmol) and aq. $H_2O_2$ (30%, 4.0 mL, 39 mmol) in AcOH (8 mL) was stirred at 80° C. overnight. The mixture was allowed to cool to ambient temperature and quenched with NaHSO$_3$ solution. The mixture was concentrated under reduced pressure and saturated aq. NaHCO$_3$ (30 mL) was added to the residue. The resulting mixture was extracted with DCM (3 times). The combined organic phases were washed with saturated aq. NaHCO$_3$, water and brine, dried over Na$_2$SO$_4$, filtered and concentrated under reduced pressure to give 2.12 g (95.4% yield) of the sub-title compound as a pink solid. LCMS calc. for $C_6H_7ClNO_2$ (M+H)$^+$: m/z=160.0. found: 160.1.

Step B. 3-Chloro-5-methoxypyridine-2-carbonitrile

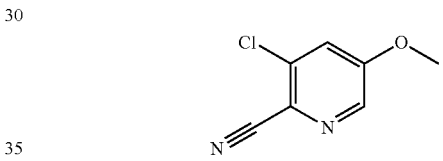

A mixture of 3-chloro-5-methoxypyridine 1-oxide (2.20 g, 13.8 mmol), trimethylsilyl cyanide (4.41 mL, 33.1 mmol) and TEA (3.84 mL, 27.6 mmol) in MeCN (20 mL) was heated under reflux overnight. The reaction mixture was concentrated under reduced pressure and the residue was partitioned between EtOAc and 10% aqueous Na$_2$CO$_3$. The organic phase was washed with water and brine, dried over Na$_2$SO$_4$, filtered and concentrated under reduced pressure to give 2.2 g (94.6% yield) of the sub-title compound as a tan solid. LCMS calc. for $C_7H_6ClN_2O$ (M+H)$^+$: m/z=169.0. found: 169.1.

Step C. Methyl 3-amino-6-methoxythieno[3,2-b]pyridine-2-carboxylate

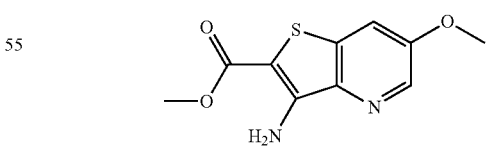

To a solution of 3-chloro-5-methoxypyridine-2-carbonitrile (2.10 g, 12.4 mmol) in MeCN (20 mL) was added 2-mercaptoacetic acid methyl ester (1.18 mL, 13.1 mmol) and potassium carbonate (3.44 g, 24.9 mmol). The mixture was heated under reflux for 2 h, then filtered and rinsed with MeCN. The filtrate was concentrated under reduced pressure and the residue was purified by column chromatography on silica gel using CombiFlash® apparatus eluting with EtOAc/hexane (0-70%). The purification gave 2.6 g (87.3% yield) of the sub-title compound as a yellow solid. LCMS calc. for $C_{10}H_{11}N_2O_3S$ (M+H)$^+$: m/z=239.0. found: 239.1.

Step D. Methyl 3-bromo-6-methoxythieno[3,2-b]pyridine-2-carboxylate

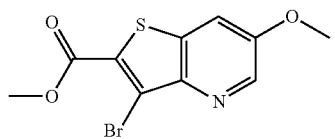

To a suspension of copper (I) bromide (1.58 g, 11.0 mmol) in HBr (26 mL, 230 mmol) at 0-5° C. was added methyl 3-amino-6-methoxythieno[3,2-b]pyridine-2-carboxylate (2.50 g, 10.5 mmol). To the mixture at this temperature was added a solution of sodium nitrite (0.870 g, 12.6 mmol) in water (13 mL) dropwise over 30 min. The reaction was continued at 0-5° C. for 1 h. The reaction mixture was slowly poured into iced water containing 20 g of NaHCO$_3$. The mixture was extracted with DCM (2 times). The combined organic phases were washed with water and brine, dried over Na$_2$SO$_4$ and concentrated under reduced pressure. The residue was purified by column chromatography on silica gel using CombiFlash® apparatus eluting with EtOAc/hexane (50-100%). The purification gave 0.25 g (7.9% yield) of the sub-title compound as a yellow solid. LCMS calc. for $C_{10}H_9BrNO_3S$ (M+H)$^+$: m/z=301.9. found: 301.9.

Step E. 3-Bromo-6-methoxythieno[3,2-b]pyridine-2-carboxylic acid

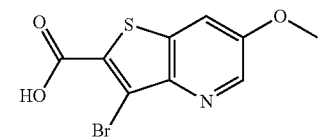

A mixture of methyl 3-bromo-6-methoxythieno[3,2-b]pyridine-2-carboxylate (0.250 g, 0.827 mmol), LiOH (0.158 g, 6.62 mmol), water (3 mL), THF (6 mL) and MeOH (3 mL) was stirred at ambient temperature for 2 h. The mixture was concentrated under reduced pressure and the residue was neutralized to pH=4-5 with 1 M aq. HCl. The solid formed was filtered to give 0.175 g (73.4% yield) of the sub-title compound as a tan solid. LCMS calc. for $C_9H_7BrNO_3S$ (M+H)$^+$: m/z=287.9. found: 287.9.

Step F. tert-Butyl (3-bromo-6-methoxythieno[3,2-b]pyridin-2-yl)carbamate

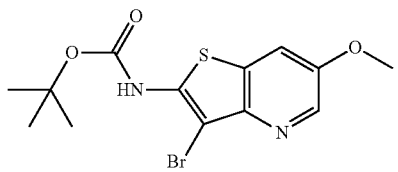 [SMILES: COc1cnc2c(Br)c(NC(=O)OC(C)(C)C)sc2c1]

A mixture of 3-bromo-6-methoxythieno[3,2-b]pyridine-2-carboxylic acid (175.0 mg, 0.6074 mmol), diphenylphosphonic azide (0.162 mL, 0.753 mmol) and DIPEA (117 µL, 0.670 mmol) in tert-butyl alcohol (4 mL) was heated under reflux overnight. The mixture was concentrated under reduced pressure and the residue was dissolved in DCM. The resulting solution was washed with 1 M aq. NaOH, water and brine, dried over Na$_2$SO$_4$, filtered and concentrated under reduced pressure. The residue was purified by column chromatography on silica gel using CombiFlash® apparatus eluting with EtOAc/hexane (0-50%). The purification gave 85.7 mg (40.1% yield) of the sub-title compound as a yellow solid. LCMS calc. for $C_{13}H_{16}BrN_2O_3S$ (M+H)$^+$: m/z=359.0. found: 359.0.

Step G. 2-[(tert-Butoxycarbonyl)amino]-6-methoxythieno[3,2-b]pyridine-3-carboxylic acid

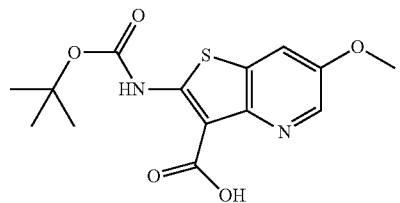 [SMILES: COc1cnc2c(C(=O)O)c(NC(=O)OC(C)(C)C)sc2c1]

To a solution of tert-butyl (3-bromo-6-methoxythieno[3,2-b]pyridin-2-yl)carbamate (87.0 mg, 0.242 mmol) in THF (3 mL) at −78° C. was added 1.6 M n-BuLi in hexane (0.378 mL, 0.605 mmol). The reaction mixture was stirred at −78° C. for 30 min. The solution was poured into dry ice. The mixture was adjusted to pH=4-5 with 1 M HCl and extracted with DCM. The organic phase was washed with water, dried over Na$_2$SO$_4$, filtered and concentrated under reduced pressure. The residue was purified by preparative LCMS (pH=10). The purification afforded the sub-title compound as a white solid. LCMS calc. for $C_{14}H_{17}N_2O_5S$ (M+H)$^+$: m/z=325.1. found: 325.1.

Step H. 2-Amino-N-{4-[(3S)-3-aminopiperidin-1-yl]pyridin-3-yl}-6-methoxythieno[3,2-b]pyridine-3-carboxamide A mixture of tert-butyl [(3S)-1-(3-aminopyridin-4-yl)piperidin-3-yl]carbamate (7.89 mg, 0.0270 mmol), 2-[(tert-butoxycarbonyl)amino]-6-methoxythieno[3,2-b]pyridine-3-carboxylic acid (8.76 mg, 0.0270 mmol), HATU (13.34 mg, 0.03509 mmol) and DIPEA (0.014 mL, 0.081 mmol) in DMF (1 mL) was stirred at ambient temperature overnight. The mixture was quenched with brine, extracted with EtOAc. The organic phase was concentrated under reduced pressure and the residue was purified by preparative LCMS (pH=2) to give the intermediate compound, tert-butyl ((3S)-1-{3-[({2-[(tert-butoxycarbonyl)amino]-6-methoxythieno[3,2-b]pyridin-3-yl}carbonyl)amino]pyridin-4-yl}piperidin-3-yl)carbamate. LCMS calc. for $C_{29}H_{39}N_6O_6S$ (M+H)$^+$: m/z=599.1. found: 599.1.

The above purified intermediate was added DCM (1 mL) and TFA (1 mL). The reaction mixture was stirred at ambient temperature for 60 min and concentrated under reduced pressure. The residue was neutralized with one drop of NH₄OH in water to pH=8-9. Purification by preparative LCMS (pH=10) afforded the title compound as a white powder. LCMS calc. for $C_{20}H_{23}N_6OS$ $(M+H)^+$: m/z=399.2. found: 399.1.

Example 13

2-Amino-N-[5-(4-aminoazepan-1-yl)-1-methyl-1H-pyrazol-4-yl]-6-methoxythieno[3,2-b]pyridine-3-carboxamide

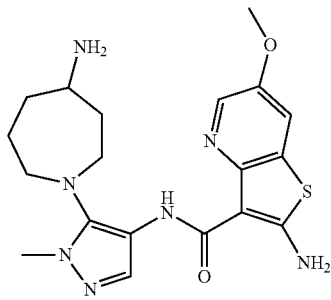 [SMILES: COc1cnc2c(C(=O)Nc3cnn(C)c3N3CCCC(N)CC3)c(N)sc2c1]

Example 13 was synthesized using an analogous procedure to that described in Example 12, except using Intermediate 1 instead of Intermediate 6 in Step H (Example 12). LCMS calc. for $C_{19}H_{26}N_7O_2S$ $(M+H)^+$: m/z=416.2. found: 416.1.

Example 14

2-Amino-N-{4-[(3S)-3-aminopiperidin-1-yl]pyridin-3-yl}-6-cyclopropoxythieno[3,2-b]pyridine-3-carboxamide

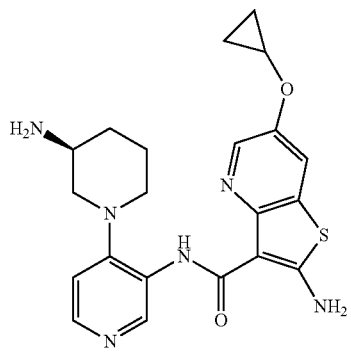 [SMILES: Nc1sc2cc(OC3CC3)cnc2c1C(=O)Nc1cnccc1N1CCC[C@H](N)C1]

Example 14 was synthesized using an analogous procedure to that described in Example 12, except using 3-chloro-5-cyclopropoxypyridine instead of 3-chloro-5-methoxypyridine in Step A (Example 12). LCMS calc. for $C_{21}H_{25}N_6O_2S$ $(M+H)^+$: m/z=425.2. found: 425.1.

Example 15

2-Amino-N-{4-[(3S,5R)-3-amino-5-methyl-piperidin-1-yl]pyridin-3-yl}-thieno[3,2-b]pyridine-3-carboxamide

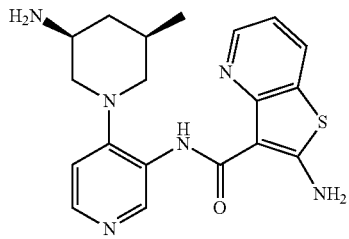 [SMILES: C[C@@H]1C[C@H](N)CN(c2ccncc2NC(=O)c2c(N)sc3cccnc23)C1]

Example 15 was synthesized using an analogous procedure to that described in Example 12, except using Intermediate 15 instead of Intermediate 6 in Step H (Example 12). LCMS calc. for $C_{19}H_{23}N_6OS$ $(M+H)^+$: m/z=383.2. found: 383.1; ¹H NMR (400 MHz, DMSO) δ 9.37 (s, 1H), 8.63 (s, 1H), 8.37 (d, J=3.6 Hz, 1H), 8.16 (d, J=5.3 Hz, 1H), 8.14 (d, J=7.9 Hz, 1H), 7.13 (dd, J=7.9, 4.9 Hz, 1H), 7.09 (d, J=5.3 Hz, 1H), 3.44-3.15 (m, 1H), 3.15-2.96 (m, 2H), 2.32-2.06 (m, 2H), 2.06-1.76 (m, 2H), 1.62-0.92 (m, 1H), 0.82 (d, J=6.4 Hz, 3H).

Example 16

2-Amino-N-{4-[(3S)-3-aminopiperidin-1-yl]pyridin-3-yl}-7-methoxythieno[3,2-b]pyridine-3-carboxamide

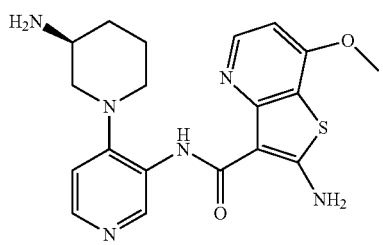 [SMILES: COc1ccnc2c(C(=O)Nc3cnccc3N3CCC[C@H](N)C3)c(N)sc12]

Step A. 3-Chloro-4-methoxypyridine

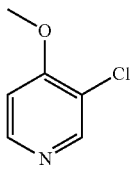

A solution of 2.0 M trimethylsilyldiazomethane in hexane (21.9 mL, 43.8 mmol) was added slowly to a suspension of 3-chloropyridin-4-ol (4.00 g, 30.9 mmol) in toluene (213.9 mL) and MeOH (32.1 mL) at 0° C. After 30 min. at 0° C., the reaction mixture was warmed to room temperature and stirred for 64 h. Aqueous AcOH was added and then enough saturated aq. Na₂CO₃ was added to bring the pH to 7.5.

The layers were separated and the aqueous phase was extracted with EtOAc. The combined organic phase was dried over Na₂SO₄, filtered and concentrated under reduced pressure. The resulting brown oil was purified on 40 g silica gel (2:1 DCM/EtOAc) to afford 2.5 g (56% yield) of the sub-title compound. LCMS calc. for C₆H₇ClNO (M+H)⁺: m/z=144.0. found: 144.1.

Step B. 3-Chloro-4-methoxypyridine 1-oxide

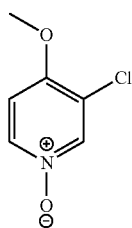

A solution of 3-chloro-4-methoxypyridine (2.5 g, 17 mmol) and mCPBA (5.87 g, 34.0 mmol) in DCM (100 mL) was stirred at room temperature overnight. The reaction mixture was washed with 1 M aq. NaOH (3 times), brine, dried over Na₂SO₄, filtered and concentrated under reduced pressure to give 2.2 g (79% yield) of the sub-title compound. LCMS calc. for C₆H₇ClNO₂ (M+H)⁺: m/z=160.0. found: 160.1.

Step C. 3-Chloro-4-methoxypyridine-2-carbonitrile

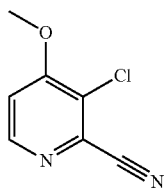

A mixture of 3-chloro-4-methoxypyridine 1-oxide (2.0 g, 12.5 mmol), trimethylsilyl cyanide (4.178 mL, 31.33 mmol) and TEA (3.717 mL, 26.67 mmol) in MeCN (33 mL) was heated under reflux overnight. The reaction mixture was concentrated under reduced pressure and the residue was partitioned between EtOAc and 10% aqueous Na₂CO₃. The organic phase was washed with water and brine, dried over Na₂SO₄, filtered and concentrated under reduced pressure to give 1.95 g (92.3% yield) of the sub-title compound as a tan solid. LCMS calc. for C₇H₆ClN₂O (M+H)⁺: m/z=169.0. found: 169.1.

Step D. Methyl 3-amino-7-methoxythieno[3,2-b]pyridine-2-carboxylate

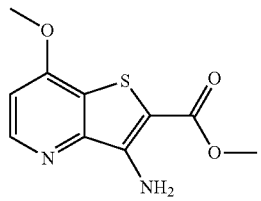 [SMILES: COC(=O)c1sc2c(OC)ccnc2c1N]

To a solution of 3-chloro-4-methoxypyridine-2-carbonitrile (3.0 g, 17.8 mmol) in MeCN (50.0 mL, 957 mmol) was added 2-mercaptoacetic acid methyl ester (1.76 mL, 19.58 mmol) and potassium carbonate (4.975 g, 36.00 mmol). The mixture was heated under reflux for 2 h, then filtered and rinsed with MeCN. The filtrate was concentrated under reduced pressure and the residue was purified by column chromatography on silica gel using CombiFlash® apparatus eluting with EtOAc/hexane (0-70%). The purification gave 3.5 g (82% yield) of the sub-title compound as a yellow solid. LCMS calc. for C₁₀H₁₁N₂O₃S (M+H)⁺: m/z=239.0. found: 239.1.

Step E. Methyl 3-bromo-7-methoxythieno[3,2-b]pyridine-2-carboxylate

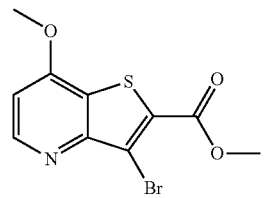 [SMILES: COC(=O)c1sc2c(OC)ccnc2c1Br]

To a suspension of copper (I) bromide (0.949 g, 6.62 mmol) in 48% HBr (15.79 mL, 139.6 mmol) at 0-5° C. was added methyl 3-amino-7-methoxythieno[3,2-b]pyridine-2-carboxylate (1.5 g, 6.3 mmol). To the mixture at this temperature was added a solution of sodium nitrite (522 mg, 7.57 mmol) in water (13 mL) dropwise over 30 min. The reaction was continued at 0-5° C. for 1 h. The reaction mixture was poured into iced water containing 20 g of NaHCO₃ slowly. The mixture was extracted with DCM (2 times). The combined organic phases were washed with water and brine, dried over Na₂SO₄ and concentrated under reduced pressure. The residue was purified by column chromatography on silica gel using CombiFlash® apparatus eluting with EtOAc/hexane (50-100%). The purification gave 1.5 g (79% yield) of the sub-title compound as a yellow solid. LCMS calc. for C₁₀H₉BrNO₃S (M+H)⁺: m/z=301.9. found: 302.0.

Step F. 3-Bromo-7-methoxythieno[3,2-b]pyridine-2-carboxylic acid

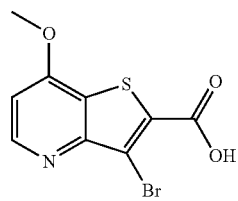

A mixture of methyl 3-bromo-7-methoxythieno[3,2-b]pyridine-2-carboxylate (1.7 g, 5.6 mmol), LiOH.H₂O (1.181 g, 28.14 mmol) in THF (51.0 mL, 629 mmol), MeOH (25.50 mL, 629.5 mmol) and water (8.50 mL, 472 mmol) was stirred at ambient temperature for 2 h. The mixture was concentrated under reduced pressure and the residue was neutralized to pH=4-5 with 1 M HCl. The solid that formed was filtered to give 1.5 g (92% yield) of the sub-title compound as a tan solid. LCMS calc. for C₉H₇BrNO₃S (M+H)⁺: m/z=287.9. found: 287.9.

Step G. tert-Butyl (3-bromo-7-methoxythieno[3,2-b]pyridin-2-yl)carbamate

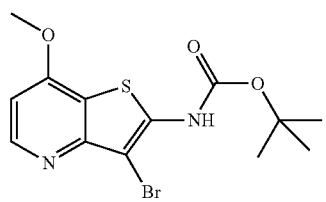 [SMILES: COc1ccnc2c(Br)c(NC(=O)OC(C)(C)C)sc12]

A mixture of 3-bromo-7-methoxythieno[3,2-b]pyridine-2-carboxylic acid (600 mg, 2.08 mmol), diphenylphosphonic azide (0.5385 mL, 2.499 mmol) and DIPEA (0.3988 mL, 2.290 mmol) in tert-butyl alcohol (19 mL) was heated under reflux overnight. The mixture was concentrated under reduced pressure and the residue was dissolved in DCM. The resulting solution was washed with 1 M aq. NaOH, water and brine, dried over Na₂SO₄, filtered and concentrated under reduced pressure. The residue was purified by column chromatography on silica gel using CombiFlash® apparatus eluting with EtOAc/hexane (0-50%). The purification gave 531 mg (71% yield) of the sub-title compound as a yellow solid. LCMS calc. for C₁₃H₁₆BrN₂O₃S (M+H)⁺: m/z=359.0. found: 359.0.

Step H. 2-[(tert-Butoxycarbonyl)amino]-7-methoxythieno[3,2-b]pyridine-3-carboxylic acid

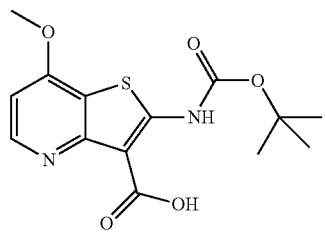 [SMILES: COc1ccnc2c(C(=O)O)c(NC(=O)OC(C)(C)C)sc12]

To a solution of tert-butyl (3-bromo-7-methoxythieno[3,2-b]pyridin-2-yl)carbamate (1.2 g, 3.34 mmol) in THF (60 mL) at −78° C. was added 1.6 M n-BuLi in hexane (5.2 mL). The reaction mixture was stirred at −78° C. for 30 min. The solution was poured into dry ice. The mixture was adjusted to pH=4-5 with 1 M HCl and extracted with DCM. The organic phase was washed with water, dried over Na₂SO₄, filtered and concentrated under reduced pressure. The residue was purified by preparative LCMS (pH=10). The purification afforded 311 mg (28.7% yield) of the sub-title compound as a white solid. LCMS calc. for C₁₄H₁₇N₂O₅S (M+H)⁺: m/z=325.1. found: 325.1.

Step I: 2-Amino-N-{4-[(3S)-3-aminopiperidin-1-yl]pyridin-3-yl}-7-methoxythieno[3,2-b]pyridine-3-carboxamide A solution of 2-[(tert-butoxycarbonyl)amino]-7-methoxythieno[3,2-b]pyridine-3-carboxylic acid (16.33 mg, 0.05035 mmol), HATU (23.08 mg, 0.06070 mmol), tert-butyl [(3S)-1-(3-aminopyridin-4-yl)piperidin-3-yl]carbamate (14.72 mg, 0.05035 mmol) and DIPEA (13.01 mg, 0.1007 mmol) in DMF (2.0 mL, 26 mmol) was stirred at room temperature overnight. Direct purification on preparative HPLC (pH=10) afforded the intermediate compound, tert-butyl ((3S)-1-{3-[({2-[(tert-butoxycarbonyl)amino]-7-methoxythieno[3,2-b]pyridin-3-yl}carbonyl)amino]pyridin-4-yl}piperidin-3-yl)carbamate. LCMS calc. for C₂₉H₃₉N₆O₆S (M+H)⁺: m/z=599.3. found: 599.1.

The above purified intermediate was dissolved in TFA (1.0 mL) and DCM (1.0 mL). The reaction mixture was stirred at room temperature for 60 min. Direct purification on Preparative HPLC (pH=10) afforded the title compound. LCMS calc. for C₁₉H₂₃N₆O₂S (M+H)⁺: m/z=399.2. found: 399.1.

Example 17

2-Amino-N-[5-(4-aminoazepan-1-yl)-1-methyl-1H-pyrazol-4-yl]-7-methoxythieno[3,2-b]pyridine-3-carboxamide

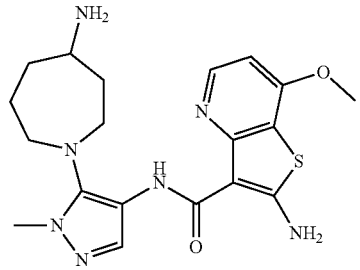 [SMILES: COc1ccnc2c(C(=O)Nc3cnn(C)c3N3CCCC(N)CC3)c(N)sc12]

Example 17 was synthesized by using an analogous procedure to that described in Example 16, except using Intermediate 1 instead of Intermediate 6 in Step H (Example 12). LCMS calc. for C₁₉H₂₆N₇O₂S (M+H)⁺: m/z=416.2. found: 416.1.

Example 18

2-Amino-N-{4-[(3S)-3-aminopiperidin-1-yl]pyridin-3-yl}-7-isopropoxythieno[3,2-b]pyridine-3-carboxamide

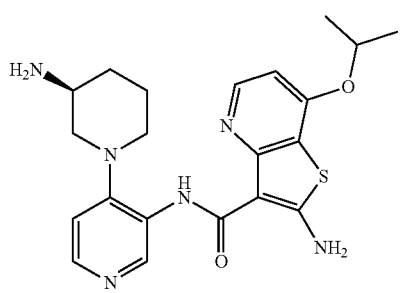 [SMILES: CC(C)Oc1ccnc2c(C(=O)Nc3cnccc3N3CCC[C@H](N)C3)c(N)sc12]

Step A. 3-Chloro-4-isopropoxypyridine 1-oxide

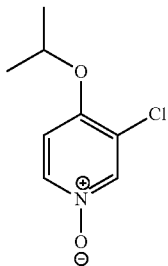

To a solution of sodium isopropoxide (5.64 g, 68.8 mmol) in i-PrOH (240 mL, 3100 mmol) was added 3-chloro-4-nitropyridine 1-oxide (8.00 g, 45.8 mmol). The reaction mixture was stirred at ambient temperature for 1 h. The reaction mixture was concentrated under reduced pressure and the residue was diluted with water. The mixture was extracted with DCM (2 times). The combined organic phases were washed with water and brine, dried over $Na_2SO_4$, filtered and concentrated under reduced pressure to give 8.5 g (98.8% yield) of the sub-title compound as a brown oil. LCMS calc. for $C_8H_{11}ClNO_2$ $(M+H)^+$: m/z=188.0. found: 188.1.

Step B. 3-Chloro-4-isopropoxypyridine-2-carbonitrile

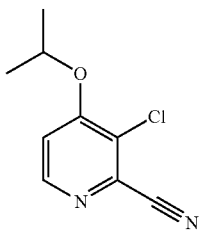

A mixture of 3-chloro-4-isopropoxypyridine 1-oxide (8.50 g, 45.3 mmol), trimethylsilyl cyanide (14.5 mL, 109 mmol) and TEA (12.6 mL, 90.6 mmol) in MeCN (70 mL, 1000 mmol) was heated under reflux overnight. The reaction mixture was concentrated under reduced pressure and the residue was partitioned between EtOAc and 10% aqueous $Na_2CO_3$. The organic phase was washed with water and brine, dried over $Na_2SO_4$ and concentrated under reduced pressure to give 8.75 g (98.2% yield) of the sub-title compound as a brown oil. LCMS calc. for $C_9H_{10}ClN_2O$ $(M+H)^+$: m/z=197.0. found: 197.1.

Step C. Methyl 3-amino-7-isopropoxythieno[3,2-b]pyridine-2-carboxylate

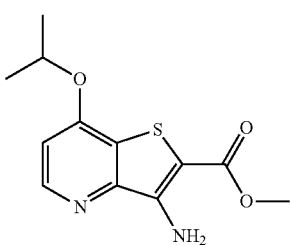 [SMILES: COC(=O)c1sc2c(OC(C)C)ccnc2c1N]

To a solution of 3-chloro-4-isopropoxypyridine-2-carbonitrile (8.75 g, 44.5 mmol) in MeCN (70 mL, 1000 mmol) was added 2-mercaptoacetic acid methyl ester (4.20 mL, 46.7 mmol) and potassium carbonate (12.3 g, 89.0 mmol). The mixture was heated under reflux for 2 h and filtered, rinsed with MeCN. The filtrate was concentrated under reduced pressure. The residue was purified by column chromatography on silica gel using CombiFlash® apparatus eluting with EtOAc/hexane (0-70%). The purification gave 3.98 g (33.6% yield) of the sub-title compound as a yellow solid. LCMS calc. for $C_{12}H_{15}N_2O_3S$ $(M+H)^+$: m/z=267.1. found: 267.1.

Step D. Methyl 3-bromo-7-isopropoxythieno[3,2-b]pyridine-2-carboxylate

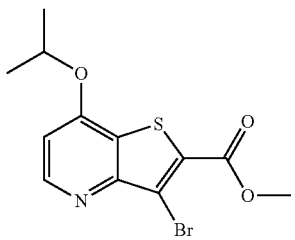 [SMILES: COC(=O)c1sc2c(OC(C)C)ccnc2c1Br]

To a mixture of methyl 3-amino-7-isopropoxythieno[3,2-b]pyridine-2-carboxylate (3.40 g, 12.8 mmol) in HBr (40 mL, 400 mmol) at 0-5° C. was added copper (I) bromide (1.92 g, 13.4 mmol). To the mixture at 0-5° C. was added a solution of sodium nitrite (1.06 g, 15.3 mmol) in water (32 mL, 1800 mmol) in 30 min. The reaction mixture was stirred at 0-5° C. for 1 h. The mixture was poured to iced water containing 30 g of $NaHCO_3$ slowly. The mixture was extracted with DCM (2 times). The combined organic phases were washed with water and brine, dried over $Na_2SO_4$, concentrated under reduced pressure. The residue was purified by column chromatography on silica gel using CombiFlash® apparatus eluting with EtOAc/hexane (10-70%). The purification gave 2.25 g (53.4% yield) of the sub-title compound as a yellow solid. LCMS calc. for $C_{12}H_{13}BrNO_3S$ $(M+H)^+$: m/z=330.0. found: 330.0.

Step E. 3-Bromo-7-isopropoxythieno[3,2-b]pyridine-2-carboxylic acid

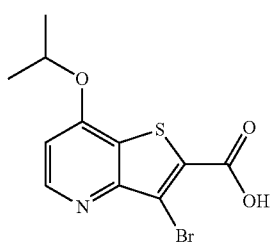 [SMILES: CC(C)Oc1ccnc2c(Br)c(C(=O)O)sc12]

A mixture of methyl 3-bromo-7-isopropoxythieno[3,2-b]pyridine-2-carboxylate (2.25 g, 6.81 mmol), LiOH (1.63 g, 68.1 mmol), THF (30 mL, 400 mmol), MeOH (15 mL, 370 mmol) and water (15 mL, 830 mmol) was stirred at ambient temperature for 2 h. The volatile was removed and the residue was adjusted to pH=4-5 with 1 M HCl. The solid that formed was filtered, rinsed with water and dried under reduced pressure to give 1.82 g (84.5% yield) of the sub-title compound as a yellow solid. LCMS calc. for $C_{11}H_{11}BrNO_3S$ (M+H)⁺: m/z=316.0. found: 316.0.

Step F. tert-Butyl (3-bromo-7-isopropoxythieno[3,2-b]pyridin-2-yl)carbamate

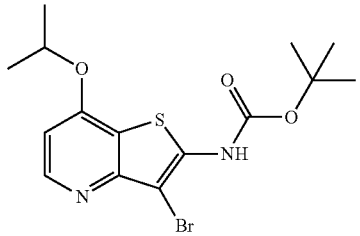 [SMILES: CC(C)Oc1ccnc2c(Br)c(NC(=O)OC(C)(C)C)sc12]

A mixture of 3-bromo-7-isopropoxythieno[3,2-b]pyridine-2-carboxylic acid (1.30 g, 4.11 mmol), diphenylphosphonic azide (1.10 mL, 5.10 mmol) and DIPEA (0.790 mL, 4.54 mmol) in tert-butyl alcohol (10 mL, 100 mmol) was heated under reflux overnight. The mixture was concentrated under reduced pressure and the residue was dissolved in DCM. The resulting solution was washed with 1 M aq. NaOH, brine, dried over $Na_2SO_4$ and concentrated under reduced pressure. The residue was purified by column chromatography on silica gel using CombiFlash® apparatus eluting with EtOAc/hexane (10-60%). The purification gave 1.05 g (65.9% yield) of the sub-title compound as a yellow solid. LCMS calc. for $C_{15}H_{20}BrN_2O_3S$ (M+H)⁺: m/z=387.0. found: 387.0.

Step G. Methyl 2-[(tert-butoxycarbonyl)amino]-7-isopropoxythieno[3,2-b]pyridine-3-carboxylate

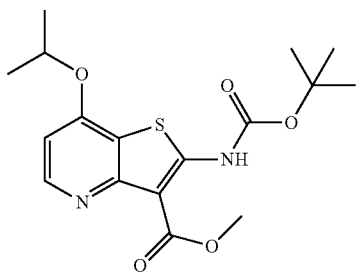 [SMILES: COC(=O)c1c(NC(=O)OC(C)(C)C)sc2c(OC(C)C)ccnc12]

To a mixture of tert-butyl (3-bromo-7-isopropoxythieno[3,2-b]pyridin-2-yl)carbamate (0.600 g, 1.55 mmol) in MeOH (10 mL, 300 mmol) was added TEA (0.432 mL, 3.10 mmol) and [1,1'-bis(diphenylphosphino)ferrocene]dichloropalladium(II), complex with dichloromethane (1:1) (0.126 g, 0.155 mmol). The mixture was heated under reflux under CO overnight. The mixture was concentrated under reduced pressure. The residue was purified by flash chromatography on silica gel eluted by EtOAc/hexane (10-70%). The purification gave 0.412 g (72.6% yield) of the sub-title compound as a yellowish oil. LCMS calc. for $C_{17}H_{23}N_2O_5S$ (M+H)⁺: m/z=367.1. found: 367.1.

Step H. 2-[(tert-Butoxycarbonyl)amino]-7-isopropoxythieno[3,2-b]pyridine-3-carboxylic acid

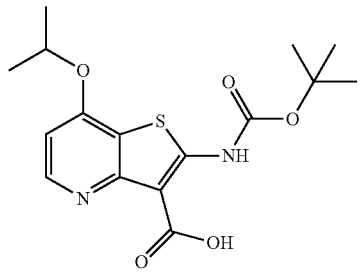 [SMILES: CC(C)Oc1ccnc2c(C(=O)O)c(NC(=O)OC(C)(C)C)sc12]

A mixture of methyl 2-[(tert-butoxycarbonyl)amino]-7-isopropoxythieno[3,2-b]pyridine-3-carboxylate (0.410 g, 1.12 mmol), LiOH (0.5 g, 20 mmol), THF (10 mL, 100 mmol), MeOH (5 mL, 100 mmol) and water (5 mL, 300 mmol) was stirred at 100° C. for 2 h. The mixture was concentrated under reduced pressure and the residue was adjusted to pH=4-5 with 1 M aq. HCl. The resulting mixture was extracted with EtOAc (2 times). The combined organic phases were washed with water and brine, dried over $Na_2SO_4$ and concentrated under reduced pressure. The residue was purified by preparative LCMS (pH=2). The purification gave 150 mg (38% yield) of the sub-title compound as a white powder. LCMS calc. for $C_{16}H_{21}N_2O_5S$ (M+H)⁺: m/z=353.1. found: 353.1.

Step I. 2-Amino-N-{4-[(3S)-3-aminopiperidin-1-yl]pyridin-3-yl}-7-isopropoxythieno[3,2-b]pyridine-3-carboxamide A mixture of tert-butyl [(3S)-1-(3-aminopyridin-4-yl)piperidin-3-yl]carbamate (8.30 mg, 0.0284 mmol), 2-[(tert-butoxycarbonyl)amino]-7-isopropoxythieno[3,2-b]pyridine-3-carboxylic acid (10.0 mg, 0.0284 mmol), HATU (14.03 mg, 0.03689 mmol) and DIPEA (0.015 mL, 0.085 mmol) in DMF (0.5 mL, 6 mmol) was stirred at ambient temperature overnight. The mixture was quenched with brine, extracted with EtOAc. The organic phases were concentrated under reduced pressure and the residue was purified by preparative LCMS (pH=2) to give tert-butyl ((3S)-1-{3-[({2-[(tert-butoxycarbonyl)amino]-7-isopropoxythieno[3,2-b]pyridin-3-yl}carbonyl)amino]pyridin-4-yl}piperidin-3-yl)carbamate. LCMS calc. for $C_{31}H_{43}N_6O_6S$ (M+H)⁺: m/z=627.3. found: 627.1.

The above purified intermediate was added DCM (0.5 mL, 8 mmol) and TFA (0.5 mL, 6 mmol). The reaction mixture was concentrated under reduced pressure and the residue was neutralized with one drop of NH₄OH in water to pH=8-9. Purification by preparative LCMS (pH=10)

afforded the title compound as a white powder. LCMS calc. for $C_{21}H_{27}N_6O_2S$ (M+H)$^+$: m/z=427.2. found: 427.0.

Example 19

2-Amino-N-[5-(4-aminoazepan-1-yl)-1-methyl-1H-pyrazol-4-yl]-7-isopropoxythieno[3,2-b]pyridine-3-carboxamide

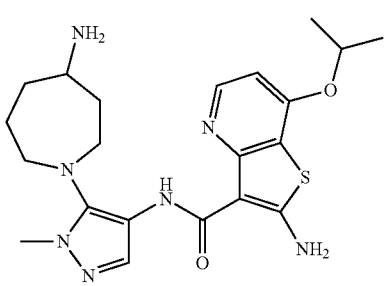 [SMILES: CC(C)Oc1ccnc2c(C(=O)Nc3cnn(C)c3N3CCCC(N)CC3)c(N)sc12]

Example 19 was synthesized by using the an analogous procedure to that described in Example 18, except using Intermediate 1 instead of Intermediate 6 in Step I (Example 18). LCMS calc. for $C_{21}H_{30}N_7O_2S$ (M+H)$^+$: m/z=444.2. found: 444.1.

Example 20

2-Amino-N-{4-[(3S)-3-aminopiperidin-1-yl]pyridin-3-yl}-7-ethoxythieno[3,2-b]pyridine-3-carboxamide

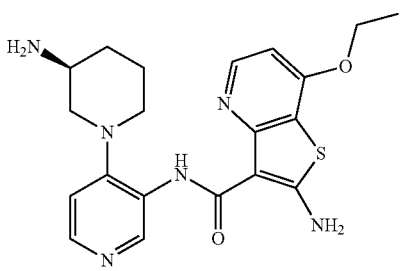 [SMILES: CCOc1ccnc2c(C(=O)Nc3cnccc3N3CCC[C@H](N)C3)c(N)sc12]

Example 20 was synthesized using an analogous procedure to that described in Example 18, except that sodium ethoxide was used instead of sodium isopropoxide in Step A (Example 18). LCMS calc. for $C_{20}H_{25}N_6O_2S$ (M+H)$^+$: m/z=413.2. found: 413.0; $^1$H NMR (300 MHz, DMSO) δ 9.56 (s, 1H), 8.79 (s, 1H), 8.58 (d, J=5.8 Hz, 1H), 8.40 (d, J=5.3 Hz, 1H), 7.30 (d, J=5.3 Hz, 1H), 7.13 (d, J=5.9 Hz, 1H), 4.54 (q, J=7.0 Hz, 2H), 3.48-3.33 (m, 1H), 3.35-3.21 (m, 1H), 3.21-3.07 (m, 1H), 2.89-2.79 (m, 1H), 2.63-2.46 (m, 1H), 2.19-2.01 (m, 1H), 2.01-1.75 (m, 2H), 1.63 (t, J=7.0 Hz, 3H), 1.44-1.21 (m, 1H).

Example 22

2-Amino-N-{4-[(3S)-3-aminopiperidin-1-yl]pyridin-3-yl}-6-ethylthieno[3,2-b]pyridine-3-carboxamide

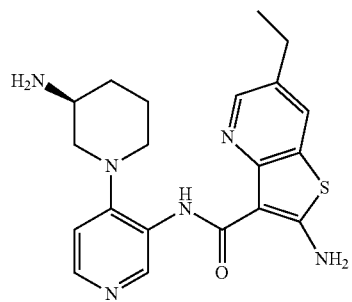

Step A. Methyl 3-amino-6-bromothieno[3,2-b]pyridine-2-carboxylate

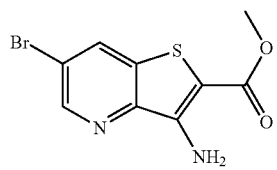

To a solution of 5-bromo-3-nitropyridine-2-carbonitrile (1.00 g, 4.38 mmol) in DMF (10 mL, 100 mmol) at 0° C. was added 2-mercaptoacetic acid methyl ester (0.414 mL, 4.60 mmol) followed by a solution of potassium hydroxide (0.492 g, 8.77 mmol) in water (1 mL, 60 mmol) dropwise. The reaction mixture was stirred at 0-5° C. for 1 h. Water (30 mL) was added to the mixture. The solid that formed was filtered, washed with water, dried under reduced pressure to give 0.990 g (78.6% yield) of the sub-title compound as a yellow solid. LCMS calc. for $C_9H_8BrN_2O_2S$ (M+H)$^+$: m/z=286.9. found: 287.1.

Step B. Methyl 3-amino-6-vinylthieno[3,2-b]pyridine-2-carboxylate

A mixture of 4,4,5,5-tetramethyl-2-vinyl-1,3,2-dioxaborolane (0.269 mL, 1.59 mmol), bis(tri-tert-butylphosphine)palladium (0.14 g, 0.26 mmol), methyl 3-amino-6-bromothieno[3,2-b]pyridine-2-carboxylate (0.380 g, 1.32 mmol) and DIPEA (0.461 mL, 2.65 mmol) in 1,4-dioxane (8 mL, 100 mmol) and water (0.400 mL, 22.2 mmol) was heated at 130° C. for 40 min. The reaction mixture was filtered through a pad of diatomaceous earth and concentrated under reduced pressure. The residue was purified by silica gel column chromatography eluted with EtOAc/hexane (0-50%). The purification gave 0.308 g (99.3% yield) of the sub-title compound as a yellow solid. LCMS calc. for $C_{11}H_{11}N_2O_2S$ (M+H)$^+$: m/z=235.1. found: 235.0.

Step C. Methyl 3-amino-6-ethylthieno[3,2-b]pyridine-2-carboxylate

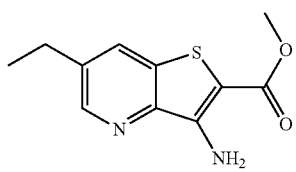 [SMILES: CCc1cnc2c(N)c(C(=O)OC)sc2c1]

A mixture of methyl 3-amino-6-vinylthieno[3,2-b]pyridine-2-carboxylate (281.4 mg, 1.201 mmol) and 10% palladium on carbon (70 mg, 0.06 mmol) in MeOH (10 mL, 200 mmol) under $H_2$ was stirred at ambient temperature for 5 h. The reaction mixture was filtered through a pad of diatomaceous earth, rinsed with MeOH, concentrated under reduced pressure to give 0.28 g (99.6% yield) of the sub-title compound as a yellow solid. LCMS calc. for $C_{11}H_{13}N_2O_2S$ (M+H)$^+$: m/z=237.1. found: 237.1.

Step D. Methyl 3-bromo-6-ethylthieno[3,2-b]pyridine-2-carboxylate

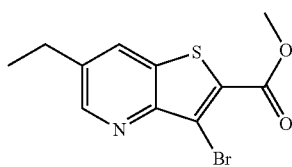 [SMILES: CCc1cnc2c(Br)c(C(=O)OC)sc2c1]

A mixture of methyl 3-amino-6-ethylthieno[3,2-b]pyridine-2-carboxylate (0.280 g, 1.18 mmol), tert-butyl nitrite (0.282 mL, 2.37 mmol) and copper (II) bromide (0.397 g, 1.78 mmol) in MeCN (20 mL, 400 mmol) was stirred at 65° C. for 2 h. The reaction mixture was filtered through a pad of diatomaceous earth and rinsed with MeCN. The filtrate was concentrated under reduced pressure and the residue was purified by column chromatography on silica gel using CombiFlash® apparatus eluting with EtOAc/hexane (10-60%). The purification gave 0.104 g (29.2% yield) of the sub-title compound as a yellowish solid. LCMS calc. for $C_{11}H_{11}BrNO_2S$ (M+H)$^+$: m/z=300.0. found: 300.0.

Step E: 3-Bromo-6-ethylthieno[3,2-b]pyridine-2-carboxylic acid

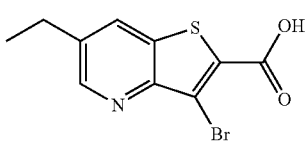

A mixture of methyl 3-bromo-6-ethylthieno[3,2-b]pyridine-2-carboxylate (0.103 g, 0.343 mmol), LiOH (0.0780 g, 3.26 mmol), THF (3 mL, 40 mmol), MeOH (2 mL, 40 mmol) and water (2 mL, 80 mmol) was stirred at ambient temperature for 2 h. The solution was concentrated under reduced pressure and the residue was adjusted to pH=4-5 with 1 M aq. HCl. The resulting solution was extracted with EtOAc (2 times). The combined organic phases were washed with water and brine, dried over $Na_2SO_4$ and concentrated under reduced pressure to give 96.2 mg (98% yield) of the sub-title compound as an off-white solid. LCMS calc. for $C_{10}H_9BrNO_2S$ (M+H)$^+$: m/z=286.0. found: 285.9.

Step F. tert-Butyl (3-bromo-6-ethylthieno[3,2-b]pyridin-2-yl)carbamate

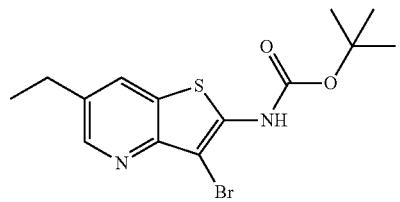 [SMILES: CCc1cnc2c(Br)c(NC(=O)OC(C)(C)C)sc2c1]

A mixture of 3-bromo-6-ethylthieno[3,2-b]pyridine-2-carboxylic acid (96.0 mg, 0.335 mmol), diphenylphosphonic azide (89.6 µL, 0.416 mmol) and DIPEA (64.5 µL, 0.370 mmol) in tert-butyl alcohol (2 mL, 20 mmol) was heated under reflux overnight. The reaction mixture was concentrated under reduced pressure and the residue was dissolved in DCM. The resulting solution was washed with 1 M aq. NaOH, brine, dried over $Na_2SO_4$ and concentrated under reduced pressure. The residue was purified by column chromatography on silica gel using CombiFlash® apparatus eluting with EtOAc/hexane (0-30%). The purification gave 96.2 mg (80.2% yield) of the sub-title compound as a colorless oil. LCMS calc. for $C_{14}H_{18}BrN_2O_2S$ (M+H)$^+$: m/z=357.0. found: 357.0.

Step G. Methyl 2-[(tert-butoxycarbonyl)amino]-6-ethylthieno[3,2-b]pyridine-3-carboxylate

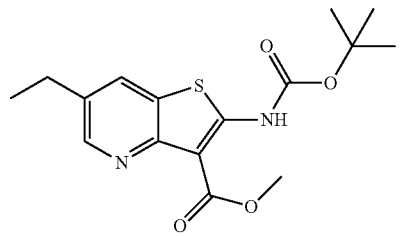 [SMILES: CCc1cnc2c(C(=O)OC)c(NC(=O)OC(C)(C)C)sc2c1]

To a mixture of tert-butyl (3-bromo-6-ethylthieno[3,2-b]pyridin-2-yl)carbamate (90.0 mg, 0.252 mmol) in MeOH (10 mL, 300 mmol) was added TEA (73.7 µL, 0.529 mmol) and [1,1'-bis(diphenylphosphino)ferrocene]dichloropalladium(II), complex with dichloromethane (1:1) (22 mg, 0.026 mmol). The mixture was heated under reflux under CO overnight. The mixture was concentrated under reduced pressure. The residue was purified by flash chromatography on silica gel eluted by EtOAc/Hexane (10-70%). The purification gave 34.5 mg (40.7% yield) of the sub-title compound as a yellowish oil. LCMS calc. for $C_{16}H_{21}N_2O_4S$ (M+H)+: m/z=337.1. found: 337.1.

Step H: 2-[(tert-Butoxycarbonyl)amino]-6-ethylthieno[3,2-b]pyridine-3-carboxylic acid

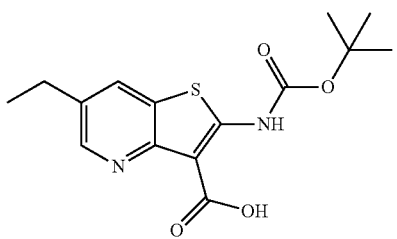

A mixture of methyl 2-[(tert-butoxycarbonyl)amino]-6-ethylthieno[3,2-b]pyridine-3-carboxylate (34.0 mg, 0.101 mmol), LiOH (24.2 mg, 1.01 mmol), THF (2 mL, 20 mmol), MeOH (1 mL, 20 mmol) and water (1 mL, 60 mmol) was stirred at 100° C. for 2 h. The reaction mixture was concentrated under reduced pressure and the residue was adjusted to pH=4-5 with 1 M aq. HCl. The resulting mixture was extracted with EtOAc (2 times). The combined organic phases were washed with water and brine, dried over $Na_2SO_4$ and concentrated under reduced pressure to give the sub-title compound as a pink solid. LCMS calc. for $C_{15}H_{10}N_2O_4S$ (M+H)+: m/z=323.1. found: 323.1.

Step I. 2-Amino-N-{4-[(3S)-3-aminopiperidin-1-yl]pyridin-3-yl}-6-ethylthieno[3,2-b]pyridine-3-carboxamide A mixture of tert-butyl [(3S)-1-(3-aminopyridin-4-yl)piperidin-3-yl]carbamate (10.9 mg, 0.0372 mmol), 2-[(tert-butoxycarbonyl)amino]-5-ethylthieno[3,2-b]pyridine-3-carboxylic acid (12.0 mg, 0.0372 mmol), HATU (18.4 mg, 0.0484 mmol) and DIPEA (19 µL, 0.11 mmol) in DMF (0.7 mL, 9 mmol) was stirred at ambient temperature overnight. The reaction was quenched with brine and the mixture was extracted with EtOAc. The organic phases were concentrated under reduced pressure and the residue was purified by preparative LCMS (pH=2) to give the intermediate compound, tert-butyl ((3S)-1-{3-[({2-[(tert-butoxycarbonyl)amino]-6-ethylthieno[3,2-b]pyridin-3-yl}carbonyl)amino]pyridin-4-yl}piperidin-3-yl)carbamate. LCMS calc. for $C_{30}H_{41}N_6O_5S$ (M+H)+: m/z=597.3. found: 597.2.

To the purified intermediate was added DCM (1 mL, 20 mmol) and TFA (1 mL, 20 mmol). The reaction mixture was stirred at ambient temperature for 1 h. The mixture was concentrated under reduced pressure and the residue was adjusted to pH=8-9 with one drop of $NH_4OH$ in water. Purification by preparative LCMS (pH=10) gave the title compound as a white powder. LCMS calc. for $C_{20}H_{25}N_6OS$ (M+H)+: m/z=397.2. found: 397.2.

Example 23

2-Amino-N-[5-(4-aminoazepan-1-yl)-1-methyl-1H-pyrazol-4-yl]-6-ethylthieno[3,2-b]pyridine-3-carboxamide

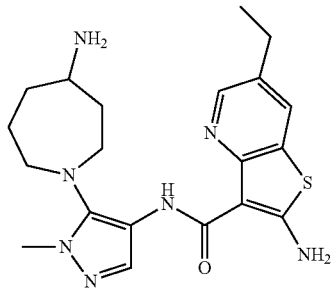 [SMILES: CCc1cnc2c(C(=O)Nc3cnn(C)c3N3CCCC(N)CC3)c(N)sc2c1]

Example 23 was synthesized by an analogous procedure to that described in Example 22, except using Intermediate 1 instead of Intermediate 6 in Step I (Example 22). LCMS calc. for $C_{20}H_{28}N_7OS$ (M+H)+: m/z=414.2. found: 414.1.

Example 24

2-Amino-N-{4-[(3S)-3-aminopiperidin-1-yl]pyridin-3-yl}-6-phenylthieno[3,2-b]pyridine-3-carboxamide

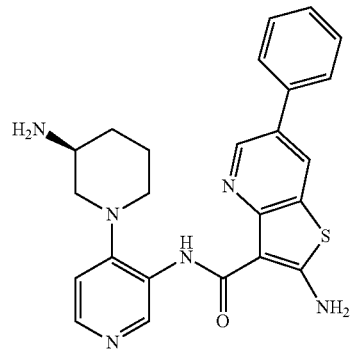 [SMILES: Nc1sc2cc(-c3ccccc3)cnc2c1C(=O)Nc1cnccc1N1CCC[C@H](N)C1]

Step A. Methyl 3-amino-6-phenylthieno[3,2-b]pyridine-2-carboxylate

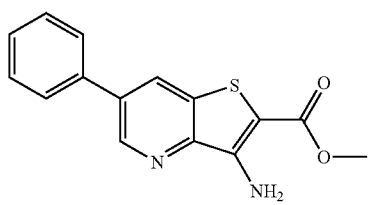 [SMILES: COC(=O)c1sc2cc(-c3ccccc3)cnc2c1N]

A mixture of phenylboronic acid (0.510 g, 4.18 mmol), bis(tri-tert-butylphosphine)palladium (0.356 g, 0.696 mmol), methyl 3-amino-6-bromothieno[3,2-b]pyridine-2-carboxylate (1.00 g, 3.48 mmol) and DIPEA (1.21 mL, 6.96 mmol) in 1,4-dioxane (10 mL, 200 mmol) and water (0.7 mL, 40 mmol) was heated under microwave irradiation at 130° C. for 40 min. The reaction mixture was filtered through a pad of diatomaceous earth and concentrated under reduced pressure. The crude product was purified by silica gel column chromatography eluting with EtOAc/hexane (0-50%) to give 0.812 g (82% yield) of the sub-title compound as a yellow solid. LCMS calc. for $C_{15}H_{13}N_2O_2S$ (M+H)$^+$: m/z=285.1. found: 285.0.

Step B. 2-[(tert-Butoxycarbonyl)amino]-6-phenylthieno[3,2-b]pyridine-3-carboxylic acid

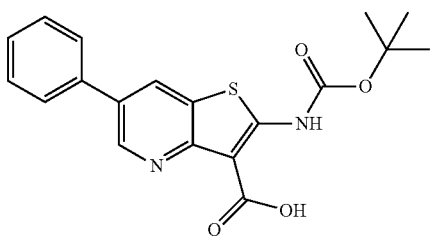 [SMILES: CC(C)(C)OC(=O)Nc1sc2cc(-c3ccccc3)cnc2c1C(=O)O]

To a solution of copper (I) bromide (0.429 g, 2.99 mmol) in HBr (10 mL, 100 mmol) at 0-5° C. was added methyl 3-amino-6-phenylthieno[3,2-b]pyridine-2-carboxylate (0.810 g, 2.85 mmol). To the mixture at this temperature was added a solution of sodium nitrite (0.236 g, 3.42 mmol) in water (4.0 mL, 220 mmol) dropwise over 30 min. The reaction was continued at 0-5° C. for 1 h. The reaction mixture was poured slowly into iced water containing 10 g of NaHCO$_3$ and extracted with DCM (2 times). The combined organic phases were washed with water and brine, dried over Na$_2$SO$_4$ and concentrated under reduced pressure. The residue was purified by column chromatography on silica gel using CombiFlash® apparatus eluting with EtOAc/hexane (0-40%). The purification gave 0.146 g (14.7% yield) of the intermediate, methyl 3-bromo-6-phenylthieno[3,2-b]pyridine-2-carboxylate, as a yellow solid. LCMS calc. for $C_{15}H_{11}BrNO_2S$ (M+H)$^+$: m/z=347.9. found: 347.9.

A mixture of methyl 3-bromo-6-phenylthieno[3,2-b]pyridine-2-carboxylate (0.146 g, 0.419 mmol), LiOH (0.0780 g, 3.26 mmol), THF (3 mL, 40 mmol), MeOH (2 mL, 40 mmol) and water (2 mL, 80 mmol) was stirred at ambient temperature for 2 h. The solution was concentrated under reduced pressure and the residue was adjusted to pH=4-5 with 1 M aq. HCl. The solid that formed was collected by filtration and dried under reduced pressure to give 75 mg (53.5% yield) of the intermediate, 3-bromo-6-phenylthieno[3,2-b]pyridine-2-carboxylic acid, as a yellow solid. LCMS calc. for $C_{14}H_9BrNO_2S$ (M+H)$^+$: m/z=333.9. found: 333.9.

A mixture of 3-bromo-6-phenylthieno[3,2-b]pyridine-2-carboxylic acid (75.0 mg, 0.224 mmol), diphenylphosphonic azide (59.9 µL, 0.278 mmol) and DIPEA (43.2 µL, 0.248 mmol) in tert-butyl alcohol (1 mL, 10 mmol) was heated under reflux overnight. The mixture was concentrated under reduced pressure and the residue was dissolved in DCM. The resulting solution was washed with 1 M aq. NaOH, water and brine, dried over Na$_2$SO$_4$, filtered and concentrated under reduced pressure. The residue was purified by column chromatography on silica gel using CombiFlash® apparatus eluting with EtOAc/hexane (0-50%). The purification gave 76.1 mg (83.7% yield) of the intermediate, tert-butyl (3-bromo-6-phenylthieno[3,2-b]pyridin-2-yl)carbamate, as a yellow solid. LCMS calc. for $C_{14}H_9BrNO_2S$ (M+H)$^+$: m/z=405.0. found: 405.0.

To a solution of tert-butyl (3-bromo-6-phenylthieno[3,2-b]pyridin-2-yl)carbamate (76.0 mg, 0.188 mmol) in THF (4 mL, 50 mmol) at −78° C. was added 1.6 M n-BuLi in hexane (0.293 mL, 0.469 mmol). The reaction mixture was stirred at −78° C. for 30 min. To the solution was added dry-ice. The mixture was stirred at −78° C. for 1 h and then adjusted to pH=4-5 with 1 M aq. HCl, extracted with DCM. The organic phases were washed with water and then concentrated under reduced pressure. The residue was purified by preparative LCMS (pH=10). The purification afforded 18.7 mg (27% yield) of the sub-title compound, 2-[(tert-butoxycarbonyl)amino]-6-phenylthieno[3,2-b]pyridine-3-carboxylic acid, as a white solid. LCMS calc. for $C_{19}K_9N_2O_4S$ (M+H)$^+$: m/z=371.1. found: 371.1.

Step C. 2-Amino-N-{4-[(3S)-3-aminopiperidin-1-yl]pyridin-3-yl}-6-phenylthieno[3,2-b]pyridine-3-carboxamide A mixture of tert-butyl [(3S)-1-(3-aminopyridin-4-yl)piperidin-3-yl]carbamate (7.89 mg, 0.0270 mmol), 2-[(tert-butoxycarbonyl)amino]-6-phenylthieno[3,2-b]pyridine-3-carboxylic acid (10.0 mg, 0.0270 mmol), HATU (13.34 mg, 0.03509 mmol) and DIPEA (0.014 mL, 0.081 mmol) in DMF (0.1 mL, 2 mmol) was stirred at ambient temperature overnight. The mixture was quenched with brine, extracted with EtOAc. The combined organic phases were concentrated under reduced pressure and the residue was purified by preparative LCMS (pH=2) to give the intermediate compound, tert-butyl ((3S)-1-{3-[({2-[(tert-butoxycarbonyl)amino]-6-phenylthieno[3,2-b]pyridin-3-yl}carbonyl)amino]pyridin-4-yl}piperidin-3-yl)carbamate. LCMS calc. for $C_{34}H_{41}N_6O_5S$ (M+H)$^+$: m/z=645.3. found: 645.1.

To the purified intermediate was added DCM (0.1 mL, 2 mmol) and TFA (0.1 mL, 2 mmol). The reaction mixture was concentrated under reduced pressure and the residue was neutralized with one drop of NH$_4$OH in water to pH=8-9. Purification by preparative LCMS (pH=10) afforded the sub-title compound as a white powder. LCMS calc. for $C_{24}H_{25}N_6OS$ (M+H)$^+$: m/z=445.2. found: 445.1.

Example 25

2-Amino-N-[5-(4-aminoazepan-1-yl)-1-methyl-1H-pyrazol-4-yl]-6-phenylthieno[3,2-b]pyridine-3-carboxamide

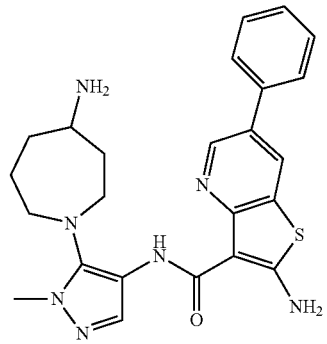 [SMILES: Cn1ncc(NC(=O)c2c(N)sc3cc(-c4ccccc4)cnc23)c1N1CCCC(N)CC1]

Example 25 was synthesized using an analogous procedure to that described in Example 24, except using Intermediate 1 instead of Intermediate 6 in Step C (Example 24). LCMS calc. for $C_{24}H_{28}N_7OS$ (M+H)$^+$: m/z=462.2. found: 462.1.

Example 26

2-Amino-N-{4-[(3S)-3-aminopiperidin-1-yl]pyridin-3-yl}-6-(2,6-difluorophenyl)-thieno[3,2-b]pyridine-3-carboxamide

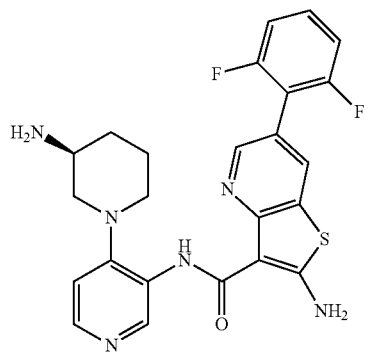 [SMILES: Nc1sc2cc(-c3c(F)cccc3F)cnc2c1C(=O)Nc1cnccc1N1CCC[C@H](N)C1]

Example 26 was synthesized using an analogous procedure to that described in Example 24, except using 2,6-difluorophenylboronic acid instead of phenylboronic acid in Step A (Example 24). LCMS calc. for $C_{24}H_{23}F_2N_6OS$ (M+H)$^+$: m/z=481.2. found: 481.1.

Example 27

2-Amino-N-[5-(4-aminoazepan-1-yl)-1-methyl-1H-pyrazol-4-yl]-6-(2,6-difluorophenyl)-thieno[3,2-b]pyridine-3-carboxamide

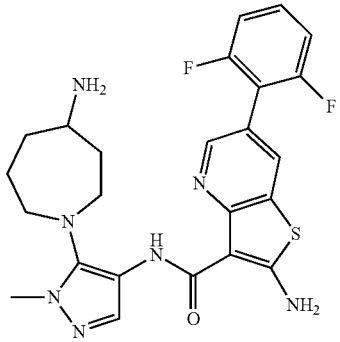 [SMILES: Cn1ncc(NC(=O)c2c(N)sc3cc(-c4c(F)cccc4F)cnc23)c1N1CCCC(N)CC1]

Example 27 was synthesized using an analogous procedure to that described in Example 24, except using 2,6-difluorophenylboronic acid instead of phenylboronic acid in Step A (Example 24) and using Intermediate 1 instead of Intermediate 6 in Step C (Example 24). LCMS calc. for $C_{24}H_{26}F_2N_7OS$ (M+H)$^+$: m/z=498.2. found: 498.1.

Example 28

2-Amino-N-{4-[(3S)-3-aminopiperidin-1-yl]pyridin-3-yl}-6-(3,5-dimethylisoxazol-4-yl)-thieno[3,2-b]pyridine-3-carboxamide

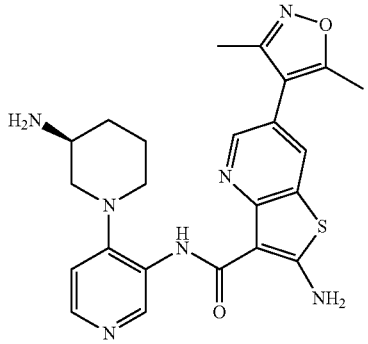 [SMILES: Cc1noc(C)c1-c1cnc2c(C(=O)Nc3cnccc3N3CCC[C@H](N)C3)c(N)sc2c1]

Example 28 was synthesized using an analogous procedure to that described in Example 24, except using 3,5-dimethyl-4-(4,4,5,5-tetramethyl-1,3,2-dioxaborolan-2-yl)isoxazole instead of phenylboronic acid in Step A (Example 24). LCMS calc. for $C_{23}H_{26}N_7O_2S$ (M+H)$^+$: m/z=464.2. found: 464.1.

Example 29

2-Amino-N-[5-(4-aminoazepan-1-yl)-1-methyl-1H-pyrazol-4-yl]-6-(3,5-dimethylisoxazol-4-yl)-thieno[3,2-b]pyridine-3-carboxamide

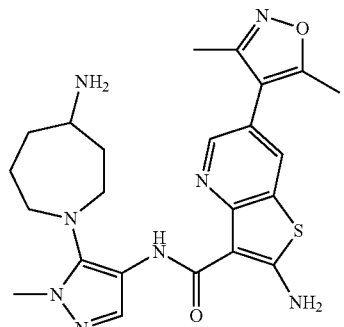

Example 29 was synthesized using an analogous procedure to that described in Example 24, except using 3,5-dimethyl-4-(4,4,5,5-tetramethyl-1,3,2-dioxaborolan-2-yl)isoxazole instead of phenylboronic acid in Step A (Example 24) and using Intermediate 1 instead of Intermediate 6 in Step C (Example 24). LCMS calc. for $C_{23}H_{29}N_8O_2S$ (M+H)$^+$: m/z=481.2. found: 481.1.

Example 30

2-Amino-N-[5-(4-aminoazepan-1-yl)-1-methyl-1H-pyrazol-4-yl]-6-(1,3-thiazol-2-yl)-thieno[3,2-b]pyridine-3-carboxamide

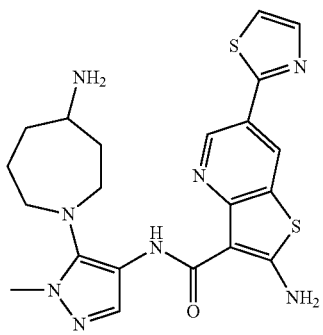 [SMILES: Cn1ncc(NC(=O)c2c(N)sc3cc(-c4nccs4)cnc23)c1N1CCCC(N)CC1]

Example 30 was synthesized using an analogous procedure to that described in Example 24, except using 2-(tributylstannyl)-1,3-thiazole instead of phenylboronic acid in Step A (Example 24) and using Intermediate 1 instead of Intermediate 6 in Step C (Example 24). LCMS calc. for $C_{21}H_{25}N_8OS_2$ (M+H)$^+$: m/z=469.2. found: 469.1.

Example 31

2-Amino-N-{4-[(3S)-3-aminopiperidin-1-yl]pyridin-3-yl}-6-(1-methylazetidin-3-yl)thieno[3,2-b]pyridine-3-carboxamide

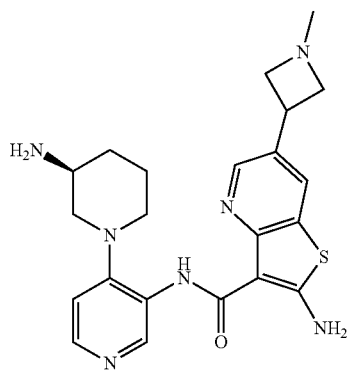 [SMILES: CN1CC(c2cnc3c(C(=O)Nc4cnccc4N4CCC[C@H](N)C4)c(N)sc3c2)C1]

Step A. Methyl 6-bromo-3-[(tert-butoxycarbonyl)amino]thieno[3,2-b]pyridine-2-carboxylate

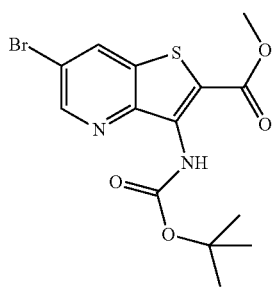 [SMILES: COC(=O)c1sc2cc(Br)cnc2c1NC(=O)OC(C)(C)C]

A solution of methyl 3-amino-6-bromothieno[3,2-b]pyridine-2-carboxylate (6.00 g, 20.9 mmol), Boc$_2$O (27.4 g, 125 mmol), DMAP (2.55 g, 20.9 mmol) in THF (120 mL, 1500 mmol) was stirred at ambient temperature overnight. The reaction mixture was concentrated under reduced pressure and the residue was re-slurred in EtOAc (20 mL). The solid that formed was filtered and rinsed with EtOAc. 8.05 g (99.5% yield) of the sub-title compound was obtained as a yellowish solid. LCMS calc. for $C_{14}H_{16}BrN_2O_4S$ (M+H)$^+$: m/z=387.0. found: 387.0.

Step B. Methyl 6-{1-[(benzyloxy)carbonyl]azetidin-3-yl}-3-[(tert-butoxycarbonyl)amino]thieno[3,2-b]pyridine-2-carboxylate

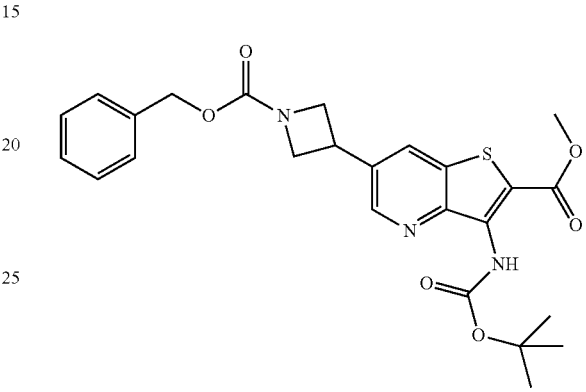

Zinc (1.93 g, 29.5 mmol) was suspended with 1,2-dibromoethane (0.169 mL, 1.96 mmol) in DMF (35 mL, 450 mmol). The mixture was heated at 70° C. for 10 min. and then cooled to ambient temperature. Chlorotrimethylsilane (0.31 mL, 2.4 mmol) was added dropwise and stirring was continued for 1 h. A solution of benzyl 3-iodoazetidine-1-carboxylate (7.80 g, 24.6 mmol) in DMF (20 mL, 200 mmol) was then added and the mixture was heated at 40° C. for 1 h before a mixture of methyl 6-bromo-3-[(tert-butoxycarbonyl)amino]thieno[3,2-b]pyridine-2-carboxylate (10.00 g, 25.82 mmol), tris(dibenzylideneacetone)dipalladium(0) (0.90 g, 0.98 mmol) and tri-(2-furyl)phosphine (0.46 g, 2.0 mmol) was added. The reaction mixture was warmed to 70° C. and stirred overnight. The mixture was then allowed to cool to room temperature and partitioned between ether and saturated NH$_4$Cl aqueous solution. The organic layer was washed with water, dried over NaSO$_4$, concentrated under reduced pressure and purified by chromatography on silica gel (0-70% EtOAc/Hexane) to give 7.38 g (60.3% yield) of the sub-title compound as a yellowish solid. LCMS calc. for $C_{25}H_{28}N_3O_6S$ (M+H)$^+$: m/z=498.2. found: 498.2.

Step C. Methyl 3-amino-6-{1-[(benzyloxy)carbonyl]azetidin-3-yl}thieno[3,2-b]pyridine-2-carboxylate

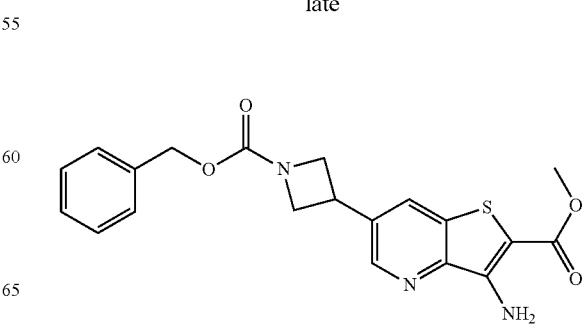

To a solution of methyl 6-{1-[(benzyloxy)carbonyl]azetidin-3-yl}-3-[(tert-butoxycarbonyl)amino]thieno[3,2-b]pyridine-2-carboxylate (7.36 g, 14.8 mmol) in DCM (40 mL, 600 mmol) was added TFA (40 mL, 500 mmol). The reaction mixture was stirred at ambient temperature for 2 h and then concentrated under reduced pressure. The residue was adjusted to pH=8-9 and then extracted with DCM. The combined organic phases were washed with water and brine, dried over $Na_2SO_4$, filtered and concentrated under reduced pressure. The residue was purified by column chromatography on silica gel using CombiFlash® apparatus eluting with EtOAc/hexane (20-70%). LCMS calc. for $C_{20}H_{20}N_3O_4S$ $(M+H)^+$: m/z=398.1. found: 398.1.

Step D. Methyl 6-{1-[(benzyloxy)carbonyl]azetidin-3-yl}-3-bromothieno[3,2-b]pyridine-2-carboxylate

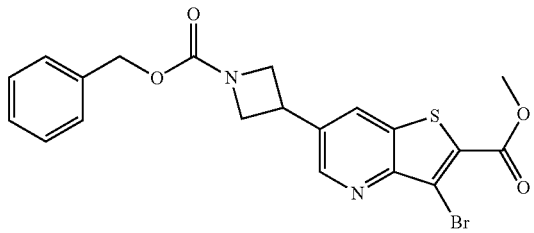 [SMILES: COC(=O)c1sc2cc(C3CN(C(=O)OCc4ccccc4)C3)cnc2c1Br]

A mixture of methyl 3-amino-6-{1-[(benzyloxy)carbonyl]azetidin-3-yl}thieno[3,2-b]pyridine-2-carboxylate (5.10 g, 12.8 mmol), tert-butyl nitrite (3.39 mL, 25.7 mmol) and copper (II) bromide (4.30 g, 19.2 mmol) in MeCN (70 mL, 1000 mmol) was stirred at 65° C. for 2 h. The reaction mixture was filtered through a pad of diatomaceous earth and rinsed with MeCN. The filtrate was concentrated under reduced pressure and the residue was dissolved in EtOAc. The organic phase was washed with 2 M $NH_4OH$ in water (3 times), brine, dried over $Na_2SO_4$, filtered and concentrated under reduced pressure to give 3.80 g (64.2% yield) of the sub-title compound as a yellow solid. LCMS calc. for $C_{20}H_{18}BrN_2O_4S$ $(M+H)^+$: m/z=461.0. found: 461.0.

Step E. 6-{1-[(Benzyloxy)carbonyl]azetidin-3-yl}-3-bromothieno[3,2-b]pyridine-2-carboxylic acid

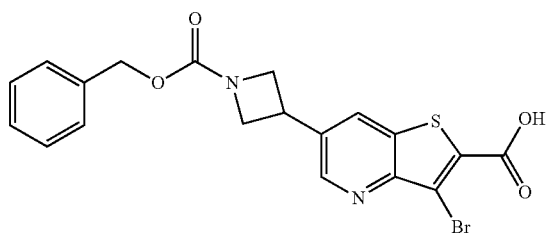 [SMILES: O=C(O)c1sc2cc(C3CN(C(=O)OCc4ccccc4)C3)cnc2c1Br]

A mixture of methyl 6-{1-[(benzyloxy)carbonyl]azetidin-3-yl}-3-bromothieno[3,2-b]pyridine-2-carboxylate (3.80 g, 8.24 mmol), LiOH (1.97 g, 82.4 mmol), THF (60 mL, 700 mmol), MeOH (30 mL, 700 mmol) and water (30 mL, 2000 mmol) was stirred at ambient temperature for 2 h. The solution was concentrated under reduced pressure and the residue was adjusted to pH=4-5 with 1 M aq. HCl. The resulting mixture was extracted with DCM (3 times). The combined organic phases were washed with water and brine, dried over $Na_2SO_4$, concentrated under reduced pressure to give 3.51 g (95.3% yield) of the sub-title compound as a yellowish solid. LCMS calc. for $C_{19}H_{16}BrN_2O_4S$ $(M+H)^+$: m/z=447.0. found: 447.0.

Step F. Benzyl 3-{3-bromo-2-[(tert-butoxycarbonyl)amino]thieno[3,2-b]pyridin-6-yl}azetidine-1-carboxylate

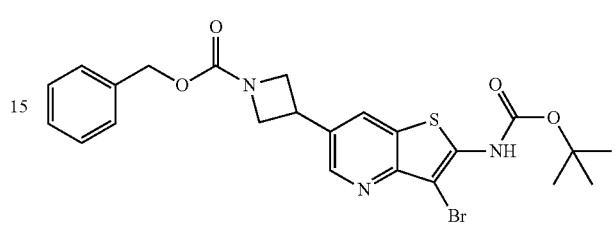

A mixture of 6-{1-[(benzyloxy)carbonyl]azetidin-3-yl}-3-bromothieno[3,2-b]pyridine-2-carboxylic acid (3.50 g, 7.82 mmol), diphenylphosphonic azide (2.09 mL, 9.70 mmol) and DIPEA (1.50 mL, 8.64 mmol) in tert-butyl alcohol (40 mL) was heated under reflux overnight. The reaction mixture was concentrated under reduced pressure and the residue was dissolved in DCM. The resulting solution was washed with 1 M aq. NaOH, brine, dried over $Na_2SO_4$, concentrated under reduced pressure. The residue was purified by column chromatography on silica gel using CombiFlash® apparatus eluting with EtOAc/hexane (0-70%). The purification gave 2.62 g (64.6% yield) of the sub-title compound as an off-white solid. LCMS calc. for $C_{23}H_{25}BrN_3O_4S$ $(M+H)^+$: m/z=518.1. found: 518.0.

Step G. Methyl 6-{1-[(benzyloxy)carbonyl]azetidin-3-yl}-2-[(tert-butoxycarbonyl)amino]thieno[3,2-b]pyridine-3-carboxylate

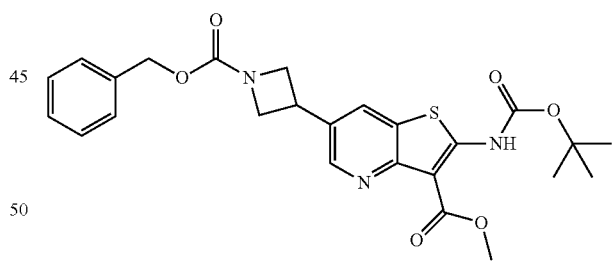

To a mixture of benzyl 3-{3-bromo-2-[(tert-butoxycarbonyl)amino]thieno[3,2-b]pyridin-6-yl}azetidine-1-carboxylate (2.60 g, 5.02 mmol) in MeOH (50 mL) was added TEA (1.47 mL, 10.5 mmol) and [1,1'-bis(diphenylphosphino)ferrocene]dichloropalladium(II), complex with dichloromethane (1:1) (0.43 g, 0.53 mmol). The mixture was heated under reflux under CO for 1 h. The reaction mixture was filtered through a pad of diatomaceous earth and rinsed with EtOAc. The filtrate was concentrated under reduced pressure. The residue was purified by flash chromatography on silica gel eluted by EtOAc/Hexane (30-100%). The purification gave 1.88 g (75.3% yield) of the sub-title compound as reddish solid. LCMS calc. for $C_{25}H_{28}N_3O_6S$ $(M+H)^+$: m/z=498.2. found: 498.1.

Step H. Methyl 6-azetidin-3-yl-2-[(tert-butoxycarbonyl)amino]thieno[3,2-b]pyridine-3-carboxylate

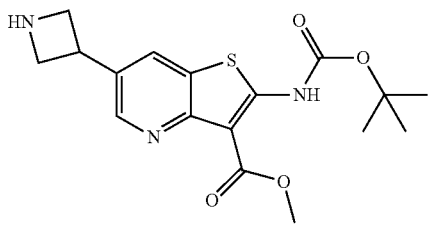 [SMILES: COC(=O)c1c(NC(=O)OC(C)(C)C)sc2cc(C3CNC3)cnc12]

A mixture of methyl 6-{1-[(benzyloxy)carbonyl]azetidin-3-yl}-2-[(tert-butoxycarbonyl)amino]thieno[3,2-b]pyridine-3-carboxylate (500.0 mg, 1.005 mmol) and 10% palladium on carbon (100 mg) in MeOH (20 mL) was stirred under $H_2$ (balloon) for 2 h. The reaction mixture was filtered through a pad of diatomaceous earth and rinsed with MeOH. The filtrate was concentrated under reduced pressure to give 304 mg (83.2% yield) of the sub-title compound as a brown oil. LCMS calc. for $C_{17}H_{22}N_3O_4S$ $(M+H)^+$: m/z=364.1. found: 364.1.

Step I. Methyl 2-[(tert-butoxycarbonyl)amino]-6-(1-methylazetidin-3-yl)thieno[3,2-b]pyridine-3-carboxylate

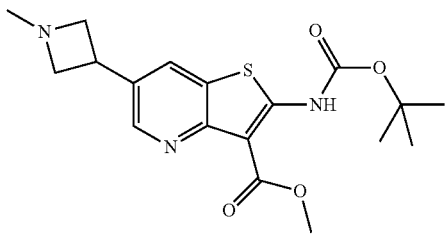 [SMILES: COC(=O)c1c(NC(=O)OC(C)(C)C)sc2cc(C3CN(C)C3)cnc12]

A mixture of methyl 6-azetidin-3-yl-2-[(tert-butoxycarbonyl)amino]thieno[3,2-b]pyridine-3-carboxylate (0.150 g, 0.413 mmol), formaldehyde (0.092 mL, 1.2 mmol) and sodium triacetoxyborohydride (0.262 g, 1.24 mmol) in THF (1 mL) was stirred at ambient temperature for 1 h. The reaction mixture was quenched with saturated aq. $NaHCO_3$, extracted with EtOAc (2 times). The combined organic phases were washed with water and brine, dried over $Na_2SO_4$ and concentrated under reduced pressure. The residue was purified by column chromatography on silica gel using CombiFlash® apparatus eluting with 10% $NH_4OH$ in MeOH/EtOAc (0-30%). The purification gave 90 mg (58% yield) of the sub-title compound as a white solid. LCMS calc. for $C_{18}H_{24}N_3O_4S$ $(M+H)^+$: m/z=378.1. found: 378.0.

Step J. 2-[(tert-Butoxycarbonyl)amino]-6-(1-methylazetidin-3-yl)thieno[3,2-b]pyridine-3-carboxylic acid

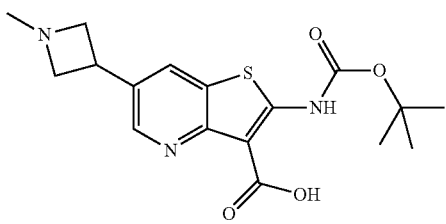 [SMILES: CN1CC(c2cnc3c(C(=O)O)c(NC(=O)OC(C)(C)C)sc3c2)C1]

A mixture of methyl 2-[(tert-butoxycarbonyl)amino]-6-(1-methylazetidin-3-yl)thieno[3,2-b]pyridine-3-carboxylate (90.0 mg, 0.238 mmol), LiOH (0.100 g, 4.18 mmol) in THF (2 mL), MeOH (1 mL) and water (1 mL) was stirred at 100° C. for 2 h. The mixture was cooled with an ice bath and neutralized to pH=6-7. Purification by preparative LCMS (pH=2) gave 36 mg (41.3% yield) of the sub-title compound as a white powder. LCMS calc. for $C_{17}H_{22}N_3O_4S$ $(M+H)^+$: m/z=364.1. found: 364.0.

Step K. 2-Amino-N-{4-[(3S)-3-aminopiperidin-1-yl]pyridin-3-yl}-6-(1-methylazetidin-3-yl)thieno[3,2-b]pyridine-3-carboxamide A mixture of tert-butyl [(3S)-1-(3-aminopyridin-4-yl)piperidin-3-yl]carbamate (8.04 mg, 0.0275 mmol), 2-[(tert-butoxycarbonyl)amino]-6-(1-methylazetidin-3-yl)thieno[3,2-b]pyridine-3-carboxylic acid (10.0 mg, 0.0275 mmol), HATU (13.60 mg, 0.03577 mmol) and DIPEA (0.014 mL, 0.082 mmol) in DMF (0.5 mL) was stirred at ambient temperature overnight. Direct purification by preparative HPLC gave the intermediate compound, tert-butyl {(3S)-1-[3-({[2-[(tert-butoxycarbonyl)amino]-6-(1-methylazetidin-3-yl)thieno[3,2-b]pyridin-3-yl]carbonyl}amino)pyridin-4-yl]piperidin-3-yl}carbamate. LCMS calc. for $C_{32}H_{44}N_7O_5S$ $(M+H)^+$: m/z=638.3. found: 638.1.

To the purified intermediate, DCM (1 mL) and TFA (1 mL) were added. The reaction mixture was stirred at ambient temperature for 2 h. The reaction mixture was concentrated under reduced pressure and the residue was adjusted to pH=7-8 with one drop of $NH_4OH$ in water. Purification by preparative LCMS (pH=10) gave the title compound as a white powder LCMS calc. for $C_{22}H_{28}N_7OS$ $(M+H)^+$: m/z=438.2. found: 438.1.

Example 32

2-Amino-N-[5-(4-aminoazepan-1-yl)-1-methyl-1H-pyrazol-4-yl]-6-(1-methylazetidin-3-yl)thieno[3,2-b]pyridine-3-carboxamide

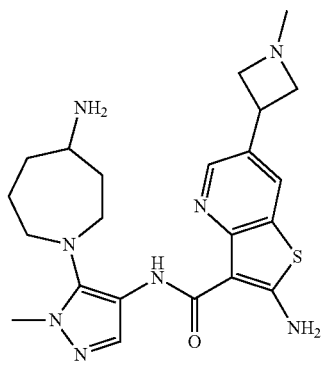 [SMILES: CN1CC(c2cnc3c(C(=O)Nc4cnn(C)c4N4CCCC(N)CC4)c(N)sc3c2)C1]

Example 32 was synthesized using an analogous procedure to that described in Example 31, excepting using Intermediate 1 instead of Intermediate 6 in Step K (Example 30). LCMS calc. for $C_{22}H_{31}N_8OS$ $(M+H)^+$: m/z=455.2. found: 455.1.

Example 33

2-Amino-N-{4-[(3S)-3-aminopiperidin-1-yl]pyridin-3-yl}-6-(1-isopropylazetidin-3-yl)thieno[3,2-b]pyridine-3-carboxamide

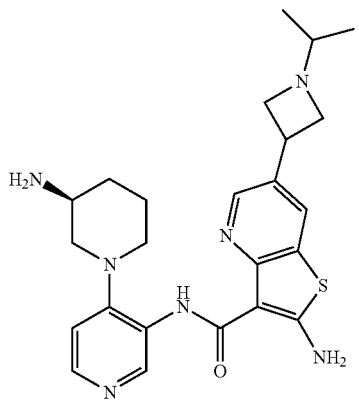 [SMILES: CC(C)N1CC(c2cnc3c(C(=O)Nc4cnccc4N4CCC[C@H](N)C4)c(N)sc3c2)C1]

Example 33 was synthesized using an analogous procedure to that described in Example 31, except that acetone was used instead of formaldehyde in Step I (Example 31). LCMS calc. for $C_{24}H_{32}N_7OS$ (M+H)$^+$: m/z=466.2. found: 466.1.

Example 34

2-Amino-N-{4-[(3S)-3-aminopiperidin-1-yl]pyridin-3-yl}-6-(methoxymethyl)thieno[3,2-b]pyridine-3-carboxamide

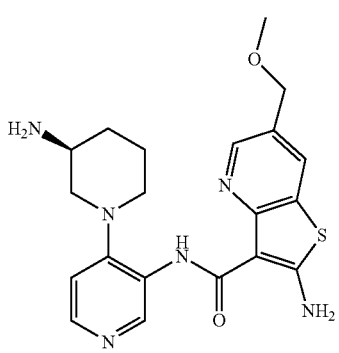 [SMILES: COCc1cnc2c(C(=O)Nc3cnccc3N3CCC[C@H](N)C3)c(N)sc2c1]

Step A. Methyl 3-[(tert-butoxycarbonyl)amino]-6-vinylthieno[3,2-b]pyridine-2-carboxylate

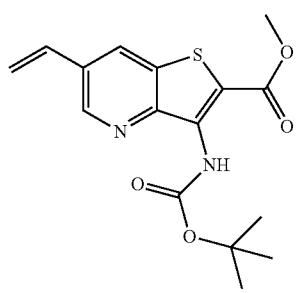 [SMILES: C=Cc1cnc2c(NC(=O)OC(C)(C)C)c(C(=O)OC)sc2c1]

A mixture of 4,4,5,5-tetramethyl-2-vinyl-1,3,2-dioxaborolane (2.63 mL, 15.5 mmol), bis(tri-tert-butylphosphine)palladium (0.66 g, 1.3 mmol), methyl 6-bromo-3-[(tert-butoxycarbonyl)amino]thieno[3,2-b]pyridine-2-carboxylate (5.00 g, 12.9 mmol) and DIPEA (4.50 mL, 25.8 mmol) in 1,4-dioxane (10 mL) and water (0.50 mL) was heated at 130° C. for 40 min. The reaction mixture was filtered through a pad of diatomaceous earth and concentrated under reduced pressure. The residue was purified by silica gel column chromatography eluting with EtOAc/hexane (0-50%). The purification gave 4.3 g (99.6% yield) of the sub-title compound as a yellow solid. LCMS calc. for $C_{16}H_{19}N_2O_4S$ (M+H)$^+$: m/z=335.1. found: 335.1.

Step B. Methyl 3-[(tert-butoxycarbonyl)amino]-6-formylthieno[3,2-b]pyridine-2-carboxylate

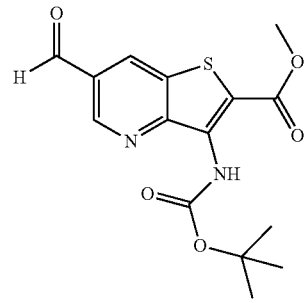 [SMILES: COC(=O)c1sc2cc(C=O)cnc2c1NC(=O)OC(C)(C)C]

Into a 1-neck round-bottom flask were added methyl 3-[(tert-butoxycarbonyl)amino]-6-vinylthieno[3,2-b]pyridine-2-carboxylate (1.40 g, 4.19 mmol) and DCM (40 mL, 600 mmol). The resulting solution was cooled to -78° C. Ozone (0.41 g, 8.5 mmol) gas was bubbled into the reaction mixture from an ozone generator until the color of the solution became blue (about 10 min.) and then N$_2$ was passed through the reaction mixture until the mixture became colorless. 20 mL of TEA was added. The reaction mixture was concentrated under reduced pressure and the residue was purified by column chromatography on silica gel using CombiFlash® apparatus eluting with EtOAc/hexane (0-50%). The purification gave 0.91 g (64.6% yield) of the sub-title compound as a brown oil. LCMS calc. for $C_{15}H_{17}N_2O_5S$ (M+H)$^+$: m/z=337.1. found: 337.0.

Step C. Methyl 3-[(tert-butoxycarbonyl)amino]-6-(hydroxymethyl)thieno[3,2-b]pyridine-2-carboxylate

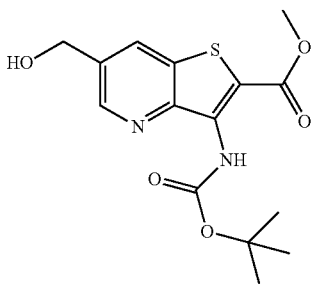 [SMILES: COC(=O)c1sc2cc(CO)cnc2c1NC(=O)OC(C)(C)C]

To a solution of methyl 3-[(tert-butoxycarbonyl)amino]-6-formylthieno[3,2-b]pyridine-2-carboxylate (900.0 mg, 2.676 mmol) in MeOH (20 mL) was added sodium tetrahydroborate (111 mg, 2.94 mmol). The mixture was stirred at ambient temperature for 1 h, then quenched with aq. $NH_4Cl$ and the resulting mixture was extracted with DCM (2 times). The combined organic extracts were washed with water and brine, dried over $Na_2SO_4$, concentrated under reduced pressure to give 0.882 g of the sub-title compound as a yellowish solid. LCMS calc. for $C_{15}H_{19}N_2O_5S$ $(M+H)^+$: m/z=339.1. found: 339.0.

Step D. Methyl 3-[(tert-butoxycarbonyl)amino]-6-(methoxymethyl)thieno[3,2-b]pyridine-2-carboxylate

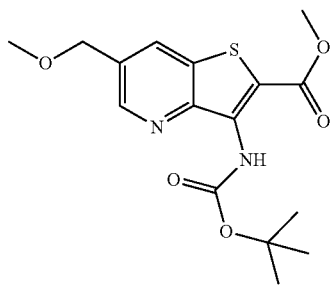 [SMILES: COCc1cnc2c(NC(=O)OC(C)(C)C)c(C(=O)OC)sc2c1]

A mixture of methyl 3-[(tert-butoxycarbonyl)amino]-6-(hydroxymethyl)thieno[3,2-b]pyridine-2-carboxylate (800.0 mg, 2.364 mmol) and thionyl chloride (0.47 mL, 6.5 mmol) in chloroform (10 mL) was heated under reflux for 2 h. TLC indicated the reaction was complete. The mixture was concentrated under reduced pressure and the residue was treated with MeOH (6 mL) and sodium methoxide (2 mL, 9 mmol). The mixture was stirred at ambient temperature for 4 h, quenched with brine, adjusted to pH=6-7 with 1 M aq. HCl, extracted with DCM (3 times). The combined organic phases were washed with water and brine, dried over $Na_2SO_4$ and concentrated under reduced pressure. The residue was purified by column chromatography on silica gel using CombiFlash® apparatus eluting with EtOAc/hexane (0-70%). The purification gave 0.148 g (17.8% yield) of the sub-title compound as a yellow solid. LCMS calc. for $C_{16}H_{21}N_2O_5S$ $(M+H)^+$: m/z=353.1. found: 353.1.

Step E. Methyl 3-amino-6-(methoxymethyl)thieno[3,2-b]pyridine-2-carboxylate

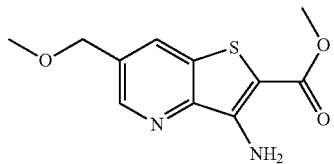 [SMILES: COCc1cnc2c(N)c(C(=O)OC)sc2c1]

A solution of methyl 3-[(tert-butoxycarbonyl)amino]-6-(methoxymethyl)thieno[3,2-b]pyridine-2-carboxylate (0.148 g, 0.420 mmol) and TFA (1 mL, 10 mmol) in DCM (1 mL, 20 mmol) was stirred at ambient temperature for 2 h. The reaction mixture was concentrated under reduced pressure and the residue was diluted with DCM. The organic phase was washed with saturated aq. $NaHCO_3$ solution, water and brine, dried over $Na_2SO_4$ and concentrated under reduced pressure to give 0.101 g (95.3% yield) of the sub-title compound. LCMS calc. for $C_{11}H_{13}N_2O_3S$ $(M+H)^+$: m/z=253.1. found: 253.1.

Step F. 2-[(tert-Butoxycarbonyl)amino]-6-(methoxymethyl)thieno[3,2-b]pyridine-3-carboxylic acid

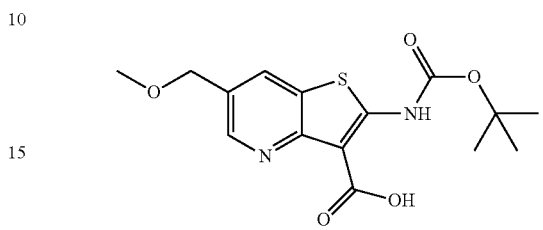

A mixture of methyl 3-amino-6-(methoxymethyl)thieno[3,2-b]pyridine-2-carboxylate (100.0 mg, 0.3964 mmol), tert-butyl nitrite (0.105 mL, 0.793 mmol) and copper (II) bromide (0.133 g, 0.594 mmol) in MeCN (2 mL) was stirred at 65° C. for 2 h. The reaction mixture was filtered through a pad of diatomaceous earth which was then rinsed with MeCN. The filtrate was concentrated under reduced pressure and the residue was dissolved in EtOAc. The organic phase was washed with 2 M $NH_4OH$ in water (3 times), brine, dried over $Na_2SO_4$, filtered and concentrated under reduced pressure to give 62 mg (49% yield) of the intermediate compound, methyl 3-bromo-6-(methoxymethyl)thieno[3,2-b]pyridine-2-carboxylate, as a yellow solid. LCMS found: 315.9 (M+H).

A mixture of methyl 3-bromo-6-(methoxymethyl)thieno[3,2-b]pyridine-2-carboxylate (60.0 mg, 0.190 mmol), LiOH (200 mg, 8 mmol), THF (2 mL), MeOH (1 mL) and water (1 mL) was stirred at ambient temperature for 2 h. The solution was concentrated under reduced pressure and the residue was neutralized to pH=4-5 with 1 M aq. HCl. The resulting mixture was extracted with DCM (3 times). The combined organic phases were washed with water and brine, dried over $Na_2SO_4$ and concentrated under reduced pressure to give 41 mg (72% yield) of the intermediate compound, 3-bromo-6-(methoxymethyl)thieno[3,2-b]pyridine-2-carboxylic acid, as a yellowish solid. LCMS found: 301.9 (M+H).

A mixture of 3-bromo-6-(methoxymethyl)thieno[3,2-b]pyridine-2-carboxylic acid (41 mg, 0.14 mmol), diphenylphosphonic azide (36.2 µL, 0.168 mmol) and DIPEA (26.1 µL, 0.150 mmol) in tert-butyl alcohol (2 mL) was heated under reflux overnight. The mixture was concentrated under reduced pressure and the residue was dissolved in DCM. The resulting solution was washed with 1 M aq. NaOH, brine, dried over $Na_2SO_4$ and concentrated under reduced pressure. The residue was purified by column chromatography on silica gel using CombiFlash® apparatus eluting with EtOAc/hexane (10-60%). The purification gave 25 mg (49% yield) of the intermediate, tert-butyl [3-bromo-6-(methoxymethyl)thieno[3,2-b]pyridin-2-yl]carbamate, as a yellow solid. LCMS found: 373.0 (M+H).

To a mixture of tert-butyl [3-bromo-6-(methoxymethyl)thieno[3,2-b]pyridin-2-yl]carbamate (24.0 mg, 0.0643 mmol) in MeOH (2 mL) was added TEA (17.9 µL, 0.128 mmol) and [1,1'-bis(diphenylphosphino)ferrocene]dichloropalladium(II), complex with dichloromethane (1:1) (5.5 mg, 0.0068 mmol). The mixture was heated under reflux under CO for 4 h. The reaction mixture was filtered through a pad of diatomaceous earth and rinsed with EtOAc. The filtrate was concentrated under reduced pressure and the residue was purified by preparative LCMS (pH=2). The purification gave 17 mg (75% yield) of the intermediate, methyl 2-[(tert-butoxycarbonyl)amino]-6-(methoxymethyl)thieno[3,2-b]pyridine-3-carboxylate, as a yellowish solid. LCMS found: 353.1 (M+H).

A mixture of methyl 2-[(tert-butoxycarbonyl)amino]-6-(methoxymethyl)thieno[3,2-b]pyridine-3-carboxylate (17.0 mg, 0.0482 mmol), LiOH (10 mg, 0.5 mmol), THF (2 mL), MeOH (1 mL) and water (1 mL) was stirred at 100° C. for 2 h. The mixture was concentrated under reduced pressure and the residue was adjusted to pH=4-5 with 1 M aq. HCl. The resulting mixture was extracted with EtOAc (2 times). The organic phase was concentrated under reduced pressure. The residue was purified by preparative LCMS (pH=2). The purification gave 12 mg (74% yield) of the sub-title compound, 2-[(tert-butoxycarbonyl)amino]-6-(methoxymethyl)thieno[3,2-b]pyridine-3-carboxylic acid, as a pink powder. LCMS calc. for $C_{15}H_{19}N_2O_5S$ $(M+H)^+$: m/z=339.1. found: 339.1.

Step G. 2-Amino-N-{4-[(3S)-3-aminopiperidin-1-yl]pyridin-3-yl}-6-(methoxymethyl)thieno[3,2-b]pyridine-3-carboxamide A mixture of tert-butyl [(3S)-1-(3-aminopyridin-4-yl)piperidin-3-yl]carbamate (10.4 mg, 0.0355 mmol), 2-[(tert-butoxycarbonyl)amino]-6-(methoxymethyl)thieno[3,2-b]pyridine-3-carboxylic acid (12.0 mg, 0.0355 mmol), HATU (17.53 mg, 0.04610 mmol) and DIPEA (0.018 mL, 0.11 mmol) in DMF (0.6 mL) was stirred at ambient temperature overnight. Direct purification by preparative HPLC afforded the intermediate compound, tert-butyl {(3S)-1-[3-({[2-[(tert-butoxycarbonyl)amino]-6-(methoxymethyl)thieno[3,2-b]pyridin-3-yl]carbonyl}amino)pyridin-4-yl]piperidin-3-yl}carbamate. LCMS calc. for $C_{30}H_{41}N_6O_6S$ $(M+H)^+$: m/z=613.3. found: 613.1.

To the purified intermediate was added DCM (1 mL) and TFA (1 mL). The reaction mixture was stirred at ambient temperature for 2 h. The mixture was concentrated under reduced pressure and the residue was adjusted to pH=7-8 with one drop of NH$_4$OH in water. Purification by preparative LCMS (pH=10) gave the title compound as a white powder. LCMS calc. for $C_{20}H_{25}N_6O_2S$ $(M+H)^+$: m/z=413.2. found: 413.2.

Example 35

2-Amino-N-{4-[(3S)-3-aminopiperidin-1-yl]pyridin-3-yl}-6-(tetrahydro-2H-pyran-4-yl)thieno[3,2-b]pyridine-3-carboxamide

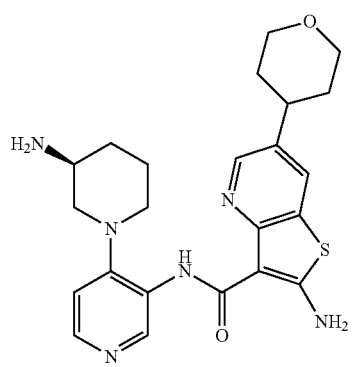 [SMILES: Nc1sc2cc(C3CCOCC3)cnc2c1C(=O)Nc1cnccc1N1CCC[C@H](N)C1]

Step A. Methyl 3[(tert-butoxycarbonyl)amino]-6-(3,6-dihydro-2H-pyran-4-yl)thieno[3,2-b]pyridine-2-carboxylate

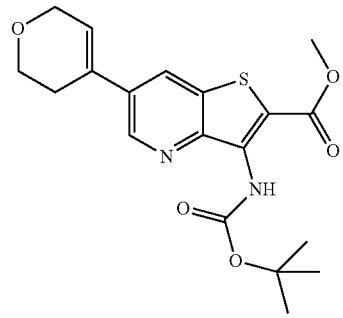 [SMILES: COC(=O)c1sc2cc(C3=CCOCC3)cnc2c1NC(=O)OC(C)(C)C]

A mixture of 4-(4,4,5,5-tetramethyl-1,3,2-dioxaborolan-2-yl)-3,6-dihydro-2H-pyran (0.716 g, 3.41 mmol), bis(tri-tert-butylphosphine)palladium (0.14 g, 0.28 mmol), methyl 6-bromo-3-[(tert-butoxycarbonyl)amino]thieno[3,2-b]pyridine-2-carboxylate (1.10 g, 2.84 mmol) and DIPEA (0.990 mL, 5.68 mmol) in 1,4-dioxane (8 mL) and water (0.50 mL) was heated under microwave irradiation at 130° C. for 20 min. The reaction mixture was filtered through a pad of diatomaceous earth and concentrated under reduced pressure. The residue was purified by silica gel column chromatography eluted with EtOAc/hexane (0-70%). The purification gave 0.902 g (81.3% yield) of the sub-title compound as a yellow solid. LCMS calc. for $C_{19}H_{23}N_2O_5S$ $(M+H)^+$: m/z=391.0. found: 391.0.

Step B. Methyl 3-[(tert-butoxycarbonyl)amino]-6-(tetrahydro-2H-pyran-4-yl)thieno[3,2-b]pyridine-2-carboxylate

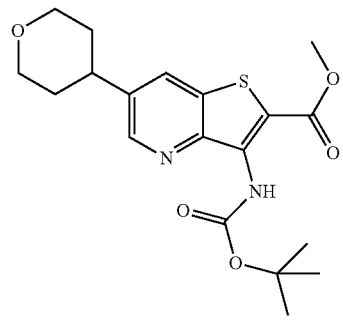 [SMILES: COC(=O)c1sc2cc(C3CCOCC3)cnc2c1NC(=O)OC(C)(C)C]

A mixture of methyl 3-[(tert-butoxycarbonyl)amino]-6-(3,6-dihydro-2H-pyran-4-yl)thieno[3,2-b]pyridine-2-carboxylate (0.900 g, 2.30 mmol) and 10% palladium on carbon (0.18 g, 0.17 mmol) in MeOH was stirred at ambient temperature under a balloon of H$_2$ for 8 h. The reaction mixture was filtered through a pad of diatomaceous earth which was then rinsed with MeOH. The filtrate was concentrated under reduced pressure and the residue was purified by column chromatography on silica gel using Combi-Flash® apparatus eluting with EtOAc/hexane (0-50%). The purification gave the sub-title compound as a yellowish oil. LCMS calc. for $C_{19}H_{25}N_2O_5S$ $(M+H)^+$: m/z=393.1. found: 393.1.

Step C. Methyl 3-amino-6-(tetrahydro-2H-pyran-4-yl)thieno[3,2-b]pyridine-2-carboxylate

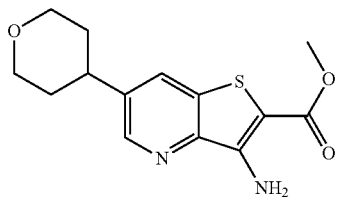 [SMILES: COC(=O)c1sc2cc(C3CCOCC3)cnc2c1N]

A solution of methyl 3-[(tert-butoxycarbonyl)amino]-6-(tetrahydro-2H-pyran-4-yl)thieno[3,2-b]pyridine-2-carboxylate (0.590 g, 1.50 mmol) and TFA (2 mL) in DCM (2 mL) was stirred at ambient temperature for 2 h. The reaction mixture was concentrated, adjusted to pH=7-8 with saturated aq. NaHCO$_3$ and extracted with DCM (2 times). The combined organic phases were washed with water and brine, dried over Na$_2$SO$_4$ and concentrated under reduced pressure to give 0.340 g (77.4% yield) of the sub-title compound as a yellowish oil. LCMS calc. for C$_{14}$H$_{17}$N$_2$O$_3$S (M+H)$^+$: m/z=293.1. found: 293.1.

Step D. 2-[(tert-Butoxycarbonyl)amino]-6-(tetrahydro-2H-pyran-4-yl)thieno[3,2-b]pyridine-3-carboxylic acid

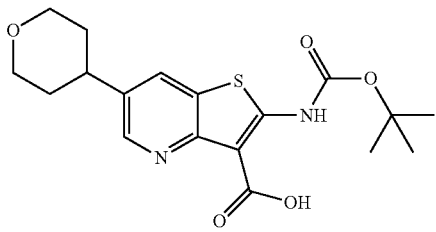 [SMILES: CC(C)(C)OC(=O)Nc1sc2cc(C3CCOCC3)cnc2c1C(=O)O]

The sub-title carboxylic acid was synthesized using an analogous procedure to that described in Step F of Example 34. LCMS calc. for C$_{18}$H$_{23}$N$_2$O$_5$S (M+H)$^+$: m/z=379.1. found: 379.1.

Step E. 2-Amino-N-{4-[(3S)-3-aminopiperidin-1-yl]pyridin-3-yl}-6-(tetrahydro-2H-pyran-4-yl)thieno[3,2-b]pyridine-3-carboxamide A mixture of tert-butyl [(3S)-1-(3-aminopyridin-4-yl)piperidin-3-yl]carbamate (7.72 mg, 0.0264 mmol), 2-[(tert-butoxycarbonyl)amino]-6-(tetrahydro-2H-pyran-4-yl)thieno[3,2-b]pyridine-3-carboxylic acid (10.0 mg, 0.0264 mmol), HATU (13.06 mg, 0.03435 mmol) and DIPEA (0.014 mL, 0.079 mmol) in DMF (0.5 mL) was stirred at ambient temperature overnight. Direct purification on preparative HPLC afforded the intermediate compound, tert-butyl [3-{[(4-{(3S)-3-[(tert-butoxycarbonyl)amino]piperidin-1-yl}pyridin-3-yl)amino]carbonyl}-6-(tetrahydro-2H-pyran-4-yl)thieno[3,2-b]pyridin-2-yl]carbamate. LCMS found: 653.2 (M+1).

To the intermediate was added DCM (1 mL) and TFA (1 mL). The reaction mixture was stirred at ambient temperature for 2 h. The mixture was concentrated under reduced pressure and the residue was adjusted to pH=7-8 with one drop of NH$_4$OH in water. Purification by preparative LCMS (pH=10) gave the title compound as a white powder. LCMS calc. for C$_{23}$H$_{29}$N$_6$O$_2$S (M+H)$^+$: m/z=453.2. found: 453.2.

Example 36

2-Amino-N-{4-[(3S)-3-aminopiperidin-1-yl]pyridin-3-yl}-6-fluoro-thieno[3,2-b]pyridine-3-carboxamide

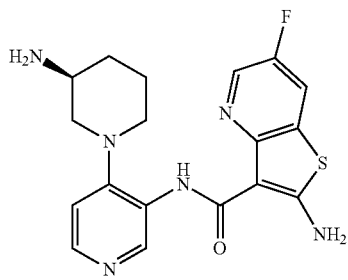 [SMILES: Nc1sc2cc(F)cnc2c1C(=O)Nc1cnccc1N1CCC[C@H](N)C1]

Step A. Methyl 3-amino-6-fluorothieno[3,2-b]pyridine-2-carboxylate

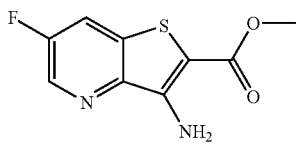

To a solution of 5-fluoro-3-nitropyridine-2-carbonitrile (2.00 g, 12.0 mmol) in DMF (30 mL) at 0° C. was added 2-mercaptoacetic acid methyl ester (1.13 mL, 12.6 mmol) followed by a solution of potassium hydroxide (1.34 g, 23.9 mmol) in water (3.0 mL) dropwise. The reaction mixture was stirred at 0-5° C. for 1 h. The mixture was quenched with water and extracted with EtOAc (2 times). The combined organic phases were washed with water and brine, dried over Na$_2$SO$_4$ and concentrated under reduced pressure to give 2.68 g (99% yield) of the sub-title compound as a yellow solid. LCMS calc. for C$_9$H$_8$FN$_2$O$_2$S (M+H)$^+$: m/z=227.0. found: 227.1.

Step B. 2[(tert-Butoxycarbonyl)amino]-6-fluorothieno[3,2-b]pyridine-3-carboxylic acid

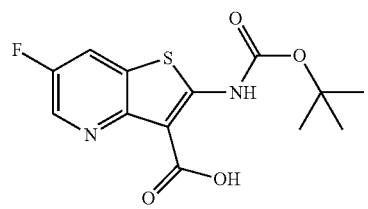 [SMILES: CC(C)(C)OC(=O)Nc1sc2cc(F)cnc2c1C(=O)O]

The sub-title carboxylic acid was synthesized using an analogous procedure to that described in Step F of Example 34. LCMS calc. for C$_{13}$H$_{14}$FN$_2$O$_4$S (M+H): 313.1. found: 313.1.

Step C. 2-Amino-N-{4-[(3S)-3-aminopiperidin-1-yl]pyridin-3-yl}-6-fluorothieno[3,2-b]pyridine-3-carboxamide A mixture of tert-butyl [(3S)-1-(3-aminopyridin-4-yl)piperidin-3-yl]carbamate (14.0 mg, 0.0480 mmol), 2-[(tert-butoxycarbonyl)amino]-6-fluorothieno[3,2-b]pyridine-3-carboxylic acid (15.0 mg, 0.0480 mmol), HATU (23.74 mg, 0.06244 mmol) and DIPEA (0.025 mL, 0.14 mmol) in DMF (0.8 mL) was stirred at ambient temperature overnight. Direct purification on preparative HPLC (pH=2) afforded the intermediate compound, tert-butyl ((3S)-1-{3-[({2-[(tert-butoxycarbonyl)amino]-6-fluorothieno[3,2-b]pyridin-3-yl}carbonyl)amino]pyridin-4-yl}piperidin-3-yl)carbamate. LCMS found: 587.1 (M+1).

To the purified intermediate was added DCM (0.8 mL) and TFA (0.8 mL). The reaction mixture was concentrated under reduced pressure and the residue was neutralized with one drop of NH$_4$OH in water to pH=8-9. Purification by preparative LCMS (pH=10) afforded the title compound as a white powder. LCMS calc. for $C_{18}H_{20}FN_6OS$ (M+H)$^+$: m/z=387.1. found: 387.1.

Example 37

2-Amino-N-[5-(4-aminoazepan-1-yl)-1-methyl-1H-pyrazol-4-yl]-6-fluoro-thieno[3,2-b]pyridine-3-carboxamide

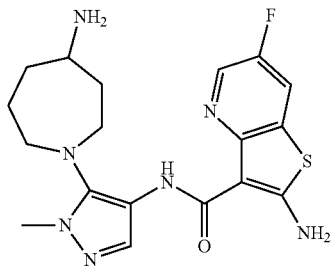 [SMILES: Cn1ncc(NC(=O)c2c(N)sc3cc(F)cnc23)c1N1CCCC(N)CC1]

Example 37 was synthesized using an analogous procedure to that described in Example 36, except using Intermediate 1 instead of Intermediate 6 in Step C (Example 36). LCMS calc. for $C_{18}H_{23}FN_7OS$ (M+H)$^+$: m/z=404.2. found: 404.1.

Example 38

2-Amino-N-{4-[(3S)-3-aminopiperidin-1-yl]pyridin-3-yl}-7-trifluoromethyl-thieno[3,2-b]pyridine-3-carboxamide

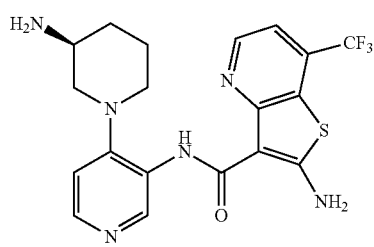 [SMILES: Nc1sc2c(C(F)(F)F)ccnc2c1C(=O)Nc1cnccc1N1CCC[C@H](N)C1]

Step A. 3-Chloro-4-(trifluoromethyl)pyridine 1-oxide

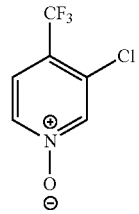 [SMILES: [O-][n+]1ccc(C(F)(F)F)c(Cl)c1]

A mixture of 3-chloro-4-(trifluoromethyl)pyridine (2.00 g, 11.0 mmol) and H$_2$O$_2$ (3.2 mL, 31 mmol) in AcOH (6 mL) was stirred at 80° C. overnight. The reaction mixture was allowed to cool to ambient temperature and quenched with NaHSO$_3$ solution. The mixture was concentrated under reduced pressure and the residue was added saturated NaHCO$_3$ solution (30 mL). The resulting mixture was extracted with DCM (3 times). The combined organic phases were washed with aq. NaHCO$_3$, water and brine, dried over Na$_2$SO$_4$ and concentrated under reduced pressure to give 2.11 g (97% yield) of the sub-title compound as a pink solid. LCMS calc. for $C_6H_4ClF_3NO$ (M+H)$^+$: m/z=198.0. found: 198.0.

Step B. 3-Chloro-4-(trifluoromethyl)pyridine-2-carbonitrile

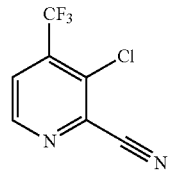 [SMILES: N#Cc1nccc(C(F)(F)F)c1Cl]

A mixture of 3-chloro-4-(trifluoromethyl)pyridine 1-oxide (2.10 g, 10.6 mmol), trimethylsilyl cyanide (3.40 mL, 25.5 mmol) and TEA (2.96 mL, 21.3 mmol) in MeCN (20 mL) was heated under reflux overnight. The reaction mixture was concentrated under reduced pressure and the residue was partitioned between EtOAc and 10% aq. Na$_2$CO$_3$. The organic phase was washed with water and brine, dried over Na$_2$SO$_4$ and concentrated under reduced pressure to give 2.18 g (99.3% yield) of the sub-title compound as a brown oil. LCMS calc. for $C_7H_3ClF_3N_2$ (M+H)$^+$: m/z=207.0. found: 207.1.

Step C. Methyl 3-amino-7-(trifluoromethyl)thieno[3,2-b]pyridine-2-carboxylate

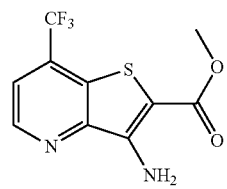 [SMILES: COC(=O)c1sc2c(C(F)(F)F)ccnc2c1N]

To a solution of 3-chloro-4-(trifluoromethyl)pyridine-2-carbonitrile (2.18 g, 10.6 mmol) in MeCN (20 mL) was added 2-mercaptoacetic acid methyl ester (1.14 mL, 12.7 mmol) and potassium carbonate (2.92 g, 21.1 mmol). The mixture was heated under reflux for 3 h, and then filtered, rinsing with MeCN. The filtrate was concentrated under reduced pressure. The residue was diluted with DCM, washed with water and brine, dried over $Na_2SO_4$ and concentrated under reduced pressure. The residue was purified by column chromatography on silica gel using CombiFlash® apparatus eluting with EtOAc/hexane (0-70%). The purification gave 1.82 g (62.4% yield) of the sub-title compound as a yellowish solid. LCMS calc. for $C_{10}H_8F_3N_2O_2S$ (M+H)$^+$: m/z=277.0. found: 277.0.

Step D. 2-[(tert-Butoxycarbonyl)amino]-7-(trifluoromethyl)thieno[3,2-b]pyridine-3-carboxylic acid

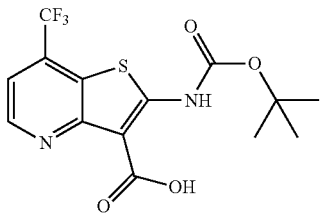 [SMILES: CC(C)(C)OC(=O)Nc1sc2c(C(F)(F)F)ccnc2c1C(=O)O]

The sub-title carboxylic acid was synthesized using an analogous procedure to that described in Step F of Example 34. LCMS calc. for $C_{14}H_{14}F_3N_2O_4S$ (M+H)$^+$: m/z=363.1. found: 363.1.

Step E. 2-Amino-N-{4-[(3S)-3-aminopiperidin-1-yl]pyridin-3-yl}-7-trifluoromethyl-thieno[3,2-b]pyridine-3-carboxamide The title compound (Example 38) was synthesized using an analogous procedure to that described in Step G of Example 34. LCMS calc. for $C_{19}H_{20}F_3N_6OS$ (M+H)$^+$: m/z=437.1. found: 437.1.

Example 39

2-Amino-N-[5-(4-aminoazepan-1-yl)-1-methyl-1H-pyrazol-4-yl]-5-chlorothieno[3,2-b]pyridine-3-carboxamide

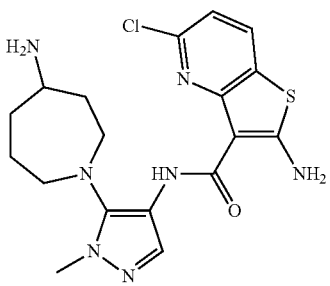 [SMILES: Cn1ncc(NC(=O)c2c(N)sc3ccc(Cl)nc23)c1N1CCCC(N)CC1]

Step A. Ethyl 2-[(tert-butoxycarbonyl)amino]-5-chlorothieno[3,2-b]pyridine-3-carboxylate

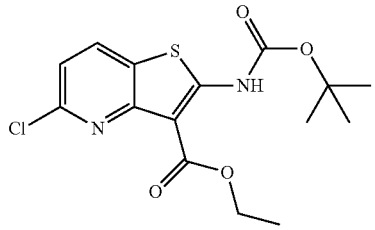 [SMILES: CCOC(=O)c1c(NC(=O)OC(C)(C)C)sc2ccc(Cl)nc12]

To a solution of ethyl 2-amino-5-chlorothieno[3,2-b]pyridine-3-carboxylate (1.0 g, 3.9 mmol) in MeCN was added DMAP (5 mg, 0.04 mmol), followed by $Boc_2O$ (0.85 g, 3.9 mmol). The reaction mixture was stirred at room temperature for 2 h and concentrated under reduced pressure. The residue was purified by column chromatography on silica gel using CombiFlash® apparatus eluting with EtOAc/hexane (20-70%). The purification gave 1.0 g (70% yield) of the sub-title compound as a yellowish solid. LCMS calc. for $C_{15}H_{18}ClN_2O_4S$ (M+H)$^+$: m/z=357.1. found: 357.0.

Step B. 2-[(tert-Butoxycarbonyl)amino]-5-chlorothieno[3,2-b]pyridine-3-carboxylic acid

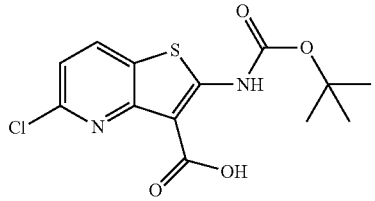 [SMILES: CC(C)(C)OC(=O)Nc1sc2ccc(Cl)nc2c1C(=O)O]

A mixture of ethyl 2-[(tert-butoxycarbonyl)amino]-5-chlorothieno[3,2-b]pyridine-3-carboxylate (1.0 g, 2.9 mmol), $LiOH.H_2O$ (600 mg, 15 mmol) in THF (6 mL), MeOH (3 mL) and water (1 mL) was stirred at 100° C. for 2 h. The mixture was concentrated under reduced pressure and neutralized to pH=6-7. The formed solid was filtered and dried under reduced pressure to give 910 mg (99% yield) of the sub-title compound as a white powder. LCMS calc. for $C_{13}H_{14}ClN_2O_4S$ (M+H)$^+$: m/z=329.0. found: 329.1.

Step C. 2-Amino-N-[5-(4-aminoazepan-1-yl)-1-methyl-1H-pyrazol-4-yl]-5-chlorothieno[3,2-b]pyridine-3-carboxamide A mixture of tert-butyl [1-(4-amino-1-methyl-1H-pyrazol-5-yl)azepan-4-yl]carbamate (20 mg, 6.5 mmol), 2-[(tert-butoxycarbonyl)amino]-5-chlorothieno[3,2-b]pyridine-3-carboxylic acid (21 mg, 6.5 mmol), HATU (29 mg, 0.078 mmol) and DIPEA (34 µL, 0.19 mmol) in DMF (1 mL) was stirred at ambient temperature for 2 h. Direct purification on preparative HPLC (pH=2) afforded an intermediate compound. LCMS calc. for $C_{28}H_{39}ClN_7O_5S$ (M+H)$^+$: m/z=620.2. found: 621.1.

To the purified intermediate was added DCM (0.8 mL) and TFA (0.8 mL). The reaction mixture was concentrated under reduced pressure and the residue was neutralized with one drop of $NH_4OH$ in water to pH=8-9. Purification by preparative LCMS (pH=10) afforded the title compound as a white powder. LCMS calc. for $C_{18}H_{23}ClN_7OS$ (M+H)$^+$: m/z=420.1. found: 420.1.

Example 40

2-Amino-N-[4-(3-aminopiperidin-1-yl)pyridin-3-yl]-5-chlorothieno[3,2-b]pyridine-3-carboxamide

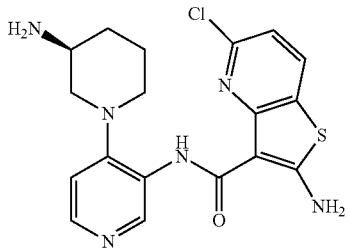 [SMILES: Nc1sc2ccc(Cl)nc2c1C(=O)Nc1cnccc1N1CCC[C@H](N)C1]

Example 40 was synthesized using an analogous procedure to that described in Example 39, except using Intermediate 6 instead of Intermediate 1 in Step c (Example 39). LCMS calc. for $C_{18}H_{20}ClN_6OS$ (M+H)$^+$: m/z=403.1. found: 403.1.

Example 41

2-Amino-N-{5-[(3S)-3-aminopiperidin-1-yl]-1-methyl-1H-pyrazol-4-yl}-5-chlorothieno[3,2-b]pyridine-3-carboxamide

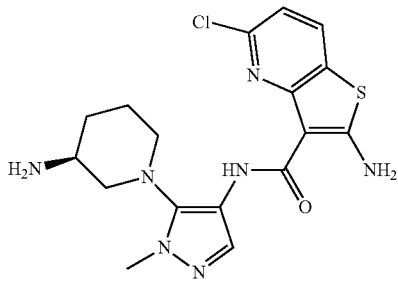 [SMILES: Cn1ncc(NC(=O)c2c(N)sc3ccc(Cl)nc23)c1N1CCC[C@H](N)C1]

Example 41 was synthesized using an analogous procedure to that described in Example 39, except using Intermediate 2 instead of Intermediate 1 in Step c (Example 39). LCMS calc. for $C_{17}H_{21}ClN_7OS$ (M+H)$^+$: m/z=406.1. found: 406.1.

Example 42

2-Amino-N-[4-(3-aminopiperidin-1-yl)pyridin-3-yl]-5-methylthieno[3,2-b]pyridine-3-carboxamide

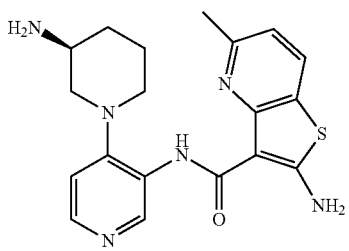 [SMILES: Cc1ccc2sc(N)c(C(=O)Nc3cnccc3N3CCC[C@H](N)C3)c2n1]

Step A. Ethyl 2-[(tert-butoxycarbonyl)amino]-5-methylthieno[3,2-b]pyridine-3-carboxylate

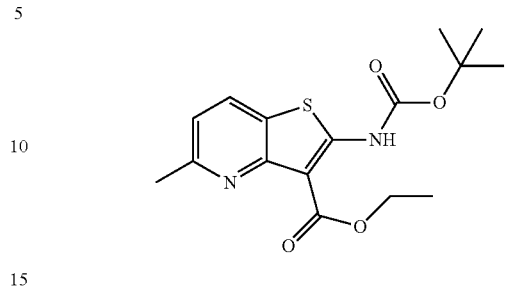

A mixture of ethyl 2-[(tert-butoxycarbonyl)amino]-5-chlorothieno[3,2-b]pyridine-3-carboxylate (100 mg, 0.3 mmol), 2.0 M methylzinc chloride in THF (0.21 mL, 0.42 mmol) and Pd(PPh$_3$)$_4$ (40 mg, 0.035 mmol) in THF (2.0 mL) in a sealed tube was heated under microwave irradiation at 110° C. for 1 h. The reaction mixture was filtered and the filtrate was concentrated under reduced pressure. The residue was purified by column chromatography on silica gel using CombiFlash® apparatus eluting with EtOAc to give 63 mg (70% yield) of the sub-title compound. LCMS calc. for $C_{16}H_{21}N_2O_4S$ (M+H)$^+$: m/z=337.1. found: 337.1.

Step B. 2-[(tert-Butoxycarbonyl)amino]-5-methylthieno[3,2-b]pyridine-3-carboxylic acid

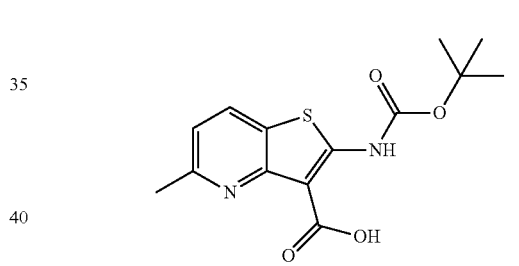

A mixture of ethyl 2-[(tert-butoxycarbonyl)amino]-5-methylthieno[3,2-b]pyridine-3-carboxylate (63 mg, 0.187 mmol), LiOH.H$_2$O (37.6 mg, 0.94 mmol) in THF (6 mL), MeOH (3 mL) and water (1 mL) was stirred at 100° C. for 2 h. The mixture was concentrated under reduced pressure and neutralized to pH=6-7. Direct purification using preparative HPLC afforded 34.7 mg (60% yield) of the sub-title compound as a white powder. LCMS calc. for $C_{14}H_{17}N_2O_4S$ (M+H)$^+$: m/z=309.1. found: 309.1.

Step C. 2-Amino-N-[4-(3-aminopiperidin-1-yl)pyridin-3-yl]-5-methylthieno[3,2-b]pyridine-3-carboxamide A mixture of tert-butyl [1-(3-aminopyridin-4-yl)piperidin-3-yl]carbamate (20 mg, 0.065 mmol), 2-[(tert-butoxycarbonyl)amino]-5-methylthieno[3,2-b]pyridine-3-carboxylic acid (21 mg, 0.065 mmol), HATU (29 mg, 0.078 mmol) and DIPEA (34 µL, 0.19 mmol) in DMF (1 mL) was stirred at ambient temperature overnight. The solution was concentrated under reduced pressure. The residue was purified by HPLC (pH=2) to afford the tert-butyloxycarbonyl-protected intermediate. LCMS calc. for $C_{29}H_{38}N_6O_5S$ (M+H)$^+$: m/z=583.3. found: 583.1.

To the purified intermediate was added DCM (0.8 mL) and TFA (0.8 mL). The reaction mixture was concentrated under reduced pressure and the residue was neutralized with one drop of NH₄OH in water to pH=8-9. Purification by preparative LCMS (pH=10) afforded the title compound as a white powder. LCMS calc. for $C_{19}H_{23}N_6OS$ (M+H)⁺: m/z=383.2. found: 383.1.

Example 43

2-Amino-N-[5-(4-aminoazepan-1-yl)-1-methyl-1H-pyrazol-4-yl]-5-methylthieno[3,2-b]pyridine-3-carboxamide

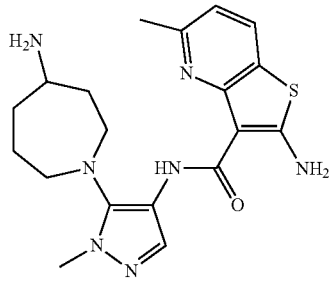 [SMILES: Cc1ccc2sc(N)c(C(=O)Nc3cnn(C)c3N3CCCC(N)CC3)c2n1]

Example 43 was synthesized using an analogous procedure to that described in Example 42, except using Intermediate 1 instead of intermediate 6 in Step C (Example 42). LCMS calc. for $C_{19}H_{26}N_7OS$ (M+H)⁺: m/z=400.2. found: 400.1.

Example 44

2-Amino-N-[5-(4-aminoazepan-1-yl)-1-methyl-1H-pyrazol-4-yl]-5-phenylthieno[3,2-b]pyridine-3-carboxamide

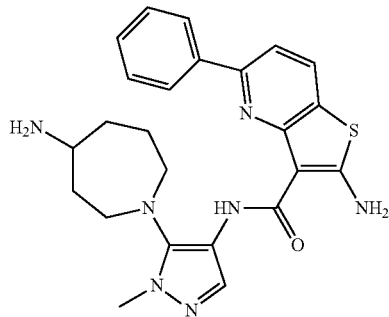 [SMILES: Cn1ncc(NC(=O)c2c(N)sc3ccc(-c4ccccc4)nc23)c1N1CCCC(N)CC1]

Step A. Ethyl 2-[(tert-butoxycarbonyl)amino]-5-phenylthieno[3,2-b]pyridine-3-carboxylate

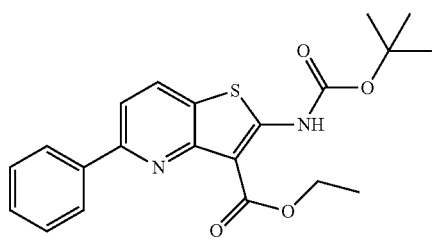 [SMILES: CCOC(=O)c1c(NC(=O)OC(C)(C)C)sc2ccc(-c3ccccc3)nc12]

A mixture of phenylboronic acid (41.0 mg, 0.336 mmol), bis(tri-tert-butylphosphine)palladium (28.6 mg, 0.0560 mmol), ethyl 2-[(tert-butoxycarbonyl)amino]-5-chlorothieno[3,2-b]pyridine-3-carboxylate (100.0 mg, 0.2802 mmol) and DIPEA (97.6 µL, 0.560 mmol) in 1,4-dioxane (1 mL) and water (50 µL) was heated under microwave irradiation at 130° C. for 40 min. The reaction mixture was filtered through a pad of diatomaceous earth and concentrated under reduced pressure. The crude product was purified by silica gel column chromatography eluted with EtOAc/hexane (0-50%) to give 77 mg (69% yield) of the sub-title compound as a yellow solid. LCMS calc. for $C_{21}H_{23}N_2O_4S$ (M+H)⁺: m/z=399.1. found: 399.1.

Step B. 2-[(tert-Butoxycarbonyl)amino]-5-phenylthieno[3,2-b]pyridine-3-carboxylic acid

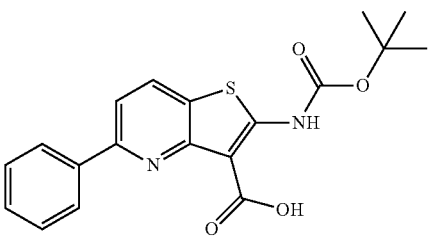 [SMILES: CC(C)(C)OC(=O)Nc1sc2ccc(-c3ccccc3)nc2c1C(=O)O]

A mixture of ethyl 2-[(tert-butoxycarbonyl)amino]-5-phenylthieno[3,2-b]pyridine-3-carboxylate (75 mg, 0.19 mmol), LiOH (22 mg, 0.94 mmol), THF (4 mL), MeOH (2 mL) and water (2 mL) was stirred at 100° C. for 2 h. The solution was concentrated under reduced pressure and the residue was adjusted to pH=4-5 with 1 M aq. HCl and the solution was extracted with EtOAc (2 times). The combined organic phases were washed with water and brine, dried over Na₂SO₄, filtered and concentrated under reduced pressure to give the sub-title compound as a yellow solid. LCMS calc. for $C_{19}H_{19}N_2O_4S$ (M+H)⁺: m/z=371.1. found: 371.1.

Step C. 2-Amino-N-[5-(4-aminoazepan-1-yl)-1-methyl-1H-pyrazol-4-yl]-5-phenylthieno[3,2-b]pyridine-3-carboxamide A mixture of tert-butyl [1-(4-amino-1-methyl-1H-pyrazol-5-yl)azepan-4-yl]carbamate (16.7 mg, 0.0540 mmol), 2-[(tert-butoxycarbonyl)amino]-5-phenylthieno[3,2-b]pyridine-3-carboxylic acid (20.0 mg, 0.0540 mmol), HATU (26.7 mg, 0.0702 mmol) and DIPEA (28 µL, 0.16 mmol) in DMF (1 mL) was stirred at ambient temperature overnight. Direct purification by preparative LCMS (pH=2) afforded the intermediate compound, tert-butyl (3-{[(5-{4-[(tert-butoxycarbonyl)amino]azepan-1-yl}-1-methyl-1H-pyrazol-4-yl)amino]carbonyl}-5-phenylthieno[3,2-b]pyridin-2-yl)carbamate. LCMS calc. for $C_{34}H_{44}N_7O_5S$ (M+H)⁺: m/z=662.3. found: 662.1.

To the purified intermediate was added DCM (2 mL) and TFA (2 mL). The reaction mixture was stirred at ambient temperature for 1 h and concentrated under reduced pressure. The residue was adjusted to pH=8-9 with one drop of NH₄OH in water. Purification by preparative LCMS (pH=10) gave the title compound as a white powder. LCMS calc. for $C_{24}H_{28}N_7OS$ (M+H)⁺: m/z=462.2. found: 462.2.

Example 45

2-Amino-N-{4-[(3S)-3-aminopiperidin-1-yl]pyridin-3-yl}furo[3,2-b]pyridine-3-carboxamide

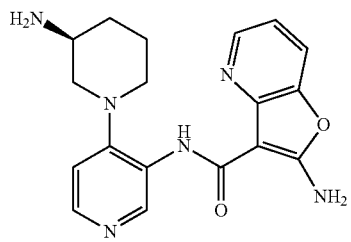

Step A. Ethyl [3-(acetyloxy)pyridin-2-yl](cyano)acetate

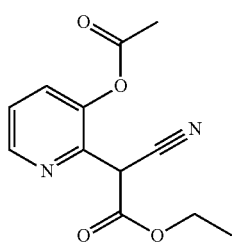 [SMILES: CCOC(=O)C(C#N)c1ncccc1OC(C)=O]

3-Hydroxy pyridine N-oxide (5 g, 45 mmol) was dissolved in 20 mL of Ac$_2$O by gently heating. After cooling, 5.3 mL of ethyl cyanoacetate was added to the solution and the mixture was allowed to stand at room temperature under N$_2$ in the dark for 3 days. A crystalline precipitate formed and was collected by filtration. The solid was recrystallized from EtOAc to give 3.5 g (31.8% yield) of the pure sub-title compound. LCMS calc. for C$_{12}$H$_{13}$N$_2$O$_4$ (M+H)$^+$: m/z=249.1. found: 249.1.

Step B. Ethyl 2-aminofuro[3,2-b]pyridine-3-carboxylate

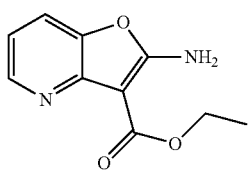

3.5 g (14.1 mmol) of ethyl [3-(acetyloxy)pyridin-2-yl](cyano)acetate was dissolved portion-wise in 20 mL of cooled concentrated sulfuric acid. After 2 h the mixture was poured into ice and the pH was adjusted to ca. 6 with 2 M NH$_4$OH. The precipitate was collected by filtration and washed with some water. The aqueous solution was extracted with chloroform. The residue combined with the precipitate was crystallized from chloroform to give 1 g (34% yield) of the sub-title compound. LCMS calc. for C$_{10}$H$_{11}$N$_2$O$_3$ (M+H)$^+$: m/z=207.1. found: 207.1.

Step C. Ethyl 2-[(tert-butoxycarbonyl)amino]furo[3,2-b]pyridine-3-carboxylate

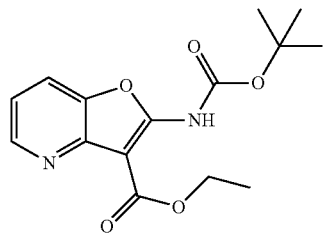 [SMILES: CCOC(=O)c1c(NC(=O)OC(C)(C)C)oc2cccnc12]

A mixture of ethyl 2-aminofuro[3,2-b]pyridine-3-carboxylate (1.00 g, 4.85 mmol), Boc$_2$O (1.27 g, 5.82 mmol) and DMAP (29.7 mg, 0.243 mmol) in MeCN (30.0 mL) was stirred at ambient temperature overnight. The reaction mixture was concentrated under reduced pressure and the residue was purified by column chromatography on silica gel using CombiFlash® apparatus to give 1.1 g (74% yield) of the sub-title compound. LCMS calc. for C$_{15}$H$_{19}$N$_2$O$_5$ (M+H)$^+$: m/z=307.1. found: 307.1.

Step D. 2-[(tert-Butoxycarbonyl)amino]furo[3,2-b]pyridine-3-carboxylic acid

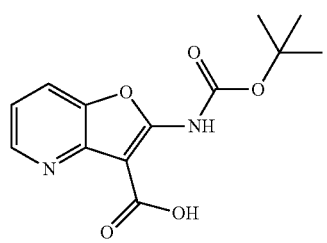 [SMILES: CC(C)(C)OC(=O)Nc1oc2cccnc2c1C(=O)O]

A mixture of ethyl 2-[(tert-butoxycarbonyl)amino]furo[3,2-b]pyridine-3-carboxylate (350.0 mg, 1.143 mmol) and LiOH.H$_2$O (239.7 mg, 5.712 mmol) in THF (12 mL), MeOH (6 mL) and water (2 mL) was stirred at 60° C. overnight. The reaction mixture was concentrated under reduced pressure and adjusted to pH=6. The solid that formed was filtered and dried under reduced pressure to give 300 mg (94% yield) of the sub-title compound. LCMS calc. for C$_{13}$H$_{15}$N$_2$O$_5$ (M+H)$^+$: m/z=279.1. found: 279.1.

Step E. 2-Amino-N-{4-[(3S)-3-aminopiperidin-1-yl]pyridin-3-yl}furo[3,2-b]pyridine-3-carboxamide A mixture of tert-butyl [(3S)-1-(3-aminopyridin-4-yl)piperidin-3-yl]carbamate (9.849 mg, 0.03368 mmol), 2-[(tert-butoxycarbonyl)amino]furo[3,2-b]pyridine-3-carboxylic acid (9.409 mg, 0.03381 mmol), HATU (13.8 mg, 0.0362 mmol) and DIPEA (0.00630 mL, 0.0362 mmol) in DMF (2.0 mL) was stirred at ambient temperature overnight. Direct purification on preparative HPLC afforded the intermediate compound, tert-butyl ((3S)-1-{3-[({2-[(tert-butoxycarbonyl)amino]furo[3,2-b]pyridin-3-yl}carbonyl)amino]pyridin-4-yl}piperidin-3-yl)carbamate. LCMS calc. for C$_{28}$H$_{37}$N$_6$O$_6$ (M+H)$^+$: m/z=553.3. found: 553.1.

To the purified intermediate was dissolved in DCM (1.0 mL) and TFA (1.0 mL). The reaction mixture was stirred at ambient temperature for 60 min. Direct purification on preparative HPLC afforded the title compound. LCMS calc. for $C_{18}H_{21}N_6O_2$ (M+H)$^+$: m/z=353.2. found: 353.1.

Example 46

2-Amino-N-[5-(4-aminoazepan-1-yl)-1-methyl-1H-pyrazol-4-yl]furo[3,2-b]pyridine-3-carboxamide

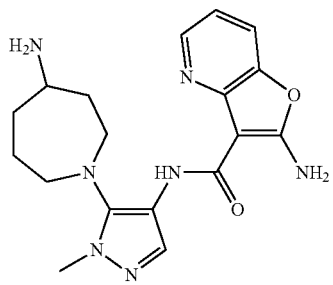

Example 46 was synthesized using an analogous procedure to that described in Example 45, except using Intermediate 1 instead of Intermediate 6 in Step E (Example 45). LCMS calc. for $C_{18}H_{24}N_7O_2$ (M+H)$^+$: m/z=370.2. found: 370.1.

Example 47

2-Amino-N-{4-[(3S)-3-aminopiperidin-1-yl]pyridin-3-yl}-6-ethylfuro[3,2-b]pyridine-3-carboxamide

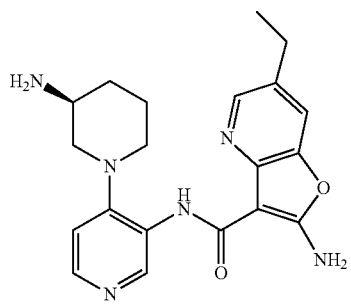 [SMILES: CCc1cnc2c(C(=O)Nc3cnccc3N3CCC[C@H](N)C3)c(N)oc2c1]

Step A. 5-Bromopyridin-3-ol 1-oxide

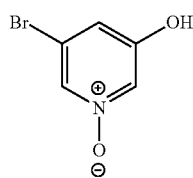

A mixture of 5-bromopyridin-3-ol (8.00 g, 46.0 mmol) and mCPBA (15.9 g, 92.0 mmol) in DCM (400 mL) was stirred at ambient temperature overnight. The solid formed was filtered and dried under reduced pressure to give 6 g (69% yield) of the sub-title compound. LCMS calc. for $C_5H_5BrNO_2$ (M+H)$^+$: m/z=189.9. found: 190.1.

Step B. Ethyl 2-amino-6-bromofuro[3,2-b]pyridine-3-carboxylate

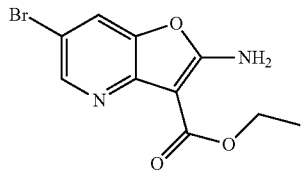 [SMILES: CCOC(=O)c1c(N)oc2cc(Br)cnc12]

A mixture of 5-bromopyridin-3-ol 1-oxide (3.0 g, 16 mmol) in Ac$_2$O (20.0 mL, 212 mmol) was heated up to 100° C. for 10 min. The reaction mixture was allowed to cool to ambient temperature. Then, into the reaction mixture was added cyanoacetic acid, ethyl ester (2.05 mL, 19.3 mmol). The resulting mixture was stirred at 100° C. overnight and concentrated under reduced pressure. The residue was dissolved in sulfuric acid (20.0 mL, 375 mmol). The reaction mixture was stirred at ambient temperature for 2 h. The mixture was adjusted to pH=6 by using 2 M aq. NH$_4$OH. The solid that formed was collected by filtration and dried under reduced pressure to give 1.0 g (22% yield) of the sub-title compound LCMS calc. for $C_{10}H_{10}BrN_2O_3$ (M+H)$^+$: m/z=285.0. found: 285.1.

Step C. Ethyl 6-bromo-2-[(tert-butoxycarbonyl)amino]furo[3,2-b]pyridine-3-carboxylate

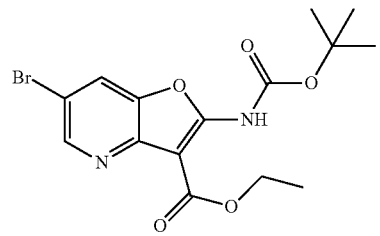 [SMILES: CCOC(=O)c1c(NC(=O)OC(C)(C)C)oc2cc(Br)cnc12]

A mixture of ethyl 2-amino-6-bromofuro[3,2-b]pyridine-3-carboxylate (260 mg, 0.91 mmol), Boc$_2$O (240.0 mg, 1.100 mmol) and DMAP (10.0 mg, 0.0818 mmol) in MeCN (30.0 mL) was stirred at ambient temperature overnight. The mixture was concentrated under reduced pressure and the residue was purified by column chromatography on silica gel using CombiFlash® apparatus to give 300 mg (85% yield) of the sub-title compound. LCMS calc. for $C_{15}H_{18}BrN_2O_5$ (M+H)$^+$: m/z=385.0. found: 385.1.

Step D. Ethyl 2-[(tert-butoxycarbonyl)amino]-6-ethylfuro[3,2-b]pyridine-3-carboxylate

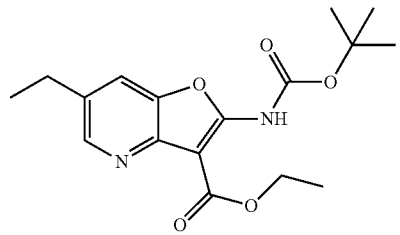 [SMILES: CCOC(=O)c1c(NC(=O)OC(C)(C)C)oc2cc(CC)cnc12]

To a solution of ethyl 6-bromo-2-[(tert-butoxycarbonyl)amino]furo[3,2-b]pyridine-3-carboxylate (100.0 mg, 0.2596 mmol) in THF (2 mL) under $N_2$ at ambient temperature was added Pd(PPh$_3$)$_4$ (15.0 mg, 0.0130 mmol). The mixture in a sealed flask was evacuated and refilled with $N_2$ several times, followed by the addition of 1.0 M diethyl zinc in hexane (2.60 mL, 2.60 mmol) at ambient temperature. The reaction mixture was heated at 70° C. for 1 h. After filtration and evaporation under reduced pressure, the residue was quenched with small amounts of water. Purification on a silica gel column afforded 60 mg (69.1% yield) of the sub-title compound. LCMS calc. for $C_{17}H_{23}N_2O_5$ (M+H)$^+$: m/z=335.2. found: 335.1.

Step E. 2-[(tert-Butoxycarbonyl)amino]-6-ethylfuro[3,2-b]pyridine-3-carboxylic acid

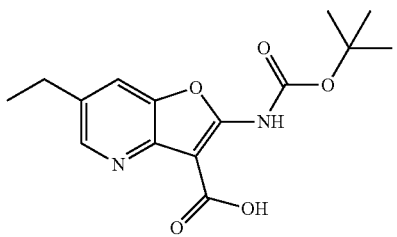 [SMILES: CCc1cnc2c(C(=O)O)c(NC(=O)OC(C)(C)C)oc2c1]

To a solution of ethyl 2-[(tert-butoxycarbonyl)amino]-6-ethylfuro[3,2-b]pyridine-3-carboxylate (60.0 mg, 0.179 mmol) in THF (12.0 mL), water (2.0 mL) and MeOH (6.0 mL) was added LiOH.H$_2$O (83.9 mg, 2.00 mmol). The resulting solution was stirred at 60° C. overnight. The reaction mixture was concentrated under reduced pressure and adjusted to pH=6. The solid formed was collected by filtration and dried under reduced pressure to give 31 mg (56.4% yield) of the sub-title compound. LCMS calc. for $C_{15}H_{19}N_2O_5$ (M+H)$^+$: m/z=307.1. found: 307.1.

Step F. 2-Amino-N-{4-[(3S)-3-aminopiperidin-1-yl]pyridin-3-yl}-6-ethylfuro[3,2-b]pyridine-3-carboxamide A mixture of tert-butyl [(3S)-1-(3-aminopyridin-4-yl)piperidin-3-yl]carbamate (10.00 mg, 0.03420 mmol), 2-[(tert-butoxycarbonyl)amino]-6-ethylfuro[3,2-b]pyridine-3-carboxylic acid (10.52 mg, 0.03433 mmol), HATU (14.0 mg, 0.0367 mmol) and DIPEA (0.00640 mL, 0.0368 mmol) in 1,2-dichloroethane (2.0 mL) was stirred at ambient temperature overnight. Direct purification on preparative HPLC afforded the intermediate compound, tert-butyl ((3S)-1-{3-[({2-[(tert-butoxycarbonyl)amino]-6-ethylfuro[3,2-b]pyridin-3-yl}carbonyl)amino]pyridin-4-yl}piperidin-3-yl)carbamate. LCMS calc. for $C_{30}H_{41}N_6O_6$ (M+H)$^+$: m/z=581.3. found: 581.1.

The purified intermediate was dissolved in DCM (1.0 mL) and TFA (1.0 mL). The reaction mixture was stirred at ambient temperature overnight. Direct purification on preparative HPLC afforded the title compound. LCMS calc. for $C_{20}H_{25}N_6O_2$ (M+H)$^+$: m/z=381.2. found: 381.1.

The following compounds in Table 1 were prepared using analogous procedures to those described in Examples 45, 46 and 47.

TABLE 1

| Example | Name | Structure | MS (M + H)$^+$ |
|---|---|---|---|
| 48 | 2-amino-N-{4-[(3S)-3-aminopiperidin-1-yl]pyridin-3-yl}-6-(trifluoromethyl)furo[3,2-b]pyridine-3-carboxamide | 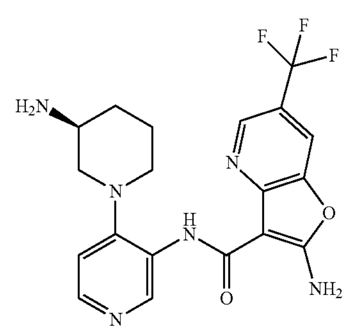 [SMILES: Nc1oc2cc(C(F)(F)F)cnc2c1C(=O)Nc1cnccc1N1CCC[C@H](N)C1] | 421.1 |
| 49 | 2-amino-N-{4-[(3S)-3-aminopiperidin-1-yl]pyridin-3-yl)-6-methyl-furo[3,2-b]pyridine-3-carboxamide | 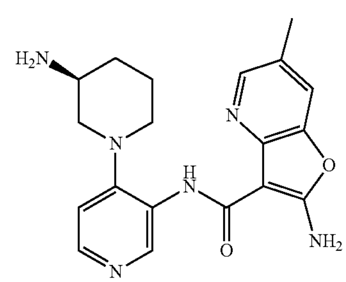 [SMILES: Cc1cnc2c(C(=O)Nc3cnccc3N3CCC[C@H](N)C3)c(N)oc2c1] | 367.1 |

TABLE 1-continued

| Example | Name | Structure | MS (M + H)+ |
|---|---|---|---|
| 50 | 2-amino-N-{4-[(3S)-3-aminopiperidin-1-yl]pyridin-3-yl}-6-(iso-propyl)furo[3,2-b]pyridine-3-carboxamide | 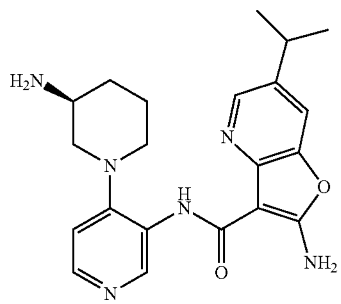 [SMILES: CC(C)c1cnc2c(C(=O)Nc3cnccc3N3CCC[C@H](N)C3)c(N)oc2c1] | 395.2 |
| 51 | 2-amino-N-{4-[(3S)-3-aminopiperidin-1-yl]pyridin-3-yl}-6-(propyl)furo[3,2-b]pyridine-3-carboxamide | 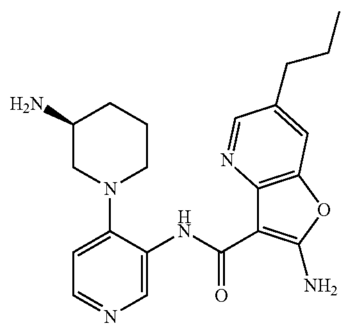 [SMILES: CCCc1cnc2c(C(=O)Nc3cnccc3N3CCC[C@H](N)C3)c(N)oc2c1] | 395.2 |
| 52 | 2-amino-N-{4-[(3S)-3-aminopiperidin-1-yl]pyridin-3-yl}-6-fluoro-furo[3,2-b]pyridine-3-carboxamide | 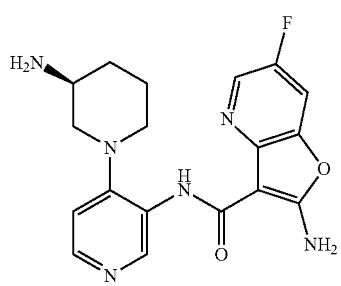 [SMILES: Nc1oc2cc(F)cnc2c1C(=O)Nc1cnccc1N1CCC[C@H](N)C1] | 371.1 |
| 53 | 2-amino-N-{4-[(3S)-3-aminopiperidin-1-yl]pyridin-3-yl}-6-chloro-furo[3,2-b]pyridine-3-carboxamide | 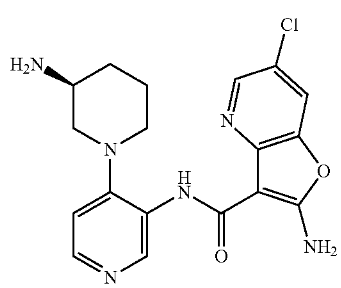 | 387.1 |
| 54 | 2-amino-N-{4-[(3S)-3-aminopiperidin-1-yl]pyridin-3-yl}-6-bromo-furo[3,2-b]pyridine-3-carboxamide | 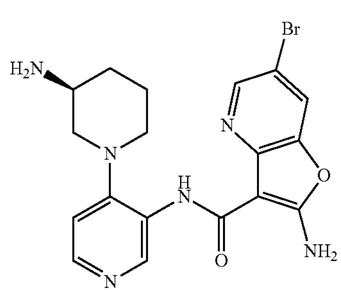 [SMILES: Nc1oc2cc(Cl)cnc2c1C(=O)Nc1cnccc1N1CCC[C@H](N)C1] | 431.1 |

TABLE 1-continued

| Example | Name | MS (M + H)+ |
|---------|------|-------------|
| 55 | 2-amino-N-{4-[(3S)-3-aminopiperidin-1-yl]pyridin-3-yl}-7-methyl-furo[3,2-b]pyridine-3-carboxamide | 367.1 |
| 56 | 2-amino-N-[5-(4-aminoazepan-1-yl)-1-methyl-1H-pyrazol-4-yl]-6-trifluoromethyl-furo[3,2-b]pyridine-3-carboxamide | 438.1 |
| 57 | 2-Amino-N-[5-(4-aminoazepan-1-yl)-1-methyl-1H-pyrazol-4-yl]-6-chlorofuro[3,2-b]pyridine-3-carboxamide | 404.1 |
| 58 | 2-amino-N-[5-(4-aminoazepan-1-yl)-1-methyl-1H-pyrazol-4-yl]-7-chlorofuro[3,2-b]pyridine-3-carboxamide | 404.1 |

TABLE 1-continued

| Example | Name | Structure | MS (M + H)+ |
|---|---|---|---|
| 59 | 2-amino-N-[5-(4-aminoazepan-1-yl)-1-methyl-1H-pyrazol-4-yl]-6-propylfuro[3,2-b]pyridine-3-carboxamide | 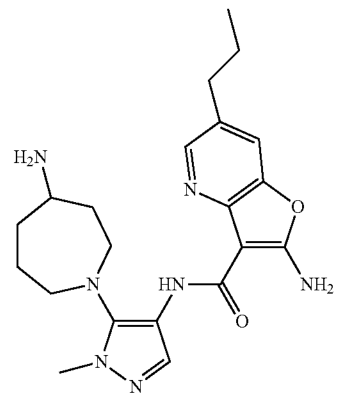 [SMILES: CCCc1cnc2c(C(=O)Nc3cnn(C)c3N3CCCC(N)CC3)c(N)oc2c1] | 412.1 |
| 60 | 2-amino-N-{4-[(3S,5R)-3-amino-5-(trifluoromethyl)piperidin-1-yl]pyridin-3-yl}-furo[3,2-b]pyridine-3-carboxamide | 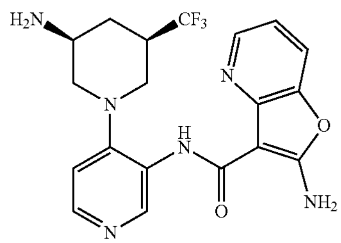 [SMILES: Nc1oc2cccnc2c1C(=O)Nc1cnccc1N1C[C@@H](N)C[C@@H](C(F)(F)F)C1] | 421.1 |
| 61 | 2-amino-N-{4-[(3S,5R)-3-amino-5-(trifluoromethyl)piperidin-1-yl]pyridin-3-yl}-6-trifluoromethyl-furo[3,2-b]pyridine-3-carboxamide | 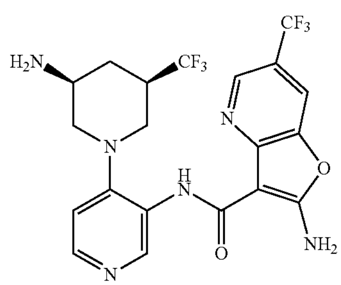 [SMILES: Nc1oc2cc(C(F)(F)F)cnc2c1C(=O)Nc1cnccc1N1C[C@@H](N)C[C@@H](C(F)(F)F)C1] | 489.1 |
| 62 | 2-amino-N-{4-[(3S,5R)-3-amino-5-(trifluoromethyl)piperidin-1-yl]pyridin-3-yl}-6-chlorofuro[3,2-b]pyridine-3-carboxamide | 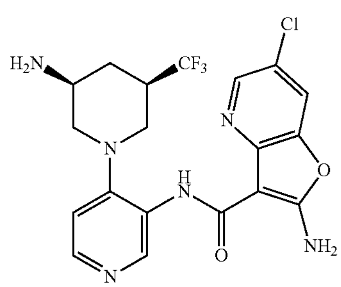 [SMILES: Nc1oc2cc(Cl)cnc2c1C(=O)Nc1cnccc1N1C[C@@H](N)C[C@@H](C(F)(F)F)C1] | 455.1 |
| 63 | 2-amino-N-{4-[(3S,5R)-3-amino-5-(trifluoromethyl)piperidin-1-yl]pyridin-3-yl}-6-fluorofuro[3,2-b]pyridine-3-carboxamide | 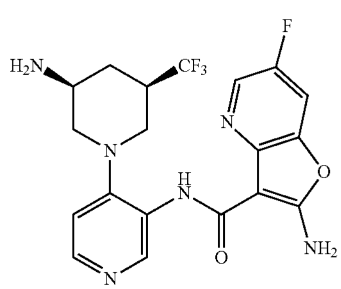 [SMILES: Nc1oc2cc(F)cnc2c1C(=O)Nc1cnccc1N1C[C@@H](N)C[C@@H](C(F)(F)F)C1] | 439.1 |

TABLE 1-continued

| Example | Name | Structure | MS (M + H)+ |
|---|---|---|---|
| 64 | 2-amino-N-{4-[(3S)-3-aminopyrrolidin-1-yl]-5-methylpyridin-3-yl}furo[3,2-b]pyridine-3-carboxamide | 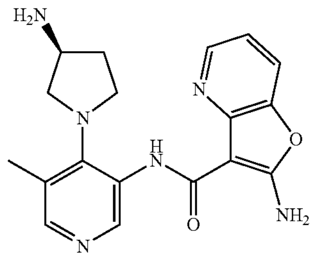 [SMILES: Cc1cncc(NC(=O)c2c(N)oc3cccnc23)c1N1CC[C@H](N)C1] | 353.1 |
| 65 | 2-amino-N-{4-[(3S,5R)-3-amino-5-methyl-piperidin-1-yl]pyridin-3-yl}-furo[3,2-b]pyridine-3-carboxamide | 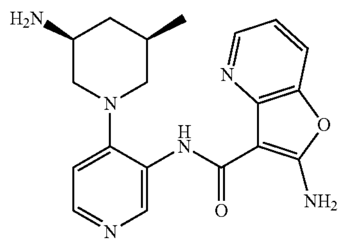 [SMILES: C[C@@H]1C[C@H](N)CN(c2ccncc2NC(=O)c2c(N)oc3cccnc23)C1] | 367.1 |
| 66 | 2-amino-N-{4-[(3R,4R,5S)-3-amino-4-hydroxy-5-methylpiperidin-1-yl]pyridin-3-yl}-6-chlorofuro[3,2-b]pyridine-3-carboxamide | 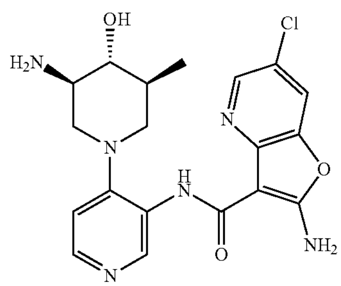 [SMILES: C[C@H]1CN(c2ccncc2NC(=O)c2c(N)oc3cc(Cl)cnc23)C[C@@H](N)[C@@H]1O] | 417.1 |

Example 67

2-Amino-N-{4-[(3R,4R,5S)-3-amino-4-hydroxy-5-methylpiperidin-1-yl]pyridin-3-yl}-6-propylfuro[3,2-b]pyridine-3-carboxamide

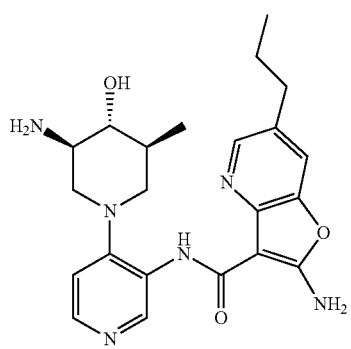 [SMILES: CCCc1cnc2c(C(=O)Nc3cnccc3N3C[C@@H](N)[C@H](O)[C@@H](C)C3)c(N)oc2c1]

Step A. Ethyl 3-amino-6-[(1Z)-prop-1-en-1-yl]furo[3,2-b]pyridine-2-carboxylate

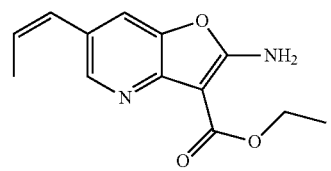 [SMILES: C/C=C\c1cnc2c(C(=O)OCC)c(N)oc2c1]

A mixture of ethyl 6-bromo-3-[(tert-butoxycarbonyl)amino]furo[3,2-b]pyridine-2-carboxylate (from Example 47 step C, 1.0 g, 2.6 mmol), bis(tri-tert-butylphosphine)palladium (0.0757 g, 0.148 mmol), (1Z)-prop-1-en-1-ylboronic acid (0.512 g, 5.96 mmol) and DIPEA (0.54 mL, 3.1 mmol) in 1,4-dioxane (2 mL) and water (0.2 mL) was stirred at 130° C. for 40 min. in a microwave oven. The mixture was concentrated under reduced pressure and the resulting residue was purified on a silica gel column to afford the sub-title compound (0.45 g, 70% yield). LCMS calc. for $C_{13}H_{15}N_2O_3$ (M+H)+: m/z=247.1. found: 247.1.

Step B. Ethyl 3-amino-6-propylfuro[3,2-b]pyridine-2-carboxylate

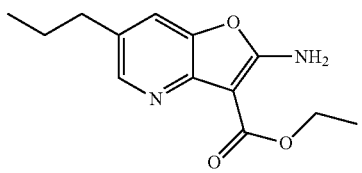 [SMILES: CCCc1cnc2c(C(=O)OCC)c(N)oc2c1]

A mixture of ethyl 3-amino-6-[(1Z)-prop-1-en-1-yl]furo[3,2-b]pyridine-2-carboxylate (498 mg, 2.02 mmol) and 10% palladium on carbon (430 mg) in EtOH (70 mL) was shaken for 2 h under $H_2$ at 5 psi. The reaction mixture was filtered through a diatomaceous earth pad and the filtrate was evaporated under reduced pressure to give the sub-title compound. LCMS calc. for $C_{13}H_{17}N_2O_3$ (M+H)$^+$: m/z=249.1. found: 249.1.

Step C. Ethyl 3-[(tert-butoxycarbonyl)amino]-6-propylfuro[3,2-b]pyridine-2-carboxylate

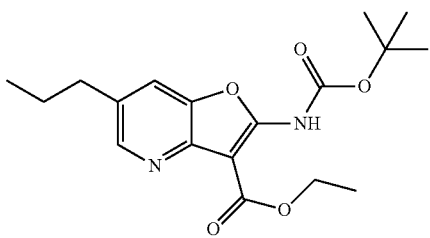 [SMILES: CCCc1cnc2c(C(=O)OCC)c(NC(=O)OC(C)(C)C)oc2c1]

A mixture of ethyl 3-amino-6-propylfuro[3,2-b]pyridine-2-carboxylate (3.0 g, 12 mmol), Boc$_2$O (3.15 g, 14.4 mmol), 4-dimethylaminopyridine (0.073 g, 0.60 mmol) and TEA (5.1 mL, 36 mmol) in MeCN (300 mL) was stirred at room temperature overnight. The mixture was concentrated under reduced pressure and the resulting residue was purified on a silica gel column to give the sub-title compound (3.0 g, 73% yield).

Step D. 3-[(tert-Butoxycarbonyl)amino]-6-propylfuro[3,2-b]pyridine-2-carboxylic acid

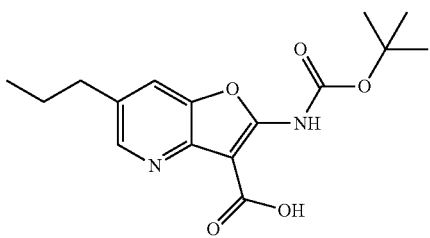 [SMILES: CCCc1cnc2c(C(=O)O)c(NC(=O)OC(C)(C)C)oc2c1]

A mixture of ethyl 3-[(tert-butoxycarbonyl)amino]-6-propylfuro[3,2-b]pyridine-2-carboxylate (0.6 g, 2 mmol), LiOH (0.6 g, 20 mmol), THF (6.0 mL), MeOH (4.0 mL) and water (2.0 mL) was stirred at 60° C. overnight. The mixture was concentrated under reduced pressure. The pH of the residue was adjusted to 5 with 1 M HCl. The mixture was extracted with EtOAc. The combined extracts were dried and concentrated under reduced pressure to give the sub-title compound. (0.3 g, 55% yield).

Step E. 2-Amino-N-{4-[(3R,4R,5S)-3-amino-4-hydroxy-5-methylpiperidin-1-yl]pyridin-3-yl}-6-propylfuro[3,2-b]pyridine-3-carboxamide

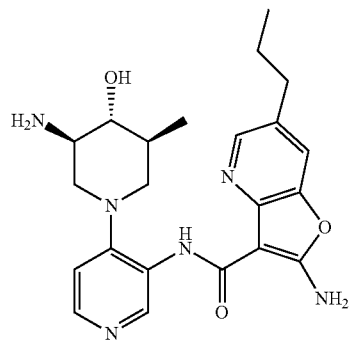

A mixture of tert-butyl ((3R,4R,5S)-1-(3-aminopyridin-4-yl)-4-{[tert-butyl(dimethyl)silyl]oxy}-5-methylpiperidin-3-yl)carbamate (1.5 g, 3.4 mmol), 2-[(tert-butoxycarbonyl)amino]-6-propylfuro[3,2-b]pyridine-3-carboxylic acid (1.3 mg, 4.1 mmol), molecular sieves (2 g) and DIPEA (1.2 mL, 6.9 mmol) in 1,2-dichloroethane (30 mL) was stirred at room temperature for 2 h, and then HATU (0.21 g, 0.55 mmol) was added. The mixture was stirred at room temperature for 24 h. The mixture was then diluted with EtOAc, washed with NaHCO$_3$ solution, dried over Na$_2$SO$_4$, filtered and concentrated under reduced pressure. The resulting residue was purified on preparative HPLC (Method A) to afford an intermediate, which was stirred in in dioxane (4 M HCl; 1 mL) for 24 h to give the final product which was concentrated under reduced pressure and purified by preparative HPLC purification (Method B) (160 mg). LCMS calc. for $C_{22}H_{29}N_6O_3$ (M+H)$^+$: m/z=425.1. found: 425.1. $^1$H NMR (500 MHz, DMSO-d$_6$) δ 10.16 (s, 1H), 9.49 (s, 1H), 8.16 (d, J=5.2 Hz, 1H), 8.13 (s, 1H), 7.60 (s, 1H), 7.10 (d, J=5.3 Hz, 1H), 4.75 (d, J=4.4 Hz, 1H), 3.14 (d, J=9.5 Hz, 1H), 3.06 (d, J=11.0 Hz, 1H), 3.01-2.91 (m, 1H), 2.75-2.65 (m, 1H), 2.61 (t, J=7.5 Hz, 2H), 2.41 (q, J=11.0 Hz, 2H), 2.09-1.92 (m, 1H), 1.71-1.52 (m, 2H), 0.90 (t, J=7.3 Hz, 3H), 0.86 (d, J=6.6 Hz, 3H) ppm.

Example 68

2-Amino-N-{4-[(3R,4R,5S)-3-amino-4-hydroxy-5-methylpiperidin-1-yl]pyridin-3-yl}-6-(trifluoromethyl)furo[3,2-b]pyridine-3-carboxamide

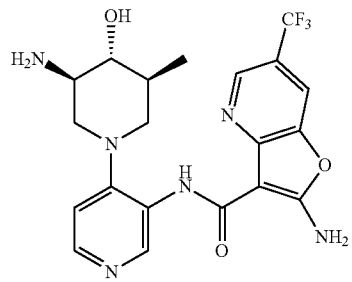 [SMILES: C[C@H]1CN(c2ccncc2NC(=O)c2c(N)oc3cc(C(F)(F)F)cnc23)C[C@@H](N)[C@@H]1O]

Step 1. tert-Butyl [3-({[4-((3R,4R,5S)-3-[(tert-butoxycarbonyl)amino]-4-{[tert-butyl(dimethyl)silyl]oxy}-5-methylpiperidin-1-yl)pyridin-3-yl]amino}carbonyl)-6-(trifluoromethyl)furo[3,2-b]pyridin-2-yl]carbamate

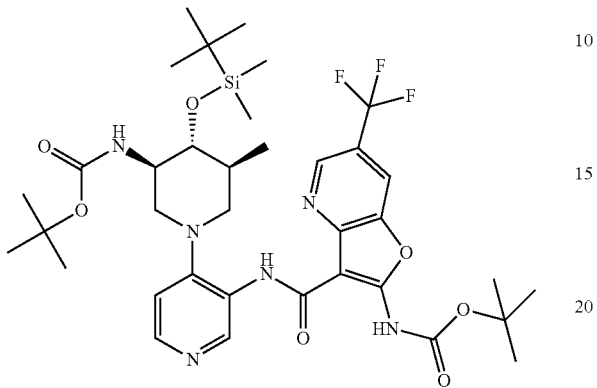

To a pre-stirred solution of 2-(tert-butoxycarbonylamino)-6-(trifluoromethyl)furo[3,2-b]pyridine-3-carboxylic acid (19 mg, 0.055 mmol), HATU (16 mg, 0.041 mmol), and DIPEA (19 µL, 0.11 mmol) in 1,2-dichloroethane (0.5 mL) was added a solution of tert-butyl ((3R,4R,5S)-1-(3-aminopyridin-4-yl)-4-{[tert-butyl(dimethyl)silyl]oxy}-5-methylpiperidin-3-yl)carbamate (15 mg, 0.034 mmol) in 1,2-dichloroethane (0.3 mL), and the resulting solution was stirred at 50° C. for 3 days. The crude reaction mixture was purified by flash chromatography (24 g silica gel column, eluting with 0-100% EtOAc/hexanes) to afford the sub-title compound. LCMS (ESI) calc. for $C_{36}H_{52}F_3N_6O_7Si(M+H)^+$: m/z=765.4. found 765.3.

Step 2. 2-Amino-N-{4-[(3R,4R,5S)-3-amino-4-hydroxy-5-methylpiperidin-1-yl]pyridin-3-yl}-6-(trifluoromethyl)furo[3,2-b]pyridine-3-carboxamide trifluoroacetate

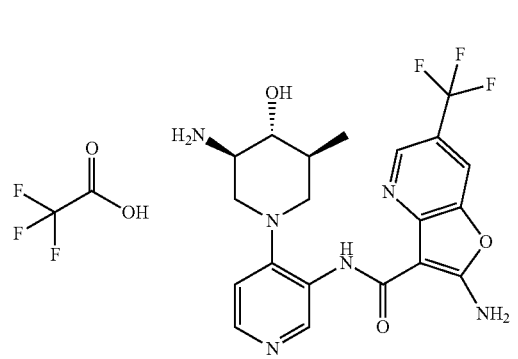 [SMILES: O=C(O)C(F)(F)F ; C[C@H]1CN(c2ccncc2NC(=O)c2c(N)oc3cc(C(F)(F)F)cnc23)C[C@@H](N)[C@@H]1O]

tert-Butyl [3-({[4-((3R,4R,5S)-3-[(tert-butoxycarbonyl)amino]-4-{[tert-butyl(dimethyl)silyl]oxy}-5-methylpiperidin-1-yl)pyridin-3-yl]amino}carbonyl)-6-(trifluoromethyl)furo[3,2-b]pyridin-2-yl]carbamate (22 mg, 0.029 mmol) was dissolved in MeCN (1.2 mL) and 1.7 M fluorosilicic acid in water (0.4 mL, 0.680 mmol) and heated with stirring at 50° C. for 3 h. The reaction mixture was diluted with MeOH and then purified by preparative-HPLC (Method A) to afford the title compound. LCMS (ESI) calc. for $C_{20}H_{22}F_3N_6O_3$ (M+H)$^+$: m/z=451.2. found 451.2.

Example 69

2-Amino-N-{4-[(3S,5R)-3-amino-5-(trifluoromethyl)piperidin-1-yl]pyridin-3-yl}-6-propylfuro[3,2-b]pyridine-3-carboxamide

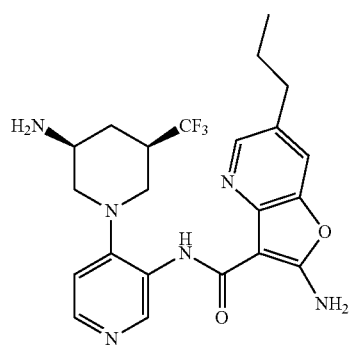 [SMILES: CCCc1cnc2c(C(=O)Nc3cnccc3N3C[C@@H](N)C[C@@H](C(F)(F)F)C3)c(N)oc2c1]

Example 69 was synthesized using analogous procedures to those described in Examples 45, 46 and 47. LCMS calc. for $C_{22}H_{26}F_3N_6O_2$ (M+H)$^+$: m/z=463.2 found: 463.1. $^1$H NMR (400 MHz, DMSO-d$_6$) δ 10.05 (s, 1H), 9.49 (s, 1H), 8.20 (d, J=5.2 Hz, 1H), 8.11 (d, J=1.3 Hz, 1H), 7.63 (d, J=1.4 Hz, 1H), 7.19 (d, J=5.3 Hz, 1H), 3.32-3.13 (m, 3H), 3.12-2.97 (m, 1H), 2.61 (t, 3H), 2.57-2.50 (m, 1H), 2.47-2.36 (m, 1H), 2.27-2.09 (m, 1H), 1.70-1.44 (m, 2H), 1.34-1.06 (m, 1H), 0.87 (t, J=7.3 Hz, 3H) ppm.

Example 70

2-Amino-N-{4-[(3S,5R)-3-amino-5-methyl-piperidin-1-yl]pyridin-3-yl}-6-propylfuro[3,2-b]pyridine-3-carboxamide

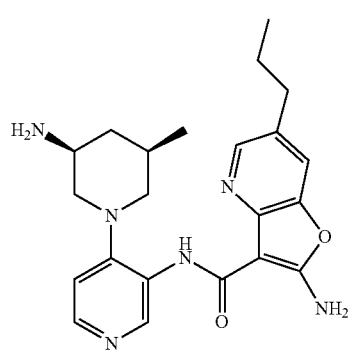 [SMILES: CCCc1cnc2c(C(=O)Nc3cnccc3N3C[C@H](C)C[C@H](N)C3)c(N)oc2c1]

Example 70 was synthesized using analogous procedures to those described in Examples 45, 46 and 47. LCMS calc. for $C_{22}H_{29}N_6O_2$ (M+H)$^+$: m/z=409.2. found: 409.1 $^1$H NMR (400 MHz, DMSO-d$_6$) δ 10.12 (s, 1H), 9.46 (s, 1H), 8.16 (d, J=5.0 Hz, 1H), 8.06 (s, 1H), 7.61 (s, 1H), 7.11 (s, 1H), 3.12-2.83 (m, 3H), 2.71-2.56 (m, 2H), 2.36-2.10 (m, 2H), 2.10-1.89 (m, 2H), 1.40-1.06 (m, 2H), 0.89 (t, J=7.4 Hz, 3H), 0.82 (d, J=6.6 Hz, 3H), 0.80-0.72 (m, 1H) ppm.

Example 71

2-Amino-N-{4-[(3S,5R)-3-amino-5-methyl-piperidin-1-yl]pyridin-3-yl}-6-fluorofuro[3,2-b]pyridine-3-carboxamide

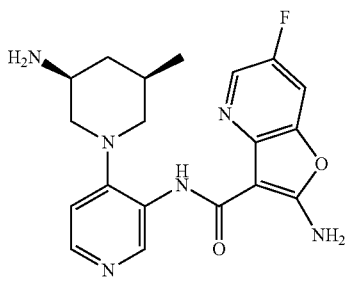 [SMILES: C[C@@H]1C[C@H](N)CN(c2ccncc2NC(=O)c2c(N)oc3cc(F)cnc23)C1]

Example 71 was synthesized using analogous procedures to those described in Examples 45, 46 and 47. LCMS calc. for $C_{19}H_{22}FN_6O_2$ (M+H)$^+$: m/z=385.2. found: 385.1.

Example 72

2-Amino-N-{4-[(3S,5R)-3-amino-5-methyl-piperidin-1-yl]pyridin-3-yl}-6-chlorofuro[3,2-b]pyridine-3-carboxamide

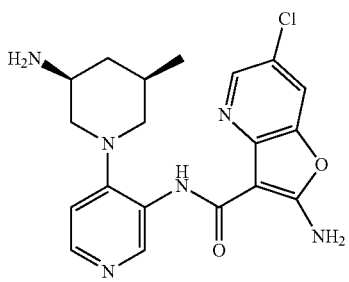 [SMILES: C[C@@H]1C[C@H](N)CN(c2ccncc2NC(=O)c2c(N)oc3cc(Cl)cnc23)C1]

Example 72 was synthesized using analogous procedures to those described in Examples 45, 46 and 47. LCMS calc. for $C_{19}H_{22}ClN_6O_2$ (M+H)$^+$: m/z=401.1. found: 401.1. $^1$H NMR (400 MHz, DMSO-d$_6$) δ 9.90 (s, 1H), 9.39 (s, 1H), 8.19 (d, J=1.9 Hz, 1H), 8.12 (d, J=5.3 Hz, 1H), 7.96 (d, J=1.9 Hz, 1H), 7.07 (d, J=5.3 Hz, 1H), 3.14-3.05 (m, 1H), 3.06-2.91 (m, 2H), 2.20-2.03 (m, 2H), 2.02-1.82 (m, 2H), 0.79 (d, J=6.4 Hz, 3H), 0.76-0.65 (m, 1H) ppm.

Example 73

2-Amino-N-{4-[(3S,5R)-3-amino-5-methyl-piperidin-1-yl]pyridin-3-yl}-6-(trifluoromethyl)-furo[3,2-b]pyridine-3-carboxamide

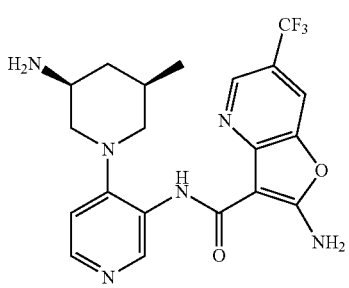

Example 73 was synthesized using analogous procedures to those described in Examples 45, 46 and 47. LCMS calc. for $C_{20}H_{22}F_3N_6O_2$ (M+H)$^+$: m/z=435.2. found: 435.1. $^1$H NMR (400 MHz, DMSO-d$_6$) δ 9.95 (s, 1H), 9.39 (s, 1H), 8.50 (s, 1H), 8.15 (d, J=5.3 Hz, 1H), 8.13 (d, J=1.5 Hz, 1H), 7.10 (d, J=5.3 Hz, 1H), 3.35-3.06 (m, 2H), 3.06-2.92 (m, 1H), 2.33-2.09 (m, 2H), 2.07-1.84 (m, 2H), 1.08-0.86 (m, 1H), 0.81 (d, J=6.3 Hz, 3H) ppm.

Example 74

2-Amino-N-{4-[(3R,4R,5S)-3-amino-4-hydroxy-5-methylpiperidin-1-yl]pyridin-3-yl}-furo[3,2-b]pyridine-3-carboxamide

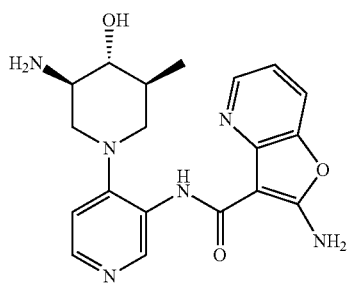

Example 74 was synthesized using analogous procedures to those described in Examples 45, 46 and 47. LCMS calc. for $C_{19}H_{23}N_6O_3$ (M+H)$^+$: m/z=383.2. found: 383.1. $^1$H NMR (400 MHz, DMSO-d$_6$) δ 10.22 (s, 1H), 9.47 (s, 1H), 8.23 (d, J=5.1 Hz, 1H), 8.12 (d, J=5.3 Hz, 1H), 7.67 (d, J=8.0 Hz, 1H), 7.09 (d, J=5.3 Hz, 1H), 7.02 (dd, J=8.0, 5.1 Hz, 1H), 5.09 (s, 1H), 3.21-3.12 (m, 1H), 3.11-2.95 (m, 2H), 2.85-2.67 (m, 1H), 2.48-2.30 (m, 2H), 1.97 (s, 1H), 0.84 (d, J=6.5 Hz, 3H) ppm.

Example 75

2-Amino-N-{4-[(3R,4R,5S)-3-amino-4-hydroxy-5-methylpiperidin-1-yl]pyridin-3-yl}-6-isopropylfuro[3,2-b]pyridine-3-carboxamide

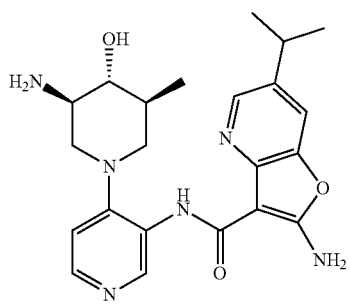 [SMILES: CC(C)c1cnc2c(C(=O)Nc3cnccc3N3C[C@@H](N)[C@H](O)[C@@H](C)C3)c(N)oc2c1]

Step A. Ethyl 3-[(tert-butoxycarbonyl)amino]-6-isopropenylfuro[3,2-b]pyridine-2-carboxylate

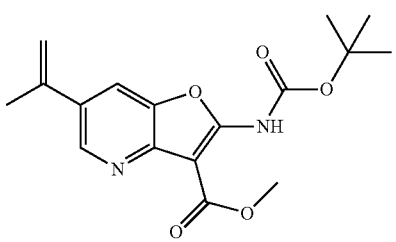 [SMILES: C=C(C)c1cnc2c(C(=O)OC)c(NC(=O)OC(C)(C)C)oc2c1]

A mixture of ethyl 6-bromo-3-[(tert-butoxycarbonyl)amino]furo[3,2-b]pyridine-2-carboxylate (1.0 g, 2.6 mmol), potassium carbonate (1.0 g, 7.2 mmol), Pd(PPh₃)₄ (0.3 g, 0.2 mmol) and 2-isopropenyl-4,4,5,5-tetramethyl-1,3,2-dioxaborolane (0.87 g, 5.2 mmol) in 1,4-dioxane (5.0 mL) and water (1.0 mL) was stirred at 110° C. for 180 min. in a microwave oven. The mixture was concentrated under reduced pressure and the resulting residue was purified by chromatography on a silica gel column (45% EtOAc in hexanes) to afford the sub-title compound (0.45 g, 70% yield).

Step B. Ethyl 3-[(tert-butoxycarbonyl)amino]-6-isopropylfuro[3,2-b]pyridine-2-carboxylate

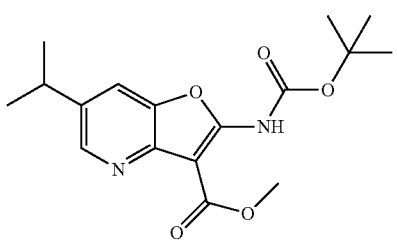 [SMILES: COC(=O)c1c(NC(=O)OC(C)(C)C)oc2cc(C(C)C)cnc12]

A mixture of ethyl 3-[(tert-butoxycarbonyl)amino]-6-isopropenylfuro[3,2-b]pyridine-2-carboxylate (4.5 g, 13 mmol), MeOH (30 mL), and 10% palladium on carbon (0.06 g) was shaken under 15 psi of H₂ for 2 h. The mixture was filtered and the resulting filtrate was concentrated under reduced pressure to give the sub-title compound (4.3 g, 96% yield).

Step C. 3-[(tert-Butoxycarbonyl)amino]-6-isoproplyfuro[3,2-b]pyridine-2-carboxylic acid

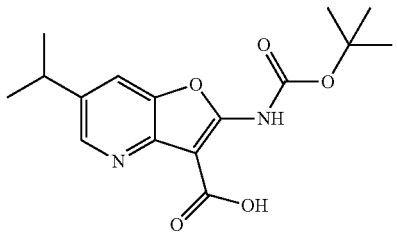 [SMILES: CC(C)c1cnc2c(C(=O)O)c(NC(=O)OC(C)(C)C)oc2c1]

A mixture of ethyl 3-[(tert-butoxycarbonyl)amino]-6-isopropylfuro[3,2-b]pyridine-2-carboxylate (4.3 g, 12 mmol), LiOH (4 g, 0.4 mol), THF (43 mL), water (14 mL) and MeOH (28 mL) was stirred at 80° C. overnight. The mixture was concentrated under reduced pressure and the pH was adjusted to 5. The resulting mixture was extracted with EtOAc. The combined extracts were dried, filtered and evaporated under reduced pressure. Further purification on silica gel eluting with 0-100% EtOAc in hexanes gave the sub-title compound (0.8 g, 20% yield).

Step D. 2-Amino-N-{4-[(3R,4R,5S)-3-amino-4-hydroxy-5-methylpiperidin-1-yl]pyridin-3-yl}-6-isopropylfuro[3,2-b]pyridine-3-carboxamide A mixture of 2-[(tert-butoxycarbonyl)amino]-6-isopropylfuro[3,2-b]pyridine-3-carboxylic acid (0.8 g, 2 mmol), tert-butyl ((3R,4R,5S)-1-(3-aminopyridin-4-yl)-4-{[tert-butyl(dimethyl)silyl]oxy}-5-methylpiperidin-3-yl)acetate (1.1 g, 2.5 mmol), Molecular Sieves (10.0 g) and DIPEA (1.3 mL, 7.5 mmol) in 1,2-dichloroethane (30 mL) was stirred at room temperature for 2 h. HATU (1.2 g, 3.2 mmol) was added and the resulting mixture was stirred at room temperature over a weekend. The volatile solvents were removed under reduced pressure. The residue was purified by HPLC (Method A) to afford an amide coupling intermediate (0.4 g, 22% yield). The intermediate (0.4 g) was dissolved in HCl in dioxane (4 M; 10 mL). The solution was stirred at room temperature for 24 h. The reaction mixture was concentrated to dryness and the resulting residue was purified by preparative HPLC (Method B) to afford the final product (120 mg, 50% yield). LCMS calc. for C₂₂H₂₉N₆O₃ (M+H)⁺: m/z=425.2. found: 425.1. ¹H NMR (500 MHz, DMSO-d₆) δ 10.16 (s, 1H), 9.50 (s, 1H), 8.19 (d, J=1.4 Hz, 1H), 8.16 (d, J=5.2 Hz, 1H), 7.67 (d, J=1.3 Hz, 1H), 7.12 (d, J=5.3 Hz, 1H), 4.85 (s, 1H), 3.16 (d, J=9.4 Hz, OH), 3.11-2.91 (m, 4H), 2.74 (s, OH), 2.47-2.39 (m, 3H), 2.11-1.90 (m, 1H), 1.25 (d, J=6.9 Hz, 7H), 0.88 (d, J=6.6 Hz, 3H) ppm.

Example 76

2-Amino-N-{5-methyl-4-[(3R,4R,5S)-3-amino-4-hydroxy-5-methylpiperidin-1-yl]pyridin-3-yl}-furo[3,2-b]pyridine-3-carboxamide

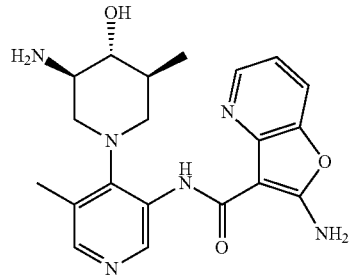 [SMILES: Cc1cncc(NC(=O)c2c(N)oc3cccnc23)c1N1C[C@@H](N)[C@H](O)[C@@H](C)C1]

Example 76 was synthesized using analogous procedures to those described in Examples 45, 46 and 47. LCMS calc. for C₂₀H₂₅N₆O₃ (M+H)⁺: m/z=397.2. found: 397.1. ¹H NMR (400 MHz, DMSO-d₆) δ 10.61 (s, 1H), 9.60 (s, 1H), 8.40 (d, J=5.0 Hz, 1H), 8.00 (s, 1H), 7.71 (d, J=8.0 Hz, 1H), 7.07 (dd, J=8.0, 5.1 Hz, 1H), 5.40 (s, 1H), 3.49-3.18 (m, 2H), 3.09-3.00 (m, 1H), 3.00-2.87 (m, 2H), 2.87-2.77 (m, 1H), 2.32 (s, 3H), 2.28-2.14 (m, 1H), 0.90 (d, J=6.5 Hz, 3H) ppm.

Example 77

2-Amino-N-{5-methyl-4-[(3R,4R,5S)-3-amino-4-hydroxy-5-methylpiperidin-1-yl]pyridin-3-yl}-6-propylfuro[3,2-b]pyridine-3-carboxamide

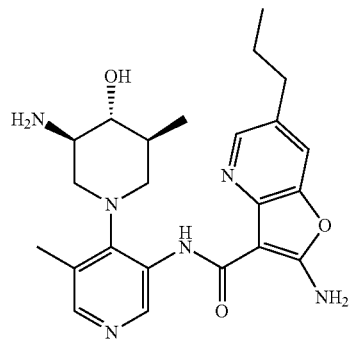 [SMILES: CCCc1cnc2c(C(=O)Nc3cncc(C)c3N3C[C@@H](N)[C@H](O)[C@@H](C)C3)c(N)oc2c1]

Example 77 was synthesized using analogous procedures to those described in Examples 45, 46 and 47. LCMS calc. for $C_{23}H_{31}N_6O_3$ (M+H)$^+$: m/z=439.2. found: 439.1. $^1$H NMR (400 MHz, DMSO-d$_6$) δ 10.54 (s, 1H), 9.56 (s, 1H), 8.25 (s, 1H), 7.98 (s, 1H), 7.59 (s, 1H), 4.95 (s, 1H), 3.24-3.04 (m, 2H), 3.04-2.85 (m, 2H), 2.85-2.70 (m, 2H), 2.68-2.52 (m, 2H), 2.38-2.09 (m, 4H), 1.79-1.40 (m, 2H), 0.90 (t, 3H), 0.88 (d, 3H) ppm.

Example 78

2-Amino-N-{5-methyl-4-[(3R,4R,5S)-3-amino-4-hydroxy-5-methylpiperidin-1-yl]pyridin-3-yl}-6-chlorofuro[3,2-b]pyridine-3-carboxamide

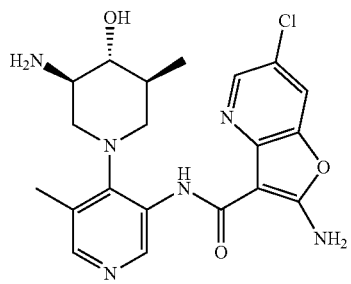 [SMILES: Cc1cncc(NC(=O)c2c(N)oc3cc(Cl)cnc23)c1N1C[C@@H](N)[C@H](O)[C@@H](C)C1]

Example 78 was synthesized using analogous procedures to those described in Examples 45, 46 and 47. LCMS calc. for $C_{20}H_{24}N_6O_3$ (M+H)$^+$: m/z=431.2. found: 431.1. $^1$H NMR (400 MHz, DMSO-d$_6$) δ 10.47 (s, 1H), 9.60 (s, 1H), 8.42 (d, J=1.9 Hz, 1H), 7.99 (s, 1H), 6.54 (s, 1H), 5.12 (s, 1H), 3.25-3.05 (m, 1H), 3.01-2.69 (m, 4H), 2.71-2.52 (m, 1H), 2.32 (s, 3H), 2.24-2.10 (m, 1H), 0.89 (d, J=6.5 Hz, 3H) ppm.

Example 79

2-Amino-N-{5-methyl-4-[(3R,4R,5S)-3-amino-4-hydroxy-5-methylpiperidin-1-yl]pyridin-3-yl}-6-(trifluoromethyl)-furo[3,2-b]pyridine-3-carboxamide

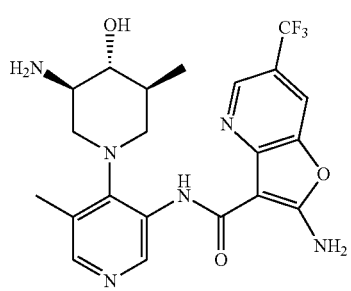 [SMILES: Cc1cncc(NC(=O)c2c(N)oc3cc(C(F)(F)F)cnc23)c1N1C[C@@H](N)[C@H](O)[C@@H](C)C1]

Example 79 was synthesized using analogous procedures to those described in Examples 45, 46 and 47. LCMS calc. for $C_{21}H_{24}F_3N_6O_3$ (M+H)$^+$: m/z=465.2. found: 465.1. $^1$H NMR (400 MHz, DMSO-d$_6$) δ 10.58 (s, 1H), 9.60 (s, 1H), 8.76 (s, 1H), 8.15 (s, 1H), 8.01 (s, 1H), 5.15 (s, 1H), 3.19-3.06 (m, 1H), 3.02-2.70 (m, 4H), 2.70-2.60 (m, 1H), 2.32 (s, 3H), 2.26-2.07 (m, 1H), 0.89 (d, J=6.5 Hz, 3H) ppm.

Example 80

2-Amino-N-{4-[(3R,4R)-3-amino-4-fluoro-piperidin-1-yl]pyridin-3-yl}-6-propylfuro[3,2-b]pyridine-3-carboxamide

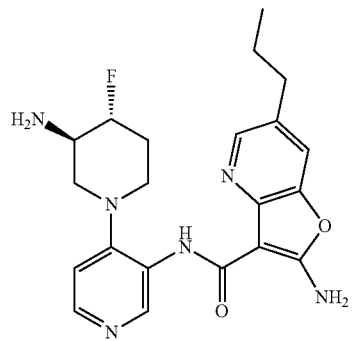 [SMILES: CCCc1cnc2c(C(=O)Nc3cnccc3N3CC[C@@H](F)[C@H](N)C3)c(N)oc2c1]

Example 80 was synthesized using analogous procedures to those described in Examples 45, 46 and 47. LCMS calc. for $C_{21}H_{26}FN_6O_2$ (M+H)$^+$: m/z=413.2. found: 413.1.

Example 81

2-Amino-N-{4-[(3S)-3-aminopiperidin-1-yl]pyridin-3-yl}-7-chloro-furo[3,2-b]pyridine-3-carboxamide

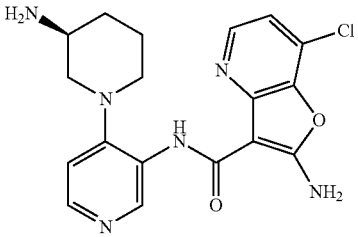 [SMILES: Nc1oc2c(Cl)ccnc2c1C(=O)Nc1cnccc1N1CCC[C@H](N)C1]

Example 81 was synthesized using analogous procedures to those described in Examples 45, 46 and 47. LCMS calc. for $C_{18}H_{20}ClN_6O_2$ (M+H)$^+$: m/z=387.1. found: 387.1. $^1$H NMR (300 MHz, DMSO-d$_6$) δ 10.07 (s, 1H), 9.41 (s, 1H), 8.18 (d, J=5.6 Hz, 1H), 8.16 (d, J=5.3 Hz, 1H), 7.18 (d, J=5.6 Hz, 1H), 7.10 (d, J=5.2 Hz, 1H), 3.17-3.05 (m, 1H), 3.04-2.81 (m, 2H), 2.74-2.55 (m, 1H), 2.39-2.31 (m, 1H), 2.26-2.10 (m, 1H), 2.02-1.82 (m, 1H), 1.85-1.59 (m, 1H), 1.39-1.19 (m, 1H) ppm.

Example 82

2-Amino-N-{4-[(3R,4R,5S)-3-amino-5-cyclopropyl-4-hydroxypiperidin-1-yl]pyridin-3-yl}-6-propylfuro[3,2-b]pyridine-3-carboxamide

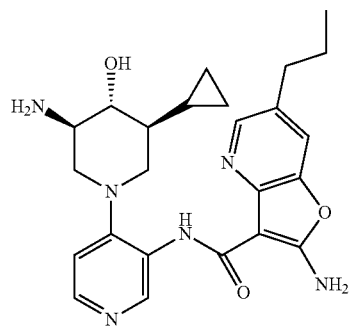 [SMILES: CCCc1cnc2c(C(=O)Nc3cnccc3N3C[C@@H](N)[C@H](O)[C@@H](C4CC4)C3)c(N)oc2c1]

Step 1. tert-Butyl (4R)-4-{(1R,2R)-3-[(4R)-4-benzyl-2-oxo-1,3-oxazolidin-3-yl]-2-cyclopropyl-1-hydroxy-3-oxopropyl}-2,2-dimethyl-1,3-oxazolidine-3-carboxylate

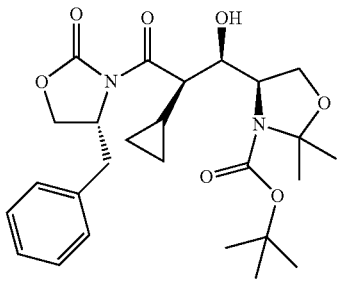 [SMILES: CC(C)(C)OC(=O)N1[C@@H]([C@H](O)[C@H](C(=O)N2C(=O)OC[C@H]2Cc2ccccc2)C2CC2)COC1(C)C]

To a solution of (4R)-4-benzyl-3-(cyclopropylacetyl)-1,3-oxazolidin-2-one (2.0 g, 7.7 mmol) in anhydrous DCM (45 mL) at −40° C. was added a solution of 1.0 M titanium tetrachloride in DCM (9.3 mL) dropwise under an atmosphere of $N_2$ to form a yellow slurry. After 10 min., DIPEA (3.36 mL, 19.3 mmol) was added dropwise, changing the color from yellow to deep purple. The reaction mixture was allowed to gradually warm to −20° C. while stirring over 1 h. The reaction mixture was cooled to −40° C. prior to the dropwise addition of a solution of tert-butyl (4R)-4-formyl-2,2-dimethyl-1,3-oxazolidine-3-carboxylate (1.8 g, 7.85 mmol) (Aldrich cat#462063) in anhydrous DCM (5 mL). The reaction mixture was allowed to gradually warm to 0° C. for 1 h and then allowed to stir for an additional 1.5 h at 0° C. The reaction was quenched by the addition of saturated aq. $NH_4Cl$ (15 mL). After separation of the two layers that formed, the organic layer was washed with water and brine, dried over $Na_2SO_4$, concentrated under reduced pressure and purified by flash chromatography (120 g silica gel, eluting with 0-60% EtOAc/hexanes) to afford the sub-title compound (1.9 g, 50%). LCMS (ESI) calc. for $C_{26}H_{36}N_2O_7Na$ (M+Na)$^+$: m/z=511.2. found 511.1.

Step 2. tert-Butyl (4R)-4-((1R,2R)-3-[(4R)-4-benzyl-2-oxo-1, 3-oxazolidin-3-yl]-1-{[tert-butyl(dimethyl)silyl]oxy}-2-cyclopropyl-3-oxopropyl)-2,2-dimethyl-1,3-oxazolidine-3-carboxylate

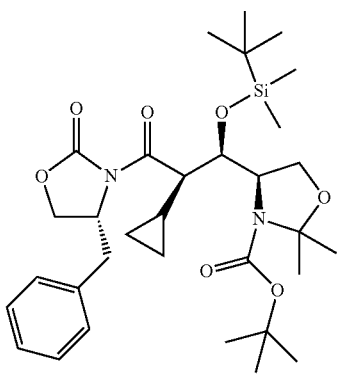 [SMILES: CC(C)(C)OC(=O)N1[C@@H]([C@H](O[Si](C)(C)C(C)(C)C)[C@H](C(=O)N2C(=O)OC[C@H]2Cc2ccccc2)C2CC2)COC1(C)C]

To a solution of tert-butyl (4R)-4-{(1R,2R)-3-[(4R)-4-benzyl-2-oxo-1,3-oxazolidin-3-yl]-2-cyclopropyl-1-hydroxy-3-oxopropyl}-2,2-dimethyl-1,3-oxazolidine-3-carboxylate (1.80 g, 3.68 mmol) in anhydrous DCM (10 mL) at −40° C., 2,6-lutidine (0.85 mL, 7.3 mmol) was added under an atmosphere of $N_2$. After 10 min., a solution of tert-butyldimethylsilyl trifluoromethanesulfonate (1.1 mL, 4.9 mmol) in anhydrous DCM (1 mL) was added. The reaction mixture was allowed to warm gradually to ambient temperature while stirring overnight. The crude reaction mixture was diluted with 1,2-dichloroethane and cooled to 0° C., then quenched with saturated aq. $NaHCO_3$. After separation of the two layers, the organic layer was washed with water and brine, dried over $Na_2SO_4$, concentrated under reduced pressure and purified by flash chromatography (120 g silica gel, eluting with 0-30% EtOAc/hexanes) to afford the sub-title compound (2.1 g, 95%). LCMS (ESI) calc. for $C_{32}H_{50}N_2O_7SiNa$ (M+Na)$^+$: m/z=625.3. found 625.1.

Step 3. tert-Butyl (4R)-4-((1R,2S)-1-{[tert-butyl(dimethyl)silyl]oxy}-2-cyclopropyl-3-hydroxypropyl)-2,2-dimethyl-1,3-oxazolidine-3-carboxylate

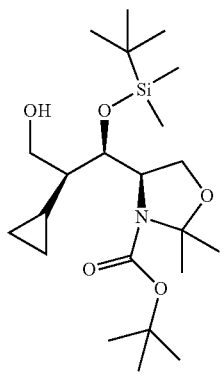 [SMILES: CC(C)(C)OC(=O)N1[C@@H]([C@H](O[Si](C)(C)C(C)(C)C)[C@H](CO)C2CC2)COC1(C)C]

A solution of tert-butyl (4R)-4-((1R,2R)-3-[(4R)-4-benzyl-2-oxo-1,3-oxazolidin-3-yl]-1-{[tert-butyl(dimethyl)silyl]oxy}-2-cyclopropyl-3-oxopropyl)-2,2-dimethyl-1,3-oxazolidine-3-carboxylate (3.3 g, 5.5 mmol) in anhydrous THF (50 mL) and EtOH (1 mL) under an atmosphere of $N_2$ was cooled to −30° C. prior to the addition of $LiBH_4$ (0.24 g, 11 mmol). The reaction mixture was allowed to gradually warm to ambient temperature while stirring for 20 h. The crude reaction mixture was diluted with diethyl ether (36 mL) and cooled to 0° C. prior to the addition of 1 M aq. NaOH (36 mL). After separation of the layers, the aqueous layer was extracted with EtOAc several times and the combined organic extracts were washed with brine, dried over $Na_2SO_4$, filtered, and concentrated under reduced pressure. The crude product was purified by flash column chromatography (120 g silica gel, eluting with 0-40% EtOAc/hexanes) to afford the sub-title compound (1.27 g, 54%). LCMS (ESI) calc. for $C_{22}H_{43}NO_5SiNa$ (M+Na)$^+$: 452.3. found 452.0.

Step 4. tert-Butyl (4R)-4-((1R,2S)-3-azido-1-{[tert-butyl(dimethyl)silyl]oxy}-2-cyclopropylpropyl)-2,2-dimethyl-1,3-oxazolidine-3-carboxylate

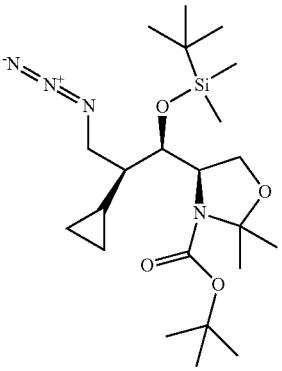

To a solution of tert-butyl (4R)-4-((1R,2S)-1-{[tert-butyl(dimethyl)silyl]oxy}-2-cyclopropyl-3-hydroxypropyl)-2,2-dimethyl-1,3-oxazolidine-3-carboxylate (1.3 g, 3.0 mmol) and PPh$_3$ (1.6 g, 6.1 mmol) in anhydrous THF (20 mL) was added diisopropyl azodicarboxylate (1.2 mL, 5.9 mmol) dropwise under an atmosphere of N$_2$. Upon completion of addition a precipitate was formed. The reaction mixture was stirred for 30 min. prior to the addition of a solution of diphenylphosphonic azide (1.3 mL, 6.2 mmol) in anhydrous THF (1.0 mL). After stirring at ambient temperature for 3 h, the volatile organic solvents were removed under reduced pressure and the crude product was purified by flash column chromatography (120 g of silica gel, eluting with 0-15% EtOAc-hexanes) to afford the sub-title compound as a light yellow oil (1.18 g, 86%). LCMS (ESI) calc. for C$_{17}$H$_{35}$N$_4$O$_2$Si (M+H-Boc+H)$^+$: 355.30. found 355.1.

Step 5. tert-Butyl [(1R,2R,3S)-4-azido-2-{[tert-butyl(dimethyl)silyl]oxy}-3-cyclopropyl-1-(hydroxymethyl)butyl]carbamate

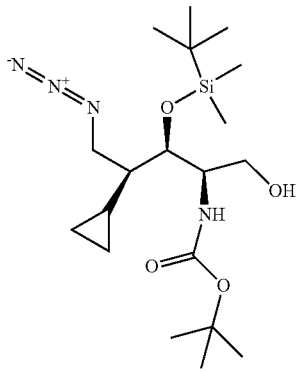

To a solution of tert-butyl (4R)-4-((1R,2S)-3-azido-1-{[tert-butyl(dimethyl)silyl]oxy}-2-cyclopropylpropyl)-2,2-dimethyl-1,3-oxazolidine-3-carboxylate (1.16 g, 2.55 mmol) in MeOH (5 mL) at 0° C. was added TFA (4.9 mL, 64 mmol) and the resulting solution was stirred at ambient temperature for 1 h. The volatile organic solvents were removed under reduced pressure and the residue was azeotropically washed with toluene (2×3 mL). The residue was dissolved in anhydrous DCM (18 mL), DIPEA (0.99 g, 7.6 mmol) and Boc$_2$O (0.84 g, 3.8 mmol) were added and the resulting solution was stirred at ambient temperature for 1 h. The volatile solvents were removed under reduced pressure and the crude product was purified by flash column chromatography (120 g silica gel, eluting with 0-100% EtOAc/hexanes) to afford the sub-title compound (0.57 g, 54%) and the desilylated product (0.2 g, 26%). LCMS (ESI) calc. for C$_{14}$H$_{31}$N$_4$O$_2$Si (M+H-Boc+H)$^+$: m/z=315.3. found 315.0.

Step 6. tert-Butyl-(2R,3R,4S)-5-azido-2-[(tert-butoxycarbonyl)amino]-3-{[tert-butyl(dimethyl)silyl]oxy}-4-cyclopropylpentyl methanesulfonate

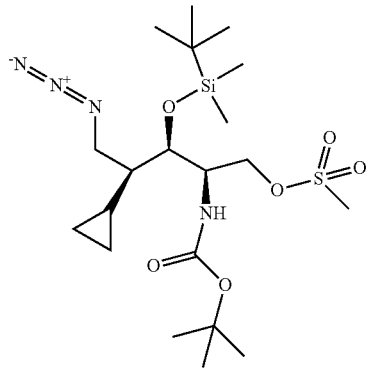

To a solution of tert-butyl [(1R,2R,3S)-4-azido-2-{[tert-butyl(dimethyl)-14-sulfanyl]oxy}-3-cyclopropyl-1-(hydroxymethyl)butyl]carbamate (0.240 g, 0.573 mmol) in anhydrous pyridine (2.0 mL) -20° C. was added DMAP (0.014 g, 0.11 mmol) and methanesulfonyl chloride (0.044 mL, 0.57 mmol). The reaction mixture was allowed to warm gradually to 5° C. and stirred for 2 h. The crude reaction mixture was diluted with EtOAc and concentrated under reduced pressure onto silica gel and purified by flash column chromatography (24 g silica gel, eluting with 0-20% EtOAc-hexanes) to afford the sub-title compound (0.240 g, 86%). LCMS (ESI) calc. for C$_{15}$H$_{33}$N$_4$O$_4$SSi (M+H-Boc+H)$^+$: m/z=393.2. found 393.0.

Step 7. ((3R,4R,5S)-4-{[tert-butyl(dimethyl)silyl]oxy}-5-cyclopropylpiperidin-3-yl)carbamate

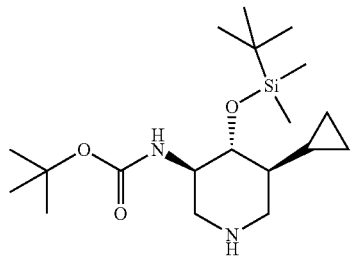 [SMILES: CC(C)(C)OC(=O)N[C@@H]1CNC[C@H](C2CC2)[C@H]1O[Si](C)(C)C(C)(C)C]

A solution of (2R,3R,4S)-5-azido-2-[(tert-butoxycarbonyl)amino]-3-{[tert-butyl (dimethyl)silyl]oxy}-4-cyclopropylpentyl methanesulfonate (0.250 g, 0.507 mmol) and DIPEA (0.26 mL, 1.5 mmol) in MeOH (8.0 mL) was purged with N$_2$ prior to the addition of 10% palladium (dry basis) on activated carbon, wet, Degussa type E101 NE/W (0.080 g, 0.076 mmol). The reaction mixture was stirred under an atmosphere of H$_2$ via a balloon for 2 h. The inorganics were filtered off, rinsed thoroughly with MeOH and EtOAc, and the filtrate was concentrated under reduced pressure to afford the sub-title compound (0.244 g). LCMS (ESI) calc. for C$_{19}$H$_{39}$N$_2$O$_3$Si (M+H)$^+$: m/z=371.3. found 371.1. $^1$H NMR (500 MHz, CDCl$_3$) δ 4.56 (s, 1H), 3.36-3.23 (m, 3H), 3.04 (dd, J=13.0, 3.1 Hz, 1H), 2.35 (ddd, J=14.7, 12.5, 11.0 Hz, 2H), 1.43 (s, 9H), 0.75 (tt, J=9.4, 4.7 Hz, 1H), 0.63-0.52 (m, 1H), 0.47 (ddt, J=13.0, 8.2, 4.1 Hz, 1H), 0.38 (qd, J=9.2, 5.5 Hz, 2H), 0.08-0.02 (m, 1H) ppm.

Step 8. tert-Butyl [(3R,4R,5S)-4-{[tert-butyl(dimethyl)silyl]oxy}-5-cyclopropyl-1-(3-nitropyridin-4-yl)piperidin-3-yl]carbamate

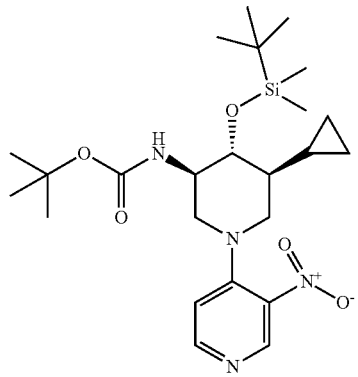 [SMILES: CC(C)(C)OC(=O)N[C@@H]1CN(c2ccncc2[N+](=O)[O-])C[C@H](C2CC2)[C@H]1O[Si](C)(C)C(C)(C)C]

A mixture of tert-butyl ((3R,4R,5S)-4-{[tert-butyl(dimethyl)silyl]oxy}-5-cyclopropylpiperidin-3-yl)carbamate (0.180 g, 0.486 mmol), 4-chloro-3-nitropyridine (0.10 g, 0.63 mmol) and TEA (0.20 mL, 1.4 mmol) in i-PrOH (1.8 mL) was heated at 75° C. in a sealed vial for 1 h. After cooling to ambient temperature, the reaction mixture was diluted with EtOAc (40 mL) and water (3 mL). The layers that formed were separated, the organic layer was washed with water (2×3 mL) and the combined aqueous phases were back extracted with EtOAc (3 mL). The combined organic layers were washed with brine (3 mL), dried over $Na_2SO_4$, filtered and concentrated under reduced pressure. The crude product was purified by flash column chromatography (20 g silica gel column, eluting with 0-20% EtOAc/hexanes) to afford the sub-title compound (0.135 g, 56%). LCMS (ESI) calc. for $C_{24}H_{41}N_4O_5Si$ $(M+H)^+$: m/z=493.3. found 493.1.

Step 9. tert-Butyl ((3R,4R,5S)-1-(3-aminopyridin-4-yl)-4-{[tert-butyl(dimethyl)silyl]oxy}-5-cyclopropylpiperidin-3-yl)carbamate

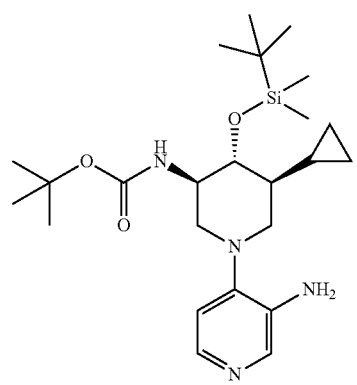 [SMILES: CC(C)(C)OC(=O)N[C@@H]1CN(c2ccncc2N)C[C@H](C2CC2)[C@H]1O[Si](C)(C)C(C)(C)C]

A mixture of tert-butyl [(3R,4R,5S)-4-{[tert-butyl(dimethyl)silyl]oxy}-5-cyclopropyl-1-(3-nitropyridin-4-yl)piperidin-3-yl]carbamate (0.140 g, 0.284 mmol) and 10% palladium (dry basis) on activated carbon, wet, Degussa type E101 NE/W (0.040 g, 0.038 mmol) in MeOH (3.5 mL) and EtOAc (0.5 mL) was purged with $N_2$ prior to stirring under an atmosphere of $H_2$ (introduced via a balloon) overnight. The crude reaction mixture was filtered through a pad of diatomaceous earth and the inorganics were washed thoroughly with EtOAc. The filtrate was concentrated under reduced pressure afford the sub-title compound (0.125 g, 95%). LCMS (ESI) calc. for $C_{24}H_{43}N_4O_3Si$ $(M+H)^+$: m/z=463.3. found 463.1.

Step 10. 2-Amino-N-{4-[(3R,4R,5S)-3-amino-5-cyclopropyl-4-hydroxypiperidin-1-yl]pyridin-3-yl}-6-propylfuro[3,2-b]pyridine-3-carboxamide A mixture of 2-[(tert-butoxycarbonyl)amino]-6-propylfuro[3,2-b]pyridine-3-carboxylic acid (0.024 g, 0.075 mmol), HATU (0.043 g, 0.11 mmol) and DIPEA (0.039 mL, 0.22 mmol) in anhydrous 1,2-dichloroethane (0.4 mL) was stirred for 10 min. prior to the addition of a solution of tert-butyl ((3R,4R,5S)-1-(3-aminopyridin-4-yl)-4-{[tert-butyl(dimethyl)silyl]oxy}-5-cyclopropylpiperidin-3-yl)carbamate (0.042 g, 0.091 mmol) in anhydrous 1,2-dichloroethane (0.2 mL). The reaction mixture was stirred at 44° C. overnight. The reaction mixture was diluted with EtOAc (40 mL) and water (3 mL). The layers were separated and the organic layer was washed with water (3×3 mL) and the combined aqueous phases were back extracted with EtOAc (3 mL). The combined organic layers were washed with brine (3 mL), dried over $Na_2SO_4$, filtered and concentrated under reduced pressure. The crude product was purified by flash column chromatography (12 g silica gel column, eluting with 0-20% EtOAc/hexanes) to afford an intermediate (8 mg, 14%). The intermediate was dissolved in MeCN (0.2 mL) and 1.7 M hexafluorosilicic acid in water (0.3 mL, 0.51 mmol) was added and was heated at 45° C. for 1 h. The volatile solvents were removed and the residue was re-dissolved in MeOH (5 mL) and neutralized by the addition of saturated $NH_4OH$. The crude reaction mixture was purified by mass triggered preparative-HPLC (Method B) to afford the title compound. LCMS (ESI) calc. for $C_{24}H_{31}N_6O_3$ $(M+H)^+$: m/z=451.2. found 451.1. $^1H$ NMR (500 MHz, DMSO-$d_6$) 9.98 (1H, s), 9.40 (1H, s), 8.17 (1H, d, J=5.0 Hz), 8.09 (1H, s), 7.60 (1H, s), 7.08 (1H, d, J=5.0 Hz), 4.73 (1H, br s), 3.16 (2H, m), 3.02 (2H, m), 2.94 (1H, m), 2.59 (3H, m), 2.36 (1H, dd, J=12.0 and 12.0 Hz), 1.61 (2H, m), 1.32 (1H, m), 0.90 (3H, t, J=7.5 Hz), 0.39 (1H, m), 0.34 (1H, m), 0.06 (1H, m), −0.01 (1H, m), −0.65 (1H, m) ppm.

Example 83

2-Amino-N-(4-((1R,3R,4R,5S)-3-amino-4-hydroxy-4,5-dimethylcyclohexyl)pyridin-3-yl)furo[3,2-b]pyridine-3-carboxamide

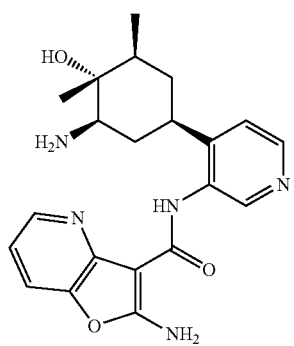 [SMILES: C[C@H]1C[C@@H](c2ccncc2NC(=O)c2c(N)oc3cccnc23)C[C@@H](N)[C@]1(C)O]

Step 1. 5-Methyl-3-oxocyclohex-1-en-1-yl trifluoromethanesulfonate

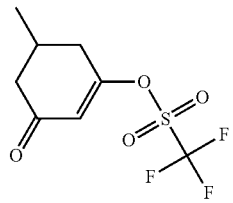 [SMILES: CC1CC(=O)C=C(OS(=O)(=O)C(F)(F)F)C1]

To a mixture of 5-methylcyclohexane-1,3-dione (8.00 g, 63.4 mmol) in DCM (100 mL) was added sodium carbonate (7.39 g, 69.8 mmol). The mixture was cooled at 0° C. and a solution of trifluoromethanesulfonic anhydride (10.7 mL, 63.4 mmol) in DCM (100 mL) was added dropwise over 1 h at 0° C. The reaction mixture was stirred at room temperature for 1 h. The solution was filtered and the filtrate was quenched by careful addition of saturated NaHCO$_3$ until pH=7. The organic layer was washed with water and brine and dried over Na$_2$SO$_4$, then filtered. The filtrate was concentrated under reduced pressure to afford the sub-title compound as a light yellow oil. The material was used for the next step without further purification. LCMS calc. for $C_8H_{10}F_3O_4S$ (M+H)$^+$ m/z: 259.0. found: 259.1.

Step 2. 5-Methyl-3-(4,4,5,5-tetramethyl-1,3,2-dioxaborolan-2-yl)cyclohex-2-en-1-one

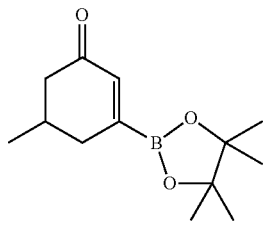

To a solution of 5-methyl-3-oxocyclohex-1-en-1-yl trifluoromethanesulfonate (12.40 g, 48.02 mmol) in deoxygenated 1,4-dioxane (70 mL) was added 4,4,5,5,4',4',5',5'-octamethyl-[2,2']bi[[1,3,2]dioxaborolanyl] (24.4 g, 96.0 mmol), KOAc (14.1 g, 144 mmol) and [1,1'-bis(diphenylphosphino)ferrocene]dichloropalladium(II), complex with dichloromethane (1:1) (3.1 g, 3.8 mmol). The reaction mixture was stirred at 80° C. overnight, then cooled to room temperature and filtered through a pad of diatomaceous earth. The filtrate solution was used for the next step without further purification.

Step 3. 5-Methyl-3-(3-nitropyridin-4-yl)cyclohex-2-en-1-one

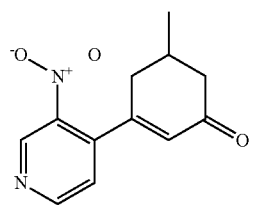

A mixture of 5-methyl-3-(4,4,5,5-tetramethyl-1,3,2-dioxaborolan-2-yl)cyclohex-2-en-1-one (11.30 g, 47.86 mmol) in 1,4-dioxane (80 mL), 4-chloro-3-nitropyridine (6.34 g, 40.0 mmol), 2.0 M aq. Na$_2$CO$_3$ (38.3 mL, 76.6 mmol) and [1,1'-bis(diphenylphosphino)ferrocene]dichloropalladium(II), complex with dichloromethane (1:1) (2.61 g, 3.20 mmol) was heated under reflux for 1 h. The mixture was cooled and filtered through a pad of diatomaceous earth, washed with EtOAc. The two layers were separated, and the aqueous layer was extracted with EtOAc (2 times). The combined organic phases were washed with water and brine and dried over Na$_2$SO$_4$. Purification by column chromatography on silica gel using CombiFlash® apparatus eluting with EtOAc/hexanes (0-60%) gave the sub-title compound as an orange oil. LCMS calc. for $C_{12}H_{13}N_2O_3$ (M+H)$^+$ m/z: 233.1. found: 233.1.

Step 4. 4-{5-Methyl-3-[(trimethylsilyl)oxy]cyclohexa-1,3-dien-1-yl}-3-nitropyridine

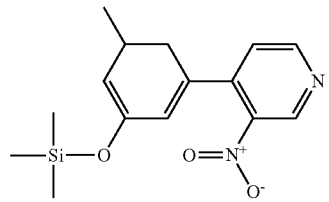 [SMILES: CC1C=C(O[Si](C)(C)C)C=C(c2ccncc2[N+](=O)[O-])C1]

To a solution of 5-methyl-3-(3-nitropyridin-4-yl)cyclohex-2-en-1-one (7.70 g, 33.2 mmol) and chlorotrimethylsilane (16.8 mL, 133 mmol) in THF (38 mL) at 0-5° C. was added 1.0 M lithium hexamethyldisilazide in THF (133 mL, 133 mmol) dropwise. The resulting solution was stirred at room temperature for 2 h. $^1$H NMR indicated the reaction was complete. The reaction mixture was diluted with EtOAc. The solid that precipitated out was filtered. The filtrate was concentrated under reduced pressure. The residue was diluted with DCM and the resulting solution was used for the next step.

Step 5. (5S)-6-[(Dimethylamino)methyl]-5-methyl-3-(3-nitropyridin-4-yl)cyclohex-2-en-1-one

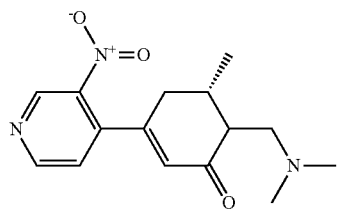

To a solution of N-methyl-N-methylenemethanaminium iodide (18.4 g, 99.5 mmol) in DCM (200 mL) at 0° C. was added a solution of 4-{5-methyl-3-[(trimethylsilyl)oxy]cyclohexa-1,3-dien-1-yl}-3-nitropyridine (10.1 g, 33.2 mmol) in DCM (200 mL) slowly. The reaction mixture was allowed to warm up to room temperature and stirred for 18 h. After cooling to 0° C. again, 1.0 M HCl in water (200 mL, 200 mmol) was added to the reaction mixture, and the resulting mixture was stirred for 20 min. at 0° C. 1.0 M NaOH in water (300 mL, 300 mmol) was then slowly added at 0° C. The reaction mixture was stirred for 1 h. The organic phase was separated, and the aqueous phase was extracted with DCM (2 times). The combined organic layers were dried over Na$_2$SO$_4$, and concentrated under reduced pressure to afford 9.50 g of sub-title compound as a brown oil. LCMS calc. for C$_{15}$H$_{20}$N$_3$O$_3$ (M+H)$^+$ m/z: 290.1. found: 290.2.

Step 6. (5S)-5-Methyl-6-methylene-3-(3-nitropyridin-4-yl)cyclohex-2-en-1-one

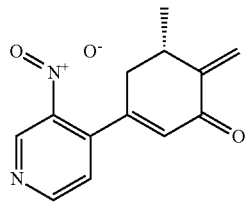

To a solution of (5S)-6-[(dimethylamino)methyl]-5-methyl-3-(3-nitropyridin-4-yl)cyclohex-2-en-1-one (9.50 g, 32.8 mmol) in THF (110 mL) at 0° C. was added methyl iodide (2.66 mL, 42.7 mmol). The reaction mixture was stirred at room temperature overnight. Saturated aq. NaHCO$_3$ was added, the reaction mixture was stirred at room temperature for 5 h and then diluted with EtOAc. The organic layer was separated. The aqueous layer was extracted with EtOAc (2 times). The combined organic extracts were washed with water and brine, dried over Na$_2$SO$_4$ and concentrated under reduced pressure to give the sub-title compound as a brown oil. LCMS calc. for C$_{13}$H$_{13}$N$_2$O$_3$ (M+H)$^+$ m/z: 245.1. found: 245.1.

Step 7. (1R,5S)-5-Methyl-6-methylene-3-(3-nitropyridin-4-yl)cyclohex-2-en-1-ol

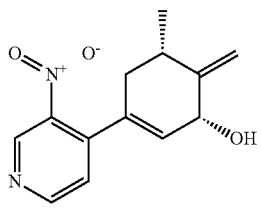

To a solution of (5S)-5-methyl-6-methylene-3-(3-nitropyridin-4-yl)cyclohex-2-en-1-one (8.00 g, 32.8 mmol) in MeOH (110 mL) was added CeCl$_3$.7H$_2$O (13.4 g, 36.0 mmol). The reaction mixture was stirred at room temperature for 1 h. After cooling to 0° C., sodium tetrahydroborate (1.24 g, 32.8 mmol) was added slowly and the resulting mixture was stirred for 30 min. The reaction was quenched with water. The volatile organic solvents were removed under reduced pressure and saturated aq. NaHCO$_3$ was added to the residue. The mixture was extracted with EtOAc (3 times). The combined organic extracts were washed with water and brine, then dried over Na$_2$SO$_4$ and concentrated under reduced pressure. The residue was purified by column chromatography on silica gel using CombiFlash® apparatus eluting with EtOAc/hexane (20-100%) to give the sub-title compound as a colorless oil. LCMS calc. for C$_{13}$H$_{15}$N$_2$O$_3$ (M+H)$^+$ m/z: 247.1. found: 247.1.

Step 8. (1R,2R,6S)-1-(Bromomethyl)-6-methyl-4-(3-nitropyridin-4-yl)cyclohex-3-ene-1,2-diol

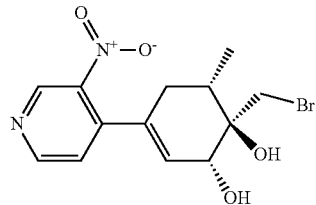 [SMILES: C[C@H]1CC(c2ccncc2[N+](=O)[O-])=C[C@@H](O)[C@@]1(O)CBr]

To a mixture of (1R,5S)-5-methyl-6-methylene-3-(3-nitropyridin-4-yl)cyclohex-2-en-1-ol (2.060 g, 8.365 mmol) in THF (13 mL) and water (13 mL) was added N-bromosuccinimide (2.23 g, 12.5 mmol) at room temperature. The reaction mixture was stirred at room temperature for 10 min., then quenched with sodium thiosulfate. The mixture was extracted with EtOAc (2 times). The combined organic phases were washed with water and brine, dried over Na$_2$SO$_4$, and concentrated under reduced pressure to give the sub-title compound (3.1 g) as a brown solid. LCMS calc. for C$_{13}$H$_{16}$BrN$_2$O$_4$ (M+H)$^+$ m/z: 343.0. found: 343.0.

Step 9. 4-[(1S,5S,6R)-6-(Bromomethyl)-5-methyl-7-oxabicyclo[4.1.0]hept-2-en-3-yl]-3-nitropyridine

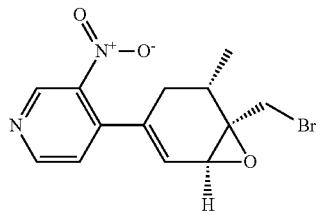 [SMILES: C[C@H]1CC(c2ccncc2[N+](=O)[O-])=C[C@@H]2O[C@@]21CBr]

To a solution of (1R,2R,6S)-1-(bromomethyl)-6-methyl-4-(3-nitropyridin-4-yl)cyclohex-3-ene-1,2-diol (2.80 g, 8.16 mmol) in DCM (60 mL) at 0° C. was added TEA (2.27 mL, 16.3 mmol), followed by methanesulfonyl chloride (0.884 mL, 11.4 mmol) dropwise. The reaction mixture was stirred at 0° C. for 1 h. The reaction was quenched with saturated aq. NaHCO$_3$ solution and stirred for 20 min. The mixture was extracted with EtOAc (2 times). The combined organic phases were washed with water and brine, dried over Na$_2$SO$_4$, and concentrated under reduced pressure to afford the sub-title compound as a brown solid (3.5 g). LCMS calc. for C$_{13}$H$_{14}$BrN$_2$O$_3$ (M+H)$^+$ m/z: 325.0. found: 325.0.

Step 10. 4-[(3R,4R,8S)-4-Azido-8-methyl-1-oxaspiro[2.5]oct-5-en-6-yl]-3-nitropyridine

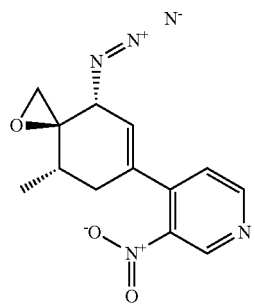

To a mixture of 4-[(1S,5S,6R)-6-(bromomethyl)-5-methyl-7-oxabicyclo[4.1.0]hept-2-en-3-yl]-3-nitropyridine (2.65 g, 8.15 mmol) in EtOH (24 mL) and water (8 mL) was added NH₄Cl (0.654 g, 12.2 mmol) and NaN₃ (0.795 g, 12.2 mmol). The reaction mixture was stirred at room temperature overnight, then treated with equal volume of saturated aq. NaHCO₃ and MeCN and stirred at room temperature for 2 h. The volatile solvent was removed under reduced pressure. The mixture was extracted with EtOAc. The combined organic phases were washed with brine and dried over Na₂SO₄, then concentrated under reduced pressure. The residue was purified by column chromatography on silica gel using CombiFlash® apparatus eluting with EtOAc/hexanes (0-20%) to give the sub-title compound as a colorless oil. LCMS calc. for $C_{13}H_{14}N_5O_3$ (M+H)⁺ m/z: 288.1. found: 288.1.

Step 11. tert-Butyl [(1R,2R,3S,5R)-5-(3-aminopyridin-4-yl)-2-hydroxy-2,3-dimethylcyclohexyl]carbamate

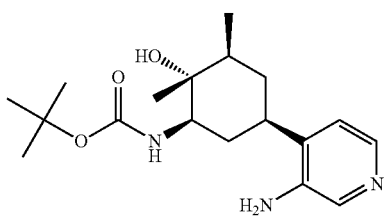 [SMILES: C[C@H]1C[C@@H](c2ccncc2N)C[C@@H](NC(=O)OC(C)(C)C)[C@]1(C)O]

A solution of 4-[(3R,4R,8S)-4-azido-8-methyl-1-oxaspiro[2.5]oct-5-en-6-yl]-3-nitropyridine (1.00 g, 3.48 mmol) in EtOH (60 mL) was deoxygenated for 10 min. Pyridine (2.82 mL, 34.8 mmol) and 10% palladium on carbon (1.1 g, 1.0 mmol) were added. The reaction mixture was stirred at room temperature under balloon pressure of H₂ for 3 days. The mixture was filtered through a pad of diatomaceous earth and the pad was rinsed with DCM/MeOH. The filtrates were concentrated under reduced pressure. To the resulting residue was added EtOH (30 mL) and Boc₂O (0.912 g, 4.18 mmol). The mixture was stirred at room temperature for 1 h, then concentrated under reduced pressure. The residue was purified by preparative LCMS (Method B) to give 283 mg of the sub-title compound as a white solid. LCMS calc. for $C_{18}H_{30}N_3O_3$ (M+H)⁺ m/z: 336.2. found: 336.3.

Step 12. 2-Amino-N-(4-((1R,3R,4R,5S)-3-amino-4-hydroxy-4,5-dimethylcyclohexyl)pyridin-3-yl)furo[3,2-b]pyridine-3-carboxamide To a solution of tert-butyl [(1R,2R,3S,5R)-5-(3-aminopyridin-4-yl)-2-hydroxy-2,3-dimethylcyclohexyl]carbamate (20 mg, 0.060 mmol) in DMF (99 µL) was added 2-[(tert-butoxycarbonyl)amino]furo[3,2-b]pyridine-3-carboxylic acid (100 mg, 0.36 mmol), DIPEA (10 µL, 0.060 mmol), and bis(2-oxo-3-oxazolidinyl)phosphinic chloride (182 mg, 0.716 mmol). The resulting mixture was stirred for 2 h. The reaction mixture was purified by preparative LCMS (Method B) to give an amide intermediate. The intermediate was treated with DCM (1 mL) and TFA (1 mL, 10 mmol). The resulting solution was stirred at room temperature for 1 h, then concentrated under reduced pressure. The residue was neutralized to pH=7-8 with NH₄OH and purified by preparative LCMS (Method B) to afford the title compound as a white solid. LCMS calc. for $C_{21}H_{26}N_5O_3$ (M+H)⁺ m/z: 396.2. found: 396.3.

Example 84

2-Amino-N-(4-((1R,3R,4R,5S)-3-amino-4-hydroxy-4,5-dimethylcyclohexyl)pyridin-3-yl)-6-propylfuro[3,2-b]pyridine-3-carboxamide

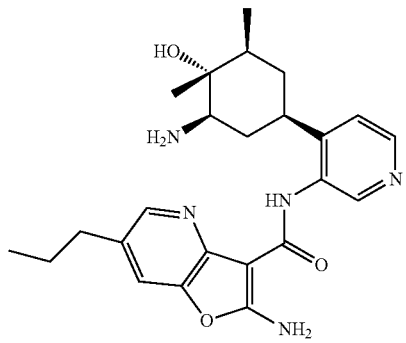 [SMILES: CCCc1cnc2c(C(=O)Nc3cnccc3[C@H]3C[C@@H](N)[C@](C)(O)[C@@H](C)C3)c(N)oc2c1]

To a solution of tert-butyl [(1R,2R,3S,5R)-5-(3-aminopyridin-4-yl)-2-hydroxy-2,3-dimethylcyclohexyl]carbamate (40 mg, 0.12 mmol) in DMF (1.0 mL) was added 2-[(tert-butoxycarbonyl)amino]-6-propylfuro[3,2-b]pyridine-3-carboxylic acid (114 mg, 0.358 mmol), DIPEA (62 µL, 0.36 mmol), and bis(2-oxo-3-oxazolidinyl)phosphinic chloride (182 mg, 0.715 mmol). The resulting mixture was stirred at 45° C. for 6 h. The mixture was purified by preparative LCMS (Method B) to give the amide intermediate. The intermediate was treated with DCM (2 mL) and TFA (2 mL, 20 mmol). The resulting solution was stirred at room temperature for 1 h, then concentrated under reduced pressure. The residue was purified by preparative LCMS (Method B) to afford the title compound as a white solid. LCMS calc. for $C_{24}H_{32}N_5O_3$ (M+H)⁺ m/z: 438.2. found: 438.3.

Example 85

2-Amino-N-{4-[(3R,4R,5S)-3-amino-4-hydroxy-4,5-dimethylpiperidin-1-yl]pyridin-3-yl}-6-propylfuro[3,2-b]pyridine-3-carboxamide

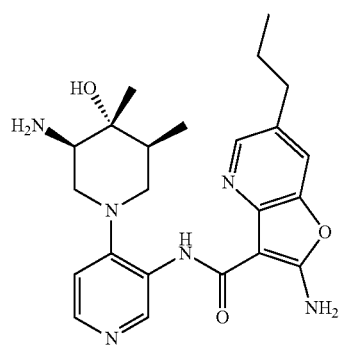 [SMILES: CCCc1cnc2c(C(=O)Nc3cnccc3N3C[C@@H](N)[C@](C)(O)[C@@H](C)C3)c(N)oc2c1]

Step 1. Benzyl-(3R,4R,5S)-3-[(tert-butoxycarbonyl)amino]-4-{[tert-butyl(dimethyl)silyl]oxy}-5-methyl-piperidine-1-carboxylate

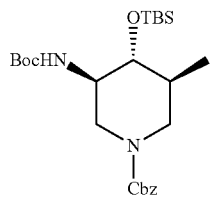 [SMILES: C[C@H]1CN(C(=O)OCc2ccccc2)C[C@@H](NC(=O)OC(C)(C)C)[C@@H]1O[Si](C)(C)C(C)(C)C]

To a solution of tert-butyl-((3R,4R,5S)-4-{[tert-butyl(dimethyl)silyl]oxy}-5-methylpiperidin-3-yl)carbamate (3.2 g, 9.4 mmol) (40% purity) in DCM (25 mL), N-(benzyloxycarbonyloxy)succinimide (2.6 g, 10 mmol) was added, followed by TEA (1.4 mL, 10 mmol). The mixture was stirred for 16 h at room temperature. The reaction mixture was then diluted with EtOAc, washed with water and brine and dried over $Na_2SO_4$. Solvent was evaporated and the resulting crude product was purified by silica gel chromatography, yielding the sub-title compound as a white solid (1.71 g, 38%). LCMS calc. for $C_{25}H_{42}N_2O_5SiNa$ $(M+Na)^+$: m/z=501.3. found 501.0.

Step 2. Benzyl-(3R,4R,5S)-3-[(tert-butoxycarbonyl)amino]-4-hydroxy-5-methylpiperidine-1-carboxylate

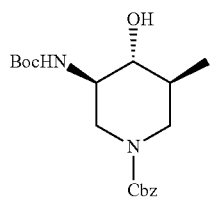 [SMILES: C[C@H]1CN(C(=O)OCc2ccccc2)C[C@@H](NC(=O)OC(C)(C)C)[C@@H]1O]

Benzyl-(3R,4R,5S)-3-[(tert-butoxycarbonyl)amino]-5-methyl-4-(1,1,2,2-tetramethylpropoxyl)piperidine-1-carboxylate (1.88 g, 4.06 mmol) was dissolved in THF (20 mL) and 1.0 M solution of TBAF in THF (4.7 mL, 4.7 mmol) was added. The reaction mixture was stirred for 30 min. at room temperature and then diluted with EtOAc. The mixture was washed 2 times with brine, dried over $Na_2SO_4$. Solvent was evaporated under reduced pressure and the resulting crude product was purified by silica gel chromatography to give white solid (1.48 g, 82%). LCMS calc. for $C_{19}H_{28}N_2NaO_5$ $(M+Na)^+$: m/z=387.2. found 387.0.

Step 3. Benzyl-3-[(tert-butoxycarbonyl)amino]-5-methyl-4-oxopiperidine-1-carboxylate

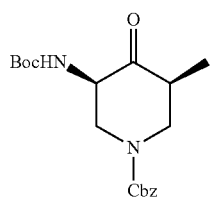 [SMILES: C[C@H]1CN(C(=O)OCc2ccccc2)C[C@@H](NC(=O)OC(C)(C)C)C1=O]

To a stirred solution of benzyl-3-[(tert-butoxycarbonyl)amino]-4-hydroxy-5-methylpiperidine-1-carboxylate (1.22 g, 3.35 mmol) in DCM (20 mL) at 0° C. was added pyridine (0.8 mL, 10 mmol) and Dess-Martin periodinane (1.8 g, 4.4 mmol). The reaction mixture was stirred at room temperature for 16 h. A solution containing a mixture of $NaHCO_3$ and $Na_2S_2O_3$ was added and the resulting mixture was stirred for 30 min. Then the product was extracted with DCM, dried and purified by silica gel chromatography to give a colorless oil (1.15 g, 95%). LCMS calc. for $C_{19}H_{26}N_2NaO_5$ $(M+Na)^+$ m/z=385.2. found 385.0.

Step 4. Benzyl-(3R,5S)-3-[(tert-butoxycarbonyl)amino]-4-hydroxy-4,5-dimethylpiperidine-1-carboxylate

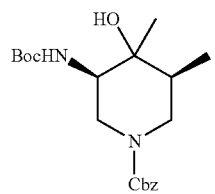 [SMILES: C[C@H]1CN(C(=O)OCc2ccccc2)C[C@@H](NC(=O)OC(C)(C)C)C1(C)O]

To a solution of benzyl-(3R,5S)-3-[(tert-butoxycarbonyl)amino]-5-methyl-4-oxopiperidine-1-carboxylate (1.61 g, 4.44 mmol) in THF (30 mL) at −78° C. was added 3.0 M solution of methylmagnesium bromide in ether (4.4 mL, 13 mmol). The reaction was quenched with a solution of $NH_4Cl$ and the products were extracted with EtOAc. The organic phase was dried, concentrated under reduced pressure and the resulting residue was purified by silica gel chromatography to give a mixture of two products as a colorless oil (0.95 g, 56%). LCMS calc. for $C_{20}H_{30}N_2NaO_5$ $(M+Na)^+$: m/z=401.2. found 401.0. 40% of unreacted starting material was also isolated.

Step 5. tert-Butyl-[(3R,5S)-4-hydroxy-4,5-dimethylpiperidin-3-yl]carbamate

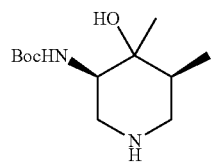 [SMILES: C[C@H]1CNC[C@@H](NC(=O)OC(C)(C)C)C1(C)O]

A mixture of benzyl-(3R,4R,5S)-3-[(tert-butoxycarbonyl)amino]-4-hydroxy-4,5-dimethylpiperidine-1-carboxylate (414 mg, 1.09 mmol) and 10% palladium on carbon (100 mg) in MeOH (10 mL) was hydrogenated under a balloon with $H_2$ at room temperature overnight. Palladium on carbon was filtered off and the filtrate was evaporated to give the sub-title compound as a colorless oil (245 mg, 92%). The crude product was used in the next step without further purification. LCMS calc. for $C_{12}H_{25}N_2O_3$ $(M+H)^+$ m/z=245.2. found 245.1.

Step 6. tert-Butyl-[(3R,5S)-4-hydroxy-4,5-dimethyl-1-(3-nitropyridin-4-yl)piperidin-3-yl]carbamate

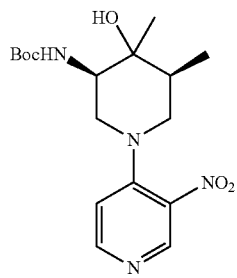 [SMILES: C[C@H]1CN(c2ccncc2[N+](=O)[O-])C[C@@H](NC(=O)OC(C)(C)C)C1(C)O]

A mixture of 4-chloro-3-nitropyridine (160 mg, 1.0 mmol), tert-butyl-[(3R,4R,5S)-4-hydroxy-4,5-dimethylpiperidin-3-yl]carbamate (245 mg, 1.00 mmol) and TEA (284 μL, 2.04 mmol) in i-PrOH (1 mL) was stirred at 80° C. for 2 h. Solvent was evaporated and the resulting residue was purified by silica gel chromatography to give yellow oil (365 mg, 99%). LCMS calc. for $C_{17}H_{27}N_4O_5$ $(M+H)^+$: m/z=367.2. found 367.1.

Step 7. tert-Butyl [(3R,5S)-1-(3-aminopyridin-4-yl)-4-hydroxy-4,5-dimethylpiperidin-3-yl]carbamate

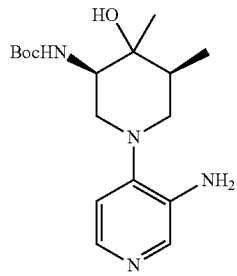 [SMILES: C[C@H]1CN(c2ccncc2N)C[C@@H](NC(=O)OC(C)(C)C)C1(C)O]

tert-Butyl-[3R,4R,5S)-4-hydroxy-4,5-dimethyl-1-(3-nitropyridin-4-yl)piperidin-3-yl]carbamate (312 mg, 0.851 mmol) was dissolved in acetic acid (5.7 mL) and iron powder (716 mg, 12.8 mmol) was added. The reaction mixture was stirred at room temperature for 2 h, then diluted with 10 mL of EtOAc and filtered through a plug of diatomaceous earth. Solvent was evaporated and the resulting residue was dissolved in EtOAc and neutralized aq. NaHCO₃ to pH 8-9. The layers were separated and the water phase was extracted 3 times with EtOAc. The combined organic layers were dried over Na₂SO₄, filtered and concentrated under reduced pressure to give the sub-title compound as a slightly yellow solid (260 mg, 91%). LCMS calc. for $C_{17}H_{29}N_4O_3$ (MAI) m/z=337.2. found 337.2.

Step 8. tert-Butyl-(3-{[(4-{(3R,5S)-3-[(tert-butoxycarbonyl)amino]-4-hydroxy-4,5-dimethylpiperidin-1-yl}pyridin-3-yl)amino]carbonyl}-6-propylfuro[3,2-b]pyridin-2-yl)carbamate

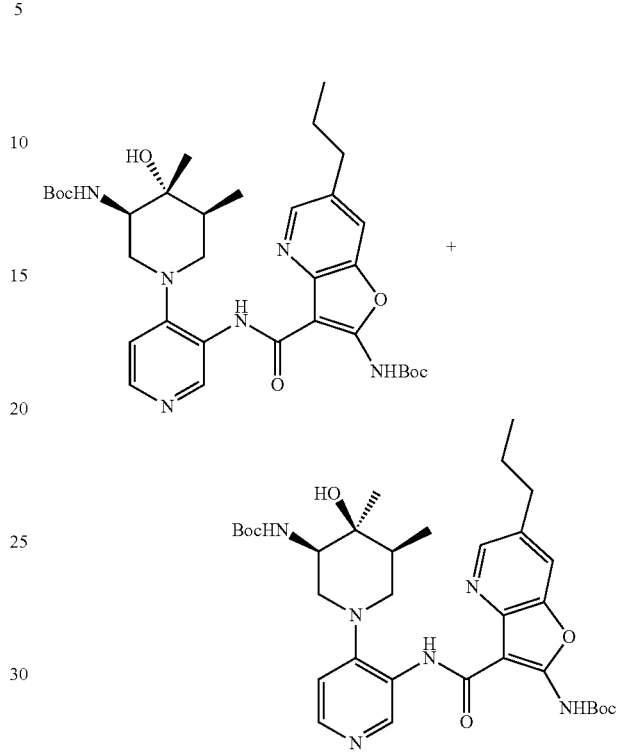

A mixture of 2-[(tert-butoxycarbonyl)amino]-6-propylfuro[3,2-b]pyridine-3-carboxylic acid (100 mg, 0.4 mmol), tert-butyl-[3R,4R,5S)-1-(3-aminopyridin-4-yl)-4-hydroxy-4,5-dimethylpiperidin-3-yl]acetate (120 mg, 0.36 mmol), HATU (330 mg, 0.88 mmol), DIPEA (180 μL, 1.0 mmol) and 4 Å molecular sieve in 1,2-dichloroethane (15 mL) was stirred at room temperature for 2 days. The reaction was quenched with aq. NaHCO₃ and the products were extracted with EtOAc. The organic phase was dried, concentrated under reduced pressure. The two diastereomers were purified and separated from each other by RP-HPLC (Waters SunFire™ C18 column, 19 mm×100 mm, 5 μm particle size, eluting with a gradient of MeCN/water containing 0.1% TFA, at flow rate of 30 mL/min.). LCMS calc. for $C_{33}H_{47}N_6O$ $(M+H)^+$: m/z=639.3. found 639.3.

Step 9. 2-Amino-N-{4-[(3R,4R,5S)-3-amino-4-hydroxy-4,5-dimethylpiperidin-1-yl]pyridin-3-yl}-6-propylfuro[3,2-b]pyridine-3-carboxamide HCl in dioxane (4.0 M; 1 mL, 4 mmol) was added to tert-butyl (3-{[(4-{(3R,4R,5S)-3-[(tert-butoxycarbonyl)amino]-4-hydroxy-4,5-dimethylpiperidin-1-yl}pyridin-3-yl)amino]carbonyl}-6-propylfuro[3,2-b]pyridin-2-yl)carbamate (10 mg, 0.02 mmol) and the reaction mixture was stirred at room temperature for 1 h. Solvent was evaporated and the title compound was purified by RP-HPLC (Waters XBridge™ C18 column, 19 mm×100 mm, 5 μm particle size, eluting with a gradient of MeCN/water containing 0.15% NH₄OH, at flow rate of 30 mL/min.) to yield 1.5 mg of the title compound as a white solid. LCMS calc. for $C_{23}H_{31}N_6O_3$ $(M+H)^+$: m/z=439.2. found 439.0. ¹H NMR (500 MHz, DMSO-d₆) δ 10.12 (s, 1H), 9.48 (s, 1H), 8.20 (s, 1H), 8.15 (d, J=5.2 Hz, 1H), 7.60 (s, 1H), 7.12 (d, J=5.3 Hz, 1H), 4.30 (s, 1H), 3.14 (dd, J=10.9, 4.1 Hz, 1H), 3.03 (d, J=11.9 Hz, 1H), 2.96 (d, J=10.5 Hz, 1H), 2.66-2.57 (m, 2H), 2.57-2.47 (m, 2H), 2.23-2.10 (m, 1H), 1.61 (q, J=7.4 Hz, 2H), 0.96 (s, 3H), 0.90 (t, J=7.3 Hz, 3H), 0.76 (d, J=6.8 Hz, 3H) ppm.

Example 86

2-Amino-N-{4-[(3R,4S,5S)-3-amino-4-hydroxy-4,5-dimethylpiperidin-1-yl]pyridin-3-yl}-6-propylfuro[3,2-b]pyridine-3-carboxamide

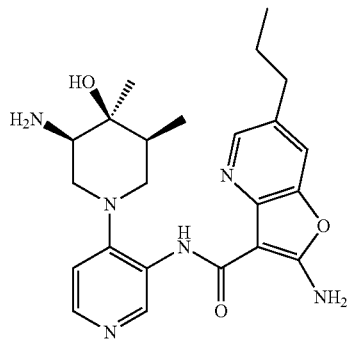 [SMILES: CCCc1cnc2c(C(=O)Nc3cnccc3N3C[C@@H](N)[C@@](C)(O)[C@@H](C)C3)c(N)oc2c1]

HCl in dioxane (4.0 M; 1 mL, 4 mmol) was added to tert-butyl (3-{[(4-{(3R,4S,5S)-3-[(tert-butoxycarbonyl)amino]-4-hydroxy-4,5-dimethylpiperidin-1-yl}pyridin-3-yl)amino]carbonyl}-6-propylfuro[3,2-b]pyridin-2-yl)carbamate (10 mg, 0.02 mmol) and the reaction stirred at room temperature for 1 h. Solvent was evaporated and the product was purified by RP-HPLC (Waters XBridge™ C18 column, 19 mm×100 mm, 5 µm particle size, eluting with a gradient of MeCN/water containing 0.15% NH$_4$OH, at flow rate of 30 mL/min.) to yield 1.7 mg of the title compound as a white solid. LCMS calc. for C$_{23}$H$_{31}$N$_6$O$_3$ (M+H)$^+$ m/z=439.2. found 439.2.

Example 87

2-Amino-N-{4-[(3R,4R,5S)-3-amino-4-hydroxy-5-(trifluoromethyl)piperidin-1-yl]pyridin-3-yl}furo[3,2-b]pyridine-3-carboxamide

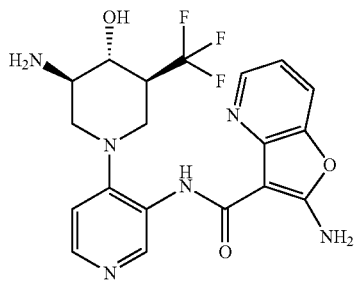 [SMILES: Nc1oc2cccnc2c1C(=O)Nc1cnccc1N1C[C@@H](N)[C@H](O)[C@@H](C(F)(F)F)C1]

Step 1. tert-Butyl (4R)-2,2-dimethyl-4-[(1R,2R)-3,3,3-trifluoro-1-hydroxy-2-(methoxycarbonyl)propyl]-1,3-oxazolidine-3-carboxylate

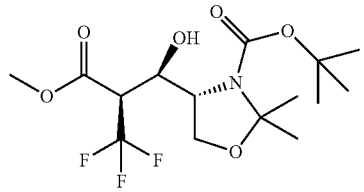 [SMILES: COC(=O)[C@@H]([C@@H](O)[C@H]1COC(C)(C)N1C(=O)OC(C)(C)C)C(F)(F)F]

To a solution of methyl 3,3,3-trifluoropropanoate (5.0 g, 35 mmol) in DCM (50 mL) (0.13 M) at –78° C. was added 1.0 M dibutylboron triflate in DCM (70 mL, 70 mmol) followed by DIPEA (18 mL, 1.02 mmol). The mixture was stirred at –78° C. for 30 min., 0° C. for 40 min., then cooled to –78° C. A solution of tert-butyl (4R)-4-formyl-2,2-dimethyl-1,3-oxazolidine-3-carboxylate (8.1 g, 35 mmol) in 10 mL DCM was added and the resulting reaction mixture was stirred at –78° C. for 1 h and 0° C. for 1 h. The reaction was quenched by the addition of pH 7 phosphate buffer solution (20 ml) and diluted with MeOH (50 mL) and oxidized with 30% H$_2$O$_2$ (5 mL) overnight. The mixture was diluted with water, then extracted with DCM. The organic phase was separated, washed with brine, dried over Na$_2$SO$_4$, then concentrated under reduced pressure. The residue was purified by chromatography on silica gel (eluting with 0-40% EtOAc/hexanes) to give 5.8 g (44%) products an an orange oil. TLC R$_f$=0.45 (25% EtOAc/hexanes). LCMS calc. for C$_{15}$H$_{24}$F$_3$NO$_6$Na (M+Na)$^+$ m/z=394.2. found: 394.1. The product was a mixture of the sub-title compound and its corresponding 1S,2S-diastereoisomer.

Step 2. tert-Butyl (4R)-4-[(1R,2R)-1-{[tert-butyl(dimethyl)silyl]oxy}-3,3,3-trifluoro-2-(methoxycarbonyl)propyl]-2,2-dimethyl-1,3-oxazolidine-3-carboxylate

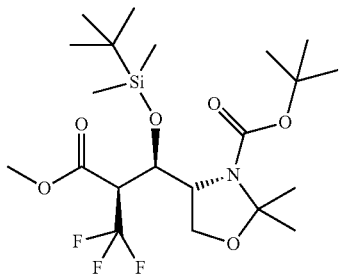

To a solution of tert-butyl (4R)-2,2-dimethyl-4-[(1R,2R)-3,3,3-trifluoro-1-hydroxy-2-(methoxycarbonyl)propyl]-1,3-oxazolidine-3-carboxylate (5.3 g, 14 mmol) and 2,6-lutidine (3.0 mL, 26 mmol) in DCM (140 mL) (0.1 M) was added tert-butyldimethylsilyl trifluoromethanesulfonate (4.6 mL, 20 mmol) at –40° C. The mixture was stirred at –40° C. for 2 h, then diluted with DCM, washed with saturated aq. NaHCO$_3$ solution, dried over Na$_2$SO$_4$, and concentrated under reduced pressure. The residue was purified by chromatography on silica gel (0-20% EtOAc/hexanes) to give the sub-title compound as a colorless oil (3.5 g, 51%). TLC $R_f$=0.85 (25% EtOAc/hexanes). LCMS calc. for $C_{16}H_{30}F_3NO_4Si$ (M+H-Boc+H)$^+$ m/z=386.2. found: 386.1. The product was a mixture of the sub-title compound and its corresponding 1S,2S-diastereoisomer.

Step 3. tert-Butyl (4R)-4-[(1R,2S)-1-{[tert-butyl (dimethyl)silyl]oxy}-3,3,3-trifluoro-2-(hydroxymethyl)propyl]-2,2-dimethyl-1,3-oxazolidine-3-carboxylate

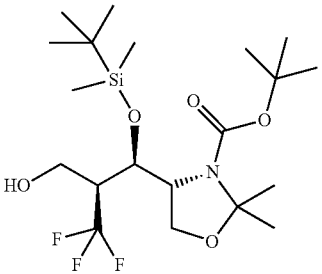

To a solution of tert-butyl (4R)-4-[(1R,2R)-1-{[tert-butyl (dimethyl)silyl]oxy}-3,3,3-trifluoro-2-(methoxycarbonyl) propyl]-2,2-dimethyl-1,3-oxazolidine-3-carboxylate (3.5 g, 7.2 mmol) and EtOH (1.3 mL, 22 mmol) in THF (80 mL) (0.09 M) was added LiBH$_4$ (0.47 g, 22 mmol) at −30° C. The mixture was warmed up to 0° C. and stirred overnight. The reaction mixture was diluted with ether and 1 M NaOH was added. The resulting mixture was extracted with EtOAc. The combined organic layers were washed with brine, dried over Na$_2$SO$_4$, then concentrated under reduced pressure. The resulting residue was purified by chromatography on silica gel (0-20% EtOAc/hexanes) to give the sub-title compound as a diastereoisomeric mixture (1.1 g, 33%, colorless oil). TLC $R_f$=0.9 and 0.75. LCMS calc. for $C_{15}H_{31}F_3NO_3Si$ (M+H-Boc+H)$^+$ m/z=358.2. found: 358.1. The product was a mixture of the sub-title compound and its corresponding 1S,2R-diastereoisomer.

Step 4. tert-Butyl (4R)-4-((1R,2S)-2-(azidomethyl)-1-{[tert-butyl(dimethyl)silyl]oxy}-3,3,3-trifluoropropyl)-2,2-dimethyl-1,3-oxazolidine-3-carboxylate

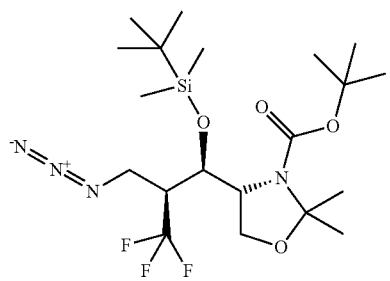

To a solution of tert-butyl (4R)-4-[(1R,2S)-1-{[tert-butyl (dimethyl)silyl]oxy}-3,3,3-trifluoro-2-(hydroxymethyl)propyl]-2,2-dimethyl-1,3-oxazolidine-3-carboxylate (1.1 g, 2.4 mmol), diisopropyl azodicarboxylate (0.95 mL, 4.8 mmol) and PPh$_3$ (1.3 g, 4.8 mmol) in THF (10 mL) (0.18 M) was added diphenylphosphonic azide (1.0 mL, 4.8 mmol). The reaction mixture was stirred at room temperature overnight. Following removal of the volatile solvent under reduced pressure, the residue was purified by chromatography on silica gel (0-15% EtOAc/hexanes) to give the sub-title compound (0.35 g) as a colorless oil. TLC $R_f$=0.80, (25% EtOAc/hexanes), LCMS calc. for $C_{15}H_{30}F_3N_4O_2Si$ (M+H-Boc+H)$^+$ m/z=383.2. found: 383.2. The product was a mixture of the sub-title compound and its corresponding 1S,2R-diastereoisomer.

Step 5. tert-Butyl [(1R,2R,3S)-3-(azidomethyl)-2-{[tert-butyl(dimethyl)silyl]oxy}-4,4,4-trifluoro-1-(hydroxymethyl)butyl]carbamate

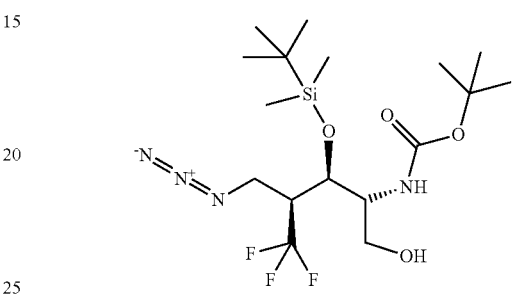

To a solution of tert-butyl (4R)-4-((1R,2S)-2-(azidomethyl)-1-{[tert-butyl(dimethyl)silyl]oxy}-3,3,3-trifluoropropyl)-2,2-dimethyl-1,3-oxazolidine-3-carboxylate (0.30 g, 0.62 mmol) in EtOH (10 mL) was added pyridinium p-toluenesulfonate (0.31 g, 1.2 mmol) and DIPEA (0.12 g, 0.93 mmol). The mixture was heated under reflux for 2 days to give (2R,3R,4S)-2-amino-4-(azidomethyl)-3-{[tert-butyl (dimethyl)silyl]oxy}-5,5,5-trifluoropentan-1-ol. LCMS calc. for $C_{12}H_{26}F_3N_4O_2Si$ (M+H)$^+$ m/z=343.2. found: 343.2. After most of the solvent was removed evaporation under reduced pressure, 5 mL DCM and 0.50 g (Boc)$_2$O were added followed by 0.35 g DIPEA. The mixture was stirred at room temperature for 2 h, then concentrated under reduced pressure. The resulting residue was purified by column chromatography on silica gel using CombiFlash® apparatus (40 g silica gel column) eluting with 0-30% EtOAc/hexanes to give 0.20 g of the sub-title compound as an oil. LCMS calc. for $C_{12}H_{26}F_3N_4O_2Si$ (M+H-Boc+H)$^+$ m/z=343.2. found: 343.2. The product was a mixture of the sub-title compound and its corresponding 1R,2S,3R-diastereoisomer.

Step 6. (2R,3R,4S)-4-(Azidomethyl)-2-[(tert-butoxycarbonyl)amino]-3-{[tert-butyl(dimethyl)silyl] oxy}-5,5,5-trifluoropentyl methanesulfonate

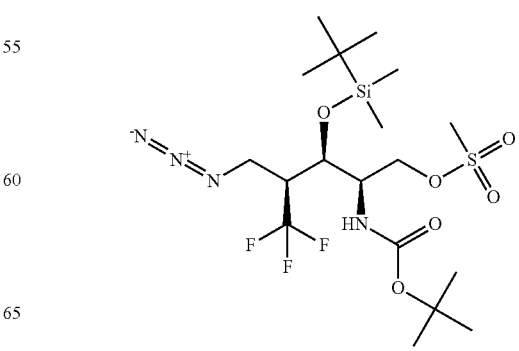

To a solution of tert-butyl [(1R,2R,3S)-3-(azidomethyl)-2-{[tert-butyl(dimethyl)silyl]oxy}-4,4,4-trifluoro-1-(hydroxymethyl)butyl]carbamate (0.22 g, 0.50 mmol) in pyridine (2.5 mL, 31 mmol) at 0° C. was added methanesulfonyl chloride (0.057 mL, 0.74 mmol) and 4-dimethylaminopyridine (0.01 g, 0.1 mmol). The resulting mixture was stirred at 0° C. for 1 h, then diluted with EtOAc, washed with saturated aq. NaHCO$_3$, then concentrated under reduced pressure. The residue was purified by chromatography on silica gel (0-25% EtOAc/hexanes) to give the sub-title compound (0.30 g) as a colorless oil. TLC R$_f$=0.45 (25% EtOAc/hexanes), LCMS calc. for C$_{13}$H$_{28}$F$_3$N$_4$O$_4$SSi (M+H-Boc+H)$^+$ m/z=421.2. found: 421.1. The product was a mixture of the sub-title compound and its corresponding 2R,3S,4R-diastereoisomer.

Step 7. tert-Butyl [(3R,4R,5S)-4-{[tert-butyl(dimethyl)silyl]oxy}-5-(trifluoromethyl)piperidin-3-yl]carbamate

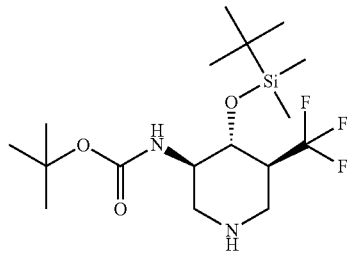 [SMILES: CC(C)(C)OC(=O)N[C@@H]1CNC[C@H](C(F)(F)F)[C@H]1O[Si](C)(C)C(C)(C)C]

A solution of (2R,3R,4S)-4-(azidomethyl)-2-[(tert-butoxycarbonyl)amino]-3-{[tert-butyl(dimethyl)silyl]oxy}-5,5,5-trifluoropentyl methanesulfonate (0.30 g, 0.58 mmol) in MeOH (18 mL) (0.09M) was deoxygenated with N$_2$ for 20 min. DIPEA (0.30 mL, 1.7 mmol) was added, followed by 10% palladium on carbon (0.31 g). The reaction mixture was stirred under a balloon containing H$_2$ for 2 h. The mixture was filtered and the filtrate was concentrated under reduced pressure to give 0.30 g of the sub-title compound as an oil which used for the next step without further purification. LCMS calc. for C$_{17}$H$_{34}$F$_3$N$_2$O$_3$Si (M+H)$^+$ m/z=399.2. found: 399.0. The product was a mixture of the sub-title compound and its corresponding 3R,4S,5R-diastereoisomer.

Step 8. tert-Butyl [(3R,4R,5S)-4-{[tert-butyl(dimethyl)silyl]oxy}-1-(3-nitropyridin-4-yl)-5-(trifluoromethyl)piperidin-3-yl]carbamate

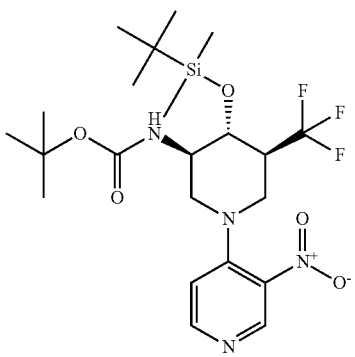

A mixture of 4-chloro-3-nitropyridine (0.120 g, 0.755 mmol), tert-butyl [(3R,4R,5S)-4-{[tert-butyl(dimethyl)silyl]oxy}-5-(trifluoromethyl)piperidin-3-yl]carbamate (0.45 g, 1.1 mmol) and TEA (0.4 mL, 3 mmol) in i-PrOH (2.2 mL) was stirred at 85° C. for 1 h. The mixture was concentrated under reduced pressure resulting residue was purified by column chromatography on silica gel using CombiFlash® apparatus eluting with EtOAc/hexanes (10-60%) to give the sub-title compound as a diastereoisomeric mixture (215 mg). LCMS calc. for C$_{22}$H$_{36}$F$_3$N$_4$O$_5$Si (M+H)$^+$ m/z=521.2. found: 521.1. The product was a mixture of the sub-title compound and its corresponding 3R,4S,5R-diastereoisomer.

Step 9. tert-Butyl [(3R,4R,5S)-1-(3-aminopyridin-4-yl)-4-{[tert-butyl(dimethyl)silyl]oxy}-5-(trifluoromethyl)piperidin-3-yl]carbamate

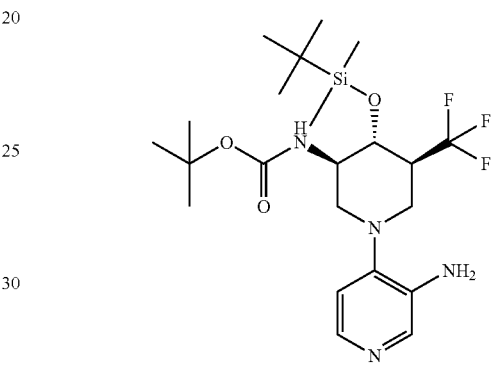

A mixture of tert-butyl [(3R,4R,5S)-4-{[tert-butyl(dimethyl)silyl]oxy}-1-(3-nitropyridin-4-yl)-5-(trifluoromethyl)piperidin-3-yl]carbamate (0.060 g, 0.12 mmol), acetic acid (2 mL) and iron (0.20 g, 3.6 mmol) was stirred at room temperature for 2 h. The mixture was diluted with 30 mL of EtOAc, then filtered through a diatomaceous earth plug. The residue was rinsed with fresh EtOAc. The combined filtrate was condensed under reduced pressure, diluted with EtOAc and then washed with 0.5 M NaOH quickly. The organic phase was further washed with water and brine, dried over Na$_2$SO$_4$, filtered and concentrated to dryness to yield 40 mg of brown solid. LCMS calc. for C$_{22}$H$_{38}$F$_3$N$_4$O$_3$Si (M+H)$^+$ m/z=521.2. found: 491.1. The product was a mixture of the sub-title compound and its corresponding 3R,4S,5R-diastereoisomer.

Step 10. 2-Amino-N-{4-[(3R,4R,5S)-3-amino-4-hydroxy-5-(trifluoromethyl)piperidin-1-yl]pyridin-3-yl}furo[3,2-b]pyridine-3-carboxamide A mixture of tert-butyl [(3R,4R,5S)-1-(3-aminopyridin-4-yl)-4-{[tert-butyl(dimethyl)silyl]oxy}-5-(trifluoromethyl)piperidin-3-yl]carbamate (20 mg, 0.04 mmol), 2-[(tert-butoxycarbonyl)amino]furo[3,2-b]pyridine-3-carboxylic acid (26 mg, 0.095 mmol) and DIPEA (20 mg, 0.2 mmol) in 1,2-dichloroethane (2 mL) and molecular sieves was stirred at room temperature for 1.5 h. Then HATU (0.031 g, 0.082 mmol) was added. The mixture was stirred at room temperature overnight. After removal of solvent, the resulting residue was purified by RP-HPLC (Waters XBridge™ C18 column, 19 mm×100 mm, 5 μm particle size, eluting with a gradient of MeCN/water containing 0.1% TFA, at flow rate of 30 mL/min.) to give tert-butyl {3-[({4-[(3R,4R,5S)-3-

[(tert-butoxycarbonyl)amino]-4-{[tert-butyl(dimethyl)silyl]oxy}-5-(trifluoromethyl)piperidin-1-yl]pyridin-3-yl}amino)carbonyl]furo[3,2-b]pyridin-2-yl}carbamate as a mixture of diastereoisomers. LCMS calc. for $C_{35}H_{50}F_3N_6O_7Si$ (M+H)$^+$ m/z=751.3. found: 751.1. The diastereoisomeric mixture was dissolved in HBr (3 mL) and stirred at 85° C. for 2 h. The solvent was removed under reduced pressure and the resulting residue was purified by RP-HPLC (Waters XBridge™ C18 column, 19 mm×100 mm, 5 μm particle size, eluting with a gradient of MeCN/water containing 0.15% NH$_4$OH, at flow rate of 30 mL/min.) to give two products.

Diastereoisomer 1. First peak is the corresponding 3R,4S,5R-diastereoisomer: retention time 1.067 min. LCMS calc. for $C_{19}H_{20}F_3N_6O_3$ (M+H)$^+$: m/z=437.2. found: 437.1. $^1$H NMR (500 MHz, CD$_3$OH)) 9.45 (1H, s), 8.37 (1H, d, J=5.5 Hz), 8.26 (1H, d, J=5.5 Hz), 7.65 (1H, d, J=8.0 Hz), 7.29 (1H, d, J=5.5 Hz), 7.14 (1H, dd, J=8.0 and 5.5 Hz), 4.27 (1H, dd, J=9.0 and 4.3 Hz), 3.82 (1H, m), 3.58 (1H, m), 3.51 (1H, dd, J=12.6 and 2.5 Hz), 3.31 (1H, dd, J=10.26 and 12.38 Hz), 3.23 (1H, m), 2.88 (1H, m) ppm.

Diastereoisomer 2. Second peak is the title compound: retention time 1.380 min. LCMS calc. for $C_{19}H_{20}F_3N_6O_3$ (M+H)$^+$: m/z=437.2. found: 437.1. $^1$H NMR (500 MHz, DMSO-d$_6$)) 10.12 (1H, s), 9.53 (1H, s), 8.34 (1H, d, J=6.0 Hz), 8.25 (1H, d, J=5.5 Hz), 7.74 (1H, d, J=8.0 Hz), 7.26 (1H, d, J=5.5 Hz), 7.09 (1H, dd, J=8.0 and 6.0 Hz), 6.25 (1H, d, J=6.0 Hz), 4.47 (1H, d, J=5.9 Hz), 3.65 (1H, br d, J=11.1 Hz), 3.46 (1H, m), 3.20 (1H, d, J=11.6 Hz), 3.13 (2H, m), 2.97 (1H, dd, J=10.9 and 11.2 Hz) ppm.

Example 88

2-Amino-N-{5-[(3S)-3-aminopiperidin-1-yl]isothiazol-4-yl}thieno[3,2-b]pyridine-3-carboxamide

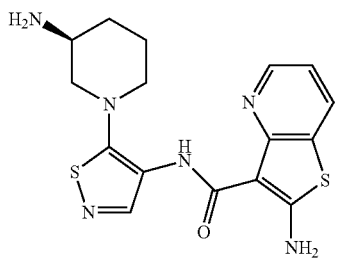 [SMILES: Nc1sc2cccnc2c1C(=O)Nc1cnsc1N1CCC[C@H](N)C1]

A mixture of tert-butyl [(3S)-1-(4-aminoisothiazol-5-yl)piperidin-3-yl]carbamate (0.020 g, 0.068 mmol), 2-[(tert-butoxycarbonyl)amino]thieno[3,2-b]pyridine-3-carboxylic acid (0.022 g, 0.075 mmol), and HATU (0.10 g, 0.27 mmol) in DMF (0.47 mL) and DIPEA (0.036 g, 0.28 mmol) was stirred at room temperature overnight. The mixture was purified by chromatography on 12 g of silica gel, eluting with 0-100% EtOAc in hexanes, to give 8 mg of tert-butyl (3-{[(5-{(3S)-3-[(tert-butoxycarbonyl)amino]piperidin-1-yl}isothiazol-4-yl)amino]carbonyl}thieno[3,2-b]pyridin-2-yl)carbamate. To the amide was added HCl in dioxane (4.0 M; 7.9 mL, 31 mmol) and the resulting mixture was stirred at room temperature for 1 h. The reaction mixture was concentrated under reduced pressure. The residue was dissolved in MeOH, neutralized with NH$_4$OH solution, and purified on RP-HPLC (Waters XBridge™ C18 column, 19 mm×100 mm, 5 μm particle size, eluting with a gradient of MeCN/water containing 0.15% NH$_4$OH, at flow rate of 30 mL/min.) to give the title compound. LCMS calc. for $C_{16}H_{19}N_6OS_2$ (M+H)$^+$: m/z=375.1. found: 375.1.

Example 89

2-Amino-N-{4-[(3R,4R,5S)-3-amino-5-cyclopropyl-4-hydroxypiperidin-1-yl]pyridin-3-yl}-6-isopropyl-furo[3,2-b]pyridine-3-carboxamide

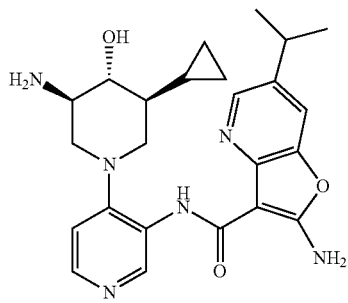 [SMILES: CC(C)c1cnc2c(C(=O)Nc3cnccc3N3C[C@@H](N)[C@H](O)[C@@H](C4CC4)C3)c(N)oc2c1]

A mixture of tert-butyl ((3R,4R,5S)-1-(3-aminopyridin-4-yl)-4-{[tert-butyl(dimethyl)silyl]oxy}-5-cyclopropylpiperidin-3-yl)carbamate (0.144 g, 0.312 mmol), 2-[(tert-butoxycarbonyl)amino]-6-isopropylfuro[3,2-b]pyridine-3-carboxylic acid (0.100 g, 0.312 mmol), DIPEA (0.163 mL, 0.936 mmol) and molecular sieves 4A (0.3 g) in 1,2-dichloroethane (0.654 mL) was stirred at room temperature for 2 h. HATU (0.237 g, 0.624 mmol) was added. The reaction mixture was stirred at room temperature overnight, then filtered through a pad of diatomaceous earth and rinsed with DCM. The filtrate was washed with 1 M NaOH, brine and dried over Na$_2$SO$_4$. The solution was concentrated under reduced pressure and the resulting residue was purified by column chromatography on silica gel using CombiFlash® apparatus eluting with EtOAc/hexanes (0-100%) to yield tert-butyl [3-({[4-((3R,4R,5S)-3-[(tert-butoxycarbonyl)amino]-4-{[tert-butyl(dimethyl)silyl]oxy}-5-cyclopropylpiperidin-1-yl)pyridin-3-yl]amino}carbonyl)-6-isopropylfuro[3,2-b]pyridin-2-yl]carbamate (67 mg) as a light green oil. This oil was treated with HCl in dioxane (4.0 M; 2 mL, 8 mmol). The reaction mixture was stirred at room temperature overnight, and then concentrated under reduced pressure. The resulting residue was purified by RP-HPLC (Waters XBridge™ C18 column, 19 mm×100 mm, 5 μm particle size, eluting with a gradient of MeCN/water containing 0.15% NH$_4$OH, at flow rate of 30 mL/min.) to afford the title compound as a white solid. LCMS calc. for $C_{24}H_{31}N_6O_3$ (M+H)$^+$: m/z=451.2. found: 451.2. $^1$H NMR (400 MHz, DMSO-d$_6$)) 10.05 (1H, s), 9.44 (1H, s), 8.22 (1H, d, J=5.2 Hz), 8.18 (1H, d, J=1.6 Hz), 7.73 (1H, d, J=1.6 Hz), 7.13 (1H, d, J=5.2 Hz), 4.71 (1H, br d, J=5.2 Hz), 3.20 (2H, m), 3.03 (2H, m), 2.93 (1H, td, J=2.4 and 10.0 Hz), 2.61 (1H, dd, J=10.8 and 10.8 Hz), 2.37 (1H, dd, J=11.6 and 11.6 Hz), 1.37 (1H, m), 1.31 (3H, d, J=6.8 Hz), 1.29 (3H, d, J=6.8 Hz), 0.39 (2H, m), 0.06 (1H, m), 0.01 (1H, m), −0.71 (1H, m) ppm.

Example 90

2-Amino-N-{5-[(3S,5R)-3-amino-5-(trifluoromethyl)piperidin-1-yl]-1-methyl-1H-pyrazol-4-yl}-6-(tetrahydro-2H-pyran-4-yl)furo[3,2-b]pyridine-3-carboxamide

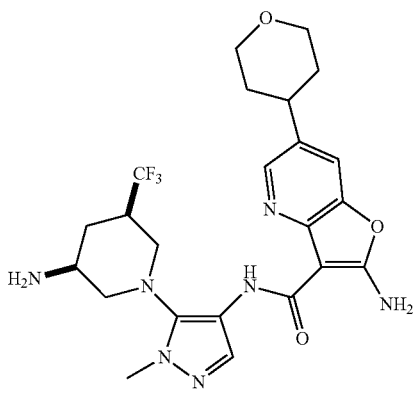 [SMILES: Cn1ncc(NC(=O)c2c(N)oc3cc(C4CCOCC4)cnc23)c1N1C[C@@H](N)C[C@@H](C(F)(F)F)C1]

Step 1. Ethyl 2-[(tert-butoxycarbonyl)amino]-6-(3,6-dihydro-2H-pyran-4-yl)furo[3,2-b]pyridine-3-carboxylate

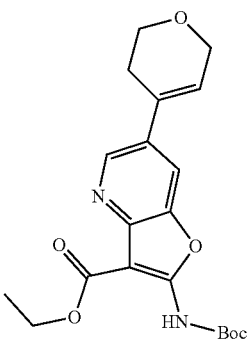 [SMILES: CCOC(=O)c1c(NC(=O)OC(C)(C)C)oc2cc(C3=CCOCC3)cnc12]

To a screw-cap vial equipped with a magnetic stir bar was added ethyl 6-bromo-2-[(tert-butoxycarbonyl)amino]furo[3,2-b]pyridine-3-carboxylate (1.041 g, 2.702 mmol), 4-(4,4,5,5-tetramethyl-1,3,2-dioxaborolan-2-yl)-3,6-dihydro-2H-pyran (755.1 mg, 3.594 mmol), dicyclohexyl(2',4',6'-triisopropylbiphenyl-2-yl)phosphine-(2'-aminobiphenyl-2-yl)(chloro)palladium (1:1) (XPhos Pd G2, Aldrich, 305.2 mg, 0.3879 mmol), and $K_3PO_4$ (1.754 g, 8.263 mmol). The vial was sealed with a PTFE-lined septum, evacuated and backfilled with $N_2$ (this process was repeated a total of three times). 1,4-Dioxane (9.00 mL) was added followed by deoxygenated water (3.00 mL). The reaction mixture was stirred at 50° C. for 2 h. After cooling to room temperature, the reaction mixture was filtered through a silica gel plug (eluted with EtOAc). The filtrate was washed with brine, dried over $Na_2SO_4$, filtered, and concentrated under reduced pressure. The resulting residue was purified by chromatography on silica gel (40 g, 0-100% EtOAc in hexanes) to give the sub-title compound as a brown foamy solid (1.012 g, 77%). LCMS calc. for $C_{20}H_{25}N_2O_6$ $(M+H)^+$: m/z=389.2. found 389.2.

Step 2. Ethyl 2-[(tert-butoxycarbonyl)amino]-6-(tetrahydro-2H-pyran-4-yl)furo[3,2-b]pyridine-3-carboxylate

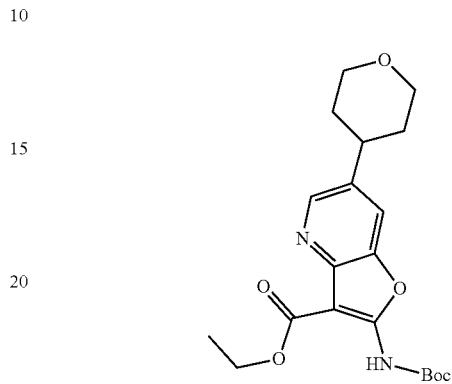

To a solution of ethyl 2-[(tert-butoxycarbonyl)amino]-6-(3,6-dihydro-2H-pyran-4-yl)furo[3,2-b]pyridine-3-carboxylate (1012 mg, 2.605 mmol) in MeOH (24.0 mL) was added 10 wt % Pd on carbon (252.4 mg, 0.2372 mmol). The mixture was stirred at room temperature under a $H_2$ atmosphere (1 atm.) for 5 h. The reaction mixture was then filtered through a pad of diatomaceous earth (eluted with MeOH). The filtrate was concentrated under reduced pressure to give the sub-title compound as a yellow foamy solid (913.2 mg, 90%) which was used directly in the next step without further purification. LCMS calc. for $C_{20}H_{27}N_2O_6$ $(M+H)^+$: m/z=391.2. found 391.2.

Step 3. 2-[(tert-butoxycarbonyl)amino]-6-(tetrahydro-2H-pyran-4-yl)furo[3,2-b]pyridine-3-carboxylic acid

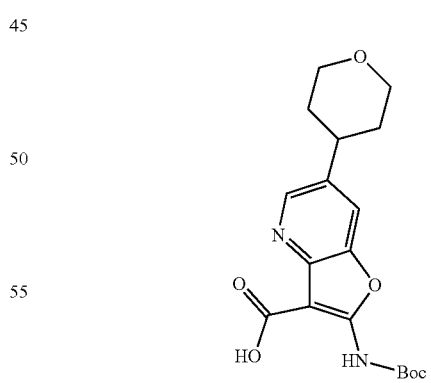

To a solution of ethyl 2-[(tert-butoxycarbonyl)amino]-6-(tetrahydro-2H-pyran-4-yl)furo[3,2-b]pyridine-3-carboxylate (913.2 mg, 2.339 mmol) in THF (6.00 mL) was added LiOH.$H_2O$ (805.4 mg, 19.19 mmol), followed by MeOH (6.00 mL) and water (3.00 mL). The reaction mixture was stirred at 70° C. for 5 h. After cooling to room temperature, the reaction mixture was diluted with DCM and water. Then Step 4. tert-Butyl [(3S,5R)-1-(1-methyl-4-nitro-1H-pyrazol-5-yl)-5-(trifluoromethyl)piperidin-3-yl]carbamate

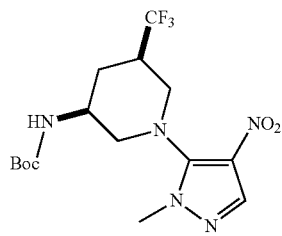 [SMILES: Cn1ncc([N+](=O)[O-])c1N1C[C@@H](NC(=O)OC(C)(C)C)C[C@@H](C(F)(F)F)C1]

To a mixture of 5-chloro-1-methyl-4-nitro-1H-pyrazole (266.5 mg, 1.650 mmol) and tert-butyl [(3S,5R)-5-(trifluoromethyl)piperidin-3-yl]carbamate (388.5 mg, 1.448 mmol) was added n-butanol (4.00 mL), followed by DIPEA (616.8 mg, 4.772 mmol). After stirring at 140° C. for 16 h, the reaction mixture was concentrated under reduced pressure. The resulting residue was purified by chromatography on silica gel (40 g, 0-50% EtOAc in hexanes) to give the title compound (432.2 mg, 76%). LCMS calc. for $C_{15}H_{23}F_3N_5O_4$ (M+H)$^+$: m/z=394.2. found 394.1.

Step 5. tert-Butyl [(3S,5R)-1-(4-amino-1-methyl-M-pyrazol-5-yl)-5-(trifluoromethyl)piperidin-3-yl]carbamate

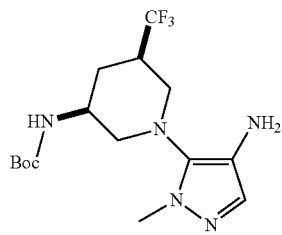 [SMILES: Cn1ncc(N)c1N1C[C@@H](NC(=O)OC(C)(C)C)C[C@@H](C(F)(F)F)C1]

To a mixture of tert-butyl [(3S,5R)-1-(1-methyl-4-nitro-1H-pyrazol-5-yl)-5-(trifluoromethyl)piperidin-3-yl]carbamate (432.2 mg, 1.099 mmol), Fe powder (700.5 mg, 12.54 mmol) and NH$_4$Cl (1201 mg, 22.45 mmol), were added EtOH (7.50 mL) followed by water (1.50 mL). The reaction mixture was stirred at 60° C. for 1 h. After cooling to the room temperature, the reaction mixture was filtered through a pad of diatomaceous earth (eluted with EtOAc). The filtrate was washed with 1.0 M Na$_2$CO$_3$ (aq.), brine, dried over Na$_2$SO$_4$, and concentrated to afford the sub-title compound as a brown foamy solid (344.5 mg, 86%) which was used directly in the next step without further purification. LCMS calc. for $C_{15}H_{25}F_3N_5O_2$ (M+H)$^+$: m/z=364.2. found 364.1.

Step 6. tert-Butyl [(3S,5R)-1-[4-({[2-[(tert-butoxycarbonyl)amino]-6-(tetrahydro-2H-pyran-4-yl)furo[3,2-b]pyridin-3-yl]carbonyl}amino)-1-methyl-1H-pyrazol-5-yl]-5-(trifluoromethyl)piperidin-3-yl]carbamate

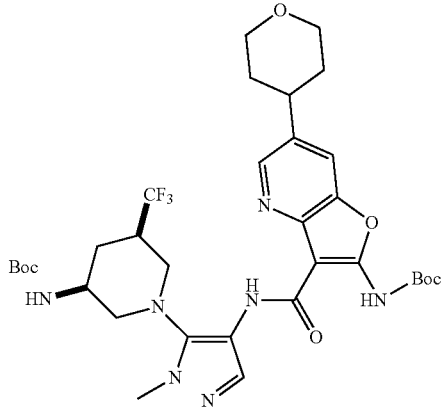 [SMILES: CN/C(=C(\C=N)NC(=O)c1c(NC(=O)OC(C)(C)C)oc2cc(C3CCOCC3)cnc12)N1C[C@@H](N)C[C@@H](C(F)(F)F)C1 ; "Boc"]

To a mixture of tert-butyl [(3S,5R)-1-(4-amino-1-methyl-1H-pyrazol-5-yl)-5-(trifluoromethyl)piperidin-3-yl]carbamate (58.6 mg, 0.161 mmol) and 2-[(tert-butoxycarbonyl)amino]-6-(tetrahydro-2H-pyran-4-yl)furo[3,2-b]pyridine-3-carboxylic acid (51.9 mg, 0.143 mmol) was added 1,2-dichloroethane (1.00 mL). The mixture was stirred at room temperature for 20 min. HATU (67.6 mg, 0.178 mmol) was then added followed by DIPEA (55.0 μL, 0.316 mmol). After stirring at room temperature for 15 h, the reaction mixture was concentrated. The resulting residue was purified by chromatography on silica gel (20 g, 0-100% EtOAc/Hexanes) to give the title compound (74.0 mg, 73%). LCMS calc. for $C_{33}H_{45}F_3N_7O_7$ (M+H)$^+$: m/z=708.3. found 708.4.

Step 7. 2-Amino-N-{5-[(3S,5R)-3-amino-5-(trifluoromethyl)piperidin-1-yl]-1-methyl-1H-pyrazol-4-yl}-6-(tetrahydro-2H-pyran-4-yl)furo[3,2-b]pyridine-3-carboxamide To a solution of tert-butyl [(3S,5R)-1-[4-({[2-[(tert-butoxycarbonyl)amino]-6-(tetrahydro-2H-pyran-4-yl)furo[3,2-b]pyridin-3-yl]carbonyl}amino)-1-methyl-1H-pyrazol-5-yl]-5-(trifluoromethyl)piperidin-3-yl]carbamate (74.0 mg, 0.104 mmol) in DCM (2.00 mL) was added TFA (2.00 mL). The mixture was stirred at room temperature for 2 h, and then concentrated. The residue was purified using RP-HPLC (Waters XBridge™ C18 column, 30 mm×100 mm, 5 μm particle size, eluting with a gradient of MeCN/water containing 0.15% NH$_4$OH, at flow rate of 30 mL/min.) to afford the title compound as a white solid (23.0 mg, 43%). LCMS calc. for $C_{23}H_{29}F_3N_7O_3$ (M+H)$^+$: m/z=508.2. found 508.3. $^1$H NMR (500 MHz, DMSO-d6) δ 9.71 (s, 1H), 8.12 (d, J=1.5 Hz, 1H), 7.77 (s, 1H), 7.70 (d, J=1.5 Hz, 1H), 3.96 (m, 2H), 3.66 (s, 3H), 3.45 (m, 2H), 3.25 (m, 1H), 3.15 (m, 1H), 3.04 (m, 1H), 2.94 (m, 1H), 2.87 (m, 2H), 2.80 (m, 1H), 2.16 (m, 1H), 1.71 (m, 4H), 1.22 (m, 1H) ppm.

Example 91

2-Amino-N-{5-[(3S,5R)-3-amino-5-(trifluoromethyl)piperidin-1-yl]isothiazol-4-yl}-6-(tetrahydro-2H-pyran-4-yl)furo[3,2-b]pyridine-3-carboxamide

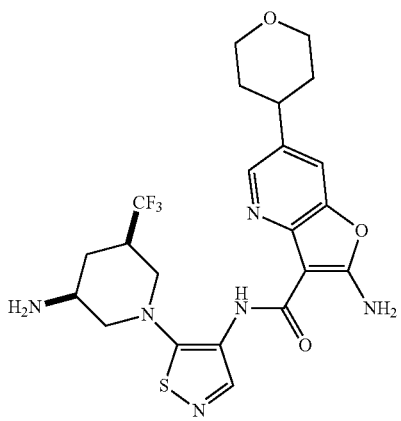 [SMILES: Nc1oc2cc(C3CCOCC3)cnc2c1C(=O)Nc1cnsc1N1C[C@@H](N)C[C@@H](C(F)(F)F)C1]

Step 1. tert-Butyl [(3S,5R)-1-(4-nitroisothiazol-5-yl)-5-(trifluoromethyl)piperidin-3-yl]carbamate

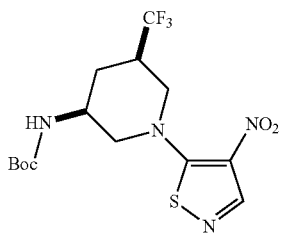 [SMILES: CC(C)(C)OC(=O)N[C@H]1C[C@@H](C(F)(F)F)CN(c2sncc2[N+](=O)[O-])C1]

To a mixture of 5-bromo-4-nitroisothiazole (258.5 mg, 1.237 mmol) and tert-butyl [(3S,5R)-5-(trifluoromethyl)piperidin-3-yl]carbamate (361.3 mg, 1.347 mmol) was added i-PrOH (4.00 mL) followed by DIPEA (488.9 mg, 3.783 mmol). After stirring at 110° C. for 5 h, the reaction mixture was concentrated under reduced pressure. The resulting residue was purified by chromatography on silica gel (40 g, 0-100% EtOAc in hexanes) to give the title compound as a pale yellow solid (471.5 mg, 96%). LCMS calc. for $C_{14}H_{20}F_3N_4O_4S$ (M+H)$^+$: m/z=397.1. found 397.1.

Step 2. tert-Butyl [(3S,5R)-1-(4-aminoisothiazol-5-yl)-5-(trifluoromethyl)piperidin-3-yl]carbamate

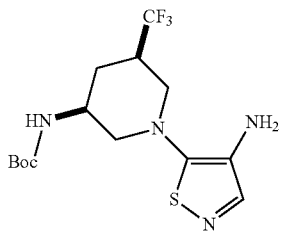 [SMILES: CC(C)(C)OC(=O)N[C@H]1C[C@@H](C(F)(F)F)CN(c2sncc2N)C1]

To a mixture of tert-butyl [(3S,5R)-1-(4-nitroisothiazol-5-yl)-5-(trifluoromethyl)piperidin-3-yl]carbamate (471.5 mg, 1.189 mmol), Fe powder (1156 mg, 20.70 mmol) and NH$_4$Cl (1389 mg, 25.97 mmol) was added EtOH (8.00 mL) followed by water (2.00 mL). The reaction mixture was stirred at 70° C. for 2 h. After cooling to the room temperature, the reaction mixture was filtered through a pad of diatomaceous earth (eluted with EtOAc). The filtrate was washed with 1.0 M Na$_2$CO$_3$ (aq.), brine, dried over Na$_2$SO$_4$, and concentrated to afford the title compound as a yellow solid (445.1 mg) which was used directly in the next step without further purification. LCMS calc. for $C_{14}H_{22}F_3N_4O_2S$ (M+H)$^+$: m/z=367.1. found 367.1.

Step 3. tert-Butyl [(3S,5R)-1-[4-({[2-[(tert-butoxycarbonyl)amino]-6-(tetrahydro-2H-pyran-4-yl)furo[3,2-b]pyridin-3-yl]carbonyl}amino)isothiazol-5-yl]-5-(trifluoromethyl)piperidin-3-yl]carbamate

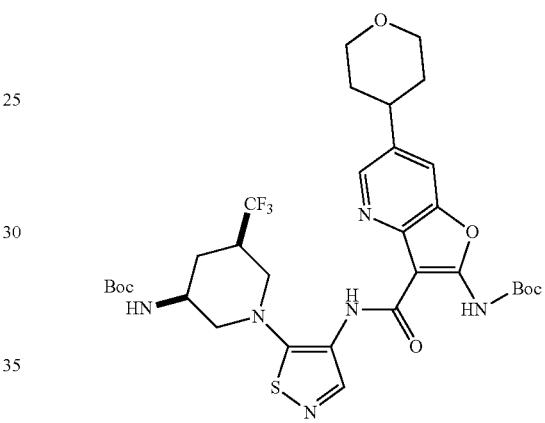

To a mixture of tert-butyl [(3S,5R)-1-(4-aminoisothiazol-5-yl)-5-(trifluoromethyl)piperidin-3-yl]carbamate (62.6 mg, 0.171 mmol), 2-[(tert-butoxycarbonyl)amino]-6-(tetrahydro-2H-pyran-4-yl)furo[3,2-b]pyridine-3-carboxylic acid (74.1 mg, 0.204 mmol), and HATU (96.6 mg, 0.254 mmol) was added 1,2-dichloroethane (1.00 mL) followed by DIPEA (75.0 µL, 0.430 mmol). After stirring at room temperature for 16 h, the reaction was concentrated under reduced pressure. The residue was purified by chromatography on silica gel (40 g, 0-100% EtOAc in hexanes) to give the sub-title compound (64.8 mg, 53%). LCMS calc. for $C_{32}H_{42}F_3N_6O_7S$ (M+H)$^+$: m/z=711.3. found 711.1.

Step 4. 2-Amino-N-{5-[(3S,5R)-3-amino-5-(trifluoromethyl)piperidin-1-yl]isothiazol-4-yl}-6-(tetrahydro-2H-pyran-4-yl)furo[3,2-b]pyridine-3-carboxamide To a solution of tert-butyl [(3S,5R)-1-[4-({[2-[(tert-butoxycarbonyl)amino]-6-(tetrahydro-2H-pyran-4-yl) furo[3,2-b]pyridin-3-yl]carbonyl}amino)isothiazol-5-yl]-5-(trifluoromethyl)piperidin-3-yl]carbamate (64.8 mg, 0.0912 mmol) in DCM (2.00 mL) was added TFA (2.00 mL). The mixture was stirred at room temperature for 2 h, and then concentrated. The residue was purified using RP-HPLC (Waters XBridge™ C18 column, 30 mm×100 mm, 5 µm particle size, eluting with a gradient of MeCN/water containing 0.15% NH$_4$OH, at flow rate of 30 mL/min.) to afford the title compound as a white solid (22.5 mg, 48%). LCMS calc. for $C_{22}H_{26}F_3N_6O_3S$ (M+H)$^+$: m/z=511.2. found 511.1. $^1$H NMR (500 MHz, DMSO-d6) δ 9.86 (s, 1H), 9.02 (s, 1H), 8.21 (d, J=1.4 Hz, 1H), 7.70 (d, J=1.4 Hz, 1H), 3.96 (m, 2H), 3.59 (m, 1H), 3.44 (m, 3H), 3.10 (m, 1H), 2.95 (m, 1H), 2.87 (m, 1H), 2.65 (m, 1H), 2.49 (m, 1H), 2.18 (m, 1H), 1.72 (m, 4H), 1.24 (m, 1H) ppm.

Example 92

2-Amino-N-{4-[(3S,5R)-3-amino-5-(trifluoromethyl)piperidin-1-yl]pyridin-3-yl}-6-(tetrahydro-2H-pyran-4-yl)furo[3,2-b]pyridine-3-carboxamide

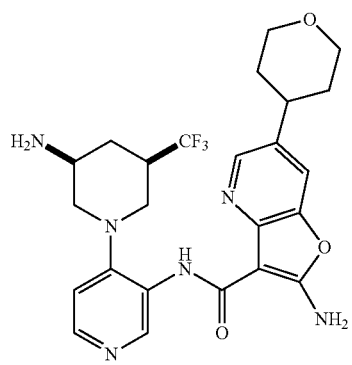 [SMILES: Nc1oc2cc(C3CCOCC3)cnc2c1C(=O)Nc1cnccc1N1C[C@@H](N)C[C@@H](C(F)(F)F)C1]

Step 1. tert-Butyl [(3S,5R)-1-[3-({[2-[(tert-butoxycarbonyl)amino]-6-(tetrahydro-2H-pyran-4-yl)furo[3,2-b]pyridin-3-yl]carbonyl}amino)pyridin-4-yl]-5-(trifluoromethyl)piperidin-3-yl]carbamate

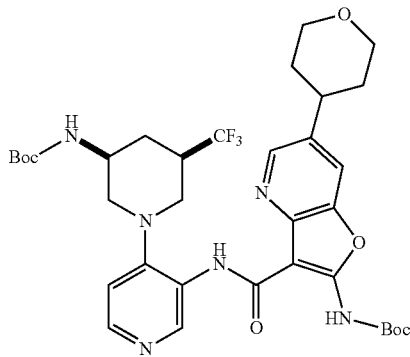

To a mixture of tert-butyl [(3S,5R)-1-(3-aminopyridin-4-yl)-5-(trifluoromethyl)piperidin-3-yl]carbamate (62.4 mg, 0.173 mmol) and 2-[(tert-butoxycarbonyl)amino]-6-(tetrahydro-2H-pyran-4-yl)furo[3,2-b]pyridine-3-carboxylic acid (51.9 mg, 0.143 mmol) was added 1,2-dichloroethane (1.00 mL). The mixture was stirred at room temperature for 20 min. HATU (68.0 mg, 0.179 mmol) was added followed by DIPEA (55.0 µL, 0.316 mmol). After stirring at room temperature for 15 h, the reaction mixture was concentrated under reduced pressure. The resulting residue was purified by chromatography on silica gel (20 g, 0-100% EtOAc/Hexanes) to give the title compound (45.9 mg, 46%). LCMS calc. for $C_{34}H_{44}F_3N_6O_7$ (M+H)$^+$: m/z=705.3. found 705.2.

Step 2. 2-Amino-N-{4-[(3S,5R)-3-amino-5-(trifluoromethyl)piperidin-1-yl]pyridin-3-yl}-6-(tetrahydro-2H-pyran-4-yl)furo[3,2-b]pyridine-3-carboxamide To a solution of tert-butyl [(3S,5R)-1-[3-({[2-[(tert-butoxycarbonyl)amino]-6-(tetrahydro-2H-pyran-4-yl)furo[3,2-b]pyridin-3-yl]carbonyl}amino)pyridin-4-yl]-5-(trifluoromethyl)piperidin-3-yl]carbamate (45.9 mg, 0.0651 mmol) in DCM (2.00 mL) was added TFA (2.00 mL). The mixture was stirred at room temperature for 2 h, and then concentrated. The residue was purified using RP-HPLC (Waters XBridge™ C18 column, 30 mm×100 mm, 5 µm particle size, eluting with a gradient of MeCN/water containing 0.15% NH$_4$OH, at flow rate of 30 mL/min.) to afford the title compound as a white solid (10.9 mg, 33%). LCMS calc. for $C_{24}H_{28}F_3N_6O_3$ (M+H)$^+$: m/z=505.2. found 505.2. $^1$H NMR (500 MHz, DMSO-d6) δ 10.04 (s, 1H), 9.50 (s, 1H), 8.20 (d, J=5.3 Hz, 1H), 8.18 (d, J=1.5 Hz, 1H), 7.71 (d, J=1.6 Hz, 1H), 7.18 (d, J=5.3 Hz, 1H), 3.95 (m, 2H), 3.45 (m, 2H), 3.28 (m, 1H), 3.19 (m, 1H), 3.13 (m, 1H), 3.06 (m, 1H), 2.90 (m, 1H), 2.55 (m, 1H), 2.40 (m, 1H), 2.19 (m, 1H), 1.72 (m, 4H), 1.19 (m, 1H) ppm.

Example 93

2-Amino-N-{4-[(3S,5R)-3-amino-5-(trifluoromethyl)piperidin-1-yl]pyridin-3-yl}-6-(1-methylpiperidin-4-yl)furo[3,2-b]pyridine-3-carboxamide

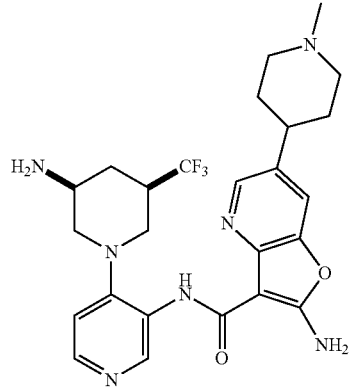 [SMILES: CN1CCC(c2cnc3c(C(=O)Nc4cnccc4N4C[C@@H](N)C[C@@H](C(F)(F)F)C4)c(N)oc3c2)CC1]

Step 1. Ethyl 2-[(tert-butoxycarbonyl)amino]-6-(1-methyl-1,2,3,6-tetrahydropyridin-4-yl)furo[3,2-b]pyridine-3-carboxylate

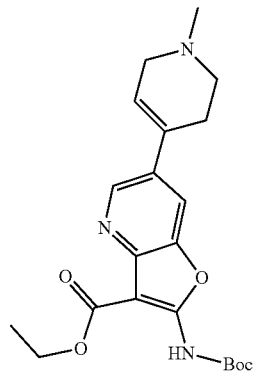 [SMILES: CCOC(=O)c1c(NC(=O)OC(C)(C)C)oc2cc(C3=CCN(C)CC3)cnc12]

To a screw-cap vial equipped with a magnetic stir bar was added ethyl 6-bromo-2-[(tert-butoxycarbonyl)amino]furo[3,2-b]pyridine-3-carboxylate (1021 mg, 2.650 mmol), 1-methyl-4-(4,4,5,5-tetramethyl-1,3,2-dioxaborolan-2-yl)-1,2,3,6-tetrahydropyridine (709.8 mg, 3.181 mmol), dicyclohexyl(2',4',6'-triisopropylbiphenyl-2-yl)phosphine-(2'-aminobiphenyl-2-yl)(chloro)palladium (1:1) (XPhos Pd G2, Aldrich, 314.7 mg, 0.4000 mmol), and $K_3PO_4$ (2.097 g, 9.879 mmol). The vial was sealed with a PTFE-lined septum, evacuated and backfilled with $N_2$ (this process was repeated a total of three times). 1,4-Dioxane (9.00 mL) was added followed by deoxygenated water (3.00 mL). The reaction mixture was stirred at 80° C. for 2 h. After cooling to room temperature, the reaction mixture was filtered through a pad of diatomaceous earth (eluted with EtOAc). The filtrate was washed with brine, dried over $Na_2SO_4$, filtered, and concentrated. The resulting residue was purified by chromatography on silica gel (40 g, 5% MeOH in DCM containing 1% $Et_3N$) to give the product as a yellow foamy solid (875.2 mg, 82%). LCMS calc. for $C_{21}H_{28}N_3O_5$ $(M+H)^+$: m/z=402.2. found 402.1.

Step 2. Ethyl 2-[(tert-butoxycarbonyl)amino]-6-(1-methylpiperidin-4-yl)furo[3,2-b]pyridine-3-carboxylate

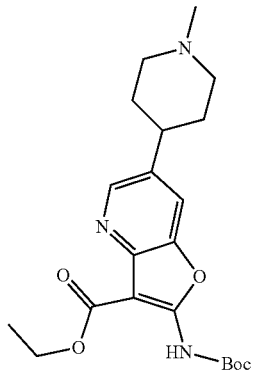 [SMILES: CCOC(=O)c1c(NC(=O)OC(C)(C)C)oc2cc(C3CCN(C)CC3)cnc12]

To a solution of ethyl 2-[(tert-butoxycarbonyl)amino]-6-(1-methyl-1,2,3,6-tetrahydropyridin-4-yl)furo[3,2-b]pyridine-3-carboxylate (875.2 mg, 2.180 mmol) in MeOH (20.0 mL) was added 10 wt % Pd on carbon (362.0 mg, 0.3402 mmol). The mixture was stirred at room temperature under $H_2$ atmosphere (1 atm.) for 1 h. The reaction was then filtered through a pad of diatomaceous earth (eluted with MeOH). The filtrate was concentrated to give the sub-title compound as a yellow foamy solid (789.2 mg, 90%) which was used directly in the next step without further purification. LCMS calc. for $C_{21}H_{30}N_3O_5$ $(M+H)^+$: m/z=404.2. found 404.2.

Step 3. 2-[(tert-Butoxycarbonyl)amino]-6-(1-methylpiperidin-4-yl)furo[3,2-b]pyridine-3-carboxylic acid[1.0]trifluoroacetic acid

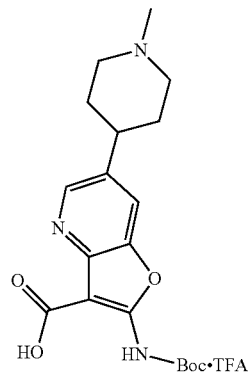

To a solution of ethyl 2-[(tert-butoxycarbonyl)amino]-6-(1-methylpiperidin-4-yl)furo[3,2-b]pyridine-3-carboxylate (722.0 mg, 1.789 mmol) in THF (4.00 mL) was added $LiOH.H_2O$ (302.7 mg, 7.213 mmol), followed by MeOH (4.00 mL) and water (2.00 mL). The reaction mixture was stirred at 70° C. for 5 h. After cooling to room temperature, the reaction mixture was adjusted to pH 4 with 1 M HCl. The mixture was purified using RP-HPLC (Waters SunFire™ C18 column, 30 mm×100 mm, 5 μm particle size, eluting with a gradient of MeCN/water containing 0.1% TFA, at flow rate of 30 mL/min.) to afford the title compound (562.4 mg, 64%). LCMS calc. for $C_{19}H_{26}N_3O_5$ $(M+H)^+$: m/z=376.2. found 376.3.

Step 4. tert-Butyl [(3S,5R)-1-[3-({[2-[(tert-butoxycarbonyl)amino]-6-(1-methylpiperidin-4-yl)furo[3,2-b]pyridin-3-yl]carbonyl}amino)pyridin-4-yl]-5-(trifluoromethyl)piperidin-3-yl]carbamate

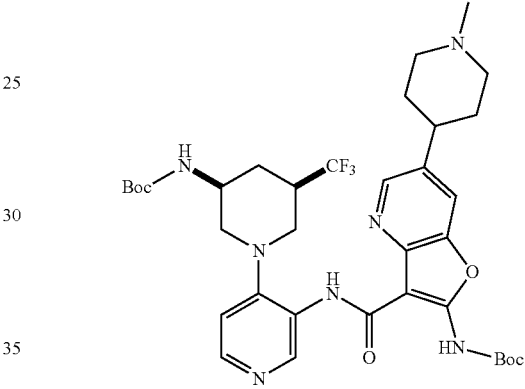

To a mixture of tert-butyl [(3S,5R)-1-(3-aminopyridin-4-yl)-5-(trifluoromethyl)piperidin-3-yl]carbamate (322.9 mg, 0.8960 mmol) and 2-[(tert-butoxycarbonyl)amino]-6-(1-methylpiperidin-4-yl)furo[3,2-b]pyridine-3-carboxylic acid [1.0]-trifluoroacetic acid (562.4 mg, 1.149 mmol) was added 1,2-dichloroethane (3.00 mL). The mixture was stirred at room temperature for 20 min. HATU (479.7 mg, 1.262 mmol) was added followed by DIPEA (354.3 mg, 2.741 mmol). After stirring at room temperature for 15 h, the reaction mixture was concentrated under reduced pressure. The resulting residue was purified using RP-HPLC (Waters XBridge™ C18 column, 30 mm×100 mm, 5 μm particle size, eluting with a gradient of MeCN/water containing 0.15% $NH_4OH$, at flow rate of 30 mL/min.) to afford the title compound (350.8 mg, 55%). LCMS calc. for $C_{35}H_{47}F_3N_7O_6$ $(M+H)^+$: m/z=718.4. found 718.5.

Step 5. 2-Amino-N-{4-[(3S,5R)-3-amino-5-(trifluoromethyl)piperidin-1-yl]pyridin-3-yl}-6-(1-methylpiperidin-4-yl)furo[3,2-b]pyridine-3-carboxamide To a solution of tert-butyl [(3S,5R)-1-[3-({[2-[(tert-butoxycarbonyl)amino]-6-(1-methylpiperidin-4-yl)furo[3,2-b]pyridin-3-yl]carbonyl}amino)pyridin-4-yl]-5-(trifluoromethyl)piperidin-3-yl]carbamate (350.8 mg, 0.4887 mmol) in DCM (2.00 mL) was added TFA (2.00 mL). The mixture was stirred at room temperature for 2 h, and then concentrated. The residue was purified using RP-HPLC (Waters XBridge™ C18 column, 30 mm×100 mm, 5 μm particle size, eluting with a gradient of MeCN/water containing 0.15% NH$_4$OH, at flow rate of 30 mL/min.) to afford the title compound as a white solid (45.9 mg, 18%). LCMS calc. for C$_{25}$H$_{31}$F$_3$N$_7$O$_2$ (M+H)$^+$: m/z=518.2. found 518.2. $^1$H NMR (500 MHz, DMSO-d6) δ 10.04 (s, 1H), 9.50 (s, 1H), 8.20 (d, J=5.3 Hz, 1H), 8.16 (d, J=1.4 Hz, 1H), 7.67 (d, J=1.4 Hz, 1H), 7.18 (d, J=5.3 Hz, 1H), 3.30 (m, 1H), 3.19 (m, 1H), 3.13 (m, 1H), 3.06 (m, 1H), 2.86 (m, 2H), 2.56 (m, 2H), 2.40 (m, 1H), 2.19 (m, 4H), 1.97 (m, 2H), 1.73 (m, 4H), 1.19 (m, 1H) ppm.

Example 94

2-Amino-N-{5-[(3S,5R)-3-amino-5-(trifluoromethyl)piperidin-1-yl]-1-methyl-1H-pyrazol-4-yl}-6-(1-methylpiperidin-4-yl)furo[3,2-b]pyridine-3-carboxamide

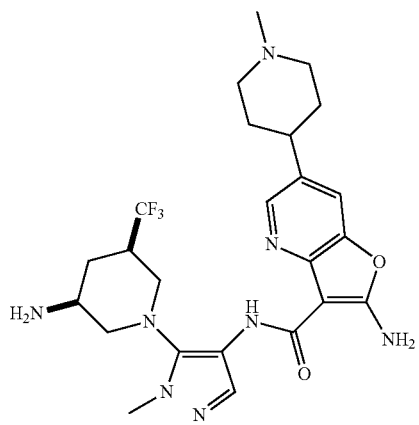 [SMILES: CN/C(=C(\C=N)NC(=O)c1c(N)oc2cc(C3CCN(C)CC3)cnc12)N1C[C@@H](N)C[C@@H](C(F)(F)F)C1]

To a mixture of tert-butyl [(3S,5R)-1-(4-amino-1-methyl-1H-pyrazol-5-yl)-5-(trifluoromethyl)piperidin-3-yl]carbamate (105.9 mg, 0.2914 mmol) and 2-[(tert-butoxycarbonyl)amino]-6-(1-methylpiperidin-4-yl)furo[3,2-b]pyridine-3-carboxylic acid [1.0]-trifluoroacetic acid (144.3 mg, 0.2948 mmol) was added 1,2-dichloroethane (2.00 mL). The mixture was stirred at room temperature for 20 min. HATU (137.7 mg, 0.3621 mmol) was then added followed by DIPEA (194.6 mg, 1.506 mmol). After stirring at room temperature for 15 h, the reaction mixture was concentrated under reduced pressure. The resulting residue was purified using RP-HPLC (Waters XBridge™ C18 column, 30 mm×100 mm, 5 μm particle size, eluting with a gradient of MeCN/water containing 0.15% NH$_4$OH, at flow rate of 30 mL/min.) to afford an amide coupling product.

To the coupling product was added DCM (2.00 mL) followed by TFA (2.00 mL). The mixture was stirred at room temperature for 2 h, and then concentrated under reduced pressure. The residue was purified using RP-HPLC (Waters XBridge™ C18 column, 30 mm×100 mm, 5 μm particle size, eluting with a gradient of MeCN/water containing 0.15% NH$_4$OH, at flow rate of 30 mL/min.) to afford the title compound as a white solid (33.4 mg, 22%). LCMS calc. for C$_{24}$H$_{32}$F$_3$N$_8$O$_2$ (M+H)$^+$: m/z=521.3. found 521.2.

Example 95

2-Amino-N-{4-[(3S,5R)-3-amino-5-methylpiperidin-1-yl]pyridin-3-yl}-6-(tetrahydro-2H-pyran-4-yl)furo[3,2-b]pyridine-3-carboxamide

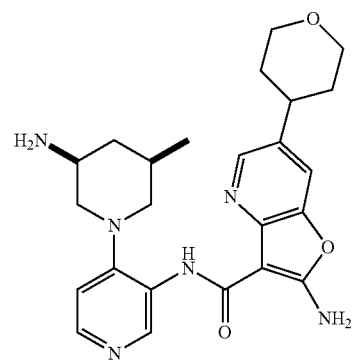 [SMILES: C[C@@H]1C[C@H](N)CN(c2ccncc2NC(=O)c2c(N)oc3cc(C4CCOCC4)cnc23)C1]

Step 1. tert-Butyl [3-{[(4-{(3S,5R)-3-[(tert-butoxycarbonyl)amino]-5-methylpiperidin-1-yl}pyridin-3-yl)amino]carbonyl}-6-(tetrahydro-2H-pyran-4-yl)furo[3,2-b]pyridin-2-yl]carbamate

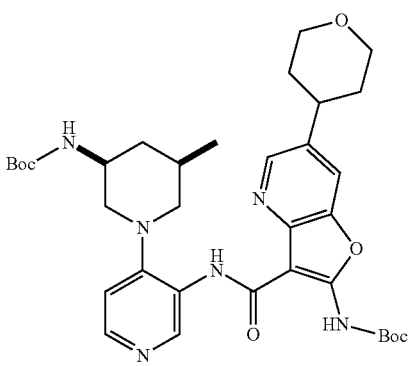 [SMILES: C[C@@H]1C[C@H](NC(=O)OC(C)(C)C)CN(c2ccncc2NC(=O)c2c(NC(=O)OC(C)(C)C)oc3cc(C4CCOCC4)cnc23)C1]

To a mixture of tert-butyl [(3S,5R)-1-(3-aminopyridin-4-yl)-5-methylpiperidin-3-yl]carbamate (56.4 mg, 0.184 mmol) and 2-[(tert-butoxycarbonyl)amino]-6-(tetrahydro-2H-pyran-4-yl)furo[3,2-b]pyridine-3-carboxylic acid (84.7 mg, 0.234 mmol) was added 1,2-dichloroethane (1.00 mL). The mixture was stirred at room temperature for 20 min. HATU (98.2 mg, 0.258 mmol) was added followed by DIPEA (75.0 μL, 0.430 mmol). After stirring at room temperature for 15 h, the reaction mixture was concentrated under reduced pressure. The resulting residue was purified by chromatography on silica gel (20 g, 0-100% EtOAc/Hexanes) to give the title compound (92.8 mg, 78%). LCMS calc. for C$_{34}$H$_{47}$N$_6$O$_7$ (M+H)$^+$: m/z=651.4. found 651.3.

Step 2. 2-Amino-N-{4-[(3S,5R)-3-amino-5-methylpiperidin-1-yl]pyridin-3-yl}-6-(tetrahydro-2H-pyran-4-yl)furo[3,2-b]pyridine-3-carboxamide To a solution of tert-butyl [3-{[(4-{(3S,5R)-3-[(tert-butoxycarbonyl)amino]-5-methylpiperidin-1-yl}pyridin-3-yl)

amino]carbonyl}-6-(tetrahydro-2H-pyran-4-yl)furo[3,2-b]pyridin-2-yl]carbamate (92.8 mg, 0.143 mmol) in DCM (2.00 mL) was added TFA (2.00 mL). The mixture was stirred at room temperature for 2 h, and then concentrated. The residue was purified using RP-HPLC (Waters XBridge™ C18 column, 30 mm×100 mm, 5 μm particle size, eluting with a gradient of MeCN/water containing 0.15% NH$_4$OH, at flow rate of 30 mL/min.) to afford the title compound as a white solid (9.5 mg, 15%). LCMS calc. for C$_{24}$H$_{31}$N$_6$O$_3$ (M+H)$^+$: m/z=451.2. found 451.3.

Example 96

2-Amino-N-{5-[(3S,5R)-3-amino-5-methylpiperidin-1-yl]isothiazol-4-yl}-6-(tetrahydro-2H-pyran-4-yl)furo[3,2-b]pyridine-3-carboxamide

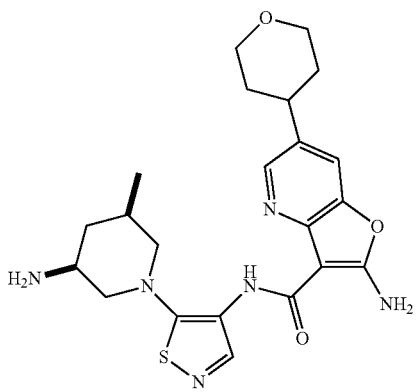 [SMILES: C[C@@H]1C[C@H](N)CN(c2sncc2NC(=O)c2c(N)oc3cc(C4CCOCC4)cnc23)C1]

Step 1. tert-Butyl [(3S,5R)-5-methyl-1-(4-nitroisothiazol-5-yl)piperidin-3-yl]carbamate

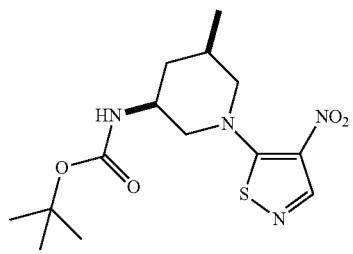

To a mixture of 5-bromo-4-nitroisothiazole (253.5 mg, 1.213 mmol) and tert-butyl [(3S,5R)-5-methylpiperidin-3-yl]carbamate (294.0 mg, 1.372 mmol) was added i-PrOH (4.00 mL) followed by DIPEA (509.2 mg, 3.940 mmol). After stirring at 110° C. for 5 h, the reaction mixture was concentrated under reduced pressure. The resulting residue was purified by chromatography on silica gel (40 g, 0-100% EtOAc in hexanes) to give the title compound as a pale yellow solid (377.9 mg, 91%). LCMS calc. for C$_{14}$H$_{23}$N$_4$O$_4$S (M+H)$^+$: m/z=343.1. found 343.1.

Step 2. tert-Butyl [(3S,5R)-1-(4-aminoisothiazol-5-yl)-5-methylpiperidin-3-yl]carbamate

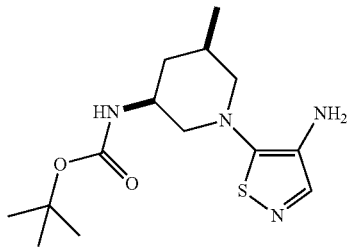 [SMILES: C[C@@H]1C[C@H](NC(=O)OC(C)(C)C)CN(c2sncc2[N+](=O)[O-])C1]

To a mixture of tert-butyl [(3S,5R)-5-methyl-1-(4-nitroisothiazol-5-yl)piperidin-3-yl]carbamate (377.9 mg, 1.104 mmol), Fe powder (1265 mg, 22.65 mmol) and NH$_4$Cl (1513 mg, 28.28 mmol) was added EtOH (8.00 mL) followed by water (2.00 mL). The reaction mixture was stirred at 70° C. for 2 h. After cooling to the room temperature, the reaction mixture was filtered through a pad of diatomaceous earth (eluted with EtOAc). The filtrate was washed with 1.0 M Na$_2$CO$_3$ (aq.), brine, dried over Na$_2$SO$_4$, and concentrated under reduced pressure to afford the title compound as a yellow solid (330.3 mg, 96%) which was used directly in the next step without further purification. LCMS calc. for C$_{14}$H$_{25}$N$_4$O$_2$S (M+H)$^+$: m/z=313.2. found 313.1.

Step 3. 2-Amino-N-{5-[(3S,5R)-3-amino-5-methylpiperidin-1-yl]isothiazol-4-yl}-6-(tetrahydro-2H-pyran-4-yl)furo[3,2-b]pyridine-3-carboxamide To a mixture of tert-butyl [(3S,5R)-1-(4-aminoisothiazol-5-yl)-5-methylpiperidin-3-yl]carbamate (52.4 mg, 0.168 mmol) and 2-[(tert-butoxycarbonyl)amino]-6-(tetrahydro-2H-pyran-4-yl)furo[3,2-b]pyridine-3-carboxylic acid (73.9 mg, 0.204 mmol) was added 1,2-dichloroethane (1.00 mL). The mixture was stirred at room temperature for 20 min. HATU (96.3 mg, 0.253 mmol) was then added followed by DIPEA (75.0 μL, 0.430 mmol). After stirring at room temperature for 15 h, the reaction mixture was concentrated. The resulting residue was purified by chromatography on silica gel (20 g, 0-100% EtOAc/Hexanes) to afford the coupling product. To the coupling product was added DCM (2.00 mL) followed by TFA (2.00 mL). The mixture was stirred at room temperature for 2 h, and then concentrated. The residue was purified using RP-HPLC (Waters XBridge™ C18 column, 30 mm×100 mm, 5 μm particle size, eluting with a gradient of MeCN/water containing 0.15% NH$_4$OH, at flow rate of 30 mL/min.) to afford the title compound as a white solid (23.8 mg, 31%). LCMS calc. for C$_{22}$H$_{29}$N$_6$O$_3$S (M+H)$^+$: m/z=457.2. found 457.2. $^1$H NMR (500 MHz, DMSO-d$_6$) δ 9.79 (s, 1H), 8.98 (s, 1H), 8.16 (d, J=1.4 Hz, 1H), 7.70 (d, J=1.4 Hz, 1H), 3.96 (m, 2H), 3.43 (m, 4H), 3.00 (m, 1H), 2.88 (m, 1H), 2.31 (m, 1H), 2.23 (m, 1H), 1.97 (m, 2H), 1.72 (m, 4H), 0.83 (m, 4H) ppm.

Example 97

2-Amino-N-{4-[(3S,5R)-3-amino-5-methylpiperidin-1-yl]pyridin-3-yl}-6-cyclobutylfuro[3,2-b]pyridine-3-carboxamide

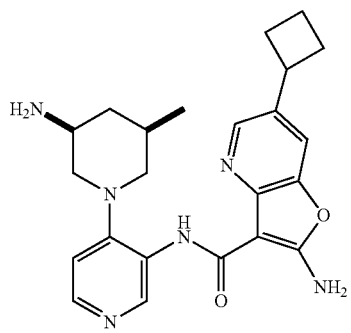 [SMILES: C[C@@H]1C[C@H](N)CN(c2ccncc2NC(=O)c2c(N)oc3cc(C4CCC4)cnc23)C1]

Step 1. Ethyl 2-[(tert-butoxycarbonyl)amino]-6-cyclobutylfuro[3,2-b]pyridine-3-carboxylate

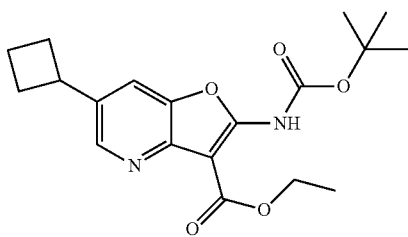 [SMILES: CCOC(=O)c1c(NC(=O)OC(C)(C)C)oc2cc(C3CCC3)cnc12]

A mixture of ethyl 6-bromo-2-[(tert-butoxycarbonyl)amino]furo[3,2-b]pyridine-3-carboxylate (300 mg, 0.8 mmol), 0.5 M bromo(cyclobutyl)zinc in THF (5.0 mL), Pd(OAc)$_2$ (15 mg, 0.07 mmol) and 2-(dicyclohexylphosphino)-2',6'-dimethoxy-1,1'-biphenyl (32 mg, 0.08 mmol) was purged with N$_2$, then heated at 60° C. for 1 h. The reaction mixture was filtered and concentrated to give the crude mixture, which was purified by silica gel column chromatography (0 to 20% EtOAc in hexanes) to give the sub-title compound as an off-white powder. LCMS calc. for C$_{19}$H$_{25}$N$_2$O$_5$ (M+H)$^+$: m/z=361.2. Found: 361.3.

Step 2. 2-[(tert-Butoxycarbonyl)amino]-6-cyclobutylfuro[3,2-b]pyridine-3-carboxylic acid

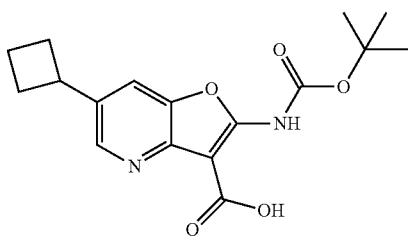 [SMILES: CC(C)(C)OC(=O)Nc1oc2cc(C3CCC3)cnc2c1C(=O)O]

A mixture of ethyl 2-[(tert-butoxycarbonyl)amino]-6-cyclobutylfuro[3,2-b]pyridine-3-carboxylate (110 mg, 0.30 mmol) and LiOH.H$_2$O (90 mg, 2.1 mmol) in THF (2.2 mL), MeOH (2.2 mL) and water (1 mL) was heated at 70° C. in a sealed vial for 18 h. After removal of the solvents, the residue was diluted with EtOAc and neutralized with 1 M HCl to pH=7. The aqueous layer was extracted with EtOAc (3 times). The combined organic layers were dried over anhydrous Na$_2$SO$_4$, filtered and concentrated to give the sub-title compound as an off-white powder. LCMS calc. for C$_{17}$H$_{21}$N$_2$O$_5$ (M+H)$^+$: m/z=333.2. Found: 333.2.

Step 3. 2-Amino-N-{4-[(3S,5R)-3-amino-5-methylpiperidin-1-yl]pyridin-3-yl}-6-cyclobutylfuro[3,2-b]pyridine-3-carboxamide To a mixture of tert-butyl [(3S,5R)-1-(3-aminopyridin-4-yl)-5-methylpiperidin-3-yl]carbamate (49.5 mg, 0.16 mmol) and 2-[(tert-butoxycarbonyl)amino]-6-cyclobutylfuro[3,2-b]pyridine-3-carboxylic acid (40 mg, 0.1 mmol) in 1,2-dichloroethane (0.53 mL) was added subsequently HATU (88 mg, 0.23 mmol) and DIPEA (38 mg, 0.29 mmol). The resulting mixture was stirred at room temperature for 17 h. The crude reaction mixture was diluted with EtOAc and 1 M NaOH was added. The aqueous layer was extracted with EtOAc (3 times). The combined organic layers were dried over anhydrous Na$_2$SO$_4$, filtered and concentrated to give the crude product, which was purified by silica gel column chromatography (0 to 100% EtOAc in hexanes) to give pure intermediate as a white powder. The intermediate was then dissolved in MeOH (0.40 mL), followed by the addition of 4.0 M HCl in dioxane (2.0 mL, 8.0 mmol). The reaction mixture was stirred at room temperature for 1 h. After removal of the solvents, the residue was diluted with MeOH and neutralized by the addition of ammonia solution, and purified by preparative LCMS (pH=10 method; XBridge™ PrepC18 5 μm OBD™ column, 30×10 mm, 60 mL/min., eluting with a gradient of MeCN and water with NH$_4$OH) to give the title compound. LCMS calc. for C$_{23}$H$_{29}$N$_6$O$_2$ (M+H)$^+$: m/z=421.1. Found: 421.3.

Example 98

2-Amino-N-{4-[(3S,5R)-3-amino-5-(trifluoromethyl)piperidin-1-yl]pyridin-3-yl}-6-cyclobutylfuro[3,2-b]pyridine-3-carboxamide

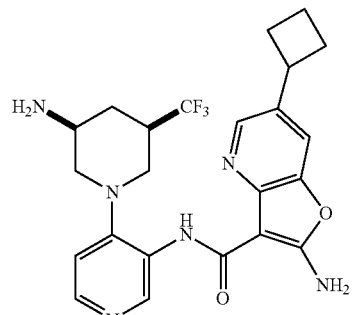

The title compound was prepared according to the procedures described for Example 97, using the following two starting materials, 2-[(tert-butoxycarbonyl)amino]-6-cyclobutylfuro[3,2-b]pyridine-3-carboxylic acid (100 mg, 0.30 mmol) (prepared in Example 97, step 2) and tert-butyl [(3S,5R)-1-(3-aminopyridin-4-yl)-5-(trifluoromethyl)piperidin-3-yl]carbamate (145 mg, 0.4 mmol) to afford the title compound as an off-white powder. LCMS calc. for $C_{23}H_{26}F_3N_6O_2$ (M+H)$^+$: m/z=475.1. Found: 475.1.

Example 99

2-Amino-N-{4-[(3S,5R)-3-amino-5-(trifluoromethyl)piperidin-1-yl]pyridin-3-yl}-6-[(3-fluoroazetidin-1-yl)methyl]furo[3,2-b]pyridine-3-carboxamide

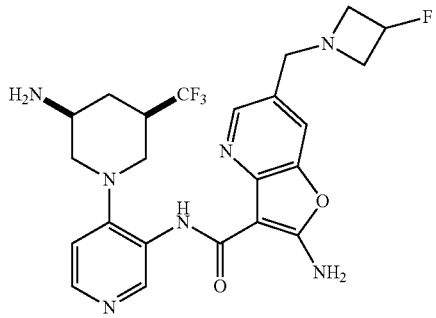 [SMILES: Nc1oc2cc(CN3CC(F)C3)cnc2c1C(=O)Nc1cnccc1N1C[C@@H](N)C[C@@H](C(F)(F)F)C1]

Step 1. Ethyl 2-[bis(tert-butoxycarbonyl)amino]-6-vinylfuro[3,2-b]pyridine-3-carboxylate

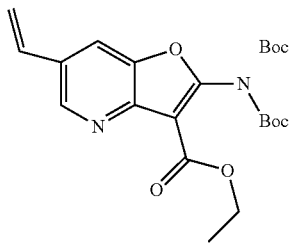 [SMILES: C=Cc1cnc2c(C(=O)OCC)c(NC(=O)OC(C)(C)C)oc2c1 ; "Boc"]

A mixture of ethyl 2-[bis(tert-butoxycarbonyl)amino]-6-bromofuro[3,2-b]pyridine-3-carboxylate (1.10 g, 2.3 mmol), 4,4,5,5-tetramethyl-2-vinyl-1,3,2-dioxaborolane (0.69 mL, 4.1 mmol), dicyclohexyl(2',4',6'-triisopropylbiphenyl-2-yl)phosphine-(2'-aminobiphenyl-2-yl)(chloro)palladium (1:1) (267 mg, 0.34 mmol) and $K_3PO_4$ (0.96 g, 4.5 mmol) in 1,4-dioxane (7.1 mL) and water (1.6 mL) was stirred at 70° C. for 4 h under $N_2$ atmosphere. The crude reaction mixture was diluted with EtOAc and water. The organic layer was separated, dried over $Na_2SO_4$ and filtered. The filtrate was concentrated under reduced pressure and the crude product was purified by silica gel column chromatography (0 to 30% EtOAc in hexanes) to give the product as light brown powder (980 mg, 98%). LCMS calc. for $C_{22}H_{29}N_2O_7$ (M+H)$^+$: m/z=433.1. Found: 433.1.

Step 2. 2-[(tert-Butoxycarbonyl)amino]-6-vinylfuro[3,2-b]pyridine-3-carboxylic acid

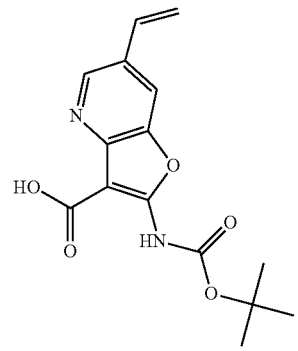 [SMILES: C=Cc1cnc2c(C(=O)O)c(NC(=O)OC(C)(C)C)oc2c1]

A mixture of ethyl 2-[bis(tert-butoxycarbonyl)amino]-6-vinylfuro[3,2-b]pyridine-3-carboxylate (800 mg, 1.85 mmol) and LiOH.H$_2$O (540 mg, 13 mmol) in THF (10 mL), MeOH (7 mL) and water (4 mL) was heated at 70° C. in a flask for 16 h. The reaction mixture was filtered to remove unreacted LiOH and neutralized with 6 M HCl. After all the solvents were removed under reduced pressure, ice water was added to the residue, and the precipitate was collected by vacuum filtration. The light yellow cake was washed with cold water, and dried under reduced pressure overnight to provide the sub-title compound as light brown powder (466 mg, 83%). LCMS calc. for $C_{15}H_{17}N_2O_5$ (M+H)$^+$: m/z=305.1. Found: 305.1.

Step 3. tert-Butyl {3-[({4-[(3S,5R)-3-[(tert-butoxycarbonyl)amino]-5-(trifluoromethyl)piperidin-1-yl]pyridin-3-yl}amino)carbonyl]-6-vinylfuro[3,2-b]pyridin-2-yl}carbamate

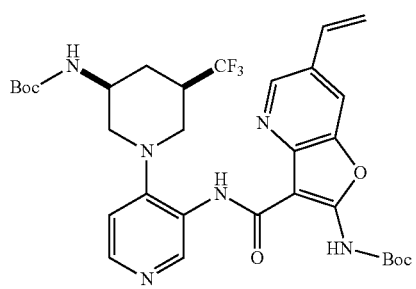 [SMILES: C=Cc1cnc2c(C(=O)Nc3cnccc3N3C[C@@H](NC(=O)OC(C)(C)C)C[C@@H](C(F)(F)F)C3)c(NC(=O)OC(C)(C)C)oc2c1]

A mixture of tert-butyl [(3S,5R)-1-(3-aminopyridin-4-yl)-5-(trifluoromethyl)piperidin-3-yl]carbamate (911 mg, 2.53 mmol), 2-[(tert-butoxycarbonyl)amino]-6-vinylfuro[3,2-b]pyridine-3-carboxylic acid (846 mg, 2.78 mmol) and molecular sieves (2.26 g, 10.1 mmol) (4 Å) in 1,2-dichloroethane (17.9 mL) was stirred vigorously at room temperature for 30 min., followed by the addition of DIPEA (1.32 mL, 7.6 mmol) and HATU (4.8 g, 12.6 mmol). The reaction mixture was stirred vigorously at room temperature for 24 h. The reaction mixture was filtered and obtained solids were washed with THF. The filtrate was concentrated under reduced pressure, and the residue was purified by silica gel column chromatography (0 to 50% EtOAc in Hexanes) to give the sub-title compound as an off-white powder (622 mg, 38%). LCMS calc. for $C_{31}H_{38}F_3N_6O_6$ (M+H)⁺: m/z=647.2. Found: 647.2.

Step 4. tert-Butyl [(3S,5R)-1-{3-[({2-[(tert-butoxy-carbonyl)amino]-6-formylfuro[3,2-b]pyridin-3-yl}carbonyl)amino]pyridin-4-yl}-5-(trifluoromethyl)piperidin-3-yl]carbamate

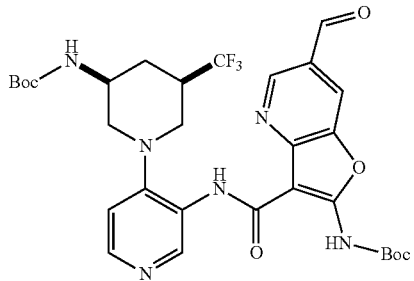 [SMILES: CC(C)(C)OC(=O)Nc1oc2cc(C=O)cnc2c1C(=O)Nc1cnccc1N1C[C@@H](NC(=O)OC(C)(C)C)C[C@@H](C(F)(F)F)C1]

tert-Butyl {3-[({4-[(3S,5R)-3-[(tert-butoxycarbonyl)amino]-5-(trifluoromethyl)piperidin-1-yl]pyridin-3-yl}amino)carbonyl]-6-vinylfuro[3,2-b]pyridin-2-yl}carbamate (500 mg, 0.77 mmol) was mixed with THF (9.4 mL), 0.16 M solution of osmium tetroxide in water (1.4 mL, 0.23 mmol) (4% aqueous solution), NaIO₄ (780 mg, 3.6 mmol) and water (0.7 mL). The reaction mixture was stirred at 70° C. for 40 min. The crude mixture was filtered, rinsed with fresh THF. The organic layer was concentrated under reduced pressure. Silica gel column purification (0 to 100% EtOAc in hexanes) gave the sub-title compound as a yellow powder (279 mg, 56%). LCMS calc. for $C_{30}H_{36}F_3N_6O_7$ (M+H)⁺: m/z=649.2. Found: 649.2.

Step 5. tert-Butyl [(3S,5R)-1-{3-[({2-[(tert-butoxycarbonyl)amino]-6-[(3-fluoroazetidin-1-yl)methyl]furo[3,2-b]pyridin-3-yl}carbonyl)amino]pyridin-4-yl}-5-(trifluoromethyl)piperidin-3-yl]carbamate

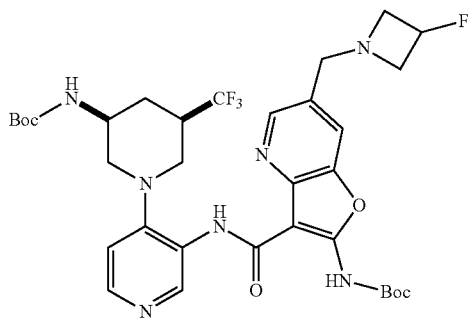 [SMILES: CC(C)(C)OC(=O)Nc1oc2cc(CN3CC(F)C3)cnc2c1C(=O)Nc1cnccc1N1C[C@@H](NC(=O)OC(C)(C)C)C[C@@H](C(F)(F)F)C1]

A mixture of 3-fluoroazetidine hydrochloride (3 mg, 0.03 mmol) and tert-butyl [(3S,5R)-1-{3-[({2-[(tert-butoxycarbonyl)amino]-6-formylfuro[3,2-b]pyridin-3-yl}carbonyl)amino]pyridin-4-yl}-5-(trifluoromethyl)piperidin-3-yl]carbamate (16.0 mg, 0.024 mmol) in dry 1,2-dichloroethane (0.10 mL) was treated with DIPEA (5.0 µL, 0.03 mmol), followed by the addition of sodium triacetoxyborohydride (10.4 mg, 0.05 mmol) and stirred at room temperature for 2 h. The reaction mixture was filtered and concentrated to give the crude product, which was used directly in the next step. LCMS calc. for $C_{33}H_{42}F_4N_7O_6$ (M+H)⁺: m/z=708.2. Found: 708.2.

Step 6. 2-Amino-N-{4-[(3S,5R)-3-amino-5-(trifluoromethyl)piperidin-1-yl]pyridin-3-yl}-6-[(3-fluoroazetidin-1-yl)methyl]furo[3,2-b]pyridine-3-carboxamide To a solution of tert-butyl [(3S,5R)-1-{3-[({2-[(tert-butoxycarbonyl)amino]-6-[(3-fluoroazetidin-1-yl)methyl]furo[3,2-b]pyridin-3-yl}carbonyl)amino]pyridin-4-yl}-5-(trifluoromethyl)piperidin-3-yl]carbamate (8.7 mg, 0.01 mmol) in MeOH (0.10 mL) was added 4.0 M solution of HCl in dioxane (0.25 mL, 0.98 mmol). The reaction mixture was stirred at room temperature for 40 min. After removal of the solvents, the residue was diluted with MeOH and NH₄OH, and purified by preparative LCMS (pH=10 method; XBridge™ PrepC18 5 µm OBD™ column, 30×10 mm, 60 mL/min., eluting with a gradient of MeCN and water with NH₄OH) to give the title compound (3 mg, 40%). LCMS calc. for $C_{23}H_{26}F_4N_7O_2$ (M+H)⁺: m/z=508.3. Found: 508.2.

Example 100

2-Amino-N-{4-[(3S,5R)-3-amino-5-(trifluoromethyl)piperidin-1-yl]pyridin-3-yl}-6-[(3,3-difluoroazetidin-1-yl)methyl]furo[3,2-b]pyridine-3-carboxamide

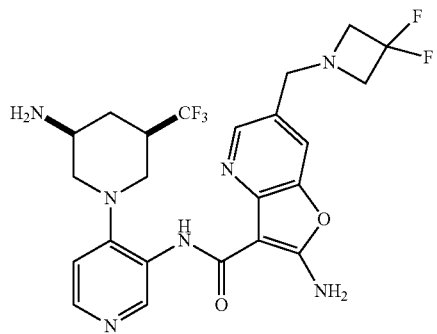 [SMILES: Nc1oc2cc(CN3CC(F)(F)C3)cnc2c1C(=O)Nc1cnccc1N1C[C@@H](N)C[C@@H](C(F)(F)F)C1]

Step 1. Methyl 2-[bis(tert-butoxycarbonyl)amino]-6-vinylfuro[3,2-b]pyridine-3-carboxylate

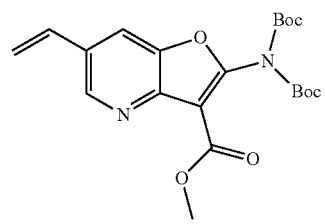 [SMILES: C=Cc1cnc2c(C(=O)OC)c(N(C(=O)OC(C)(C)C)C(=O)OC(C)(C)C)oc2c1]

To a pressure flask was added methyl 2-[bis(tert-butoxycarbonyl)amino]-6-bromofuro[3,2-b]pyridine-3-carboxylate (3.0 g, 6.4 mmol), K₃PO₄ (2.70 g, 12.7 mmol), 1,4- dioxane (15 mL), water (3.4 mL) and 4,4,5,5-tetramethyl-2-vinyl-1,3,2-dioxaborolane (1.8 g, 11 mmol). The mixture was flushed with $N_2$ for 10 min., followed by the addition of dicyclohexyl(2',4',6'-triisopropylbiphenyl-2-yl)phosphine-(2'-aminobiphenyl-2-yl)(chloro)palladium (1:1) (0.40 g, 0.51 mmol). The reaction mixture was sealed and heated at 85° C. for 3 h. The crude reaction mixture was filtered and concentrated to give the residue, which was purified by silica gel column chromatography (0 to 50% EtOAc in hexanes) to give the sub-title compound as a thick oil. LCMS calc. for $C_{21}H_{27}N_2O_7$ $(M+H)^+$: m/z=419.1. Found: 419.1.

Step 2. Methyl 2-[bis(tert-butoxycarbonyl)amino]-6-formylfuro[3,2-b]pyridine-3-carboxylate

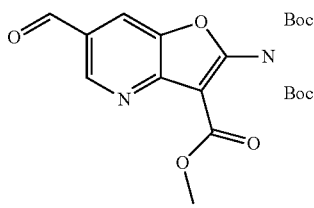 [SMILES: COC(=O)c1c(N)oc2cc(C=O)cnc12 ; "Boc" ; "Boc"]

Methyl 2-[bis(tert-butoxycarbonyl)amino]-6-vinylfuro[3,2-b]pyridine-3-carboxylate (1.66 g, 3.1 mmol) was mixed with THF (37 mL), 0.16 M solution of osmium tetroxide in water (5.6 mL, 0.9 mmol), $NaIO_4$ (3.0 g, 14 mmol) and water (3 mL). The reaction mixture was stirred at 70° C. for 1 h. The mixture was filtered, rinsed with fresh THF. The organic layer was concentrated under reduced pressure. Silica gel column purification (0 to 50% EtOAc in hexanes) gave the sub-title compound as a yellow powder (1.27 g, 98%). LCMS calc. for $C_{20}H_{25}N_2O_8$ $(M+H)^+$: m/z=421.1. Found: 421.1.

Step 3. Methyl 2-[bis(tert-butoxycarbonyl)amino]-6-[(3,3-difluoroazetidin-1-yl)methyl]furo[3,2-b]pyridine-3-carboxylate

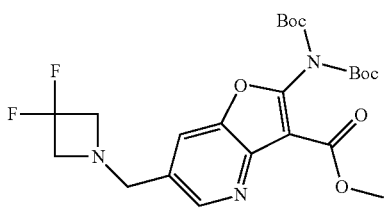 [SMILES: COC(=O)c1c(N(C(=O)OC(C)(C)C)C(=O)OC(C)(C)C)oc2cc(CN3CC(F)(F)C3)cnc12]

To a mixture of methyl 2-[bis(tert-butoxycarbonyl)amino]-6-formylfuro[3,2-b]pyridine-3-carboxylate (150 mg, 0.36 mmol), 3,3-difluoroazetidine HCl (51 mg, 0.39 mmol) and DCM (1.9 mL) was added resin of sodium triacetoxyborohydride (290 mg, 0.66 mmol). The resulting reaction mixture was stirred at room temperature for 16 h. The reaction mixture was filtered and concentrated. The crude product was used in the next step without further purification. LCMS calc. for $C_{23}H_{30}F_2N_3O_7$ $(M+H)^+$: m/z=498.3. Found: 498.3.

Step 4. 2-[(tert-Butoxycarbonyl)amino]-6-[(3,3-difluoroazetidin-1-yl)methyl]furo[3,2-b]pyridine-3-carboxylic acid

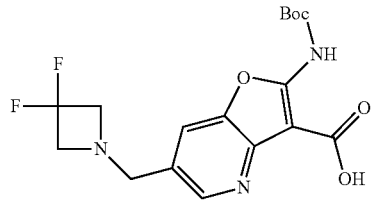 [SMILES: CC(C)(C)OC(=O)Nc1oc2cc(CN3CC(F)(F)C3)cnc2c1C(=O)O]

A mixture of methyl 2-[bis(tert-butoxycarbonyl)amino]-6-[(3,3-difluoroazetidin-1-yl)methyl]furo[3,2-b]pyridine-3-carboxylate (0.15 g, 0.30 mmol), $LiOH.H_2O$ (87 mg, 2.1 mmol), water (0.33 mL), THF (0.40 mL) and MeOH (0.40 mL) was heated at 70° C. for 3 h. The reaction mixture was neutralized with 1 M HCl to pH=5. The aqueous layer was extracted with EtOAc twice. The organic layers were combined, dried over $Na_2SO_4$, filtered and concentrated to give the crude product, which was purified by preparative LCMS (pH=10 method; XBridge™ PrepC18 5 μm OBD™ column, 30×10 mm, 60 mL/min., eluting with a gradient of MeCN and water with $NH_4OH$) to give the sub-title compound. LCMS calc. for $C_{17}H_{20}F_2N_3O_5$ $(M+H)^+$: m/z=384.2. Found: 384.2.

Step 5. tert-Butyl [(3S,5R)-1-{3[({2-[(tert-butoxycarbonyl)amino]-6-[(3,3-difluoroazetidin-1-yl)methyl]furo[3,2-b]pyridin-3-yl}carbonyl)amino]pyridin-4-yl}-5-(trifluoromethyl)piperidin-3-yl]carbamate

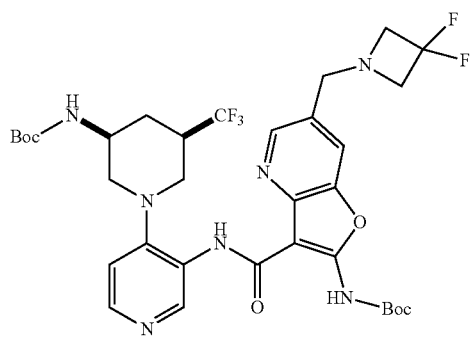 [SMILES: CC(C)(C)OC(=O)Nc1oc2cc(CN3CC(F)(F)C3)cnc2c1C(=O)Nc1cnccc1N1C[C@@H](NC(=O)OC(C)(C)C)C[C@@H](C(F)(F)F)C1]

A mixture of tert-butyl [(3S,5R)-1-(3-aminopyridin-4-yl)-5-(trifluoromethyl)piperidin-3-yl]carbamate (25 mg, 0.07 mmol), 2-[(tert-butoxycarbonyl)amino]-6-[(3,3-difluoroazetidin-1-yl)methyl]furo[3,2-b]pyridine-3-carboxylic acid (25 mg, 0.07 mmol) and molecular sieves (0.063 g, 0.28 mmol) (4 Å) in 1,2-dichloroethane (0.53 mL) was stirred vigorously at room temperature for 25 min., followed by the addition of DIPEA (0.048 mL, 0.27 mmol) and HATU (80 mg, 0.21 mmol). The reaction mixture was stirred vigorously at room temperature for 24 h. The crude reaction mixture was diluted with MeOH, filtered, and purified by preparative LCMS (pH=10 method; XBridge™ PrepC18 5 μm OBD™ column, 30×10 mm, 60 mL/min., eluting with a gradient of MeCN and water with $NH_4OH$) to give the sub-title compound. LCMS calc. for $C_{33}H_{41}F_5N_7O_6$ $(M+H)^+$: m/z=726.3. Found: 726.3.

Step 6. 2-Amino-N-{4-[(3S,5R)-3-amino-5-(trifluoromethyl)piperidin-1-yl]pyridin-3-yl}-6-[(3,3-difluoroazetidin-1-yl)methyl]furo[3,2-b]pyridine-3-carboxamide tert-Butyl [(3S,5R)-1-{3-[({2-[(tert-butoxycarbonyl)amino]-6-[(3,3-difluoroazetidin-1-yl)methyl]furo[3,2-b]pyridin-3-yl}carbonyl)amino]pyridin-4-yl}-5-(trifluoromethyl)piperidin-3-yl]carbamate (4 mg, 0.005 mmol) was dissolved in MeOH (0.5 mL), followed by the addition of 4.0 M solution of HCl in dioxane (1.0 mL, 4.0 mmol). The reaction mixture was stirred at room temperature for 1 h. After removal of the solvents, the residue was diluted with MeOH and NH$_4$OH, and purified by preparative LCMS (pH=10 method; XBridge™ PrepC18 5 μm OBD™ column, 30×10 mm, 60 mL/min., eluting with a gradient of MeCN and water with NH$_4$OH) to give the title compound. LCMS calc. for $C_{23}H_{25}F_5N_7O_2$ (M+H)$^+$: m/z=526.3. Found: 526.3.

Example 101

2-Amino-N-{4-[(3S,5R)-3-amino-5-(trifluoromethyl)piperidin-1-yl]pyridin-3-yl}-6-[(3-hydroxyazetidin-1-yl)methyl]furo[3,2-b]pyridine-3-carboxamide

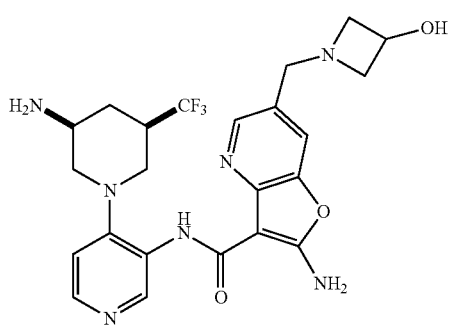 [SMILES: Nc1oc2cc(CN3CC(O)C3)cnc2c1C(=O)Nc1cnccc1N1C[C@@H](N)C[C@@H](C(F)(F)F)C1]

Step 1. tert-Butyl [(3S,5R)-1-{3-[({2-[(tert-butoxycarbonyl)amino]-6-[(3-hydroxyazetidin-1-yl)methyl]furo[3,2-b]pyridin-3-yl}carbonyl)amino]pyridin-4-yl}-5-(trifluoromethyl)piperidin-3-yl]carbamate

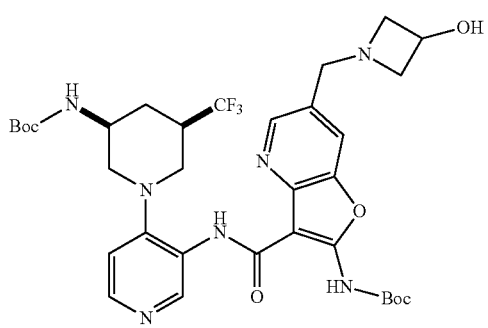 [SMILES: CC(C)(C)OC(=O)Nc1oc2cc(CN3CC(O)C3)cnc2c1C(=O)Nc1cnccc1N1C[C@@H](NC(=O)OC(C)(C)C)C[C@@H](C(F)(F)F)C1]

A mixture of azetidin-3-ol hydrochloride (6 mg, 0.06 mmol) and tert-butyl [(3S,5R)-1-{3-[({2-[(tert-butoxycarbonyl)amino]-6-formylfuro[3,2-b]pyridin-3-yl}carbonyl)amino]pyridin-4-yl}-5-(trifluoromethyl)piperidin-3-yl]carbamate (32.0 mg, 0.05 mmol) (prepared in Example 99, step 4) in dry 1,2-dichloroethane (0.20 mL) was treated with sodium triacetoxyborohydride (20.8 mg, 0.10 mmol) and stirred at room temperature for 2 h. The reaction mixture was filtered and concentrated under reduced pressure to give the crude product, which was used directly in the next step. LCMS calc. for $C_{33}H_{43}F_3N_7O_6$ (M+H)$^+$: m/z=706.3. Found: 706.3.

Step 2. 2-Amino-N-{4-[(3S,5R)-3-amino-5-(trifluoromethyl)piperidin-1-yl]pyridin-3-yl}-6-[(3-hydroxyazetidin-1-yl)methyl]furo[3,2-b]pyridine-3-carboxamide tert-Butyl [(3S,5R)-1-{3-[({2-[(tert-butoxycarbonyl)amino]-6-[(3-hydroxyazetidin-1-yl)methyl]furo[3,2-b]pyridin-3-yl}carbonyl)amino]pyridin-4-yl}-5-(trifluoromethyl)piperidin-3-yl]carbamate (9 mg, 0.01 mmol) was dissolved in MeOH (0.5 mL), followed by the addition of 4.0 M solution of HCl in dioxane (1.0 mL, 4.0 mmol). The reaction mixture was stirred at room temperature for 1 h. After removal of the solvents under reduced pressure, the residue was diluted with MeOH and NH$_4$OH, and purified by preparative LCMS (pH=10 method; XBridge™ PrepC18 5 μm OBD™ column, 30×10 mm, 60 mL/min., eluting with a gradient of MeCN and water with NH$_4$OH) to give the title compound. LCMS calc. for $C_{23}H_{27}F_3N_7O_3$ (M+H)$^+$: m/z=506.3. Found: 506.3.

Example 102

2-Amino-N-{4-[(3R,4S,5S)-3-amino-5-methyl-4-(1H-1,2,3-triazol-1-yl)piperidin-1-yl]pyridin-3-yl}-6-isopropylfuro[3,2-b]pyridine-3-carboxamide

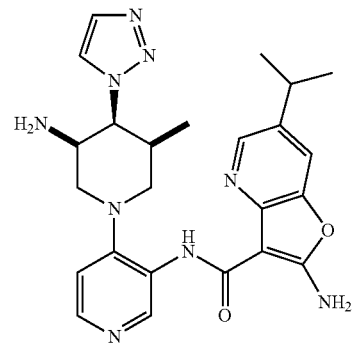 [SMILES: CC(C)c1cnc2c(C(=O)Nc3cnccc3N3C[C@@H](N)[C@@H](n4ccnn4)[C@@H](C)C3)c(N)oc2c1]

Step 1. tert-Butyl [(3R,4R,5S)-4-{[tert-butyl(dimethyl)silyl]oxy}-5-methyl-1-(3-nitropyridin-4-yl)piperidin-3-yl]carbamate

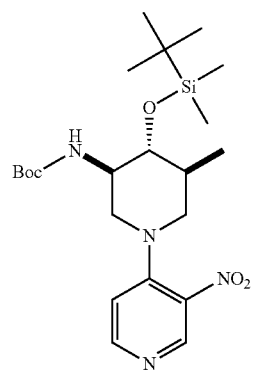 [SMILES: C[C@H]1CN(c2ccncc2[N+](=O)[O-])C[C@@H](NC(=O)OC(C)(C)C)[C@@H]1O[Si](C)(C)C(C)(C)C]

A mixture of 4-chloro-3-nitropyridine (5.11 g, 32.2 mmol), tert-butyl ((3R,4R,5S)-4-{[tert-butyl(dimethyl)silyl]oxy}-5-methylpiperidin-3-yl)carbamate[0.5]-oxalic acid (13.2 g, 33.8 mmol) and i-PrOH (63.0 mL) was stirred at 90° C. for 3 h. The mixture was concentrated under reduced pressure, and diluted with EtOAc and water. The aqueous layer was extracted with EtOAc (three times). The combined organic layers were dried, filtered and concentrated under reduced pressure to give a residue, which was purified by silica gel column chromatography (0-50% EtOAc in hexanes) to give the sub-title compound as a yellow powder (13.4 g, 89%). LCMS calc. for $C_{22}H_{38}N_4O_5Si$ (M+H)$^+$: m/z=467.3. Found: 467.3.

Step 2. tert-Butyl ((3R,4R,5S)-1-(3-aminopyridin-4-yl)-4-{[tert-butyl(dimethyl)silyl]oxy}-5-methylpiperidin-3-yl)carbamate

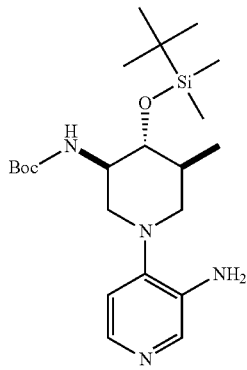

tert-Butyl [(3R,4R,5S)-4-{[tert-butyl(dimethyl)silyl]oxy}-5-methyl-1-(3-nitropyridin-4-yl)piperidin-3-yl]carbamate (13.4 g, 28.7 mmol) was dissolved in MeOH (80 mL), flushed with $N_2$, then mixed with 10 wt % of palladium on carbon (4.6 g, 4.3 mmol) and hydrogenated under $H_2$ at 60 psi for 16 h. The reaction mixture was filtered through diatomaceous earth and the filtrate was concentrated under reduced pressure to give the sub-title compound (12.5 g, 99%). LCMS calc. for $C_{22}H_{40}N_4O_3Si$ (M+H)$^+$: m/z=437.4. Found: 437.4.

Step 3. Di-tert-butyl [4-((3R,4R,5S)-3-[(tert-butoxycarbonyl)amino]-4-{[tert-butyl (dimethyl)silyl]oxy}-5-methylpiperidin-1-yl)pyridin-3-yl]imidodicarbonate

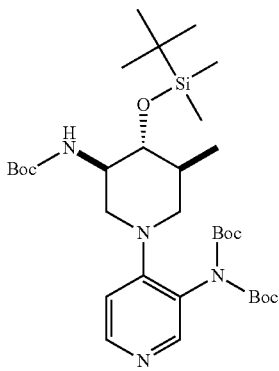 [SMILES: C[C@H]1CN(c2ccncc2N(C(=O)OC(C)(C)C)C(=O)OC(C)(C)C)C[C@@H](NC(=O)OC(C)(C)C)[C@@H]1O[Si](C)(C)C(C)(C)C]

To a solution of tert-butyl ((3R,4R,5S)-1-(3-aminopyridin-4-yl)-4-{[tert-butyl(dimethyl)silyl]oxy}-5-methylpiperidin-3-yl)carbamate (1.20 g, 2.75 mmol) in DCM (5.5 mL) at room temperature was added Boc$_2$O (3.60 g, 16.5 mmol), followed by DMAP (0.671 g, 5.50 mmol). The reaction mixture was stirred at room temperature for 6 h, and was then diluted with EtOAc and water. The organic layer was washed with brine, dried over Na$_2$SO$_4$, concentrated and purified by column chromatography on silica gel using CombiFlash® apparatus (eluting with 0-50% EtOAc in hexanes) to give the sub-title compound as a brown gum (1.05 g, 60%). LCMS calc. for $C_{32}H_{56}N_4O_7Si$ (M+H)$^+$: m/z=637.4. Found: 637.3.

Step 4. Di-tert-butyl (4-{(3R,4R,5S)-3-[(tert-butoxycarbonyl)amino]-4-hydroxy-5-methylpiperidin-1-yl}pyridin-3-yl)imidodicarbonate

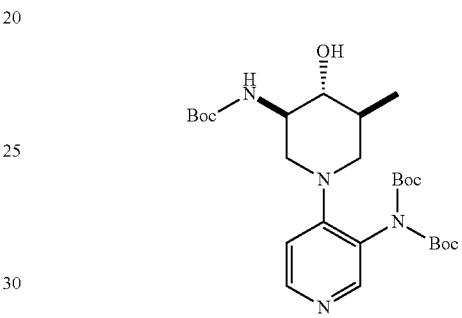

To a solution of di-tert-butyl [4-((3R,4R,5S)-3-[(tert-butoxycarbonyl)amino]-4-{[tert-butyl(dimethyl)silyl]oxy}-5-methylpiperidin-1-yl)pyridin-3-yl]imido dicarbonate (1.01 g, 1.58 mmol) in THF (7.90 mL) at room temperature was added 1.0 M TBAF in THF (1.66 mL, 1.66 mmol). The reaction mixture was stirred at room temperature for 2 h. The mixture was then diluted with EtOAc and water. The organic layer was washed with brine, dried, concentrated and purified by column chromatography on silica gel using CombiFlash® apparatus (eluting with 0 to 80% EtOAc in hexanes) to give the sub-title compound (771 mg, 93%). LCMS calc. for $C_{26}H_{42}N_4O_7$ (M+H)$^+$: m/z=523.2. Found: 523.2.

Step 5. (3R,4R,5S)-1-{3-[Bis(tert-butoxycarbonyl)amino]pyridin-4-yl}-3-[(tert-butoxycarbonyl)amino]-5-methylpiperidin-4-yl methanesulfonate

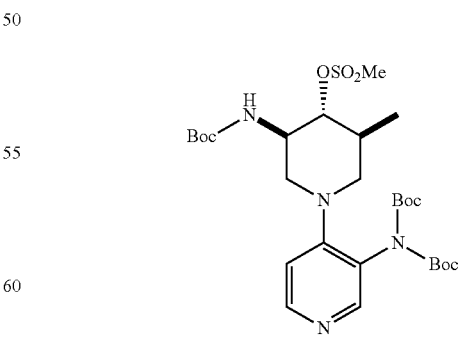

To a solution of di-tert-butyl (4-{(3R,4R,5S)-3-[(tert-butoxycarbonyl)amino]-4-hydroxy-5-methylpiperidin-1-yl}pyridin-3-yl)imidodicarbonate (500 mg, 0.957 mmol) in DCM (4.5 mL) was added TEA (0.227 mL, 1.63 mmol), followed by methanesulfonyl chloride (0.096 mL, 1.24 mmol). The solution obtained was stirred in a closed vial at room temperature for 1 h. The reaction mixture was quenched with NaHCO₃ (aq.), extracted with EtOAc. The organic layer was washed with brine, dried, filtered and concentrated under reduced pressure to give the sub-title compound as a light yellow powder (574 mg, 100%). LCMS calc. for $C_{27}H_{44}N_4O_9S$ (M+H)⁺: m/z=601.2. Found: 601.2.

Step 6. Di-tert-butyl (4-{(3R,4S,5S)-4-azido-3-[(tert-butoxycarbonyl)amino]-5-methylpiperidin-1-yl}pyridin-3-yl)imidodicarbonate

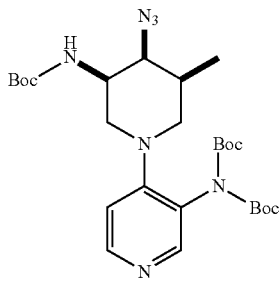 [SMILES: C[C@H]1CN(c2ccncc2N(C(=O)OC(C)(C)C)C(=O)OC(C)(C)C)C[C@@H](NC(=O)OC(C)(C)C)[C@H]1N=[N+]=[N-]]

To a solution of (3R,4R,5S)-1-{3-[bis(tert-butoxycarbonyl)amino]pyridin-4-yl}-3-[(tert-butoxycarbonyl)amino]-5-methylpiperidin-4-yl methanesulfonate (0.57 g, 0.96 mmol) in DMF (5.0 mL) was added NaN₃ (0.31 g, 4.8 mmol). The tube containing the reaction mixture was sealed and the reaction mixture was heated at 90° C. for 5 h. After cooling down to room temperature, the solution was partitioned between EtOAc and water. The organic layer was washed with Na₂CO₃, brine, dried, filtered and concentrated under reduced pressure to give the sub-title compound (0.52 g, 99%). LCMS calc. for $C_{26}H_{41}N_7O_6$ (M+H)⁺: m/z=548.3. Found: 548.4.

Step 7. Di-tert-butyl {4-[(3R,4S,5S)-3-[(tert-butoxycarbonyl)amino]-5-methyl-4-(1H-1,2,3-triazol-1-yl)piperidin-1-yl]pyridin-3-yl}imidodicarbonate

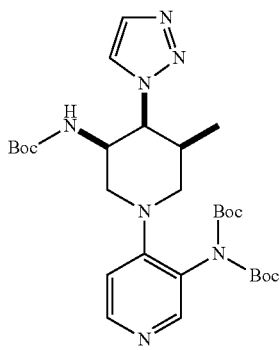

A solution of di-tert-butyl (4-{(3R,4S,5S)-4-azido-3-[(tert-butoxycarbonyl)amino]-5-methylpiperidin-1-yl}pyridin-3-yl)imidodicarbonate (0.28 g, 0.51 mmol) in acetic acid ethenyl ester (4.2 mL, 46 mmol) in a sealed flask was heated at 115° C. for 96 h. The reaction mixture was concentrated under reduced pressure and purified by column chromatography on silica gel using CombiFlash® apparatus (eluting with 50 to 100% EtOAc in hexanes) to give the sub-title compound (97 mg, 33%). LCMS calc. for $C_{28}H_{43}N_7O_6$ (M+H)⁺: m/z=574.4. Found: 574.4.

Step 8. tert-Butyl [(3R,4S,5S)-1-(3-aminopyridin-4-yl)-5-methyl-4-(1H-1,2,3-triazol-1-yl)piperidin-3-yl]carbamate

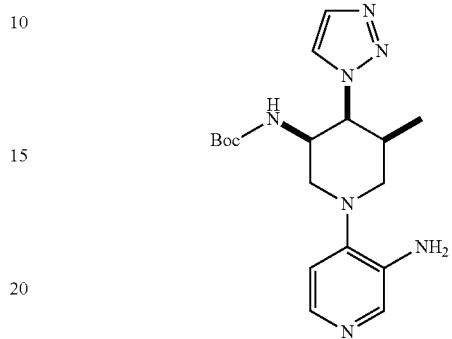

To di-tert-butyl {4-[(3R,4S,5S)-3-[(tert-butoxycarbonyl)amino]-5-methyl-4-(1H-1,2,3-triazol-1-yl)piperidin-1-yl]pyridin-3-yl}imidodicarbonate (97 mg, 0.17 mmol) was added a 4.0 M solution of HCl in dioxane (1.27 mL, 5.1 mmol). After 1 h, the volatile solvents were removed under reduced pressure. Then the residue (HCl salt) was dried under high vacuum for 20 min. Then it was dissolved in DCM (1.1 mL) and DIPEA (0.44 mL, 2.5 mmol), and 1-[(tert-butoxycarbonyl)oxy]pyrrolidine-2,5-dione (36.4 mg, 0.17 mmol) were added at 0° C. After 90 min. stirring at room temperature, the reaction mixture was quenched with NaHCO₃ (aq.) and diluted with EtOAc. The aqueous layer was separated and extracted with EtOAc two times. The combined organic layers were dried, concentrated under reduced pressure to give a yellow residue, which was purified by column chromatography on silica gel using CombiFlash® apparatus (eluting with 0 to 25% MeOH in EtOAc) to give the sub-title compound as a light yellow powder (40 mg, 63%). LCMS calc. for $C_{18}H_{27}N_7O_2$ (M+H)⁺: m/z=374.2. Found: 374.2.

Step 9. 2-Amino-N-{4-[(3R,4S,5S)-3-amino-5-methyl-4-(1H-1,2,3-triazol-1-yl)piperidin-1-yl]pyridin-3-yl}-6-isopropylfuro[3,2-b]pyridine-3-carboxamide A mixture of tert-butyl [(3R,4S,5S)-1-(3-aminopyridin-4-yl)-5-methyl-4-(1H-1,2,3-triazol-1-yl)piperidin-3-yl]carbamate (40.0 mg, 0.107 mmol), 2-[(tert-butoxycarbonyl)amino]-6-isopropylfuro[3,2-b]pyridine-3-carboxylic acid (51.5 mg, 0.16 mmol) and molecular sieves (96.0 mg, 0.43 mmol) (4 Å) in 1,2-dichloroethane (0.8 mL) was stirred at room temperature for 30 min., followed by the addition of DIPEA (56.0 µL, 0.32 mmol) and HATU (102 mg, 0.27 mmol). The reaction mixture was stirred at room temperature for 24 h. The mixture was filtered, concentrated under reduced pressure, and the residue was purified by preparative LCMS (pH=10 method; XBridge™ PrepC18 5 µm OBD™ column, 30×10 mm, 60 mL/min., eluting with a gradient of MeCN and water with NH₄OH) to give the pure intermediate (9.0 mg, 12%). The intermediate was dissolved in MeOH (0.10 mL), followed by the addition of 4.0 M solution of HCl in dioxane (2.7 mL, 10.7 mmol). The reaction mixture was stirred for 60 min. After removal of the solvents under reduced pressure, the residue was diluted with MeOH and NH₄OH, and purified by preparative LCMS (pH=10 method; XBridge™ PrepC 18 5 μm OBD™ column, 30×10 mm, 60 mL/min., eluting with a gradient of MeCN and water with NH₄OH) to give the title compound (3.5 mg, 7% yield). LCMS calc. for C₂₄H₃₀N₉O₂ (M+H)⁺: m/z=476.2. Found: 476.2.

Example 103

2-Amino-N-{4-[(3S,5R)-3-amino-5-(trifluoromethyl)piperidin-1-yl]pyridin-3-yl}-6-[(3-methoxypyrrolidin-1-yl)methyl]furo[3,2-b]pyridine-3-carboxamide

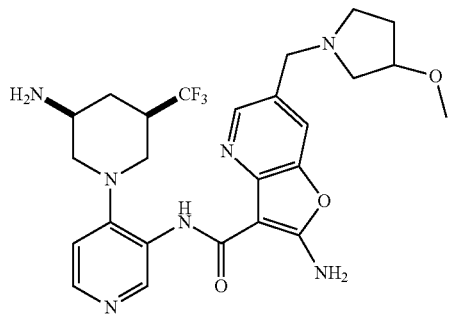 [SMILES: COC1CCN(Cc2cnc3c(C(=O)Nc4cnccc4N4C[C@@H](N)C[C@@H](C(F)(F)F)C4)c(N)oc3c2)C1]

Step 1. Methyl 2-[bis(tert-butoxycarbonyl)amino]-6-[(3-methoxypyrrolidin-1-yl)methyl]furo[3,2-b]pyridine-3-carboxylate

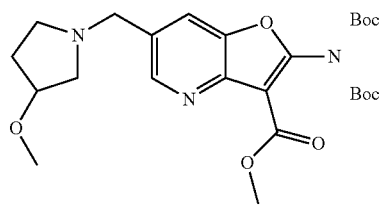 [SMILES: COC(=O)c1c(N)oc2cc(CN3CCC(OC)C3)cnc12 ; "Boc" ; "Boc"]

To a mixture of methyl 2-[bis(tert-butoxycarbonyl)amino]-6-formylfuro[3,2-b]pyridine-3-carboxylate (150 mg, 0.36 mmol) (prepared in Example 100, step 2) and 3-methoxypyrrolidine HCl (56 mg, 0.4 mmol) in DCM (1.9 mL) was added resin of sodium triacetoxyborohydride (290 mg, 0.66 mmol). The resulting mixture was stirred at room temperature for 16 h. The mixture was filtered and concentrated under reduced pressure. The crude product was used in the next step without further purification. LCMS calc. for C₂₅H₃₆N₃O₈ (M+H)⁺: m/z=506.2. Found: 506.2.

Step 2. 2[(tert-Butoxycarbonyl)amino]-6-[(3-methoxypyrrolidin-1-yl)methyl]furo[3,2-b]pyridine-3-carboxylic acid

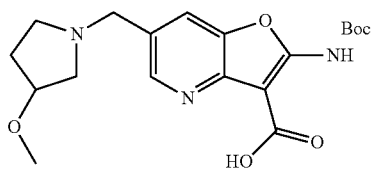 [SMILES: COC1CCN(Cc2cnc3c(C(=O)O)c(N)oc3c2)C1 ; "Boc"]

A mixture of methyl 2-[bis(tert-butoxycarbonyl)amino]-6-[(3-methoxypyrrolidin-1-yl)methyl]furo[3,2-b]pyridine-3-carboxylate (0.15 g, 0.30 mmol), LiOH.H₂O (87 mg, 2.1 mmol), water (0.33 mL), THF (0.40 mL) and MeOH (0.40 mL) was heated at 70° C. for 1 h. The solution was filtered and then diluted with MeOH, and purified by preparative LCMS (pH=10 method; XBridge™ PrepC18 5 μm OBD™ column, 30×10 mm, 60 mL/min., eluting with a gradient of MeCN and water with NH₄OH) to give the sub-title compound. LCMS calc. for C₁₉H₂₆N₃O₆ (M+H)⁺: m/z=392.2. Found: 392.2.

Step 3. tert-Butyl [(3S,5R)-1-{3-[({2-[(tert-butoxycarbonyl)amino]-6-[(3-methoxypyrrolidin-1-yl)methyl]furo[3,2-b]pyridin-3-yl}carbonyl)amino]pyridin-4-yl}-5-(trifluoromethyl)piperidin-3-yl]carbamate

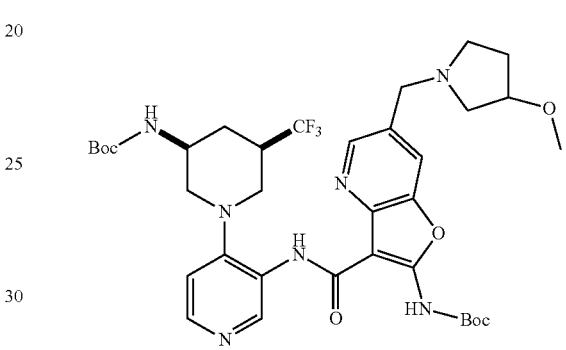

A mixture of tert-butyl [(3S,5R)-1-(3-aminopyridin-4-yl)-5-(trifluoromethyl)piperidin-3-yl]carbamate (72 mg, 0.20 mmol), 2-[(tert-butoxycarbonyl)amino]-6-[(3-methoxypyrrolidin-1-yl)methyl]furo[3,2-b]pyridine-3-carboxylic acid (72 mg, 0.18 mmol) and molecular sieves (0.16 g, 0.71 mmol) (4 Å) in 1,2-dichloroethane (1.5 mL) was stirred vigorously at room temperature for 25 min., then DIPEA (80.0 mg, 0.62 mmol) and HATU (0.25 g, 0.66 mmol) were added. The reaction mixture was stirred vigorously at room temperature for 24 h. The mixture was diluted with MeOH, filtered, and purified by preparative LCMS (pH=10 method; XBridge™ PrepC18 5 μm OBD™ column, 30×10 mm, 60 mL/min., eluting with a gradient of MeCN and water with NH₄OH) to give the sub-title compound. LCMS calc. for C₃₅H₄₇F₃N₇O₇ (M+H)⁺: m/z=734.4. Found: 734.4.

Step 4. 2-Amino-N-{4-[(3S,5R)-3-amino-5-(trifluoromethyl)piperidin-1-yl]pyridin-3-yl}-6-[(3-methoxypyrrolidin-1-yl)methyl]furo[3,2-b]pyridine-3-carboxamide tert-Butyl [(3S,5R)-1-{3-[({2-[(tert-butoxycarbonyl)amino]-6-[(3-methoxypyrrolidin-1-yl)methyl]furo[3,2-b]pyridin-3-yl}carbonyl)amino]pyridin-4-yl}-5-(trifluoromethyl)piperidin-3-yl]carbamate (10 mg, 0.014 mmol) was dissolved in MeOH (0.5 mL), then a 4.0 M solution of HCl in dioxane (1.0 mL, 4.0 mmol) was added. The reaction mixture was stirred at room temperature for 1 h. After removal of the solvents, the residue was diluted with MeOH and NH₄OH, and purified by preparative LCMS (pH=10 method; XBridge™ PrepC18 5 μm OBD™ column, 30×10 mm, 60 mL/min., eluting with a gradient of MeCN and water with NH₄OH) to give the title compound. LCMS calc. for C₂₅H₃₁F₃N₇O₃ (M+H)⁺: m/z=534.3. Found: 534.3.

Example 104

2-Amino-N-{4-[(3S,5R)-3-amino-5-(trifluoromethyl)piperidin-1-yl]pyridin-3-yl}-6-[(3-ethoxypyrrolidin-1-yl)methyl]furo[3,2-b]pyridine-3-carboxamide

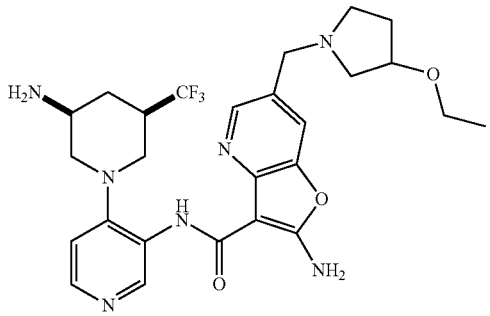 [SMILES: CCOC1CCN(Cc2cnc3c(C(=O)Nc4cnccc4N4C[C@@H](N)C[C@@H](C(F)(F)F)C4)c(N)oc3c2)C1]

Step 1. tert-Butyl [(3S,5R)-1-{3-[({2-[(tert-butoxycarbonyl)amino]-6-[(3-ethoxypyrrolidin-1-yl)methyl]furo[3,2-b]pyridin-3-yl}carbonyl)amino]pyridin-4-yl}-5-(trifluoromethyl)piperidin-3-yl]carbamate

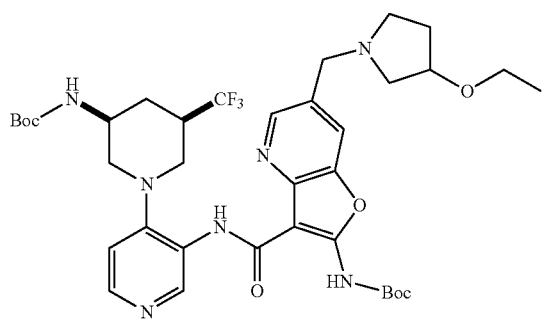 [SMILES: CCOC1CCN(Cc2cnc3c(C(=O)Nc4cnccc4N4C[C@@H](NC(=O)OC(C)(C)C)C[C@@H](C(F)(F)F)C4)c(NC(=O)OC(C)(C)C)oc3c2)C1]

A mixture of 3-ethoxypyrrolidine hydrochloride (4 mg, 0.03 mmol) and tert-butyl [(3S,5R)-1-{3-[({2-[(tert-butoxycarbonyl)amino]-6-formylfuro[3,2-b]pyridin-3-yl}carbonyl) amino]pyridin-4-yl}-5-(trifluoromethyl)piperidin-3-yl]carbamate (16.0 mg, 0.024 mmol) (prepared in Example 99, step 4) in dry 1,2-dichloroethane (0.10 mL) was treated with sodium triacetoxyborohydride resin (10.4 mg, 0.05 mmol) and stirred at room temperature for 2 h. The reaction mixture was filtered and concentrated to give the crude product, which was used directly in the next step. LCMS calc. for $C_{36}H_{49}F_3N_7O_7$ (M+H)$^+$: m/z=748.4. Found: 748.4.

Step 2. 2-Amino-N-{4-[(3S,5R)-3-amino-5-(trifluoromethyl)piperidin-1-yl]pyridin-3-yl}-6-[(3-ethoxypyrrolidin-1-yl)methyl]furo[3,2-b]pyridine-3-carboxamide tert-Butyl [(3S,5R)-1-{3-[({2-[(tert-butoxycarbonyl)amino]-6-[(3-ethoxypyrrolidin-1-yl)methyl]furo[3,2-b]pyridin-3-yl}carbonyl)amino]pyridin-4-yl}-5-(trifluoromethyl)piperidin-3-yl]carbamate (9 mg, 0.01 mmol) was dissolved in MeOH (0.5 mL), followed by the addition of 4.0 M solution of HCl in dioxane (1.0 mL, 4.0 mmol). The reaction mixture was stirred at room temperature for 1 h. After removal of the solvents under reduced pressure, the residue was diluted with MeOH and NH$_4$OH, and purified by preparative LCMS (pH=10 method; XBridge™ PrepC18 5 μm OBD™ column, 30×10 mm, 60 mL/min., eluting with a gradient of MeCN and water with NH$_4$OH) to give the title compound. LCMS calc. for $C_{26}H_{33}F_3N_7O_3$ (M+H)$^+$: m/z=548.3. Found: 548.3.

Example 105

2-Amino-N-{4-[(3S,5R)-3-amino-5-(trifluoromethyl)piperidin-1-yl]pyridin-3-yl}-6-{[(3R)-3-fluoropyrrolidin-1-yl]methyl}furo[3,2-b]pyridine-3-carboxamide

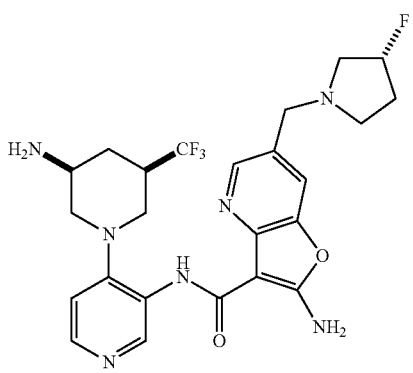 [SMILES: Nc1oc2cc(CN3CC[C@@H](F)C3)cnc2c1C(=O)Nc1cnccc1N1C[C@@H](N)C[C@@H](C(F)(F)F)C1]

Step 1. tert-Butyl [(3S,5R)-1-(3-{[(2-[(tert-butoxycarbonyl)amino]-6-{[(3R)-3-fluoropyrrolidin-1-yl]methyl}furo[3,2-b]pyridin-3-yl)carbonyl]amino}pyridin-4-yl)-5-(trifluoromethyl)piperidin-3-yl]carbamate

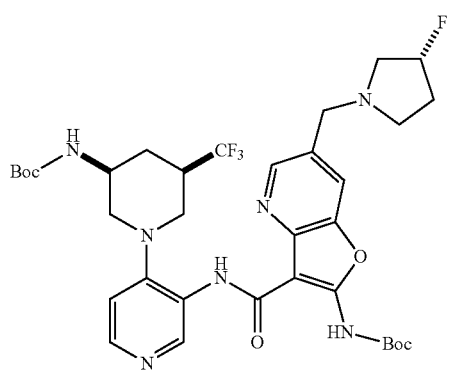 [SMILES: CC(C)(C)OC(=O)Nc1oc2cc(CN3CC[C@@H](F)C3)cnc2c1C(=O)Nc1cnccc1N1C[C@@H](NC(=O)OC(C)(C)C)C[C@@H](C(F)(F)F)C1]

A mixture of tert-butyl [(3S,5R)-1-{3-[({2-[(tert-butoxycarbonyl)amino]-6-formylfuro[3,2-b]pyridin-3-yl}carbonyl)amino]pyridin-4-yl}-5-(trifluoromethyl)piperidin-3-yl]carbamate (90.0 mg, 0.14 mmol) (prepared in Example 99, step 4) and (3R)-3-fluoropyrrolidine hydrochloride (20.9 mg, 0.17 mmol) in dry 1,2-dichloroethane (0.66 mL) was treated with DIPEA (31.4 μL, 0.18 mmol), followed by the addition of sodium triacetoxyborohydride resin (58.8 mg, 0.28 mmol) and stirred at room temperature for 3 h. The reaction mixture was filtered and concentrated under reduced pressure to give the crude product, which was used directly in the next step. LCMS calc. for $C_{34}H_{44}F_4N_7O_6$ (M+H)$^+$: m/z=722.2. Found: 722.2.

223

Step 2. 2-Amino-N-{4-[(3S,5R)-3-amino-5-(trifluoromethyl)piperidin-1-yl]pyridin-3-yl}-6-{[(3R)-3-fluoropyrrolidin-1-yl]methyl}furo[3,2-b]pyridine-3-carboxamide To a solution of tert-butyl [(3S,5R)-1-(3-{[(2-[(tert-butoxycarbonyl)amino]-6-{[(3R)-3-fluoropyrrolidin-1-yl]methyl}furo[3,2-b]pyridin-3-yl)carbonyl]amino}pyridin-4-yl)-5-(trifluoromethyl)piperidin-3-yl]carbamate (96.0 mg, 0.13 mmol) in MeOH (0.22 mL) was added 4.0 M solution of HCl in dioxane (2.66 mL, 10.6 mmol). The reaction mixture was stirred at room temperature for 40 min. After removal of the solvents, the residue was diluted with MeOH and NH$_4$OH, and purified by preparative LCMS (pH=10 method; XBridge™ PrepC18 5 μm OBD™ column, 30×10 mm, 60 mL/min., eluting with a gradient of MeCN and water with NH$_4$OH) to give the title compound (33 mg, 48%). LCMS calc. for $C_{24}H_{28}F_4N_7O_2$ (M+H)$^+$: m/z=522.2. Found: 522.2. $^1$H NMR (500 MHz, DMSO-d$_6$): δ 10.08 (s, 1H), 9.48 (s, 1H), 8.21 (d, J=5.3 Hz, 2H), 7.66 (d, J=1.5 Hz, 1H), 7.18 (d, J=5.3 Hz, 1H), 5.24 (t, J=5.8 Hz, 1H), 5.13 (t, J=5.8 Hz, 1H), 3.68 (d, J=4.9 Hz, 2H), 3.19 (d, J=10.8 Hz, 1H), 3.16-3.07 (m, 1H), 3.03 (s, 2H), 2.86-2.67 (m, 3H), 2.68-2.52 (m, 2H), 2.41 (t, J=10.6 Hz, 1H), 2.34 (d, J=7.7 Hz, 1H), 2.12 (ddd, J=27.4, 13.6, 7.6 Hz, 3H), 1.86 (ddt, J=28.6, 14.3, 6.8 Hz, 2H), 1.19 (q, J=12.3 Hz, 2H) ppm.

Example 106

2-Amino-N-{4-[(3S,5R)-3-amino-5-(trifluoromethyl)piperidin-1-yl]pyridin-3-yl}-6-{[(3S)-3-fluoropyrrolidin-1-yl]methyl}furo[3,2-b]pyridine-3-carboxamide

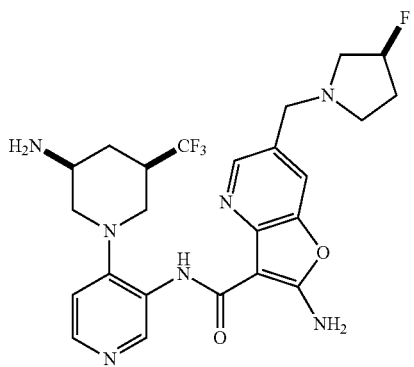 [SMILES: Nc1oc2cc(CN3CC[C@H](F)C3)cnc2c1C(=O)Nc1cnccc1N1C[C@@H](N)C[C@@H](C(F)(F)F)C1]

Step 1. tert-Butyl [(3S,5R)-1-(3-{[(2-[(tert-butoxycarbonyl)amino]-6-{[(3S)-3-fluoropyrrolidin-1-yl]methyl}furo[3,2-b]pyridin-3-yl)carbonyl]amino}pyridin-4-yl)-5-(trifluoromethyl)piperidin-3-yl]carbamate

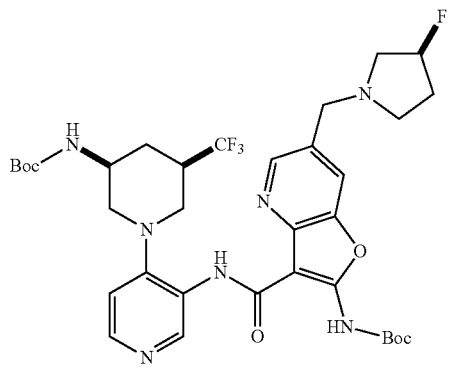 [SMILES: CC(C)(C)OC(=O)Nc1oc2cc(CN3CC[C@H](F)C3)cnc2c1C(=O)Nc1cnccc1N1C[C@@H](NC(=O)OC(C)(C)C)C[C@@H](C(F)(F)F)C1]

224

A mixture of tert-butyl [(3S,5R)-1-{3-[({2-[(tert-butoxycarbonyl)amino]-6-formylfuro[3,2-b]pyridin-3-yl}carbonyl)amino]pyridin-4-yl}-5-(trifluoromethyl)piperidin-3-yl]carbamate (10.0 mg, 0.015 mmol) (prepared in Example 99, step 4) and (3S)-3-fluoropyrrolidine hydrochloride (2.3 mg, 0.02 mmol) in dry 1,2-dichloroethane (0.07 mL) was treated with DIPEA (4 μL, 0.02 mmol), followed by sodium triacetoxyborohydride resin (6.5 mg, 0.03 mmol). The mixture was then stirred at room temperature for 1 h. The reaction mixture was filtered and concentrated under reduced pressure to give the crude product, which was used directly in the next step. LCMS calc. for $C_{34}H_{44}F_4N_7O_6$ (M+H)$^+$: m/z=722.2. Found: 722.2.

Step 2. 2-Amino-N-{4-[(3S,5R)-3-amino-5-(trifluoromethyl)piperidin-1-yl]pyridin-3-yl}-6-{[(3S)-3-fluoropyrrolidin-1-yl]methyl}furo[3,2-b]pyridine-3-carboxamide To a solution of tert-butyl [(3S,5R)-1-(3-{[(2-[(tert-butoxycarbonyl)amino]-6-{[(3S)-3-fluoropyrrolidin-1-yl]methyl}furo[3,2-b]pyridin-3-yl)carbonyl]amino}pyridin-4-yl)-5-(trifluoromethyl)piperidin-3-yl]carbamate (11.1 mg, 0.015 mmol) in MeOH (0.10 mL) was added 4.0 M HCl in dioxane (0.31 mL, 1.2 mmol). The reaction mixture was stirred at room temperature for 1 h. The solvents were removed under reduced pressure, then the residue was diluted with MeOH and NH$_4$OH, and purified by preparative LCMS (pH=10 method; XBridge™ PrepC18 5 μm OBD™ column, 30×10 mm, 60 mL/min., eluting with a gradient of MeCN and water with NH$_4$OH) to give the title compound (4.8 mg, 60%). LCMS calc. for $C_{24}H_{28}F_4N_7O_2$ (M+H)$^+$: m/z=522.2. Found: 522.2.

Example 107

2-Amino-N-{4-[(3S,5R)-3-amino-5-(trifluoromethyl)piperidin-1-yl]pyridin-3-yl}-6-[(4-methoxypiperidin-1-yl)methyl]furo[3,2-b]pyridine-3-carboxamide

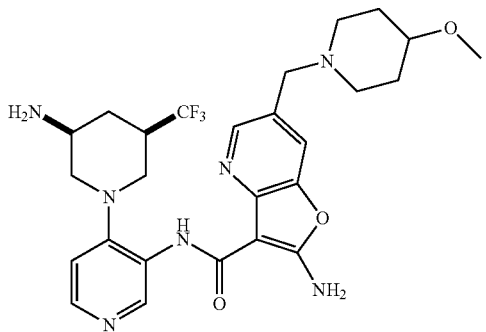 [SMILES: COC1CCN(Cc2cnc3c(C(=O)Nc4cnccc4N4C[C@@H](N)C[C@@H](C(F)(F)F)C4)c(N)oc3c2)CC1]

Step 1. tert-Butyl [(3S,5R)-1-{3-[({2-[(tert-butoxycarbonyl)amino]-6-[(4-methoxypiperidin-1-yl)methyl]furo[3,2-b]pyridin-3-yl}carbonyl)amino]pyridin-4-yl}-5-(trifluoromethyl)piperidin-3-yl]carbamate

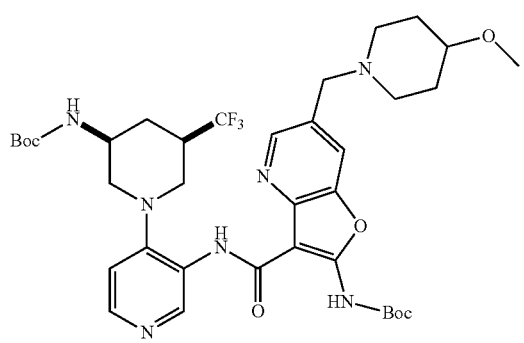 [SMILES: COC1CCN(Cc2cnc3c(C(=O)Nc4cnccc4N4C[C@@H](NC(=O)OC(C)(C)C)C[C@@H](C(F)(F)F)C4)c(NC(=O)OC(C)(C)C)oc3c2)CC1]

A mixture of 4-methoxypiperidine hydrochloride (2.1 mg, 0.014 mmol) and tert-butyl [(3S,5R)-1-{3-[({2-[(tert-butoxycarbonyl)amino]-6-formylfuro[3,2-b]pyridin-3-yl}carbonyl)amino]pyridin-4-yl}-5-(trifluoromethyl)piperidin-3-yl]carbamate (8.0 mg, 0.01 mmol) (prepared in Example 99, step 4) in dry 1,2-dichloroethane (0.10 mL, 1.3 mmol) was treated with sodium triacetoxyborohydride resin (5.2 mg, 0.025 mmol) and stirred at room temperature for 2 h. The reaction mixture was filtered and concentrated under reduced pressure to give the crude product, which was used directly in the next step. LCMS calc. for $C_{36}H_{49}F_3N_7O_7$ (M+H)$^+$: m/z=748.4. Found: 748.4.

Step 2. 2-Amino-N-{4-[(3S,5R)-3-amino-5-(trifluoromethyl)piperidin-1-yl]pyridin-3-yl}-6-[(4-methoxypiperidin-1-yl)methyl]furo[3,2-b]pyridine-3-carboxamide tert-Butyl [(3S,5R)-1-{3-[({2-[(tert-butoxycarbonyl)amino]-6-[(4-methoxypiperidin-1-yl)methyl]furo[3,2-b]pyridin-3-yl}carbonyl)amino]pyridin-4-yl}-5-(trifluoromethyl)piperidin-3-yl]carbamate (9 mg, 0.01 mmol) was dissolved in MeOH (0.20 mL), then 4.0 M solution of HCl in dioxane (1.0 mL, 4.0 mmol) was added. The reaction mixture was stirred at room temperature for 1 h. After removal of the solvents under reduced pressure, the residue was diluted with MeOH and NH$_4$OH, and purified by preparative LCMS (pH=10 method; XBridge™ PrepC18 5 μm OBD™ column, 30×10 mm, 60 mL/min., eluting with a gradient of MeCN and water with NH$_4$OH) to give the title compound. LCMS calc. for $C_{26}H_{33}F_3N_7O_3$ (M+H)$^+$: m/z=548.3. Found: 548.3.

Example 108

2-Amino-N-{4-[(3S,5R)-3-amino-5-(trifluoromethyl)piperidin-1-yl]pyridin-3-yl}-6-[(4-methylpiperazin-1-yl)methyl]furo[3,2-b]pyridine-3-carboxamide

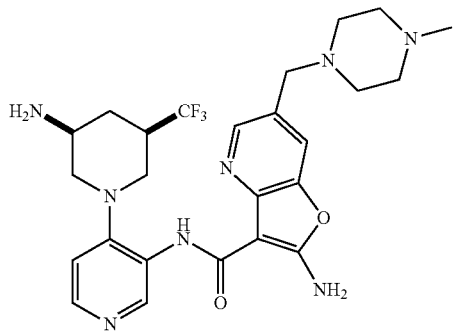 [SMILES: CN1CCN(Cc2cnc3c(C(=O)Nc4cnccc4N4C[C@@H](N)C[C@@H](C(F)(F)F)C4)c(N)oc3c2)CC1]

Step 1. tert-Butyl [(3S,5R)-1-{3-[({2-[(tert-butoxycarbonyl)amino]-6-[(4-methylpiperazin-1-yl)methyl]furo[3,2-b]pyridin-3-yl}carbonyl)amino]pyridin-4-yl}-5-(trifluoromethyl)piperidin-3-yl]carbamate

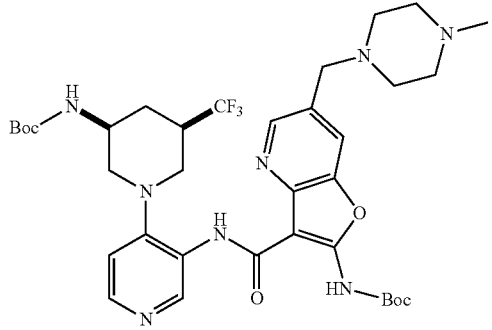 [SMILES: CN1CCN(Cc2cnc3c(C(=O)Nc4cnccc4N4C[C@@H](NC(=O)OC(C)(C)C)C[C@@H](C(F)(F)F)C4)c(NC(=O)OC(C)(C)C)oc3c2)CC1]

A mixture of tert-butyl [(3S,5R)-1-{3-[({2-[(tert-butoxycarbonyl)amino]-6-formylfuro[3,2-b]pyridin-3-yl}carbonyl)amino]pyridin-4-yl}-5-(trifluoromethyl)piperidin-3-yl]carbamate (90.0 mg, 0.14 mmol) (prepared in Example 99, step 4) and 1-methylpiperazine (16.7 mg, 0.17 mmol) in dry 1,2-dichloroethane (0.66 mL) was treated by the addition of sodium triacetoxyborohydride resin (58.8 mg, 0.28 mmol) and stirred at room temperature for 1 h. The reaction mixture was filtered and concentrated under reduced pressure to give the crude product, which was used directly in the next step. LCMS calc. for $C_{35}H_{48}F_3N_8O_6$ (M+H)$^+$: m/z=733.2. Found: 733.2.

Step 2. 2-Amino-N-{4-[(3S,5R)-3-amino-5-(trifluoromethyl)piperidin-1-yl]pyridin-3-yl}-6-[(4-methylpiperazin-1-yl)methyl]furo[3,2-b]pyridine-3-carboxamide To a solution of tert-butyl [(3S,5R)-1-{3-[({2-[(tert-butoxycarbonyl)amino]-6-[(4-methylpiperazin-1-yl)methyl]furo[3,2-b]pyridin-3-yl}carbonyl)amino]pyridin-4-yl}-5-(trifluoromethyl)piperidin-3-yl]carbamate (102 mg, 0.14 mmol) in MeOH (0.23 mL) was added 4.0 M solution of HCl in dioxane (2.78 mL, 11 mmol). The reaction mixture was stirred at room temperature for 2 h. After removal of the solvents under reduced pressure, the residue was diluted with MeOH and NH$_4$OH, and purified by preparative LCMS (pH=10 method; XBridge™ PrepC18 5 μm OBD™ column, 30×10 mm, 60 mL/min., eluting with a gradient of MeCN and water with NH$_4$OH) to give the title compound (41.4 mg, 56%). LCMS calc. for $C_{25}H_{32}F_3N_8O_2$ (M+H)$^+$: m/z=533.2. Found: 533.2. $^1$H NMR (500 MHz, DMSO-d$_6$): δ 10.00 (s, 1H), 9.46 (s, 2H), 8.56 (d, J=6.6 Hz, 3H), 8.39 (d, J=13.4 Hz, 3H), 7.86 (s, 3H), 7.70 (d, J=6.6 Hz, 3H), 3.90 (dd, J=43.3, 9.0 Hz, 3H), 3.66 (s, 1H), 3.10 (d, J=8.0 Hz, 3H), 2.95 (t, J=11.8 Hz, 3H), 2.43 (d, J=11.9 Hz, 2H), 1.75 (s, 2H), 1.66 (q, J=11.8 Hz, 2H) ppm.

Example 109

2-Amino-N-{4-[(3S,5R)-3-amino-5-(trifluoromethyl)piperidin-1-yl]pyridin-3-yl}-6-(1-methyl-1H-pyrazol-4-yl)furo[3,2-b]pyridine-3-carboxamide

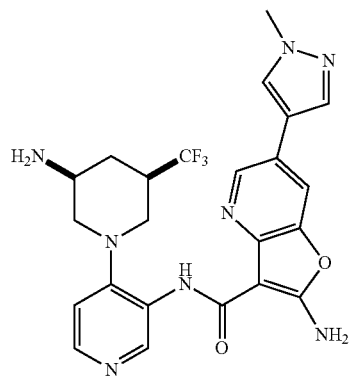 [SMILES: Cn1cc(-c2cnc3c(C(=O)Nc4cnccc4N4C[C@@H](N)C[C@@H](C(F)(F)F)C4)c(N)oc3c2)cn1]

Step 1. Ethyl 2-[(tert-butoxycarbonyl)amino]-6-(1-methyl-1H-pyrazol-4-yl)furo[3,2-b]pyridine-3-carboxylate

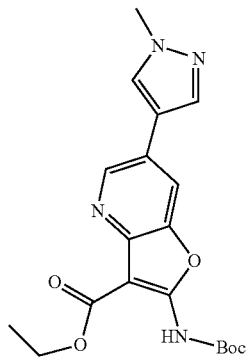 [SMILES: CCOC(=O)c1c(NC(=O)OC(C)(C)C)oc2cc(-c3cnn(C)c3)cnc12]

A mixture of ethyl 6-bromo-2-[(tert-butoxycarbonyl)amino]furo[3,2-b]pyridine-3-carboxylate (150 mg, 0.39 mmol), 1-methyl-4-(4,4,5,5-tetramethyl-1,3,2-dioxaborolan-2-yl)-1H-pyrazole (97.2 mg, 0.47 mmol), dicyclohexyl(2',4',6'-triisopropylbiphenyl-2-yl)phosphine-(2'-aminobiphenyl-2-yl)(chloro)palladium (1:1) (49.0 mg, 0.062 mmol) and K$_3$PO$_4$ (165 mg, 0.78 mmol) in 1,4-dioxane (1.22 mL) and water (0.28 mL) was stirred at 100° C. for 2 h under a N$_2$ atmosphere. The crude mixture was diluted with EtOAc and water. The organic layer was separated and dried over Na$_2$SO$_4$ and filtered. The filtrate was concentrated under reduced pressure. The residue was purified by silica gel column chromatography (0 to 10% MeOH in EtOAc) to give the sub-title compound as an off-white powder (69 mg, 46%). LCMS calc. for C$_{19}$H$_{23}$N$_4$O$_5$ (M+H)$^+$: m/z=387.2. Found: 387.2.

Step 2. 2[(tert-Butoxycarbonyl)amino]-6-(1-methyl-1H-pyrazol-4-yl)furo[3,2-b]pyridine-3-carboxylic acid

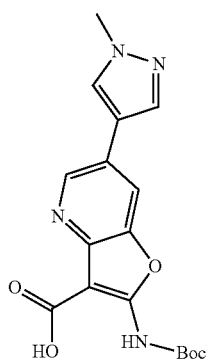 [SMILES: Cn1cc(-c2cnc3c(C(=O)O)c(NC(=O)OC(C)(C)C)oc3c2)cn1]

A mixture of ethyl 2-[(tert-butoxycarbonyl)amino]-6-(1-methyl-1H-pyrazol-4-yl)furo[3,2-b]pyridine-3-carboxylate (69.0 mg, 0.18 mmol), LiOH.H$_2$O (42.8 mg, 1.8 mmol), THF (0.46 mL), water (0.15 mL) and MeCN (0.35 mL) was stirred at 70° C. for 6 h. The solvents were removed under reduced pressure and the pH was adjusted to 7 with 3 M HCl. The crude mixture was diluted with MeOH and purified by preparative LCMS (pH=10 method; XBridge™ PrepC18 5 μm OBD™ column, 30×10 mm, 60 mL/min., eluting with a gradient of MeCN and water with NH$_4$OH) to give the sub-title compound as an off-white powder (44 mg, 69%). LCMS calc. for C$_{17}$H$_{19}$N$_4$O$_5$ (M+H)$^+$: m/z=359.2. Found: 359.2.

Step 3. tert-Butyl [(3S,5R)-1-[3-({[2-[(tert-butoxycarbonyl)amino]-6-(1-methyl-1H-pyrazol-4-yl)furo[3,2-b]pyridin-3-yl]carbonyl}amino)pyridin-4-yl]-5-(trifluoromethyl)piperidin-3-yl]carbamate

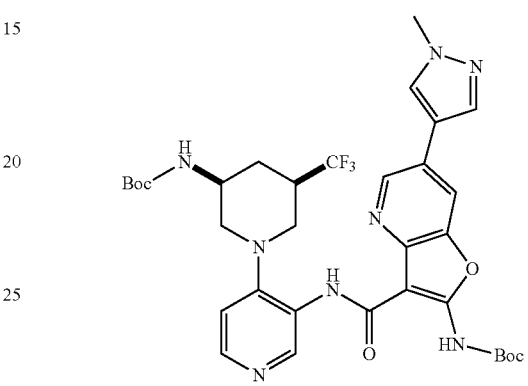

A mixture of tert-butyl [(3S,5R)-1-(3-aminopyridin-4-yl)-5-(trifluoromethyl)piperidin-3-yl]carbamate (16.9 mg, 0.047 mmol), 2-[(tert-butoxycarbonyl)amino]-6-(1-methyl-1H-pyrazol-4-yl)furo[3,2-b]pyridine-3-carboxylic acid (14.0 mg, 0.039 mmol) and molecular sieves (35.0 mg, 0.16 mmol) (4 Å) in 1,2-dichloroethane (0.25 mL) was stirred vigorously at room temperature for 30 min., then DIPEA (20.4 μL, 0.12 mmol) and HATU (74.3 mg, 0.20 mmol) were added. The reaction mixture was stirred vigorously at room temperature for 2 h. The mixture was filtered, and solids were washed with THF. The filtrate was concentrated under reduced pressure, and the residue was diluted with MeOH and purified by preparative LCMS (pH=10 method; XBridge™ PrepC18 5 μm OBD™ column, 30×10 mm, 60 mL/min., eluting with a gradient of MeCN and water with NH$_4$OH) to give the sub-title compound as an off-white powder (4 mg, 10%). LCMS calc. for C$_{33}$H$_{40}$F$_3$N$_8$O$_6$ (M+H)$^+$: m/z=701.3. Found: 701.3.

Step 4. 2-Amino-N-{4-[(3S,5R)-3-amino-5-(trifluoromethyl)piperidin-1-yl]pyridin-3-yl}-6-(1-methyl-1H-pyrazol-4-yl)furo[3,2-b]pyridine-3-carboxamide To a solution of tert-butyl [(3S,5R)-1-[3-({[2-[(tert-butoxycarbonyl)amino]-6-(1-methyl-1H-pyrazol-4-yl)furo[3,2-b]pyridin-3-yl]carbonyl}amino)pyridin-4-yl]-5-(trifluoromethyl)piperidin-3-yl]carbamate (4 mg, 0.01 mmol) in MeOH (0.02 mL) was added 4.0 M solution of HCl in dioxane (0.11 mL, 0.43 mmol). The reaction mixture was stirred at room temperature for 1 h. After removal of the solvents, the residue was diluted with MeOH and NH$_4$OH, and purified by preparative LCMS (pH=10 method; XBridge™ PrepC 18 5 μm OBD™ column, 30×10 mm, 60 mL/min., eluting with a gradient of MeCN and water with NH$_4$OH) to give the title compound (2 mg, 74%). LCMS calc. for C$_{23}$H$_{24}$F$_3$N$_8$O$_2$ (M+H)$^+$: m/z=501.2. Found: 501.2.

Example 110

2-Amino-N-{4-[(3S,5R)-3-amino-5-methylpiperidin-1-yl]pyridin-3-yl}-6-(1-methyl-1H-pyrazol-4-yl)furo[3,2-b]pyridine-3-carboxamide

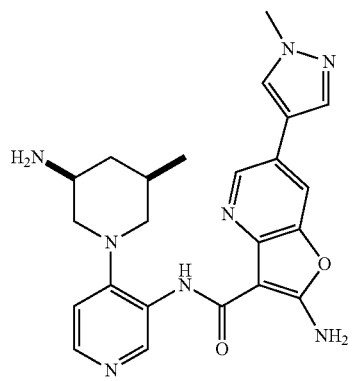 [SMILES: C[C@@H]1C[C@H](N)CN(c2ccncc2NC(=O)c2c(N)oc3cc(-c4cnn(C)c4)cnc23)C1]

Step 1. tert-Butyl [3-{[(4-{(3S,5R)-3-[(tert-butoxycarbonyl)amino]-5-methylpiperidin-1-yl}pyridin-3-yl)amino]carbonyl}-6-(1-methyl-1H-pyrazol-4-yl)furo[3,2-b]pyridin-2-yl]carbamate

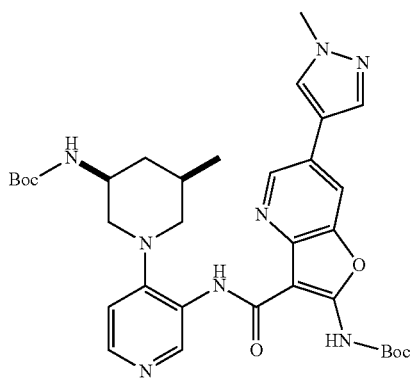 [SMILES: C[C@@H]1C[C@H](NC(=O)OC(C)(C)C)CN(c2ccncc2NC(=O)c2c(NC(=O)OC(C)(C)C)oc3cc(-c4cnn(C)c4)cnc23)C1]

A mixture of tert-butyl [(3S,5R)-1-(3-aminopyridin-4-yl)-5-methylpiperidin-3-yl]carbamate (14.4 mg, 0.047 mmol), 2-[(tert-butoxycarbonyl)amino]-6-(1-methyl-1H-pyrazol-4-yl)furo[3,2-b]pyridine-3-carboxylic acid (14.0 mg, 0.039 mmol) (prepared in Example 109, step 2) and molecular sieves (35.0 mg, 0.16 mmol) (4 Å) in 1,2-dichloroethane (0.22 mL) was stirred vigorously at room temperature for 30 min., then DIPEA (20.4 µL, 0.12 mmol) and HATU (74.3 mg, 0.20 mmol) were added. The reaction mixture was stirred vigorously at room temperature for 2 h. The mixture was filtered, and solids were washed with THF. The filtrate was concentrated under reduced pressure, and the residue was diluted with MeOH and purified by preparative LCMS (pH=10 method; XBridge™ PrepC18 5 µm OBD™ column, 30×10 mm, 60 mL/min., eluting with a gradient of MeCN and water with NH₄OH) to give the sub-title compound as an off-white powder (4.3 mg, 17%). LCMS calc. for $C_{33}H_{43}N_8O_6$ $(M+H)^+$: m/z=647.3. Found: 647.3.

Step 2. 2-Amino-N-{4-[(3S,5R)-3-amino-5-methylpiperidin-1-yl]pyridin-3-yl}-6-(1-methyl-1H-pyrazol-4-yl)furo[3,2-b]pyridine-3-carboxamide To a solution of tert-butyl [3-{[(4-{(3S,5R)-3-[(tert-butoxycarbonyl)amino]-5-methylpiperidin-1-yl}pyridin-3-yl)amino]carbonyl}-6-(1-methyl-1H-pyrazol-4-yl)furo[3,2-b]pyridin-2-yl]carbamate (4.3 mg, 0.01 mmol) in MeOH (0.05 mL) was added a 4.0 M solution of HCl in dioxane (0.13 mL, 0.53 mmol). The reaction mixture was stirred at room temperature for 1 h. After removal of the solvents, the residue was diluted with MeOH and NH₄OH, and purified by preparative LCMS (pH=10 method; XBridge™ PrepC18 5 µm OBD™ column, 30×10 mm, 60 mL/min., eluting with a gradient of MeCN and water with NH₄OH) to give the title compound (3 mg, 84%). LCMS calc. for $C_{23}H_{27}N_8O_2$ $(M+H)^+$: m/z=447.2. Found: 447.2.

Example 111

2-Amino-N-{4-[(3S,5R)-3-amino-5-(trifluoromethyl)piperidin-1-yl]pyridin-3-yl}-6-pyrimidin-5-ylfuro[3,2-b]pyridine-3-carboxamide

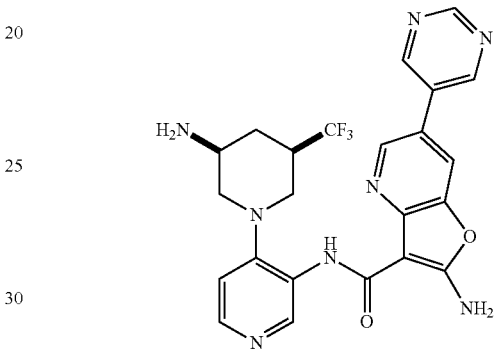

Step 1. Methyl 2-[bis(tert-butoxycarbonyl)amino]-6-pyrimidin-5-ylfuro[3,2-b]pyridine-3-carboxylate

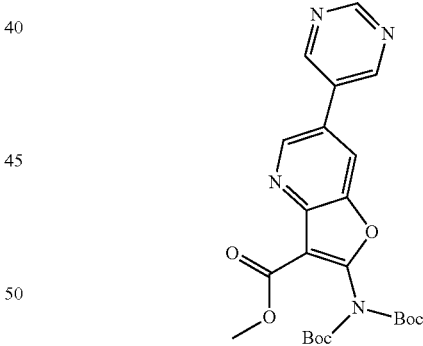

A mixture of methyl 2-[bis(tert-butoxycarbonyl)amino]-6-bromofuro[3,2-b]pyridine-3-carboxylate (300 mg, 0.64 mmol), pyrimidin-5-ylboronic acid (94.6 mg, 0.76 mmol), dicyclohexyl(2',4',6'-triisopropylbiphenyl-2-yl)phosphine-(2'-aminobiphenyl-2-yl)(chloro)palladium (1:1) (80.1 mg, 0.10 mmol) and K₃PO₄ (270 mg, 1.27 mmol) in 1,4-dioxane (1.99 mL) and water (0.46 mL) was stirred at 90° C. for 2 h under N₂ atmosphere. The crude product was diluted with EtOAc and water. The organic layer was separated, dried over anhydrous Na₂SO₄ and filtered. The filtrate was concentrated under reduced pressure. The residue was purified by silica gel column chromatography (0 to 10% MeOH in EtOAc) to give the product as a light yellow powder (108 mg, 36%). LCMS calc. for $C_{23}H_{27}N_4O_7$ $(M+H)^+$: m/z=471.2. Found: 471.2.

Step 2. 2-[(tert-Butoxycarbonyl)amino]-6-pyrimidin-5-ylfuro[3,2-b]pyridine-3-carboxylic acid

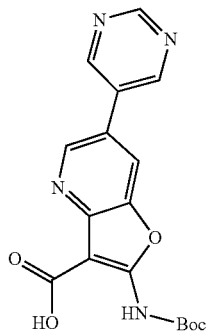 [SMILES: CC(C)(C)OC(=O)Nc1oc2cc(-c3cncnc3)cnc2c1C(=O)O]

A mixture of methyl 2-[bis(tert-butoxycarbonyl)amino]-6-pyrimidin-5-ylfuro[3,2-b]pyridine-3-carboxylate (108 mg, 0.23 mmol) and LiOH.H$_2$O (44 mg, 1.8 mmol) in THF (0.60 mL), water (0.20 mL) and MeOH (0.30 mL) was stirred at 70° C. for 2 h. The solvents were removed and pH was adjusted to 7 with 3 M HCl. The crude mixture was diluted with MeOH and purified by preparative LCMS (pH=10 method; XBridge™ PrepC 18 5 μm OBD™ column, 30×10 mm, 60 mL/min., eluting with a gradient of MeCN and water with NH$_4$OH) to give the sub-title compound as an off-white powder (24 mg, 29%). LCMS calc. for C$_{17}$H$_{17}$N$_4$O$_5$ (M+H)$^+$: m/z=357.2. Found: 357.2.

Step 3. tert-Butyl [(3S,5R)-1-{3-[({2-[(tert-butoxycarbonyl)amino]-6-pyrimidin-5-ylfuro[3,2-b]pyridin-3-yl}carbonyl)amino]pyridin-4-yl}-5-(trifluoromethyl)piperidin-3-yl]carbamate

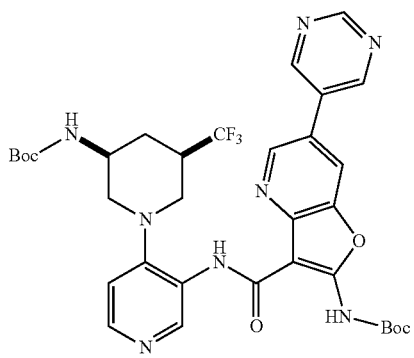

A mixture of tert-butyl [(3S,5R)-1-(3-aminopyridin-4-yl)-5-(trifluoromethyl)piperidin-3-yl]carbamate (12.1 mg, 0.034 mmol), 2-[(tert-butoxycarbonyl)amino]-6-pyrimidin-5-ylfuro[3,2-b]pyridine-3-carboxylic acid (10.0 mg, 0.03 mmol) and molecular sieves (25.1 mg, 0.11 mmol) (4 Å) in 1,2-dichloroethane (0.155 mL) was stirred vigorously at room temperature for 30 min., then DIPEA (14.7 μL, 0.08 mmol) and HATU (53.4 mg, 0.14 mmol) were added. The reaction mixture was stirred vigorously at room temperature for 2 h. The mixture was filtered, washed with THF. The filtrate was concentrated under reduced pressure, and the residue was diluted with MeOH and purified by preparative LCMS (pH=10 method; XBridge™ PrepC18 5 μm OBD™ column, 30×10 mm, 60 mL/min., eluting with a gradient of MeCN and water with NH$_4$OH) to give the sub-title compound as an off-white powder (3.0 mg, 15%). LCMS calc. for C$_{33}$H$_{38}$F$_3$N$_8$O$_6$ (M+H)$^+$: m/z=699.2. Found: 699.2.

Step 4. 2-Amino-N-{4-[(3S,5R)-3-amino-5-(trifluoromethyl)piperidin-1-yl]pyridin-3-yl}-6-pyrimidin-5-ylfuro[3,2-b]pyridine-3-carboxamide To a solution of tert-butyl [(3S,5R)-1-{3-[({2-[(tert-butoxycarbonyl)amino]-6-pyrimidin-5-ylfuro[3,2-b]pyridin-3-yl}carbonyl)amino]pyridin-4-yl}-5-(trifluoromethyl)piperidin-3-yl]carbamate (3.0 mg, 0.004 mmol) in MeOH (0.04 mL) was added a 4.0 M solution of HCl in dioxane (0.1 mL, 0.4 mmol). The reaction mixture was stirred at room temperature for 45 min. After removal of the solvents, the residue was diluted with MeOH and NH$_4$OH, and purified by preparative LCMS (pH=10 method; XBridge™ PrepC18 5 μm OBD™ column, 30×10 mm, 60 mL/min., eluting with a gradient of MeCN and water with NH$_4$OH) to give the title compound (2 mg, 94%). LCMS calc. for C$_{23}$H$_{22}$F$_3$N$_8$O$_2$ (M+H)$^+$: m/z=499.2. Found: 499.2.

Example 112

2-Amino-N-{4-[(3S,5R)-3-amino-5-methylpiperidin-1-yl]pyridin-3-yl}-6-pyrimidin-5-ylfuro[3,2-b]pyridine-3-carboxamide

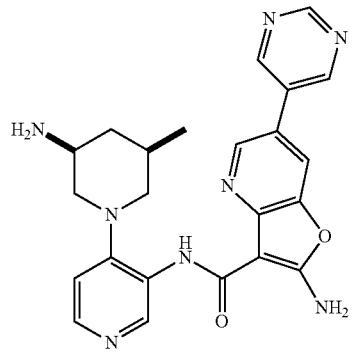 [SMILES: C[C@@H]1C[C@H](N)CN(c2ccncc2NC(=O)c2c(N)oc3cc(-c4cncnc4)cnc23)C1]

Step 1. tert-Butyl (3-{[(4-{(3S,5R)-3-[(tert-butoxycarbonyl)amino]-5-methylpiperidin-1-yl}pyridin-3-yl)amino]carbonyl}-6-pyrimidin-5-ylfuro[3,2-b]pyridin-2-yl)carbamate

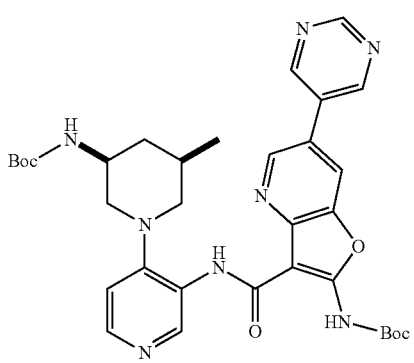 [SMILES: C[C@@H]1C[C@H](NC(=O)OC(C)(C)C)CN(c2ccncc2NC(=O)c2c(NC(=O)OC(C)(C)C)oc3cc(-c4cncnc4)cnc23)C1]

A mixture of tert-butyl [(3S,5R)-1-(3-aminopyridin-4-yl)-5-methylpiperidin-3-yl]carbamate (10.3 mg, 0.03 mmol), 2-[(tert-butoxycarbonyl)amino]-6-pyrimidin-5-ylfuro[3,2-b]pyridine-3-carboxylic acid (10.0 mg, 0.03 mmol) and molecular sieves (25 mg, 0.11 mmol) (4 Å) in 1,2-dichloroethane (0.16 mL) was stirred vigorously at room temperature for 30 min., then DIPEA (14.7 μL, 0.08 mmol) and HATU (53.4 mg, 0.14 mmol) were added. The reaction mixture was stirred vigorously at room temperature for 2 h. The mixture was filtered, and the solids were washed with THF. The filtrate was concentrated under reduced pressure, and the residue was diluted with MeOH and purified by preparative LCMS (pH=10 method; XBridge™ PrepC18 5 μm OBD™ column, 30×10 mm, 60 mL/min., eluting with a gradient of MeCN and water with NH₄OH) to give the sub-title compound as an off-white powder (10 mg). LCMS calc. for $C_{33}H_{41}N_8O_6$ (M+H)⁺: m/z=645.3. Found: 645.3.

Step 2. 2-Amino-N-{4-[(3S,5R)-3-amino-5-methylpiperidin-1-yl]pyridin-3-yl}-6-pyrimidin-5-ylfuro[3,2-b]pyridine-3-carboxamide To a solution of tert-butyl (3-{[(4-{(3S,5R)-3-[(tert-butoxycarbonyl)amino]-5-methylpiperidin-1-yl}pyridin-3-yl)amino]carbonyl}-6-pyrimidin-5-ylfuro[3,2-b]pyridin-2-yl)carbamate (10.0 mg, 0.01 mmol) in MeOH (0.02 mL) was added a 4.0 M solution of HCl in dioxane (0.12 mL, 0.5 mmol). The reaction mixture was stirred at room temperature for 1 h. After removal of the solvents, the residue was diluted with MeOH and NH₄OH, and purified by preparative LCMS (pH=10 method; XBridge™ PrepC18 5 μm OBD™ column, 30×10 mm, 60 mL/min., eluting with a gradient of MeCN and water with NH₄OH) to give the title compound (2 mg, 54%). LCMS calc. for $C_{23}H_{25}N_8O_2$ (M+H)⁺: m/z=445.3. Found: 445.3.

Example 113

2-Amino-N-{4-[(3S,5R)-3-amino-5-(trifluoromethyl)piperidin-1-yl]pyridin-3-yl}-6-cyclopropylfuro[3,2-b]pyridine-3-carboxamide

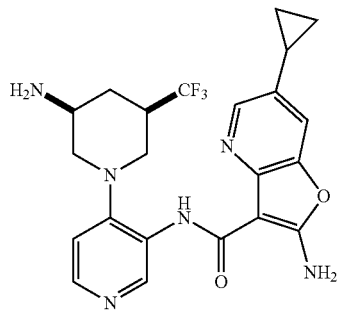 [SMILES: Nc1oc2cc(C3CC3)cnc2c1C(=O)Nc1cnccc1N1C[C@@H](N)C[C@@H](C(F)(F)F)C1]

Step 1. Ethyl 2-[(tert-butoxycarbonyl)amino]-6-cyclopropylfuro[3,2-b]pyridine-3-carboxylate

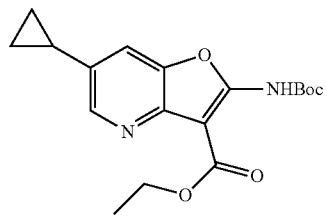 [SMILES: CCOC(=O)c1c(NC(=O)OC(C)(C)C)oc2cc(C3CC3)cnc12]

To a microwave vial was added ethyl 6-bromo-2-[(tert-butoxycarbonyl)amino]furo[3,2-b]pyridine-3-carboxylate (300 mg, 0.78 mmol), potassium cyclopropyltrifluoroborate (210 mg, 1.4 mmol), Cs₂CO₃ (761 mg, 2.34 mmol), Pd(OAc)₂ (35 mg, 0.16 mmol) and di-1-adamantyl(butyl)phosphine (42 mg, 0.12 mmol). The vial was sealed, evacuated and filled with N₂ three times. Toluene (2.86 mL) and water (0.28 mL) were added. The reaction mixture was heated at 110° C. for 26 h. The reaction mixture was diluted with water and EtOAc. The aqueous layer was extracted with EtOAc. The combined organic layers were dried over Na₂SO₄, filtered and concentrated under reduced pressure. The residue was dissolved in THF (3 mL), followed by the addition of Boc₂O (0.13 g) and DMAP (13 mg). The reaction mixture was stirred at room temperature for 16 h. The solvent was removed and the crude product was purified by silica gel column chromatography (0 to 80% EtOAc in hexanes) to give the sub-title compound as a yellow foam. LCMS calc. for $C_{18}H_{23}N_2O_5$ (M+H)⁺: m/z=347.2. Found: 347.2.

Step 2. 2-[(tert-Butoxycarbonyl)amino]-6-cyclopropylfuro[3,2-b]pyridine-3-carboxylic acid

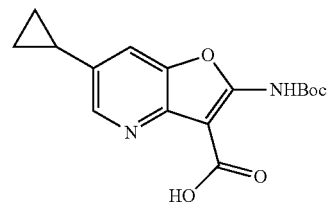 [SMILES: CC(C)(C)OC(=O)Nc1oc2cc(C3CC3)cnc2c1C(=O)O]

A mixture of ethyl 2-[(tert-butoxycarbonyl)amino]-6-cyclopropylfuro[3,2-b]pyridine-3-carboxylate (157 mg, 0.45 mmol) and LiOH.H₂O (59 mg, 2.5 mmol) in THF (1.7 mL), water (0.57 mL) and MeOH (1.1 mL) was stirred at 60° C. for 16 h. The solvents were removed under reduced pressure and the pH was adjusted to 7 with 3 M HCl. The aqueous layer was extracted with EtOAc. The organic layer was separated and washed with brine, dried over Na₂SO₄ and concentrated under reduced pressure to give the sub-title compound as light brown powder (103 mg, 71%). LCMS calc. for $C_{16}H_{19}N_2O_5$ (M+H)⁺: m/z=319.2. Found: 319.2.

Step 3. tert-Butyl [(3S,5R)-1-{3-[({2-[(tert-butoxycarbonyl)amino]-6-cyclopropylfuro[3,2-b]pyridin-3-yl}carbonyl)amino]pyridin-4-yl}-5-(trifluoromethyl)piperidin-3-yl]carbamate

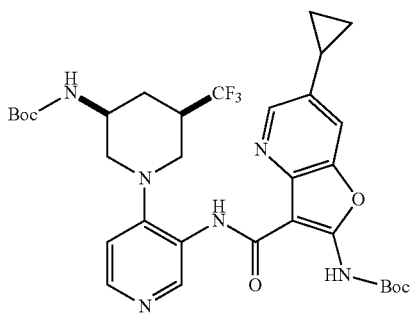 [SMILES: CC(C)(C)OC(=O)Nc1oc2cc(C3CC3)cnc2c1C(=O)Nc1cnccc1N1C[C@@H](NC(=O)OC(C)(C)C)C[C@@H](C(F)(F)F)C1]

A mixture of tert-butyl [(3S,5R)-1-(3-aminopyridin-4-yl)-5-(trifluoromethyl)piperidin-3-yl]carbamate (20.4 mg, 0.06 mmol), 2-[(tert-butoxycarbonyl)amino]-6-cyclopropylfuro[3,2-b]pyridine-3-carboxylic acid (15.0 mg, 0.05 mmol) and molecular sieves (42 mg, 0.19 mmol) (4 Å) in 1,2-dichloroethane (0.26 m) was stirred vigorously at room temperature for 30 min., followed by the addition of DIPEA (25 μL, 0.14 mmol) and HATU (89.6 mg, 0.24 mmol). The reaction mixture was stirred vigorously at room temperature for 2 h. The mixture was filtered and washed with THF. The filtrate was concentrated under reduced pressure, and the residue was purified by preparative LCMS (pH=10 method; XBridge™ PrepC18 5 μm OBD™ column, 30×10 mm, 60 mL/min., eluting with a gradient of MeCN and water with NH₄OH) to give the sub-title compound as an off-white powder (7.0 mg, 22%). LCMS calc. for $C_{32}H_{40}F_3N_6O_6$ $(M+H)^+$: m/z=661.2. Found: 661.2.

Step 4. 2-Amino-N-{4-[(3S,5R)-3-amino-5-(trifluoromethyl)piperidin-1-yl]pyridin-3-yl}-6-cyclopropylfuro[3,2-b]pyridine-3-carboxamide To a solution of tert-butyl [(3S,5R)-1-{3-[({2-[(tert-butoxycarbonyl)amino]-6-cyclopropylfuro[3,2-b]pyridin-3-yl}carbonyl)amino]pyridin-4-yl}-5-(trifluoromethyl)piperidin-3-yl]carbamate (6.1 mg, 0.01 mmol) in MeOH (0.02 mL) was added a 4.0 M solution of HCl in dioxane (0.19 mL, 0.74 mmol). The reaction mixture was stirred at room temperature for 16 h. After removal of the solvents under reduced pressure, the residue was diluted with MeOH and NH₄OH, and purified by preparative LCMS (pH=10 method; XBridge™ PrepC18 5 μm OBD™ column, 30×10 mm, 60 mL/min., eluting with a gradient of MeCN and water with NH₄OH) to give the title compound (2.0 mg, 47%). LCMS calc. for $C_{22}H_{24}F_3N_6O_2$ $(M+H)^+$: m/z=461.3. Found: 461.3.

Example 114

2-Amino-N-{4-[(3S,5R)-3-amino-5-methylpiperidin-1-yl]pyridin-3-yl}-6-cyclopropylfuro[3,2-b]pyridine-3-carboxamide

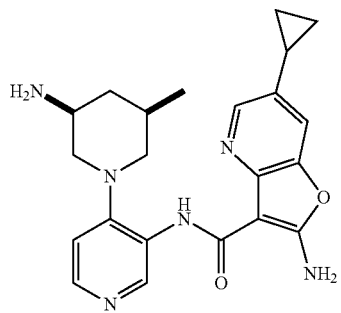 [SMILES: C[C@@H]1C[C@H](N)CN(c2ccncc2NC(=O)c2c(N)oc3cc(C4CC4)cnc23)C1]

Step 1. tert-Butyl ((3S,5R)-1-{3-[({2-[(tert-butoxycarbonyl)amino]-6-cyclopropylfuro[3,2-b]pyridin-3-yl}carbonyl)amino]pyridin-4-yl}-5-methylpiperidin-3-yl)carbamate

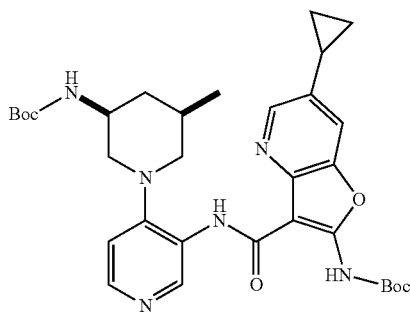 [SMILES: C[C@@H]1C[C@H](NC(=O)OC(C)(C)C)CN(c2ccncc2NC(=O)c2c(NC(=O)OC(C)(C)C)oc3cc(C4CC4)cnc23)C1]

A mixture of tert-butyl [(3S,5R)-1-(3-aminopyridin-4-yl)-5-methylpiperidin-3-yl]carbamate (17.3 mg, 0.06 mmol), 2-[(tert-butoxycarbonyl)amino]-6-cyclopropylfuro[3,2-b]pyridine-3-carboxylic acid (15 mg, 0.05 mmol) (prepared in Example 113, step 2) and molecular sieves (42 mg, 0.19 mmol) (4 Å) in 1,2-dichloroethane (0.26 mL) was stirred vigorously at room temperature for 30 min., then DIPEA (25 μL, 0.14 mmol) and HATU (89.6 mg, 0.24 mmol) were added. The reaction mixture was stirred vigorously at room temperature for 2 h. The mixture was filtered and solids were washed with THF. The filtrate was concentrated under reduced pressure, and the residue was purified by preparative LCMS (pH=10 method; XBridge™ PrepC18 5 μm OBD™ column, 30×10 mm, 60 mL/min., eluting with a gradient of MeCN and water with NH₄OH) to give the sub-title compound as an off-white powder (3 mg, 10%). LCMS calc. for $C_{32}H_{43}N_6O_6$ $(M+H)^+$: m/z=607.2. Found: 607.2.

Step 2. 2-Amino-N-{4-[(3S,5R)-3-amino-5-methylpiperidin-1-yl]pyridin-3-yl}-6-cyclopropylfuro[3,2-b]pyridine-3-carboxamide To a solution of tert-butyl ((3S,5R)-1-{3-[({2-[(tert-butoxycarbonyl)amino]-6-cyclopropylfuro[3,2-b]pyridin-3-yl}carbonyl)amino]pyridin-4-yl}-5-methylpiperidin-3-yl)carbamate (6.0 mg, 0.01 mmol) in MeOH (0.02 mL) was added a 4.0 M solution of HCl in dioxane (0.20 mL, 0.79 mmol). The reaction mixture was stirred at room temperature for 16 h. After removal of the solvents, the residue was diluted with MeOH and NH₄OH, and purified by preparative LCMS (pH=10 method; XBridge™ PrepC18 5 μm OBD™ column, 30×10 mm, 60 mL/min., eluting with a gradient of MeCN and water with NH₄OH) to give the title compound (2.3 mg, 57%). LCMS calc. for $C_{22}H_{27}N_6O_2$ $(M+H)^+$: m/z=407.2. Found: 407.2. ¹H NMR (400 MHz, DMSO-d₆): δ 10.09 (s, 1H), 9.44 (s, 1H), 8.22-8.08 (m, 2H), 7.34 (d, J=1.6 Hz, 1H), 7.10 (d, J=5.3 Hz, 1H), 3.15 (d, J=10.4 Hz, 2H), 3.06 (t, J=10.6 Hz, 2H), 2.16 (q, J=10.8 Hz, 2H), 2.06 (dq, J=8.4, 4.2, 3.3 Hz, 3H), 1.96 (d, J=12.4 Hz, 1H), 0.97 (dd, J=8.3, 2.1 Hz, 3H), 0.83 (d, J=6.5 Hz, 4H), 0.77-0.63 (m, 3H) ppm.

Example 115

2-Amino-N-{4-[(3S,5R)-3-amino-5-(trifluoromethyl)piperidin-1-yl]pyridin-3-yl}-6-methylfuro[3,2-b]pyridine-3-carboxamide

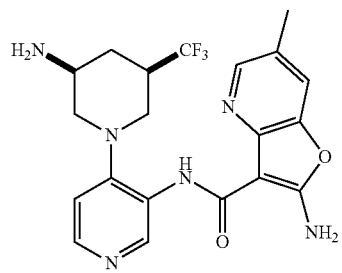 [SMILES: Cc1cnc2c(C(=O)Nc3cnccc3N3C[C@@H](N)C[C@@H](C(F)(F)F)C3)c(N)oc2c1]

Step 1. Methyl 2-[(tert-butoxycarbonyl)amino]-6-methylfuro[3,2-b]pyridine-3-carboxylate

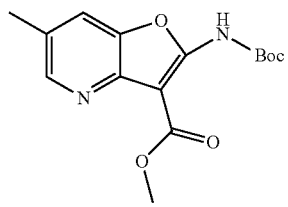 [SMILES: COC(=O)c1c(NC(=O)OC(C)(C)C)oc2cc(C)cnc12]

A mixture of methyl 6-bromo-2-[(tert-butoxycarbonyl)amino]furo[3,2-b]pyridine-3-carboxylate (150 mg, 0.40 mmol), trimethylboroxine (0.12 mL, 0.83 mmol), dicyclohexyl(2',4',6'-triisopropylbiphenyl-2-yl)phosphine-(2'-aminobiphenyl-2-yl)(chloro)palladium (1:1) (32 mg, 0.04 mmol) and $Cs_2CO_3$ (330 mg, 1.0 mmol) in 1,4-dioxane (3.0 mL) and water (0.40 mL) was evacuated and backfilled with $N_2$ three times. The reaction mixture was heated at 90° C. for 16 h. The crude mixture was filtered and purified by silica gel column chromatography (0 to 100% EtOAc in hexanes) to give the sub-title compound (113 mg, 91%). LCMS calc. for $C_{15}H_{19}N_2O_5$ $(M+H)^+$: m/z=307.1. Found: 307.1.

Step 2. 2-[(tert-Butoxycarbonyl)amino]-6-methyl-furo[3,2-b]pyridine-3-carboxylic acid

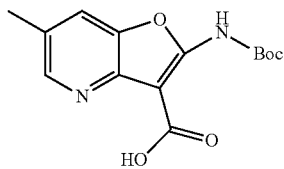 [SMILES: Cc1cnc2c(C(=O)O)c(NC(=O)OC(C)(C)C)oc2c1]

A mixture of methyl 2-[(tert-butoxycarbonyl)amino]-6-methylfuro[3,2-b]pyridine-3-carboxylate (429 mg, 1.4 mmol) and $LiOH·H_2O$ (270 mg, 11 mmol) in THF (5.3 mL), water (1.8 mL) and MeOH (3.5 mL) was stirred at 75° C. for 16 h. The solvents were removed under reduced pressure and pH was adjusted to 7 with 6 M HCl. The crude mixture was diluted with THF and MeOH. The mixture was placed in the fridge and the sub-title compound precipitated out over the weekend. It was collected by vacuum filtration, and washed with cold water twice. The cake was dried overnight under reduced pressure to give the sub-title compound as an off-white powder (240.3 mg, 59%). LCMS calc. for $C_{14}H_{17}N_2O_5$ $(M+H)^+$: m/z=293.1. Found: 293.1.

Step 3. tert-Butyl [(3S,5R)-1-{3-[({2-[(tert-butoxycarbonyl)amino]-6-methylfuro[3,2-b]pyridin-3-yl}carbonyl)amino]pyridin-4-yl}-5-(trifluoromethyl)piperidin-3-yl]carbamate

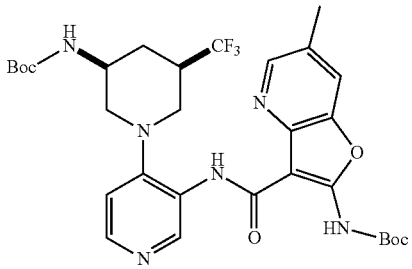 [SMILES: Cc1cnc2c(C(=O)Nc3cnccc3N3C[C@@H](NC(=O)OC(C)(C)C)C[C@@H](C(F)(F)F)C3)c(NC(=O)OC(C)(C)C)oc2c1]

A mixture of tert-butyl [(3S,5R)-1-(3-aminopyridin-4-yl)-5-(trifluoromethyl)piperidin-3-yl]carbamate (342 mg, 0.95 mmol), 2-[(tert-butoxycarbonyl)amino]-6-methylfuro[3,2-b]pyridine-3-carboxylic acid (231 mg, 0.79 mmol) and molecular sieves (710 mg, 3.2 mmol) (4 Å) in 1,2-dichloroethane (4.4 mL) was stirred vigorously at room temperature for 30 min., followed by the addition of DIPEA (0.41 mL, 2.4 mmol) and HATU (1.50 g, 3.95 mmol). The reaction mixture was stirred vigorously at room temperature for 4 h. The mixture was filtered and solids were washed with THF. The filtrate was concentrated under reduced pressure, and the residue was purified by column chromatography on silica gel using CombiFlash® apparatus (eluting with 0 to 100% EtOAc in hexanes) to give the sub-title compound as an off-white powder (133.6 mg, 27%). LCMS calc. for $C_{30}H_{38}F_3N_6O_6$ $(M+H)^+$: m/z=635.2. Found: 635.2.

Step 4. 2-Amino-N-{4-[(3S,5R)-3-amino-5-(trifluoromethyl)piperidin-1-yl]pyridin-3-yl}-6-methylfuro[3,2-b]pyridine-3-carboxamide To a solution of tert-butyl [(3S,5R)-1-{3-[({2-[(tert-butoxycarbonyl)amino]-6-methylfuro[3,2-b]pyridin-3-yl}carbonyl)amino]pyridin-4-yl}-5-(trifluoromethyl)piperidin-3-yl]carbamate (133 mg, 0.21 mmol) in MeOH (0.34 mL) was added 4.0 M solution of HCl in dioxane (4.2 mL, 16.8 mmol). The reaction mixture was stirred at room temperature for 60 min. After removal of the solvents, the residue was diluted with MeOH and $NH_4OH$, and purified by preparative LCMS (pH=10 method; XBridge™ PrepC18 5 μm OBD™ column, 30×10 mm, 60 mL/min., eluting with a gradient of MeCN and water with $NH_4OH$) to give the title compound (53 mg, 58%). LCMS calc. for $C_{20}H_{22}F_3N_6O_2$ $(M+H)^+$: m/z=435.2. Found: 425.2. $^1H$ NMR (500 MHz, DMSO-$d_6$): δ 10.34 (s, 1H), 9.34 (s, 1H), 9.18 (d, J=1.5, 1H), 8.75 (m, 1H), 8.58 (m, 2H), 8.28 (d, J=5.3, 1H), 7.14 (d, J=5.4, 1H), 7.01 (d, J=10.1, 2H), 4.60 (d, J=6.0, 1H), 3.89 (s, 3H), 3.27 (m, 2H), 2.96 (m, 2H), 2.59 (t, J=10.8, 1H), 2.55-2.49 (m, 1H), 1.66 (s, 2H), 1.25 (m, 1H), 0.57 (m, 1H), 0.30 (m, 1H), 0.17 (m, 1H), 0.04 (m, 2H) ppm.

Example 116

2-Amino-N-{4-[(3S,5R)-3-amino-5-methylpiperidin-1-yl]pyridin-3-yl}-6-methylfuro[3,2-b]pyridine-3-carboxamide

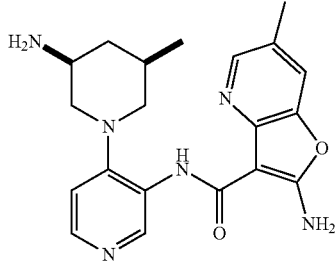 [SMILES: Cc1cnc2c(C(=O)Nc3cnccc3N3C[C@H](C)C[C@H](N)C3)c(N)oc2c1]

Step 1. tert-Butyl ((3S,5R)-1-{3-[({2-[(tert-butoxycarbonyl)amino]-6-methylfuro[3,2-b]pyridin-3-yl}carbonyl)amino]pyridin-4-yl}-5-methylpiperidin-3-yl)carbamate

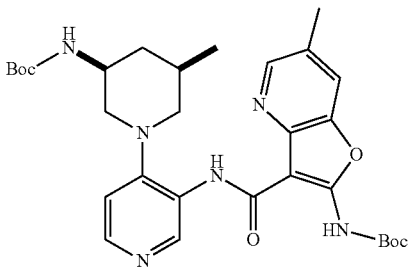 [SMILES: Cc1cnc2c(C(=O)Nc3cnccc3N3C[C@H](C)C[C@H](NC(=O)OC(C)(C)C)C3)c(NC(=O)OC(C)(C)C)oc2c1]

A mixture of tert-butyl [(3S,5R)-1-(3-aminopyridin-4-yl)-5-methylpiperidin-3-yl]carbamate (18.9 mg, 0.06 mmol), 2-[(tert-butoxycarbonyl)amino]-6-methylfuro[3,2-b]pyridine-3-carboxylic acid (15 mg, 0.05 mmol) (prepared in Example 115, step 2) and molecular sieves (46 mg, 0.21 mmol) (4 Å) in 1,2-dichloroethane (0.28 mL) was stirred vigorously at room temperature for 30 min., then DIPEA (27

µL, 0.15 mmol) and HATU (97.6 mg, 0.26 mmol) were added. The reaction mixture was stirred vigorously at room temperature for 16 h. The reaction mixture was filtered and solids were washed with THF. The filtrate was concentrated under reduced pressure, and the residue was purified by preparative LCMS (pH=10 method; XBridge™ PrepC18 5 µm OBD™ column, 30×10 mm, 60 mL/min., eluting with a gradient of MeCN and water with NH$_4$OH) to give the sub-title compound as an off-white powder (6 mg, 20%). LCMS calc. for C$_{30}$H$_{41}$N$_6$O$_6$ (M+H)$^+$: m/z=581.2. Found: 581.2.

Step 2. 2-Amino-N-{4-[(3S,5R)-3-amino-5-methyl-piperidin-1-yl]pyridin-3-yl}-6-methylfuro[3,2-b]pyridine-3-carboxamide To a solution of tert-butyl ((3S,5R)-1-{3-[({2-[(tert-butoxycarbonyl)amino]-6-methylfuro[3,2-b]pyridin-3-yl}carbonyl)amino]pyridin-4-yl}-5-methylpiperidin-3-yl) carbamate (6.0 mg, 0.01 mmol) in MeOH (0.02 mL) was added a 4.0 M solution of HCl in dioxane (0.10 mL, 0.4 mmol). The reaction mixture was stirred at room temperature for 30 min. After removal of the solvents, the residue was diluted with MeOH and NH$_4$OH, and purified by preparative LCMS (pH=10 method; XBridge™ PrepC18 5 µm OBD™ column, 30×10 mm, 60 mL/min., eluting with a gradient of MeCN and water with NH$_4$OH) to give the title compound (2 mg, 51%). LCMS calc. for C$_{20}$H$_{25}$N$_6$O$_2$ (M+H)$^+$: m/z=381.2. Found: 381.2.

Example 117

2-Amino-N-{4-[(3S,5R)-3-amino-5-methylpiperidin-1-yl]pyridin-3-yl}-6-ethylfuro[3,2-b]pyridine-3-carboxamide

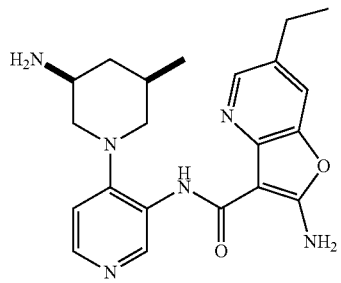 [SMILES: CCc1cnc2c(C(=O)Nc3cnccc3N3C[C@H](C)C[C@H](N)C3)c(N)oc2c1]

Step 1. Ethyl 2-[bis(tert-butoxycarbonyl)amino]-6-vinylfuro[3,2-b]pyridine-3-carboxylate

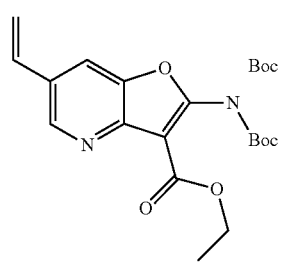 [SMILES: C=Cc1cnc2c(C(=O)OCC)c(NC(=O)OC(C)(C)C)oc2c1 ; "Boc"]

A mixture of ethyl 2-[bis(tert-butoxycarbonyl)amino]-6-bromofuro[3,2-b]pyridine-3-carboxylate (1.10 g, 2.3 mmol), 4,4,5,5-tetramethyl-2-vinyl-1,3,2-dioxaborolane (0.69 mL, 4.1 mmol), dicyclohexyl(2',4',6'-triisopropylbiphenyl-2-yl)phosphine-(2'-aminobiphenyl-2-yl)(chloro)palladium (1:1) (267 mg, 0.34 mmol) and K$_3$PO$_4$ (0.96 g, 4.5 mmol) in 1,4-dioxane (7.1 mL) and water (1.6 mL) was stirred at 70° C. for 4 h under N$_2$ atmosphere. The crude reaction mixture was diluted with EtOAc and water. The organic layer was dried over anhydrous Na$_2$SO$_4$ and filtered. The filtrate was concentrated under reduced pressure. The resulting residue was purified by silica gel column chromatography (0 to 30% EtOAc in hexanes) to give the product as light brown powder (980 mg, 98%). LCMS calc for C$_{22}$H$_{29}$N$_2$O$_7$ (M+H)$^+$: m/z=433.1. Found: 433.1.

Step 2. 2-[(tert-Butoxycarbonyl)amino]-6-vinylfuro[3,2-b]pyridine-3-carboxylic acid

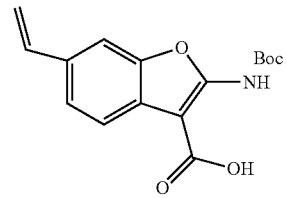

A solution of ethyl 2-[bis(tert-butoxycarbonyl)amino]-6-vinylfuro[3,2-b]pyridine-3-carboxylate (800 mg, 1.85 mmol) and LiOH.H$_2$O (540 mg, 13 mmol) in THF (10 mL), MeOH (7 mL), and water (4 mL) was heated at 70° C. in a flask for 16 h. The reaction mixture was filtered to remove unreacted LiOH and neutralized with 6 M HCl. After all the solvents were removed under reduced pressure, the residue was mixed with ice water, and the resulting precipitate was collected by vacuum filtration. The light yellow cake was washed with cold water, and dried under reduced pressure overnight to provide the sub-title compound as fluffy light brown powder (466 mg, 83%). LCMS calc. for C$_{15}$H$_{17}$N$_2$O$_5$ (M+H)$^+$: m/z=305.1. Found: 305.1.

Step 3. tert-Butyl (3-{[(4-{(3S,5R)-3-[(tert-butoxycarbonyl)amino]-5-methylpiperidin-1-yl}pyridin-3-yl)amino]carbonyl}-6-vinylfuro[3,2-b]pyridin-2-yl) carbamate

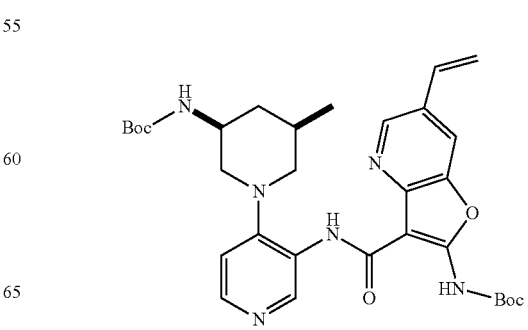

A mixture of tert-butyl [(3S,5R)-1-(3-aminopyridin-4-yl)-5-methylpiperidin-3-yl]carbamate (362 mg, 1.2 mmol), 2-[(tert-butoxycarbonyl)amino]-6-vinylfuro[3,2-b]pyridine-3-carboxylic acid (300 mg, 0.99 mmol) and molecular sieves (0.88 g, 3.9 mmol) (4 Å) in 1,2-dichloroethane (5.4 mL) was stirred vigorously at room temperature for 30 min., then DIPEA (0.52 mL, 3.0 mmol) and HATU (1.87 g, 4.9 mmol) were added. The reaction mixture was stirred vigorously at room temperature for 20 h. The mixture was filtered and solids were washed with THF. The filtrate was concentrated under reduced pressure, and the residue was purified by silica gel column chromatography (0 to 100% EtOAc in hexanes) to give the sub-title compound as an off-white powder (167 mg, 29%). LCMS calc. for $C_{31}H_{41}N_6O_6$ (M+H)$^+$: m/z=593.2. Found: 593.2.

Step 4. tert-Butyl ((3S,5R)-1-{3-[({2-[(tert-butoxycarbonyl)amino]-6-ethylfuro[3,2-b]pyridin-3-yl}carbonyl)amino]pyridin-4-yl}-5-methylpiperidin-3-yl)carbamate

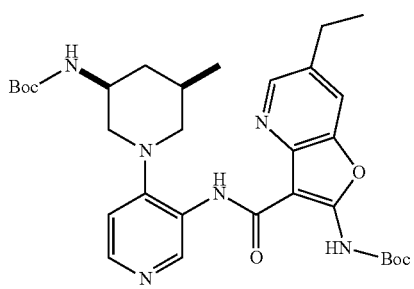 [SMILES: CCc1cnc2c(C(=O)Nc3cnccc3N3C[C@H](C)C[C@H](NC(=O)OC(C)(C)C)C3)c(NC(=O)OC(C)(C)C)oc2c1]

To a solution of tert-butyl (3-{[(4-{(3S,5R)-3-[(tert-butoxycarbonyl)amino]-5-methylpiperidin-1-yl}pyridin-3-yl)amino]carbonyl}-6-vinylfuro[3,2-b]pyridin-2-yl)carbamate (167 mg, 0.28 mmol) in MeOH (1.00 mL) under $N_2$ was added 5 wt % of Pd on carbon (46 mg, 0.04 mmol). The reaction mixture was hydrogenated under $H_2$ balloon at 1 atm. for 16 h. The reaction mixture was filtered through diatomaceous earth and the filtrate was concentrated and dried under high vacuum to give the sub-title compound as an off-white foamy powder (125 mg, 75%). LCMS calc. for $C_{31}H_{43}N_6O_6$ (M+H)$^+$: m/z=595.3. Found: 595.3.

Step 5. 2-Amino-N-{4-[(3S,5R)-3-amino-5-methylpiperidin-1-yl]pyridin-3-yl}-6-ethylfuro[3,2-b]pyridine-3-carboxamide To a solution of tert-butyl ((3S,5R)-1-{3-[({2-[(tert-butoxycarbonyl)amino]-6-ethylfuro[3,2-b]pyridin-3-yl}carbonyl)amino]pyridin-4-yl}-5-methylpiperidin-3-yl)carbamate (125 mg, 0.21 mmol) in MeOH (0.34 mL) was added a 4.0 M solution of HCl in dioxane (4.2 mL, 17 mmol). The reaction mixture was stirred at room temperature for 60 min. After removal of the solvents, the residue was diluted with MeOH and NH$_4$OH, and purified by preparative LCMS (pH=10 method; XBridge™ PrepC18 5 μm OBD™ column, 30×10 mm, 60 mL/min., eluting with a gradient of MeCN and water with NH$_4$OH) to give the title compound (44.0 mg, 53%). LCMS calc. for $C_{21}H_{27}N_6O_2$ (M+H)$^+$: m/z=395.2. Found: 395.2. $^1$H NMR (500 MHz, DMSO-d$_6$): δ 10.11 (s, 1H), 9.46 (s, 1H), 8.16 (d, J=5.3 Hz, 1H), 8.09 (d, J=1.1 Hz, 2H), 7.62 (d, J=1.3 Hz, 2H), 7.10 (d, J=5.3 Hz, 1H), 3.15 (d, J=10.8 Hz, 1H), 3.11-2.99 (m, 4H), 2.68 (q, J=7.5 Hz, 2H), 2.22-2.12 (m, 3H), 1.95 (d, J=12.5 Hz, 2H), 1.21 (t, J=7.6 Hz, 3H), 0.82 (d, J=6.6 Hz, 3H) ppm.

Example 118

2-Amino-N-{4-[(3S,5R)-3-amino-5-(trifluoromethyl)piperidin-1-yl]pyridin-3-yl}-6-ethylfuro[3,2-b]pyridine-3-carboxamide

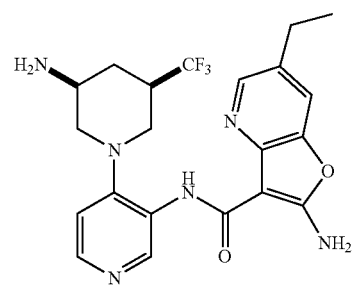 [SMILES: CCc1cnc2c(C(=O)Nc3cnccc3N3C[C@@H](N)C[C@@H](C(F)(F)F)C3)c(N)oc2c1]

Step 1. tert-Butyl {3-[({4-[(3S,5R)-3-[(tert-butoxycarbonyl)amino]-5-(trifluoromethyl)piperidin-1-yl]pyridin-3-yl}amino)carbonyl]-6-vinylfuro[3,2-b]pyridin-2-yl}carbamate

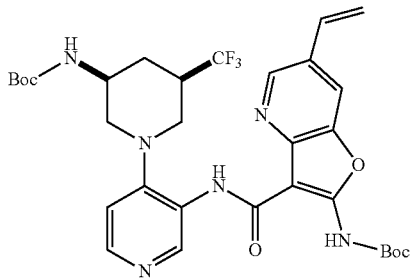

A mixture of tert-butyl [(3S,5R)-1-(3-aminopyridin-4-yl)-5-(trifluoromethyl)piperidin-3-yl]carbamate (911 mg, 2.5 mmol), 2-[(tert-butoxycarbonyl)amino]-6-vinylfuro[3,2-b]pyridine-3-carboxylic acid (846 mg, 2.78 mmol) (prepared in Example 117, step 2) and molecular sieves (2.26 g, 10.1 mmol) (4 Å) in 1,2-dichloroethane (17.9 mL) was stirred vigorously at room temperature for 30 min., followed by the addition of DIPEA (1.32 mL, 7.6 mmol) and HATU (4.80 g, 12.6 mmol). The reaction mixture was stirred vigorously at room temperature for 24 h. The reaction mixture was filtered solids were washed with THF. The filtrate was concentrated under reduced pressure, and the residue was purified by silica gel column chromatography (0 to 50% EtOAc in hexanes) to give the sub-title compound as an off-white powder (622 mg, 38%). LCMS calc. for $C_{31}H_{38}F_3N_6O_6$ (M+H)$^+$: m/z=647.2. Found: 647.2.

243

Step 2. tert-Butyl [(3S,5R)-1-{3-[({2-[(tert-butoxy-carbonyl)amino]-6-ethylfuro[3,2-b]pyridin-3-yl}carbonyl)amino]pyridin-4-yl}-5-(trifluoromethyl)piperidin-3-yl]carbamate

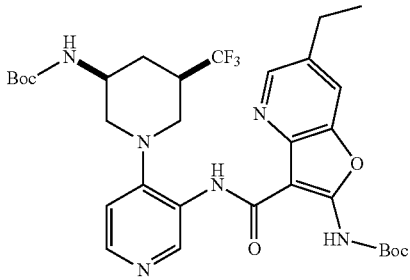 [SMILES: CCc1cnc2c(C(=O)Nc3cnccc3N3C[C@@H](NC(=O)OC(C)(C)C)C[C@@H](C(F)(F)F)C3)c(NC(=O)OC(C)(C)C)oc2c1]

To a solution of tert-butyl {3-[({4-[(3S,5R)-3-[(tert-butoxycarbonyl)amino]-5-(trifluoromethyl)piperidin-1-yl]pyridin-3-yl}amino)carbonyl]-6-vinylfuro[3,2-b]pyridin-2-yl}carbamate (12 mg, 0.019 mmol) in MeOH (0.15 mL) under $N_2$ was added 5 wt % of Pd on carbon (4 mg, 0.01 mmol). The reaction mixture was hydrogenated under $H_2$ balloon at 1 atm. for 16 h. The reaction mixture was filtered through diatomaceous earth and the filtrate was concentrated and dried under high vacuum to give the sub-title compound as an off-white foamy powder (11.8 mg, 98%). LCMS calc. for $C_{31}H_{40}F_3N_6O_6$ $(M+H)^+$: m/z=649.3. Found: 649.3.

Step 3. 2-Amino-N-{4-[(3S,5R)-3-amino-5-(trifluoromethyl)piperidin-1-yl]pyridin-3-yl}-6-ethylfuro[3,2-b]pyridine-3-carboxamide To a solution of tert-butyl [(3S,5R)-1-{3-[({2-[(tert-butoxycarbonyl)amino]-6-ethylfuro[3,2-b]pyridin-3-yl}carbonyl)amino]pyridin-4-yl}-5-(trifluoromethyl)piperidin-3-yl]carbamate (11.8 mg, 0.02 mmol) in MeOH (0.02 mL) was added 4.0 M solution of HCl in dioxane (0.23 mL, 0.9 mmol). The reaction mixture was stirred at room temperature for 16 h. After removal of the solvents, the residue was diluted with MeOH and $NH_4OH$, and purified by preparative LCMS (pH=10 method; XBridge™ PrepC18 5 µm OBD™ column, 30×10 mm, 60 mL/min., eluting with a gradient of MeCN and water with $NH_4OH$) to give the title compound (3.7 mg, 45%). LCMS calc. for $C_{21}H_{24}F_3N_6O_2$ $(M+H)^+$: m/z=449.2. Found: 449.2.

Example 119

2-Amino-N-{4-[(3S,5R)-3-amino-5-methylpiperidin-1-yl]pyridin-3-yl}-6-(2,6-difluorophenyl)furo[3,2-b]pyridine-3-carboxamide

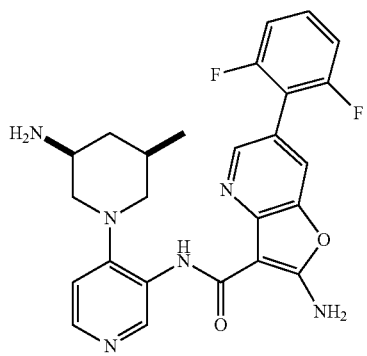 [SMILES: C[C@@H]1C[C@H](N)CN(c2ccncc2NC(=O)c2c(N)oc3cc(-c4c(F)cccc4F)cnc23)C1]

244

Step 1. Ethyl 2-[(tert-butoxycarbonyl)amino]-6-(2,6-difluorophenyl)furo[3,2-b]pyridine-3-carboxylate

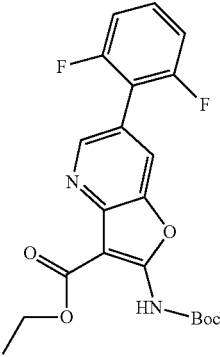 [SMILES: CCOC(=O)c1c(NC(=O)OC(C)(C)C)oc2cc(-c3c(F)cccc3F)cnc12]

A mixture of ethyl 6-bromo-2-[(tert-butoxycarbonyl)amino]furo[3,2-b]pyridine-3-carboxylate (200 mg, 0.52 mmol), (2,6-difluorophenyl)boronic acid (98 mg, 0.62 mmol), dicyclohexyl(2',4',6'-triisopropylbiphenyl-2-yl)phosphine-(2'-aminobiphenyl-2-yl)(chloro)palladium (1:1) (65.4 mg, 0.083 mmol) and $K_3PO_4$ (220 mg, 1.04 mmol) in 1,4-dioxane (1.62 mL) and water (0.38 mL) was stirred at 100° C. for 2 h (only low conversion was achieved). The crude product was filtered to remove $K_3PO_4$, then $Pd(tBu_3P)_2$ (60 mg) and DIPEA (230 µL) were added. The reaction mixture was heated at 100° C. for 1 h and the reaction was complete. The crude reaction mixture was diluted with EtOAc and water. The organic layer was separated, dried over $Na_2SO_4$ and filtered. The filtrate was concentrated under reduced pressure. The resulting residue was purified by silica gel column chromatography (0 to 40% EtOAc in hexanes) to give the product as a light yellow gum (189 mg, 87%). LCMS calc. for $C_{21}H_{21}F_2N_2O_5$ $(M+H)^+$: m/z=419.1. Found: 419.1.

Step 2. 2[(tert-Butoxycarbonyl)amino]-6-(2,6-difluorophenyl)furo[3,2-b]pyridine-3-carboxylic acid

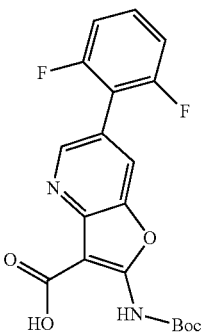 [SMILES: CC(C)(C)OC(=O)Nc1oc2cc(-c3c(F)cccc3F)cnc2c1C(=O)O]

A mixture of ethyl 2-[(tert-butoxycarbonyl)amino]-6-(2,6-difluorophenyl)furo[3,2-b]pyridine-3-carboxylate (188 mg, 0.45 mmol) and $LiOH \cdot H_2O$ (108 mg, 4.5 mmol) in THF (1.2 mL), MeOH (0.87 mL) and water (0.39 mL) was stirred at 80° C. for 3 h. The solvents were removed under reduced pressure and pH was adjusted to 4-5 with 6 M HCl. The resulted precipitate was collected by vacuum filtration. The cake was washed with cold water and dried under reduced pressure overnight to give the sub-title compound as a light yellow powder (137.4 mg, 78%). LCMS calc. for $C_{19}H_{17}F_2N_2O_5$ (M+H)$^+$: m/z=391.1. Found: 391.1.

Step 3. tert-Butyl {(3S,5R)-1-[3-({[2-[(tert-butoxycarbonyl)amino]-6-(2,6-difluorophenyl)furo[3,2-b]pyridin-3-yl]carbonyl}amino)pyridin-4-yl]-5-methylpiperidin-3-yl}carbamate

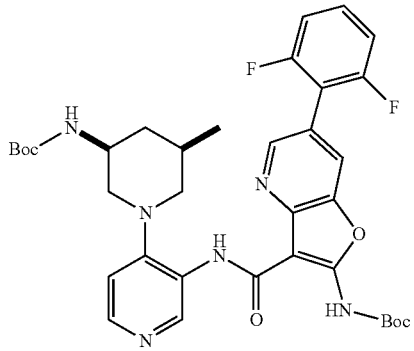 [SMILES: C[C@@H]1C[C@H](NC(=O)OC(C)(C)C)CN(c2ccncc2NC(=O)c2c(NC(=O)OC(C)(C)C)oc3cc(-c4c(F)cccc4F)cnc23)C1]

A mixture of tert-butyl [(3S,5R)-1-(3-aminopyridin-4-yl)-5-methylpiperidin-3-yl]carbamate (18.8 mg, 0.062 mmol), 2-[(tert-butoxycarbonyl)amino]-6-(2,6-difluorophenyl)furo[3,2-b]pyridine-3-carboxylic acid (20 mg, 0.05 mmol) and molecular sieves (46 mg, 0.21 mmol) (4 Å) in 1,2-dichloroethane (0.28 mL) was stirred vigorously at room temperature for 30 min., then DIPEA (27 µL, 0.15 mmol) and HATU (97.4 mg, 0.26 mmol) were added. The reaction mixture was stirred vigorously at room temperature for 3 h. The crude reaction mixture was filtered and solids were washed with THF. The filtrate was concentrated under reduced pressure, and the residue was diluted with MeOH and purified by preparative LCMS MS (pH=10 method; XBridge™ PrepC18 5 µm OBD™ column, 30×10 mm, 60 mL/min., eluting with a gradient of MeCN and water with NH$_4$OH) to give the sub-title compound as an off-white powder (4.0 mg, 12%). LCMS calc. for $C_{35}H_{41}F_2N_6O_6$ (M+H)$^+$: m/z=679.3. Found: 679.3.

Step 4. 2-Amino-N-{4-[(3S,5R)-3-amino-5-methylpiperidin-1-yl]pyridin-3-yl}-6-(2,6-difluorophenyl)furo[3,2-b]pyridine-3-carboxamide To a solution of tert-butyl {(3S,5R)-1-[3-({[2-[(tert-butoxycarbonyl)amino]-6-(2,6-difluorophenyl)furo[3,2-b]pyridin-3-yl]carbonyl}amino)pyridin-4-yl]-5-methylpiperidin-3-yl}carbamate (3.0 mg, 0.004 mmol) in MeOH (0.02 mL) was added 4.0 M HCl in dioxane (0.10 mL, 0.5 mmol). The reaction mixture was stirred at room temperature for 16 h. After removal of the solvents, the residue was diluted with MeOH and NH$_4$OH, and purified by preparative LCMS MS (pH=10 method; XBridge™ PrepC18 5 µm OBD™ column, 30×10 mm, 60 mL/min., eluting with a gradient of MeCN and water with NH$_4$OH) to give the title compound (2 mg, 80%). LCMS calc. for $C_{25}H_{25}F_2N_6O_2$ (M+H)$^+$: m/z=479.2. Found: 479.2.

Example 120

2-Amino-N-(4-((3S,5R)-3-amino-5-methylpiperidin-1-yl)pyridin-3-yl)-6-(difluoromethoxy)furo[3,2-b]pyridine-3-carboxamide

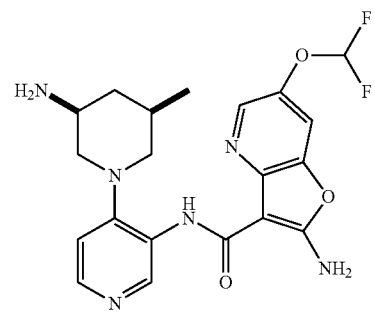 [SMILES: C[C@@H]1C[C@H](N)CN(c2ccncc2NC(=O)c2c(N)oc3cc(OC(F)F)cnc23)C1]

Step 1. Ethyl 6-bromo-2-(tert-butoxycarbonylamino)furo[3,2-b]pyridine-3-carboxylate

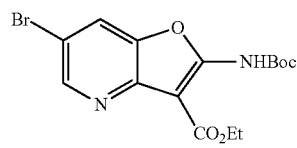 [SMILES: CCOC(=O)c1c(NC(=O)OC(C)(C)C)oc2cc(Br)cnc12]

The mixture of 5-bromo-2-iodopyridin-3-ol (3.00 g, 10.0 mmol), ethyl cyanoacetate (2.26 g, 20.0 mmol), copper(I) iodide (343 mg, 1.80 mmol), 2-pyridinecarboxylic acid (443 mg, 3.60 mmol) and Cs$_2$CO$_3$ (11.7 g, 36.0 mmol) in dioxane (66.7 mL) was stirred at room temperature for 3 h. The reaction mixture was then adjusted to pH 8 with 1 M aq. HCl solution. The mixture was extracted with EtOAc. The organic layer was dried over Na$_2$SO$_4$, filtered, and concentrated to give a cyclization product.

To the above cyclization product was add DMAP (122 mg, 1.00 mmol) followed by THF (40.5 mL). Then a solution of Boc$_2$O (3.05 g, 14.0 mmol) in DCM (32.0 mL) was added dropwise. The mixture was stirred at room temperature for 6 h. Additional Boc$_2$O (1.52 g, 7.00 mmol) was added. After stirring for another 2 h, the reaction mixture was concentrated under reduced pressure. The residue was purified by chromatography on silica gel (10-20% EtOAc/Hex) to give the product (2.61 g, 68% yield, two steps). LCMS calc. for $C_{15}H_{18}BrN_2O_5$ (M+H)$^+$: m/z=385.0. Found: 385.2. $^1$H NMR (300 MHz, CDCl$_3$) δ 9.66 (s, 1H), 8.63 (s, 1H), 7.88 (d, J=1.9 Hz, 1H), 4.52 (q, J=7.1 Hz, 2H), 1.57 (s, 9H), 1.46 (t, J=7.1 Hz, 3H) ppm.

Step 2. Ethyl 2-(tert-butoxycarbonylamino)-6-hydroxyfuro[3,2-b]pyridine-3-carboxylate

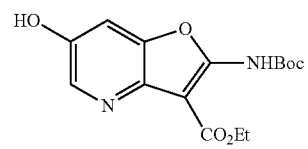 [SMILES: CCOC(=O)c1c(NC(=O)OC(C)(C)C)oc2cc(O)cnc12]

To a mixture of KOAc (1.72 g, 17.5 mmol), ethyl 6-bromo-2-[(tert-butoxycarbonyl)amino]furo[3,2-b]pyridine-3-carboxylate (2.50 g, 5.84 mmol) and bis(pinacolato) diboron (2.37 g, 9.34 mmol) dioxane (29.2 mL) was added, followed by Pd(dppf)Cl$_2$-DCM complex (477 mg, 584 μmol). After stirring at 90° C. for 3 h, the mixture was diluted with DCM, filtered through a pad of diatomaceous earth. The filtrate was concentrated under reduced pressure to give the boronic ester.

To the boronic ester were added neutral Al$_2$O$_3$ (200 mg), DCM (28.5 mL) and water (28.5 mL), followed by H$_2$O$_2$ (30%) in water (11.9 mL, 116 mmol). The mixture was stirred at room temperature for 2 h, and then filtered. The filtrate was diluted with DCM and washed with water. The organic phase was dried over Na$_2$SO$_4$, filtered, and concentrated under reduced pressure. The residue was purified by chromatography on silica gel (40-80% EtOAc/Hex) to give the product (1.10 g, 59% yield, two steps). R$_f$=0.15 (50% EtOAc/Hex). LCMS calc. for C$_{15}$H$_{19}$N$_2$O$_6$ (M+H)$^+$: m/z=323.1. Found: 323.2. $^1$H NMR (500 MHz, CDCl$_3$) δ 9.50 (s, 1H), 8.25 (s, 1H), 7.40 (s, 1H), 4.43 (d, J=6.9 Hz, 2H), 1.55 (s, 9H), 1.36 (t, J=6.7 Hz, 3H) ppm.

Step 3. Ethyl 2-(tert-butoxycarbonylamino)-6-(difluoromethoxy)furo[3,2-b]pyridine-3-carboxylate

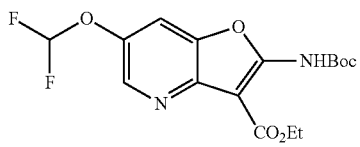 [SMILES: CC(C)(C)OC(=O)Nc1oc2cc(OC(F)F)cnc2c1C(=O)O]

To a mixture of ethyl 2-[(tert-butoxycarbonyl)amino]-6-hydroxyfuro[3,2-b]pyridine-3-carboxylate (660 mg, 2.05 mmol) and potassium hydroxide (1620 mg, 24.6 mmol) was added MeCN (10.3 mL), followed by H$_2$O (10.3 mL). The mixture was cooled to −78° C. Diethyl [bromo(difluoro)methyl]phosphonate (1.46 mL, 8.19 mmol) was then added. The reaction mixture was allowed to warm to room temperature and stirred for 1 h. The reaction was quenched with aq. HCl (1 M) to pH 7 and then extracted with EtOAc. The organic phase was dried over Na$_2$SO$_4$, filtered, and concentrated. The residue was purified by chromatography on silica gel (10-25% EtOAc/Hex) to give the product (458 mg, 60% yield). R$_f$=0.70 (50% EtOAc/Hex). LCMS calc. for C$_{16}$H$_{19}$F$_2$N$_2$O$_6$ (M+H)$^+$: m/z=373.1. Found: 373.2.

Step 4. 2-(tert-Butoxycarbonylamino)-6-(difluoromethoxy)furo[3,2-b]pyridine-3-carboxylic acid

To a solution of ethyl 2-[(tert-butoxycarbonyl)amino]-6-(difluoromethoxy)furo[3,2-b]pyridine-3-carboxylate (450 mg, 1.21 mmol) in THF (3.92 mL) was added water (2.61 mL), MeOH (2.94 mL), and LiOH (347 mg, 14.5 mmol). After stirring at 40° C. for 18 h, the mixture was adjusted to pH 5 with aqueous solution of HCl (1 M). The mixture was extracted with EtOAc. The organic phase was dried over Na$_2$SO$_4$, filtered, and concentrated. The residue (378 mg, 91% yield) was used directly in the next step without further purification. LCMS calc. for C$_{14}$H$_{15}$F$_2$N$_2$O$_6$ (M+H)$^+$: m/z=345.1. Found: 345.1.

Step 5. 2-Amino-N-(4-((3S,5R)-3-amino-5-methyl-piperidin-1-yl)pyridin-3-yl)-6-(difluoromethoxy)furo[3,2-b]pyridine-3-carboxamide HATU (223 mg, 0.586 mmol) was added to the solution of tert-butyl [(3S,5R)-1-(3-aminopyridin-4-yl)-5-methylpiperidin-3-yl]carbamate (157 mg, 0.512 mmol) and 2-[(tert-butoxycarbonyl)amino]-6-(difluoromethoxy)furo[3,2-b]pyridine-3-carboxylic acid (126 mg, 0.366 mmol) in 1,2-dichloroethane (1.12 mL), followed by N,N-diisopropylethylamine (153 μL, 0.878 mmol). The mixture was stirred at room temperature for 14 h. The mixture was concentrated under reduced pressure, and the residue was purified by chromatography on silica gel (40-70% EtOAc/Hexanes) to give the coupling product as a yellow oil (116 mg, 50% yield). R$_f$=0.12 (50% EtOAc/Hexanes).

The solution of HCl in dioxane (4 M, 2.75 mL) was added to the solution of the coupling product (116 mg, 0.183 mmol) in MeOH (0.371 mL). The mixture was stirred at room temperature for 1 h. The crude product was concentrated under reduced pressure and purified by RP-HPLC (water XBridge C18 column, 30 mm×100 mm, 5 μm particle size, eluting with a gradient of MeCN/water containing 0.1% NH$_4$OH, at flow rate of 60 mL/min.) to give the title compound. LCMS calc. for C$_{20}$H$_{23}$F$_2$N$_6$O$_3$ (M+H)$^+$ m/z=433.2. found: 433.3. $^1$H NMR (400 MHz, DMSO-d$_6$) δ 10.01 (s, 1H), 9.46 (s, 1H), 8.20-8.12 (m, 2H), 7.83 (d, J=2.1 Hz, 1H), 7.21 (t, J=73.9 Hz, 1H), 7.11 (d, J=5.3 Hz, 1H), 3.19-3.10 (m, 1H), 3.09-2.99 (m, 2H), 2.18 (ddd, J=10.7, 5.5, 5.5 Hz, 1H), 2.16 (ddd, J=10.7, 5.5, 5.5 Hz, 1H), 2.07-1.92 (m, 2H), 0.82 (d, J=6.5 Hz, 3H), 0.79-0.70 (m, 1H).

Example 121

2-Amino-N-(4-((3S,5R)-3-amino-5-methylpiperidin-1-yl)pyridin-3-yl)-6-isopropoxyfuro[3,2-b]pyridine-3-carboxamide

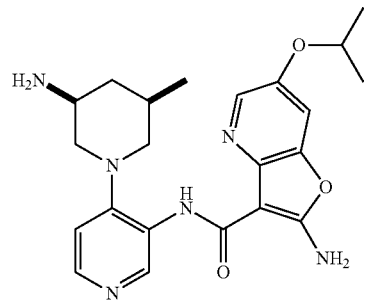 [SMILES: CC(C)Oc1cnc2c(C(=O)Nc3cnccc3N3C[C@H](C)C[C@H](N)C3)c(N)oc2c1]

Step 1. Ethyl 2-(bis(tert-butoxycarbonyl)amino)-6-bromofuro[3,2-b]pyridine-3-carboxylate

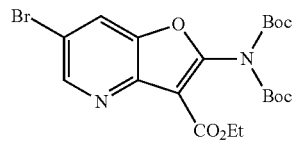

This compound was synthesized using an analogous procedure to that described in Example 120 (step 1) with excess Boc$_2$O. LCMS calc. for C$_{20}$H$_{26}$BrN$_2$O$_7$ (M+H)$^+$: m/z=485.1. Found: 485.2.

Step 2. Ethyl 2-(bis(tert-butoxycarbonyl)amino)-6-hydroxyfuro[3,2-b]pyridine-3-carboxylate

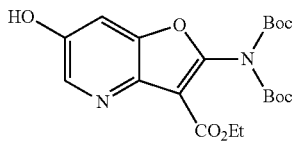 [SMILES: CCOC(=O)c1c(N(C(=O)OC(C)(C)C)C(=O)OC(C)(C)C)oc2cc(O)cnc12]

This compound was synthesized using an analogous procedure to that described in Example 120 (step 2). LCMS calc. for $C_{20}H_{27}N_2O_8$ (M+H)$^+$: m/z=423.1. Found: 422.8.

Step 3. Ethyl 2-(bis(tert-butoxycarbonyl)amino)-6-isopropoxyfuro[3,2-b]pyridine-3-carboxylate

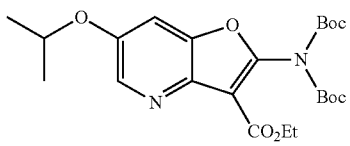 [SMILES: CCOC(=O)c1c(N(C(=O)OC(C)(C)C)C(=O)OC(C)(C)C)oc2cc(OC(C)C)cnc12]

PPh$_3$ (0.149 g, 0.567 mmol) was added to the solution of ethyl 2-bis(tert-butoxycarbonyl)amino]-6-hydroxyfuro[3,2-b]pyridine-3-carboxylate (79.8 mg, 0.189 mmol) and i-PrOH (43.4 μL, 0.567 mmol) in THF (1.26 mL). The mixture was cooled to 0° C., and then diisopropyl azodicarboxylate (112 μL, 0.567 mmol) was added. The reaction mixture was stirred at room temperature for 15 h, and then concentrated under reduced pressure. The residue was purified by chromatography on silica gel (20-40% EtOAc/Hex) to give the sub-title compound as a white solid (75.5 mg, 86% yield). LCMS calc. for $C_{23}H_{33}N_2O_8$ (M+H)$^+$: m/z=465.2. Found: 464.8.

Step 4. 2-Amino-N-(4-((3S,5R)-3-amino-5-methylpiperidin-1-yl)pyridin-3-yl)-6-isopropoxyfuro[3,2-b]pyridine-3-carboxamide This compound was synthesized using an analogous procedure to that described in Example 120 (step 4 and 5). LCMS calc. for $C_{22}H_{29}N_6O_3$ (M+H)$^+$: m/z=425.2. Found: 425.3.

Example 122

2-Amino-N-(4-((3S,5R)-3-amino-5-methylpiperidin-1-yl)pyridin-3-yl)-6-(tetrahydrofuran-3-yl)furo[3,2-b]pyridine-3-carboxamide

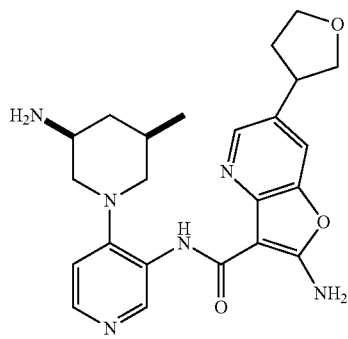 [SMILES: C[C@@H]1C[C@H](N)CN(c2ccncc2NC(=O)c2c(N)oc3cc(C4CCOC4)cnc23)C1]

Step A. Ethyl 2-[(tert-butoxycarbonyl)amino]-6-(4,5-dihydrofuran-3-yl)furo[3,2-b]pyridine-3-carboxylate

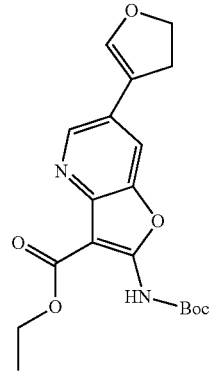 [SMILES: CCOC(=O)c1c(NC(=O)OC(C)(C)C)oc2cc(C3=COCC3)cnc12]

A mixture of ethyl 6-bromo-2-[(tert-butoxycarbonyl)amino]furo[3,2-b]pyridine-3-carboxylate (1.82 g, 4.7 mmol), 2-(4,5-dihydrofuran-3-yl)-4,4,5,5-tetramethyl-1,3,2-dioxaborolane (1.38 g, 7.03 mmol), [1,1'-bis(diphenylphosphino)ferrocene]dichloropalladium (II) (340 mg, 0.47 mmol), and potassium carbonate (2.0 g, 14 mmol) in 1,4-dioxane (19 mL) was de-gassed and purged with N$_2$ (g) several times prior to heating at 90° C. in a sealed vial for 12 h. The crude reaction mixture was allowed to cool to ambient temperature prior to filtering through a pad of diatomaceous earth. The inorganics were washed thoroughly with EtOAc. The filtrate was concentrated under reduced pressure and the residue was purified by column chromatography on silica gel using a CombiFlash® apparatus eluting with MeOH/DCM (0-10%) to afford 1.77 g of the sub-title compound (100% yield). LCMS calc. for $C_{19}H_{23}N_2O_6$ (M+H)$^+$: m/z=375.2. found: 375.2.

Step B. Ethyl 2-[bis(tert-butoxycarbonyl)amino]-6-(4,5-dihydrofuran-3-yl)furo[3,2-b]pyridine-3-carboxylate

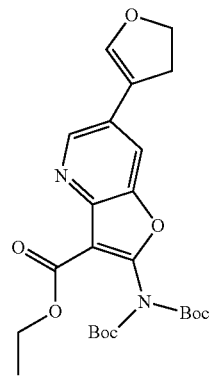 [SMILES: CCOC(=O)c1c(N(C(=O)OC(C)(C)C)C(=O)OC(C)(C)C)oc2cc(C3=COCC3)cnc12]

To a solution of ethyl 2-[(tert-butoxycarbonyl)amino]-6-(4,5-dihydrofuran-3-yl)furo[3,2-b]pyridine-3-carboxylate (1.77 g, 4.73 mmol) and DMAP (87 mg, 0.71 mmol) in THF (10 mL) was added Boc$_2$O (1.6 mL, 7.1 mmol) and the resulting solution was stirred at ambient temperature for 12 h. The crude reaction mixture was concentrated under reduced pressure and the residue was purified by column chromatography on silica gel using a CombiFlash® apparatus eluting with MeOH/DCM (0-5%) to afford 1.38 g of the sub-title compound (62% yield). LCMS calc. for $C_{24}H_{31}N_2O_8$ (M+H)⁺: m/z=475.2. found: 475.2.

Step C. Ethyl 2-[bis(tert-butoxycarboyl)amino]-6-(tetrahydrofuran-3-yl)furo[3,2-b]pyridine-3-carboxylate

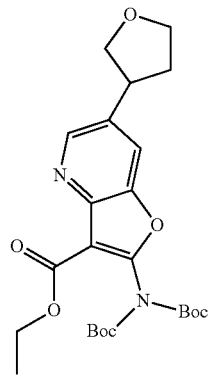 [SMILES: CCOC(=O)c1c(N(C(=O)OC(C)(C)C)C(=O)OC(C)(C)C)oc2cc(C3CCOC3)cnc12]

A mixture of ethyl 2-[bis(tert-butoxycarbonyl)amino]-6-(4,5-dihydrofuran-3-yl)furo[3,2-b]pyridine-3-carboxylate (1.38 g, 2.91 mmol) and 10% Pd on carbon (0.31 g, 0.29 mmol) in MeOH (10 mL) was stirred under an atmosphere of H₂ (g) via a balloon for 4 h. The crude reaction mixture was filtered through a pad of diatomaceous earth and the inorganics were washed thoroughly with EtOAc. The filtrate was concentrated under reduced pressure to afford 0.975 g of the sub-title compound (71% yield). LCMS calc. for $C_{24}H_{33}N_2O_8$ (M+H)⁺: m/z=477.2. found: 477.3.

Step D. 2-[(tert-Butoxycarbonyl)amino]-6-[tetrahydrofuran-3-yl]furo[3,2-b]pyridine-3-carboxylic acid

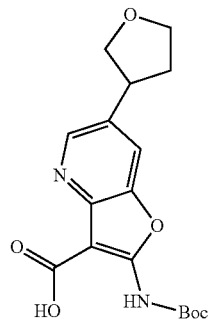 [SMILES: CC(C)(C)OC(=O)Nc1oc2cc(C3CCOC3)cnc2c1C(=O)O]

A solution of ethyl 2-[bis(tert-butoxycarbonyl)amino]-6-[tetrahydrofuran-3-yl]furo[3,2-b]pyridine-3-carboxylate (377 mg, 0.79 mmol) and LiOH.H₂O (260 mg, 6.3 mmol) in THF (1.2 mL), MeOH (0.8 mL), and water (0.4 mL) was stirred at 60° C. for 12 h. The reaction mixture was allowed to cool to room temperature, diluted with EtOAc (30 mL), and neutralized to pH=7 with 1 M HCl(aq.). The layers were separated and the organic layer was washed with H₂O (3 mL). The combined aqueous phases were back extracted with EtOAc (5 mL) and the combined organic layers were washed with brine (3 mL), dried over Na₂SO₄, filtered, and concentrated under reduced pressure to afford 281 mg of the sub-title compound (100% yield). The product was used in the subsequent reaction without further purification. LCMS calc. for $C_{17}H_{21}N_2O_6$ (M+H)⁺: m/z=349.1. found: 349.1.

Step E. 2-Amino-N-(4-((3S,5R)-3-amino-5-methylpiperidin-1-yl)pyridin-3-yl)-6-(tetrahydrofuran-3-yl)furo[3,2-b]pyridine-3-carboxamide To a solution of 2-[(tert-butoxycarbonyl)amino]-6-[tetrahydrofuran-3-yl]furo[3,2-b]pyridine-3-carboxylic acid (67 mg, 0.19 mmol) and tert-butyl [(3S,5R)-1-(3-aminopyridin-4-yl)-5-methylpiperidin-3-yl]carbamate (66 mg, 0.22 mmol) in 1,2-dichloroethane (0.8 mL) were added sequentially HATU (88 mg, 0.23 mmol) and DIPEA (84 µL, 0.48 mmol). The resulting solution was stirred at ambient temperature for 12 h. The crude reaction mixture was concentrated under reduced pressure and the residue was purified by column chromatography on silica gel using a CombiFlash® apparatus eluting with MeOH/DCM (0-10%) to afford 126 mg of the title compound, which was contaminated with DIPEA. LCMS calc. for $C_{33}H_{45}N_6O_7$ (M+H)⁺: m/z=637.3. found: 637.0.

To the purified intermediate were added DCM (1 mL) and TFA (1 mL) and the solution was stirred at ambient temperature for 1 h. The reaction mixture was concentrated under reduced pressure and the residue was diluted with MeOH and purified by preparative LCMS (pH=2) to afford the title compound as a white powder. LCMS calc. for $C_{23}H_{29}N_6O_3$ (M+H)⁺: m/z=437.2. found: 437.3.

Example 123

2-Amino-N-{4-[(3S,5R)-3-amino-5-(trifluoromethyl)piperidin-1-yl]pyridin-3-yl}-6-(tetrahydrofuran-3-yl)furo[3,2-b]pyridine-3-carboxamide

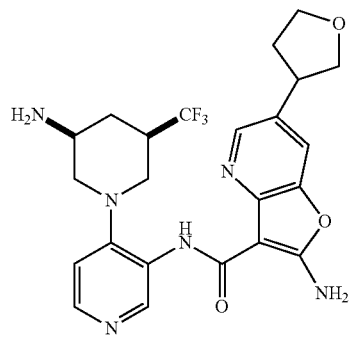

To a solution of 2-[(tert-butoxycarbonyl)amino]-6-(tetrahydrofuran-3-yl)furo[3,2-b]pyridine-3-carboxylic acid (221 mg, 0.634 mmol) and tert-butyl [(3S,5R)-1-(3-aminopyridin-4-yl)-5-(trifluoromethyl)piperidin-3-yl]carbamate (320 mg, 0.89 mmol) in 1,2-dichloroethane (1 mL) was added sequentially HATU (290 mg, 0.76 mmol) and DIPEA (330 µL, 1.9 mmol) and the resulting solution was stirred at ambient temperature overnight. HATU (150 mg, 0.39 mmol) and DIPEA (110 µL, 0.63 mmol) were added, and stirring was continued for 3 h. The crude reaction mixture was concentrated under reduced pressure and the residue was purified by column chromatography on silica gel using CombiFlash® apparatus eluting with MeOH/DCM (0-10%)

to afford 281 mg of the title compound, which was not completely pure. LCMS calc. for $C_{33}H_{42}F_3N_6O_7$ (M+H)$^+$: m/z=691.3. found: 691.3.

To the purified intermediate were added 4 M HCl in 1,4-dioxane (4 mL) and MeOH (0.2 mL) and the solution was stirred at ambient temperature for 1 h. The reaction mixture was concentrated under reduced pressure and the residue was diluted with MeOH and purified by preparative LCMS (pH=2) to afford the title compound as a white powder. LCMS calc. for $C_{23}H_{26}F_3N_6O_3$ (M+H)$^+$: m/z=491.2. found: 491.3.

Example 124

2-Amino-N-{4-[(3R,4R,5S)-3-amino-4-hydroxy-5-methylpiperidin-1-yl]pyridin-3-yl}-6-cyclobutylfuro[3,2-b]pyridine-3-carboxamide

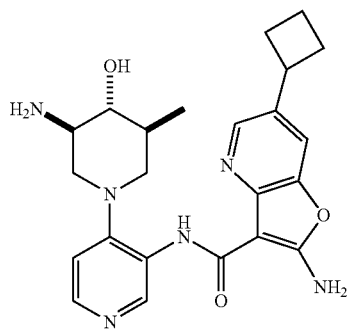 [SMILES: C[C@H]1CN(c2ccncc2NC(=O)c2c(N)oc3cc(C4CCC4)cnc23)C[C@@H](N)[C@@H]1O]

Step A. Ethyl 2-[(tert-butoxycarbonyl)amino]-6-cyclobutylfuro[3,2-b]pyridine-3-carboxylate

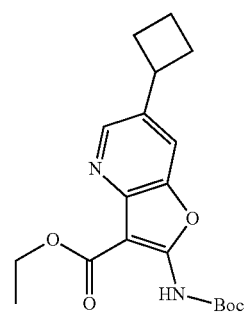 [SMILES: CCOC(=O)c1c(NC(=O)OC(C)(C)C)oc2cc(C3CCC3)cnc12]

A mixture of ethyl 6-bromo-2-[(tert-butoxycarbonyl)amino]furo[3,2-b]pyridine-3-carboxylate (250 mg, 0.65 mmol), 0.5 M bromo(cyclobutyl)zinc in THF (2.0 mL, 0.98 mmol), Pd(OAc)$_2$ (7 mg, 0.05 mmol) and 2-(dicyclohexylphosphino)-2',6'-dimethoxy-1,1'-biphenyl (26 mg, 0.06 mmol) was de-gassed and purged with N$_2$ several times prior to stirring at ambient temperature for 12 h. The crude reaction mixture was concentrated under reduced pressure and the residue was purified by column chromatography on silica gel using a CombiFlash® apparatus eluting with MeOH/DCM (0-5%) to afford 157 mg of the sub-title compound (68% yield). LCMS calc. for $C_{19}H_{25}N_2O_5$ (M+H)$^+$: m/z=361.2. found: 361.1.

Step B. 2-[(tert-Butoxycarbonyl)amino]-6-cyclobutylfuro[3,2-b]pyridine-3-carboxylic acid

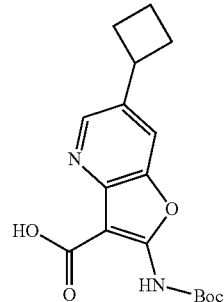

A mixture of ethyl 2-[(tert-butoxycarbonyl)amino]-6-cyclobutylfuro[3,2-b]pyridine-3-carboxylate (203 mg, 0.56 mmol) and LiOH.H$_2$O (160 mg, 3.9 mmol) in THF (1.2 mL), MeOH (0.8 mL), and water (0.4 mL) was stirred at 60° C. overnight. The reaction mixture was diluted with EtOAc (40 mL) and neutralized by the addition of 1.0 M HCl in water until pH=7 was reached. The layers were separated and the organic layer was washed with H$_2$O (4 mL) and the combined aqueous phases were back-extracted with EtOAc (5 mL). The combined organic layers were washed with brine (5 mL), dried over Na$_2$SO$_4$, filtered, and concentrated under reduced pressure to afford 192 mg of the sub-title compound (100% yield). The crude product was used directly in the next step without further purification. LCMS calc. for $C_{17}H_{21}N_2O_5$ (M+H)$^+$: m/z=333.1. found: 333.1.

Step C. 2-Amino-N-{4-[(3R,4R,5S)-3-amino-4-hydroxy-5-methylpiperidin-1-yl]pyridin-3-yl}-6-cyclobutylfuro[3,2-b]pyridine-3-carboxamide An amide coupling and subsequent deprotection procedure analogous to that described in Example 122 was used with the exception that 2-[(tert-butoxycarbonyl)amino]-6-cyclobutylfuro[3,2-b]pyridine-3-carboxylic acid and ((3R,4R,5S)-1-(3-aminopyridin-4-yl)-4-{[tert-butyl (dimethyl)silyl]oxy}-5-methylpiperidin-3-yl)carbamate were used to afford the title compound. LCMS calc. for $C_{23}H_{29}N_6O_3$ (M+H)$^+$: m/z=437.2. found: 437.2.

Example 125

2-Amino-N-{4-[(3R,4R,5S)-3-amino-5-cyclopropyl-4-hydroxypiperidin-1-yl]pyridin-3-yl}-6-cyclobutylfuro[3,2-b]pyridine-3-carboxamide

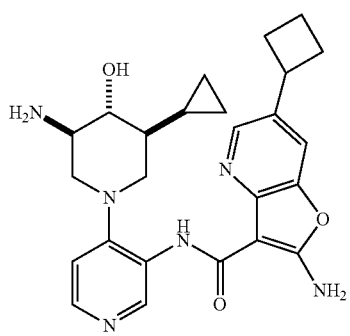 [SMILES: Nc1oc2cc(C3CCC3)cnc2c1C(=O)Nc1cnccc1N1C[C@@H](N)[C@H](O)[C@@H](C2CC2)C1]

A procedure analogous to that described in Example 123 was used except that tert-butyl (3R,4R,5S)-1-(3-aminopyridin-4-yl)-4-{[tert-butyl(dimethyl)silyl]oxy}-5-cyclopropylpiperidin-3-yl)carbamate and 2-[(tert-butoxycarbonyl)

amino]-6-cyclobutylfuro[3,2-b]pyridine-3-carboxylic acid were used in the amide coupling/deprotection sequence to afford the title compound. LCMS calc. for $C_{25}H_{31}N_6O_3$ (M+H)$^+$: m/z=463.2. found: 463.3.

Example 126

2-Amino-N-{4-[(3S,5R)-3-amino-5-(trifluoromethyl)piperidin-1-yl]pyridin-3-yl}-6-{6-[(methylamino)carbonyl]pyridin-3-yl}furo[3,2-b]pyridine-3-carboxamide

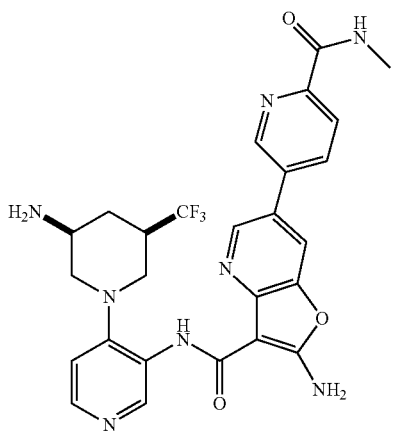 [SMILES: CNC(=O)c1ccc(-c2cnc3c(C(=O)Nc4cnccc4N4C[C@@H](N)C[C@@H](C(F)(F)F)C4)c(N)oc3c2)cn1]

Step A. ethyl 2-[(tert-butoxycarbonyl)amino]-6-{6-[(methylamino)carbonyl]pyridin-3-yl}furo[3,2-b]pyridine-3-carboxylate

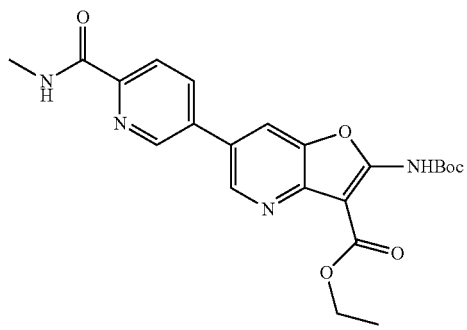 [SMILES: CCOC(=O)c1c(NC(=O)OC(C)(C)C)oc2cc(-c3ccc(C(=O)NC)nc3)cnc12]

A mixture of ethyl 6-bromo-2-[(tert-butoxycarbonyl)amino]furo[3,2-b]pyridine-3-carboxylate (0.300 g, 0.779 mmol), N-methyl-5-(4,4,5,5-tetramethyl-1,3,2-dioxaborolan-2-yl) pyridine-2-carboxamide (0.2654 g, 1.012 mmol), N-methyl-5-(4,4,5,5-tetramethyl-1,3,2-dioxaborolan-2-yl) pyridine-2-carboxamide, DIPEA (0.27 mL, 1.6 mmol) in 1,4-dioxane (4 mL) and water (0.2 mL) was deoxygenated and purged with $N_2$ several times prior to the addition of Pd(tBu$_3$P)$_2$ (0.0796 g, 0.16 mmol). The reaction mixture was heated at 85° C. for 1.5 h. Upon cooling to ambient temperature the reaction mixture was diluted with EtOAc and was filtered through a pad of diatomaceous earth. The resulting filtrate was washed with water, brine, dried over Na$_2$SO$_4$, filtered and concentrated under reduced pressure. The crude product was purified by silica gel flash column chromatography using a CombiFlash® apparatus eluting with EtOAc/hexanes (0-100%) to afford 285 mg of the sub-title compound (83% yield). LCMS calc. for $C_{22}H_{25}N_4O_6$ (M+H)$^+$: m/z=441.2. found: 441.2.

Step B. 2-[(tert-Butoxycarbonyl)amino]-6-{6-[(methylamino)carbonyl]pyridin-3-yl}furo[3,2-b]pyridine-3-carboxylic acid

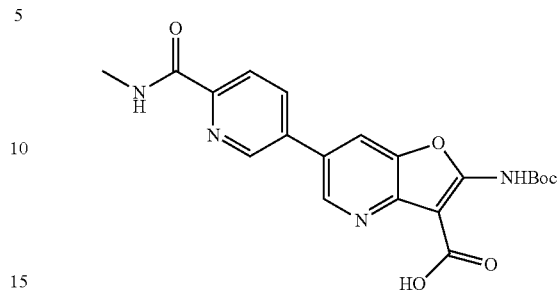

The intermediate from Step A was dissolved in THF (3 mL), MeOH (2 mL), and water (1 mL). LiOH.H$_2$O (0.13 g, 5.4 mmol) was added and the resulting solution was heated at 62° C. overnight. The reaction mixture was diluted with EtOAc (40 mL) and neutralized by the addition of 1.0 M HCl in water until the pH=7. The layers were separated and the organic layer was washed with H$_2$O (4 mL) then the combined aqueous phases were back-extracted with EtOAc (5 mL). The combined organic layers were washed with brine (5 mL), dried over Na$_2$SO$_4$, filtered, and concentrated under reduced pressure to afford the sub-title compound (285 mg, 89% yield). The crude product was used directly in the next step without further purification. LCMS calc. for $C_{20}H_{21}N_4O_6$ (M+H)$^+$: m/z=413.1. found: 413.3.

Step C. 2-Amino-N-{4-[(3S,5R)-3-amino-5-(trifluoromethyl)piperidin-1-yl]pyridin-3-yl}-6-{6-[(methylamino)carbonyl]pyridin-3-yl}furo[3,2-b]pyridine-3-carboxamide An amide coupling and subsequent de-protection procedure analogous to that described in Example 122 was used except that 2-[(tert-butoxycarbonyl)amino]-6-{6-[(methylamino) carbonyl]pyridin-3-yl}furo[3,2-b]pyridine-3-carboxylic acid and tert-butyl [(3S,5R)-1-(3-aminopyridin-4-yl)-5-(trifluoromethyl)piperidin-3-yl]carbamate were used as starting materials to afford the title compound. LCMS calc. for $C_{26}H_{26}F_3N_8O_3$ (M+H)$^+$: m/z=555.2. found: 555.3.

Example 127

2-Amino-N-(4-((3S,5R)-3-amino-5-methylpiperidin-1-yl)pyridin-3-yl)-6-(6-(methylcarbamoyl)pyridin-3-yl)furo[3,2-b]pyridine-3-carboxamide

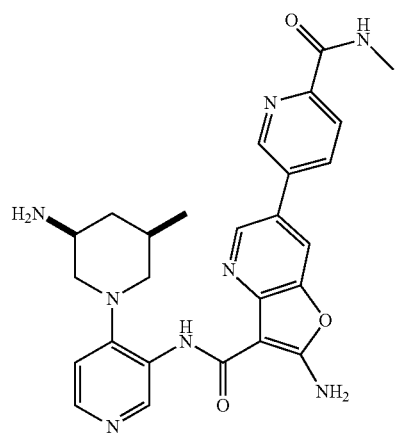 [SMILES: CNC(=O)c1ccc(-c2cnc3c(C(=O)Nc4cnccc4N4C[C@H](C)C[C@H](N)C4)c(N)oc3c2)cn1]

A procedure analogous to that described in Example 122 was used except that tert-butyl [(3S,5R)-1-(3-aminopyridin-4-yl)-5-methylpiperidin-3-yl]carbamate and 2-[(tert-butoxycarbonyl)amino]-6-{6-[(methylamino)carbonyl]pyridin-3-yl}furo[3,2-b]pyridine-3-carboxylic acid were used as the starting materials to afford the title compound. LCMS calc. for $C_{26}H_{29}N_8O_3$ (M+H)$^+$: m/z=501.2. found: 501.3.

Example 128

2-Amino-N-(4-((3R,4R,5S)-3-amino-5-cyclopropyl-4-hydroxypiperidin-1-yl)pyridin-3-yl)-6-cyclopropylfuro[3,2-b]pyridine-3-carboxamide

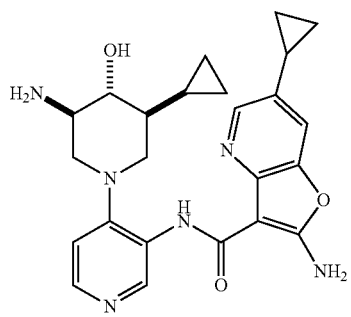 [SMILES: Nc1oc2cc(C3CC3)cnc2c1C(=O)Nc1cnccc1N1C[C@@H](N)[C@H](O)[C@@H](C2CC2)C1]

Step A. Ethyl 2-[(tert-butoxycarbonyl)amino]-6-cyclopropylfuro[3,2-b]pyridine-3-carboxylate

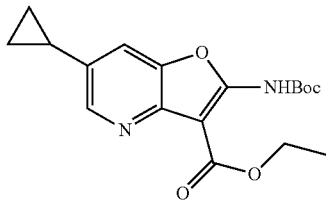 [SMILES: CCOC(=O)c1c(NC(=O)OC(C)(C)C)oc2cc(C3CC3)cnc12]

A mixture of ethyl 6-bromo-2-[(tert-butoxycarbonyl)amino]furo[3,2-b]pyridine-3-carboxylate (300. mg, 0.779 mmol), potassium cyclopropyltrifluoroborate (340 mg, 2.3 mmol), $K_3PO_4$ (500 mg, 2.3 mmol) and Pd(PPh$_3$)$_4$ (45 mg, 0.039 mmol) in toluene (3 mL) and water (1 mL) was de-gassed and purged with N$_2$ several times prior to heating at 100° C. overnight. The reaction mixture was diluted with MeOH, filtered through a pad of diatomaceous earth and purified by silica gel flash column chromatography using a CombiFlash® apparatus eluting with MeOH/DCM (0-10%) to afford 183 mg of the sub-title compound (95% yield). LCMS calc. for $C_{18}H_{23}N_2O_5$ (M+H)$^+$: m/z=347.2. found: 347.1.

Step B. 2-[(tert-Butoxycarbonyl)amino]-6-cyclopropylfuro[3,2-b]pyridine-3-carboxylic acid

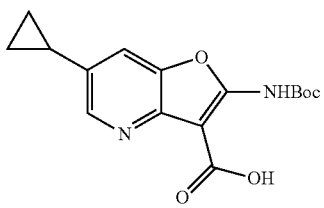 [SMILES: CC(C)(C)OC(=O)Nc1oc2cc(C3CC3)cnc2c1C(=O)O]

A mixture of ethyl 2-[(tert-butoxycarbonyl)amino]-6-cyclopropylfuro[3,2-b]pyridine-3-carboxylate (183 mg, 0.53 mmol) and LiOH.H$_2$O (135 mg, 3.22 mmol) in THF (2.0 mL), MeOH (1.8 mL), and water (0.8 mL) was stirred at 60° C. overnight. The reaction mixture was diluted with EtOAc (40 mL) and neutralized by the addition of 1.0 M HCl in water until pH=7. The layers were separated and the organic layer was washed with H$_2$O (4 mL) and the combined aqueous phases were back-extracted with EtOAc (5 mL). The combined organic layers were washed with brine (5 mL), dried over Na$_2$SO$_4$, filtered, and concentrated under reduced pressure to afford 122 mg of the sub-title compound (73% yield). The crude product was used directly in the next step without further purification. LCMS calc. for $C_{16}H_{19}N_2O_5$ (M+H)$^+$: m/z=319.1. found: 319.1.

Step C. 2-Amino-N-(4-((3R,4R,5S)-3-amino-5-cyclopropyl-4-hydroxypiperidin-1-yl)pyridin-3-yl)-6-cyclopropylfuro[3,2-b]pyridine-3-carboxamide An amide coupling and subsequent de-protection procedure analogous to that described in Example 122 was used with the exception that 2-[(tert-butoxycarbonyl)amino]-6-cyclopropylfuro[3,2-b]pyridine-3-carboxylic acid and tert-butyl ((3R,4R,5S)-1-(3-aminopyridin-4-yl)-4-{[tert-butyl(dimethyl)silyl]oxy}-5-cyclopropylpiperidin-3-yl)carbamate were used as the starting materials to afford the title compound. LCMS calc. for $C_{24}H_{29}N_6O_3$ (M+H)$^+$: m/z=449.2. found: 449.2.

Example 129

2-Amino-N-(4-((3R,4R,5S)-3-amino-5-cyclopropyl-4-hydroxypiperidin-1-yl)pyridin-3-yl)-6-(trifluoromethyl)furo[3,2-b]pyridine-3-carboxamide

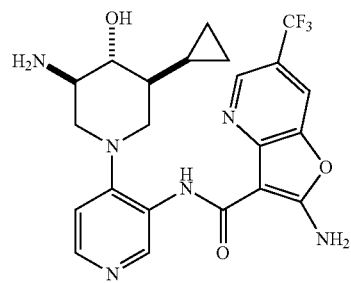 [SMILES: Nc1oc2cc(C(F)(F)F)cnc2c1C(=O)Nc1cnccc1N1C[C@@H](N)[C@H](O)[C@@H](C2CC2)C1]

An amide coupling and subsequent de-protection procedure analogous to that described Example 122 was used with the exception that 2-[(tert-butoxycarbonyl)amino]-6-(trifluormethyl)furo[3,2-b]pyridine-3-carboxylic acid and tert-butyl((3R,4R,5S)-1-(3-aminopyridin-4-yl)-4-{[tert-butyl(dimethyl)silyl]oxy}-5-cyclopropylpiperidin-3-yl)carbamate were used as the starting materials to afford the title compound. LCMS calc. for $C_{22}H_{24}F_3N_6O_3$ (M+H)$^+$: m/z=477.2. found: 477.1.

Example 130

2-Amino-N-{4-[(1R,3S,5S)-3-amino-5-methylcyclohexyl]pyridin-3-yl}-6-isopropylfuro[3,2-b]pyridine-3-carboxamide

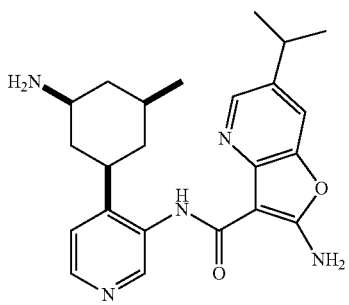 [SMILES: CC(C)c1cnc2c(C(=O)Nc3cnccc3[C@@H]3C[C@H](C)C[C@H](N)C3)c(N)oc2c1]

Step 1. 5-Methyl-3-oxocyclohex-1-en-1-yl trifluoromethanesulfonate

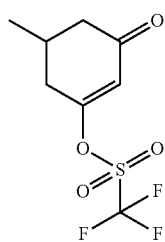 [SMILES: CC1CC(=O)C=C(OS(=O)(=O)C(F)(F)F)C1]

To a solution of 5-methylcyclohexane-1,3-dione (50.1 g, 397 mmol) in DCM (700 mL) was added sodium carbonate (46.3 g, 437 mmol) and cooled to 0° C. A solution of trifluoromethanesulfonic anhydride (66.8 mL, 397 mmol) in DCM (600 mL) was added to reaction flask dropwise over 1 h at 0° C. The reaction mixture was stirred at room temperature for 2 h. The solution was filtered and the filtrate was quenched by careful addition of saturated NaHCO₃ until pH=7. The organic layer was washed with water, brine, dried over Na₂SO₄ and concentrate to give the sub-title compound as a light yellow oil. The crude product was used for the next step without purification. LCMS calc. for $C_8H_{10}F_3O_4S$ (M+H)⁺: m/z=259.0. Found: 259.1.

Step 2. 5-Methyl-3-(4,4,5,5-tetramethyl-1,3,2-dioxaborolan-2-yl)cyclohex-2-en-1-one

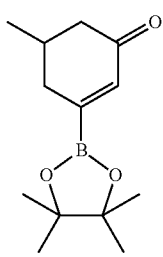 [SMILES: CC1CC(=O)C=C(B2OC(C)(C)C(C)(C)O2)C1]

To a mixture of 4,4,5,5,4',4',5',5'-octamethyl-[2,2']bi[[1,3,2]dioxaborolanyl] (77.6 g, 306 mmol), KOAc (77.1 g, 785 mmol) and [1,1'-bis(diphenylphosphino)ferrocene]dichloropalladium(II), complex with DCM (1:1) (8.6 g, 10.0 mmol) under N₂ was added a solution of 5-methyl-3-oxocyclohex-1-en-1-yl trifluoromethanesulfonate (67.6 g, 262 mmol) in 1,4-dioxane (420 mL). The reaction mixture was deoxygenated with N₂. The mixture was stirred at 80° C. overnight. After cooling to room temperature, the mixture was filtered through a pad of diatomaceous earth (eluted with EtOAc). The filtrate was concentrated under reduced pressure to give the crude product, which was used in next step without purification.

Step 3. 5-Methyl-3-(3-nitropyridin-4-yl)cyclohex-2-en-1-one

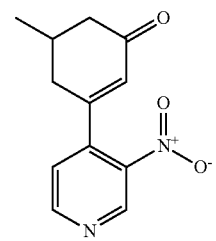 [SMILES: CC1CC(=O)C=C(c2ccncc2[N+](=O)[O-])C1]

A solution of 5-methyl-3-(4,4,5,5-tetramethyl-1,3,2-dioxaborolan-2-yl)cyclohex-2-en-1-one (20.0 g, 84.7 mmol) in 1,4-dioxane (120 mL), 4-chloro-3-nitropyridine (10.0 g, 63.1 mmol), 2.0 M aq. Na₂CO₃ (63.1 mL, 126 mmol) and [1,1'-bis(diphenylphosphino)ferrocene]dichloropalladium (II), complex with DCM (1:1) (2.58 g, 3.15 mmol) was heated under reflux under a N₂ atmosphere for 1 h. The reaction mixture was diluted with EtOAc and water, then filtered through a pad of diatomaceous earth, which was washed with EtOAc. The two layers were separated and the aqueous layer was extracted with EtOAc (2 times). The combined organic phases were washed with water, brine and dried over Na₂SO₄. The crude product was purified by flash chromatography (eluting with a gradient 0-60% EtOAc in hexanes) to give the sub-title compound as an orange oil (6.6 g, 45%). LCMS calc. for $C_{12}H_{13}N_2O_3$ (M+H)⁺: m/z=233.1. Found: 233.1.

Step 4. cis-(±)-5-Methyl-3-(3-nitropyridin-4-yl)cyclohex-2-en-1-ol

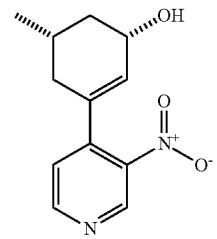 [SMILES: C[C@H]1CC(c2ccncc2[N+](=O)[O-])=C[C@@H](O)C1]

To a solution of 5-methyl-3-(3-nitropyridin-4-yl)cyclohex-2-en-1-one (6.6 g, 28 mmol) in EtOH (93 mL) was added CeCl₃.7H₂O (12.7 g, 34.1 mmol). The resulting mixture was cooled to 0° C. and sodium tetrahydroborate (1.29 g, 34.1 mmol) was added portionwise. After stirring at 0° C. for 1 h, the reaction was quenched with water and concentrated under reduced pressure to remove the EtOH and extracted with EtOAc. The organic extract was washed with brine, dried over $Na_2SO_4$, filtered and concentrated under reduced pressure. The crude product was purified by flash chromatography (eluting with a gradient of 20-90% EtOAc in hexanes) to give the sub-title compound as racemic mixture (6.4 g, 96%). LCMS calc. for $C_{12}H_{15}N_2O_3$ $(M+H)^+$: m/z=235.1. Found: 235.1.

Step 5. 4-(3-(tert-Butyldimethylsilyloxy)-5-methyl-cyclohex-1-enyl)3-nitropyridine

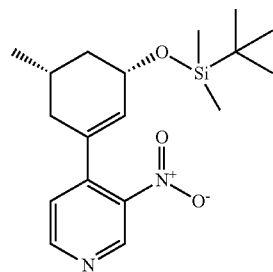 [SMILES: C[C@H]1CC(c2ccncc2[N+](=O)[O-])=C[C@@H](O[Si](C)(C)C(C)(C)C)C1]

A solution of cis(±)-5-methyl-3-(3-nitropyridin-4-yl)cyclohex-2-en-1-ol (6.4 g, 27 mmol) in DMF (51 mL) was added 1H-imidazole (3.7 g, 55 mmol) and tert-butyldimethylsilyl chloride (5.8 g, 38 mmol). The resulting mixture was stirred at room temperature overnight. The reaction solution was diluted with water and EtOAc. The organic layer was washed with water (2 times), brine, dried over $Na_2SO_4$ and concentrated under reduced pressure to give product as an orange oil. LCMS calc. for $C_{18}H_{29}N_2O_3Si$ $(M+H)^+$: m/z=349.2. Found: 349.2.

Step 6. 4-(3-(tert-Butyldimethylsilyloxy)-5-methyl-cyclohex-1-enyl)pyridin-3-amine

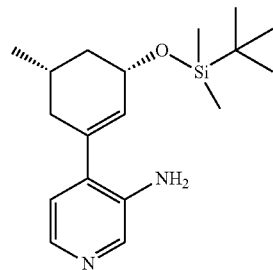 [SMILES: C[C@H]1CC(c2ccncc2N)=C[C@@H](O[Si](C)(C)C(C)(C)C)C1]

The mixture of 4-(3-(tert-butyldimethylsilyloxy)-5-methylcyclohex-1-enyl)3-nitropyridine (9.3 g, 27 mmol), iron (8.9 g, 160 mmol) and AcOH (67 mL) was stirred at room temperature for 2 h. The reaction mixture was filtered through a pad of diatomaceous earth, washed with MeOH. The filtrate was concentrated under reduced pressure to remove the volatile solvents, and the residue was dissolved in EtOAc, washed with saturated $Na_2CO_3$, brine and dried over $Na_2SO_4$, filtered and concentrated under reduced pressure to give the sub-title compound as a yellow oil (7.7 g, 90%). LCMS calc. for $C_{18}H_{31}N_2OSi$ $(M+H)^+$: m/z=319.2. Found: 319.2.

Step 7. 4-(3-(tert-Butyldimethylsilyloxy)-5-methyl-cyclohexyl)pyridin-3-amine

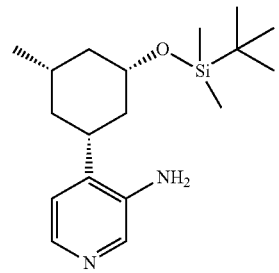 [SMILES: C[C@@H]1C[C@H](O[Si](C)(C)C(C)(C)C)C[C@H](c2ccncc2N)C1]

To a suspension of 4-(3-(tert-butyldimethylsilyloxy)-5-methylcyclohex-1-enyl)pyridin-3-amine (7.7 g, 24 mmol) in MeOH (203 mL) under $N_2$ was added 10% Pd on carbon (2.64 g, 2.48 mmol). The mixture was purged with $H_2$ and stirred under a balloon of $H_2$ for 3 h. The mixture was filtered through a pad of diatomaceous earth and eluted with MeOH. The filtrate was concentrated under reduced pressure to give the crude product as an off-white foamy solid (7.3 g, 93%). The crude product was used directly in the next step without further purification. LCMS calc. for $C_{18}H_{33}N_2OSi$ $(M+H)^+$: m/z=321.2. Found: 321.3.

Step 8. cis (±) Benzyl 4-3-(tert-butyldimethylsilyloxy)-5-methylcyclohexylpyridin-3-ylcarbamate

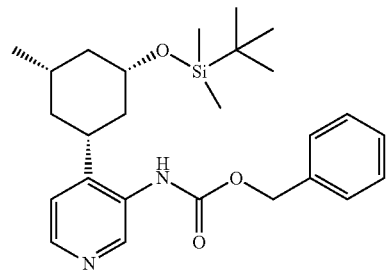 [SMILES: C[C@@H]1C[C@H](O[Si](C)(C)C(C)(C)C)C[C@H](c2ccncc2NC(=O)OCc2ccccc2)C1]

To a solution of 4-(3-(tert-butyldimethylsilyloxy)-5-methylcyclohexyl)pyridin-3-amine (7.3 g, 23 mmol) in DCM (50 mL) was added N-(benzyloxycarbonyloxy)succinimide (6.5 g, 26 mmol) and DMAP (0.14 g, 1.2 mmol). After stirring for 16 h, another portion of N-(benzyloxycarbonyloxy)succinimide (3.1 g, 12 mmol) was added, followed by DMAP. The reaction mixture was stirred overnight. The reaction solution was partitioned between EtOAc and saturated aq. $Na_2CO_3$. The organic layer was washed with saturated aq. $Na_2CO_3$ and brine, dried over $Na_2SO_4$, filtered and concentrated. The residue was purified by flash chromatography (eluting with a gradient of 0-40% EtOAc in hexanes) to give the sub-title compound as a brown oil (7.0

Step 9. cis-(±)Benzyl 4-(-3-hydroxy-5-methylcyclohexyl)pyridin-3-ylcarbamate

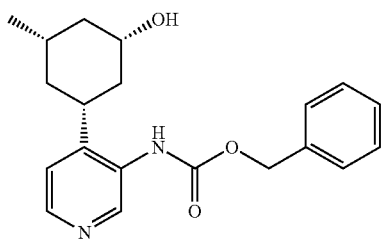 [SMILES: C[C@@H]1C[C@H](O)C[C@H](c2ccncc2NC(=O)OCc2ccccc2)C1]

To a solution of cis (±) benzyl 4-3-(tert-butyldimethylsilyloxy)-5-methylcyclohexylpyridin-3-ylcarbamate (7.0 g, 15 mmol) in MeOH (100 mL) was added 6.0 M HCl in water (50.0 mL, 300 mmol). The resulting mixture was stirred at room temperature for 6 h. The pH was then adjusted to pH=7 by addition of 6 M NaOH and the volatile solvents were removed under reduced pressure. The aqueous layer was extracted with EtOAc and the organic extract was washed with brine, dried over MgSO$_4$, filtered and concentrated under reduced pressure to give the crude product which was used in next step without purification (4.8 g, 92%). LCMS calc. for C$_{20}$H$_{25}$N$_2$O$_3$ (M+H)$^+$: m/z=341.2. Found: 341.1.

Step 10. cis-(±)-Benzyl 4-(3-methyl-5-oxocyclohexyl)pyridin-3-ylcarbamate

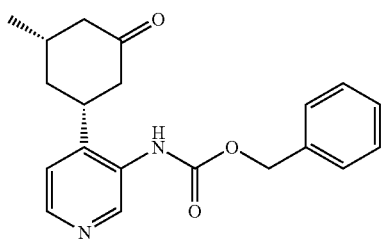 [SMILES: C[C@@H]1CC(=O)C[C@H](c2ccncc2NC(=O)OCc2ccccc2)C1]

To a solution of cis-(±)benzyl 4-(-3-hydroxy-5-methylcyclohexyl)pyridin-3-ylcarbamate (4.8 g, 14 mmol) in DCM (90. mL) was added Dess-Martin periodinane (8.97 g, 21.2 mmol). The reaction mixture was stirred at room temperature for 2 h. The reaction mixture was diluted with ether and saturated aq. NaHCO$_3$ and stirred for 30 min. The organic layer was separated and washed with brine, dried over Na$_2$SO$_4$, filtered and concentrated under reduced pressure. The crude product was purified by flash chromatography (eluting with a gradient of 0-50% EtOAc in hexanes) to give the sub-title compound (2.5 g, 52%). LCMS calc. for C$_{20}$H$_{23}$N$_2$O$_3$ (M+H)$^+$: m/z=339.2. Found: 339.1.

Step 11. cis-(±)-Benzyl 4-(3-(benzylamino)-5-methylcyclohexyl)pyridin-3-ylcarbamate

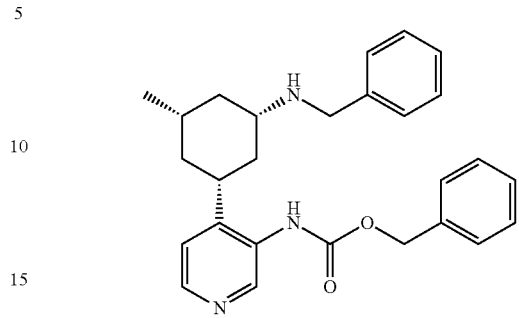

To a solution of cis-(±)-benzyl 4-(3-methyl-5-oxocyclohexyl)pyridin-3-ylcarbamate (2.50 g, 7.39 mmol) in MeOH (30. mL) was added benzylamine (2.42 mL, 22.2 mmol). The resulting mixture was stirred at room temperature for 2 h. After cooling to −78° C., 2.0 M LiBH$_4$ in THF (4.1 mL, 8.1 mmol) was added. The reaction mixture was allowed to warm to room temperature and stirred overnight. The solution was partitioned between EtOAc and saturated aq. NaHCO$_3$, the layers were separated, and the organic extract was washed further with saturated aq. NaHCO$_3$ and brine, then dried over MgSO$_4$, filtered and concentrated under reduced pressure. The crude product was used in the next step without purification (3.1 g, 98%). LCMS calc. for C$_{27}$H$_{32}$N$_3$O$_2$ (M+H)$^+$: m/z=430.2. Found: 430.2.

Step 12. 4 tert-Butyl [(1S,3R,5S)-3-(3-aminopyridin-4-yl)-5-methylcyclohexyl]carbamate and 4 tert-Butyl [(1R,3S,5R)-3-(3-aminopyridin-4-yl)-5-methylcyclohexyl]carbamate

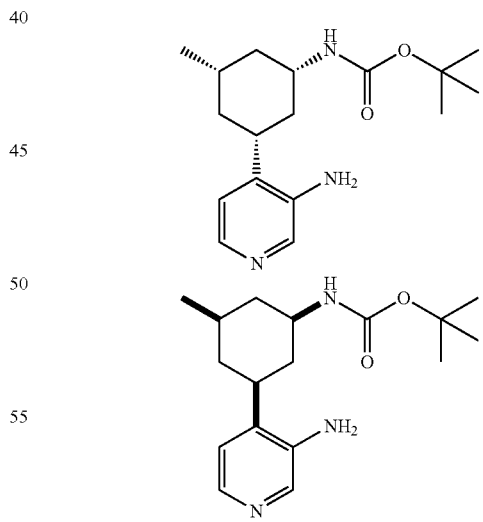

To a solution of cis-(±)-benzyl 4-(3-(benzylamino)-5-methylcyclohexyl)pyridin-3-ylcarbamate (3.10 g, 7.22 mmol) in MeOH (100 mL) was added 20% palladium hydroxide (1.0 g, 1.4 mmol). The resulting heterogeneous solution was put under an atmosphere of H$_2$ and was stirred for 14 h. At this time the reaction mixture was purged with N$_2$, Boc$_2$O (1.6 g, 7.2 mmol) was added and the solution was stirred for 7 h. Additional Boc₂O (1.6 g, 7.2 mmol) was added and the solution was stirred overnight. The solvent was removed under reduced pressure and the residue was purified by flash chromatography (eluting with a gradient of 20-100% EtOAc in hexanes) to give the racemic product.

The racemic mixture was separated by chiral column (CHIRALPAK IA Col, 15% EtOH/85% Hex, 12 ml/min.) to give two peaks.

Peak 1 retention time: 14.3 min. LCMS calc. for $C_{17}H_{28}N_3O_2$ (M+H)⁺: m/z=306.2. Found: 306.2. This compound was tentatively identified as the (1R,3S,5R) enantiomer.

Peak 2 retention time: 18.6 min. LCMS calc. for $C_{17}H_{28}N_3O_2$ (M+H)⁺: m/z=306.2. Found: 306.2. This compound was tentatively identified as the (1S,3R,5S) enantiomer.

Step 13. Ethyl 2-[bis(tert-butoxycarbonyl)amino]-6-isopropenylfuro[3,2-b]pyridine-3-carboxylate

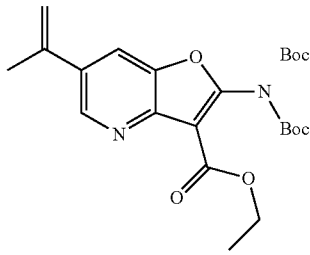 [SMILES: C=C(C)c1cnc2c(C(=O)OCC)c(NC(=O)OC(C)(C)C)oc2c1 ; "Boc"]

A mixture of ethyl 2-[bis(tert-butoxycarbonyl)amino]-6-bromofuro[3,2-b]pyridine-3-carboxylate (1.40 g, 2.88 mmol), 2-isopropenyl-4,4,5,5-tetramethyl-1,3,2-dioxaborolane (0.582 mL, 3.46 mmol), dicyclohexyl(2',4',6'-triisopropylbiphenyl-2-yl)phosphine-(2'-aminobiphenyl-2-yl)(chloro)palladium (1:1) (2.0 mg, 0.25 mmol) and K₃PO₄·H₂O (1.46 g, 6.35 mmol) in 1,4-dioxane (8.0 mL) and water (2.7 mL) was stirred under N₂ atmosphere at 70° C. for 2 h. The crude product was diluted with DCM and washed with water. The organic layer was dried over Na₂SO₄, filtered, and concentrated. The residue was purified by chromatography on silica gel (eluting with a gradient of 15-40% EtOAc in hexanes) to give the sub-title compound (1.20 g, 98% yield). LCMS calc. for $C_{23}H_{31}N_2O_7$ (M+H)⁺: m/z=447.2. Found: 447.2.

Step 14. Ethyl 2-[bis(tert-butoxycarbonyl)amino]-6-isopropylfuro[3,2-b]pyridine-3-carboxylate

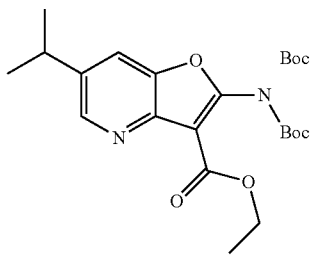 [SMILES: CCOC(=O)c1c(NC(=O)OC(C)(C)C)oc2cc(C(C)C)cnc12 ; "Boc"]

To a flask containing ethyl 2-[bis(tert-butoxycarbonyl)amino]-6-isopropenylfuro[3,2-b]pyridine-3-carboxylate (1.50 g, 3.36 mmol) in MeOH (34 mL) under N₂ atmosphere was added 10% Pd on carbon (540 mg, 0.50 mmol). The reaction mixture was purged with H₂ and stirred at H₂ atmosphere for 2 h. The reaction mixture was filtered through a pad of diatomaceous earth (eluted with MeOH). The filtrate was concentrated under reduced pressure to give the product as a brown foamy solid (1.27 g, 84%). LCMS calc. for $C_{23}H_{33}N_2O_7$ (M+H)⁺: m/z=449.2. Found: 449.2.

Step 15. 2-[(tert-Butoxycarbonyl)amino]-6-isopropylfuro[3,2-b]pyridine-3-carboxylic acid

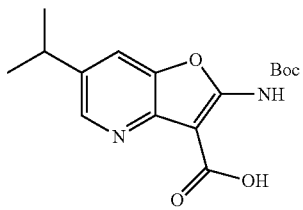 [SMILES: CC(C)c1cnc2c(C(=O)O)c(N)oc2c1 ; "Boc"]

A mixture of ethyl 2-[bis(tert-butoxycarbonyl)amino]-6-isopropylfuro[3,2-b]pyridine-3-carboxylate (1.50 g, 3.34 mmol), LiOH (440 mg, 18 mmol) in THF (11 mL)/water (3.8 mL)/MeOH (7.5 mL) was stirred at 60° C. overnight. Solvent was evaporated and water was added. The pH was adjusted to 7 with 1 M aqueous solution of HCl. The aqueous layer was extracted with EtOAc (2 times). The combined organic layers were washed with brine, dried over Na₂SO₄, filtered and concentrated to give the sub-title compound (0.78 g, 73%). LCMS calc. for $C_{16}H_{21}N_2O_5$ (M+H)⁺: m/z=321.1. Found: 321.1.

Step 16. tert-Butyl ((1S,3R,5S)-3-{3-[({2-[(tert-butoxycarbonyl)amino]-6-isopropylfuro[3,2-b]pyridin-3-yl}carbonyl)amino]pyridin-4-yl}-5-methylcyclohexyl)carbamate

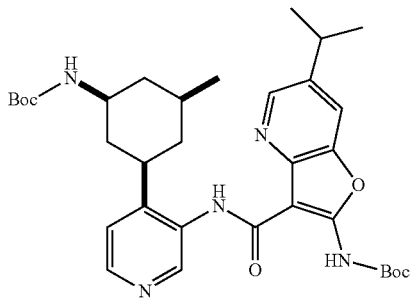 [SMILES: CC(C)c1cnc2c(C(=O)Nc3cnccc3[C@@H]3C[C@H](C)C[C@H](NC(=O)OC(C)(C)C)C3)c(NC(=O)OC(C)(C)C)oc2c1]

A solution of 2-[(tert-butoxycarbonyl)amino]-6-isopropylfuro[3,2-b]pyridine-3-carboxylic acid (893 mg, 2.37 mmol) and tert-butyl [(1S,3R,5S)-3-(3-aminopyridin-4-yl)-5-methylcyclohexyl]carbamate (603 mg, 1.97 mmol) (step 12, peak 2) in 1,2-dichloroethane (6.24 mL) was added HATU (1.13 g, 2.96 mmol) and DIPEA (760 μL, 4.3 mmol). The reaction mixture was stirred at room temperature overnight. The reaction mixture was diluted with water, and the aqueous layer was extracted with DCM. The combined organic layers were dried over Na₂SO₄, filtered and concentrated. The residue was purified by preparative LCMS (XBridge C18 column, eluting with a gradient of MeCN/water containing 0.05% TFA, at flow rate of 60 mL/min.) give the sub-title compound (0.48 g, 40%). LCMS calc. for $C_{33}H_{46}N_5O_6$ (M+H)$^+$: m/z=608.3. Found: 608.3.

Step 17. 2-Amino-N-{4-[(1R,3S,5S)-3-amino-5-methylcyclohexyl]pyridin-3-yl}-6-isopropylfuro[3,2-b]pyridine-3-carboxamide tert-Butyl ((1S,3R,5S)-3-{3-[({2-[(tert-butoxycarbonyl)amino]-6-isopropylfuro[3,2-b]pyridin-3-yl}carbonyl)amino]pyridin-4-yl}-5-methylcyclohexyl)carbamate (0.48 g, 0.79 mmol) was treated with 1:1 TFA/DCM (6 mL) for 1 h. The volatile was removed under reduced pressure and the residue was dissolved in MeOH and purified by preparative LCMS (XBridge C18 column, eluting with a gradient of MeCN/water containing 0.05% TFA, at flow rate of 60 mL/min.) to give the title compound as the tris(trifluoroacetate) salt (305 mg, 51%) as a white solid. LCMS calc. for $C_{23}H_{30}N_5O_2$ (M+H)$^+$: m/z=408.2. Found: 408.2. $^1$H NMR (500 MHz, DMSO) δ 10.31 (s, 1H), 9.63 (s, 1H), 8.48 (d, J=5.5 Hz, 1H), 8.35 (s, 2H), 8.18 (d, J=1.3 Hz, 1H), 8.02 (s, 2H), 7.76 (d, J=1.4 Hz, 1H), 7.65 (d, J=5.6 Hz, 1H), 3.34 (m, 1H), 3.25 (t, J=12.0 Hz, 1H), 3.04 (m, 1H), 2.18-2.05 (m, 2H), 1.89 (m, 2H), 1.53 (m, 1H), 1.35-1.06 (m, 8H), 1.02 (d, J=6.4 Hz, 3H).

2-Amino-N-{4-[(1S,3R,5R)-3-amino-5-methylcyclohexyl]pyridin-3-yl}-6-isopropylfuro[3,2-b]pyridine-3-carboxamide is prepared by an analogous route using the alternative enantiomer of the starting material in Step 16.

Example 131

2-Amino-N-{4-[(3S,5R)-3-amino-5-(trifluoromethyl)piperidin-1-yl]pyridin-3-yl}-6-(3-methoxypropyl)furo[3,2-b]pyridine-3-carboxamide

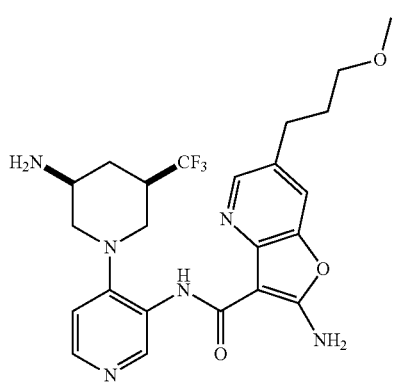 [SMILES: COCCCc1cnc2c(C(=O)Nc3cnccc3N3C[C@@H](N)C[C@@H](C(F)(F)F)C3)c(N)oc2c1]

Step 1. Ethyl 2-[bis(tert-butoxycarbonyl)amino]-6-[(1E)-3-methoxyprop-1-en-1-yl]furo[3,2-b]pyridine-3-carboxylate

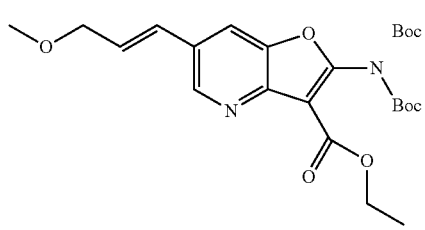 [SMILES: CCOC(=O)c1c(NC(=O)OC(C)(C)C)oc2cc(/C=C/COC)cnc12 ; "Boc"]

A mixture of ethyl 2-[bis(tert-butoxycarbonyl)amino]-6-bromofuro[3,2-b]pyridine-3-carboxylate (7.30 g, 15.0 mmol), potassium trifluoro[(1E)-3-methoxyprop-1-en-1-yl]borate(1-) (2.80 g, 15.7 mmol), dicyclohexyl(2',4',6'-triisopropylbiphenyl-2-yl)phosphine-(2'-aminobiphenyl-2-yl)(chloro)palladium (1:1) (960 mg, 1.2 mmol) and $K_3PO_4 \cdot H_2O$ (7.06 g, 30.6 mmol) in 1,4-dioxane (47.8 mL) and water (11.0 mL) was stirred at 75° C. under $N_2$ atmosphere for 6 h. The crude product was diluted with DCM and washed with water. The organic layer was dried over $Na_2SO_4$, filtered and concentrated under reduced pressure. The residue was purified by flash chromatography (eluting with a gradient of 15-40% EtOAc in hexanes) to give the sub-title compound (6.3 g, 88% yield). LCMS calc. for $C_{24}H_{33}N_2O_8$ (M+H)$^+$: m/z=477.2. Found: 477.2.

Step 2. Ethyl 2-[bis(tert-butoxycarbonyl)amino]-6-(3-methoxypropyl)furo[3,2-b]pyridine-3-carboxylate

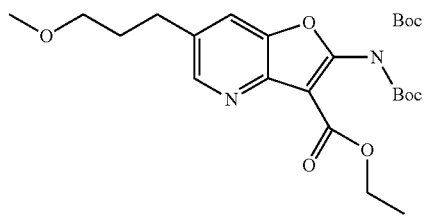 [SMILES: CCOC(=O)c1c(NC(=O)OC(C)(C)C)oc2cc(CCCOC)cnc12 ; "Boc"]

To a solution of ethyl 2-[bis(tert-butoxycarbonyl)amino]-6-[(1E)-3-methoxyprop-1-en-1-yl]furo[3,2-b]pyridine-3-carboxylate (6.3 g, 13 mmol) in MeOH (100 mL) was added 10% Pd on carbon (2.1 g, 2.0 mmol). The reaction mixture was stirred under an atmosphere of $H_2$ for 1.5 h. The reaction mixture was filtered through a pad of diatomaceous earth. The filtrate was concentrated under reduced pressure to give product as a yellow solid (6.1 g, 96%). LCMS calc. for $C_{24}H_{35}N_2O_8$ (M+H)$^+$: m/z=479.2. Found: 479.2.

Step 3. 2-[(tert-Butoxycarbonyl)amino]-6-(3-methoxypropyl)furo[3,2-b]pyridine-3-carboxylic acid

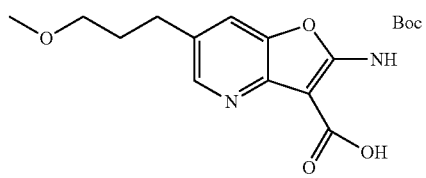 [SMILES: COCCCc1cnc2c(C(=O)O)c(N)oc2c1 ; "Boc"]

A mixture of ethyl 2-[bis(tert-butoxycarbonyl)amino]-6-(3-methoxypropyl)furo[3,2-b]pyridine-3-carboxylate (6.10 g, 12.7 mmol), LiOH (1.5 g, 64 mmol) in THF (48 mL)/water (16 mL)/MeOH (32 mL) was stirred at 60° C. overnight. LiOH (0.61 g, 25 mmol) was added and heated at 60° C. for another 6 h. Solvent was evaporated and water added. The solution was neutralized with 1 M HCl to pH 7. The aqueous layer was extracted with EtOAc. The combined organic layers were dried over $Na_2SO_4$, filtered and concentrated reduced pressure to give the sub-title compound as a white solid (3.8 g, 85%). LCMS calc. for $C_{17}H_{23}N_2O_6$ (M+H)$^+$: m/z=351.2. Found: 351.2.

Step 4. tert-Butyl [(3S,5R)-1-[3-({[2-[(tert-butoxycarbonyl)amino]-6-(3-methoxypropyl)furo[3,2-b]pyridin-3-yl]carbonyl}amino)pyridin-4-yl]-5-(trifluoromethyl)piperidin-3-yl]carbamate

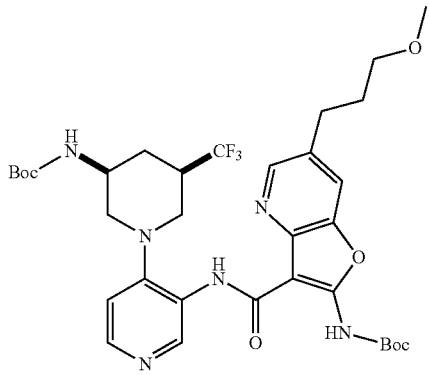 [SMILES: COCCCc1cnc2c(C(=O)Nc3cnccc3N3C[C@@H](NC(=O)OC(C)(C)C)C[C@@H](C(F)(F)F)C3)c(NC(=O)OC(C)(C)C)oc2c1]

A solution of 2-[(tert-butoxycarbonyl)amino]-6-(3-methoxypropyl)furo[3,2-b]pyridine-3-carboxylic acid (1.07 g, 3.06 mmol) and tert-butyl [(3S,5R)-1-(3-aminopyridin-4-yl)-5-(trifluoromethyl)piperidin-3-yl]carbamate (849 mg, 2.36 mmol) in 1,2-dichloroethane (7.3 mL) were added HATU (1.25 g, 3.30 mmol) and DIPEA (820 μL, 4.7 mmol). The reaction mixture was stirred at room temperature overnight. The reaction mixture was diluted with water and DCM. The aqueous layer was extracted with DCM. The combined organic layers were dried over $Na_2SO_4$, filtered and concentrated under reduced pressure. The residue was purified by flash chromatography (eluting with a gradient of 50-100% EtOAc in hexanes and 0-10% MeOH in DCM) to give the sub-title compound (1.3 g, 80%). LCMS calc. for $C_{33}H_{44}F_3N_6O_7$ (M+H)$^+$: m/z=693.3. Found: 693.3.

Step 5. 2-Amino-N-{4-[(3S,5R)-3-amino-5-(trifluoromethyl)piperidin-1-yl]pyridin-3-yl}-6-(3-methoxypropyl)furo[3,2-b]pyridine-3-carboxamide tert-Butyl [(3S,5R)-1-[3-({[2-[(tert-butoxycarbonyl)amino]-6-(3-methoxypropyl)furo[3,2-b]pyridin-3-yl]carbonyl}amino)pyridin-4-yl]-5-(trifluoromethyl)piperidin-3-yl]carbamate (1.3 g, 1.89 mmol) was treated with 1:1 (DCM/TFA) (10 mL) for 1.5 h. The volatile solvent was removed under reduced pressure and the residue was diluted with MeOH and purified by preparative LCMS (XBridge C18 column, eluting with a gradient of MeCN/water containing 0.1% NH$_4$OH, at flow rate of 60 mL/min.) to give the title compound as a white solid (0.32 g, 34%). LCMS calc. for $C_{23}H_{28}F_3N_6O_3$ (M+H)$^+$: m/z=493.2. Found: 493.2, $^1$H NMR (500 MHz, DMSO) δ 10.06 (s, 1H), 9.49 (s, 1H), 8.20 (d, J=5.2 Hz, 1H), 8.10 (d, J=1.4 Hz, 1H), 7.63 (d, J=1.5 Hz, 1H), 7.18 (d, J=5.3 Hz, 1H), 3.30 (m, 5H), 3.23 (s, 3H), 3.18 (m, 1H), 3.12 (m, 1H), 3.04 (m, 1H), 2.74-2.61 (m, 2H), 2.55 (t, J=11.3 Hz, 1H), 2.40 (t, J=10.5 Hz, 1H), 2.18 (d, J=12.2 Hz, 1H), 1.81 (m, 2H), 1.19 (q, J=12.3 Hz, 1H).

Example 132

2-Amino-N-{4-[(3S,5R)-3-amino-5-(trifluoromethyl)piperidin-1-yl]pyridin-3-yl}-6-(3-morpholin-4-ylpropyl)furo[3,2-b]pyridine-3-carboxamide

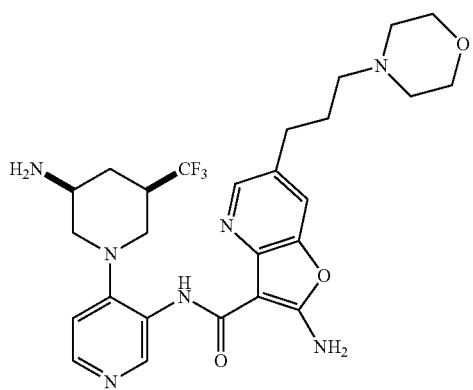 [SMILES: Nc1oc2cc(CCCN3CCOCC3)cnc2c1C(=O)Nc1cnccc1N1C[C@@H](N)C[C@@H](C(F)(F)F)C1]

Step 1. Ethyl 2-[bis(tert-butoxycarbonyl)amino]-6-((1E)-3-{[tert-butyl(dimethyl)silyl]oxy}prop-1-en-1-yl)furo[3,2-b]pyridine-3-carboxylate

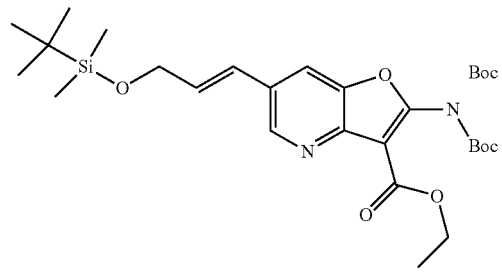 [SMILES: CCOC(=O)c1c(NC(=O)OC(C)(C)C)oc2cc(/C=C/CO[Si](C)(C)C(C)(C)C)cnc12 ; "Boc"]

A mixture of ethyl 2-[bis(tert-butoxycarbonyl)amino]-6-bromofuro[3,2-b]pyridine-3-carboxylate (10.6 g, 21.8 mmol), tert-butyl(dimethyl){[(2E)-3-(4,4,5,5-tetramethyl-1,3,2-dioxaborolan-2-yl)prop-2-en-1-yl]oxy}silane (10.0 mL, 30.6 mmol), dicyclohexyl(2',4',6'-triisopropylbiphenyl-2-yl)phosphine-(2'-aminobiphenyl-2-yl)(chloro)palladium (1:1) (1.7 g, 2.2 mmol) and $K_3PO_4$·$H_2O$ (10.0 g, 43.7 mmol) in 1,4-dioxane (68.2 mL) and water (15.7 mL) was stirred at 75° C. under $N_2$ atmosphere for 3 h. The reaction mixture was diluted with DCM and washed with water. The organic layer was dried over $Na_2SO_4$, filtered and concentrated under reduced pressure. The residue was purified by flash chromatography (eluting with a gradient of 15 to 40% EtOAc in hexanes) to give the sub-title compound (13.0 g, 100%). LCMS calc. for $C_{29}H_{45}N_2O_8Si$ (M+H)$^+$: m/z=577.3. Found: 577.3.

Step 2. Ethyl 2-[bis(tert-butoxycarbonyl)amino]-6-(3-{[tert-butyl(dimethyl)silyl]oxy}propyl)furo[3,2-b]pyridine-3-carboxylate

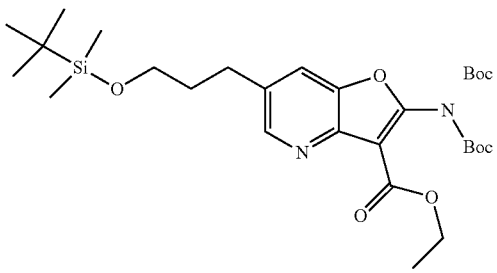 [SMILES: CCOC(=O)c1c(NC(=O)OC(C)(C)C)oc2cc(CCCO[Si](C)(C)C(C)(C)C)cnc12 ; "Boc"]

To a solution of ethyl 2-[bis(tert-butoxycarbonyl)amino]-6-41E)-3-{[tert-butyl(dimethyl)silyl]oxy}prop-1-en-1-yl)furo[3,2-b]pyridine-3-carboxylate (12.6 g, 21.8 mmol) in MeOH (50 mL) was added was added 10% Pd on carbon (2.1 g, 2.0 mmol). The reaction mixture was stirred under an atmosphere of hydrogen for 1.5 h. The reaction mixture was filtered through a pad of diatomaceous earth. The filtrate was concentrated under reduced pressure to give the sub-title compound as a yellow solid (12.5 g, 99%). LCMS calc. for $C_{29}H_{47}N_2O_8Si$ (M+H)$^+$: m/z=579.3. Found: 579.4.

Step 3. Ethyl 2-[(tert-butoxycarbonyl)amino]-6-(3-hydroxypropyl)furo[3,2-b]pyridine-3-carboxylate

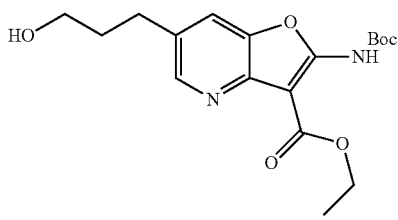 [SMILES: CCOC(=O)c1c(N)oc2cc(CCCO)cnc12]

To a solution of ethyl 2-[bis(tert-butoxycarbonyl)amino]-6-(3-{[tert-butyl(dimethyl)silyl]oxy}propyl)furo[3,2-b]pyridine-3-carboxylate (12.6 g, 21.8 mmol) in THF (100 mL) was added 1.0 M TBAF in THF (26.3 mL, 26.3 mmol). The mixture was stirred at room temperature overnight. The reaction was diluted with EtOAc and water. The aqueous layer was extracted with EtOAc. The combined organic solutions were washed with brine, dried over Na$_2$SO$_4$, filtered and concentrated under reduced pressure. The crude product was purified by flash chromatography (eluting with a gradient of 20-100% EtOAc in hexanes) to give the sub-title compound (5.0 g, 63%). LCMS calc. for $C_{18}H_{25}N_2O_6$ (M+H)$^+$: m/z=365.2. Found: 365.2.

Step 4. Ethyl 2-[(tert-butoxycarbonyl)amino]-6-(3-oxopropyl)furo[3,2-b]pyridine-3-carboxylate

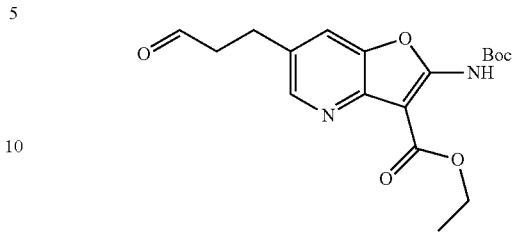

To a solution of ethyl 2-[(tert-butoxycarbonyl)amino]-6-(3-hydroxypropyl)furo[3,2-b]pyridine-3-carboxylate (4.99 g, 13.7 mmol) in DCM (110 mL) was added Dess-Martin periodinane (6.97 g, 16.4 mmol). The reaction mixture was stirred at room temperature for 2 h. The reaction was diluted with ether and saturated aq. NaHCO$_3$ solution and stirred for 30 min. The organic layer was separated and washed with brine, dried over Na$_2$SO$_4$, filtered and concentrated under reduced pressure to give the sub-title compound which was used in next step without purification. LCMS calc. for $C_{18}H_{23}N_2O_6$ (M+H)$^+$: m/z=363.2. Found: 363.1.

Step 5. Ethyl 2-[(tert-butoxycarbonyl)amino]-6-(3-morpholin-4-ylpropyl)furo[3,2-b]pyridine-3-carboxylate

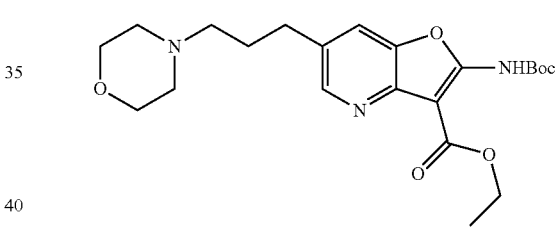

To a mixture of ethyl 2-[(tert-butoxycarbonyl)amino]-6-(3-oxopropyl)furo[3,2-b]pyridine-3-carboxylate (4.60 g, 12.7 mmol), and morpholine (1.3 mL, 15 mmol) in DCM (95 mL) was added sodium triacetoxyborohydride resin (10 g, 23 mmol). The resulting mixture was stirred at room temperature overnight. The mixture was filtered and concentrated under reduced pressure. The crude product was purified by flash chromatography (eluting with a gradient of 30%-100% EtOAc in hexane, then 0-10% MeOH in DCM) to give the sub-title compound (4.5 g, 82%). LCMS calc. for $C_{22}H_{32}N_3O_6$ (M+H)$^+$: m/z=434.2. Found: 434.2.

Step 6. 2-[(tert-Butoxycarbonyl)amino]-6-(3-morpholin-4-ylpropyl)furo[3,2-b]pyridine-3-carboxylic acid

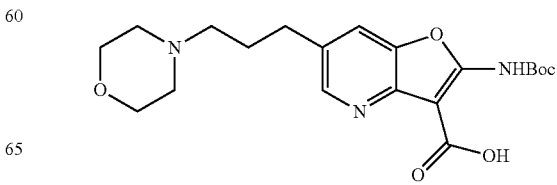

A mixture of ethyl 2-[(tert-butoxycarbonyl)amino]-6-(3-morpholin-4-ylpropyl)furo[3,2-b]pyridine-3-carboxylate (4.4 g, 10. mmol), LiOH (1.3 g, 55 mmol) in THF (39 mL), water (13 mL) and MeOH (26 mL) was stirred at 60° C. overnight. Solvent was evaporated under reduced pressure and water was added. The solution was neutralized with 1 M HCl to pH 7. The mixture was purified by preparative LCMS (XBridge C18 column, eluting with a gradient of MeCN/water containing 0.1% NH₄OH, at flow rate of 60 mL/min.) to give the sub-title compound as a white solid (3.6 g, 87%). LCMS calc. for $C_{20}H_{28}N_3O_6$ (M+H)⁺: m/z=406.2. Found: 406.1.

Step 7. tert-Butyl [(3S,5R)-1-[3-({[2-[(tert-butoxycarbonyl)amino]-6-(3-morpholin-4-ylpropyl)furo[3,2-b]pyridin-3-yl]carbonyl}amino)pyridin-4-yl]-5-(trifluoromethyl)piperidin-3-yl]carbamate

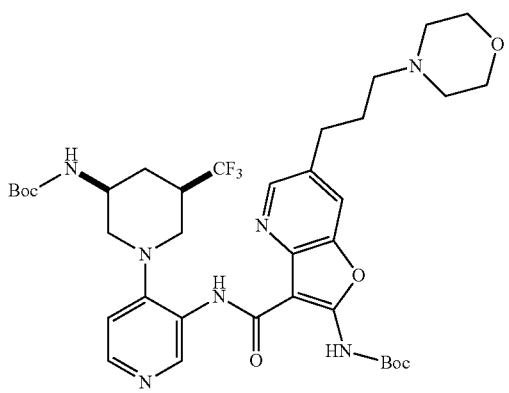 [SMILES: CC(C)(C)OC(=O)Nc1oc2cc(CCCN3CCOCC3)cnc2c1C(=O)Nc1cnccc1N1C[C@@H](NC(=O)OC(C)(C)C)C[C@@H](C(F)(F)F)C1]

The sub-title compound was prepared according to an analogous procedure to described in Example 2, Step 4, using 2-[(tert-butoxycarbonyl)amino]-6-(3-morpholin-4-ylpropyl)furo[3,2-b]pyridine-3-carboxylic acid (from Example 3, step 6) instead of 2-[(tert-butoxycarbonyl)amino]-6-(3-methoxypropyl)furo[3,2-b]pyridine-3-carboxylic acid as the starting material. LCMS calc. for $C_{36}H_{49}F_3N_7O_7$ (M+H)⁺: m/z=748.4. Found: 748.3.

Step 8. 2-Amino-N-{4-[(3S,5R)-3-amino-5-(trifluoromethyl)piperidin-1-yl]pyridin-3-yl}-6-(3-morpholin-4-ylpropyl)furo[3,2-b]pyridine-3-carboxamide This compound was prepared according to a procedure analogous to that described in Example 131, Step 5, using tert-butyl [(3S,5R)-1-[3-({[2-[(tert-butoxycarbonyl)amino]-6-(3-morpholin-4-ylpropyl)furo[3,2-b]pyridin-3-yl]carbonyl}amino)pyridin-4-yl]-5-(trifluoromethyl)piperidin-3-yl]carbamate instead of tert-butyl [(3S,5R)-1-[3-({[2-[(tert-butoxycarbonyl)amino]-6-(3-methoxypropyl)furo[3,2-b]pyridin-3-yl]carbonyl}amino)pyridin-4-yl]-5-(trifluoromethyl)piperidin-3-yl]carbamate as the starting material. LCMS calc. for $C_{26}H_{33}F_3N_7O_3$ (M+H)⁺: m/z=548.3. Found: 548.3. ¹H NMR (500 MHz, DMSO) δ 10.04 (s, 1H), 9.48 (s, 1H), 8.20 (d, J=5.3 Hz, 1H), 8.10 (d, J=1.3 Hz, 1H), 7.64 (d, J=1.4 Hz, 1H), 7.18 (d, J=5.3 Hz, 1H), 3.68-3.46 (m, 4H), 3.29 (m, 1H), 3.22-2.91 (m, 3H), 2.67 (t, J=7.4 Hz, 2H), 2.56 (m, 1H), 2.39 (m, 1H), 2.33-2.09 (m, 7H), 1.74 (m, 2H), 1.19 (m, 1H).

Example 133

2-Amino-N-{4-[(1R,3S,5S)-3-amino-5-methylcyclohexyl]pyridin-3-yl}-6-cyclopropylfuro[3,2-b]pyridine-3-carboxamide

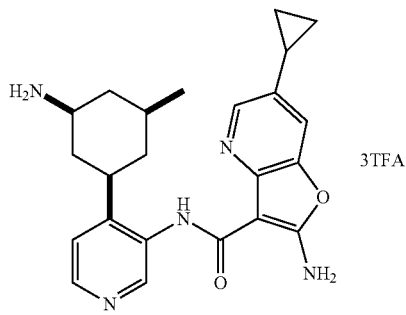

Step 1. Ethyl 3-[(tert-butoxycarbonyl)amino]-6-cyclopropylfuro[3,2-b]pyridine-2-carboxylate

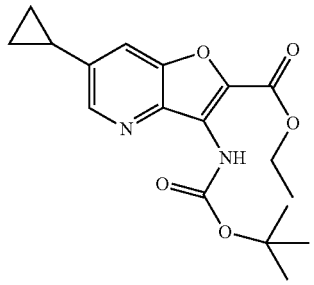 [SMILES: CCOC(=O)c1oc2cc(C3CC3)cnc2c1NC(=O)OC(C)(C)C]

To a microwave vial was added ethyl 6-bromo-3-[(tert-butoxycarbonyl)amino]furo[3,2-b]pyridine-2-carboxylate (1.05 g, 2.72 mmol), potassium cyclopropyltrifluoroborate (480 mg, 3.3 mmol), Cs₂CO₃ (2.66 g, 8.18 mmol), Pd(OAc)₂ (61.2 mg, 0.272 mmol) and di-1-adamantyl(butyl)phosphine (150 mg, 0.41 mmol). The vialed was seal and evacuated and filled with N₂ three times. Toluene (10.0 mL, 93.9 mmol) and water (1.0 mL, 56 mmol) were added. The reaction mixture was heated at 110° C. for 24 h. The reaction mixture was diluted with water and EtOAc. The aqueous layer was extracted with EtOAc. The combined organic layers were dried over Na₂SO₄, filtered and concentrated under reduced pressure. The residue was dissolved in THF (10 mL), and Boc₂O (0.40 g) was added followed by DMAP (40 mg). The resulting solution was stirred at room temperature overnight. The solvent was removed under reduced pressure and the residue was purified by flash chromatography (eluting with a gradient of 0-30% EtOAc in hexanes) to give the sub-title compound as a yellow foam (0.91 g, 96%). LCMS calc. for $C_{18}H_{23}N_2O_5$ (M+H)⁺: m/z=347.2. Found: 346.9.

Step 2. 2-[(tert-Butoxycarbonyl)amino]-6-cyclopropylfuro[3,2-b]pyridine-3-carboxylic acid

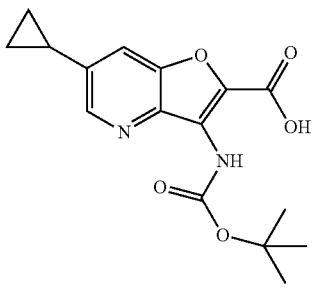 [SMILES: CC(C)(C)OC(=O)Nc1c(C(=O)O)oc2cc(C3CC3)cnc12]

A mixture of ethyl 2-[(tert-butoxycarbonyl)amino]-6-cyclopropylfuro[3,2-b]pyridine-3-carboxylate (703 mg, 2.03 mmol), LiOH (330 mg, 14 mmol) in THF (7.5 mL)/water (2.5 mL)/MeOH (5.0 mL) was stirred at 60° C. overnight. The solvent was evaporated under reduced pressure and water was added. The pH of the solution was adjusted to pH=6 with 1 M aq. HCl solution. The aqueous layer was extracted with EtOAc. The organic layer was separated and washed with brine, dried over $Na_2SO_4$, filtered and concentrated under reduce pressure to give the sub-title compound as a yellow solid (0.51 g, 78%). LCMS calc. for $C_{16}H_{19}N_2O_5$ $(M+H)^+$: m/z=319.1. Found: 319.1.

Step 3. tert-Butyl ((1S,3R,5S)-3-{3-[({2-[(tert-butoxycarbonyl)amino]-6-cyclopropylfuro[3,2-b]pyridin-3-yl}carbonyl)amino]pyridin-4-yl}-5-methylcyclohexyl)carbamate

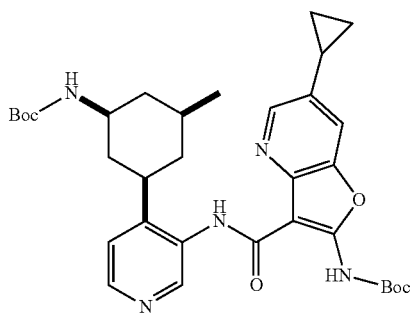

This compound was prepared according to a procedure analogous to that described in Example 130, Step 16, using 2-[(tert-butoxycarbonyl)amino]-6-cyclopropylfuro[3,2-b]pyridine-3-carboxylic acid (from Example 133, step 2) instead of 2-[(tert-butoxycarbonyl)amino]-6-isopropylfuro[3,2-b]pyridine-3-carboxylic acid as the starting material. LCMS calc. for $C_{33}H_{44}N_5O_6$ $(M+H)^+$: m/z=606.3. Found: 606.3.

Step 4. 2-Amino-N-{4-[(1R,3S,5S)-3-amino-5-methylcyclohexyl]pyridin-3-yl}-6-cyclopropylfuro[3,2-b]pyridine-3-carboxamide The title compound was prepared as a tris(trifluoroacetate) salt using a procedure analogous to that described in Example 130, Step 17, using tert-butyl ((1S,3R,5S)-3-{3-[({2-[(tert-butoxycarbonyl)amino]-6-cyclopropylfuro[3,2-b]pyridin-3-yl}carbonyl)amino]pyridin-4-yl}-5-methylcyclohexyl)carbamate (from Example 133, step 3) instead of tert-butyl ((1S,3R,5S)-3-{3-[({2-[(tert-butoxycarbonyl)amino]-6-isopropylfuro[3,2-b]pyridin-3-yl}carbonyl)amino]pyridin-4-yl}-5-methylcyclohexyl)carbamate as the starting material. LCMS calc. for $C_{23}H_{28}N_5O_2$ $(M+H)^+$: m/z=406.2. Found: 406.2. $^1$H NMR (400 MHz, DMSO) δ 10.25 (s, 1H), 9.59 (s, 1H), 8.52-8.25 (m, 3H), 8.19 (d, J=1.5 Hz, 1H), 8.03 (s, 2H), 7.60 (s, 1H), 7.43 (d, J=1.5 Hz, 1H), 3.23 (m, 1H), 3.21 (m, 1H), 2.22-1.87 (m, 5H), 1.52 (m, 1H), 1.35-0.87 (m, 7H), 0.74 (m, 2H).

2-Amino-N-{4-[(1S,3R,5R)-3-amino-5-methylcyclohexyl]pyridin-3-yl}-6-cyclopropylfuro[3,2-b]pyridine-3-carboxamide is prepared by an analogous procedure.

Example 134

2-Amino-N-{4-[(3S,5R)-3-amino-5-methylpiperidin-1-yl]pyridin-3-yl}-6-(3-methoxypropyl)furo[3,2-b]pyridine-3-carboxamide

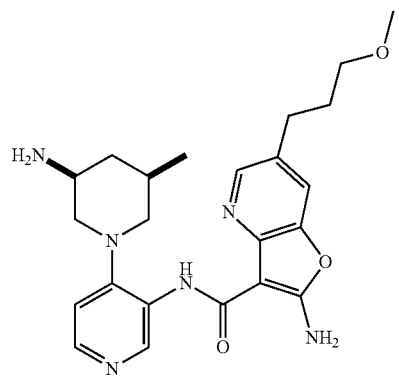 [SMILES: COCCCc1cnc2c(C(=O)Nc3cnccc3N3C[C@H](C)C[C@H](N)C3)c(N)oc2c1]

Step 1. tert-Butyl {(3S,5R)-1-[3-({[2-[(tert-butoxycarbonyl)amino]-6-(3-methoxypropyl)furo[3,2-b]pyridin-3-yl]carbonyl}amino)pyridin-4-yl]-5-methylpiperidin-3-yl}carbamate

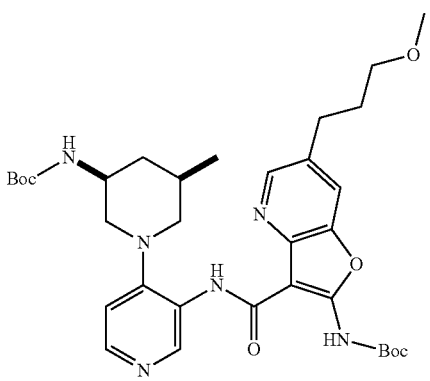 [SMILES: COCCCc1cnc2c(C(=O)Nc3cnccc3N3C[C@H](C)C[C@H](NC(=O)OC(C)(C)C)C3)c(NC(=O)OC(C)(C)C)oc2c1]

The sub-title compound was prepared according to a procedure analogous to that described in Example 131, Step 4, using tert-butyl [(3S,5R)-1-(3-aminopyridin-4-yl)-5-methylpiperidin-3-yl]carbamate instead of tert-butyl [(3S,5R)-1-(3-aminopyridin-4-yl)-5-(trifluoromethyl)piperidin- 3-yl]carbamate as the starting material. LCMS calc. for C$_{33}$H$_{47}$N$_6$O$_7$ (M+H)$^+$: m/z=639.4. Found: 639.5.

Step 2. 2-Amino-N-{4-[(3S,5R)-3-amino-5-methyl-piperidin-1-yl]pyridin-3-yl}-6-(3-methoxypropyl)furo[3,2-b]pyridine-3-carboxamide The title compound was prepared by a procedure analogous to that described in Example 131, Step 5, using tert-butyl {(3S,5R)-1-[3-({[2-[(tert-butoxycarbonyl)amino]-6-(3-methoxypropyl) furo[3,2-b]pyridin-3-yl]carbonyl}amino)pyridin-4-yl]-5-methylpiperidin-3-yl}carbamate (from last step) instead of tert-butyl [(3S,5R)-1-[3-({[2-[(tert-butoxycarbonyl)amino]-6-(3-methoxypropyl)furo[3,2-b]pyridin-3-yl]carbonyl}amino)pyridin-4-yl]-5-(trifluoromethyl)piperidin-3-yl]carbamate as the starting material. LCMS calc. for C$_{23}$H$_{31}$N$_6$O$_3$ (M+H)$^+$: m/z=439.2. Found: 439.2. $^1$H NMR (500 MHz, CD$_3$OD) δ 9.42 (s, 1H), 8.18-8.10 (m, 2H), 7.45 (d, J=1.5 Hz, 1H), 7.16 (d, J=5.5 Hz, 1H), 3.47-3.24 (m, 6H), 3.20 (m, 1H), 2.76 (t, J=7.7 Hz, 2H), 2.38-2.14 (m, 4H), 2.10 (m, 1H), 1.94-1.84 (m, 2H), 0.97-0.86 (m, 4H).

Example 135

2-Amino-N-{4-[(3S,5R)-3-amino-5-(trifluoromethyl)piperidin-1-yl]pyridin-3-yl}-6-[3-(dimethylamino)propyl]furo[3,2-b]pyridine-3-carboxamide

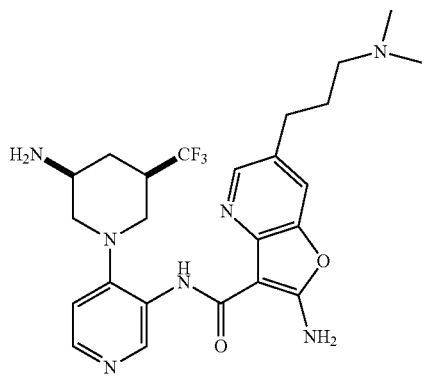 [SMILES: CN(C)CCCc1cnc2c(C(=O)Nc3cnccc3N3C[C@@H](N)C[C@@H](C(F)(F)F)C3)c(N)oc2c1]

Step 1. Ethyl 2-[(tert-butoxycarbonyl)amino]-6-[3-(dimethylamino)propyl]furo[3,2-b]pyridine-3-carboxylate

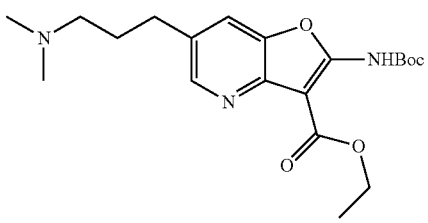 [SMILES: CCOC(=O)c1c(NC(=O)OC(C)(C)C)oc2cc(CCCN(C)C)cnc12]

This compound was prepared according to a procedure analogous to that of Example 132, Step 5, using dimethylamine instead of morpholine as the starting material. LCMS calc. for C$_{20}$H$_{30}$N$_3$O$_5$ (M+H)$^+$: m/z=392.2. Found: 392.2.

Step 2. 2-[(tert-Butoxycarbonyl)amino]-6-[3-(dimethylamino)propyl]furo[3,2-b]pyridine-3-carboxylic acid

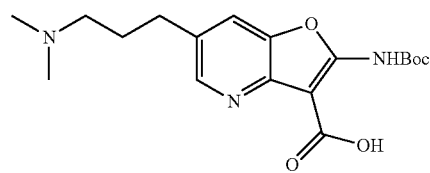 [SMILES: CN(C)CCCc1cnc2c(C(=O)O)c(NC(=O)OC(C)(C)C)oc2c1]

The sub-title compound was prepared according to the procedure analogous to that of Example 132, Step 6, using ethyl 2-[(tert-butoxycarbonyl)amino]-6-[3-(dimethylamino)propyl]furo[3,2-b]pyridine-3-carboxylate instead of ethyl 2-[(tert-butoxycarbonyl)amino]-6-(3-morpholin-4-ylpropyl)furo[3,2-b]pyridine-3-carboxylate as the starting material. LCMS calc. for C$_{18}$H$_{26}$N$_3$O$_5$ (M+H)$^+$: m/z=364.2. Found: 364.2.

Step 3. tert-Butyl [(3S,5R)-1-{3-[({2-[(tert-butoxycarbonyl)amino]-6-[3-(dimethylamino)propyl]furo[3,2-b]pyridin-3-yl}carbonyl)amino]pyridin-4-yl}-5-(trifluoromethyl)piperidin-3-yl]carbamate

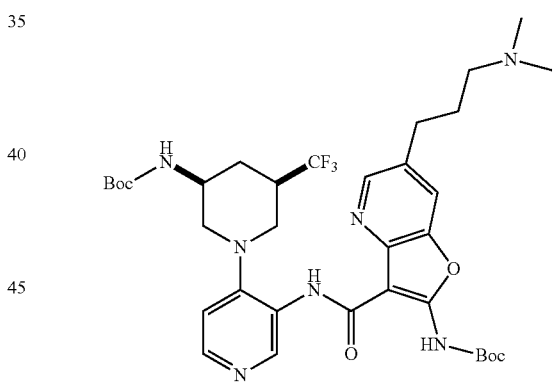

The sub-title compound was prepared according to a procedure analogous to that of Example 131, Step 4, using 2-[(tert-butoxycarbonyl)amino]-6-[3-(dimethylamino)propyl]furo[3,2-b]pyridine-3-carboxylic acid instead of 2-[(tert-butoxycarbonyl)amino]-6-(3-methoxypropyl)furo[3,2-b]pyridine-3-carboxylic acid as the starting material. LCMS calc. for C$_{34}$H$_{47}$F$_3$N$_7$O$_6$ (M+H)$^+$: m/z=706.4. Found: 706.4.

Step 4. 2-Amino-N-{4-[(3S,5R)-3-amino-5-(trifluoromethyl)piperidin-1-yl]pyridin-3-yl}-6-[3-(dimethylamino)propyl]furo[3,2-b]pyridine-3-carboxamide The sub-title compound was prepared according to a procedure analogous to that of Example 131, Step 5, using tert-butyl [(3S,5R)-1-{3-[({2-[(tert-butoxycarbonyl)amino]-

6-[3-(dimethylamino)propyl]furo[3,2-b]pyridin-3-yl}carbonyl)amino]pyridin-4-yl}-5-(trifluoromethyl)piperidin-3-yl]carbamate instead of tert-butyl [(3S,5R)-1-[3-({[2-[(tert-butoxycarbonyl)amino]-6-(3-methoxypropyl)furo[3,2-b]pyridin-3-yl]carbonyl}amino)pyridin-4-yl]-5-(trifluoromethyl)piperidin-3-yl]carbamate as the starting material. LCMS calc. for $C_{24}H_{31}F_3N_7O_2$ (M+H)$^+$: m/z=506.2. Found: 506.2. $^1$H NMR (500 MHz, DMSO) δ 10.06 (s, 1H), 9.49 (s, 1H), 8.20 (d, J=5.3 Hz, 1H), 8.10 (d, J=1.2 Hz, 1H), 7.63 (d, J=1.3 Hz, 1H), 7.18 (d, J=5.3 Hz, 1H), 3.22-2.98 (m, 3H), 2.65 (m, 2H), 2.54 (m, 1H), 2.40 (t, J=10.5 Hz, 1H), 2.18 (m, 3H), 2.11 (s, 6H), 1.70 (m, 3H), 1.19 (m, 1H).

Example 136

2-Amino-N-{4-[(1R,3R,5S)-3-amino-5-(trifluoromethyl)cyclohexyl]pyridin-3-yl}furo[3,2-b]pyridine-3-carboxamide

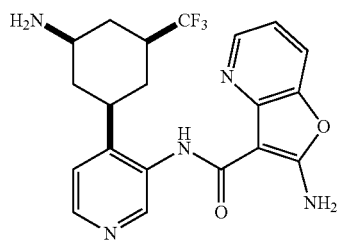

Step 1. 3-Oxo-5-(trifluoromethyl)cyclohex-1-en-1-yl trifluoromethanesulfonate

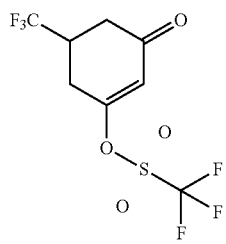

To a suspension of 5-(trifluoromethyl)cyclohexane-1,3-dione (50.0 g, 278 mmol) (Anichem, Inc.) in DCM (1000 mL) was added TEA (46.4 mL, 333 mmol). The mixture was cooled to 0° C., and then trifluoromethanesulfonic anhydride (49.0 mL, 291 mmol) in DCM (300 mL) was added dropwise. The reaction mixture was stirred at 0° C. for 2 h. The reaction mixture was diluted with DCM. The organic layer was washed with water, aq. NaHCO$_3$, brine, and dried over Na$_2$SO$_4$, filtered and concentrated under reduced pressure to give the sub-title compound which was used directly in the next step without further purification. LCMS calc. for $C_8H_7F_6O_4S$ (M+H)$^+$: m/z=313.0. Found: 313.0.

Step 2. 3-(4,4,5,5-Tetramethyl-1,3,2-dioxaborolan-2-yl)-5-(trifluoromethyl)cyclohex-2-en-1-one

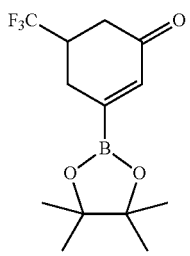

A mixture of 3-oxo-5-(trifluoromethyl)cyclohex-1-en-1-yl trifluoromethanesulfonate (86.6 g, 277 mmol), 4,4,5,5,4',4',5',5'-octamethyl-[2,2']bi[[1,3,2]dioxaborolanyl] (84.5 g, 333 mmol) and sodium acetate (68.3 g, 832 mmol) in 1,4-dioxane (1000 mL) was deoxygenated by bubbling N$_2$ gas through for 10 min. [1,1'-bis(diphenylphosphino)ferrocene]dichloropalladium(II), complex with DCM (1:1) (22.6 g, 27.7 mmol) was added. After stirring at 80° C. for 2 h, the reaction mixture was filtered through a coarse frit glass funnel, and the cake was rinsed with 1,4-dioxane. The filtrate was concentrated under reduced pressure to give the crude product which was used directly in the next step without further purification.

Step 3. 3-(3-Nitropyridin-4-yl)-5-(trifluoromethyl)cyclohex-2-en-1-one

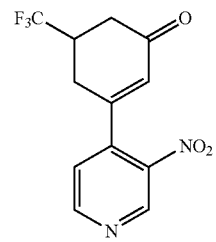 [SMILES: O=C1C=C(c2ccncc2[N+](=O)[O-])CC(C(F)(F)F)C1]

To a mixture of 3-(4,4,5,5-tetramethyl-1,3,2-dioxaborolan-2-yl)-5-(trifluoromethyl)cyclohex-2-en-1-one (80.5 g, 278 mmol) and 4-chloro-3-nitropyridine (52.8 g, 333 mmol) was added 1,4-dioxane (1000 mL) followed by 2.0 M aq. Na$_2$CO$_3$ (278 mL, 555 mmol). The mixture was deoxygenated by bubbling N$_2$ gas through for 10 min. [1,1'-Bis(diphenylphosphino)ferrocene]dichloropalladium(II), complex with DCM (1:1) (22.7 g, 27.8 mmol) was added. The mixture was stirred at 1000° C. for 2 h. The resulting mixture was filtered through a pad of diatomaceous earth, and the diatomaceous earth pad was rinsed with EtOAc. The filtrate was concentrated under reduced pressure, and the residue was diluted with EtOAc and water. The separated organic layer was washed with brine, dried over Na$_2$SO$_4$ filtered and concentrated under reduced pressure. The residue was purified by flash chromatography (eluting with a gradient of 0-70% EtOAc in hexanes) to give the sub-title compound as colorless oil (41.2 g, 52%). LCMS calc. for $C_{12}H_{10}F_3N_2O_3$ (M+H)$^+$: m/z=287.1. Found: 287.1.

Step 4. (1S,5S)-3-(3-Nitropyridin-4-yl)-5-(trifluoromethyl)cyclohex-2-en-1-ol

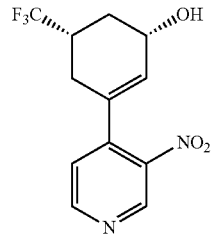 [SMILES: O=[N+]([O-])c1cnccc1C1=C[C@@H](O)C[C@@H](C(F)(F)F)C1]

To a mixture of 3-(3-nitropyridin-4-yl)-5-(trifluoromethyl)cyclohex-2-en-1-one (16.6 g, 58.0 mmol) in EtOH (300 mL) was added CeCl$_3$·7H$_2$O (21.6 g, 58.0 mmol). The mixture was stirred at room temperature until all solids dissolved. The reaction mixture was then cooled to 0° C., and sodium tetrahydroborate (2.63 g, 69.6 mmol) was added portionwise. After stirring at 0° C. for 1 h, the mixture was diluted with EtOAc, washed with brine. The organic layer was dried over Na$_2$SO$_4$, filtered and concentrated under reduced pressure. The residue was purified by flash chromatography (eluting with a gradient of 20-90% EtOAc in hexanes) to give the sub-title compound as a racemic mixture (11.7 g, 70%). LCMS calc. for C$_{12}$H$_{12}$F$_3$N$_2$O$_3$ (M+H)$^+$: m/z=289.1. Found: 289.0.

Step 5. 4-[(3S,5S)-3-Azido-5-(trifluoromethyl)cyclohex-1-en-1-yl]-3-nitropyridine

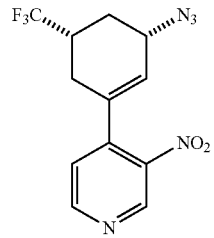 [SMILES: [N-]=[N+]=N[C@@H]1C=C(c2ccncc2[N+](=O)[O-])C[C@H](C(F)(F)F)C1]

To a solution of (1S,5S)-3-(3-nitropyridin-4-yl)-5-(trifluoromethyl)cyclohex-2-en-1-ol (11.7 g, 40.6 mmol) in DCM (200 mL) at 0° C. were added TEA (14.1 mL, 101 mmol), followed by methanesulfonyl chloride (5.66 mL, 73.1 mmol). The reaction was allowed to warm to room temperature. After stirring at room temperature for 2 h, the mixture was concentrated under reduced pressure. The residue was dissolved in DMF (70 mL), and NaN$_3$ (6.33 g, 97.4 mmol) was added. The mixture was stirred at room temperature overnight. The mixture was diluted with EtOAc, and washed with brine. The organic layer was dried over Na$_2$SO$_4$, filtered and concentrated under reduced pressure. The residue was purified by flash chromatography (eluting with a gradient of 0-70% EtOAc in hexane) to give the sub-title compound as colorless oil (4.1 g, 32%). LCMS calc. for C$_{12}$H$_{11}$F$_3$N$_5$O$_2$ (M+H)$^+$: m/z=314.1. Found: 314.0.

Step 6. tert-butyl [(1S,3R,5R)-3-(3-aminopyridin-4-yl)-5-(trifluoromethyl)cyclohexyl]carbamate tert-butyl [(1R,3R,5S)-3-(3-aminopyridin-4-yl)-5-(trifluoromethyl)cyclohexyl]carbamate

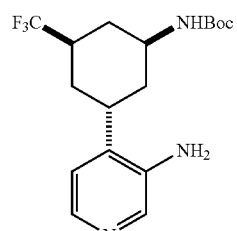

C

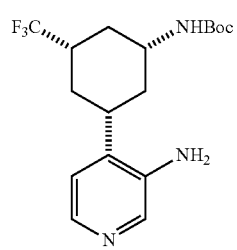

D

To a mixture of cis-4-[(3S,5S)-3-azido-5-(trifluoromethyl)cyclohex-1-en-1-yl]-3-nitropyridine (4.10 g, 13.1 mmol) and Boc$_2$O (4.28 g, 19.6 mmol) under N$_2$ were added MeOH (70 mL) followed by 20 wt % palladium hydroxide (1.84 g, 2.62 mmol). The mixture was purged with H$_2$ and stirred under a H$_2$ atmosphere (1 atm.) overnight. The mixture was filtered through a pad of diatomaceous earth, and the diatomaceous earth pad was rinsed with MeOH. The filtrate was concentrated under reduced pressure. The residue was purified by preparative LCMS (XBridge™ C18 column, eluting with a gradient of MeCN/water containing 0.1% NH$_4$OH, at flow rate of 60 mL/min.) to give 220 mg of compound C (racemic) and 450 mg of compound D (racemic). The two enantiomers of compound D were separated using chiral column (CHIRALPAK IA Col, 10% EtOH/90% Hex, 16 ml/min.).

Peak 1: retention time: 12.6 min., LCMS calc. for C$_{17}$H$_{25}$F$_3$N$_3$O$_2$ (M+H)$^+$: m/z=360.2. Found: 360.2. The product was tentatively assigned as the (1S,3S,5R) enantiomer.

Peak 2: retention time: 17.2 min., LCMS calc. for C$_{17}$H$_{25}$F$_3$N$_3$O$_2$ (M+H)$^+$: m/z=360.2. Found: 360.2. The product was tentatively assigned as the [(1R,3R,5S)-enantiomer.

Step 7. 2-Amino-N-{4-[(1R,3R,5S)-3-amino-5-(trifluoromethyl)cyclohexyl]pyridin-3-yl}furo[3,2-b]pyridine-3-carboxamide A mixture of tert-butyl [1R,3R,5S)-3-(3-aminopyridin-4-yl)-5-(trifluoromethyl)cyclohexyl]carbamate (70.0 mg, 0.195 mmol) (from last step peak 2 of compound D), 2-[(tert-butoxycarbonyl)amino]furo[3,2-b]pyridine-3-carboxylic acid (75.9 mg, 0.273 mmol), HATU (133.3 mg, 0.3506 mmol) and DIPEA (67.8 μL, 0.390 mmol) in 1,2-dichloroethane (0.6 mL) was stirred at room temperature overnight. The mixture was filtered through a pad of diatomaceous earth, and the diatomaceous earth pad was rinsed with DCM. The filtrate was concentrated under reduced pressure, the residue was purified by flash chromatography (eluting with a gradient of 0-100% EtOAc in hexanes) to give an amide coupling product.

To the amide was added DCM (2 mL) followed by TFA (2 mL). The mixture was stirred at room temperature for 1 h, and then concentrated under reduced pressure. The residue was purified by preparative LCMS (XBridge™ C18 column, eluting with a gradient of MeCN/water containing 0.1% NH$_4$OH, at flow rate of 60 mL/min.) to give the title compound as a white solid (15.8 mg, 19%). LCMS calc. for $C_{20}H_{21}F_3N_5O_2$ (M+H)$^+$: m/z=420.2. Found: 420.2. $^1$H NMR (500 MHz, DMSO) δ 10.12 (s, 1H), 9.38 (s, 1H), 8.28 (m, 2H), 7.77-7.71 (m, 1H), 7.35 (d, J=5.1 Hz, 1H), 7.08 (dd, J=8.0, 5.2 Hz, 1H), 3.13 (t, J=12.2 Hz, 1H), 2.91 (t, J=11.0 Hz, 1H), 2.59 (m, 1H), 2.08-1.93 (m, 3H), 1.50 (m, 1H), 1.26 (m, 1H), 1.13 (m, 1H).

2-Amino-N-{4-[(1S,3S,5R)-3-amino-5-(trifluoromethyl)cyclohexyl]pyridin-3-yl}furo[3,2-b]pyridine-3-carboxamide is prepared by an analogous procedure.

Example 137

2-Amino-N-(4-((3R,4R,5S)-3-amino-4-hydroxy-5-methylpiperidin-1-yl)pyridin-3-yl)-6-(3-fluoropropyl)furo[3,2-b]pyridine-3-carboxamide

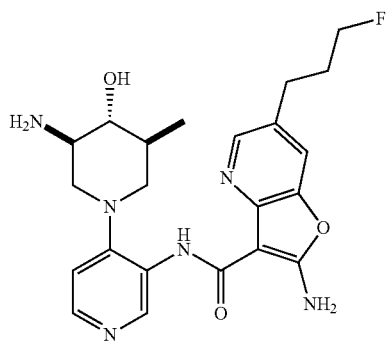 [SMILES: C[C@H]1CN(c2ccncc2NC(=O)c2c(N)oc3cc(CCCF)cnc23)C[C@@H](N)[C@@H]1O]

Step 1. Ethyl 2-[(tert-butoxycarbonyl)amino]-6-(3-fluoropropyl)furo[3,2-b]pyridine-3-carboxylate

To a mixture of ethyl 2-[(tert-butoxycarbonyl)amino]-6-(3-hydroxypropyl)furo[3,2-b]pyridine-3-carboxylate (500.0 mg, 1.372 mmol) in DCM (5.0 mL), diethylaminosulfur trifluoride (0.31 mL, 2.3 mmol) was added at 0° C. and the reaction mixture was stirred at room temperature overnight. The reaction mixture was diluted with saturated aq. NaHCO$_3$. The aqueous layer was extracted with EtOAc. The organic layer was washed with brine, dried over Na$_2$SO$_4$, filtered and concentrated. The residue was purified by flash chromatography (eluting with a gradient of 0-45% EtOAc in hexanes) to give the sub-title compound (0.4 g, 80%). LCMS calc. for $C_{18}H_{24}FN_2O_5$ (M+H)$^+$: m/z=367.2. Found: 367.2.

Step 2. 2-[(tert-Butoxycarbonyl)amino]-6-(3-fluoropropyl)furo[3,2-b]pyridine-3-carboxylic acid

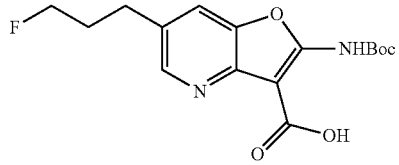 [SMILES: CC(C)(C)OC(=O)Nc1oc2cc(CCCF)cnc2c1C(=O)O]

The sub-title compound was prepared according to a procedure analogous to that of Example 132, Step 6, using ethyl 2-[(tert-butoxycarbonyl)amino]-6-(3-fluoropropyl)furo[3,2-b]pyridine-3-carboxylate instead of ethyl 2-[(tert-butoxycarbonyl)amino]-6-(3-morpholin-4-ylpropyl)furo[3,2-b]pyridine-3-carboxylate as the starting material. LCMS calc. for $C_{16}H_{20}FN_2O_5$ (M+H)$^+$: m/z=339.1. Found: 338.1.

Step 3. tert-Butyl [3-({[4-((3R,4R,5S)-3-[(tert-butoxycarbonyl)amino]-4-{[tert-butyl(dimethyl)silyl]oxy}-5-methylpiperidin-1-yl)pyridin-3-yl]amino}carbonyl)-6-(3-fluoropropyl)furo[3,2-b]pyridin-2-yl]carbamate

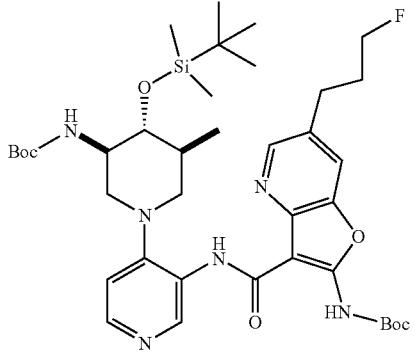 [SMILES: C[C@H]1CN(c2ccncc2NC(=O)c2c(NC(=O)OC(C)(C)C)oc3cc(CCCF)cnc23)C[C@@H](NC(=O)OC(C)(C)C)[C@@H]1O[Si](C)(C)C(C)(C)C]

The sub-title compound was prepared according to a procedure analogous to that of Example 131, Step 4, using 2-[(tert-butoxycarbonyl)amino]-6-(3-fluoropropyl)furo[3,2-b]pyridine-3-carboxylic acid and tert-butyl ((3R,4R,5S)-1-(3-aminopyridin-4-yl)-4-{[tert-butyl(dimethyl)silyl]oxy}-5-methylpiperidin-3-yl)carbamate instead of 2-[(tert-butoxycarbonyl)amino]-6-(3-methoxypropyl)furo[3,2-b]pyridine-3-carboxylic acid and tert-butyl [(3S,5R)-1-(3-aminopyridin-4-yl)-5-(trifluoromethyl)piperidin-3-yl]carbamate as the starting material. LCMS calc. for $C_{38}H_{58}FN_6O_7Si$ (M+H)$^+$: m/z=757.4. Found: 757.4.

Step 4. 2-Amino-N-(4-((3R,4R,5S)-3-amino-4-hydroxy-5-methylpiperidin-1-yl)pyridin-3-yl)-6-(3-fluoropropyl)furo[3,2-b]pyridine-3-carboxamide The title compound was prepared according to a procedure analogous to that of Example 131, Step 5, using tert-butyl [3-({[4-((3R,4R,5S)-3-[(tert-butoxycarbonyl)amino]-4-{[tert-butyl(dimethyl)silyl]oxy}-5-methylpiperidin-1-yl)pyridin-3-yl]amino}carbonyl)-6-(3-fluoropropyl)furo[3,2-b]pyridin-2-yl]carbamate instead of tert-butyl [(3S,5R)-1-[3-({[2-[(tert-butoxycarbonyl)amino]-6-(3-methoxypropyl)furo[3,2-b]pyridin-3-yl]carbonyl}amino)pyridin-4-yl]-5-(trifluoromethyl)piperidin-3-yl]carbamate as the starting material. LCMS calc. for $C_{22}H_{28}FN_6O_3$ (M+H)$^+$: m/z=443.2. Found: 443.2. $^1$H NMR (500 MHz, DMSO) δ 10.15 (s, 1H), 9.49 (s, 1H), 8.16 (m, 2H), 7.65 (d, J=1.5 Hz, 1H), 7.11 (d, J=5.3 Hz, 1H), 4.52 (t, J=6.0 Hz, 1H), 4.42 (t, J=6.0 Hz, 1H), 3.18-3.11 (m, 1H), 3.10-3.03 (m, 1H), 2.98 (m, 1H), 2.78-2.67 (m, 3H), 2.45-2.37 (m, 2H), 2.05-1.91 (m, 3H), 0.87 (d, J=6.6 Hz, 3H).

Example 138

2-Amino-N-{4-[(3S,5R)-3-amino-5-(trifluoromethyl)piperidin-1-yl]pyridin-3-yl}-6-{2-[(3R)-3-fluoropyrrolidin-1-yl]ethyl}furo[3,2-b]pyridine-3-carboxamide

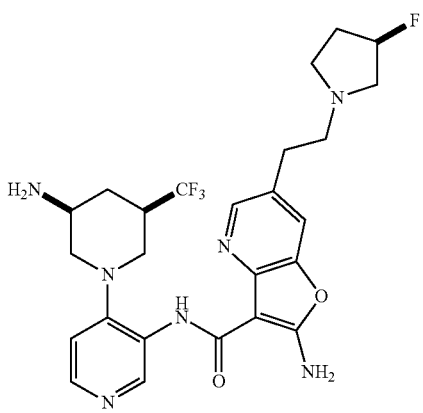 [SMILES: Nc1oc2cc(CCN3CC[C@@H](F)C3)cnc2c1C(=O)Nc1cnccc1N1C[C@@H](N)C[C@@H](C(F)(F)F)C1]

Step 1. Ethyl 6-allyl-2-[(tert-butoxycarbonyl)amino]furo[3,2-b]pyridine-3-carboxylate

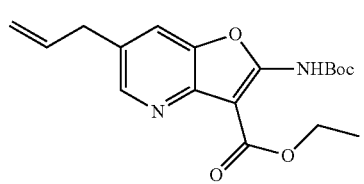 [SMILES: C=CCc1cnc2c(C(=O)OCC)c(NC(=O)OC(C)(C)C)oc2c1]

A mixture of Pd(PPh$_3$)$_4$ (340 mg, 0.29 mmol) ethyl 6-bromo-2-[(tert-butoxycarbonyl)amino]furo[3,2-b]pyridine-3-carboxylate (1.12 g, 2.91 mmol) was evacuated under reduced pressure and backfilled with N$_2$ (repeated three times). Allyltributyltin (1.17 mL, 3.77 mmol) and toluene (11.0 mL) were added. The reaction mixture was heated at 110° C. overnight. The solvent was removed under reduced pressure, and the residue was purified by flash chromatography to give the sub-title compound. LCMS calc. for $C_{18}H_{23}N_2O_5$ (M+H)$^+$: m/z=347.2. Found: 347.1. $^1$H NMR (400 MHz, CDCl$_3$) δ 9.64 (s, 1H), 8.41 (d, J=1.7 Hz, 1H), 7.56 (d, J=1.7 Hz, 1H), 5.98-5.88 (m, 1H), 5.15-5.01 (m, 2H), 4.52 (m, 2H), 3.46 (d, J=6.5 Hz, 2H), 1.55 (s, 9H), 1.50-1.29 (m, 3H).

Step 2. Ethyl 2-[(tert-butoxycarbonyl)amino]-6-(2-oxoethyl)furo[3,2-b]pyridine-3-carboxylate

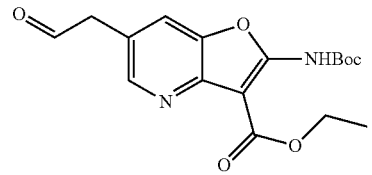 [SMILES: CCOC(=O)c1c(NC(=O)OC(C)(C)C)oc2cc(CC=O)cnc12]

To a solution of ethyl 6-allyl-2-[(tert-butoxycarbonyl)amino]furo[3,2-b]pyridine-3-carboxylate (2.6 g, 7.5 mmol) in THF (40 mL) and water (7 mL) was added 5% osmium tetroxide (3.8 mL, 0.61 mmol), followed by N-methylmorpholine N-oxide (1.8 g, 15 mmol). The mixture was stirred at 0° C. then allowed to warm to room temperature overnight. To the reaction mixture was added 10% aq. sodium sulfite and stirred for 30 min. The reaction mixture was extracted with EtOAc (2 times) and the combined organic layers were dried over MgSO$_4$, filtered and concentrated under reduced pressure. The residue was dissolved in THF (20 mL) and water (12 mL). To the reaction flask was added AcOH (60 μL) and NaIO$_4$ (5.3 g, 25 mmol) at 0° C. After stirring for 3 h at the same temperature, water was added to the reaction flask and extracted with DCM (3 times). The combined extracts were washed with brine, dried over Na$_2$SO$_4$, filtered and concentrated under reduced pressure to give the sub-title compound (1.6 g, 61%). LCMS calc. for $C_{17}H_{21}N_2O_6$ (M+H)$^+$: m/z=349.1. Found: 349.1.

Step 3. Ethyl 2-[(tert-butoxycarbonyl)amino]-6-{2-[(3R)-3-fluoropyrrolidin-1-yl]ethyl}furo[3,2-b]pyridine-3-carboxylate

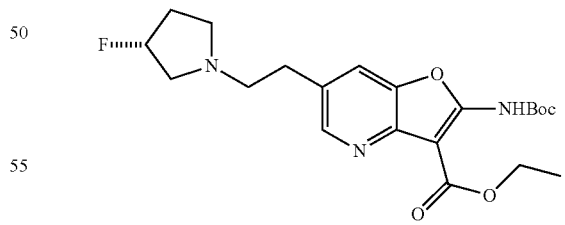

The sub-title compound was prepared according to a procedure analogous to that of Example 132, Step 5, using ethyl 2-[(tert-butoxycarbonyl)amino]-6-(2-oxoethyl)furo[3,2-b]pyridine-3-carboxylate (3R)-3-fluoropyrrolidine hydrochloride instead of ethyl 2-[(tert-butoxycarbonyl)amino]-6-(3-oxopropyl)furo[3,2-b]pyridine-3-carboxylate and morpholine as starting material. LCMS calc. for $C_{21}H_{29}FN_3O_5$ (M+H)$^+$: m/z=422.2. Found: 422.2.

Step 4. 2-[(tert-Butoxycarbonyl)amino]-6-{2-[(3R)-3-fluoropyrrolidin-1-yl]ethyl}furo[3,2-b]pyridine-3-carboxylic acid

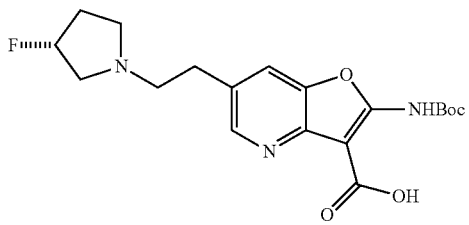 [SMILES: CC(C)(C)OC(=O)Nc1oc2cc(CCN3CC[C@@H](F)C3)cnc2c1C(=O)O]

The sub-title compound was prepared according to a procedure analogous to that of Example 132, Step 6, using ethyl 2-[(tert-butoxycarbonyl)amino]-6-{2-[(3R)-3-fluoropyrrolidin-1-yl]ethyl}furo[3,2-b]pyridine-3-carboxylate instead of ethyl 2-[(tert-butoxycarbonyl)amino]-6-(3-morpholin-4-ylpropyl)furo[3,2-b]pyridine-3-carboxylate as starting material. LCMS calc. for $C_{19}H_{25}FN_3O_5$ (M+H)$^+$: m/z=394.2. Found: 394.1.

Step 5. tert-Butyl [(3S,5R)-1-(3-{[(2-[(tert-butoxycarbonyl)amino]-6-{2-[(3R)-3-fluoropyrrolidin-1-yl]ethyl}furo[3,2-b]pyridin-3-yl)carbonyl]amino}pyridin-4-yl)-5-(trifluoromethyl)piperidin-3-yl]carbamate

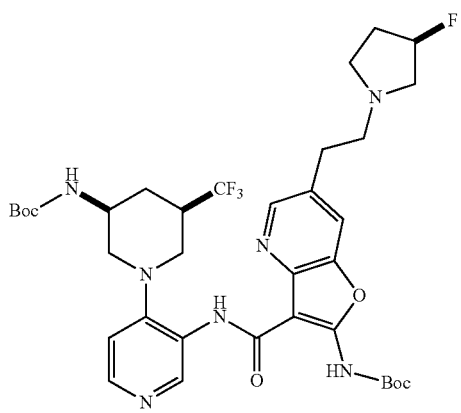 [SMILES: CC(C)(C)OC(=O)Nc1oc2cc(CCN3CC[C@@H](F)C3)cnc2c1C(=O)Nc1cnccc1N1C[C@@H](NC(=O)OC(C)(C)C)C[C@@H](C(F)(F)F)C1]

The sub-title compound was prepared according to a procedure analogous to that of Example 131, Step 4, using 2-[(tert-butoxycarbonyl)amino]-6-{2-[(3R)-3-fluoropyrrolidin-1-yl]ethyl}furo[3,2-b]pyridine-3-carboxylic acid instead of 2-[(tert-butoxycarbonyl)amino]-6-(3-methoxypropyl)furo[3,2-b]pyridine-3-carboxylic acid as starting material. LCMS calc. for $C_{35}H_{46}F_4N_7O_6$ (M+H)$^+$: m/z=736.3. Found: 736.3.

Step 6. 2-Amino-N-{4-[(3S,5R)-3-amino-5-(trifluoromethyl)piperidin-1-yl]pyridin-3-yl}-6-{2-[(3R)-3-fluoropyrrolidin-1-yl]ethyl}furo[3,2-b]pyridine-3-carboxamide The title compound was prepared according to a procedure analogous to that of Example 131, Step 5, using tert-butyl [(3S,5R)-1-(3-{[(2-[(tert-butoxycarbonyl)amino]-6-{2-[(3R)-3-fluoropyrrolidin-1-yl]ethyl}furo[3,2-b]pyridin-3-yl)carbonyl]amino}pyridin-4-yl)-5-(trifluoromethyl)piperidin-3-yl]carbamate instead of tert-butyl [(3S,5R)-1-[3-({[2-[(tert-butoxycarbonyl)amino]-6-(3-methoxypropyl)furo[3,2-b]pyridin-3-yl]carbonyl}amino)pyridin-4-yl]-5-(trifluoromethyl)piperidin-3-yl]carbamate as starting material. LCMS calc. for $C_{25}H_{30}F_4N_7O_2$ (M+H)$^+$: m/z=536.2. Found: 536.2.

Example 139

2-Amino-N-(4-((3R,4R,5S)-3-amino-4-hydroxy-5-methylpiperidin-1-yl)pyridin-3-yl)-6-isopropylthieno[3,2-b]pyridine-3-carboxamide

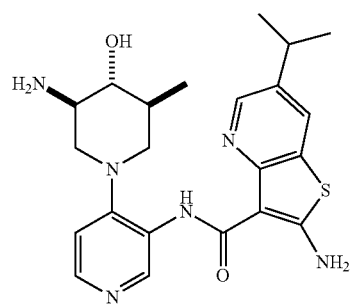 [SMILES: CC(C)c1cnc2c(C(=O)Nc3cnccc3N3C[C@@H](N)[C@H](O)[C@@H](C)C3)c(N)sc2c1]

Step 1. tert-Butyl ethyl (5-bromo-3-fluoropyridin-2-yl)malonate

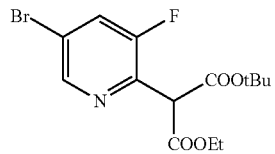

5-Bromo-2,3-difluoropyridine (3.23 g, 16.6 mmol, Matrix Scientific) and tert-butyl ethyl propane-1,3-dioate (3.4 mL, 18 mmol, Sigma-Aldrich) were dissolved in dimethyl sulfoxide (40 mL). After addition of $Cs_2CO_3$ (11 g, 33 mmol), the reaction mixture was stirred at room temperature overnight. Then the reaction mixture was quenched with water and pH adjusted to 7 by addition of 1 M aq. HCl. The reaction mixture was then extracted with EtOAc and the organic phase was washed with brine and dried over $Na_2SO_4$. After solvent evaporation under reduced pressure, a liquid product was obtained which was used in the next step without further purification. LCMS calc. for $C_{10}H_{10}BrFNO_4$ (M-tBu+2H)$^+$ m/z=306.0 and 308.0. found: 306.0 and 308.0.

Step 2. Ethyl (5-bromo-3-fluoropyridin-2-yl)acetate

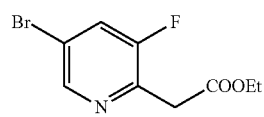 [SMILES: CCOC(=O)Cc1ncc(Br)cc1F]

tert-Butyl ethyl (5-bromo-3-fluoropyridin-2-yl)malonate (from previous step) was dissolved in DCM (50 mL) and TFA (10 mL, 200 mmol). The reaction mixture was stirred at room temperature until consumption of the starting material was complete (about 4 h). Solvent was then evaporated under reduced pressure and DCM was added again. The resulting solution was neutralized by addition of saturated aq. NaHCO$_3$ and product was extracted with DCM. The organic phase was washed with brine, dried over Na$_2$SO$_4$ and solvent was evaporated under reduced pressure. Crude material was purified by chromatography on silica gel using Biotage Isolera™ apparatus to give the sub-title compound (4.26 g, 98% over 2 steps). LCMS calc. for C$_9$H$_{10}$BrFNO$_2$ (M+H)$^+$ m/z=262.0 and 264.0. found: 262.0 and 264.0.

Step 3. Ethyl 6-bromo-2-[(4-methoxybenzyl)amino]thieno[3,2-b]pyridine-3-carboxylate

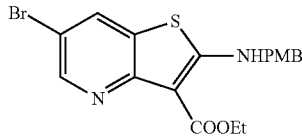

Ethyl (5-bromo-3-fluoropyridin-2-yl)acetate (4.08 g, 15.6 mmol) was dissolved in dimethyl sulfoxide (60 mL) and NaH (60% in mineral oil) (750 mg, 19 mmol) was slowly added. The reaction mixture was stirred at room temperature for 30 min. After this, 1-(isothiocyanatomethyl)-4-methoxybenzene (3.1 g, 17 mmol) was added and reaction mixture was stirred at room temperature for 20 min., and at 120° C. for 1 h. Then the reaction mixture was allowed to cool to room temperature and water was added. The product was extracted with EtOAc and organic phase was washed with brine and dried over Na$_2$SO$_4$. After evaporation of the solvent under reduced pressure, the crude product was purified by chromatography on silica gel using Biotage Isolera™ apparatus to give the sub-title compound as a yellow solid (3.2 g, 49%). LCMS calc. for C$_{18}$H$_{18}$BrN$_2$O$_3$S (M+H)$^+$ m/z=421.0 and 423.0. found: 421.0 and 423.0.

Step 4. Ethyl 6-isopropenyl-2-[(4-methoxybenzyl)amino]thieno[3,2-b]pyridine-3-carboxylate

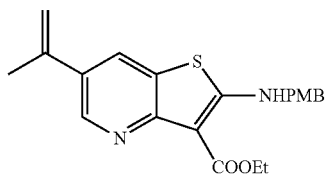

Ethyl 6-bromo-2-[(4-methoxybenzyl)amino]thieno[3,2-b]pyridine-3-carboxylate (880 mg, 2.1 mmol), dicyclohexyl (2',4',6'-triisopropylbiphenyl-2-yl)phosphine-(2'-aminobiphenyl-2-yl)(chloro)palladium (1:1) (160 mg, 0.21 mmol), K$_3$PO$_4$ (1000 mg, 6 mmol) and a magnetic stir bar were placed in a vial with septum. The vial was then evacuated and backfilled with N$_2$ three times. 1,4-Dioxane (8 mL) and deoxygenated water (3 mL) were added, followed by 2-isopropenyl-4,4,5,5-tetramethyl-1,3,2-dioxaborolane (700 µL, 4.2 mmol). The reaction mixture was stirred at 55° C. for 1 h. The reaction mixture was diluted with EtOAc, washed with brine, dried with Na$_2$SO$_4$ and concentrated under reduced pressure. The residue was purified by chromatography on silica gel using Biotage Isolera™ apparatus to give the sub-title compound (725 mg, 91%). LCMS calc. for C$_{21}$H$_{23}$N$_2$O$_3$S (M+H)$^+$ m/z=383.1. found: 383.1.

Step 5. Ethyl 6-isopropyl-2-[(4-methoxybenzyl)amino]thieno[3,2-b]pyridine-3-carboxylate

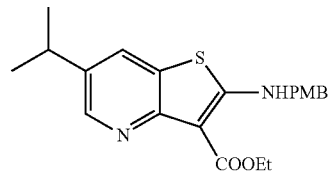

Ethyl 6-isopropenyl-2-[(4-methoxybenzyl)amino]thieno[3,2-b]pyridine-3-carboxylate (725 mg, 1.90 mmol) was dissolved in MeOH (10.0 mL) and 5 wt % of palladium on carbon (150 mg, 0.070 mmol) was added. The vial was closed with a septum and was connected to a balloon with hydrogen and stirred at room temperature overnight. LCMS showed complete conversion of the starting material. The reaction mixture was then filtered through a pad of diatomaceous earth. The filtrate was concentrated under reduced pressure to give the sub-title compound which was used in the next step without further purification (652 mg, 89%). LCMS calc. for C$_{21}$H$_{25}$N$_2$O$_3$S (M+H)$^+$ m/z=385.2. found: 385.1.

Step 6. 6-isopropyl-2-[(4-methoxybenzyl)amino]thieno[3,2-b]pyridine-3-carboxylic acid

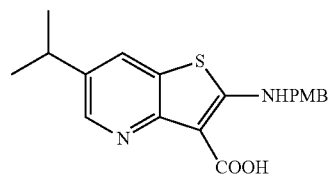

Ethyl 6-isopropyl-2-[(4-methoxybenzyl)amino]thieno[3,2-b]pyridine-3-carboxylate (652 mg, 1.70 mmol) was dissolved in THF (12 mL). Then water (4.3 mL) and MeOH (8.6 mL) were added. After addition of LiOH (300 mg, 10 mmol), reaction mixture was stirred at 60° C. for 4 h. The solution was then allowed to cool to room temperature and was adjusted to pH 5 with 1 M aq. HCl. The mixture was extracted with EtOAc, and the organic phase was washed with brine, dried with Na$_2$SO$_4$ and concentrated under reduced pressure to give the sub-title compound which was used in the next step without further purification (604 mg, 99%). LCMS calc. for C$_{19}$H$_{21}$N$_2$O$_3$S (M+H)$^+$ m/z=357.1. found: 357.1.

Step 7. tert-Butyl ((3R,4R,5S)-4-{[tert-butyl(dimethyl)silyl]oxy}-1-{3-[({6-isopropyl-2-[(4-methoxybenzyl)amino]thieno[3,2-b]pyridin-3-yl}carbonyl)amino]pyridin-4-yl}-5-methylpiperidin-3-yl)carbamate

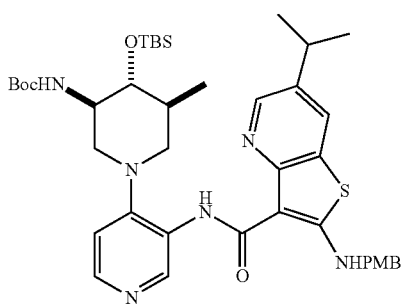

tert-Butyl ((3R,4R,5S)-1-(3-aminopyridin-4-yl)-4-{[tert-butyl(dimethyl)silyl]oxy}-5-methylpiperidin-3-yl)carbamate (1.60 mg, 0.367 mmol) and 6-isopropyl-2-[(4-methoxybenzyl)amino]thieno[3,2-b]pyridine-3-carboxylic acid (140 mg, 0.40 mmol) were dissolved in DMF (10 mL). Then DIPEA (130 µL, 0.73 mmol) and HATU (210 mg, 0.55 mmol) were added and reaction mixture was stirred at 60° C. overnight. After full conversion of the starting material was achieved, the reaction mixture was quenched with saturated aq. NaHCO₃. The mixture was extracted with EtOAc. The organic phase was washed with brine, then dried with Na₂SO₄. The solvent was evaporated under reduced pressure and the product was purified by chromatography on silica gel using Biotage Isolera™ apparatus to give the sub-title compound (315 mg, 99%). LCMS calc. for $C_{41}H_{59}N_6O_5SSi$ (M+H)⁺ m/z=775.4. found: 775.3.

Step 8. 2-amino-N-(4-((3R,4R,5S)-3-amino-4-hydroxy-5-methylpiperidin-1-yl)pyridin-3-yl)-6-isopropylthieno[3,2-b]pyridine-3-carboxamide tert-Butyl ((3R,4R,5S)-4-{[tert-butyl(dimethyl)silyl]oxy}-1-{3-[({6-isopropyl-2-[(4-methoxybenzyl)amino]thieno[3,2-b]pyridin-3-yl}carbonyl)amino]pyridin-4-yl}-5-methylpiperidin-3-yl)carbamate (208 mg, 0.268 mmol) was dissolved in DCM (2.0 mL) and TFA (2 mL, 14 mmol). Then 4.0 M HCl in dioxane (2 mL, 4 mmol) was added. The reaction mixture was stirred at 40° C. for overnight. The reaction mixture was diluted with MeCN and purified by RP-HPLC (Waters SunFire™ C18 column, 19 mm×100 mm, 5 µm particle size, eluting with a gradient of MeCN/water containing 0.1% TFA, at flow rate of 30 mL/min.) to give the title compound as a white solid. LCMS calc. for $C_{22}H_{29}N_6O_2S$ (M+H)⁺ m/z=441.2. found 441.2. ¹H NMR (500 MHz, DMSO-d₆) δ 11.87 (s, 1H), 9.39 (s, 1H), 8.61 (s, 2H), 8.43 (d, J=6.5 Hz, 1H), 8.34 (d, J=1.8 Hz, 1H), 8.14 (d, J=1.8 Hz, 1H), 8.05 (s, 1H), 7.53 (d, J=6.5 Hz, 1H), 3.97 (d, J=11.7 Hz, 1H), 3.62 (d, J=12.4 Hz, 1H), 3.20 (d, J=9.0 Hz, 2H), 3.00 (dt, J=13.8, 7.1 Hz, 2H), 2.87 (t, J=12.4 Hz, 1H), 1.99-1.84 (m, 1H), 1.26 (dd, J=6.9, 3.0 Hz, 6H), 0.95 (d, J=6.5 Hz, 3H).

Example 140

2-Amino-N-(4-((3R,4R,5S)-3-amino-4-hydroxy-5-methylpiperidin-1-yl)pyridin-3-yl)-6-propylthieno[3,2-b]pyridine-3-carboxamide

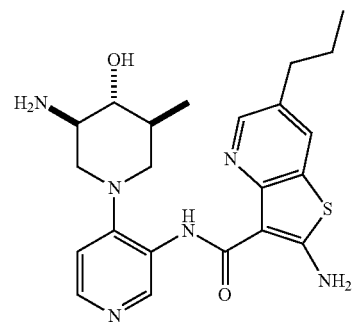 [SMILES: CCCc1cnc2c(C(=O)Nc3cnccc3N3C[C@@H](N)[C@H](O)[C@@H](C)C3)c(N)sc2c1]

The title compound was synthesized according a procedure analogous to that of Example 139, using (Z)-4,4,5,5-tetramethyl-2-(prop-1-enyl)-1,3,2-dioxaborolane as the starting material. LCMS calc. for $C_{22}H_{29}N_6O_2S$ (M+H)⁺ m/z=441.2. found: 441.2. ¹H NMR (500 MHz, DMSO-d₆) δ 11.84 (s, 1H), 9.38 (s, 1H), 8.61 (s, 2H), 8.40 (d, J=6.3 Hz, 1H), 8.29 (d, J=1.7 Hz, 1H), 8.16-7.98 (m, 3H), 7.47 (d, J=6.3 Hz, 1H), 3.91 (d, J=11.8 Hz, 1H), 3.56 (d, J=11.9 Hz, 1H), 3.19 (d, J=8.3 Hz, 2H), 2.99-2.91 (m, 1H), 2.82 (t, J=12.2 Hz, 1H), 2.61 (t, 2H), 2.01-1.83 (m, 1H), 1.62 (q, J=7.4 Hz, 2H), 0.95 (d, J=6.5 Hz, 3H), 0.91 (t, J=7.3 Hz, 3H).

Example 141

6-(Acetylamino)-2-amino-N-{4-[(3R,4R,5S)-3-amino-4-hydroxy-5-methylpiperidin-1-yl]pyridin-3-yl}thieno[3,2-b]pyridine-3-carboxamide

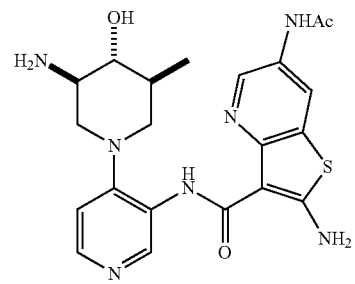 [SMILES: CC(=O)Nc1cnc2c(C(=O)Nc3cnccc3N3C[C@@H](N)[C@H](O)[C@@H](C)C3)c(N)sc2c1]

Step 1. tert-Butyl ethyl (3-chloro-5-nitropyridin-2-yl)malonate

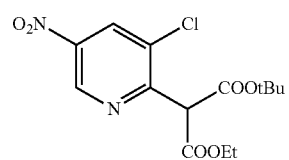

2,3-Dichloro-5-nitropyridine (1.78 g, 9.22 mmol, Matrix Scientific) and tert-butyl ethyl propane-1,3-dioate (1.9 mL, 10 mmol, Sigma-Aldrich) were dissolved in dimethyl sulfoxide (20 mL). $K_2CO_3$ (2.5 g, 18 mmol) was added and the reaction mixture was stirred at room temperature overnight. Then water was added and the pH was adjusted to pH 7 with 1 M aq. HCl. The mixture was then extracted with EtOAc and the organic phase was washed with brine and dried over $Na_2SO_4$. After solvent evaporation under reduced pressure, a liquid product was obtained which was used in the next step without further purification. LCMS calc. for $C_{10}H_{10}ClN_2O_6$ $(M-tBu+2H)^+$ m/z=289.0. found: 289.0.

Step 2. Ethyl (3-chloro-5-nitropyridin-2-yl)acetate

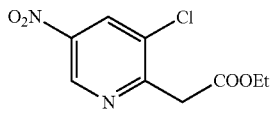 [SMILES: CCOC(=O)Cc1ncc([N+](=O)[O-])cc1Cl]

tert-Butyl ethyl (3-chloro-5-nitropyridin-2-yl)malonate (was dissolved in DCM (30 mL) and TFA (7 mL, 100 mmol). The reaction mixture was stirred at room temperature until consumption of the starting material was complete (about 4 h). The solvent was then evaporated under reduced pressure and DCM was added again. The resulting solution was neutralized by addition of saturated aq. $NaHCO_3$ and product was extracted with DCM. The organic phase was washed with brine, dried over $Na_2SO_4$ and solvent was evaporated under reduced pressure. The residue was purified by chromatography on silica gel using Biotage Isolera™ apparatus to give the sub-title compound (1.83 g, 81% over 2 steps). LCMS calc. for $C_9H_{10}ClN_2O_4$ $(M+H)^+$ m/z=245.0. found: 245.1.

Step 3. Ethyl 2-[(4-methoxybenzyl)amino]-6-nitrothieno[3,2-b]pyridine-3-carboxylate

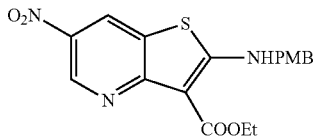

Ethyl (3-chloro-5-nitropyridin-2-yl)acetate (1.82 g, 7.42 mmol) was dissolved in dimethyl sulfoxide (30 mL) and NaH (60% in mineral oil) (360 mg, 8.9 mmol) was slowly added. The reaction mixture was then stirred at room temperature for 30 min. After this, 1-(isothiocyanatomethyl)-4-methoxybenzene (1.5 g, 8.2 mmol) was added and the reaction mixture was stirred at room temperature for 20 min and at 120° C. for 1 h. The reaction mixture was then allowed to cool to room temperature and water was added. The product was extracted with EtOAc and organic phase was washed with brine and dried over $Na_2SO_4$. After evaporation of the solvent under reduced pressure, the residue was purified by chromatography on silica gel using Biotage Isolera™ apparatus to give the sub-title compound as a yellow solid (1.14 g, 41%). LCMS calc. for $C_{18}H_{18}N_3O_5S$ $(M+H)^+$ m/z=388.1. found: 388.1.

Step 4. Ethyl 6-amino-2-[(4-methoxybenzyl)amino] thieno[3,2-b]pyridine-3-carboxylate

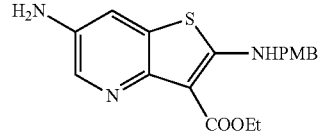

Ethyl 2-[(4-methoxybenzyl)amino]-6-nitrothieno[3,2-b] pyridine-3-carboxylate (1.187 g, 3.064 mmol) was dissolved in AcOH (40 mL). Then Fe powder (2 g, 30 mmol) was added and reaction mixture was stirred at room temperature for 2 h. The reaction mixture was then diluted with EtOAc and all the solids were filtered off with diatomaceous earth. The solvent was then evaporated under reduced pressure and fresh EtOAc was added. The mixture was neutralized with saturated aq. $NaHCO_3$. The mixture was extracted with EtOAc and organic phase was washed with brine and dried over $Na_2SO_4$. After evaporation of the solvent under reduced pressure, the residue was purified by chromatography on silica gel using Biotage Isolera™ apparatus to give the sub-title compound (0.74 g, 68%). LCMS calc. for $C_{18}H_{20}N_3O_3S$ $(M+H)^+$ m/z=358.1. found: 358.1.

Step 5. Ethyl 6-(acetylamino)-2-[(4-methoxybenzyl) amino]thieno[3,2-b]pyridine-3-carboxylate

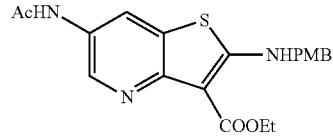

Ethyl 6-amino-2-[(4-methoxybenzyl)amino]thieno[3,2-b] pyridine-3-carboxylate (245 mg, 0.685 mmol) was dissolved in DCM (3 mL) and $Ac_2O$ (67.9 µL, 0.720 mmol) was added. The reaction mixture was stirred at room temperature for 2 h. The reaction was then quenched by addition of saturated aq. $NaHCO_3$. The product was then extracted with EtOAc and the organic phase was washed with brine and dried over $Na_2SO_4$. After solvent evaporation under reduced pressure, a pure product was obtained which was used in the next step without further purification (215 mg, 79%). LCMS calc. for $C_{20}H_{22}N_3O_4S$ $(M+H)^+$ m/z=400.1. found: 400.1.

Step 6. 6-(acetylamino)-2-[(4-methoxybenzyl) amino]thieno[3,2-b]pyridine-3-carboxylic acid

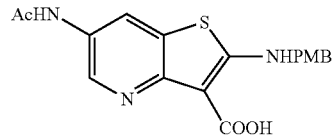

Ethyl 6-(acetylamino)-2-[(4-methoxybenzyl)amino] thieno[3,2-b]pyridine-3-carboxylate (205 mg, 0.513 mmol) was dissolved in THF (3.6 mL). Then water (1.3 mL) and MeOH (2.6 mL) were added. After addition of LiOH (90 mg, 4 mmol), the reaction mixture was stirred at 60° C. for 4 h. The reaction mixture was then allowed to cool to room temperature and the pH was adjusted to 5 by addition of 1 M aq. HCl. The mixture was then extracted with EtOAc and the organic phase washed with brine, dried with Na₂SO₄ and the solvent was evaporated under reduced pressure to give the sub-title compound, which was used in the next step without further purification (175 mg, 92%). LCMS calc. for C₁₈H₁₈N₃O₄S (M+H)⁺ m/z=372.1. found: 372.1.

Step 7. tert-Butyl ((3R,4R,5S)-1-{3-[({6-(acety-lamino)-2-[(4-methoxybenzyl)amino]thieno[3,2-b]pyridin-3-yl}carbonyl)amino]pyridin-4-yl}-4-{[tert-butyl(dimethyl)silyl]oxy}-5-methylpiperidin-3-yl)carbamate

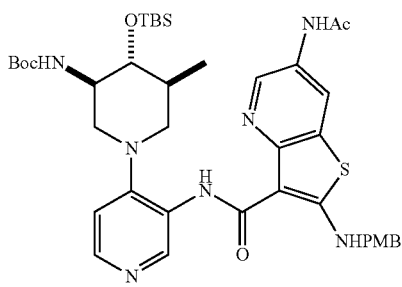

tert-Butyl ((3R,4R,5S)-1-(3-aminopyridin-4-yl)-4-{[tert-butyl(dimethyl)silyl]oxy}-5-methylpiperidin-3-yl)carbamate (182 mg, 0.416 mmol) and 6-(acetylamino)-2-[(4-methoxybenzyl)amino]thieno[3,2-b]pyridine-3-carboxylic acid (170 mg, 0.46 mmol) were dissolved in DMF (12 mL). Then DIPEA (140 µL, 0.83 mmol) and HATU (240 mg, 0.62 mmol) were added and reaction mixture was stirred at 60° C. overnight. After full conversion of the starting material was achieved, the reaction was quenched with saturated aq. NaHCO₃ and the mixture was extracted with EtOAc. The organic phase was washed with brine, dried with Na₂SO₄, and the solvent was evaporated under reduced pressure. The residue was purified by chromatography on silica gel using Biotage Isolera™ apparatus to give the sub-title compound (212 mg, 65%). LCMS calc. for C₄₀H₅₆N₇O₆SSi (M+H)⁺ m/z=790.4. found: 790.3.

Step 8. 6-(acetylamino)-2-amino-N-{4-[(3R,4R,5S)-3-amino-4-hydroxy-5-methylpiperidin-1-yl]pyridin-3-yl}thieno[3,2-b]pyridine-3-carboxamide tert-Butyl ((3R,4R,5S)-1-{3-[({6-(acetylamino)-2-[(4-methoxybenzyl)amino]thieno[3,2-b]pyridin-3-yl}carbonyl)amino]pyridin-4-yl}-4-{[tert-butyl(dimethyl)silyl]oxy}-5-methylpiperidin-3-yl)carbamate (212 mg, 0.268 mmol) was dissolved in DCM (2.0 mL) and TFA (2 mL, 14 mmol). Then 4.0 M HCl in dioxane (2 mL, 4 mmol) was added. The reaction mixture was stirred at 40° C. for overnight. The reaction mixture was then diluted with MeCN and purified by RP-HPLC (Waters SunFire™ C18 column, 19 mm×100 mm, 5 µm particle size, eluting with a gradient of MeCN/water containing 0.1% TFA, at flow rate of 30 mL/min.) to give the title compound as a white solid. LCMS calc. for C₂₁H₂₆N₇O₃S (M+H)⁺ m/z=456.2. found 456.2. ¹H NMR (500 MHz, DMSO-d₆) δ 11.63 (s, 1H), 10.23 (s, 1H), 9.31 (s, 1H), 8.58 (s, 2H), 8.49 (d, J=6.5 Hz, 1H), 8.37 (d, J=6.1 Hz, 1H), 7.97 (s, 2H), 7.43 (d, J=6.1 Hz, 1H), 3.88 (d, J=12.0 Hz, 1H), 3.54 (d, J=11.7 Hz, 1H), 3.21-3.06 (m, 2H), 2.81 (t, J=12.1 Hz, 2H), 2.08 (s, 3H), 1.93-1.77 (m, 1H), 0.99 (d, J=6.4 Hz, 3H).

Example 142

2-Amino-N-(4-((3R,4R,5S)-3-amino-4-hydroxy-5-methylpiperidin-1-yl)pyridin-3-yl)-6-(cyclopropanecarboxamido)thieno[3,2-b]pyridine-3-carboxamide

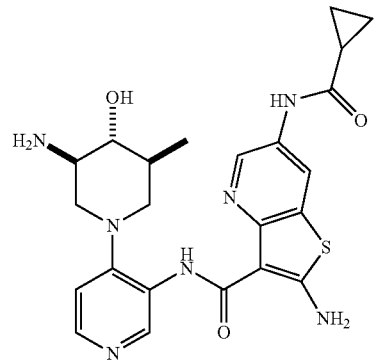 [SMILES: C[C@H]1CN(c2ccncc2NC(=O)c2c(N)sc3cc(NC(=O)C4CC4)cnc23)C[C@@H](N)[C@@H]1O]

The title compound was prepared using a method analogous to that of Example 141, using cyclopropanecarbonyl chloride as the starting material. LCMS calc. for C₂₃H₂₈N₇O₃S (M+H)⁺ m/z=482.2. found: 482.2. ¹H NMR (500 MHz, DMSO-d₆) δ 11.63 (s, 1H), 10.49 (s, 1H), 9.31 (s, 1H), 8.58 (s, 2H), 8.52 (d, J=2.1 Hz, 1H), 8.49 (d, J=2.0 Hz, 1H), 8.39 (d, J=6.3 Hz, 1H), 7.99 (s, 2H), 7.46 (d, J=6.3 Hz, 1H), 3.93 (d, J=11.7 Hz, 1H), 3.58 (d, J=12.6 Hz, 1H), 3.21-3.08 (m, 2H), 2.91-2.79 (m, 2H), 1.92-1.76 (m, 2H), 0.99 (d, J=6.5 Hz, 3H), 0.88-0.77 (m, 4H).

Example 143

2-Amino-N-(4-((3R,4R,5S)-3-amino-4-hydroxy-5-methylpiperidin-1-yl)pyridin-3-yl)-6-isobutyramidothieno[3,2-b]pyridine-3-carboxamide

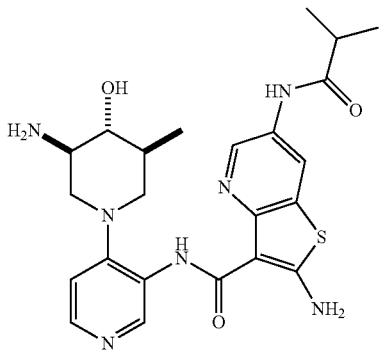 [SMILES: CC(C)C(=O)Nc1cnc2c(C(=O)Nc3cnccc3N3C[C@@H](N)[C@H](O)[C@@H](C)C3)c(N)sc2c1]

The title compound was prepared by a method analogous to that of Example 141, using isobutyryl chloride. LCMS calc. for C₂₃H₃₀N₇O₃S (M+H)⁺ m/z=484.2. found: 484.2. ¹H NMR (500 MHz, DMSO-d₆) δ 11.63 (s, 1H), 10.13 (s, 1H), 9.29 (s, 1H), 8.58 (s, 2H), 8.55 (d, J=2.1 Hz, 1H), 8.50 (d, J=2.0 Hz, 1H), 8.40 (d, J=6.4 Hz, 1H), 7.99 (s, 2H), 7.48 (d, J=6.4 Hz, 1H), 3.96 (d, J=11.1 Hz, 1H), 3.62 (d, J=11.6 Hz, 1H), 3.18 (t, J=9.8 Hz, 1H), 3.15-3.06 (m, 1H), 2.94-2.82 (m, 2H), 2.63 (p, J=6.8 Hz, 1H), 1.90-1.77 (m, 1H), 1.12 (dd, J=6.8, 1.2 Hz, 6H), 0.98 (d, J=6.5 Hz, 3H).

Example 144

2-Amino-N-(4-((3S,5R)-3-amino-5-(trifluoromethyl)piperidin-1-yl)pyridin-3-yl)-6-morpholinothieno[3,2-b]pyridine-3-carboxamide

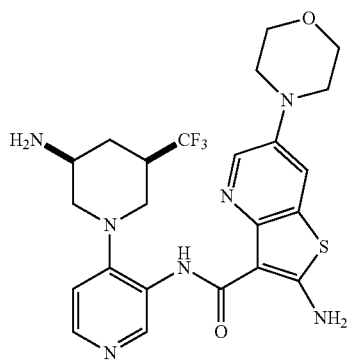 [SMILES: Nc1sc2cc(N3CCOCC3)cnc2c1C(=O)Nc1cnccc1N1C[C@@H](N)C[C@@H](C(F)(F)F)C1]

Step 1. Ethyl 2-[(4-methoxybenzyl)amino]-6-morpholin-4-ylthieno[3,2-b]pyridine-3-carboxylate

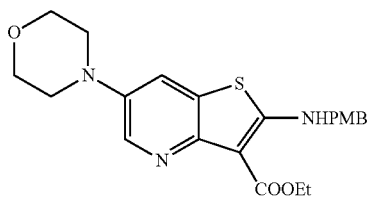

Ethyl 6-bromo-2-[(4-methoxybenzyl)amino]thieno[3,2-b]pyridine-3-carboxylate (250 mg, 0.59 mmol, from Example 1), Cs₂CO₃ (390 mg, 1.2 mmol) and chloro-(2-dicyclohexylphosphino-22,62-diisopropoxy-1,12-biphenyl)[2-(2-aminoethyl)phenyl]palladium(II)-methyl-t-butyl ether adduct (48 mg, 0.059 mmol) were placed in a vial. The vial was then evacuated and backfilled with N₂ three times. Then toluene (10 mL) and morpholine (100 µL, 1.2 mmol) was added through a septum and reaction mixture was heated at 100° C. overnight. The reaction mixture was allowed to cool to room temperature and diluted with EtOAc and washed twice with brine. The organic phase was then dried over Na₂SO₄, filtered and concentrated under reduced pressure. The residue was purified by chromatography on silica gel using Biotage Isolera™ apparatus to give the sub-title compound (130 mg, 51%). LCMS calc. for $C_{22}H_{26}N_3O_4S$ (M+H)⁺ m/z=428.2. found 428.2.

Step 2. 2-[(4-methoxybenzyl)amino]-6-morpholin-4-ylthieno[3,2-b]pyridine-3-carboxylic acid

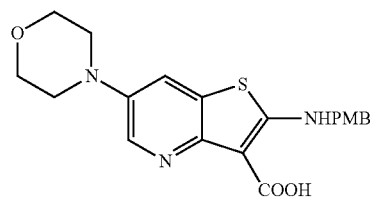

Ethyl 2-[(4-methoxybenzyl)amino]-6-morpholin-4-ylthieno[3,2-b]pyridine-3-carboxylate (130 mg, 0.30 mmol) was dissolved in THF (2.1 mL). Then water (0.77 mL) and MeOH (1.5 mL) were added. After addition of LiOH (50 mg, 2 mmol), the reaction mixture was stirred at 60° C. for 4 h. The reaction mixture was then allowed to cool to room temperature and the pH was adjusted to pH 5 by addition of 1 M aq. HCl. The mixture was then extracted with EtOAc and the organic phase was washed with brine, dried with Na₂SO₄ and the solvent was evaporated. The resulting product was used in the next step without further purification (110 mg, 90%). LCMS calc. for $C_{20}H_{22}N_3O_4S$ (M+H)⁺ m/z=400.1. found: 400.1.

Step 3. tert-Butyl [(3S,5R)-1-{3-[({2-[(4-methoxybenzyl)amino]-6-piperidin-1-ylthieno[3,2-b]pyridin-3-yl}carbonyl)amino]pyridin-4-yl}-5-(trifluoromethyl)piperidin-3-yl]carbamate

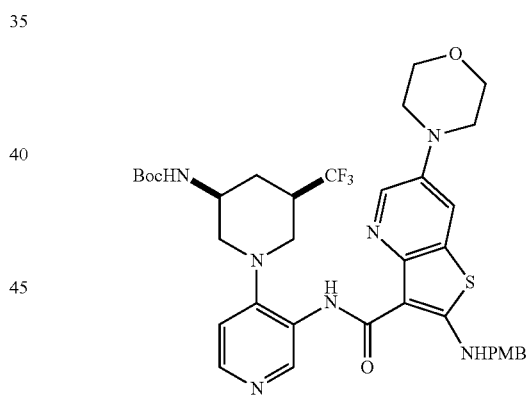

tert-Butyl [(3S,5R)-1-(3-aminopyridin-4-yl)-5-(trifluoromethyl)piperidin-3-yl]carbamate (45.1 mg, 0.125 mmol) and 2-[(4-methoxybenzyl)amino]-6-morpholin-4-ylthieno[3,2-b]pyridine-3-carboxylic acid (55 mg, 0.14 mmol) were dissolved in DMF (2.7 mL). Then DIPEA (44 µL, 0.25 mmol) and HATU (95 mg, 0.25 mmol) were added and reaction mixture was stirred at 60° C. overnight. After full conversion was achieved, the reaction was quenched by the addition of saturated aq. NaHCO₃ and reaction mixture was extracted with EtOAc. The organic phase was washed with brine, dried with Na₂SO₄ and the solvent was evaporated under reduced pressure. The solvent was evaporated, and the product was then purified by chromatography on silica gel using Biotage Isolera™ apparatus to give the sub-title compound (71 mg, 77%). LCMS calc. for $C_{36}H_{43}F_3N_7O_5S$ (M+H)⁺ m/z=742.3. found: 742.2.

Step 4. 2-amino-N-(4-((3S,5R)-3-amino-5-(trifluoromethyl)piperidin-1-yl)pyridin-3-yl)-6-morpholinothieno[3,2-b]pyridine-3-carboxamide tert-Butyl [(3S,5R)-1-{3-[({2-[(4-methoxybenzyl)amino]-6-morpholin-4-ylthieno[3,2-b]pyridin-3-yl}carbonyl)amino]pyridin-4-yl}-5-(trifluoromethyl)piperidin-3-yl]carbamate (40 mg, 0.06 mmol) was dissolved in DCM (2.0 mL) and TFA (2 mL, 14 mmol). Then, the reaction mixture was stirred at 40° C. for overnight. After being allowed to cool to room temperature, the reaction mixture was diluted with MeCN and purified by RP-HPLC (Waters SunFire™ C18 column, 19 mm×100 mm, 5 μm particle size, eluting with a gradient of MeCN/water containing 0.1% TFA, at flow rate of 30 mL/min.) to give the title compound as a white solid. LCMS calc. for $C_{23}H_{27}F_3N_7O_2S$ $(M+H)^+$ m/z=522.2. found 522.1. $^1H$ NMR (500 MHz, DMSO-$d_6$) δ 11.62 (s, 1H), 9.37 (s, 1H), 8.51-8.41 (m, 3H), 8.26 (s, 1H), 8.17 (s, 2H), 7.91 (d, J=2.5 Hz, 1H), 7.53 (d, J=6.4 Hz, 1H), 3.94 (d, J=9.8 Hz, 1H), 3.86-3.74 (m, 5H), 3.22-3.03 (m, 7H), 2.92 (t, J=11.7 Hz, 1H), 2.35 (d, J=11.2 Hz, 1H).

Example A

Pim Enzyme Assays

Pim-1 and Pim-3 kinase assays-20 μL reactions were run in white 384 well polystyrene plates dotted with 0.8 μL compound/DMSO in the assay buffer (50 mM Tris, pH 7.5, 0.01% Tween-20, 5 mM $MgCl_2$, 0.01% BSA, 5 mM DTT), containing 0.05 μm Biotin-labeled BAD peptide substrate (AnaSpec 62269), 1 mM ATP, and 2.5 pM (Pim-1, Invitrogen PV3503) or 1.25 pM (Pim-3, Millipore 14-738) enzyme for 1 h at 25° C. Reactions were stopped by addition of 10 μL STOP Buffer (150 mM Tris, pH=7.5, 150 mM NaCl, 75 mM EDTA, 0.01% Tween-20, 0.3% BSA) supplemented with Phospho-Bad (Ser112) Antibody (Cell Signaling 9291) diluted 666-fold, and Streptavidin donor beads (PerkinElmer 6760002) along with Protein-A acceptor beads (PerkinElmer 6760137) at 15 μg/mL each. Supplementation of the STOP buffer with beads and stopping the reactions were done under reduced light. Prior to the stopping reactions STOP buffer with beads was pre-incubated for 1 h in the dark at room temperature. After stopping the reactions, plates were incubated for 1 h in the dark at room temperature before reading on a PHERAstar FS plate reader (BMG Labtech) under reduced light.

Pim-2 kinase assay-20 μL reactions were run in white 384 well polystyrene plates dotted with 0.8 μL compound/DMSO in the assay buffer (50 mM Tris, pH 7.5, 0.01% Tween-20, 5 mM $MgCl_2$, 0.01% BSA, 5 mM DTT), containing 0.05 μm Fluorescein-labeled CREBtide peptide substrate (Invitrogen PV3508), 1 mM ATP, and 1 nM enzyme (Invitrogen PV3649) for 2 h at 25° C. Reactions were stopped by addition of 10 μL TR-FRET Dilution Buffer (Invitrogen PV3574) with 30 mM EDTA and 1.5 nM LanthaScreen Tb-CREB pSer133 antibody (Invitrogen PV3566). After 30 min. incubation at room temperature, plates were read on a PHERAstar FS plate reader (BMG Labtech).

Compounds of the invention having an $IC_{50}$ of 2 μm or less when tested for PIM kinase activity under the assay conditions disclosed above are considered active.

Although the above in vitro assays are conducted at 1 mM ATP compounds can also be evaluated for potency and in vitro activity against PIM targets utilizing $K_m$ conditions, where the concentration of ATP is set to the $K_m$ value and the assay is more sensitive to PIM inhibition activity.

Example B

Pim Cellular Assays

One or more compounds of the invention were tested for inhibitory activity of PIM according to at least one of the following cellular assays. Compounds of the invention having an $IC_{50}$ of 10 μm or less when tested for PIM kinase activity under the cellular assay conditions disclosed below would be and were considered active.

Pim Cell Proliferation Assay

KG-1A cells are purchased from ATCC (Manassas, Va.) and KMS.12.BM cells are purchased from NIBIO, JCRB cell bank (Tokyo, Japan) and maintained in the culture mediums recommended, RPMI, 10% FBS (Roswell Park Memorial Institute 1640 Medium supplemented with 10% fetal bovine serum) and IMDM 20% FBS (Iscove's Modified Dulbecco's Medium (MDM) with 20% fetal bovine strum) (Mediatech, Manassas, Va.) respectively. To measure the anti-proliferation activity of test compounds, both cell lines are plated with the culture medium ($2 \times 10^3$ cells/well/in 200 μL) into 96-well polystyrene ultralow binding (Costar®) in the presence or absence of a concentration range of test compounds. After 4 days, [$^3$H]-thymidine, 1 μCi/10 μL/well (PerkinElmer, Boston, Mass.) in culture medium is then added to the cell culture for an additional 16 h before the incorporated radioactivity is separated by filtration with a Packard Microplate Harvester with water through a 0.3% polyethylenimine pre-wetted glass fiber GF/B filter plates (Packard Bioscience/PerkinElmer, Boston, Mass.). The plate is measured by liquid scintillation counting with a TopCount® scintillation sounter (PerkinElmer). $IC_{50}$ determination is performed by fitting the curve of percent inhibition versus the log of the inhibitor concentration using GraphPad Prism® 5.0 software.

Pim Cell Proliferation Assay

MOLM-16 cells are purchased from DSMZ (Germany) and maintained in the culture medium recommended, RPMI, 20% FBS. To measure the anti-proliferation activity of test compounds, the cells are plated with the RPMI, 10% FBS ($1 \times 10^4$ cells/well/in 200 μL) into 96-well polystyrene ultralow binding plates (Costar) in the presence or absence of a concentration range of test compounds. After 4 days, [$^3$H]-thymidine, 1 μCi/10 μL/well (PerkinElmer, Boston, Mass.) in RPMI, 10% FBS is then added to the cell culture for an additional 16 h before the incorporated radioactivity is separated by filtration with a Packard Micro plate Harvester with water through a 0.3% PEI pre wetted GF/B filter plates (Packard Bioscience/PerkinElmer, Boston, Mass.). The plate is measured by liquid scintillation counting with a TopCount (PerkinElmer). $IC_{50}$ determination is performed by fitting the curve of percent inhibition versus the log of the inhibitor concentration using the GraphPad Prism 5.0 software.

Pim pBAD Signaling Assay

KG-1A cells are purchased from ATCC (Manassas, Va.) and KMS.12.BM cells are purchased from NIBIO, JCRB cell bank (Tokyo, Japan) and maintained in the culture mediums recommended, RPMI, 10% FBS and IMDM 20% FBS (Mediatech, Manassas, Va.) respectively. To measure the pBAD inhibitory activity of the compounds, both cell lines are plated with the culture medium ($1 \times 10^6$/well/100 μL for KG1A and $4 \times 10^5$ cells/well/in 100 μL for KMS12BM) into 96-well V bottom polypropylene plates (Matrix, Thermo Fisher, USA) and incubated 30 min. at 37° C. to normalize cell signaling from handling. Test compounds are added at an appropriate concentration range and further incubated for 2.5 h for KMS.12.BM cells and 4 h for KG1-A cells. Plates are centrifuged at 2000 RPM for 10 min. and supernatants aspirated. 100 μL lysis buffer with protease inhibitors (Cell Signaling Technologies, Danver, Mass., Sigma, St Louis Mo., EMD, USA) is added to the pellets, mixed well and set on ice for 30 min. Lysates are frozen overnight at −80° C. To measure the pBAD activity, a Cell Signaling ELISA (enzyme-linked immunosorbent assay) kit (Cell Signaling Path Scan phosphor pBAD ELISA) is utilized. 50 μL of the lysate is tested per the ELISA protocol and the data analysis is performed by software on a SpectraMax® M5 plate reader (Molecular Devices, Sunnyvale, Calif.). $IC_{50}$ determination is performed by fitting the curve of percent inhibition versus the log of the inhibitor concentration using GraphPad Prism® 5.0 software.

Data obtained for the Example compounds, obtained using the methods described in Example A, are provided in Table 2.

TABLE 2

Pim Enzyme Assay Data

| Example | Pim1 $IC_{50}$ (nM)[a] | Pim2 $IC_{50}$ (nM)[a] | Pim3 $IC_{50}$ (nM)[a] |
|---|---|---|---|
| 1 | * | *** | * |
| 2 | * | *** | * |
| 3 | * | >2000 | * |
| 4 | * | >1000 | * |
| 5 | * | *** | * |
| 6 | * | *** | * |
| 7 | * | >2000 | >40 |
| 8 | * | >2000 | >40 |
| 9 | ** | >2000 | >40 |
| 12 | * | *** | * |
| 13 | * | ** | * |
| 14 | * | >2000 | * |
| 15 | * | *** | * |
| 16 | * | *** | * |
| 17 | * | * | * |
| 18 | >40 | >1000 | * |
| 19 | * | ** | * |
| 20 | * | *** | * |
| 22 | * | ** | * |
| 23 | * | ** | * |
| 24 | * | >1000 | * |
| 25 | * | ** | * |
| 26 | * | ** | * |
| 27 | * | ** | * |
| 28 | * | >2000 | >40 |
| 29 | * | *** | * |
| 30 | * | ** | * |
| 31 | * | *** | * |
| 32 | * | *** | * |
| 33 | * | >2000 | ** |
| 34 | * | *** | * |
| 35 | * | ** | * |
| 36 | * | *** | * |
| 37 | * | *** | * |
| 38 | * | *** | * |
| 39 | * | *** | * |
| 40 | * | >2000 | ** |
| 41 | * | *** | * |
| 42 | >40 | >2000 | >40 |
| 43 | * | >1000 | ** |
| 44 | * | >2000 | * |
| 45 | * | *** | * |
| 46 | * | >2000 | ** |
| 47 | * | ** | * |
| 48 | * | ** | * |
| 49 | * | ** | * |
| 50 | * | ** | * |
| 51 | * | ** | * |
| 52 | * | *** | * |
| 53 | * | ** | * |
| 54 | * | ** | * |
| 55 | ** | >2000 | * |
| 56 | * | ** | * |
| 57 | * | *** | * |
| 58 | * | *** | * |
| 59 | * | ** | * |
| 60 | * | ** | * |
| 61 | * | ** | * |
| 62 | * | ** | * |
| 63 | * | ** | * |
| 64 | * | **** | * |
| 65 | * | ** | * |
| 66 | * | ** | * |
| 67 | * | * | * |
| 68 | * | ** | * |
| 69 | * | * | * |
| 70 | * | ** | * |
| 71 | * | ** | * |
| 72 | * | ** | * |
| 73 | * | ** | * |
| 74 | * | ** | * |
| 75 | * | ** | * |
| 76 | * | *** | * |
| 77 | * | * | * |
| 78 | * | ** | * |
| 79 | * | ** | * |
| 80 | * | *** | * |
| 81 | * | * | * |
| 82 | * | * | * |
| 83 | * | *** | * |
| 84 | * | ** | * |
| 85 | * | * | * |
| 86 | * | * | * |
| 87 (Diastereoisomer 1) | * | *** | * |
| 87 (Diastereoisomer 2) | * | ** | * |
| 88 | * | *** | * |
| 89 | * | * | * |
| 90 | * | ** | * |
| 91 | * | ** | * |
| 92 | * | * | * |
| 93 | * | ** | * |
| 94 | * | ** | * |
| 95 | * | ** | * |
| 96 | * | ** | * |
| 97 | * | * | * |
| 98 | * | * | * |
| 99 | * | ** | * |
| 100 | * | ** | * |
| 101 | * | ** | * |
| 102 | * | ** | * |
| 103 | * | ** | * |
| 104 | * | ** | * |
| 105 | * | ** | * |
| 106 | * | ** | * |
| 107 | * | ** | * |
| 108 | * | ** | * |
| 109 | * | ** | * |
| 110 | * | ** | * |
| 111 | * | ** | * |
| 112 | * | ** | * |
| 113 | * | * | * |
| 114 | * | * | * |
| 115 | * | * | * |
| 116 | * | ** | * |
| 117 | * | * | * |
| 118 | * | * | * |
| 119 | * | ** | * |
| 120 | * | ** | * |
| 121 | * | ** | * |
| 122 | * | * | * |

TABLE 2-continued

Pim Enzyme Assay Data

| Example | Pim1 IC$_{50}$ (nM)$^a$ | Pim2 IC$_{50}$ (nM)$^a$ | Pim3 IC$_{50}$ (nM)$^a$ |
|---|---|---|---|
| 123 | * | * | * |
| 124 | * | * | * |
| 125 | * | * | * |
| 126 | * | ** | * |
| 127 | * | ** | * |
| 128 | * | ** | * |
| 129 | * | ** | * |
| 130 | * | * | * |
| 131 | * | * | * |
| 132 | * | * | * |
| 133 | * | * | * |
| 134 | * | * | * |
| 135 | * | ** | * |
| 136 | * | ** | * |
| 137 | * | * | * |
| 138 | * | * | * |
| 139 | * | * | * |
| 140 | * | * | * |
| 141 | * | ** | * |
| 142 | * | ** | * |
| 143 | * | ** | * |
| 144 | * | ** | * |

$^a$IC$_{50}$ ≤ 10 nM: *; 10 nM < IC$_{50}$ ≤ 100 nM: ; 100 nM < IC$_{50}$ ≤ 1000 nM: *; 100 nM < IC$_{50}$ ≤ 2000 nM: ****.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:
1. A compound of Formula (I):

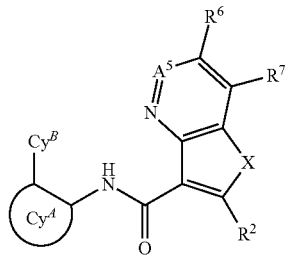

(I)

or a pharmaceutically acceptable salt thereof, wherein:
X is S or O;
$A^5$ is C—$R^5$;
$Cy^A$ is a pyridinyl ring, wherein the pyridinyl ring is unsubstituted or substituted with 1, 2, or 3 $R^A$;
each $R^A$ is independently selected from $R^{A1}$, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$;
each $R^{A1}$ is independently selected from $C_{1-6}$ alkyl, $C_{2-6}$ alkenyl and $C_{2-6}$ alkynyl, wherein each $C_{1-6}$ alkyl, $C_{2-6}$ alkenyl and $C_{2-6}$ alkynyl forming $R^{A1}$ is unsubstituted or substituted with 1, 2, 3, 4 or 5 substituents independently selected from halogen, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$;

$Cy^B$ is a 3-aminopiperidin-1-yl, wherein said piperidinyl is optionally substituted with 1, 2, 3, or 4 $R^B$;
each $R^B$ is independently selected from $R^{B1}$, $R^{B2}$, halogen, $C_{1-6}$ haloalkyl, CN, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $NR^{c2}R^{d2}$, $NR^{c2}C(=O)R^{b2}$, $NR^{c2}C(=O)NR^{c2}R^{d2}$, $NR^{c2}C(=O)OR^{a2}$, $C(=NR^{e2})NR^{c2}R^{d2}$, $NR^{c2}C(=NR^{e2})NR^{c2}R^{d2}$, $S(=O)NR^{c2}R^{d2}$, $S(=O)_2R^{b2}$, $NR^{c2}S(=O)_2R^{b2}$ and $S(=O)NR^{c2}R^{d2}$;
each $R^{B1}$ is independently selected from $C_{1-6}$ alkyl, $C_{2-6}$ alkenyl and $C_{2-6}$ alkynyl, wherein each of said $C_{1-6}$ alkyl, $C_{2-6}$ alkenyl and $C_{2-6}$ alkynyl of $R^{B1}$ is unsubstituted or substituted with 1, 2, 3, 4 or 5 $R^{B3}$;
each $R^{B2}$ is independently selected from $C_{6-10}$ aryl, $C_{3-7}$ cycloalkyl, 5-10 membered heteroaryl and 4-10 membered heterocycloalkyl, wherein each of said $C_{6-10}$ aryl, $C_{3-7}$ cycloalkyl, 5-10 membered heteroaryl and 4-10 membered heterocycloalkyl forming $R^{B2}$ is unsubstituted or substituted with 1, 2, 3, 4 or 5 $R^{B4}$;
each $R^{B3}$ is independently selected from $R^{B2}$, halogen, $C_{1-6}$ haloalkyl, CN, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $NR^{c2}R^{d2}$, $NR^{c2}C(=O)R^{b2}$, $NR^{c2}C(=O)NR^{c2}R^{d2}$, $NR^{c2}C(=O)OR^{a2}$, $C(=NR^{e2})NR^{c2}R^{d2}$, $NR^{c2}C(=NR^{e2})NR^{c2}R^{d2}$, $S(=O)R^{b2}$, $S(=O)NR^{c2}R^{d2}$, $S(=O)_2R^{b2}$, $NR^{c2}S(=O)_2R^{b2}$ and $S(=O)_2NR^{c2}R^{d2}$;
each $R^{B4}$ is independently selected from halogen, $C_{1-6}$ haloalkyl, CN, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $NR^{c2}R^{d2}$, $NR^{c2}C(=O)R^{b2}$, $NR^{c2}C(=O)NR^{c2}R^{d2}$, $NR^{c2}C(=O)OR^{a2}$, $C(=NR^{e2})NR^{c2}R^{d2}$, $NR^{c2}C(=NR^{e2})NR^{c2}R^{d2}$, $S(=O)R^{b2}$, $S(=O)NR^{c2}R^{d2}$, $S(=O)_2R^{b2}$, $NR^{c2}S(=O)_2R^{b2}$ and $S(=O)_2NR^{c2}R^{d2}$;
$R^2$ is H, halogen or $NH_2$;
$R^5$ is H, halogen, $R^{5A}$, $C_{1-6}$ haloalkyl, CN, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $C(=NR^{e3})NR^{c3}R^{d3}$, $NR^{c3}C(=NR^{e3})NR^{c3}R^{d3}$, $S(=O)R^{b3}$, $S(=O)NR^{c3}R^{d3}$, $S(=O)_2R^{b3}$, $NR^{c3}S(=O)_2R^{b3}$ or $S(=O)_2NR^{c3}R^{d3}$;
$R^{5A}$ is $C_{1-6}$ alkyl, $C_{2-6}$ alkenyl, $C_{2-6}$ alkynyl, $C_{3-7}$ cycloalkyl or phenyl, wherein each of said $C_{1-6}$ alkyl, $C_{2-6}$ alkenyl, $C_{2-6}$ alkynyl, $C_{3-7}$ cycloalkyl or phenyl forming $R^{5A}$ is unsubstituted or substituted with 1, 2, 3, 4 or 5 substituents independently selected from halogen, CN, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $C(=NR^{e3})NR^{c3}R^{d3}$, $NR^{c3}C(=NR^{e3})NR^{c3}R^{d3}$, $S(=O)R^{b3}$, $S(=O)NR^{c3}R^{d3}$, $S(=O)_2R^{b3}$, $NR^{c3}S(=O)_2R^{b3}$ and $S(=O)_2NR^{c3}R^{d3}$;
$R^6$ is H, halogen, $R^{6A}$, $C_{1-6}$ haloalkyl, CN, $OR^{a4}$, $SR^{a4}$, $C(=O)R^{b4}$, $C(=O)NR^{c4}R^{d4}$, $C(=O)OR^{a4}$, OC(=O)R$^{b4}$, OC(=O)NR$^{c4}$R$^{d4}$, NR$^{c4}$R$^{d4}$, NR$^{c4}$C(=O)R$^{b4}$, NR$^{c4}$C(=O)NR$^{c4}$R$^{d4}$, NR$^{c4}$C(=O)OR$^{a4}$, C(=NR$^{e4}$)NR$^{c4}$R$^{d4}$, NR$^{c4}$C(=NR$^{e4}$)NR$^{c4}$R$^{d4}$, S(=O)R$^{b4}$, S(=O)NR$^{c4}$R$^{d4}$, S(=O)$_2$R$^{b4}$, NR$^{c4}$S(=O)$_2$R$^{b4}$ or S(=O)$_2$NR$^{c4}$R$^{d4}$;

R$^{6A}$ is C$_{1-6}$ alkyl, C$_{2-6}$ alkenyl, C$_{2-6}$ alkynyl, C$_{3-7}$ cycloalkyl, C$_{6-10}$ aryl, 5-10 membered heteroaryl, 4-10 membered heterocycloalkyl, C$_{3-7}$ cycloalkyl-C$_{1-4}$ alkyl-, C$_{6-10}$ aryl-C$_{1-4}$ alkyl-, 5-10 membered heteroaryl-C$_{1-4}$ alkyl- or 4-10 membered heterocycloalkyl-C$_{1-4}$ alkyl-, wherein each of said C$_{1-6}$ alkyl, C$_{2-6}$ alkenyl, C$_{2-6}$ alkynyl, C$_{3-7}$ cycloalkyl, C$_{6-10}$ aryl, 5-10 membered heteroaryl, 4-10 membered heterocycloalkyl, C$_{3-7}$ cycloalkyl-C$_{1-4}$ alkyl-, C$_{6-10}$ aryl-C$_{1-4}$ alkyl-, 5-10 membered heteroaryl-C$_{1-4}$ alkyl- or 4-10 membered heterocycloalkyl-C$_{1-4}$ alkyl- forming R$^{6A}$ is unsubstituted or substituted with 1, 2, 3, 4 or 5 substituents independently selected from C$_{1-6}$ alkyl, halogen, C$_{1-6}$ haloalkyl, CN, OR$^{a4}$, SR$^{a4}$, C(=O)R$^{b4}$, C(=O)NR$^{c4}$R$^{d4}$, C(=O)OR$^{a4}$, OC(=O)R$^{b4}$, OC(=O)NR$^{c4}$R$^{d4}$, NR$^{c4}$R$^{d4}$, NR$^{c4}$C(=O)R$^{b4}$, NR$^{c4}$C(=O)NR$^{c4}$R$^{d4}$ NR$^{c4}$C(=O)OR$^{a4}$, C(=NR$^{e4}$)NR$^{c4}$R$^{d4}$, NR$^{c4}$C(=NR$^{e4}$)NR$^{c4}$R$^{d4}$S(=O)R$^{b4}$, S(=O)NR$^{c4}$R$^{d4}$, S(=O)$_2$R$^{b4}$, NR$^{c4}$S(=O)$_2$R$^{b4}$ and S(=O)$_2$NR$^{c4}$R$^{d4}$;

R$^7$ is H, halogen, R$^{7A}$, C$_{1-6}$ haloalkyl, CN, OR$^{a5}$, SR$^{a5}$, C(=O)R$^{b5}$, C(=O)NR$^{c5}$R$^{d5}$, C(=O)OR$^{a5}$, OC(=O)R$^{b5}$, OC(=O)NR$^{c5}$R$^{d5}$, NR$^{c5}$R$^{d5}$, NR$^{c5}$C(=O)R$^{b5}$, NR$^{c5}$C(=O)NR$^{c5}$R$^{d5}$, NR$^{c5}$C(=O)OR$^{a5}$, C(=NR$^{e5}$)NR$^{c5}$R$^{d5}$, NR$^{c5}$C(=NR$^{e5}$)NR$^{c5}$R$^{d5}$, S(=O)R$^{b5}$, S(=O)NR$^{c5}$R$^{d5}$, S(=O)$_2$R$^{b5}$, NR$^{c5}$S(=O)$_2$R$^{b5}$ or S(=O)$_2$NR$^{c5}$R$^{d5}$;

R$^{7A}$ is C$_{1-6}$ alkyl, C$_{2-6}$ alkenyl, C$_{2-6}$ alkynyl, C$_{3-7}$ cycloalkyl, C$_{6-10}$ aryl, 5-10 membered heteroaryl, 4-10 membered heterocycloalkyl, C$_{3-7}$ cycloalkyl-C$_{1-4}$ alkyl-, C$_{6-10}$ aryl-C$_{1-4}$ alkyl-, 5-10 membered heteroaryl-C$_{1-4}$ alkyl- or 4-10 membered heterocycloalkyl-C$_{1-4}$ alkyl-, wherein each of said C$_{1-6}$ alkyl, C$_{2-6}$ alkenyl, C$_{2-6}$ alkynyl, C$_{3-7}$ cycloalkyl, C$_{6-10}$ aryl, 5-10 membered heteroaryl, 4-10 membered heterocycloalkyl, C$_{3-7}$ cycloalkyl-C$_{1-4}$ alkyl-, C$_{6-10}$ aryl-C$_{1-4}$ alkyl-, 5-10 membered heteroaryl-C$_{1-4}$ alkyl- or 4-10 membered heterocycloalkyl-C$_{1-4}$ alkyl- forming R$^{7A}$ is unsubstituted or substituted with 1, 2, 3, 4 or 5 substituents independently selected from C$_{1-6}$ alkyl, halogen, C$_{1-6}$ haloalkyl, CN, OR$^{a5}$, SR$^{a5}$, C(=O)R$^{b5}$, (=O)NR$^{c5}$R$^{d5}$, C(=O)OR$^{a5}$, OC(=O)R$^{b5}$, OC(=O)NR$^{c5}$R$^{d5}$, NR$^{c5}$R$^{d5}$, NR$^{c5}$C(=O)R$^{b5}$, NR$^{c5}$C(=O)NR$^{c5}$R$^{d5}$, NR$^{c5}$C(=O)OR$^{a5}$, C(=NR$^{e5}$)NR$^{c5}$R$^{d5}$, NR$^{c5}$C(=NR$^{e5}$)NR$^{c5}$R$^{d5}$, S(=O)R$^{b5}$, S(=O)NR$^{c5}$R$^{d5}$, S(=O)$_2$R$^{b5}$, NR$^{c5}$S(=O)$_2$R$^{b5}$ and S(=O)$_2$NR$^{c5}$R$^{d5}$;

R$^{a1}$, R$^{b1}$, R$^{c1}$ and R$^{d1}$ are each independently selected from H, C$_{1-6}$ alkyl, C$_{2-6}$ alkenyl and C$_{2-6}$ alkynyl;

R$^{a2}$, R$^{b2}$, R$^{c2}$ and R$^{d2}$ are each independently selected from H, C$_{1-6}$ alkyl, C$_{2-6}$ alkenyl and C$_{2-6}$ alkynyl;

R$^{a3}$, R$^{b3}$, R$^{c3}$ and R$^{d3}$ are each independently selected from H, C$_{1-6}$ alkyl, C$_{2-6}$ alkenyl and C$_{2-6}$ alkynyl;

R$^{a4}$, R$^{b4}$, R$^{c4}$ and R$^{d4}$ are each independently selected from H, C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl forming R$^{a4}$, R$^{b4}$, R$^{c4}$ and R$^{d4}$ are each unsubstituted or substituted with 1, 2, 3, 4 or 5 substituents independently selected from C$_{1-6}$ alkyl, halo, CN, OR$^{a6}$, SR$^{a6}$, C(=O)R$^{b6}$, C(=O)NR$^{c6}$R$^{d6}$, C(=O)OR$^{a6}$, OC(=O)R$^{b6}$, OC(=O)NR$^{c6}$R$^{d6}$, NR$^{c6}$R$^{d6}$, NR$^{c6}$C(=O)R$^{b6}$, NR$^{c6}$C(=O)NR$^{c6}$R$^{d6}$, NR$^{c6}$C(=O)OR$^{a6}$, C(=NR$^{e6}$)NR$^{c6}$R$^{d6}$, NR$^{c6}$C(=NR$^{e6}$)NR$^{c6}$R$^{d6}$, S(=O)R$^{b6}$, S(=O)NR$^{c6}$R$^{d6}$, S(=O)$_2$R$^{b6}$, NR$^{c6}$S(=O)$_2$R$^{b6}$ and S(=O)$_2$NR$^{c6}$R$^{d6}$;

or R$^{c4}$ and R$^{d4}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from C$_{1-6}$ alkyl, halo, CN, OR$^{a6}$, SR$^{a6}$, C(=O)R$^{b6}$, C(=O)NR$^{c6}$R$^{d6}$, C(=O)OR$^{a6}$, OC(=O)R$^{b6}$, OC(=O)NR$^{c6}$R$^{d6}$, NR$^{c6}$R$^{d6}$, NR$^{c6}$C(=O)R$^{b6}$, NR$^{c6}$C(=O)NR$^{c6}$R$^{d6}$, NR$^{c6}$C(=O)OR$^{a6}$, C(=NR$^{e6}$)NR$^{c6}$R$^{d6}$, NR$^{c6}$C(=NR$^{e6}$)NR$^{c6}$R$^{d6}$, S(=O)R$^{b6}$, S(=O)NR$^{c6}$R$^{d6}$, S(=O)$_2$R$^{b6}$, NR$^{c6}$S(=O)$_2$R$^{b6}$ and S(=O)$_2$NR$^{c6}$R$^{d6}$;

R$^{a5}$, R$^{b5}$, R$^{c5}$ and R$^{d5}$ are each independently selected from H, C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl forming R$^{a5}$, R$^{b5}$, R$^{c5}$ and R$^{d5}$ are each unsubstituted or substituted with 1, 2, 3, 4 or 5 substituents independently selected from C$_{1-6}$ alkyl, halo, CN, OR$^{a6}$, SR$^{a6}$, C(=O)R$^{b6}$, C(=O)NR$^{c6}$R$^{d6}$, C(=O)OR$^{a6}$, OC(=O)R$^{b6}$, OC(=O)NR$^{c6}$R$^{d6}$, NR$^{c6}$R$^{d6}$, NR$^{c6}$C(=O)R$^{b6}$, NR$^{c6}$C(=O)NR$^{c6}$R$^{d6}$, NR$^{c6}$C(=O)OR$^{a6}$, C(=NR$^{e6}$)NR$^{c6}$R$^{d6}$, NR$^{c6}$C(=NR$^{e6}$)NR$^{c6}$R$^{d6}$, S(=O)R$^{b6}$, S(=O)NR$^{c6}$R$^{d6}$, S(=O)$_2$R$^{b6}$, NR$^{c6}$S(=O)$_2$R$^{b6}$ and S(=O)$_2$NR$^{c6}$R$^{d6}$;

or R$^{c5}$ and R$^{d5}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from C$_{1-6}$ alkyl, halo, CN, OR$^{a6}$, SR$^{a6}$, C(=O)R$^{b6}$, C(=O)NR$^{c6}$R$^{d6}$, C(=O)OR$^{a6}$, OC(=O)R$^{b6}$, OC(=O)NR$^{c6}$R$^{d6}$, NR$^{c6}$R$_{d6}$, NR$^{c6}$C(=O)R$^{b6}$, NR$^{c6}$C(=O)NR$^{c6}$R$^{d6}$, NR$^{c6}$C(=O)OR$^{a6}$, C(=NR$^{e6}$)NR$^{c6}$R$^{d6}$, NR$^{c6}$C(=NR$^{e6}$)NR$^{c6}$R$^{d6}$, S(=O)R$^{b6}$, S(=O)NR$^{c6}$R$^{d6}$, S(=O)$_2$R$^{b6}$, NR$^{c6}$S(=O)$_2$R$^{b6}$ and S(=O)$_2$NR$^{c6}$R$^{d6}$;

R$^{a6}$, R$^{b6}$, R$^{c6}$ and R$^{d6}$ are each independently selected from H, C$_{1-6}$ alkyl, C$_{1-6}$ haloalkyl, C$_{2-6}$ alkenyl, C$_{2-6}$ alkynyl, C$_{6-10}$ aryl, 5-10 membered heteroaryl, C$_{3-7}$ cycloalkyl and 4-10 membered heterocycloalkyl, wherein said C$_{1-6}$ alkyl, C$_{2-6}$ alkenyl, C$_{2-6}$ alkynyl, C$_{6-10}$ aryl, 5-10 membered heteroaryl, C$_{3-7}$ cycloalkyl and 4-10 membered heterocycloalkyl forming R$^{a6}$, R$^{b6}$, R$^{c6}$ and R$^{d6}$ are each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy;

or $R^{c6}$ and $R^{d6}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy; and $R^{e1}$, $R^{e2}$, $R^{e3}$, $R^{e4}$, $R^{e5}$ and $R^{e6}$ are each, independently, H, $C_{1-4}$ alkyl, CN or $NO_2$.

2. The compound of claim 1, or a pharmaceutically acceptable salt thereof, wherein X is O.

3. The compound of claim 1, or a pharmaceutically acceptable salt thereof, wherein X is S.

4. The compound of claim 1, or a pharmaceutically acceptable salt thereof, wherein each $R^A$ is independently selected from $C_{1-6}$ alkyl, $C_{2-6}$ alkenyl $C_{2-6}$ alkynyl, halogen, $C_{1-6}$ haloalkyl, CN, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $C(=NR^{e1})NR^{c1}R^{d1}$, $NR^{c1}C(=NR^{e1})NR^{c1}R^{d1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$.

5. The compound of claim 4, or a pharmaceutically acceptable salt thereof, wherein each $R^A$ is $C_{1-6}$ alkyl.

6. The compound of claim 1, or a pharmaceutically acceptable salt thereof, wherein $Cy^A$ is pyridin-3-yl or 5-methylpyridin-3-yl.

7. The compound of claim 1, wherein each $R^B$ is independently selected from halogen, $C_{1-6}$ alkyl, $C_{1-6}$ haloalkyl, $C_{3-7}$ cycloalkyl, CN, $OR^{a2}$ and $NR^{c2}R^{d2}$.

8. The compound of claim 7, or a pharmaceutically acceptable salt thereof, wherein each $R^B$ is independently selected from methyl, ethyl, cyclopropyl, $CF_3$, OH and $NH_2$.

9. The compound of claim 1, or a pharmaceutically acceptable salt thereof, wherein $Cy^B$ is a piperidinyl group of the following Formula (B-1):

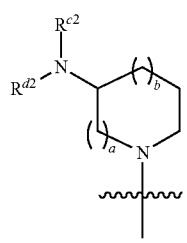

(B-1)

wherein:
$R^{c2}$ is H;
$R^{d2}$ is H;
a is 1;
b is 1; and
wherein the piperidinyl group of Formula (B-1) is further substituted by 0, 1, 2, or 3 $R^B$, wherein $R^B$ is independently, at each occurrence, selected from F, Cl, methyl, ethyl, cyclopropyl, $CF_3$, CN, OH, and methoxy.

10. The compound of claim 1, or a pharmaceutically acceptable salt thereof, wherein $Cy^B$ is a group of Formula $Cy^B$-1:

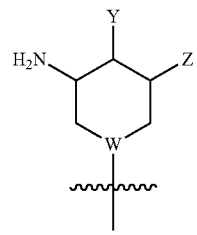

($Cy^B$-1)

wherein:
W is N;
Y is H or OH; and
Z is H, $C_{1-6}$ alkyl, $C_{1-3}$ haloalkyl, or $C_{3-7}$ cycloalkyl.

11. The compound of claim 1, or a pharmaceutically acceptable salt thereof, wherein $Cy^B$ is a group of Formula $Cy^B$-2:

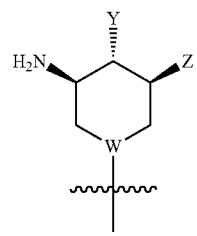

($Cy^B$-2)

wherein:
W is N;
Y is H or OH; and
Z is H, $C_{1-6}$ alkyl, $C_{1-3}$ haloalkyl, or $C_{3-7}$ cycloalkyl.

12. The compound of claim 1, or a pharmaceutically acceptable salt thereof, wherein $Cy^B$ is a group selected from groups of the following Formulae (B-2) to (B-8):

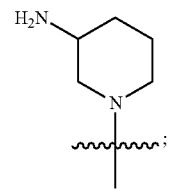

(B-2)

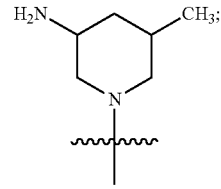

(B-3)

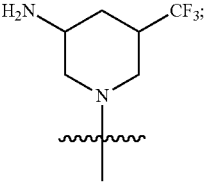

(B-4)

-continued (B-5)
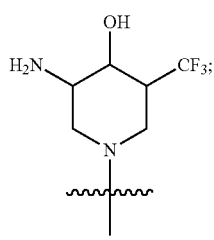

(B-6)
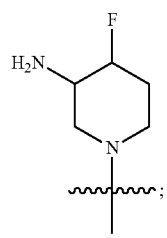

(B-7)
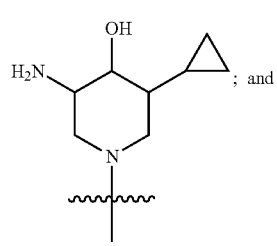; and

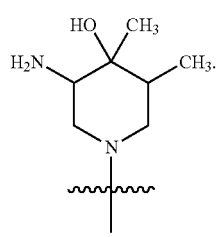

-continued (B-4a)
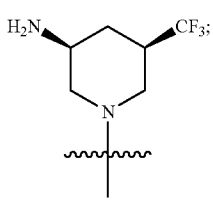

(B-5a)
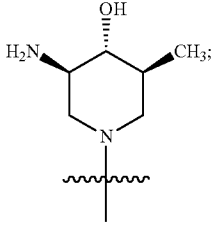

(B-6a)
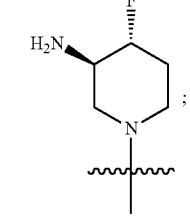

(B-7a)
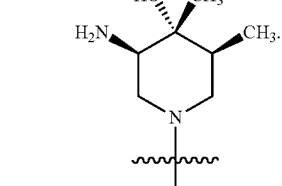; and (B-8a)
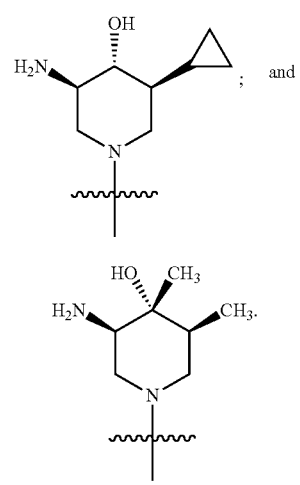

13. The compound of claim 1, or a pharmaceutically acceptable salt thereof, wherein $Cy^B$ is a group selected from groups of the following Formulae (B-2a) to (B-8a):

(B-2a)
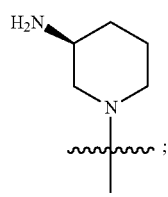

(B-3a)
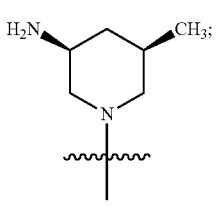

14. The compound of claim 13, or a pharmaceutically acceptable salt thereof, wherein $Cy^B$ is a group of Formula (B-8a):

(B-8a)
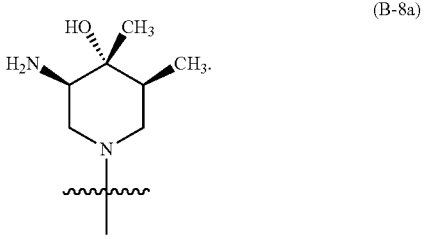 [SMILES: *N1C[C@@H](N)[C@](C)(O)[C@@H](C)C1]

15. The compound of claim 13, or a pharmaceutically acceptable salt thereof, wherein $Cy^B$ is a group of Formula (B-7a):

(B-7a)

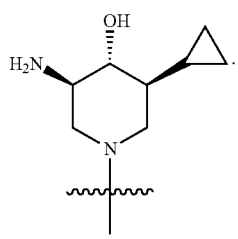

16. The compound of claim 13, or a pharmaceutically acceptable salt thereof, wherein $Cy^B$ is a group of Formula (B-5a):

(B-5a)

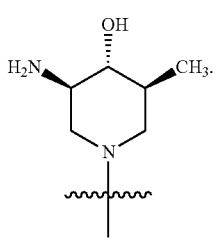

17. The compound of claim 13, or a pharmaceutically acceptable salt thereof, wherein $Cy^B$ is a group of Formula (B-4a):

(B-4a)

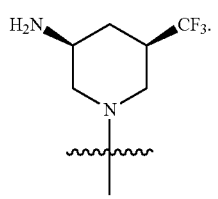

18. The compound of claim 13, or a pharmaceutically acceptable salt thereof, wherein $Cy^B$ is a group of Formula (B-3a):

(B-3a)

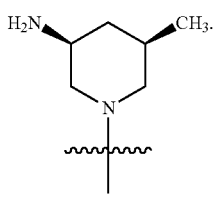

19. The compound of claim 1, or a pharmaceutically acceptable salt thereof, wherein $Cy^B$ is a group selected from groups of the following Formulae (B-101) to (B-107) and (B-115) to (B-121):

(B-101)

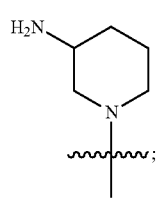

(B-102)

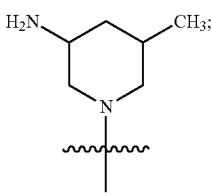

(B-103)

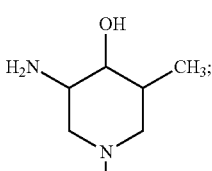

(B-104)

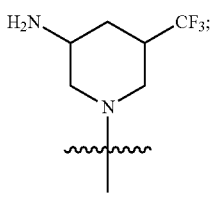

(B-105)

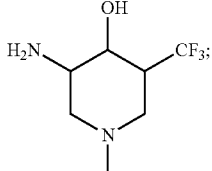

(B-106)

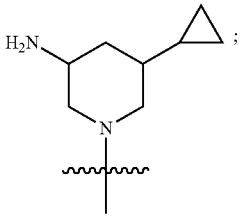

(B-107)

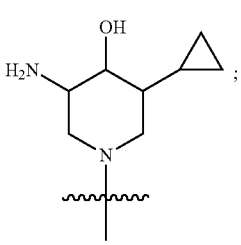

(B-115)

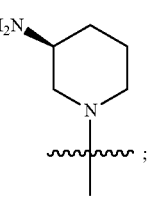

-continued
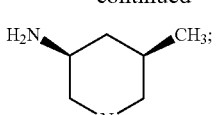 (B-116)
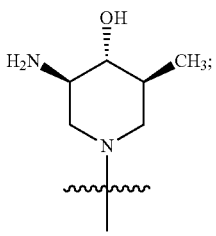 (B-117)
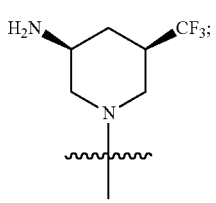 (B-118)
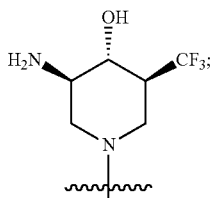 (B-119)
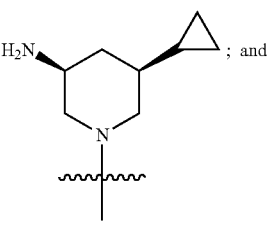 (B-120)
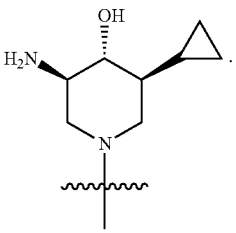 (B-121)
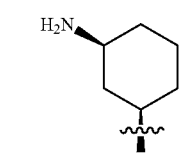 (B-125)
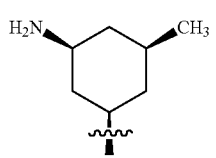 (B-126)
-continued
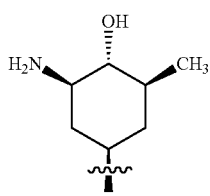 (B-127)
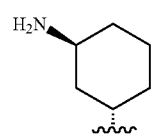 (B-128)
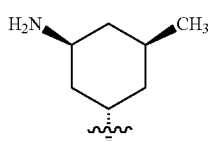 (B-129)
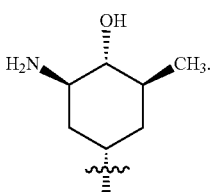 (B-130)
20. The compound of claim 1, or a pharmaceutically acceptable salt thereof, wherein the group:
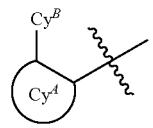
is selected from groups of Formulae (Cy-1) to (Cy-12):
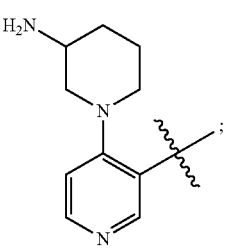 (Cy-1)
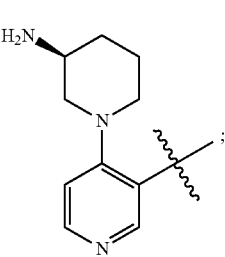 (Cy-2)

-continued

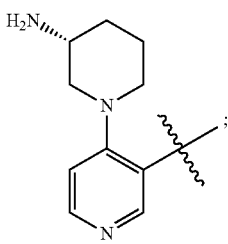 (Cy-3)

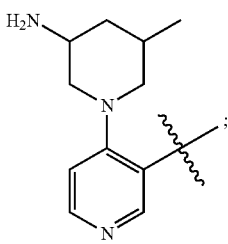 (Cy-4)

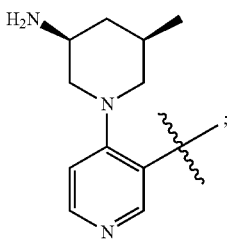 (Cy-5)

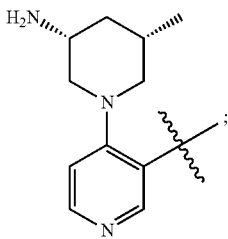 (Cy-6)

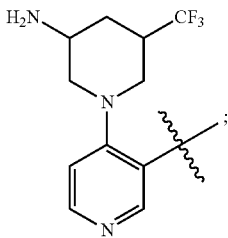 (Cy-7)

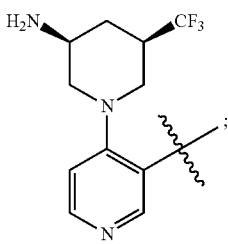 (Cy-8)

-continued

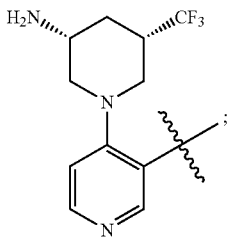 (Cy-9)

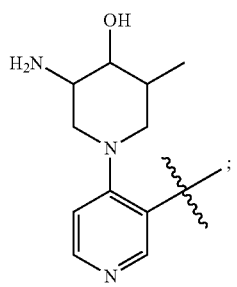 (Cy-10)

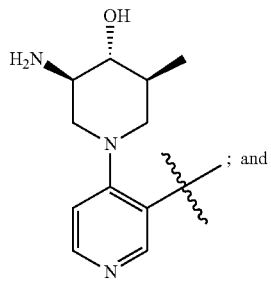 (Cy-11)

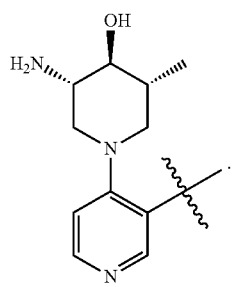 (Cy-12)

21. The compound of claim 1, or a pharmaceutically acceptable salt thereof, wherein $R^2$ is $NH_2$.

22. The compound of claim 1, or a pharmaceutically acceptable salt thereof, wherein $R^5$ is H, halogen, $R^{5A}$, CN or $OR^{a3}$.

23. The compound of claim 1, or a pharmaceutically acceptable salt thereof, wherein $R^5$ is $R^{5A}$ and $R^{5A}$ is $C_{1-6}$ alkyl, $C_{2-6}$ alkenyl, $C_{2-6}$ alkynyl, $C_{1-6}$ haloalkyl, $C_{3-7}$ cycloalkyl or phenyl, wherein each of said $C_{1-6}$ alkyl, $C_{2-6}$ alkenyl, $C_{2-6}$ alkynyl, $C_{3-7}$ cycloalkyl or phenyl forming $R^{5A}$ is unsubstituted or substituted with 1, 2 or 3 substituents independently selected from halogen, CN and $OR^{a3}$.

24. The compound of claim 1, or a pharmaceutically acceptable salt thereof, wherein $R^5$ is H, halogen, $C_{1-6}$ alkyl, $C_{2-6}$ alkenyl, $C_{2-6}$ alkynyl, $C_{1-6}$ haloalkyl, $C_{3-7}$ cycloalkyl, phenyl, $R^{5A}$, CN, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $C(=NR^{e3})NR^{c3}R^{d3}$, $NR^{c3}C(=NR^{e3})NR^{c3}R^{d3}$, $S(=O)R^{b3}$, $S(=O)NR^{c3}R^{d3}$, $S(=O)_2R^{b3}$, $NR^{c3}S(=O)_2R^{b3}$ or $S(=O)_2NR^{c3}R^{d3}$.

25. The compound of claim 1, or a pharmaceutically acceptable salt thereof, wherein $R^5$ is H, halogen or $C_{1-6}$ alkyl.

26. The compound of claim 1, or a pharmaceutically acceptable salt thereof, wherein $R^5$ is H.

27. The compound of claim 1, or a pharmaceutically acceptable salt thereof, wherein $R^6$ is H, halogen, $R^{6A}$, $C_{1-6}$ haloalkyl, CN or $OR^{a4}$.

28. The compound of claim 1, or a pharmaceutically acceptable salt thereof, wherein $R^6$ is H, halogen, $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkyl-, $C_{6-10}$ aryl-$C_{1-4}$ alkyl-, 5-10 membered heteroaryl-$C_{1-4}$ alkyl-, 4-10 membered heterocycloalkyl-$C_{1-4}$ alkyl-, $C_{1-6}$ haloalkyl, CN, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$, $NR^{c4}C(=O)R^{b4}$, $NR^{c4}C(=O)NR^{c4}R^{d4}$, $NR^{c4}C(=O)OR^{a4}$, $C(=NR^{e4})NR^{c4}R^{d4}$, $NR^{c4}C(=NR^{e4})NR^{c4}R^{d4}$, $S(=O)R^{b4}$, $S(=O)NR^{c4}R^{d4}$, $S(=O)_2R^{b4}$, $NR^{c4}S(=O)_2R^{b4}$ or $S(=O)_2NR^{c4}R^{d4}$.

29. The compound of claim 1, or a pharmaceutically acceptable salt thereof, wherein $R^6$ is H, halogen, $C_{1-6}$ alkyl, OH, $OC_{1-6}$ alkyl, $OC_{3-7}$ cycloalkyl, $C_{1-6}$ haloalkyl, $C_{6-10}$ aryl, 5-6-membered heteroaryl or 4-7 membered heterocycloalkyl.

30. The compound of claim 1, or a pharmaceutically acceptable salt thereof, wherein $R^6$ is H, F, Cl, Br, methyl, ethyl, propyl, isopropyl, $CF_3$, OH, OMe, OEt, On-Pr, Oi-Pr, Ocyclopropyl, phenyl, 2,6-difluorophenyl, 3,5-dimethylisoxazol-4-yl, 1,3-thiazol-2-yl, 1-methylazetidin-3-yl, 1-isopropylazetidin-3-yl, methoxymethyl or tetrahydro-2H-pyran-4-yl.

31. The compound of claim 1, or a pharmaceutically acceptable salt thereof, wherein $R^6$ is H.

32. The compound of claim 1, or a pharmaceutically acceptable salt thereof, wherein $R^6$ is $R^{6A}$ and $R^{6A}$ is $C_{1-6}$ alkyl, $C_{2-6}$ alkenyl, $C_{2-6}$ alkynyl, $C_{3-7}$ cycloalkyl, phenyl, 5-6 membered heteroaryl or 4-7 membered heterocycloalkyl, wherein each of said $C_{1-6}$ alkyl, $C_{2-6}$ alkenyl, $C_{2-6}$ alkynyl, $C_{3-7}$ cycloalkyl, phenyl, 5-6 membered heteroaryl or 4-7 membered heterocycloalkyl forming $R^{6A}$ is unsubstituted or substituted with 1, 2, 3, 4 or 5 substituents independently selected from $C_{1-6}$ alkyl, halogen, CN and $OR^{a4}$.

33. The compound of claim 32, or a pharmaceutically acceptable salt thereof, wherein $R^6$ is $R^{6A}$ and $R^{6A}$ is unsubstituted phenyl or phenyl substituted with 1, 2, 3, 4 or 5 substituents independently selected from $C_{1-6}$ alkyl, halogen, CN and $OR^{a4}$.

34. The compound of claim 32, or a pharmaceutically acceptable salt thereof, wherein $R^6$ is $R^{6A}$ and $R^{6A}$ is unsubstituted phenyl or phenyl 2,6-disubstituted with substituents independently selected from $C_{1-6}$ alkyl, halogen, CN and $OR^{a4}$.

35. The compound of claim 1, or a pharmaceutically acceptable salt thereof, wherein $R^7$ is H, halogen, $R^{7A}$, $C_{1-6}$ haloalkyl, CN, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)NR^{c5}R^{d5}$, $NR^{c5}C(=O)OR^{a5}$, $C(=NR^{e5})NR^{c5}R^{d5}$, $NR^{c5}C(=NR^{e5})NR^{c5}R^{d5}$, $S(=O)R^{b5}$, $S(=O)NR^{c5}R^{d5}$, $S(=O)_2R^{b5}$, $NR^{c5}S(=O)_2R^{b5}$ or $S(=O)_2NR^{c5}R^{d5}$.

36. The compound of claim 1, or a pharmaceutically acceptable salt thereof, wherein $R^7$ is H, halogen, $R^{7A}$, $C_{1-6}$ haloalkyl, CN or $OR^{a5}$.

37. The compound of claim 1, or a pharmaceutically acceptable salt thereof, wherein $R^7$ is $R^{7A}$ and $R^{7A}$ is $C_{1-6}$ alkyl, $C_{2-6}$ alkenyl, $C_{2-6}$ alkynyl, $C_{3-7}$ cycloalkyl or phenyl, wherein each $C_{1-6}$ alkyl, $C_{2-6}$ alkenyl, $C_{2-6}$ alkynyl, $C_{3-7}$ cycloalkyl and phenyl forming $R^{7A}$ is unsubstituted or substituted with 1, 2, 3, 4 or 5 substituents independently selected from $C_{1-6}$ alkyl, halogen, $C_{1-6}$ haloalkyl, CN, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)NR^{c5}R^{d5}$, $NR^{c5}C(=O)OR^{a5}$, $C(=NR^{e5})NR^{c5}R^{d5}$, $NR^{c5}C(=NR^{e5})NR^{c5}R^{d5}$, $S(=O)R^{b5}$, $S(=O)NR^{c5}R^{d5}$, $S(=O)_2R^{b5}$, $NR^{c5}S(=O)_2R^{b5}$ and $S(=O)_2NR^{c5}R^{d5}$.

38. The compound of claim 1, or a pharmaceutically acceptable salt thereof, wherein $R^7$ is H, halogen, $C_{1-6}$ alkyl, $C_{1-6}$ haloalkyl, or $O(C_{1-6}$ alkyl).

39. The compound of claim 1, or a pharmaceutically acceptable salt thereof, wherein $R^7$ is H, Cl, methyl, ethyl, $CF_3$, OMe, OEt, On-Pr or Oi-Pr.

40. The compound of claim 1, or a pharmaceutically acceptable salt thereof, wherein $R^7$ is H.

41. The compound of claim 1 of Formula (I-A):

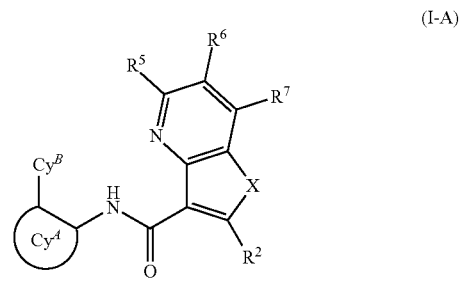

(I-A)

or a pharmaceutically acceptable salt thereof, wherein:

X is S or O;

$Cy^A$ is a pyridinyl ring, wherein the pyridinyl ring is unsubstituted or substituted with 1, 2, or 3 $R^A$;

each $R^A$ is independently selected from halogen, CN, OH, $C_{1-6}$ alkyl, $C_{1-6}$ haloalkyl and $C_{1-6}$ alkoxy;

$Cy^B$ is a 3-aminopiperidin-1-yl, wherein the piperidinyl ring is optionally substituted with 1, 2, 3, or 4 $R^B$;

each $R^B$ is independently selected from halogen, $C_{1-6}$ alkyl, $C_{1-6}$ haloalkyl, $C_{3-7}$ cycloalkyl, CN, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $NR^{c2}R^{d2}$, $NR^{c2}C(=O)R^{b2}$, $NR^{c2}C(=O)NR^{c2}R^{d2}$, $NR^{c2}C(=O)OR^{a2}$, $C(=NR^{e2})NR^{c2}R^{d2}$, $NR^{c2}C(=NR^{e2})NR^{c2}R^{d2}$, $S(=O)R^{b2}$, $S(=O)NR^{c2}R^{d2}$, $S(=O)_2R^{b2}$, $NR^{c2}S(=O)_2R^{b2}$ and $S(=O)_2NR^{c2}R^{d2}$;

$R^2$ is H, halogen or $NH_2$;

$R^5$ is H, halogen, $R^{5A}$, $C_{1-6}$ haloalkyl, CN, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $C(=NR^{e3})NR^{c3}R^{d3}$, $NR^{c3}C(=NR^{e3})NR^{c3}R^{d3}$, $S(=O)R^{b3}$, $S(=O)NR^{c3}R^{d3}$, $S(=O)_2R^{b3}$, $NR^{c3}S(=O)_2R^{b3}$ or $S(=O)_2NR^{c3}R^{d3}$;

$R^{5A}$ is $C_{1-6}$ alkyl, $C_{2-6}$ alkenyl, $C_{2-6}$ alkynyl, $C_{3-7}$ cycloalkyl or phenyl wherein each of said $C_{1-6}$ alkyl, $C_{2-6}$ alkenyl, $C_{2-6}$ alkynyl, $C_{3-7}$ cycloalkyl or phenyl forming $R^{5A}$ is unsubstituted or substituted with 1, 2, 3, 4 or 5 substituents independently selected from halogen, CN, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)$ $NR^{c3}R^{d3}$, $N^{R3}C(=O)OR^{a3}$, $C(=NR^{e3})NR^{c3}R^{d3}$, NR$^{c3}$C(=NR$^{e3}$)NR$^{c3}$R$^{d3}$, S(=O)R$^{b3}$, S(=O)NR$^{c3}$R$^{d3}$, S(=O)$_2$R$^{b3}$, NR$^{c3}$S(=O)$_2$R$^{b3}$ and S(=O)$_2$NR$^{c3}$R$^{d3}$;

R$^6$ is H, halogen, R$^{6A}$, C$_{1-6}$ haloalkyl, CN, OR$^{a4}$, SR$^{a4}$, C(=O)R$^{b4}$, C(=O)NR$^{c4}$R$^{d4}$, C(=O)OR$^{a4}$, OC(=O)R$^{b4}$, OC(=O)NR$^{c4}$R$^{d4}$, NR$^{c4}$R$^{d4}$ NR$^{c4}$C(=O)R$^{b4}$, NR$^{c4}$C(=O)NR$^{c4}$R$^{d4}$, NR$^{c4}$C(=O)OR$^{a4}$, C(=NR$^{e4}$)NR$^{c4}$R$^{d4}$, NR$^{c4}$C(=NR$^{e4}$)NR$^{c4}$R$^{d4}$, S(=O)R$^{b4}$, S(=O)NR$^{c4}$R$^{d4}$, S(=O)$_2$R$^{b4}$, NR$^{c4}$S(=O)$_2$R$^{b4}$ or S(=O)$_2$NR$^{c4}$R$^{d4}$;

R$^{6A}$ is C$_{1-6}$ alkyl, C$_{2-6}$ alkenyl, C$_{2-6}$ alkynyl, C$_{3-7}$ cycloalkyl, C$_{6-10}$ aryl, 5-10 membered heteroaryl, 4-10 membered heterocycloalkyl, C$_{3-7}$ cycloalkyl-C$_{1-4}$ alkyl-, C$_{6-10}$ aryl-C$_{1-4}$ alkyl-, 5-10 membered heteroaryl-C$_{1-4}$ alkyl- or 4-10 membered heterocycloalkyl-C$_{1-4}$ alkyl- wherein each of said C$_{1-6}$ alkyl, C$_{2-6}$ alkenyl, C$_{2-6}$ alkynyl, C3-7 cycloalkyl, C$_{6-10}$ aryl, 5-10 membered heteroaryl, 4-10 membered heterocycloalkyl, C$_{3-7}$ cycloalkyl-C$_{1-4}$ alkyl-, C$_{6-10}$ aryl-C$_{1-4}$ alkyl-, 5-10 membered heteroaryl-C$_{1-4}$ alkyl- or 4-10 membered heterocycloalkyl-C$_{1-4}$ alkyl- forming R$^{6A}$ is unsubstituted or substituted with 1, 2, 3, 4 or 5 substituents independently selected from C$_{1-6}$ alkyl, halogen, C$_{1-6}$ haloalkyl, CN, OR$^{a4}$, SR$^{a4}$, C(=O)R$^{b4}$, C(=O)NR$^{c4}$R$^{d4}$, C(=O)OR$^{a4}$, OC(=O)R$^{b4}$, OC(=O)NR$^{c4}$R$^{d4}$, NR$^{c4}$R$^{d4}$, NR$^{c4}$C(=O)NR$^{b4}$, NR$^{c4}$C(=O)NR$^{c4}$R$^{d4}$, NR$^{c4}$C(=O)OR$^{a4}$, C(=NR$^{e4}$)NR$^{c4}$R$^{d4}$, NR$^{c4}$C(=NR$^{e4}$)NR$^{c4}$R$^{d4}$, S(=O)R$^{b4}$, S(=O)NR$^{c4}$R$^{d4}$, S(=O)$_2$R$^{b4}$, NR$^{c4}$S(=O)$_2$R$^{b4}$ and S(=O)$_2$NR$^{c4}$R$^{d4}$;

R$^7$ is H, halogen, R$^{7A}$, C$_{1-6}$ haloalkyl, CN, OR$^{a5}$, SR$^{a5}$, C(=O)R$^{b5}$, C(=O)NR$^{c5}$R$^{d5}$, C(=O)OR$^{a5}$, OC(=O)R$^{b5}$, OC(=O)NR$^{c5}$R$^{d5}$, NR$^{c5}$R$^{d5}$, NR$^{c5}$C(=O)R$^{b5}$, NR$^{c5}$C(=O)NR$^{c5}$R$^{d5}$, NR$^{c5}$C(=O)OR$^{a5}$, C(=NR$^{e5}$)NR$^{c5}$R$^{d5}$, NR$^{c5}$C(=NR$^{e5}$)N$^{c5}$R$^{d5}$, S(=O)R$^{b5}$, S(=O)NR$^{c5}$R$^{d5}$, S(=O)$_2$R$^{b5}$, NR$^{c5}$S(=O)$_2$R$^{b5}$ or S(=O)$_2$NR$^{c5}$R$^{d5}$;

R$^{7A}$ is C$_{1-6}$ alkyl, C$_{2-6}$ alkenyl, C$_{2-6}$ alkynyl, C$_{3-7}$ cycloalkyl, C$_{6-10}$ aryl, 5-10 membered heteroaryl, 4-10 membered heterocycloalkyl, C$_{3-7}$ cycloalkyl-C$_{1-4}$ alkyl-, C$_{6-10}$ aryl-C$_{1-4}$ alkyl-, 5-10 membered heteroaryl-C$_{1-4}$ alkyl- or 4-10 membered heterocycloalkyl-C$_{1-4}$ alkyl-, wherein each of said C$_{1-6}$ alkyl, C$_{2-6}$ alkenyl, C$_{2-6}$ alkynyl, C$_{3-7}$ cycloalkyl, C$_{6-10}$ aryl, 5-10 membered heteroaryl, 4-10 membered heterocycloalkyl, C$_{3-7}$ cycloalkyl-C$_{1-4}$ alkyl-, C$_{6-10}$ aryl-C$_{1-4}$ alkyl-, 5-10 membered heteroaryl-C$_{1-4}$ alkyl- and 4-10 membered heterocycloalkyl-C$_{1-4}$ alkyl- forming R$^{7A}$ is unsubstituted or substituted with 1, 2, 3, 4 or 5 substituents independently selected from C$_{1-6}$ alkyl, halogen, C$_{1-6}$ haloalkyl, CN, OR$^{a5}$, SR$^{a5}$, C(=O)R$^{b5}$, C(=O)NR$^{c5}$R$^{d5}$, C(=O)OR$^{a5}$, OC(=O)R$^{b5}$, OC(=O)NR$^{c5}$R$^{d5}$, NR$^{c5}$R$^{d5}$, NR$^{c5}$C(=O)R$^{b5}$, NR$^{c5}$C(=O)NR$^{c5}$R$^{d5}$, NR$^{c5}$C(=O)OR$^{a5}$, C(=NR$^{e5}$)NR$^{c5}$R$^{d5}$, NR$^{c5}$C(=NR$^{e5}$)NR$^{c5}$R$^{d5}$, S(=O)R$^{b5}$, S(=O)NR$^{c5}$R$^{d5}$, S(=O)$_2$R$^{b5}$, NR$^{c5}$S(=O)$_2$R$^{b5}$ and S(=O)$_2$NR$^{c5}$R$^{d5}$;

R$^{a1}$, R$^{b1}$, R$^{c1}$ and R$^{d1}$ are each independently selected from H, C$_{1-6}$ alkyl, C$_{2-6}$ alkenyl and C$_{2-6}$ alkynyl;

R$^{a2}$, R$^{b2}$, R$^{c2}$ and R$^{d2}$ are each independently selected from H, C$_{1-6}$ alkyl, C$_{2-6}$ alkenyl and C$_{2-6}$ alkynyl;

R$^{a3}$, R$^{b3}$, R$^{c3}$ and R$^{d3}$ are each independently selected from H, C$_{1-6}$ alkyl, C$_{2-6}$ alkenyl and C$_{2-6}$ alkynyl;

R$^{a4}$, R$^{b4}$, R$^{c4}$ and R$^{d4}$ are each independently selected from H, C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl forming R$^{a4}$, R$^{b4}$, R$^{c4}$ and R$^{d4}$ are each unsubstituted or substituted with 1, 2, 3, 4 or 5 substituents independently selected from C$_{1-6}$ alkyl, halo, CN, OR$^{a6}$, SR$^{a6}$, C(=O)R$^{b6}$, C(=O)NR$^{c6}$R$^{d6}$, C(=O)OR$^{a6}$, OC(=O)R$^{b6}$, OC(=O)NR$^{c6}$R$^{d6}$, NR$^{c6}$R$^{d6}$, NR$^{c6}$C(=O)R$^{b6}$, NR$^{c6}$C(=O)NR$^{c6}$R$^{d6}$, NR$^{c6}$C(=O)OR$^{a6}$, C(=NR$^{e6}$)NR$^{c6}$R$^{d6}$, NR$^{c6}$C(=NR$^{e6}$)NR$^{c6}$R$^{d6}$, S(=O)R$^{b6}$, S(=O)NR$^{c6}$R$^{d6}$, S(=O)$_2$R$^{b6}$, NR$^{c6}$S(=O)$_2$R$^{b6}$ and S(=O)$_2$NR$^{c6}$R$^{d6}$;

or R$^{c4}$ and R$^{d4}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from C$_{1-6}$ alkyl, halo, CN, OR$^{a6}$, SR$^{a6}$, C(=O)R$^{b6}$, C(=O)NR$^{c6}$R$^{d6}$, C(=O)OR$^{a6}$, OC(=O)R$^{b6}$, OC(=O)NR$^{c6}$R$^{d6}$, NR$^{c6}$R$^{d6}$, NR$^{c6}$C(=O)R$^{b6}$, NR$^{c6}$C(=O)NR$^{c6}$R$^{d6}$, NR$^{c6}$C(=O)OR$^{a6}$, C(=NR$^{e6}$)NR$^{c6}$R$^{d6}$, NR$^{c6}$C(=NR$^{e6}$)NR$^{c6}$R$^{d6}$, S(=O)R$^{b6}$, S(=O)NR$^{c6}$R$^{d6}$, S(=O)$_2$R$^{b6}$, NR$^{c6}$S(=O)$_2$R$^{b6}$ and S(=O)$_2$NR$^{c6}$R$^{d6}$;

R$^{a5}$, R$^{b5}$, R$^{c5}$ and R$^{d5}$ are each independently selected from H, C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl forming R$^{a5}$, R$^{b5}$, R$^{c5}$ and R$^{d5}$ are each unsubstituted or substituted with 1, 2, 3, 4 or 5 substituents independently selected from C$_{1-6}$ alkyl, halo, CN, OR$^{a6}$, SR$^{a6}$, C(=O)R$^{b6}$, C(=O)NR$^{c6}$R$^{d6}$, C(=O)OR$^{a6}$, OC(=O)R$^{b6}$, OC(=O)NR$^{c6}$R$^{d6}$, NR$^{c6}$R$^{d6}$, NR$^{c6}$C(=O)R$^{b6}$, NR$^{c6}$C(=O)NR$^{c6}$R$^{d6}$, NR$^{c6}$C(=O)OR$^{a6}$, C(=NR$^{e6}$)NR$^{c6}$R$^{d6}$, NR$^{c6}$C(=NR$^{e6}$)NR$^{c6}$R$^{d6}$, S(=O)R$^{b6}$, S(=O)NR$^{c6}$R$^{d6}$, S(=O)$_2$R$^{b6}$, NR$^{c6}$S(=O)$_2$R$^{b6}$ and S(=O)$_2$NR$^{c6}$R$^{d6}$;

or R$^{c5}$ and R$^{d5}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from C$_{1-6}$ alkyl, halo, CN, OR$^{a6}$, SR$^{a6}$, C(=O)R$^{b6}$, C(=O)NR$^{c6}$R$^{d6}$, C(=O)OR$^{a6}$, OC(=O)R$^{b6}$, OC(=O)NR$^{c6}$R$^{d6}$, NR$^{c6}$R$^{d6}$, NR$^{c6}$C(=O)R$^{b6}$, NR$^{c6}$C(=O)NR$^{c6}$R$^{d6}$, NR$^{c6}$C(=O)OR$^{a6}$, C(=NR$^{e6}$)NR$^{c6}$R$^{d6}$, NR$^{c6}$C(=NR$^{e6}$)NR$^{c6}$R$^{d6}$, S(=O)R$^{b6}$, S(=O)NR$^{c6}$R$^{d6}$, S(=O)$_2$R$^{b6}$, NR$^{c6}$S(=O)$_2$R$^{b6}$ and S(=O)$_2$NR$^{c6}$R$^{d6}$;

R$^{a6}$, R$^{b6}$, R$^{c6}$ and R$^{d6}$ are each independently selected from H, C$_{1-6}$ alkyl, C$_{1-6}$ haloalkyl, C$_{2-6}$ alkenyl, C$_{2-6}$ alkynyl, aryl, C$_{6-10}$ aryl, 5-10 membered heteroaryl, $C_{3-7}$ cycloalkyl and 4-10 membered heterocycloalkyl, wherein said $C_{1-6}$ alkyl, $C_{2-6}$ alkenyl, C2-6 alkynyl $C_{6-10}$ aryl, 5-10 membered heteroaryl, $C_{3-7}$ cycloalkyl and 4-10 membered heterocycloalkyl forming $R^{a6}$, $R^{b6}$, $R^{c6}$ and $R^{d6}$ are each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy;

or $R^{c6}$ and $R^{d6}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy; and $R^{e1}$, $R^{e2}$, $R^{e3}$, $R^{e4}$, $R^{e5}$ and $R^{e6}$ are each, independently, H, $C_{1-4}$ alkyl, CN or NO$_2$.

42. The compound of claim 41 of Formula (I-A):

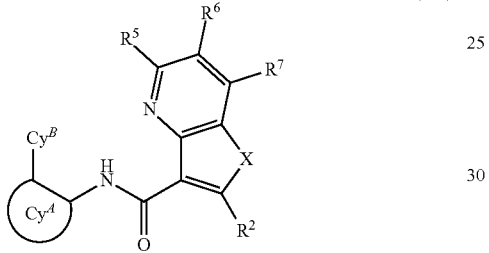

(I-A)

or a pharmaceutically acceptable salt thereof, wherein:
X is S or O;
Cy$^A$ is a pyridinyl ring, wherein the pyridinyl ring is unsubstituted or substituted with 1, 2, or 3 R$^A$;
each R$^A$ is independently selected from halogen, CN, OH, $C_{1-6}$ alkyl, $C_{1-6}$ haloalkyl and $C_{1-6}$ alkoxy;
Cy$^B$ is a 3-aminopiperidin-1-yl, wherein the piperidinyl ring is optionally substituted with 1, 2, 3, or 4 R$^B$;
each R$^B$ is independently selected from halogen, $C_{1-6}$ alkyl, $C_{1-6}$ haloalkyl, $C_{3-7}$ cycloalkyl, CN, OH, $C_{1-6}$ alkoxy and NH$_2$;
$R^2$ is H, halogen or NH$_2$;
$R^5$ is H, halogen, $R^{5A}$, $C_{1-6}$ haloalkyl, CN or OR$^{a3}$;
$R^{5A}$ is $C_{1-6}$ alkyl, $C_{2-6}$ alkenyl, $C_{2-6}$ alkynyl, $C_{3-7}$ cycloalkyl or phenyl wherein each of said $C_{1-6}$ alkyl, $C_{2-6}$ alkenyl, $C_{2-6}$ alkynyl, $C_{3-7}$ cycloalkyl or phenyl forming $R^{5A}$ is unsubstituted or substituted with 1, 2 or 3 substituents independently selected from halogen, CN and OR$^{a3}$;
$R^6$ is H, halogen, $R^{6A}$, $C_{1-6}$ haloalkyl, CN or OR$^{a4}$;
$R^{6A}$ is $C_{1-6}$ alkyl, $C_{2-6}$ alkenyl, $C_{2-6}$ alkynyl, $C_{3-7}$ cycloalkyl, phenyl, 5-6 membered heteroaryl or 4-7 membered heterocycloalkyl, wherein each of said $C_{1-6}$ alkyl, $C_{2-6}$ alkenyl, $C_{2-6}$ alkynyl, $C_{3-7}$ cycloalkyl, phenyl, 5-6 membered heteroaryl or 4-7 membered heterocycloalkyl forming $R^{6A}$ is unsubstituted or substituted with 1, 2, 3, 4 or 5 substituents independently selected from $C_{1-6}$ alkyl, halogen, CN and OR$^{a4}$;
$R^7$ is H, halogen, $R^{7A}$, $C_{1-6}$ haloalkyl, CN or OR$^{a5}$;
$R^{7A}$ is $C_{1-6}$ alkyl, $C_{2-6}$ alkenyl, $C_{2-6}$ alkynyl, $C_{3-7}$ cycloalkyl, phenyl, 5-6 membered heteroaryl or 4-7 membered heterocycloalkyl forming $R^{7A}$ is unsubstituted or substituted with 1, 2, 3, 4 or 5 substituents independently selected from H, $C_{1-6}$ alkyl, halogen, CN and OR$^{a5}$;
each R$^{a3}$ is independently selected from H, $C_{1-6}$ alkyl, $C_{2-6}$ alkenyl, $C_{2-6}$ alkynyl and $C_{3-7}$ cycloalkyl;
each R$^{a4}$ is independently selected from H, $C_{1-6}$ alkyl, $C_{1-6}$ haloalkyl, $C_{2-6}$ alkenyl and $C_{2-6}$ alkynyl; and
each R$^{a5}$ is independently selected from H, $C_{1-6}$ alkyl, $C_{1-6}$ haloalkyl, $C_{2-6}$ alkenyl and $C_{2-6}$ alkynyl.

43. The compound of claim 1 of Formula (II-5):

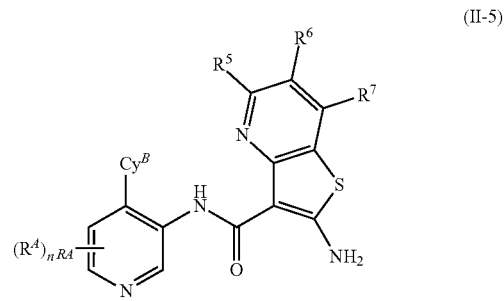

(II-5)

or a pharmaceutically acceptable salt thereof, wherein n$^{RA}$ is 0, 1, 2 or 3.

44. The compound of claim 1 of Formula (II-6):

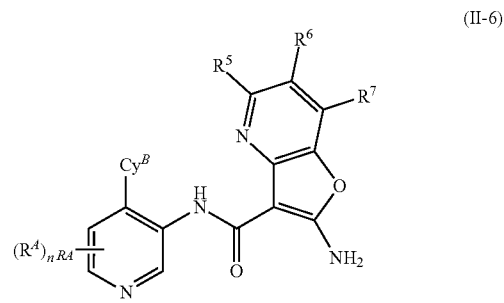

(II-6)

or a pharmaceutically acceptable salt thereof, wherein n$^{RA}$ is 0, 1, 2 or 3.

45. The compound of claim 1, or a pharmaceutically acceptable salt thereof, wherein each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a6}$, $R^{b6}$, $R^{c6}$ and $R^{d6}$ is independently selected from H and $C_{1-6}$ alkyl and each $R^{e1}$, $R^{e2}$, $R^{e3}$, $R^{e4}$, $R^{e5}$ and $R^{e6}$ is independently selected from H and $C_{1-6}$ alkyl.

46. The compound of claim 1 selected from the following compounds:
2-amino-N-{4-[3-aminopiperidin-1-yl]pyridin-3-yl}thieno[3,2-b]pyridine-3-carboxamide;
2-amino-N-{4-[(3S)-3-aminopiperidin-1-yl]pyridin-3-yl}thieno[3,2-b]pyridine-3-carboxamide;
2-amino-N-{4-[(3R)-3-aminopiperidin-1-yl]pyridin-3-yl}thieno[3,2-b]pyridine-3-carboxamide;
2-amino-N-{4-[3-aminopiperidin-1-yl]pyridin-3-yl}-6-methoxythieno[3,2-b]pyridine-3-carboxamide;
2-amino-N-{4-[(3S)-3-aminopiperidin-1-yl]pyridin-3-yl}-6-methoxythieno[3,2-b]pyridine-3-carboxamide;
2-amino-N-{4-[(3R)-3-aminopiperidin-1-yl]pyridin-3-yl}-6-methoxythieno[3,2-b]pyridine-3-carboxamide;
2-amino-N-{4-[3-aminopiperidin-1-yl]pyridin-3-yl}-6-cyclopropoxythieno[3,2-b]pyridine-3-carboxamide;

2-amino-N-{4-[(3S)-3-aminopiperidin-1-yl]pyridin-3-yl}-6-cyclopropoxythieno[3,2-b]pyridine-3-carboxamide;
2-amino-N-{4-[(3R)-3-aminopiperidin-1-yl]pyridin-3-yl}-6-cyclopropoxythieno[3,2-b]pyridine-3-carboxamide;
2-amino-N-{4-[(3-amino-5-methyl-piperidin-1-yl]pyridin-3-yl}-thieno[3,2-b]pyridine-3-carboxamide;
2-amino-N-{4-[(cis-3-amino-5-methyl-piperidin-1-yl]pyridin-3-yl}-thieno[3,2-b]pyridine-3-carboxamide;
2-amino-N-{4-[(3S,5R)-3-amino-5-methyl-piperidin-1-yl]pyridin-3-yl}-thieno[3,2-b]pyridine-3-carboxamide;
2-amino-N-{4-[(3-aminopiperidin-1-yl]pyridin-3-yl}-7-methoxythieno[3,2-b]pyridine-3-carboxamide;
2-amino-N-{4-[(3S)-3-aminopiperidin-1-yl]pyridin-3-yl}-7-methoxythieno[3,2-b]pyridine-3-carboxamide;
2-amino-N-{4-[(3R)-3-aminopiperidin-1-yl]pyridin-3-yl}-7-methoxythieno[3,2-b]pyridine-3-carboxamide;
2-amino-N-{4-[3-aminopiperidin-1-yl]pyridin-3-yl}-7-isopropoxythieno[3,2-b]pyridine-3-carboxamide;
2-amino-N-{4-[(3S)-3-aminopiperidin-1-yl]pyridin-3-yl}-7-isopropoxythieno[3,2-b]pyridine-3-carboxamide;
2-amino-N-{4-[(3R)-3-aminopiperidin-1-yl]pyridin-3-yl}-7-isopropoxythieno[3,2-b]pyridine-3-carboxamide;
2-amino-N-{4-[3-aminopiperidin-1-yl]pyridin-3-yl}-7-ethoxythieno[3,2-b]pyridine-3-carboxamide;
2-amino-N-{4-[(3S)-3-aminopiperidin-1-yl]pyridin-3-yl}-7-ethoxythieno[3,2-b]pyridine-3-carboxamide;
2-amino-N-{4-[(3R)-3-aminopiperidin-1-yl]pyridin-3-yl}-7-ethoxythieno[3,2-b]pyridine-3-carboxamide;
2-amino-N-{4-[3-aminopiperidin-1-yl]pyridin-3-yl}-6-ethylthieno[3,2-b]pyridine-3-carboxamide;
2-amino-N-{4-[(3S)-3-aminopiperidin-1-yl]pyridin-3-yl}-6-ethylthieno[3,2-b]pyridine-3-carboxamide;
2-amino-N-{4-[(3R)-3-aminopiperidin-1-yl]pyridin-3-yl}-6-ethylthieno[3,2-b]pyridine-3-carboxamide;
2-amino-N-{4-[3-aminopiperidin-1-yl]pyridin-3-yl}-6-phenylthieno[3,2-b]pyridine-3-carboxamide;
2-amino-N-{4-[3-aminopiperidin-1-yl]pyridin-3-yl}-6-phenylthieno[3,2-b]pyridine-3-carboxamide;
2-amino-N-{4-[(3S)-3-aminopiperidin-1-yl]pyridin-3-yl}-6-phenylthieno[3,2-b]pyridine-3-carboxamide;
2-amino-N-{4-[(3R)-3-aminopiperidin-1-yl]pyridin-3-yl}-6-phenylthieno[3,2-b]pyridine-3-carboxamide;
2-amino-N-{4-[3-aminopiperidin-1-yl]pyridin-3-yl}-6-(2,6-difluorophenyl)-thieno[3,2-b]pyridine-3-carboxamide;
2-amino-N-{4-[(3S)-3-aminopiperidin-1-yl]pyridin-3-yl}-6-(2,6-difluorophenyl)-thieno[3,2-b]pyridine-3-carboxamide;
2-amino-N-{4-[(3R)-3-aminopiperidin-1-yl]pyridin-3-yl}-6-(2,6-difluorophenyl)-thieno[3,2-b]pyridine-3-carboxamide;
2-amino-N-{4-[3-aminopiperidin-1-yl]pyridin-3-yl}-6-(3,5-dimethylisoxazol-4-yl)-thieno[3,2-b]pyridine-3-carboxamide;
2-amino-N-{4-[(3S)-3-aminopiperidin-1-yl]pyridin-3-yl}-6-(3, 5-dimethylisoxazol-4-yl)-thieno[3,2-b]pyridine-3-carboxamide;
2-amino-N-{4-[(3R)-3-aminopiperidin-1-yl]pyridin-3-yl}-6-(3,5-dimethylisoxazol-4-yl)-thieno[3,2-b]pyridine-3-carboxamide;
2-amino-N-{4-[3-aminopiperidin-1-yl]pyridin-3-yl}-6-(1-methylazetidin-3-yl)thieno[3,2-b]pyridine-3-carboxamide;
2-amino-N-{4-[(3S)-3-aminopiperidin-1-yl]pyridin-3-yl}-6-(1-methylazetidin-3-yl)thieno[3,2-b]pyridine-3-carboxamide;
2-amino-N-{4-[(3R)-3-aminopiperidin-1-yl]pyridin-3-yl}-6-(1-methylazetidin-3-yl)thieno[3,2-b]pyridine-3-carboxamide;
2-amino-N-{4-[(3-aminopiperidin-1-yl]pyridin-3-yl}-6-(1 isopropylazetidin-3-yl)thieno[3,2-b]pyridine-3-carboxamide;
2-amino-N-{4-[(3S)-3-aminopiperidin-1-yl]pyridin-3-yl}-6-(4-isopropylazetidin-3-yl)thieno[3,2-b]pyridine-3-carboxamide;
2-amino-N-{4-[(3R)-3-aminopiperidin-1-yl]pyridin-3-yl}-6-(1-isopropylazetidin-3-yl)thieno[3,2-b]pyridine-3-carboxamide;
2-amino-N-{4-[(3-aminopiperidin-1-yl]pyridin-3-yl}-6-(methoxymethyl)thieno[3,2-b]pyridine-3-carboxamide;
2-amino-N-{4-[(3S)-3-aminopiperidin-1-yl]pyridin-3-yl}-6-(methoxymethyl)thieno[3,2-b]pyridine-3-carboxamide;
2-amino-N-{4-[(3R)-3-aminopiperidin-1-yl]pyridin-3-yl}-6-(methoxymethyl)thieno[3,2-b]pyridine-3-carboxamide;
2-amino-N-{4-[3-aminopiperidin-1-yl]pyridin-3-yl}-6-(tetrahydro-2H-pyran-4-yl)thieno[3,2-b]pyridine-3-carboxamide;
2-amino-N-{4-[(3S)-3-aminopiperidin-1-yl]pyridin-3-yl}-6-(tetrahydro-2H-pyran-4-yl)thieno[3,2-b]pyridine-3-carboxamide;
2-amino-N-{4-[(3R)-3-aminopiperidin-1-yl]pyridin-3-yl}-6-(tetrahydro-2H-pyran-4-yl)thieno[3,2-b]pyridine-3-carboxamide;
2-amino-N-{4-[3-aminopiperidin-1-yl]pyridin-3-yl}-6-fluoro-thieno[3,2-b]pyridine-3-carboxamide;
2-amino-N-{4-[(3S)-3-aminopiperidin-1-yl]pyridin-3-yl}-6-fluoro-thieno[3,2-b]pyridine-3-carboxamide;
2-amino-N-{4-[(3R)-3-aminopiperidin-1-yl]pyridin-3-yl}-6-fluoro-thieno[3,2-b]pyridine-3-carboxamide;
2-amino-N-{4-[3-aminopiperidin-1-yl]pyridin-3-yl}-7-trifluoromethyl-thieno[3,2-b]pyridine-3-carboxamide;
2-amino-N-{4-[(3S)-3-aminopiperidin-1-yl]pyridin-3-yl}-7-trifluoromethyl-thieno[3,2-b]pyridine-3-carboxamide;
2-amino-N-{4-[(3R)-3-aminopiperidin-1-yl]pyridin-3-yl}-7-trifluoromethyl-thieno[3,2-b]pyridine-3-carboxamide;
2-amino-N-[4-(3-aminopiperidin-1-yl)pyridin-3-yl]-5-chlorothieno[3,2-b]pyridine-3-carboxamide;
2-amino-N-[4-((3S)-3-aminopiperidin-1-yl)pyridin-3-yl]-5-chlorothieno[3,2-b]pyridine-3-carboxamide;
2-amino-N-[4-((3R)-3-aminopiperidin-1-yl)pyridin-3-yl]-5-chlorothieno[3,2-b]pyridine-3-carboxamide;
2-amino-N-[4-(3-aminopiperidin-1-yl)pyridin-3-yl]-5-methylthieno[3,2-b]pyridine-3-carboxamide;
2-amino-N-[4-((3S)-3-aminopiperidin-1-yl)pyridin-3-yl]-5-methylthieno[3,2-b]pyridine-3-carboxamide;
2-amino-N-[4-((3R)-3-aminopiperidin-1-yl)pyridin-3-yl]-5-methylthieno[3,2-b]pyridine-3-carboxamide;
2-amino-N-{4-[3-aminopiperidin-1-yl]pyridin-3-yl}furo[3,2-b]pyridine-3-carboxamide;
2-amino-N-{4-[(3S)-3-aminopiperidin-1-yl]pyridin-3-yl}furo[3,2-b]pyridine-3-carboxamide;
2-amino-N-{4-[(3R)-3-aminopiperidin-1-yl]pyridin-3-yl}furo[3,2-b]pyridine-3-carboxamide;
2-amino-N-{4-[(3-aminopiperidin-1-yl]pyridin-3-yl}-6-ethylfuro[3,2-b]pyridine-3-carboxamide;

2-amino-N-{4-[(3S)-3-aminopiperidin-1-yl]pyridin-3-yl}-6-ethylfuro[3,2-b]pyridine-3-carboxamide;
2-amino-N-{4-[(3R)-3-aminopiperidin-1-yl]pyridin-3-yl}-6-ethylfuro[3,2-b]pyridine-3-carboxamide;
2-amino-N-{4-[3-aminopiperidin-1-yl]pyridin-3-yl}-6-(trifluoromethyl)furo[3,2-b]pyridine-3-carboxamide;
2-amino-N-{4-[(3S)-3-aminopiperidin-1-yl]pyridin-3-yl}-6-(trifluoromethyl)furo[3,2-b]pyridine-3-carboxamide;
2-amino-N-{4-[(3R)-3-aminopiperidin-1-yl]pyridin-3-yl}-6-(trifluoromethyl)furo[3,2-b]pyridine-3-carboxamide;
2-amino-N-{4-[(3-aminopiperidin-1-yl]pyridin-3-yl}-6-methyl-furo[3,2-b]pyridine-3-carboxamide;
2-amino-N-{4-[(3S)-3-aminopiperidin-1-yl]pyridin-3-yl}-6-methyl-furo[3,2-b]pyridine-3-carboxamide;
2-amino-N-{4-[(3R)-3-aminopiperidin-1-yl]pyridin-3-yl}-6-methyl-furo[3,2-b]pyridine-3-carboxamide;
2-amino-N-{4-[3-aminopiperidin-1-yl]pyridin-3-yl}-6-(iso-propyl)furo[3,2-b]pyridine-3-carboxamide;
2-amino-N-{4-[(3S)-3-aminopiperidin-1-yl]pyridin-3-yl}-6-(iso-propyl)furo[3,2-b]pyridine-3-carboxamide;
2-amino-N-{4-[(3R)-3-aminopiperidin-1-yl]pyridin-3-yl}-6-(iso-propyl)furo[3,2-b]pyridine-3-carboxamide;
2-amino-N-{4-[3-aminopiperidin-1-yl]pyridin-3-yl}-6-(propyl)furo[3,2-b]pyridine-3-carboxamide;
2-amino-N-{4-[(3S)-3-aminopiperidin-1-yl]pyridin-3-yl}-6-(propyl)furo[3,2-b]pyridine-3-carboxamide;
2-amino-N-{4-[(3R)-3-aminopiperidin-1-yl]pyridin-3-yl}-6-(propyl)furo[3,2-b]pyridine-3-carboxamide;
2-amino-N-{4-[3-aminopiperidin-1-yl]pyridin-3-yl}-6-fluoro-furo[3,2-b]pyridine-3-carboxamide;
2-amino-N-{4-[(3S)-3-aminopiperidin-1-yl]pyridin-3-yl}-6-fluoro-furo[3,2-b]pyridine-3-carboxamide;
2-amino-N-{4-[(3R)-3-aminopiperidin-1-yl]pyridin-3-yl}-6-fluoro-furo[3,2-b]pyridine-3-carboxamide;
2-amino-N-{4-[3-aminopiperidin-1-yl]pyridin-3-yl}-6-chloro-furo[3,2-b]pyridine-3-carboxamide;
2-amino-N-{4-[(3S)-3-aminopiperidin-1-yl]pyridin-3-yl}-6-chloro-furo[3,2-b]pyridine-3-carboxamide;
2-amino-N-{4-[(3R)-3-aminopiperidin-1-yl]pyridin-3-yl}-6-chloro-furo[3,2-b]pyridine-3-carboxamide;
2-amino-N-{4-[3-aminopiperidin-1-yl]pyridin-3-yl}-6-bromo-furo[3,2-b]pyridine-3-carboxamide;
2-amino-N-{4-[(3S)-3-aminopiperidin-1-yl]pyridin-3-yl}-6-bromo-furo[3,2-b]pyridine-3-carboxamide;
2-amino-N-{4-[(3R)-3-aminopiperidin-1-yl]pyridin-3-yl}-6-bromo-furo[3,2-b]pyridine-3-carboxamide;
2-amino-N-{4-[3-aminopiperidin-1-yl]pyridin-3-yl}-7-methyl-furo[3,2-b]pyridine-3-carboxamide;
2-amino-N-{4-[(3S)-3-aminopiperidin-1-yl]pyridin-3-yl}-7-methyl-furo[3,2-b]pyridine-3-carboxamide;
2-amino-N-{4-[(3R)-3-aminopiperidin-1-yl]pyridin-3-yl}-7-methyl-furo[3,2-b]pyridine-3-carboxamide;
2-amino-N-{4-[3-amino-5-(trifluoromethyl)piperidin-1-yl]pyridin-3-yl}-furo[3,2-b]pyridine-3-carboxamide;
2-amino-N-{4-[cis-3-amino-5-(trifluoromethyl)piperidin-1-yl]pyridin-3-yl}-furo[3,2-b]pyridine-3-carboxamide;
2-amino-N-{4-[(3S,5R)-3-amino-5-(trifluoromethyl)piperidin-1-yl]pyridin-3-yl}-furo[3,2-b]pyridine-3-carboxamide;
2-amino-N-{4-[3-amino-5-(trifluoromethyl)piperidin-1-yl]pyridin-3-yl}-6-trifluoromethyl-furo[3,2-b]pyridine-3-carboxamide;
2-amino-N-{4-[cis-3-amino-5-(trifluoromethyl)piperidin-1-yl]pyridin-3-yl}-6-trifluoromethyl-furo[3,2-b]pyridine-3-carboxamide;
2-amino-N-{4-[(3S,5R)-3-amino-5-(trifluoromethyl)piperidin-1-yl]pyridin-3-yl}-6-trifluoromethyl-furo[3,2-b]pyridine-3-carboxamide;
2-amino-N-{4-[3-amino-5-(trifluoromethyl)piperidin-1-yl]pyridin-3-yl}-6-chlorofuro[3,2-b]pyridine-3-carboxamide;
2-amino-N-{4-[cis-3-amino-5-(trifluoromethyl)piperidin-1-yl]pyridin-3-yl}-6-chlorofuro[3,2-b]pyridine-3-carboxamide;
2-amino-N-{4-[(3S,5R)-3-amino-5-(trifluoromethyl)piperidin-1-yl]pyridin-3-yl}-6-chlorofuro[3,2-b]pyridine-3-carboxamide;
2-amino-N-{4-[3-amino-5-(trifluoromethyl)piperidin-1-yl]pyridin-3-yl}-6-fluorofuro[3,2-b]pyridine-3-carboxamide;
2-amino-N-{4-[cis-3-amino-5-(trifluoromethyl)piperidin-1-yl]pyridin-3-yl}-6-fluorofuro[3,2-b]pyridine-3-carboxamide;
2-amino-N-{4-[(3S,5R)-3-amino-5-(trifluoromethyl)piperidin-1-yl]pyridin-3-yl}-6-fluorofuro[3,2-b]pyridine-3-carboxamide;
2-amino-N-{4-[3-amino-5-methyl-piperidin-1-yl]pyridin-3-yl}-furo[3,2-b]pyridine-3-carboxamide;
2-amino-N-{4-[cis-3-amino-5-methyl-piperidin-1-yl]pyridin-3-yl}-furo[3,2-b]pyridine-3-carboxamide;
2-amino-N-{4-[(3S,5R)-3-amino-5-methyl-piperidin-1-yl]pyridin-3-yl}-furo[3,2-b]pyridine-3-carboxamide;
2-amino-N-{4-[3-amino-4-hydroxy-5-methylpiperidin-1-yl]pyridin-3-yl}-6-chlorofuro[3,2-b]pyridine-3-carboxamide;
2-amino-N-{4-[(3R,4R,5S)-3-amino-4-hydroxy-5-methylpiperidin-1-yl]pyridin-3-yl}-6-chlorofuro[3,2-b]pyridine-3-carboxamide;
2-amino-N-{4-[3-amino-4-hydroxy-5-methylpiperidin-1-yl]pyridin-3-yl}-6-propylfuro[3,2-b]pyridine-3-carboxamide;
2-amino-N-{4-[(3R,4R,5S)-3-amino-4-hydroxy-5-methylpiperidin-1-yl]pyridin-3-yl}-6-propylfuro[3,2-b]pyridine-3-carboxamide;
2-amino-N-{4-[3-amino-4-hydroxy-5-methylpiperidin-1-yl]pyridin-3-yl}-6-(trifluoromethyl)furo[3,2-b]pyridine-3-carboxamide;
2-amino-N-{4-[(3R,4R,5S)-3-amino-4-hydroxy-5-methylpiperidin-1-yl]pyridin-3-yl}-6-(trifluoromethyl)furo[3,2-b]pyridine-3-carboxamide;
2-amino-N-{4-[3-amino-5-(trifluoromethyl)piperidin-1-yl]pyridin-3-yl}-6-propylfuro[3,2-b]pyridine-3-carboxamide;
2-amino-N-{4-[cis-3-amino-5-(trifluoromethyl)piperidin-1-yl]pyridin-3-yl}-6-propylfuro[3,2-b]pyridine-3-carboxamide;
2-amino-N-{4-[(3S,5R)-3-amino-5-(trifluoromethyl)piperidin-1-yl]pyridin-3-yl}-6-propylfuro[3,2-b]pyridine-3-carboxamide;
2-amino-N-{4-[3-amino-5-methyl-piperidin-1-yl]pyridin-3-yl}-6-propylfuro[3,2-b]pyridine-3-carboxamide;
2-amino-N-{4-[cis-3-amino-5-methyl-piperidin-1-yl]pyridin-3-yl}-6-propylfuro[3,2-b]pyridine-3-carboxamide;
2-amino-N-{4-[(3S,5R)-3-amino-5-methyl-piperidin-1-yl]pyridin-3-yl}-6-propylfuro[3,2-b]pyridine-3-carboxamide;
2-amino-N-{4-[3-amino-5-methyl-piperidin-1-yl]pyridin-3-yl}-6-fluorofuro[3,2-b]pyridine-3-carboxamide;

2-amino-N-{4-[cis-3-amino-5-methyl-piperidin-1-yl]pyridin-3-yl}-6-fluorofuro[3,2-b]pyridine-3-carboxamide;
2-amino-N-{4-[(3S,5R)-3-amino-5-methyl-piperidin-1-yl]pyridin-3-yl}-6-fluorofuro[3,2-b]pyridine-3-carboxamide;
2-amino-N-{4-[(3-amino-5-methyl-piperidin-1-yl]pyridin-3-yl}-6-chlorofuro[3,2-b]pyridine-3-carboxamide;
2-amino-N-{4-[cis3-amino-5-methyl-piperidin-1-yl]pyridin-3-yl}-6-chlorofuro[3,2-b]pyridine-3-carboxamide;
2-amino-N-{4-[(3S,5R)-3-amino-5-methyl-piperidin-1-yl]pyridin-3-yl}-6-chlorofuro[3,2-b]pyridine-3-carboxamide;
2-amino-N-{4-[3-amino-5-methyl-piperidin-1-yl]pyridin-3-yl}-6-(trifluoromethyl)-furo[3,2-b]pyridine-3-carboxamide;
2-amino-N-{4-[cis-3-amino-5-methyl-piperidin-1-yl]pyridin-3-yl}-6-(trifluoromethyl)-furo[3,2-b]pyridine-3-carboxamide;
2-amino-N-{4-[(3S,5R)-3-amino-5-methyl-piperidin-1-yl]pyridin-3-yl}-6-(trifluoromethyl)-furo[3,2-b]pyridine-3-carboxamide;
2-amino-N-{4-[3-amino-4-hydroxy-5-methylpiperidin-1-yl]pyridin-3-yl}-furo[3,2-b]pyridine-3-carboxamide;
2-amino-N-{4-[(3R,4R,5S)-3-amino-4-hydroxy-5-methylpiperidin-1-yl]pyridin-3-yl}-furo[3,2-b]pyridine-3-carboxamide;
2-amino-N-{4-[3-amino-4-hydroxy-5-methylpiperidin-1-yl]pyridin-3-yl}-6-isopropylfuro[3,2-b]pyridine-3-carboxamide;
2-amino-N-{4-[(3R,4R,5S)-3-amino-4-hydroxy-5-methylpiperidin-1-yl]pyridin-3-yl}-6-isopropylfuro[3,2-b]pyridine-3-carboxamide;
2-amino-N-{5-methyl-4-[3-amino-4-hydroxy-5-methylpiperidin-1-yl]pyridin-3-yl}-furo[3,2-b]pyridine-3-carboxamide;
2-amino-N-{5-methyl-4-[(3R,4R,5S)-3-amino-4-hydroxy-5-methylpiperidin-1-yl]pyridin-3-yl}-furo[3,2-b]pyridine-3-carboxamide;
2-amino-N-{5-methyl-4-[3-amino-4-hydroxy-5-methylpiperidin-1-yl]pyridin-3-yl}-6-propylfuro[3,2-b]pyridine-3-carboxamide;
2-amino-N-{5-methyl-4-[(3R,4R,5S)-3-amino-4-hydroxy-5-methylpiperidin-1-yl]pyridin-3-yl}-6-propylfuro[3,2-b]pyridine-3-carboxamide;
2-amino-N-{5-methyl-4-[3-amino-4-hydroxy-5-methylpiperidin-1-yl]pyridin-3-yl}-6-chlorofuro[3,2-b]pyridine-3-carboxamide;
2-amino-N-{5-methyl-4-[(3R,4R,5S)-3-amino-4-hydroxy-5-methylpiperidin-1-yl]pyridin-3-yl}-6-chlorofuro[3,2-b]pyridine-3-carboxamide;
2-amino-N-{5-methyl-4-[3-amino-4-hydroxy-5-methylpiperidin-1-yl]pyridin-3-yl}-6-(trifluoromethyl)-furo[3,2-b]pyridine-3-carboxamide;
2-amino-N-{5-methyl-4-[(3R,4R,5S)-3-amino-4-hydroxy-5-methylpiperidin-1-yl]pyridin-3-yl}-6-(trifluoromethyl)-furo[3,2-b]pyridine-3-carboxamide;
2-amino-N-{4-[3-amino-4-fluoro-piperidin-1-yl]pyridin-3-yl}-6-propylfuro[3,2-b]pyridine-3-carboxamide;
2-amino-N-{4-[trans-3-amino-4-fluoro-piperidin-1-yl]pyridin-3-yl}-6-propylfuro[3,2-b]pyridine-3-carboxamide;
2-amino-N-{4-[(3R,4R)-3-amino-4-fluoro-piperidin-1-yl]pyridin-3-yl}-6-propylfuro[3,2-b]pyridine-3-carboxamide;
2-amino-N-{4-[3-aminopiperidin-1-yl]pyridin-3-yl}-7-chloro-furo[3,2-b]pyridine-3-carboxamide;
2-amino-N-{4-[(3S)-3-aminopiperidin-1-yl]pyridin-3-yl}-7-chloro-furo[3,2-b]pyridine-3-carboxamide;
2-amino-N-{4-[(3R)-3-aminopiperidin-1-yl]pyridin-3-yl}-7-chloro-furo[3,2-b]pyridine-3-carboxamide;
2-amino-N-{4-[3-amino-5-cyclopropyl-4-hydroxypiperidin-1-yl]pyridin-3-yl}-6-propylfuro[3,2-b]pyridine-3-carboxamide;
2-amino-N-{4-[(3R,4R,5S)-3-amino-5-cyclopropyl-4-hydroxypiperidin-1-yl]pyridin-3-yl}-6-propylfuro[3,2-b]pyridine-3-carboxamide;
2-amino-N-{4-[3-amino-4-hydroxy-4,5-dimethylpiperidin-1-yl]pyridin-3-yl}-6-propylfuro[3,2-b]pyridine-3-carboxamide;
2-amino-N-{4-[(3R,4R,5S)-3-amino-4-hydroxy-4, 5-dimethylpiperidin-1-yl]pyridin-3-yl}-6-propylfuro[3,2-b]pyridine-3-carboxamide;
2-amino-N-{4-[3-amino-4-hydroxy-4,5-dimethylpiperidin-1-yl]pyridin-3-yl}-6-propylfuro[3,2-b]pyridine-3-carboxamide;
2-amino-N-{4-[(3R,4S,5S)-3-amino-4-hydroxy-4, 5-dimethylpiperidin-1-yl]pyridin-3-yl}-6-propylfuro[3,2-b]pyridine-3-carboxamide;
2-amino-N-{4-[3-amino-4-hydroxy-5-(trifluoromethyl)piperidin-1-yl]pyridin-3-yl}furo[3,2-b]pyridine-3-carboxamide;
2-amino-N-{4-[(3R,4R,5S)-3-amino-4-hydroxy-5-(trifluoromethyl)piperidin-1-yl]pyridin-3-yl}furo[3,2-b]pyridine-3-carboxamide;
2-amino-N-{4-[3-amino-5-(trifluoromethyl)piperidin-1-yl]pyridin-3-yl}-6-(tetrahydro-2H-pyran-4-yl)furo[3,2-b]pyridine-3-carboxamide;
2-amino-N-{4-[trans-3-amino-5-(trifluoromethyl)piperidin-1-yl]pyridin-3-yl}-6-(tetrahydro-2H-pyran-4-yl)furo[3,2-b]pyridine-3-carboxamide;
2-amino-N-{4-[(3S,5R)-3-amino-5-(trifluoromethyl)piperidin-1-yl]pyridin-3-yl}-6-(tetrahydro-2H-pyran-4-yl)furo[3,2-b]pyridine-3-carboxamide;
2-amino-N-{4-[3-amino-5-(trifluoromethyl)piperidin-1-yl]pyridin-3-yl}-6-(1-methylpiperidin-4-yl)furo[3,2-b]pyridine-3-carboxamide;
2-amino-N-{4-[cis-3-amino-5-(trifluoromethyl)piperidin-1-yl]pyridin-3-yl}-6-(1-methylpiperidin-4-yl)furo[3,2-b]pyridine-3-carboxamide;
2-amino-N-{4-[(3S,5R)-3-amino-5-(trifluoromethyl)piperidin-1-yl]pyridin-3-yl}-6-(1-methylpiperidin-4-yl)furo[3,2-b]pyridine-3-carboxamide;
2-amino-N-{4-[3-amino-5-methylpiperidin-1-yl]pyridin-3-yl}-6-(tetrahydro-2H-pyran-4-yl)furo[3,2-b]pyridine-3-carboxamide;
2-amino-N-{4-[cis-3-amino-5-methylpiperidin-1-yl]pyridin-3-yl}-6-(tetrahydro-2H-pyran-4-yl)furo[3,2-b]pyridine-3-carboxamide;
2-amino-N-{4-[(3S,5R)-3-amino-5-methylpiperidin-1-yl]pyridin-3-yl}-6-(tetrahydro-2H-pyran-4-yl)furo[3,2-b]pyridine-3-carboxamide;
2-amino-N-{4-[3-amino-5-methylpiperidin-1-yl]pyridin-3-yl}-6-cyclobutylfuro[3,2-b]pyridine-3-carboxamide;
2-amino-N-{4-[cis-3-amino-5-methylpiperidin-1-yl]pyridin-3-yl}-6-cyclobutylfuro[3,2-b]pyridine-3-carboxamide;
2-amino-N-{4-[(3S,5R)-3-amino-5-methylpiperidin-1-yl]pyridin-3-yl}-6-cyclobutylfuro[3,2-b]pyridine-3-carboxamide;
2-amino-N-{4-[3-amino-5-(trifluoromethyl)piperidin-1-yl]pyridin-3-yl}-6-cyclobutylfuro[3,2-b]pyridine-3-carboxamide;

2-amino-N-{4-[cis-3-amino-5-(trifluoromethyl)piperidin-1-yl]pyridin-3-yl}-6-cyclobutylfuro[3,2-b]pyridine-3-carboxamide;
2-amino-N-{4-[(3S,5R)-3-amino-5-(trifluoromethyl)piperidin-1-yl]pyridin-3-yl}-6-cyclobutylfuro[3,2-b]pyridine-3-carboxamide;
2-amino-N-{4-[3-amino-5-(trifluoromethyl)piperidin-1-yl]pyridin-3-yl}-6-[(3-fluoroazetidin-1-yl)methyl]furo[3,2-b]pyridine-3-carboxamide;
2-amino-N-{4-[cis-3-amino-5-(trifluoromethyl)piperidin-1-yl]pyridin-3-yl}-6-[(3-fluoroazetidin-1-yl)methyl]furo[3,2-b]pyridine-3-carboxamide;
2-amino-N-{4-[(3S,5R)-3-amino-5-(trifluoromethyl)piperidin-1-yl]pyridin-3-yl]-1-6-[(3-fluoroazetidin-1-yl)methyl]furo[3,2-b]pyridine-3-carboxamide;
2-amino-N-{4-[3-amino-5-(trifluoromethyl)piperidin-1-yl]pyridin-3-yl}-6-[(3,3-difluoroazetidin-1-yl)methyl]furo[3,2-b]pyridine-3-carboxamide;
2-amino-N-{4-[cis-3-amino-5-(trifluoromethyl)piperidin-1-yl]pyridin-3-yl}-6-[(3,3-difluoroazetidin-1-yl)methyl]furo[3,2-b]pyridine-3-carboxamide;
2-amino-N-{4-[(3S,5R)-3-amino-5-(trifluoromethyl)piperidin-1-yl]pyridin-3-yl}-6-[(3,3-difluoroazetidin-1-yl)methyl]furo[3,2-b]pyridine-3-carboxamide;
2-amino-N-{4-[3-amino-5-(trifluoromethyl)piperidin-1-yl]pyridin-3-yl}-6-[(3-hydroxyazetidin-1-yl)methyl]furo[3,2-b]pyridine-3-carboxamide;
2-amino-N-{4-[cis-3-amino-5-(trifluoromethyl)piperidin-1-yl]pyridin-3-yl}-6-[(3-hydroxyazetidin-1-yl)methyl]furo[3,2-b]pyridine-3-carboxamide;
2-amino-N-{4-[(3S,5R)-3-amino-5-(trifluoromethyl)piperidin-1-yl]pyridin-3-yl}-6-[(3-hydroxyazetidin-1-yl)methyl]furo[3,2-b]pyridine-3-carboxamide;
2-amino-N-{4-[3-amino-5-methyl-4-(1H-1,2,3-triazol-1-yl)piperidin-1-yl]pyridin-3-yl}-6-isopropylfuro[3,2-b]pyridine-3-carboxamide;
2-amino-N-{4-[(3R,4S,5S)-3-amino-5-methyl-4-(1H-1,2,3-triazol-1-yl)piperidin-1-yl]pyridin-3-yl}-6-isopropylfuro[3,2-b]pyridine-3-carboxamide;
2-amino-N-{4-[3-amino-5-(trifluoromethyl)piperidin-1-yl]pyridin-3-yl}-6-[(3-methoxypyrrolidin-1-yl)methyl]furo[3,2-b]pyridine-3-carboxamide;
2-amino-N-{4-[cis-3-amino-5-(trifluoromethyl)piperidin-1-yl]pyridin-3-yl}-6-[(3-methoxypyrrolidin-1-yl)methyl]furo[3,2-b]pyridine-3-carboxamide;
2-amino-N-{4-[(3S,5R)-3-amino-5-(trifluoromethyl)piperidin-1-yl]pyridin-3-yl}-6-[(3-methoxypyrrolidin-1-yl)methyl]furo[3,2-b]pyridine-3-carboxamide;
2-amino-N-{4-[3-amino-5-(trifluoromethyl)piperidin-1-yl]pyridin-3-yl}-6-[(3-ethoxypyrrolidin-1-yl)methyl]furo[3,2-b]pyridine-3-carboxamide;
2-amino-N-{4-[cis-3-amino-5-(trifluoromethyl)piperidin-1-yl]pyridin-3-yl}-6-[(3-ethoxypyrrolidin-1-yl)methyl]furo[3,2-b]pyridine-3-carboxamide;
2-amino-N-{4-[(3S,5R)-3-amino-5-(trifluoromethyl)piperidin-1-yl]pyridin-3-yl}-6-[(3-ethoxypyrrolidin-1-yl)methyl]furo[3,2-b]pyridine-3-carboxamide;
2-amino-N-{4-[3-amino-5-(trifluoromethyl)piperidin-1-yl]pyridin-3-yl}-6-{[(3R)-3-fluoropyrrolidin-1-yl]methyl}furo[3,2-b]pyridine-3-carboxamide;
2-amino-N-{4-[cis-3-amino-5-(trifluoromethyl)piperidin-1-yl]pyridin-3-yl}-6-{[(3R)-3-fluoropyrrolidin-1-yl]methyl}furo[3,2-b]pyridine-3-carboxamide;
2-amino-N-{4-[(3S,5R)-3-amino-5-(trifluoromethyl)piperidin-1-yl]pyridin-3-yl}-6-{[(3R)-3-fluoropyrrolidin-1-yl]methyl}furo[3,2-b]pyridine-3-carboxamide;
2-amino-N-{4-[3-amino-5-(trifluoromethyl)piperidin-1-yl]pyridin-3-yl}-6-{[(3S)-3-fluoropyrrolidin-1-yl]methyl}furo[3,2-b]pyridine-3-carboxamide;
2-amino-N-{4-[cis-3-amino-5-(trifluoromethyl)piperidin-1-yl]pyridin-3-yl}-6-{[(3S)-3-fluoropyrrolidin-1-yl]methyl}furo[3,2-b]pyridine-3-carboxamide;
2-amino-N-{4-[(3S,5R)-3-amino-5-(trifluoromethyl)piperidin-1-yl]pyridin-3-yl}-6-{[(3S)-3-fluoropyrrolidin-1-yl]methyl}furo[3,2-b]pyridine-3-carboxamide;
2-amino-N-{4-[3-amino-5-(trifluoromethyl)piperidin-1-yl]pyridin-3-yl}-6-[(4-methoxypiperidin-1-yl)methyl]furo[3,2-b]pyridine-3-carboxamide;
2-amino-N-{4-[cis-3-amino-5-(trifluoromethyl)piperidin-1-yl]pyridin-3-yl}-6-[(4-methoxypiperidin-1-yl)methyl]furo[3,2-b]pyridine-3-carboxamide;
2-amino-N-{4-[(3S,5R)-3-amino-5-(trifluoromethyl)piperidin-1-yl]pyridin-3-yl}-6-[(4-methoxypiperidin-1-yl)methyl]furo[3,2-b]pyridine-3-carboxamide;
2-amino-N-{4-[3-amino-5-(trifluoromethyl)piperidin-1-yl]pyridin-3-yl}-6-[(4-methylpiperazin-1-yl)methyl]furo[3,2-b]pyridine-3-carboxamide;
2-amino-N-{4-[cis-3-amino-5-(trifluoromethyl)piperidin-1-yl]pyridin-3-yl}-6-[(4-methylpiperazin-1-yl)methyl]furo[3,2-b]pyridine-3-carboxamide;
2-amino-N-{4-[(3S,5R)-3-amino-5-(trifluoromethyl)piperidin-1-yl]pyridin-3-yl}-6-[(4-methylpiperazin-1-yl)methyl]furo[3,2-b]pyridine-3-carboxamide;
2-amino-N-{4-[3-amino-5-(trifluoromethyl)piperidin-1-yl]pyridin-3-yl}-6-(1-methyl-1H-pyrazol-4-yl)furo[3,2-b]pyridine-3-carboxamide;
2-amino-N-{4-[cis-3-amino-5-(trifluoromethyl)piperidin-1-yl]pyridin-3-yl}-6-(1-methyl-1H-pyrazol-4-yl)furo[3,2-b]pyridine-3-carboxamide;
2-amino-N-{4-[(3S,5R)-3-amino-5-(trifluoromethyl)piperidin-1-yl]pyridin-3-yl}-6-(1-methyl-1H-pyrazol-4-yl)furo[3,2-b]pyridine-3-carboxamide;
2-amino-N-{4-[3-amino-5-methylpiperidin-1-yl]pyridin-3-yl}-6-(1-methyl-1H-pyrazol-4-yl)furo[3,2-b]pyridine-3-carboxamide;
2-amino-N-{4-[(cis)-3-amino-5-methylpiperidin-1-yl]pyridin-3-yl}-6-(1-methyl-1H-pyrazol-4-yl)furo[3,2-b]pyridine-3-carboxamide;
2-amino-N-{4-[(3S,5R)-3-amino-5-methylpiperidin-1-yl]pyridin-3-yl}-6-(1-methyl-1H-pyrazol-4-yl)furo[3,2-b]pyridine-3-carboxamide;
2-amino-N-{4-[(3S,5R)-3-amino-5-(trifluoromethyl)piperidin-1-yl]pyridin-3-yl}-6-pyrimidin-5-ylfuro[3,2-b]pyridine-3-carboxamide;
2-amino-N-{4-[3-amino-5-(trifluoromethyl)piperidin-1-yl]pyridin-3-yl}-6-pyrimidin-5-ylfuro[3,2-b]pyridine-3-carboxamide;
2-amino-N-{4-[cis-3-amino-5-(trifluoromethyl)piperidin-1-yl]pyridin-3-yl}-6-pyrimidin-5-ylfuro[3,2-b]pyridine-3-carboxamide;
2-amino-N-{4-[3-amino-5-methylpiperidin-1-yl]pyridin-3-yl}-6-pyrimidin-5-ylfuro[3,2-b]pyridine-3-carboxamide;
2-amino-N-{4-[cis-3-amino-5-methylpiperidin-1-yl]pyridin-3-yl}-6-pyrimidin-5-ylfuro[3,2-b]pyridine-3-carboxamide;
2-amino-N-{4-[(3S,5R)-3-amino-5-methylpiperidin-1-yl]pyridin-3-yl}-6-pyrimidin-5-ylfuro[3,2-b]pyridine-3-carboxamide;
2-amino-N-{4-[3-amino-5-(trifluoromethyl)piperidin-1-yl]pyridin-3-yl}-6-cyclopropylfuro[3,2-b]pyridine-3-carboxamide;

2-amino-N-{4-[cis-3-amino-5-(trifluoromethyl)piperidin-1-yl]pyridin-3-yl}-6-cyclopropylfuro[3,2-b]pyridine-3-carboxamide;
2-amino-N-{4-[(3S,5R)-3-amino-5-(trifluoromethyl)piperidin-1-yl]pyridin-3-yl}-6-cyclopropylfuro[3,2-b]pyridine-3-carboxamide;
2-amino-N-{4-[3-amino-5-methylpiperidin-1-yl]pyridin-3-yl}-6-cyclopropylfuro[3,2-b]pyridine-3-carboxamide;
2-amino-N-{4-[cis-3-amino-5-methylpiperidin-1-yl]pyridin-3-yl}-6-cyclopropylfuro[3,2-b]pyridine-3-carboxamide;
2-amino-N-{4-[(3S,5R)-3-amino-5-methylpiperidin-1-yl]pyridin-3-yl}-6-cyclopropylfuro[3,2-b]pyridine-3-carboxamide;
2-amino-N-{4-[3-amino-5-(trifluoromethyl)piperidin-1-yl]pyridin-3-yl}-6-methylfuro[3,2-b]pyridine-3-carboxamide;
2-amino-N-{4-[cis-3-amino-5-(trifluoromethyl)piperidin-1-yl]pyridin-3-yl}-6-methylfuro[3,2-b]pyridine-3-carboxamide;
2-amino-N-{4-[(3S,5R)-3-amino-5-(trifluoromethyl)piperidin-1-yl]pyridin-3-yl}-6-methylfuro[3,2-b]pyridine-3-carboxamide;
2-amino-N-{4-[3-amino-5-methylpiperidin-1-yl]pyridin-3-yl}-6-methylfuro[3,2-b]pyridine-3-carboxamide;
2-amino-N-{4-[cis-3-amino-5-methylpiperidin-1-yl]pyridin-3-yl}-6-methylfuro[3,2-b]pyridine-3-carboxamide;
2-amino-N-{4-[(3S,5R)-3-amino-5-methylpiperidin-1-yl]pyridin-3-yl}-6-methylfuro[3,2-b]pyridine-3-carboxamide;
2-amino-N-{4-[3-amino-5-methylpiperidin-1-yl]pyridin-3-yl}-6-ethylfuro[3,2-b]pyridine-3-carboxamide;
2-amino-N-{4-[cis-3-amino-5-methylpiperidin-1-yl]pyridin-3-yl}-6-ethylfuro[3,2-b]pyridine-3-carboxamide;
2-amino-N-{4-[(3S,5R)-3-amino-5-methylpiperidin-1-yl]pyridin-3-yl}-6-ethylfuro[3,2-b]pyridine-3-carboxamide;
2-amino-N-{4-[3-amino-5-(trifluoromethyl)piperidin-1-yl]pyridin-3-yl}-6-ethylfuro[3,2-b]pyridine-3-carboxamide;
2-amino-N-{4-[cis)-3-amino-5-(trifluoromethyl)piperidin-1-yl]pyridin-3-yl}-6-ethylfuro[3,2-b]pyridine-3-carboxamide;
2-amino-N-{4-[(3S,5R)-3-amino-5-(trifluoromethyl)piperidin-1-yl]pyridin-3-yl}-6-ethylfuro[3,2-b]pyridine-3-carboxamide;
2-amino-N-{4-[3-amino-5-methylpiperidin-1-yl]pyridin-3-yl}difluorophenyl)furo[3,2-b]pyridine-3-carboxamide;
2-amino-N-{4-[cis-3-amino-5-methylpiperidin-1-yl]pyridin-3-yl}difluorophenyl)furo[3,2-b]pyridine-3-carboxamide;
2-amino-N-{4-[(3S,5R)-3-amino-5-methylpiperidin-1-yl]pyridin-3}-6-(2,6-difluorophenyl)furo[3,2-b]pyridine-3-carboxamide;
2-amino-N-(4-(3-amino-5-methylpiperidin-1-yl)pyridin-3-yl)-6-(difluoromethoxy)furo[3,2-b]pyridine-3-carboxamide;
2-amino-N-(4-(cis-3-amino-5-methylpiperidin-1-yl)pyridin-3-yl)-6-(difluoromethoxy)furo[3,2-b]pyridine-3-carboxamide;
2-amino-N-(4-((3S,5R)-3-amino-5-methylpiperidin-1-yl)pyridin-3-yl)-6-(difluoromethoxy)furo[3,2-b]pyridine-3-carboxamide;
2-amino-N-(4-(3-amino-5-methylpiperidin-1-yl)pyridin-3-yl)-6-isopropoxyfuro[3,2-b]pyridine-3-carboxamide;
2-amino-N-(4-(cis-3-amino-5-methylpiperidin-1-yl)pyridin-3-yl)-6-isopropoxyfuro[3,2-b]pyridine-3-carboxamide;
2-amino-N-(4-((3S,5R)-3-amino-5-methylpiperidin-1-yl)pyridin-3-yl)-6-isopropoxyfuro[3,2-b]pyridine-3-carboxamide;
2-amino-N-(4-(3-amino-5-methylpiperidin-1-yl)pyridin-3-yl)-6-(tetrahydrofuran-3-yl)furo[3,2-b]pyridine-3-carboxamide;
2-amino-N-(4-(cis-3-amino-5-methylpiperidin-1-yl)pyridin-3-yl)-6-(tetrahydrofuran-3-yl)furo[3,2-b]pyridine-3-carboxamide;
2-amino-N-(4-((3S,5R)-3-amino-5-methylpiperidin-1-yl)pyridin-3-yl)-6-(tetrahydrofuran-3-yl)furo[3,2-b]pyridine-3-carboxamide;
2-amino-N-{4-[3-amino-5-(trifluoromethyl)piperidin-1-yl]pyridin-3-yl}-6-(tetrahydrofuran-3-yl)furo[3,2-b]pyridine-3-carboxamide;
2-amino-N-{4-[cis-3-amino-5-(trifluoromethyl)piperidin-1-yl]pyridin-3-yl}-6-(tetrahydrofuran-3-yl)furo[3,2-b]pyridine-3-carboxamide;
2-amino-N-{4-[(3S,5R)-3-amino-5-(trifluoromethyl)piperidin-1-yl]pyridin-3-yl}-6-(tetrahydrofuran-3-yl)furo[3,2-b]pyridine-3-carboxamide;
2-amino-N-{4-[3-amino-4-hydroxy-5-methylpiperidin-1-yl]pyridin-3-yl}-6-cyclobutylfuro[3,2-b]pyridine-3-carboxamide;
2-amino-N-{4-[(3R,4R,5S)-3-amino-4-hydroxy-5-methylpiperidin-1-yl]pyridin-3-yl}-6-cyclobutylfuro[3,2-b]pyridine-3-carboxamide;
2-amino-N-{4-[3-amino-5-cyclopropyl-4-hydroxypiperidin-1-yl]pyridin-3-yl}-6-cyclobutylfuro[3,2-b]pyridine-3-carboxamide;
2-amino-N-{4-[(3R,4R,5S)-3-amino-5-cyclopropyl-4-hydroxypiperidin-1-yl]pyridin-3-yl}-6-cyclobutylfuro[3,2-b]pyridine-3-carboxamide;
2-amino-N-{4-[3-amino-5-(trifluoromethyl)piperidin-1-yl]pyridin-3-yl}-6-{6-[(methylamino)carbonyl]pyridin-3-yl}furo[3,2-b]pyridine-3-carboxamide;
2-amino-N-{4-[cis-3-amino-5-(trifluoromethyl)piperidin-1-yl]pyridin-3-yl}-6-{6-[(methylamino)carbonyl]pyridin-3-yl}furo[3,2-b]pyridine-3-carboxamide;
2-amino-N-{4-[(3S,5R)-3-amino-5-(trifluoromethyl)piperidin-1-yl]pyridin-3-yl}-6-{6-[(methylamino)carbonyl]pyridin-3-yl}furo[3,2-b]pyridine-3-carboxamide;
2-amino-N-(4-(3-amino-5-methylpiperidin-1-yl)pyridin-3-yl)-6-(6-(methylcarbamoyl)pyridin-3-yl)furo[3,2-b]pyridine-3-carboxamide;
2-amino-N-(4-(cis-3-amino-5-methylpiperidin-1-yl)pyridin-3-yl)-6-(6-(methylcarbamoyl)pyridin-3-yl)furo[3,2-b]pyridine-3-carboxamide;
2-amino-N-(4-((3S,5R)-3-amino-5-methylpiperidin-1-yl)pyridin-3-yl)-6-(6-(methylcarbamoyl)pyridin-3-yl)furo[3,2-b]pyridine-3-carboxamide;
2-amino-N-(4-(3-amino-5-cyclopropyl-4-hydroxypiperidin-1-yl)pyridin-3-yl)-6-cyclopropylfuro[3,2-b]pyridine-3-carboxamide;
2-amino-N-(4-((3R,4R,5S)-3-amino-5-cyclopropyl-4-hydroxypiperidin-1-yl)pyridin-3-yl)-6-cyclopropylfuro[3,2-b]pyridine-3-carboxamide;
2-amino-N-(4-(3-amino-5-cyclopropyl-4-hydroxypiperidin-1-yl)pyridin-3-yl)-6-(trifluoromethyl)furo[3,2-b]pyridine-3-carboxamide;
2-amino-N-(4-((3R,4R,5S)-3-amino-5-cyclopropyl-4-hydroxypiperidin-1-yl)pyridin-3-yl)-6-(trifluoromethyl)furo[3,2-b]pyridine-3-carboxamide;

2-amino-N-{4-[3-amino-5-(trifluoromethyl)piperidin-1-yl]pyridin-3-yl}-6-(3-methoxypropyl)furo[3,2-b]pyridine-3-carboxamide;

2-amino-N-{4-[cis-3-amino-5-(trifluoromethyl)piperidin-1-yl]pyridin-3-yl}-6-(3-methoxypropyl)furo[3,2-b]pyridine-3-carboxamide;

2-amino-N-{4-[(3S,5R)-3-amino-5-(trifluoromethyl)piperidin-1-yl]pyridin-3-yl}-6-(3-methoxypropyl)furo[3,2-b]pyridine-3-carboxamide;

2-amino-N-{4-[3-amino-5-(trifluoromethyl)piperidin-1-yl]pyridin-3-yl}-6-(3-morpholin-4-ylpropyl)furo[3,2-b]pyridine-3-carboxamide;

2-amino-N-{4-[cis-3-amino-5-(trifluoromethyl)piperidin-1-yl]pyridin-3-yl}-6-(3-morpholin-4-ylpropyl)furo[3,2-b]pyridine-3-carboxamide;

2-amino-N-{4-[(3S,5R)-3-amino-5-(trifluoromethyl)piperidin-1-yl]pyridin-3-yl}-6-(3-morpholin-4-ylpropyl)furo[3,2-b]pyridine-3-carboxamide;

2-amino-N-{4-[3-amino-5-methylpiperidin-1-yl]pyridin-3-yl}-6-(3-methoxypropyl)furo[3,2-b]pyridine-3-carboxamide;

2-amino-N-{4-[cis-3-amino-5-methylpiperidin-1-yl]pyridin-3-yl}-6-(3-methoxypropyl)furo[3,2-b]pyridine-3-carboxamide;

2-amino-N-{4-[(3S,5R)-3-amino-5-methylpiperidin-1-yl]pyridin-3-yl}-6-(3-methoxypropyl)furo[3,2-b]pyridine-3-carboxamide;

2-amino-N-{4-[3-amino-5-(trifluoromethyl)piperidin-1-yl]pyridin-3-yl}-6-[3-(dimethylamino)propyl]furo[3,2-b]pyridine-3-carboxamide;

2-amino-N-{4-[cis-3-amino-5-(trifluoromethyl)piperidin-1-yl]pyridin-3-yl}-6-[3-(dimethylamino)propyl]furo[3,2-b]pyridine-3-carboxamide;

2-amino-N-{4-[(3S,5R)-3-amino-5-(trifluoromethyl)piperidin-1-yl]pyridin-3-yl}-6-[3-(dimethylamino)propyl]furo[3,2-b]pyridine-3-carboxamide;

2-amino-N-{4-[3-amino-4-hydroxy-5-methylpiperidin-1-yl]pyridin-3-yl}-6-(3-fluoropropyl)furo[3,2-b]pyridine-3-carboxamide;

2-amino-N-{4-[cis-3-amino-4-hydroxy-5-methylpiperidin-1-yl]pyridin-3-yl}-6-(3-fluoropropyl)furo[3,2-b]pyridine-3-carboxamide;

2-amino-N-{4-[(3R,5S)-3-amino-4-hydroxy-5-methylpiperidin-1-yl]pyridin-3-yl}-6-(3-fluoropropyl)furo[3,2-b]pyridine-3-carboxamide;

2-amino-N-{4-[3-amino-5-(trifluoromethyl)piperidin-1-yl]pyridin-3-yl}-6-{2-[3-fluoropyrrolidin-1-yl]ethyl}furo[3,2-b]pyridine-3-carboxamide;

2-amino-N-{4-[cis-3-amino-5-(trifluoromethyl)piperidin-1-yl]pyridin-3-yl}-6-{2-[3-fluoropyrrolidin-1-yl]ethyl}furo[3,2-b]pyridine-3-carboxamide;

2-amino-N-{4-[(3S,5R)-3-amino-5-(trifluoromethyl)piperidin-1-yl]pyridin-3-yl}-6-{2-[(3R)-3-fluoropyrrolidin-1-yl]ethyl}furo[3,2-b]pyridine-3-carboxamide;

2-amino-N-(4-(3-amino-4-hydroxy-5-methylpiperidin-1-yl)pyridin-3-yl)-6-isopropylthieno[3,2-b]pyridine-3-carboxamide;

2-amino-N-(4-((3R,4R,5S)-3-amino-4-hydroxy-5-methylpiperidin-1-yl)pyridin-3-yl)-6-isopropylthieno[3,2-b]pyridine-3-carboxamide;

2-amino-N-(4-(3-amino-4-hydroxy-5-methylpiperidin-1-yl)pyridin-3-yl)-6-propylthieno[3,2-b]pyridine-3-carboxamide;

2-amino-N-(4-((3R,4R,5S)-3-amino-4-hydroxy-5-methylpiperidin-1-yl)pyridin-3-yl)-6-propylthieno[3,2-b]pyridine-3-carboxamide;

6-(acetylamino)-2-amino-N-{4-[3-amino-4-hydroxy-5-methylpiperidin-1-yl]pyridin-3-yl}thieno[3,2-b]pyridine-3-carboxamide;

6-(acetylamino)-2-amino-N-{4-[(3R,4R,5S)-3-amino-4-hydroxy-5-methylpiperidin-1-yl]pyridin-3-yl}thieno[3,2-b]pyridine-3-carboxamide;

2-amino-N-(4-(3-amino-4-hydroxy-5-methylpiperidin-1-yl)pyridin-3-yl)-6-(cyclopropanecarboxamido)thieno[3,2-b]pyridine-3-carboxamide;

2-amino-N-(4-((3R,4R,5S)-3-amino-4-hydroxy-5-methylpiperidin-1-yl)pyridin-3-yl)-6-(cyclopropanecarboxamido)thieno[3,2-b]pyridine-3-carboxamide;

2-amino-N-(4-(3-amino-4-hydroxy-5-methylpiperidin-1-yl)pyridin-3-yl)-6-isobutyramidothieno[3,2-b]pyridine-3-carboxamide;

2-amino-N-(4-((3R,4R,5S)-3-amino-4-hydroxy-5-methylpiperidin-1-yl)pyridin-3-yl)-6-isobutyramidothieno[3,2-b]pyridine-3-carboxamide;

2-amino-N-(4-(3-amino-5-(trifluoromethyl)piperidin-1-yl)pyridin-3-yl)-6-morpholinothieno[3,2-b]pyridine-3-carboxamide;

2-amino-N-(4-(cis-3-amino-5-(trifluoromethyl)piperidin-1-yl)pyridin-3-yl)-6-morpholinothieno[3,2-b]pyridine-3-carboxamide; and 2-amino-N-(4-(3S,5R)-3-amino-5-(trifluoromethyl)piperidin-1-yl)pyridin-3-yl)-6-morpholinothieno[3,2-b]pyridine-3-carboxamide;

or a pharmaceutically acceptable salt thereof.

47. A composition comprising a compound of claim 1, or a pharmaceutically acceptable salt thereof, and at least one pharmaceutically acceptable carrier.

48. A method of inhibiting Pim1, Pim2 or Pim3 enzyme comprising contacting the enzyme with a compound of claim 1, or a pharmaceutically acceptable salt thereof.

* * * * *

UNITED STATES PATENT AND TRADEMARK OFFICE
CERTIFICATE OF CORRECTION

PATENT NO. : 9,556,197 B2
APPLICATION NO. : 14/465910
DATED : January 31, 2017
INVENTOR(S) : Yun-Long Li et al.

It is certified that error appears in the above-identified patent and that said Letters Patent is hereby corrected as shown below:

In the Claims

Column 303, Line 63, Claim 1, delete "$S(=O)_2R^{c1}R^{d1};$" and insert -- $S(=O)_2NR^{c1}R^{d1};$ --, Column 304, Line 13, Claim 1, delete "$C(=O)R^{a2},$" and insert -- $C(=O)OR^{a2},$ --, Column 304, Line 16, Claim 1, after "$NR^{c2}C(=NR^{e2})NR^{c2}R^{d2},$" insert -- $S(=O)R^{b2},$ --, Column 304, Line 18, Claim 1, delete "$S(=O)NR^{c2}R^{d2},$" and insert -- $S(=O)_2NR^{c2}R^{d2};$ --, Column 305, Line 22, Claim 1, delete "$NR^{c4}C(=O)NR^{c4}R^{d4}$" and insert -- $NR^{c4}C(=O)NR^{c4}R^{d4},$ --, Column 305, Lines 23-24, Claim 1, delete "$NR^{c4}C(=NR^{e4})NR^{c4}R^{d4}$" and insert -- $NR^{c4}C(=NR^{e4})NR^{c4}R^{d4},$ --, Column 307, Line 22, Claim 4, delete "$C_{2-6}$ alkenyl" and insert -- $C_{2-6}$ alkenyl, --, Column 313-314, Lines 55-65, Claim 19, delete "

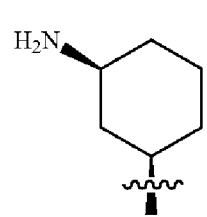

(B-125)

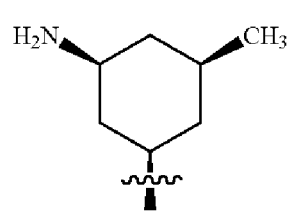

(B-126)

Signed and Sealed this
Twenty-eighth Day of November, 2017

Joseph Matal
*Performing the Functions and Duties of the
Under Secretary of Commerce for Intellectual Property and
Director of the United States Patent and Trademark Office*

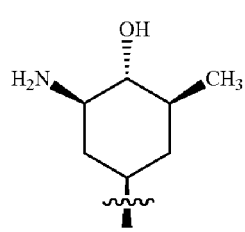
(B-127)
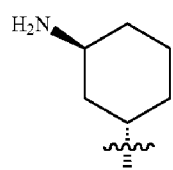
(B-128)
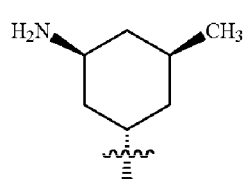
(B-129)
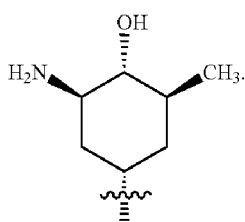
(B-130)
",
Column 318, Line 8, Claim 37, delete "S(=O)$_2$NR$^{c5}$R$^{d5}$," and insert -- S(=O)NR$^{c5}$R$^{d5}$, --,
Column 319, Line 27, Claim 41, delete "NR$^{c4}$C(=O)NR$^{b4}$," and insert -- NR$^{c4}$C(=O)R$^{b4}$, --,
Column 320, Line 14, Claim 41, delete "(=O)R$^{b6}$," and insert -- C(=O)R$^{b6}$, --,
Column 321, Lines 2-3, Claim 41, delete "C2-6 alkynyl" and insert -- C$_{2-6}$ alkynyl, --,
Column 324, Line 8, Claim 46, delete "(1 isopropylazetidin-3- yl)" and insert -- (1-isopropylazetidin-3-yl) --.